United States Patent
Møller et al.

(10) Patent No.: US 11,414,464 B2
(45) Date of Patent: Aug. 16, 2022

(54) **CHIMERIC PROTEINS FOR INDUCING IMMUNITY TOWARDS INFECTION WITH *S. AUREUS***

(71) Applicant: Evaxion Biotech ApS, København K (DK)

(72) Inventors: Niels Iversen Møller, København K (DK); Andreas Holm Mattsson, København K (DK); Jens Kringelum, Copenhagen Ø (DK)

(73) Assignee: Evaxion Biotech A/S, Hørsholm (DK)

( * ) Notice: Subject to any disclaimer, the term of this patent is extended or adjusted under 35 U.S.C. 154(b) by 119 days.

(21) Appl. No.: 16/319,729

(22) PCT Filed: Jul. 24, 2017

(86) PCT No.: PCT/EP2017/068694
§ 371 (c)(1),
(2) Date: Jan. 22, 2019

(87) PCT Pub. No.: WO2018/015575
PCT Pub. Date: Jan. 25, 2018

(65) Prior Publication Data
US 2019/0241623 A1  Aug. 8, 2019

(30) Foreign Application Priority Data

Jul. 22, 2016  (EP) .................................. 16180748

(51) Int. Cl.
*A61K 39/085* (2006.01)
*A61K 39/00* (2006.01)
*C07K 14/31* (2006.01)
*A61P 31/04* (2006.01)

(52) U.S. Cl.
CPC ............ *C07K 14/31* (2013.01); *A61K 39/085* (2013.01); *A61P 31/04* (2018.01); *A61K 39/00* (2013.01); *C07K 2319/00* (2013.01)

(58) Field of Classification Search
None
See application file for complete search history.

(56) References Cited

U.S. PATENT DOCUMENTS

| | | |
|---|---|---|
| 4,684,611 A | 8/1987 | Schilperoort et al. |
| 4,879,236 A | 11/1989 | Smith et al. |
| 4,952,500 A | 8/1990 | Finnerty et al. |
| 5,302,523 A | 4/1994 | Coffee et al. |
| 5,322,783 A | 6/1994 | Tomes et al. |
| 5,384,253 A | 1/1995 | Krzyzek et al. |
| 5,464,765 A | 11/1995 | Coffee et al. |
| 5,538,877 A | 7/1996 | Lundquist et al. |
| 5,538,880 A | 7/1996 | Lundquist et al. |
| 5,550,318 A | 8/1996 | Adams et al. |
| 5,563,055 A | 10/1996 | Townsend et al. |
| 5,580,859 A | 12/1996 | Feigner et al. |
| 5,589,466 A | 12/1996 | Feigner et al. |
| 5,591,616 A | 1/1997 | Hiei et al. |
| 5,610,042 A | 3/1997 | Chang et al. |
| 5,656,610 A | 8/1997 | Shuler et al. |
| 5,702,932 A | 12/1997 | Hoy et al. |
| 5,736,524 A | 4/1998 | Content et al. |
| 5,780,448 A | 7/1998 | Davis |
| 5,789,215 A | 8/1998 | Berns et al. |
| 5,871,986 A | 2/1999 | Boyce |
| 5,925,565 A | 7/1999 | Berlioz et al. |
| 5,935,819 A | 8/1999 | Eichner et al. |
| 5,945,100 A | 8/1999 | Fick |
| 5,981,274 A | 11/1999 | Tyrrell et al. |
| 5,994,624 A | 11/1999 | Trolinder et al. |
| 8,545,853 B2 | 10/2013 | Filee et al. |
| 2012/0014983 A1 | 1/2012 | Filee et al. |

FOREIGN PATENT DOCUMENTS

| | | |
|---|---|---|
| EP | 1769068 | 9/2005 |
| EP | 2192172 | 2/2010 |
| EP | 2853599 | 1/2015 |
| WO | WO9014837 | 12/1990 |
| WO | WO9409699 | 5/1994 |
| WO | WO9506128 | 3/1995 |
| WO | WO2010081875 | 7/2010 |
| WO | WO2012136653 | 10/2012 |

OTHER PUBLICATIONS

David et al. Clin. Microbiol. Rev. 23: 616-687, 2010.*
Greenspan et al. Nature Biotechnology 7: 936-937, 1999.*
Ellis RW. Vaccines, (Eds) Plotkin et al., W.B. Saunders Company, Philadelphia, Chapter29, 568-575, 1988.*
Skolnick et al. Trends in Biotechnology 18: 34-39, 2000.*
Zhang et al. mBio 9: e01949-18, pp. 1-13, 2018.*
Yang, L. et al, "Protective efficacy of the chimeric *Staphylococcus aureus* vaccine candidate IC in sepsis and pneumonia models", Scientific Reports, vol. 6(1), pp. 1-13, XP055414062, (Feb. 2016).
Zhou, H. et al, "An immunogenicity study of a newly fusion protein Cna-FnBP vaccinated against *Staphylococcus aureus* infections in a mice model", Vaccine, vol. 24(22) pp. 4830-4837, XP02801722, (May 2006).
Qian-Fei, Z. et al, "Evaluation of the protective immunity of a novel subunit fusion vaccine in a murine model of systemic MRSA infection", PLoS ONE, vol. 8(12), p. e81212, XP055414085, (Dec. 2013).

(Continued)

*Primary Examiner* — Sarvamangala Devi
(74) *Attorney, Agent, or Firm* — McHale & Slavin, P.A.

(57) ABSTRACT

Disclosed is chimeric polypeptides derived from *S. aureus* proteins having SEQ ID NOs: 1-9 and 139-146. The chimeric polypeptides are useful as immunogens for providing protective immunity against *S. aureus* infection. Also disclosed are compositions, methods of treatment and prophylaxis, nucleic acids and vectors comprising the nucleic acids.

32 Claims, 18 Drawing Sheets

Figure 1A:
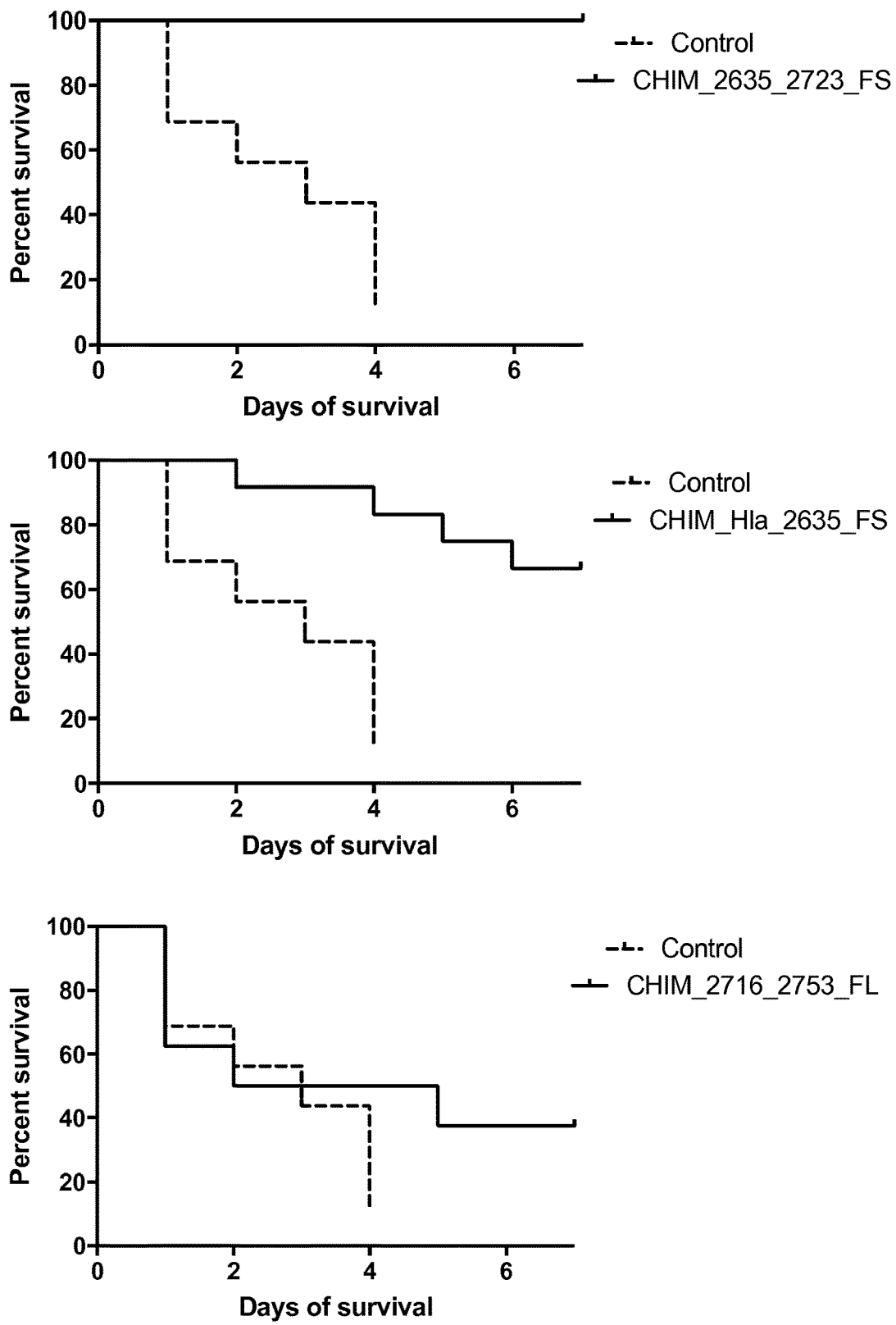

Specification includes a Sequence Listing.

(56) References Cited

OTHER PUBLICATIONS

Yu, L et al, "Cross-protective effect of a novel multi-antigen-chimeric vaccine against *Streptococcus* and *Staphylococcus aureus* infection in mice", Journal of Medical Microbiology, vol. 63(pt 12), pp. 1732-1740, XP055414083, (Oct. 2014).
Chen, X. et al, "Fusion protein linkers: property, design and functionality", Advanced Drug Delivery Rev., vol. 65(10), pp. 1357-1369, (2013).
Robinson, H. et al, "DNA Vaccines", Seminars in Immunology, vol. 9(5), pp. 271-283, (1997).
Donnelly, J. et al., "DNA Vaccines", Annual Review of Immunology, vol. 15, pp. 617-648, (Apr. 1997).
Agger, E. et al., "Catatonic liposomes formulated with synthetic mycobacterial cordfactor (CAF01): a versatile adjuvant for vaccines with different immunological requirements", PLoS ONE, vol. 3(9), p. e3116, (2008).

\* cited by examiner

SEQUENCE LISTING

```
<160> NUMBER OF SEQ ID NOS: 146

<210> SEQ ID NO 1
<211> LENGTH: 199
<212> TYPE: PRT
<213> ORGANISM: Staphylococcus aureus

<400> SEQUENCE: 1

Met Thr Glu Lys Glu Lys Met Leu Ala Glu Lys Trp Tyr Asp Ala Asn
1               5                   10                  15

Phe Asp Gln Asp Leu Ile Asn Glu Arg Ala Arg Ala Lys Asp Ile Cys
                20                  25                  30

Phe Glu Leu Asn His Thr Lys Pro Ser Asp Lys Asn Lys Arg Lys Glu
            35                  40                  45

Leu Ile Asp Glu Leu Phe Gln Thr Thr Thr Asp Asn Val Ser Ile Ser
        50                  55                  60

Ile Pro Phe Asp Thr Asp Tyr Gly Trp Asn Val Lys Leu Gly Lys Asn
65                  70                  75                  80

Val Tyr Val Asn Thr Asn Cys Tyr Phe Met Asp Gly Gly Gln Ile Thr
                85                  90                  95

Ile Gly Asp Asn Val Phe Ile Gly Pro Asn Cys Gly Phe Tyr Thr Ala
                100                 105                 110

Thr His Pro Leu Asn Phe His His Arg Asn Glu Gly Phe Glu Lys Ala
            115                 120                 125

Gly Pro Ile Asn Ile Gly Ser Asn Thr Trp Phe Gly Gly His Val Ala
```

```
                130                 135                 140
Val Leu Pro Gly Val Thr Ile Gly Glu Gly Ser Val Ile Gly Ala Gly
145                 150                 155                 160

Ser Val Val Thr Lys Asp Ile Pro Pro His Ser Leu Ala Val Gly Asn
                165                 170                 175

Pro Cys Lys Val Val Arg Lys Ile Asp Asn Glu Val Pro Ser Glu Ala
            180                 185                 190

Leu Asn Asp Glu Thr Leu Asn
        195

<210> SEQ ID NO 2
<211> LENGTH: 202
<212> TYPE: PRT
<213> ORGANISM: Staphylococcus aureus

<400> SEQUENCE: 2

Lys Arg Ile Lys Gln His Pro Asp Val Gln Lys Val Thr Asp Ala Thr
1               5                   10                  15

Ser Lys Val Ala Ser Lys Thr Ser Ala Ala Ile Ser Asn Thr Ala Ser
                20                  25                  30

Asp Val Lys Glu Tyr Val Gly Asp Lys Lys Gln Asp Phe Glu Asn Lys
            35                  40                  45

Arg Glu Leu Lys Lys Phe Ala Arg Glu His Asp Pro Ala Tyr Ile Glu
        50                  55                  60

Lys Lys Gly Glu Lys Leu Ala Lys Gln Asn Arg Lys Asp Ala Asp Lys
65                  70                  75                  80

Met Asn Lys Ile Leu Gln Lys Asn Ile Glu Lys Arg His Lys Glu Glu
                85                  90                  95

Gln Lys Ala Arg Glu Lys Asn Glu Ile Gln Arg Ile Lys Asp Met Lys
            100                 105                 110

Lys Ser Gln Lys Tyr Glu Val Lys Ala Gly Leu Thr Pro Asn Lys Leu
        115                 120                 125

Asp Glu Lys Thr Glu Lys Lys Gly Asp Lys Leu Ala Glu Lys Asn Arg
130                 135                 140

Lys Glu Ile Ala Lys Met Asn Lys Lys Leu Gln Lys Asn Ile Glu Lys
145                 150                 155                 160

Arg His Lys Glu Glu Gln Lys Arg Gln Gln Glu Ala Asp Lys Ala Arg
                165                 170                 175

Ile Lys Ser Phe Lys Lys Tyr Lys Asp Tyr Val Ala Lys Ser Ala Ser
            180                 185                 190

Gln Gln Asn Lys Glu Asn Asn Thr Glu Ala
        195                 200

<210> SEQ ID NO 3
<211> LENGTH: 293
<212> TYPE: PRT
<213> ORGANISM: Staphylococcus aureus

<400> SEQUENCE: 3

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
                20                  25                  30

Gly Met Leu Lys Lys Val Phe Tyr Ser Phe Ile Asp Asp Lys Asn His
            35                  40                  45

Asn Lys Lys Leu Leu Val Ile Arg Thr Lys Gly Thr Ile Ala Gly Gln
```

```
            50                  55                  60
Tyr Arg Val Tyr Ser Glu Glu Gly Ala Asn Lys Ser Gly Leu Ala Trp
 65                  70                  75                  80

Pro Ser Ala Phe Lys Val Gln Leu Gln Leu Pro Asp Asn Glu Val Ala
                 85                  90                  95

Gln Ile Ser Asp Tyr Tyr Pro Arg Asn Ser Ile Asp Thr Lys Glu Tyr
                100                 105                 110

Met Ser Thr Leu Thr Tyr Gly Phe Asn Gly Asn Val Thr Gly Asp Asp
                115                 120                 125

Thr Gly Lys Ile Gly Gly Leu Ile Gly Ala Asn Val Ser Ile Gly His
                130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
                180                 185                 190

Asn Gln Leu Phe Met Lys Thr Arg Asn Gly Ser Met Lys Ala Ala Asp
                195                 200                 205

Asn Phe Leu Asp Pro Asn Lys Ala Ser Ser Leu Leu Ser Ser Gly Phe
210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
                260                 265                 270

Lys Trp Ile Asp Arg Ser Ser Glu Arg Tyr Lys Ile Asp Trp Glu Lys
                275                 280                 285

Glu Glu Met Thr Asn
    290

<210> SEQ ID NO 4
<211> LENGTH: 351
<212> TYPE: PRT
<213> ORGANISM: Staphylococcus aureus

<400> SEQUENCE: 4

Ala Lys Asp Asn Leu Asn Gly Glu Lys Pro Thr Thr Asn Leu Asn His
 1               5                  10                  15

Asn Val Thr Ser Pro Ser Val Asn Ser Glu Met Asn Asn Asn Glu Thr
                20                  25                  30

Gly Thr Pro His Glu Ser Asn Gln Ala Gly Asn Glu Gly Thr Gly Ser
                35                  40                  45

Asn Ser Arg Asp Ala Asn Pro Asp Ser Asn Val Lys Pro Asp Ser
 50                 55                  60

Asn Asn Gln Asn Pro Ser Pro Asp Ser Lys Pro Asp Pro Asn Asn Pro
 65                 70                  75                  80

Asn Pro Gly Pro Asn Pro Lys Pro Asp Pro Asp Lys Pro Lys Pro Asn
                 85                 90                  95

Pro Glu Pro Lys Pro Asp Pro Lys Pro Asp Pro Lys Pro Lys Pro
                100                 105                 110

Asn Pro Asp Pro Lys Pro Asp Pro Asp Lys Pro Lys Pro Asn Pro Asp
                115                 120                 125
```

```
Pro Lys Pro Asp Pro Asp Lys Pro Lys Pro Asn Pro Asp Lys Pro
    130                 135                 140

Asp Pro Asn Pro Asn Pro Lys Pro Asp Pro Asn Lys Pro Asn Pro Asn
145                 150                 155                 160

Pro Ser Pro Asn Pro Asn Gln Pro Gly Asp Ser Asn Gln Ser Gly Gly
                165                 170                 175

Ser Lys Asn Gly Gly Thr Trp Asn Pro Asn Ala Ser Asp Gly Ser Asn
            180                 185                 190

Gln Gly Gln Trp Gln Pro Asn Gly Asn Gln Gly Asn Ser Gln Asn Pro
        195                 200                 205

Thr Gly Asn Asp Phe Val Ser Gln Arg Phe Leu Ala Leu Ala Asn Gly
    210                 215                 220

Ala Tyr Lys Tyr Asn Pro Tyr Ile Leu Asn Gln Ile Asn Gln Leu Gly
225                 230                 235                 240

Lys Glu Tyr Gly Glu Val Thr Asp Glu Asp Ile Tyr Asn Ile Ile Arg
                245                 250                 255

Lys Gln Asn Phe Ser Gly Asn Ala Tyr Leu Asn Gly Leu Gln Gln Gln
            260                 265                 270

Ser Asn Tyr Phe Arg Phe Gln Tyr Phe Asn Pro Leu Lys Ser Glu Arg
        275                 280                 285

Tyr Tyr Arg Asn Leu Asp Glu Gln Val Leu Ala Leu Ile Thr Gly Glu
    290                 295                 300

Ile Gly Ser Met Pro Asp Leu Lys Lys Pro Glu Asp Lys Pro Asp Ser
305                 310                 315                 320

Lys Gln Arg Ser Phe Glu Pro His Glu Lys Asp Asp Phe Thr Val Val
                325                 330                 335

Lys Lys Gln Glu Asp Asn Lys Lys Ser Ala Ser Thr Ala Tyr Ser
            340                 345                 350

<210> SEQ ID NO 5
<211> LENGTH: 365
<212> TYPE: PRT
<213> ORGANISM: Staphylococcus aureus

<400> SEQUENCE: 5

Gly Phe Leu Asn Lys Ser Lys Asn Glu Gln Ala Ala Leu Lys Ala Gln
1               5                   10                  15

Gln Ala Ala Ile Lys Glu Glu Ala Ser Ala Asn Asn Leu Ser Asp Thr
            20                  25                  30

Ser Gln Glu Ala Gln Glu Ile Gln Glu Ala Lys Arg Glu Ala Gln Ala
        35                  40                  45

Glu Ala Asp Lys Ser Val Ala Val Ser Asn Lys Glu Ser Lys Ala Val
50                  55                  60

Ala Leu Lys Ala Gln Gln Ala Ala Ile Lys Glu Ala Ser Ala Asn
65                  70                  75                  80

Asn Leu Ser Asp Thr Ser Gln Glu Ala Gln Glu Ile Gln Glu Ala Lys
                85                  90                  95

Lys Glu Ala Gln Ala Glu Thr Asp Lys Ser Ala Ala Val Ser Asn Glu
            100                 105                 110

Glu Pro Lys Ala Val Ala Leu Lys Ala Gln Gln Ala Ala Ile Lys Glu
        115                 120                 125

Glu Ala Ser Ala Asn Asn Leu Ser Asp Ile Ser Gln Glu Ala Gln Glu
    130                 135                 140

Val Gln Glu Ala Lys Lys Glu Ala Gln Ala Glu Lys Asp Ser Asp Thr
145                 150                 155                 160
```

-continued

Leu Thr Lys Asp Ala Ser Ala Ala Lys Val Glu Val Ser Lys Pro Glu
                165                 170                 175

Ser Gln Ala Glu Arg Leu Ala Asn Ala Ala Lys Gln Lys Gln Ala Lys
            180                 185                 190

Leu Thr Pro Gly Ser Lys Glu Ser Gln Leu Thr Glu Ala Leu Phe Ala
        195                 200                 205

Glu Lys Pro Val Ala Lys Asn Asp Leu Lys Glu Ile Pro Gln Leu Val
    210                 215                 220

Thr Lys Asn Asp Val Ser Glu Thr Glu Thr Val Asn Ile Asp Asn
225                 230                 235                 240

Lys Asp Thr Val Lys Gln Lys Glu Ala Lys Phe Glu Asn Gly Val Ile
                245                 250                 255

Thr Arg Lys Ala Asp Glu Lys Thr Thr Asn Asn Thr Ala Val Asp Lys
            260                 265                 270

Lys Ser Gly Lys Gln Ser Lys Lys Thr Thr Pro Ser Asn Lys Arg Asn
        275                 280                 285

Ala Ser Lys Ala Ser Thr Asn Lys Thr Ser Gly Gln Lys Lys Gln His
    290                 295                 300

Asn Lys Lys Ser Ser Gln Gly Ala Lys Lys Gln Ser Ser Ser Ser Lys
305                 310                 315                 320

Ser Thr Gln Lys Asn Asn Gln Thr Ser Asn Lys Asn Ser Lys Thr Thr
                325                 330                 335

Asn Ala Lys Ser Ser Asn Ala Ser Lys Thr Pro Asn Ala Lys Val Glu
            340                 345                 350

Lys Ala Lys Ser Lys Ile Glu Lys Arg Thr Phe Asn Asp
        355                 360                 365

<210> SEQ ID NO 6
<211> LENGTH: 390
<212> TYPE: PRT
<213> ORGANISM: Staphylococcus aureus

<400> SEQUENCE: 6

Lys Val Ala Lys Gln Gly Gln Tyr Lys Asn Gln Asp Pro Ile Val Leu
1               5                   10                  15

Val His Gly Phe Asn Gly Phe Thr Asp Asp Ile Asn Pro Ser Val Leu
            20                  25                  30

Ala His Tyr Trp Gly Gly Asn Lys Met Asn Ile Arg Gln Asp Leu Glu
        35                  40                  45

Glu Asn Gly Tyr Lys Ala Tyr Glu Ala Ser Ile Ser Ala Phe Gly Ser
    50                  55                  60

Asn Tyr Asp Arg Ala Val Glu Leu Tyr Tyr Ile Lys Gly Gly Arg
65                  70                  75                  80

Val Asp Tyr Gly Ala Ala His Ala Ala Lys Tyr Gly His Glu Arg Tyr
                85                  90                  95

Gly Lys Thr Tyr Glu Gly Ile Tyr Lys Asp Trp Lys Pro Gly Gln Lys
            100                 105                 110

Val His Leu Val Gly His Ser Met Gly Gly Gln Thr Ile Arg Gln Leu
        115                 120                 125

Glu Glu Leu Leu Arg Asn Gly Ser Arg Glu Glu Ile Glu Tyr Gln Lys
    130                 135                 140

Lys His Gly Gly Glu Ile Ser Pro Leu Phe Lys Gly Asn Asn Asp Asn
145                 150                 155                 160

Met Ile Ser Ser Ile Thr Thr Leu Gly Thr Pro His Asn Gly Thr His

```
            165                 170                 175
Ala Ser Asp Leu Ala Gly Asn Glu Ala Leu Val Arg Gln Ile Val Phe
            180                 185                 190

Asp Ile Gly Lys Met Phe Gly Asn Lys Asn Ser Arg Val Asp Phe Gly
            195                 200                 205

Leu Ala Gln Trp Gly Leu Lys Gln Lys Pro Asn Glu Ser Tyr Ile Asp
            210                 215                 220

Tyr Val Lys Arg Val Lys Gln Ser Asn Leu Trp Lys Ser Lys Asp Asn
225                 230                 235                 240

Gly Phe Tyr Asp Leu Thr Arg Glu Gly Ala Thr Asp Leu Asn Arg Lys
                245                 250                 255

Thr Ser Leu Asn Pro Asn Ile Val Tyr Lys Thr Tyr Thr Gly Glu Ala
                260                 265                 270

Thr His Lys Ala Leu Asn Ser Asp Arg Gln Lys Ala Asp Leu Asn Met
                275                 280                 285

Phe Phe Pro Phe Val Ile Thr Gly Asn Leu Ile Gly Lys Ala Thr Glu
            290                 295                 300

Lys Glu Trp Arg Glu Asn Asp Gly Leu Val Ser Val Ile Ser Ser Gln
305                 310                 315                 320

His Pro Phe Asn Gln Ala Tyr Thr Asn Ala Thr Asp Lys Ile Gln Lys
                325                 330                 335

Gly Ile Trp Gln Val Thr Pro Thr Lys His Asp Trp Asp His Val Asp
            340                 345                 350

Phe Val Gly Gln Asp Ser Ser Asp Thr Val Arg Thr Arg Glu Glu Leu
            355                 360                 365

Gln Asp Phe Trp His His Leu Ala Asp Asp Leu Val Lys Thr Glu Lys
            370                 375                 380

Val Thr Asp Thr Lys Gln
385                 390

<210> SEQ ID NO 7
<211> LENGTH: 409
<212> TYPE: PRT
<213> ORGANISM: Staphylococcus aureus

<400> SEQUENCE: 7

Met Asp Ile Gly Lys Lys His Val Ile Pro Lys Ser Gln Tyr Arg Arg
1               5                   10                  15

Lys Arg Arg Glu Phe Phe His Asn Glu Asp Arg Glu Glu Asn Leu Asn
            20                  25                  30

Gln His Gln Asp Lys Gln Asn Ile Asp Asn Thr Thr Ser Lys Lys Ala
        35                  40                  45

Asp Lys Gln Ile His Lys Asp Ser Ile Asp Lys His Glu Arg Phe Lys
    50                  55                  60

Asn Ser Leu Ser Ser His Leu Glu Gln Arg Asn Arg Asp Val Asn Glu
65                  70                  75                  80

Asn Lys Ala Glu Glu Ser Lys Ser Asn Gln Asp Ser Lys Ser Ala Tyr
                85                  90                  95

Asn Arg Asp His Tyr Leu Thr Asp Asp Val Ser Lys Lys Gln Asn Ser
                100                 105                 110

Leu Asp Ser Val Asp Gln Asp Thr Glu Lys Ser Lys Tyr Tyr Glu Gln
            115                 120                 125

Asn Ser Glu Ala Thr Leu Ser Thr Lys Ser Thr Asp Lys Val Glu Ser
        130                 135                 140
```

```
Thr Glu Met Arg Lys Leu Ser Ser Asp Lys Asn Lys Val Gly His Glu
145                 150                 155                 160

Glu Gln His Val Leu Ser Lys Pro Ser Glu His Asp Lys Glu Thr Arg
                165                 170                 175

Ile Asp Ser Glu Ser Ser Arg Thr Asp Ser Asp Ser Ser Met Gln Thr
                180                 185                 190

Glu Lys Ile Lys Lys Asp Ser Ser Asp Gly Asn Lys Ser Ser Asn Leu
            195                 200                 205

Lys Ser Glu Val Ile Ser Asp Lys Ser Asn Thr Val Pro Lys Leu Ser
        210                 215                 220

Glu Ser Asp Asp Glu Val Asn Asn Gln Lys Pro Leu Thr Leu Pro Glu
225                 230                 235                 240

Glu Gln Lys Leu Lys Arg Gln Gln Ser Gln Asn Glu Gln Thr Lys Thr
                245                 250                 255

Tyr Thr Tyr Gly Asp Ser Glu Gln Asn Asp Lys Ser Asn His Glu Asn
                260                 265                 270

Asp Leu Ser His His Ile Pro Ser Ile Ser Asp Lys Asp Asn Val
            275                 280                 285

Met Arg Glu Asn His Ile Val Asp Asp Asn Pro Asp Asn Asp Ile Asn
290                 295                 300

Thr Pro Ser Leu Ser Lys Thr Asp Asp Arg Lys Leu Asp Glu Lys
305                 310                 315                 320

Ile His Val Glu Asp Lys His Lys Gln Asn Ala Asp Ser Ser Glu Thr
                325                 330                 335

Val Gly Tyr Gln Ser Gln Ser Thr Ala Ser His Arg Ser Thr Glu Lys
            340                 345                 350

Arg Asn Ile Ser Ile Asn Asp His Asp Lys Leu Asn Gly Gln Lys Thr
        355                 360                 365

Asn Thr Lys Thr Ser Ala Asn Asn Gln Lys Lys Ala Thr Ser Lys
370                 375                 380

Leu Asn Lys Gly Arg Ala Thr Asn Asn Asn Tyr Ser Asp Ile Leu Lys
385                 390                 395                 400

Lys Phe Trp Met Met Tyr Trp Pro Lys
                405

<210> SEQ ID NO 8
<211> LENGTH: 412
<212> TYPE: PRT
<213> ORGANISM: Staphylococcus aureus

<400> SEQUENCE: 8

Ile Asp Ser Lys Asn Lys Pro Ala Asn Ser Asp Ile Lys Phe Glu Val
1                   5                   10                  15

Thr Gln Lys Ser Asp Ala Val Lys Ala Leu Lys Glu Leu Pro Lys Ser
                20                  25                  30

Glu Asn Val Lys Asn Ile Tyr Gln Asp Tyr Ala Val Thr Asp Val Lys
            35                  40                  45

Thr Asp Lys Lys Gly Phe Thr His Tyr Thr Leu Gln Pro Ser Val Asp
        50                  55                  60

Gly Val His Ala Pro Asp Lys Glu Val Lys Val His Ala Asp Lys Ser
65                  70                  75                  80

Gly Lys Val Val Leu Ile Asn Gly Asp Thr Asp Ala Lys Lys Val Lys
                85                  90                  95

Pro Thr Asn Lys Val Thr Leu Ser Lys Asp Asp Ala Ala Asp Lys Ala
            100                 105                 110
```

Phe Lys Ala Val Lys Ile Asp Lys Asn Lys Ala Lys Asn Leu Lys Asp
                115                 120                 125

Lys Val Ile Lys Glu Asn Lys Val Glu Ile Asp Gly Asp Ser Asn Lys
            130                 135                 140

Tyr Val Tyr Asn Val Glu Leu Ile Thr Val Thr Pro Glu Ile Ser His
145                 150                 155                 160

Trp Lys Val Lys Ile Asp Ala Gln Thr Gly Glu Ile Leu Glu Lys Met
                165                 170                 175

Asn Leu Val Lys Glu Ala Ala Glu Thr Gly Lys Gly Lys Gly Val Leu
            180                 185                 190

Gly Asp Thr Lys Asp Ile Asn Ile Asn Ser Ile Asp Gly Gly Phe Ser
                195                 200                 205

Leu Glu Asp Leu Thr His Gln Gly Lys Leu Ser Ala Phe Ser Phe Asn
210                 215                 220

Asp Gln Thr Gly Gln Ala Thr Leu Ile Thr Asn Glu Asp Glu Asn Phe
225                 230                 235                 240

Val Lys Asp Glu Gln Arg Ala Gly Val Asp Ala Asn Tyr Tyr Ala Lys
                245                 250                 255

Gln Thr Tyr Asp Tyr Tyr Lys Asp Thr Phe Gly Arg Glu Ser Tyr Asp
            260                 265                 270

Asn Gln Gly Ser Pro Ile Val Ser Leu Thr His Val Asn Asn Tyr Gly
            275                 280                 285

Gly Gln Asp Asn Arg Asn Asn Ala Ala Trp Ile Gly Asp Lys Met Ile
            290                 295                 300

Tyr Gly Asp Gly Asp Gly Arg Thr Phe Thr Ser Leu Ser Gly Ala Asn
305                 310                 315                 320

Asp Val Val Ala His Glu Leu Thr His Gly Val Thr Gln Glu Thr Ala
                325                 330                 335

Asn Leu Glu Tyr Lys Asp Gln Ser Gly Ala Leu Asn Glu Ser Phe Ser
            340                 345                 350

Asp Val Phe Gly Tyr Phe Val Asp Asp Glu Asp Phe Leu Met Gly Glu
            355                 360                 365

Asp Val Tyr Thr Pro Gly Lys Glu Gly Asp Ala Leu Arg Ser Met Ser
            370                 375                 380

Asn Pro Glu Gln Phe Gly Gln Pro Ala His Met Lys Asp Tyr Val Phe
385                 390                 395                 400

Thr Glu Lys Asp Asn Gly Gly Val His Thr Asn Ser
                405                 410

<210> SEQ ID NO 9
<211> LENGTH: 592
<212> TYPE: PRT
<213> ORGANISM: Staphylococcus aureus

<400> SEQUENCE: 9

Asp Thr Pro Gln Lys Asp Thr Thr Ala Lys Thr Thr Ser His Asp Ser
1               5                   10                  15

Lys Lys Ser Asn Asp Asp Glu Thr Ser Lys Thr Thr Ser Lys Asp
            20                  25                  30

Ile Asp Lys Ala Asp Asn Asn Thr Ser Asn Gln Asp Asn Asn Asp
                35                  40                  45

Lys Lys Phe Lys Thr Ile Asp Asp Ser Thr Ser Asp Ser Asn Asn Ile
50                  55                  60

Ile Asp Phe Ile Tyr Lys Asn Leu Pro Gln Thr Asn Ile Asn Gln Leu

```
                65                  70                  75                  80
Leu Thr Lys Asn Lys Tyr Asp Asp Asn Tyr Ser Leu Thr Thr Leu Ile
                    85                  90                  95
Gln Asn Leu Phe Asn Leu Asn Ser Asp Ile Ser Asp Tyr Glu Gln Pro
                100                 105                 110
Arg Asn Gly Glu Lys Ser Thr Asn Asp Ser Asn Lys Asn Ser Asp Asn
                115                 120                 125
Ser Ile Lys Asn Asp Thr Asp Thr Gln Ser Ser Lys Gln Asp Lys Ala
            130                 135                 140
Asp Asn Gln Lys Ala Pro Lys Ser Asn Asn Thr Lys Pro Ser Thr Ser
145                 150                 155                 160
Asn Lys Gln Pro Asn Ser Pro Lys Pro Thr Gln Pro Asn Gln Ser Asn
                    165                 170                 175
Ser Gln Pro Ala Ser Asp Asp Lys Ala Asn Gln Lys Ser Ser Ser Lys
                180                 185                 190
Asp Asn Gln Ser Met Ser Asp Ser Ala Leu Asp Ser Ile Leu Asp Gln
            195                 200                 205
Tyr Ser Glu Asp Ala Lys Lys Thr Gln Lys Asp Tyr Ala Ser Gln Ser
            210                 215                 220
Lys Lys Asp Lys Asn Glu Lys Ser Asn Thr Lys Asn Pro Gln Leu Pro
225                 230                 235                 240
Thr Gln Asp Glu Leu Lys His Lys Ser Lys Pro Ala Gln Ser Phe Asn
                    245                 250                 255
Asn Asp Val Asn Gln Lys Asp Thr Arg Ala Thr Ser Leu Phe Glu Thr
                260                 265                 270
Asp Pro Ser Ile Ser Asn Asn Asp Ser Gly Gln Phe Asn Val Val
            275                 280                 285
Asp Ser Lys Asp Thr Arg Gln Phe Val Lys Ser Ile Ala Lys Asp Ala
            290                 295                 300
His Arg Ile Gly Gln Asp Asn Asp Ile Tyr Ala Ser Val Met Ile Ala
305                 310                 315                 320
Gln Ala Ile Leu Glu Ser Asp Ser Gly Arg Ser Ala Leu Ala Lys Ser
                    325                 330                 335
Pro Asn His Asn Leu Phe Gly Ile Lys Gly Ala Phe Glu Gly Asn Ser
                340                 345                 350
Val Pro Phe Asn Thr Leu Glu Ala Asp Gly Asn Lys Leu Tyr Ser Ile
            355                 360                 365
Asn Ala Gly Phe Arg Lys Tyr Pro Ser Thr Lys Glu Ser Leu Lys Asp
            370                 375                 380
Tyr Ser Asp Leu Ile Lys Asn Gly Ile Asp Gly Asn Arg Thr Ile Tyr
385                 390                 395                 400
Lys Pro Thr Trp Lys Ser Glu Ala Asp Ser Tyr Lys Asp Ala Thr Ser
                    405                 410                 415
His Leu Ser Lys Thr Tyr Ala Thr Asp Pro Asn Tyr Ala Lys Lys Leu
                420                 425                 430
Asn Ser Ile Ile Lys His Tyr Gln Leu Thr Gln Phe Asp Asp Glu Arg
            435                 440                 445
Met Pro Asp Leu Asp Lys Tyr Glu Arg Ser Ile Lys Asp Tyr Asp Asp
            450                 455                 460
Ser Ser Asp Glu Phe Lys Pro Phe Arg Glu Val Ser Asp Ser Met Pro
465                 470                 475                 480
Tyr Pro His Gly Gln Cys Thr Trp Tyr Val Tyr Asn Arg Met Lys Gln
                    485                 490                 495
```

-continued

```
Phe Gly Thr Ser Ile Ser Gly Asp Leu Gly Asp Ala His Asn Trp Asn
                500                 505                 510
Asn Arg Ala Gln Tyr Arg Asp Tyr Gln Val Ser His Thr Pro Lys Arg
            515                 520                 525
His Ala Ala Val Val Phe Glu Ala Gly Gln Phe Gly Ala Asp Gln His
        530                 535                 540
Tyr Gly His Val Ala Phe Val Glu Lys Val Asn Ser Asp Gly Ser Ile
545                 550                 555                 560
Val Ile Ser Glu Ser Asn Val Lys Gly Leu Gly Ile Ile Ser His Arg
                565                 570                 575
Thr Ile Asn Ala Ala Ala Ala Glu Glu Leu Ser Tyr Ile Thr Gly Lys
            580                 585                 590
```

```
<210> SEQ ID NO 10
<211> LENGTH: 6
<212> TYPE: PRT
<213> ORGANISM: Artificial sequence
<220> FEATURE:
<223> OTHER INFORMATION: Peptide linker

<400> SEQUENCE: 10

Gly Ser Gly Gly Gly Ala
1               5

<210> SEQ ID NO 11
<211> LENGTH: 12
<212> TYPE: PRT
<213> ORGANISM: Artificial sequence
<220> FEATURE:
<223> OTHER INFORMATION: Peptide linker

<400> SEQUENCE: 11

Gly Ser Gly Gly Gly Ala Gly Ser Gly Gly Gly Ala
1               5                   10

<210> SEQ ID NO 12
<211> LENGTH: 617
<212> TYPE: PRT
<213> ORGANISM: Artificial sequence
<220> FEATURE:
<223> OTHER INFORMATION: Chimeric polypeptide
<220> FEATURE:
<221> NAME/KEY: MISC_FEATURE
<222> LOCATION: (1)..(409)
<223> OTHER INFORMATION: SEQ ID NO: 9
<220> FEATURE:
<221> NAME/KEY: MISC_FEATURE
<222> LOCATION: (410)..(415)
<223> OTHER INFORMATION: GSGGGA linker
<220> FEATURE:
<221> NAME/KEY: MISC_FEATURE
<222> LOCATION: (416)..(617)
<223> OTHER INFORMATION: SEQ ID NO: 2

<400> SEQUENCE: 12

Met Asp Ile Gly Lys Lys His Val Ile Pro Lys Ser Gln Tyr Arg Arg
1               5                   10                  15
Lys Arg Arg Glu Phe Phe His Asn Glu Asp Arg Glu Glu Asn Leu Asn
            20                  25                  30
Gln His Gln Asp Lys Gln Asn Ile Asp Asn Thr Thr Ser Lys Lys Ala
        35                  40                  45
Asp Lys Gln Ile His Lys Asp Ser Ile Asp Lys His Glu Arg Phe Lys
    50                  55                  60
```

-continued

```
Asn Ser Leu Ser Ser His Leu Glu Gln Arg Asn Arg Asp Val Asn Glu
 65                  70                  75                  80

Asn Lys Ala Glu Glu Ser Lys Ser Asn Gln Asp Ser Lys Ser Ala Tyr
                 85                  90                  95

Asn Arg Asp His Tyr Leu Thr Asp Asp Val Ser Lys Lys Gln Asn Ser
            100                 105                 110

Leu Asp Ser Val Asp Gln Asp Thr Glu Lys Ser Lys Tyr Tyr Glu Gln
            115                 120                 125

Asn Ser Glu Ala Thr Leu Ser Thr Lys Ser Thr Asp Lys Val Glu Ser
        130                 135                 140

Thr Glu Met Arg Lys Leu Ser Ser Asp Lys Asn Lys Val Gly His Glu
145                 150                 155                 160

Glu Gln His Val Leu Ser Lys Pro Ser Glu His Asp Lys Glu Thr Arg
                165                 170                 175

Ile Asp Ser Glu Ser Ser Arg Thr Asp Ser Asp Ser Ser Met Gln Thr
            180                 185                 190

Glu Lys Ile Lys Lys Asp Ser Ser Asp Gly Asn Lys Ser Ser Asn Leu
            195                 200                 205

Lys Ser Glu Val Ile Ser Asp Lys Ser Asn Thr Val Pro Lys Leu Ser
210                 215                 220

Glu Ser Asp Asp Glu Val Asn Asn Gln Lys Pro Leu Thr Leu Pro Glu
225                 230                 235                 240

Glu Gln Lys Leu Lys Arg Gln Gln Ser Gln Asn Glu Gln Thr Lys Thr
                245                 250                 255

Tyr Thr Tyr Gly Asp Ser Glu Gln Asn Asp Lys Ser Asn His Glu Asn
            260                 265                 270

Asp Leu Ser His His Ile Pro Ser Ile Ser Asp Asp Lys Asp Asn Val
            275                 280                 285

Met Arg Glu Asn His Ile Val Asp Asp Asn Pro Asp Asn Asp Ile Asn
        290                 295                 300

Thr Pro Ser Leu Ser Lys Thr Asp Asp Arg Lys Leu Asp Glu Lys
305                 310                 315                 320

Ile His Val Glu Asp Lys His Lys Gln Asn Ala Asp Ser Ser Glu Thr
                325                 330                 335

Val Gly Tyr Gln Ser Gln Ser Thr Ala Ser His Arg Ser Thr Glu Lys
            340                 345                 350

Arg Asn Ile Ser Ile Asn Asp His Asp Lys Leu Asn Gly Gln Lys Thr
            355                 360                 365

Asn Thr Lys Thr Ser Ala Asn Asn Gln Lys Lys Ala Thr Ser Lys
        370                 375                 380

Leu Asn Lys Gly Arg Ala Thr Asn Asn Asn Tyr Ser Asp Ile Leu Lys
385                 390                 395                 400

Lys Phe Trp Met Met Tyr Trp Pro Lys Gly Ser Gly Gly Gly Ala Lys
                405                 410                 415

Arg Ile Lys Gln His Pro Asp Val Gln Lys Val Thr Asp Ala Thr Ser
            420                 425                 430

Lys Val Ala Ser Lys Thr Ser Ala Ala Ile Ser Asn Thr Ala Ser Asp
            435                 440                 445

Val Lys Glu Tyr Val Gly Asp Lys Lys Gln Asp Phe Glu Asn Lys Arg
        450                 455                 460

Glu Leu Lys Lys Phe Ala Arg Glu His Asp Pro Ala Tyr Ile Glu Lys
465                 470                 475                 480

Lys Gly Glu Lys Leu Ala Lys Gln Asn Arg Lys Asp Ala Asp Lys Met
```

```
              485                 490                 495
Asn Lys Ile Leu Gln Lys Asn Ile Glu Lys Arg His Lys Glu Glu Gln
            500                 505                 510

Lys Ala Arg Glu Lys Asn Glu Ile Gln Arg Ile Lys Asp Met Lys Lys
            515                 520                 525

Ser Gln Lys Tyr Glu Val Lys Ala Gly Leu Thr Pro Asn Lys Leu Asp
            530                 535                 540

Glu Lys Thr Glu Lys Lys Gly Asp Lys Leu Ala Glu Lys Asn Arg Lys
545                 550                 555                 560

Glu Ile Ala Lys Met Asn Lys Lys Leu Gln Lys Asn Ile Glu Lys Arg
                565                 570                 575

His Lys Glu Glu Gln Lys Arg Gln Glu Ala Asp Lys Ala Arg Ile
            580                 585                 590

Lys Ser Phe Lys Lys Tyr Lys Asp Tyr Val Ala Lys Ser Ala Ser Gln
            595                 600                 605

Gln Asn Lys Glu Asn Asn Thr Glu Ala
            610                 615
```

<210> SEQ ID NO 13
<211> LENGTH: 797
<212> TYPE: PRT
<213> ORGANISM: Artificial sequence
<220> FEATURE:
<223> OTHER INFORMATION: Chimeric polypeptide
<220> FEATURE:
<221> NAME/KEY: MISC_FEATURE
<222> LOCATION: (1)..(199)
<223> OTHER INFORMATION: SEQ ID NO: 1
<220> FEATURE:
<221> NAME/KEY: MISC_FEATURE
<222> LOCATION: (200)..(205)
<223> OTHER INFORMATION: GSGGGA linker
<220> FEATURE:
<221> NAME/KEY: MISC_FEATURE
<222> LOCATION: (206)..(797)
<223> OTHER INFORMATION: SEQ ID NO: 7

<400> SEQUENCE: 13

```
Met Thr Glu Lys Glu Lys Met Leu Ala Glu Lys Trp Tyr Asp Ala Asn
1               5                   10                  15

Phe Asp Gln Asp Leu Ile Asn Glu Arg Ala Arg Ala Lys Asp Ile Cys
            20                  25                  30

Phe Glu Leu Asn His Thr Lys Pro Ser Asp Lys Asn Lys Arg Lys Glu
        35                  40                  45

Leu Ile Asp Glu Leu Phe Gln Thr Thr Thr Asp Asn Val Ser Ile Ser
    50                  55                  60

Ile Pro Phe Asp Thr Asp Tyr Gly Trp Asn Val Lys Leu Gly Lys Asn
65                  70                  75                  80

Val Tyr Val Asn Thr Asn Cys Tyr Phe Met Asp Gly Gln Ile Thr
                85                  90                  95

Ile Gly Asp Asn Val Phe Ile Gly Pro Asn Cys Gly Phe Tyr Thr Ala
            100                 105                 110

Thr His Pro Leu Asn Phe His His Arg Asn Glu Gly Phe Glu Lys Ala
        115                 120                 125

Gly Pro Ile Asn Ile Gly Ser Asn Thr Trp Phe Gly Gly His Val Ala
    130                 135                 140

Val Leu Pro Gly Val Thr Ile Gly Glu Gly Ser Val Ile Gly Ala Gly
145                 150                 155                 160

Ser Val Val Thr Lys Asp Ile Pro Pro His Ser Leu Ala Val Gly Asn
```

-continued

```
                165                 170                 175
Pro Cys Lys Val Val Arg Lys Ile Asp Asn Glu Val Pro Ser Glu Ala
                180                 185                 190
Leu Asn Asp Glu Thr Leu Asn Gly Ser Gly Gly Gly Ala Asp Thr Pro
                195                 200                 205
Gln Lys Asp Thr Thr Ala Lys Thr Thr Ser His Asp Ser Lys Lys Ser
                210                 215                 220
Asn Asp Asp Glu Thr Ser Lys Asp Thr Thr Ser Lys Asp Ile Asp Lys
225                 230                 235                 240
Ala Asp Asn Asn Asn Thr Ser Asn Gln Asp Asn Asn Asp Lys Lys Phe
                245                 250                 255
Lys Thr Ile Asp Asp Ser Thr Ser Asp Ser Asn Asn Ile Ile Asp Phe
                260                 265                 270
Ile Tyr Lys Asn Leu Pro Gln Thr Asn Ile Asn Gln Leu Leu Thr Lys
                275                 280                 285
Asn Lys Tyr Asp Asp Asn Tyr Ser Leu Thr Thr Leu Ile Gln Asn Leu
                290                 295                 300
Phe Asn Leu Asn Ser Asp Ile Ser Asp Tyr Glu Gln Pro Arg Asn Gly
305                 310                 315                 320
Glu Lys Ser Thr Asn Asp Ser Asn Lys Asn Ser Asp Asn Ser Ile Lys
                325                 330                 335
Asn Asp Thr Asp Thr Gln Ser Ser Lys Gln Asp Lys Ala Asp Asn Gln
                340                 345                 350
Lys Ala Pro Lys Ser Asn Asn Thr Lys Pro Ser Thr Ser Asn Lys Gln
                355                 360                 365
Pro Asn Ser Pro Lys Pro Thr Gln Pro Asn Gln Ser Asn Ser Gln Pro
                370                 375                 380
Ala Ser Asp Asp Lys Ala Asn Gln Lys Ser Ser Ser Lys Asp Asn Gln
385                 390                 395                 400
Ser Met Ser Asp Ser Ala Leu Asp Ser Ile Leu Asp Gln Tyr Ser Glu
                405                 410                 415
Asp Ala Lys Lys Thr Gln Lys Asp Tyr Ala Ser Gln Ser Lys Lys Asp
                420                 425                 430
Lys Asn Glu Lys Ser Asn Thr Lys Asn Pro Gln Leu Pro Thr Gln Asp
                435                 440                 445
Glu Leu Lys His Lys Ser Lys Pro Ala Gln Ser Phe Asn Asn Asp Val
                450                 455                 460
Asn Gln Lys Asp Thr Arg Ala Thr Ser Leu Phe Glu Thr Asp Pro Ser
465                 470                 475                 480
Ile Ser Asn Asn Asp Asp Ser Gly Gln Phe Asn Val Val Asp Ser Lys
                485                 490                 495
Asp Thr Arg Gln Phe Val Lys Ser Ile Ala Lys Asp Ala His Arg Ile
                500                 505                 510
Gly Gln Asp Asn Asp Ile Tyr Ala Ser Val Met Ile Ala Gln Ala Ile
                515                 520                 525
Leu Glu Ser Asp Ser Gly Arg Ser Ala Leu Ala Lys Ser Pro Asn His
                530                 535                 540
Asn Leu Phe Gly Ile Lys Gly Ala Phe Glu Gly Asn Ser Val Pro Phe
545                 550                 555                 560
Asn Thr Leu Glu Ala Asp Gly Asn Lys Leu Tyr Ser Ile Asn Ala Gly
                565                 570                 575
Phe Arg Lys Tyr Pro Ser Thr Lys Glu Ser Leu Lys Asp Tyr Ser Asp
                580                 585                 590
```

```
Leu Ile Lys Asn Gly Ile Asp Gly Asn Arg Thr Ile Tyr Lys Pro Thr
            595                 600                 605

Trp Lys Ser Glu Ala Asp Ser Tyr Lys Asp Ala Thr Ser His Leu Ser
        610                 615                 620

Lys Thr Tyr Ala Thr Asp Pro Asn Tyr Ala Lys Lys Leu Asn Ser Ile
625                 630                 635                 640

Ile Lys His Tyr Gln Leu Thr Gln Phe Asp Asp Glu Arg Met Pro Asp
                645                 650                 655

Leu Asp Lys Tyr Glu Arg Ser Ile Lys Asp Tyr Asp Ser Ser Asp
            660                 665                 670

Glu Phe Lys Pro Phe Arg Glu Val Ser Asp Ser Met Pro Tyr Pro His
        675                 680                 685

Gly Gln Cys Thr Trp Tyr Val Tyr Asn Arg Met Lys Gln Phe Gly Thr
    690                 695                 700

Ser Ile Ser Gly Asp Leu Gly Asp Ala His Asn Trp Asn Asn Arg Ala
705                 710                 715                 720

Gln Tyr Arg Asp Tyr Gln Val Ser His Thr Pro Lys Arg His Ala Ala
                725                 730                 735

Val Val Phe Glu Ala Gly Gln Phe Gly Ala Asp Gln His Tyr Gly His
            740                 745                 750

Val Ala Phe Val Glu Lys Val Asn Ser Asp Gly Ser Ile Val Ile Ser
        755                 760                 765

Glu Ser Asn Val Lys Gly Leu Gly Ile Ile Ser His Arg Thr Ile Asn
    770                 775                 780

Ala Ala Ala Glu Glu Leu Ser Tyr Ile Thr Gly Lys
785                 790                 795
```

```
<210> SEQ ID NO 14
<211> LENGTH: 814
<212> TYPE: PRT
<213> ORGANISM: Artificial sequence
<220> FEATURE:
<223> OTHER INFORMATION: Chimeric polypeptide
<220> FEATURE:
<221> NAME/KEY: MISC_FEATURE
<222> LOCATION: (1)..(412)
<223> OTHER INFORMATION: SEQ ID NO: 6
<220> FEATURE:
<221> NAME/KEY: MISC_FEATURE
<222> LOCATION: (413)..(424)
<223> OTHER INFORMATION: GSGGGAGSGGGA linker
<220> FEATURE:
<221> NAME/KEY: MISC_FEATURE
<222> LOCATION: (425)..(814)
<223> OTHER INFORMATION: SEQ ID NO: 8

<400> SEQUENCE: 14
```

```
Ile Asp Ser Lys Asn Lys Pro Ala Asn Ser Asp Ile Lys Phe Glu Val
1               5                   10                  15

Thr Gln Lys Ser Asp Ala Val Lys Ala Leu Lys Glu Leu Pro Lys Ser
            20                  25                  30

Glu Asn Val Lys Asn Ile Tyr Gln Asp Tyr Ala Val Thr Asp Val Lys
        35                  40                  45

Thr Asp Lys Lys Gly Phe Thr His Tyr Thr Leu Gln Pro Ser Val Asp
    50                  55                  60

Gly Val His Ala Pro Asp Lys Glu Val Lys Val His Ala Asp Lys Ser
65                  70                  75                  80

Gly Lys Val Val Leu Ile Asn Gly Asp Thr Asp Ala Lys Lys Val Lys
                85                  90                  95
```

```
Pro Thr Asn Lys Val Thr Leu Ser Lys Asp Asp Ala Asp Lys Ala
                100             105                 110

Phe Lys Ala Val Lys Ile Asp Lys Asn Lys Ala Lys Asn Leu Lys Asp
            115                 120                 125

Lys Val Ile Lys Glu Asn Lys Val Glu Ile Asp Gly Asp Ser Asn Lys
        130                 135                 140

Tyr Val Tyr Asn Val Glu Leu Ile Thr Val Thr Pro Glu Ile Ser His
145                 150                 155                 160

Trp Lys Val Lys Ile Asp Ala Gln Thr Gly Glu Ile Leu Glu Lys Met
                165                 170                 175

Asn Leu Val Lys Glu Ala Ala Glu Thr Gly Lys Gly Lys Gly Val Leu
            180                 185                 190

Gly Asp Thr Lys Asp Ile Asn Ile Asn Ser Ile Asp Gly Gly Phe Ser
        195                 200                 205

Leu Glu Asp Leu Thr His Gln Gly Lys Leu Ser Ala Phe Ser Phe Asn
    210                 215                 220

Asp Gln Thr Gly Gln Ala Thr Leu Ile Thr Asn Glu Asp Glu Asn Phe
225                 230                 235                 240

Val Lys Asp Glu Gln Arg Ala Gly Val Asp Ala Asn Tyr Tyr Ala Lys
                245                 250                 255

Gln Thr Tyr Asp Tyr Tyr Lys Asp Thr Phe Gly Arg Glu Ser Tyr Asp
            260                 265                 270

Asn Gln Gly Ser Pro Ile Val Ser Leu Thr His Val Asn Asn Tyr Gly
        275                 280                 285

Gly Gln Asp Asn Arg Asn Asn Ala Ala Trp Ile Gly Asp Lys Met Ile
    290                 295                 300

Tyr Gly Asp Gly Asp Gly Arg Thr Phe Thr Ser Leu Ser Gly Ala Asn
305                 310                 315                 320

Asp Val Val Ala His Glu Leu Thr His Gly Val Thr Gln Glu Thr Ala
                325                 330                 335

Asn Leu Glu Tyr Lys Asp Gln Ser Gly Ala Leu Asn Glu Ser Phe Ser
            340                 345                 350

Asp Val Phe Gly Tyr Phe Val Asp Asp Glu Asp Phe Leu Met Gly Glu
        355                 360                 365

Asp Val Tyr Thr Pro Gly Lys Glu Gly Asp Ala Leu Arg Ser Met Ser
    370                 375                 380

Asn Pro Glu Gln Phe Gly Gln Pro Ala His Met Lys Asp Tyr Val Phe
385                 390                 395                 400

Thr Glu Lys Asp Asn Gly Gly Val His Thr Asn Ser Gly Ser Gly Gly
                405                 410                 415

Gly Ala Gly Ser Gly Gly Ala Lys Val Ala Lys Gln Gly Gln Tyr
            420                 425                 430

Lys Asn Gln Asp Pro Ile Val Leu Val His Gly Phe Asn Gly Phe Thr
        435                 440                 445

Asp Asp Ile Asn Pro Ser Val Leu Ala His Tyr Trp Gly Gly Asn Lys
    450                 455                 460

Met Asn Ile Arg Gln Asp Leu Glu Glu Asn Gly Tyr Lys Ala Tyr Glu
465                 470                 475                 480

Ala Ser Ile Ser Ala Phe Gly Ser Asn Tyr Asp Arg Ala Val Glu Leu
                485                 490                 495

Tyr Tyr Tyr Ile Lys Gly Gly Arg Val Asp Tyr Gly Ala Ala His Ala
            500                 505                 510
```

```
Ala Lys Tyr Gly His Glu Arg Tyr Gly Lys Thr Tyr Glu Gly Ile Tyr
    515                 520                 525
Lys Asp Trp Lys Pro Gly Gln Lys Val His Leu Val Gly His Ser Met
530                 535                 540
Gly Gly Gln Thr Ile Arg Gln Leu Glu Glu Leu Leu Arg Asn Gly Ser
545                 550                 555                 560
Arg Glu Glu Ile Glu Tyr Gln Lys Lys His Gly Gly Glu Ile Ser Pro
                565                 570                 575
Leu Phe Lys Gly Asn Asn Asp Asn Met Ile Ser Ser Ile Thr Thr Leu
            580                 585                 590
Gly Thr Pro His Asn Gly Thr His Ala Ser Asp Leu Ala Gly Asn Glu
        595                 600                 605
Ala Leu Val Arg Gln Ile Val Phe Asp Ile Gly Lys Met Phe Gly Asn
    610                 615                 620
Lys Asn Ser Arg Val Asp Phe Gly Leu Ala Gln Trp Gly Leu Lys Gln
625                 630                 635                 640
Lys Pro Asn Glu Ser Tyr Ile Asp Tyr Val Lys Arg Val Lys Gln Ser
                645                 650                 655
Asn Leu Trp Lys Ser Lys Asp Asn Gly Phe Tyr Asp Leu Thr Arg Glu
            660                 665                 670
Gly Ala Thr Asp Leu Asn Arg Lys Thr Ser Leu Asn Pro Asn Ile Val
        675                 680                 685
Tyr Lys Thr Tyr Thr Gly Glu Ala Thr His Lys Ala Leu Asn Ser Asp
    690                 695                 700
Arg Gln Lys Ala Asp Leu Asn Met Phe Phe Pro Phe Val Ile Thr Gly
705                 710                 715                 720
Asn Leu Ile Gly Lys Ala Thr Glu Lys Glu Trp Arg Glu Asn Asp Gly
                725                 730                 735
Leu Val Ser Val Ile Ser Ser Gln His Pro Phe Asn Gln Ala Tyr Thr
            740                 745                 750
Asn Ala Thr Asp Lys Ile Gln Lys Gly Ile Trp Gln Val Thr Pro Thr
        755                 760                 765
Lys His Asp Trp Asp His Val Asp Phe Val Gly Gln Asp Ser Ser Asp
    770                 775                 780
Thr Val Arg Thr Arg Glu Glu Leu Gln Asp Phe Trp His His Leu Ala
785                 790                 795                 800
Asp Asp Leu Val Lys Thr Glu Lys Val Thr Asp Thr Lys Gln
                805                 810

<210> SEQ ID NO 15
<211> LENGTH: 988
<212> TYPE: PRT
<213> ORGANISM: Artificial sequence
<220> FEATURE:
<223> OTHER INFORMATION: Chimeric polypeptide
<220> FEATURE:
<221> NAME/KEY: MISC_FEATURE
<222> LOCATION: (1)..(592)
<223> OTHER INFORMATION: SEQ ID NO: 7
<220> FEATURE:
<221> NAME/KEY: MISC_FEATURE
<222> LOCATION: (593)..(598)
<223> OTHER INFORMATION: GSGGGA linker
<220> FEATURE:
<221> NAME/KEY: MISC_FEATURE
<222> LOCATION: (599)..(988)
<223> OTHER INFORMATION: SEQ ID NO: 8

<400> SEQUENCE: 15
```

```
Asp Thr Pro Gln Lys Asp Thr Thr Ala Lys Thr Thr Ser His Asp Ser
1               5                   10                  15

Lys Lys Ser Asn Asp Asp Glu Thr Ser Lys Asp Thr Thr Ser Lys Asp
            20                  25                  30

Ile Asp Lys Ala Asp Asn Asn Asn Thr Ser Asn Gln Asp Asn Asn Asp
            35                  40                  45

Lys Lys Phe Lys Thr Ile Asp Asp Ser Thr Ser Asp Ser Asn Asn Ile
50                      55                  60

Ile Asp Phe Ile Tyr Lys Asn Leu Pro Gln Thr Asn Ile Asn Gln Leu
65                  70                  75                  80

Leu Thr Lys Asn Lys Tyr Asp Asp Asn Tyr Ser Leu Thr Thr Leu Ile
                85                  90                  95

Gln Asn Leu Phe Asn Leu Asn Ser Asp Ile Ser Asp Tyr Glu Gln Pro
                100                 105                 110

Arg Asn Gly Glu Lys Ser Thr Asn Asp Ser Asn Lys Asn Ser Asp Asn
                115                 120                 125

Ser Ile Lys Asn Asp Thr Asp Thr Gln Ser Ser Lys Gln Asp Lys Ala
        130                 135                 140

Asp Asn Gln Lys Ala Pro Lys Ser Asn Asn Thr Lys Pro Ser Thr Ser
145                 150                 155                 160

Asn Lys Gln Pro Asn Ser Pro Lys Pro Thr Gln Pro Asn Gln Ser Asn
                165                 170                 175

Ser Gln Pro Ala Ser Asp Asp Lys Ala Asn Gln Lys Ser Ser Ser Lys
            180                 185                 190

Asp Asn Gln Ser Met Ser Asp Ser Ala Leu Asp Ser Ile Leu Asp Gln
            195                 200                 205

Tyr Ser Glu Asp Ala Lys Lys Thr Gln Lys Asp Tyr Ala Ser Gln Ser
    210                 215                 220

Lys Lys Asp Lys Asn Glu Lys Ser Asn Thr Lys Asn Pro Gln Leu Pro
225                 230                 235                 240

Thr Gln Asp Glu Leu Lys His Lys Ser Lys Pro Ala Gln Ser Phe Asn
                245                 250                 255

Asn Asp Val Asn Gln Lys Asp Thr Arg Ala Thr Ser Leu Phe Glu Thr
                260                 265                 270

Asp Pro Ser Ile Ser Asn Asn Asp Ser Gly Gln Phe Asn Val Val
                275                 280                 285

Asp Ser Lys Asp Thr Arg Gln Phe Val Lys Ser Ile Ala Lys Asp Ala
            290                 295                 300

His Arg Ile Gly Gln Asp Asn Asp Ile Tyr Ala Ser Val Met Ile Ala
305                 310                 315                 320

Gln Ala Ile Leu Glu Ser Asp Ser Gly Arg Ser Ala Leu Ala Lys Ser
                325                 330                 335

Pro Asn His Asn Leu Phe Gly Ile Lys Gly Ala Phe Glu Gly Asn Ser
            340                 345                 350

Val Pro Phe Asn Thr Leu Glu Ala Asp Gly Asn Lys Leu Tyr Ser Ile
            355                 360                 365

Asn Ala Gly Phe Arg Lys Tyr Pro Ser Thr Lys Glu Ser Leu Lys Asp
    370                 375                 380

Tyr Ser Asp Leu Ile Lys Asn Gly Ile Asp Gly Asn Arg Thr Ile Tyr
385                 390                 395                 400

Lys Pro Thr Trp Lys Ser Glu Ala Asp Ser Tyr Lys Asp Ala Thr Ser
                405                 410                 415

His Leu Ser Lys Thr Tyr Ala Thr Asp Pro Asn Tyr Ala Lys Lys Leu
```

-continued

```
            420                 425                 430
Asn Ser Ile Ile Lys His Tyr Gln Leu Thr Gln Phe Asp Asp Glu Arg
            435                 440                 445
Met Pro Asp Leu Asp Lys Tyr Glu Arg Ser Ile Lys Asp Tyr Asp Asp
        450                 455                 460
Ser Ser Asp Glu Phe Lys Pro Phe Arg Glu Val Ser Asp Ser Met Pro
465                 470                 475                 480
Tyr Pro His Gly Gln Cys Thr Trp Tyr Val Tyr Asn Arg Met Lys Gln
                485                 490                 495
Phe Gly Thr Ser Ile Ser Gly Asp Leu Gly Asp Ala His Asn Trp Asn
            500                 505                 510
Asn Arg Ala Gln Tyr Arg Asp Tyr Gln Val Ser His Thr Pro Lys Arg
        515                 520                 525
His Ala Ala Val Val Phe Glu Ala Gly Gln Phe Gly Ala Asp Gln His
    530                 535                 540
Tyr Gly His Val Ala Phe Val Glu Lys Val Asn Ser Asp Gly Ser Ile
545                 550                 555                 560
Val Ile Ser Glu Ser Asn Val Lys Gly Leu Gly Ile Ile Ser His Arg
                565                 570                 575
Thr Ile Asn Ala Ala Ala Glu Glu Leu Ser Tyr Ile Thr Gly Lys
            580                 585                 590
Gly Ser Gly Gly Gly Ala Lys Val Ala Lys Gln Gly Gln Tyr Lys Asn
        595                 600                 605
Gln Asp Pro Ile Val Leu Val His Gly Phe Asn Gly Phe Thr Asp Asp
    610                 615                 620
Ile Asn Pro Ser Val Leu Ala His Tyr Trp Gly Gly Asn Lys Met Asn
625                 630                 635                 640
Ile Arg Gln Asp Leu Glu Glu Asn Gly Tyr Lys Ala Tyr Glu Ala Ser
                645                 650                 655
Ile Ser Ala Phe Gly Ser Asn Tyr Asp Arg Ala Val Glu Leu Tyr Tyr
            660                 665                 670
Tyr Ile Lys Gly Gly Arg Val Asp Tyr Gly Ala Ala His Ala Ala Lys
        675                 680                 685
Tyr Gly His Glu Arg Tyr Gly Lys Thr Tyr Glu Gly Ile Tyr Lys Asp
    690                 695                 700
Trp Lys Pro Gly Gln Lys Val His Leu Val Gly His Ser Met Gly Gly
705                 710                 715                 720
Gln Thr Ile Arg Gln Leu Glu Glu Leu Arg Asn Gly Ser Arg Glu
                725                 730                 735
Glu Ile Glu Tyr Gln Lys Lys His Gly Gly Glu Ile Ser Pro Leu Phe
            740                 745                 750
Lys Gly Asn Asn Asp Asn Met Ile Ser Ser Ile Thr Thr Leu Gly Thr
        755                 760                 765
Pro His Asn Gly Thr His Ala Ser Asp Leu Ala Gly Asn Glu Ala Leu
    770                 775                 780
Val Arg Gln Ile Val Phe Asp Ile Gly Lys Met Phe Gly Asn Lys Asn
785                 790                 795                 800
Ser Arg Val Asp Phe Gly Leu Ala Gln Trp Gly Leu Lys Gln Lys Pro
                805                 810                 815
Asn Glu Ser Tyr Ile Asp Tyr Val Lys Arg Val Lys Gln Ser Asn Leu
            820                 825                 830
Trp Lys Ser Lys Asp Asn Gly Phe Tyr Asp Leu Thr Arg Glu Gly Ala
        835                 840                 845
```

```
Thr Asp Leu Asn Arg Lys Thr Ser Leu Asn Pro Asn Ile Val Tyr Lys
    850                 855                 860

Thr Tyr Thr Gly Glu Ala Thr His Lys Ala Leu Asn Ser Asp Arg Gln
865                 870                 875                 880

Lys Ala Asp Leu Asn Met Phe Phe Pro Phe Val Ile Thr Gly Asn Leu
                885                 890                 895

Ile Gly Lys Ala Thr Glu Lys Glu Trp Arg Glu Asn Asp Gly Leu Val
            900                 905                 910

Ser Val Ile Ser Ser Gln His Pro Phe Asn Gln Ala Tyr Thr Asn Ala
        915                 920                 925

Thr Asp Lys Ile Gln Lys Gly Ile Trp Gln Val Thr Pro Thr Lys His
    930                 935                 940

Asp Trp Asp His Val Asp Phe Val Gly Gln Asp Ser Ser Asp Thr Val
945                 950                 955                 960

Arg Thr Arg Glu Glu Leu Gln Asp Phe Trp His His Leu Ala Asp Asp
                965                 970                 975

Leu Val Lys Thr Glu Lys Val Thr Asp Thr Lys Gln
            980                 985

<210> SEQ ID NO 16
<211> LENGTH: 722
<212> TYPE: PRT
<213> ORGANISM: Artificial sequence
<220> FEATURE:
<223> OTHER INFORMATION: Chimeric polypeptide
<220> FEATURE:
<221> NAME/KEY: MISC_FEATURE
<222> LOCATION: (1)..(351)
<223> OTHER INFORMATION: SEQ ID NO: 5
<220> FEATURE:
<221> NAME/KEY: MISC_FEATURE
<222> LOCATION: (352)..(357)
<223> OTHER INFORMATION: GSGGGA linker
<220> FEATURE:
<221> NAME/KEY: MISC_FEATURE
<222> LOCATION: (358)..(722)
<223> OTHER INFORMATION: SEQ ID NO: 4

<400> SEQUENCE: 16

Ala Lys Asp Asn Leu Asn Gly Glu Lys Pro Thr Thr Asn Leu Asn His
1               5                   10                  15

Asn Val Thr Ser Pro Ser Val Asn Ser Glu Met Asn Asn Asn Glu Thr
            20                  25                  30

Gly Thr Pro His Glu Ser Asn Gln Ala Gly Asn Glu Gly Thr Gly Ser
        35                  40                  45

Asn Ser Arg Asp Ala Asn Pro Asp Ser Asn Asn Val Lys Pro Asp Ser
    50                  55                  60

Asn Asn Gln Asn Pro Ser Pro Asp Ser Lys Pro Asp Pro Asn Asn Pro
65                  70                  75                  80

Asn Pro Gly Pro Asn Pro Lys Pro Asp Pro Asp Lys Pro Lys Pro Asn
                85                  90                  95

Pro Glu Pro Lys Pro Asp Pro Lys Pro Asp Pro Asp Lys Pro Lys Pro
            100                 105                 110

Asn Pro Asp Pro Lys Pro Asp Pro Asp Lys Pro Lys Pro Asn Pro Asp
        115                 120                 125

Pro Lys Pro Asp Pro Asp Lys Pro Lys Pro Asn Pro Asp Pro Lys Pro
    130                 135                 140

Asp Pro Asn Pro Asn Pro Lys Pro Asp Pro Asn Lys Pro Asn Pro Asn
145                 150                 155                 160
```

```
Pro Ser Pro Asn Pro Asn Gln Pro Gly Asp Ser Asn Gln Ser Gly Gly
                165                 170                 175

Ser Lys Asn Gly Gly Thr Trp Asn Pro Asn Ala Ser Asp Gly Ser Asn
                180                 185                 190

Gln Gly Gln Trp Gln Pro Asn Gly Asn Gln Gly Asn Ser Gln Asn Pro
                195                 200                 205

Thr Gly Asn Asp Phe Val Ser Gln Arg Phe Leu Ala Leu Ala Asn Gly
            210                 215                 220

Ala Tyr Lys Tyr Asn Pro Tyr Ile Leu Asn Gln Ile Asn Gln Leu Gly
225                 230                 235                 240

Lys Glu Tyr Gly Glu Val Thr Asp Glu Asp Ile Tyr Asn Ile Ile Arg
                245                 250                 255

Lys Gln Asn Phe Ser Gly Asn Ala Tyr Leu Asn Gly Leu Gln Gln Gln
                260                 265                 270

Ser Asn Tyr Phe Arg Phe Gln Tyr Phe Asn Pro Leu Lys Ser Glu Arg
                275                 280                 285

Tyr Tyr Arg Asn Leu Asp Glu Gln Val Leu Ala Leu Ile Thr Gly Glu
                290                 295                 300

Ile Gly Ser Met Pro Asp Leu Lys Lys Pro Glu Asp Lys Pro Asp Ser
305                 310                 315                 320

Lys Gln Arg Ser Phe Glu Pro His Glu Lys Asp Asp Phe Thr Val Val
                325                 330                 335

Lys Lys Gln Glu Asp Asn Lys Lys Ser Ala Ser Thr Ala Tyr Ser Gly
                340                 345                 350

Ser Gly Gly Gly Ala Gly Phe Leu Asn Lys Ser Lys Asn Glu Gln Ala
                355                 360                 365

Ala Leu Lys Ala Gln Gln Ala Ala Ile Lys Glu Glu Ala Ser Ala Asn
                370                 375                 380

Asn Leu Ser Asp Thr Ser Gln Glu Ala Gln Glu Ile Gln Glu Ala Lys
385                 390                 395                 400

Arg Glu Ala Gln Ala Glu Ala Asp Lys Ser Val Ala Val Ser Asn Lys
                405                 410                 415

Glu Ser Lys Ala Val Ala Leu Lys Ala Gln Gln Ala Ala Ile Lys Glu
                420                 425                 430

Glu Ala Ser Ala Asn Asn Leu Ser Asp Thr Ser Gln Glu Ala Gln Glu
                435                 440                 445

Ile Gln Glu Ala Lys Lys Glu Ala Gln Ala Glu Thr Asp Lys Ser Ala
450                 455                 460

Ala Val Ser Asn Glu Glu Pro Lys Ala Val Ala Leu Lys Ala Gln Gln
465                 470                 475                 480

Ala Ala Ile Lys Glu Glu Ala Ser Ala Asn Asn Leu Ser Asp Ile Ser
                485                 490                 495

Gln Glu Ala Gln Glu Val Gln Glu Ala Lys Lys Glu Ala Gln Ala Glu
                500                 505                 510

Lys Asp Ser Asp Thr Leu Thr Lys Asp Ala Ser Ala Ala Lys Val Glu
                515                 520                 525

Val Ser Lys Pro Glu Ser Gln Ala Glu Arg Leu Ala Asn Ala Ala Lys
530                 535                 540

Gln Lys Gln Ala Lys Leu Thr Pro Gly Ser Lys Glu Ser Gln Leu Thr
545                 550                 555                 560

Glu Ala Leu Phe Ala Glu Lys Pro Val Ala Lys Asn Asp Leu Lys Glu
                565                 570                 575
```

```
Ile Pro Gln Leu Val Thr Lys Lys Asn Asp Val Ser Glu Thr Glu Thr
            580                 585                 590

Val Asn Ile Asp Asn Lys Asp Thr Val Lys Gln Lys Glu Ala Lys Phe
        595                 600                 605

Glu Asn Gly Val Ile Thr Arg Lys Ala Asp Glu Lys Thr Thr Asn Asn
    610                 615                 620

Thr Ala Val Asp Lys Lys Ser Gly Lys Gln Ser Lys Thr Thr Pro
625                 630                 635                 640

Ser Asn Lys Arg Asn Ala Ser Lys Ala Ser Thr Asn Lys Thr Ser Gly
                645                 650                 655

Gln Lys Lys Gln His Asn Lys Ser Ser Gln Gly Ala Lys Lys Gln
            660                 665                 670

Ser Ser Ser Ser Lys Ser Thr Gln Lys Asn Asn Gln Thr Ser Asn Lys
            675                 680                 685

Asn Ser Lys Thr Thr Asn Ala Lys Ser Ser Ala Ser Lys Thr Pro
            690                 695                 700

Asn Ala Lys Val Glu Lys Ala Lys Ser Lys Ile Glu Lys Arg Thr Phe
705                 710                 715                 720

Asn Asp

<210> SEQ ID NO 17
<211> LENGTH: 620
<212> TYPE: PRT
<213> ORGANISM: Artificial sequence
<220> FEATURE:
<223> OTHER INFORMATION: Chimeric polypeptide
<220> FEATURE:
<221> NAME/KEY: MISC_FEATURE
<222> LOCATION: (1)..(409)
<223> OTHER INFORMATION: SEQ ID NO: 9
<220> FEATURE:
<221> NAME/KEY: MISC_FEATURE
<222> LOCATION: (410)..(421)
<223> OTHER INFORMATION: GSGGGAGSGGGA linker
<220> FEATURE:
<221> NAME/KEY: MISC_FEATURE
<222> LOCATION: (422)..(620)
<223> OTHER INFORMATION: SAR35 (SEQ ID NO: 1)
<220> FEATURE:
<221> NAME/KEY: MISC_FEATURE
<222> LOCATION: (422)..(620)
<223> OTHER INFORMATION: SEQ ID NO: 1

<400> SEQUENCE: 17

Met Asp Ile Gly Lys Lys His Val Ile Pro Lys Ser Gln Tyr Arg Arg
1               5                   10                  15

Lys Arg Arg Glu Phe Phe His Asn Glu Asp Arg Glu Glu Asn Leu Asn
            20                  25                  30

Gln His Gln Asp Lys Gln Asn Ile Asp Asn Thr Thr Ser Lys Lys Ala
        35                  40                  45

Asp Lys Gln Ile His Lys Asp Ser Ile Asp Lys His Glu Arg Phe Lys
    50                  55                  60

Asn Ser Leu Ser Ser His Leu Glu Gln Arg Asn Arg Asp Val Asn Glu
65                  70                  75                  80

Asn Lys Ala Glu Glu Ser Lys Ser Asn Gln Asp Ser Lys Ser Ala Tyr
                85                  90                  95

Asn Arg Asp His Tyr Leu Thr Asp Asp Val Ser Lys Lys Gln Asn Ser
            100                 105                 110

Leu Asp Ser Val Asp Gln Asp Thr Glu Lys Ser Lys Tyr Tyr Glu Gln
        115                 120                 125
```

```
Asn Ser Glu Ala Thr Leu Ser Thr Lys Ser Thr Asp Lys Val Glu Ser
    130                 135                 140
Thr Glu Met Arg Lys Leu Ser Ser Asp Lys Asn Lys Val Gly His Glu
145                 150                 155                 160
Glu Gln His Val Leu Ser Lys Pro Ser Glu His Asp Lys Glu Thr Arg
                165                 170                 175
Ile Asp Ser Glu Ser Ser Arg Thr Asp Ser Asp Ser Ser Met Gln Thr
            180                 185                 190
Glu Lys Ile Lys Lys Asp Ser Ser Asp Gly Asn Lys Ser Ser Asn Leu
        195                 200                 205
Lys Ser Glu Val Ile Ser Asp Lys Ser Asn Thr Val Pro Lys Leu Ser
210                 215                 220
Glu Ser Asp Asp Glu Val Asn Asn Gln Lys Pro Leu Thr Leu Pro Glu
225                 230                 235                 240
Glu Gln Lys Leu Lys Arg Gln Gln Ser Gln Asn Glu Gln Thr Lys Thr
                245                 250                 255
Tyr Thr Tyr Gly Asp Ser Glu Gln Asn Asp Lys Ser Asn His Glu Asn
            260                 265                 270
Asp Leu Ser His His Ile Pro Ser Ile Ser Asp Asp Lys Asp Asn Val
        275                 280                 285
Met Arg Glu Asn His Ile Val Asp Asp Asn Pro Asp Asn Asp Ile Asn
290                 295                 300
Thr Pro Ser Leu Ser Lys Thr Asp Asp Arg Lys Leu Asp Glu Lys
305                 310                 315                 320
Ile His Val Glu Asp Lys His Lys Gln Asn Ala Asp Ser Ser Glu Thr
                325                 330                 335
Val Gly Tyr Gln Ser Gln Ser Thr Ala Ser His Arg Ser Thr Glu Lys
            340                 345                 350
Arg Asn Ile Ser Ile Asn Asp His Asp Lys Leu Asn Gly Gln Lys Thr
        355                 360                 365
Asn Thr Lys Thr Ser Ala Asn Asn Gln Lys Lys Ala Thr Ser Lys
370                 375                 380
Leu Asn Lys Gly Arg Ala Thr Asn Asn Asn Tyr Ser Asp Ile Leu Lys
385                 390                 395                 400
Lys Phe Trp Met Met Tyr Trp Pro Lys Gly Ser Gly Gly Ala Gly
                405                 410                 415
Ser Gly Gly Gly Ala Met Thr Glu Lys Glu Lys Met Leu Ala Glu Lys
            420                 425                 430
Trp Tyr Asp Ala Asn Phe Asp Gln Asp Leu Ile Asn Glu Arg Ala Arg
        435                 440                 445
Ala Lys Asp Ile Cys Phe Glu Leu Asn His Thr Lys Pro Ser Asp Lys
450                 455                 460
Asn Lys Arg Lys Glu Leu Ile Asp Glu Leu Phe Gln Thr Thr Thr Asp
465                 470                 475                 480
Asn Val Ser Ile Ser Ile Pro Phe Asp Thr Asp Tyr Gly Trp Asn Val
                485                 490                 495
Lys Leu Gly Lys Asn Val Tyr Val Asn Thr Asn Cys Tyr Phe Met Asp
            500                 505                 510
Gly Gly Gln Ile Thr Ile Gly Asp Asn Val Phe Ile Gly Pro Asn Cys
        515                 520                 525
Gly Phe Tyr Thr Ala Thr His Pro Leu Asn Phe His His Arg Asn Glu
530                 535                 540
Gly Phe Glu Lys Ala Gly Pro Ile Asn Ile Gly Ser Asn Thr Trp Phe
```

```
                545                 550                 555                 560
Gly Gly His Val Ala Val Leu Pro Gly Val Thr Ile Gly Glu Gly Ser
            565                 570                 575
Val Ile Gly Ala Gly Ser Val Val Thr Lys Asp Ile Pro His Ser
            580                 585                 590
Leu Ala Val Gly Asn Pro Cys Lys Val Val Arg Lys Ile Asp Asn Glu
            595                 600                 605
Val Pro Ser Glu Ala Leu Asn Asp Glu Thr Leu Asn
            610                 615                 620

<210> SEQ ID NO 18
<211> LENGTH: 498
<212> TYPE: PRT
<213> ORGANISM: Artificial sequence
<220> FEATURE:
<223> OTHER INFORMATION: Chimeric polypeptide
<220> FEATURE:
<221> NAME/KEY: MISC_FEATURE
<222> LOCATION: (1)..(293)
<223> OTHER INFORMATION: Residues 27-319 of S. aureus alpha hemolysin
      (residues 27-319 of SEQ ID NO: 2)
<220> FEATURE:
<221> NAME/KEY: MISC_FEATURE
<222> LOCATION: (294)..(299)
<223> OTHER INFORMATION: GSGGGA linker
<220> FEATURE:
<221> NAME/KEY: MISC_FEATURE
<222> LOCATION: (300)..(498)
<223> OTHER INFORMATION: SEQ ID NO: 1

<400> SEQUENCE: 18

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met Leu Lys Lys Val Phe Tyr Ser Phe Ile Asp Asp Lys Asn His
        35                  40                  45

Asn Lys Lys Leu Leu Val Ile Arg Thr Lys Gly Thr Ile Ala Gly Gln
    50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly His
    130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220
```

```
Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
            245                 250                 255

Gln Leu His Trp Thr Ser Thr Asn Trp Lys Gly Thr Asn Thr Lys Asp
        260                 265                 270

Lys Trp Ile Asp Arg Ser Ser Glu Arg Tyr Lys Ile Asp Trp Glu Lys
    275                 280                 285

Glu Glu Met Thr Asn Gly Ser Gly Gly Gly Ala Met Thr Glu Lys Glu
290                 295                 300

Lys Met Leu Ala Glu Lys Trp Tyr Asp Ala Asn Phe Asp Gln Asp Leu
305                 310                 315                 320

Ile Asn Glu Arg Ala Arg Ala Lys Asp Ile Cys Phe Glu Leu Asn His
            325                 330                 335

Thr Lys Pro Ser Asp Lys Asn Lys Arg Lys Glu Leu Ile Asp Glu Leu
        340                 345                 350

Phe Gln Thr Thr Thr Asp Asn Val Ser Ile Ser Ile Pro Phe Asp Thr
    355                 360                 365

Asp Tyr Gly Trp Asn Val Lys Leu Gly Lys Asn Val Tyr Val Asn Thr
370                 375                 380

Asn Cys Tyr Phe Met Asp Gly Gln Ile Thr Ile Gly Asp Asn Val
385                 390                 395                 400

Phe Ile Gly Pro Asn Cys Gly Phe Tyr Thr Ala Thr His Pro Leu Asn
            405                 410                 415

Phe His His Arg Asn Glu Gly Phe Glu Lys Ala Gly Pro Ile Asn Ile
        420                 425                 430

Gly Ser Asn Thr Trp Phe Gly Gly His Val Ala Val Leu Pro Gly Val
    435                 440                 445

Thr Ile Gly Glu Gly Ser Val Ile Gly Ala Gly Ser Val Val Thr Lys
450                 455                 460

Asp Ile Pro Pro His Ser Leu Ala Val Gly Asn Pro Cys Lys Val Val
465                 470                 475                 480

Arg Lys Ile Asp Asn Glu Val Pro Ser Glu Ala Leu Asn Asp Glu Thr
            485                 490                 495

Leu Asn

<210> SEQ ID NO 19
<211> LENGTH: 689
<212> TYPE: PRT
<213> ORGANISM: Artificial sequence
<220> FEATURE:
<223> OTHER INFORMATION: Chimeric polypeptide
<220> FEATURE:
<221> NAME/KEY: MISC_FEATURE
<222> LOCATION: (1)..(293)
<223> OTHER INFORMATION: Residues 27-319 of S. aureus alpha hemolysin
      (residues 27-319 of SEQ ID NO: 2)
<220> FEATURE:
<221> NAME/KEY: MISC_FEATURE
<222> LOCATION: (294)..(299)
<223> OTHER INFORMATION: GSGGGA linker
<220> FEATURE:
<221> NAME/KEY: MISC_FEATURE
<222> LOCATION: (300)..(689)
<223> OTHER INFORMATION: SEQ ID NO: 8

<400> SEQUENCE: 19

Ala Asp Ser Asp Ile Asn Ile Lys Thr Gly Thr Thr Asp Ile Gly Ser
1               5                   10                  15
```

-continued

```
Asn Thr Thr Val Lys Thr Gly Asp Leu Val Thr Tyr Asp Lys Glu Asn
                20                  25                  30

Gly Met Leu Lys Lys Val Phe Tyr Ser Phe Ile Asp Asp Lys Asn His
         35                  40                  45

Asn Lys Lys Leu Leu Val Ile Arg Thr Lys Gly Thr Ile Ala Gly Gln
 50                  55                  60

Tyr Arg Val Tyr Ser Glu Glu Gly Ala Asn Lys Ser Gly Leu Ala Trp
 65                  70                  75                  80

Pro Ser Ala Phe Lys Val Gln Leu Gln Leu Pro Asp Asn Glu Val Ala
                 85                  90                  95

Gln Ile Ser Asp Tyr Tyr Pro Arg Asn Ser Ile Asp Thr Lys Glu Tyr
            100                 105                 110

Met Ser Thr Leu Thr Tyr Gly Phe Asn Gly Asn Val Thr Gly Asp Asp
            115                 120                 125

Thr Gly Lys Ile Gly Gly Leu Ile Gly Ala Asn Val Ser Ile Gly His
        130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Ile Asp Arg Ser Ser Glu Arg Tyr Lys Ile Asp Trp Glu Lys
        275                 280                 285

Glu Glu Met Thr Asn Gly Ser Gly Gly Ala Lys Val Ala Lys Gln
    290                 295                 300

Gly Gln Tyr Lys Asn Gln Asp Pro Ile Val Leu Val His Gly Phe Asn
305                 310                 315                 320

Gly Phe Thr Asp Asp Ile Asn Pro Ser Val Leu Ala His Tyr Trp Gly
                325                 330                 335

Gly Asn Lys Met Asn Ile Arg Gln Asp Leu Glu Glu Asn Gly Tyr Lys
            340                 345                 350

Ala Tyr Glu Ala Ser Ile Ser Ala Phe Gly Ser Asn Tyr Asp Arg Ala
        355                 360                 365

Val Glu Leu Tyr Tyr Tyr Ile Lys Gly Gly Arg Val Asp Tyr Gly Ala
    370                 375                 380

Ala His Ala Ala Lys Tyr Gly His Glu Arg Tyr Gly Lys Thr Tyr Glu
385                 390                 395                 400

Gly Ile Tyr Lys Asp Trp Lys Pro Gly Gln Lys Val His Leu Val Gly
                405                 410                 415

His Ser Met Gly Gly Gln Thr Ile Arg Gln Leu Glu Glu Leu Leu Arg
            420                 425                 430

Asn Gly Ser Arg Glu Glu Ile Glu Tyr Gln Lys Lys His Gly Gly Glu
```

```
                435                 440                 445
Ile Ser Pro Leu Phe Lys Gly Asn Asn Asp Asn Met Ile Ser Ser Ile
    450                 455                 460

Thr Thr Leu Gly Thr Pro His Asn Gly Thr His Ala Ser Asp Leu Ala
465                 470                 475                 480

Gly Asn Glu Ala Leu Val Arg Gln Ile Val Phe Asp Ile Gly Lys Met
                485                 490                 495

Phe Gly Asn Lys Asn Ser Arg Val Asp Phe Gly Leu Ala Gln Trp Gly
            500                 505                 510

Leu Lys Gln Lys Pro Asn Glu Ser Tyr Ile Asp Tyr Val Lys Arg Val
        515                 520                 525

Lys Gln Ser Asn Leu Trp Lys Ser Lys Asp Asn Gly Phe Tyr Asp Leu
    530                 535                 540

Thr Arg Glu Gly Ala Thr Asp Leu Asn Arg Lys Thr Ser Leu Asn Pro
545                 550                 555                 560

Asn Ile Val Tyr Lys Thr Tyr Thr Gly Glu Ala Thr His Lys Ala Leu
                565                 570                 575

Asn Ser Asp Arg Gln Lys Ala Asp Leu Asn Met Phe Phe Pro Phe Val
            580                 585                 590

Ile Thr Gly Asn Leu Ile Gly Lys Ala Thr Glu Lys Glu Trp Arg Glu
        595                 600                 605

Asn Asp Gly Leu Val Ser Val Ile Ser Ser Gln His Pro Phe Asn Gln
    610                 615                 620

Ala Tyr Thr Asn Ala Thr Asp Lys Ile Gln Lys Gly Ile Trp Gln Val
625                 630                 635                 640

Thr Pro Thr Lys His Asp Trp Asp His Val Asp Phe Val Gly Gln Asp
                645                 650                 655

Ser Ser Asp Thr Val Arg Thr Arg Glu Glu Leu Gln Asp Phe Trp His
            660                 665                 670

His Leu Ala Asp Asp Leu Val Lys Thr Glu Lys Val Thr Asp Thr Lys
        675                 680                 685

Gln

<210> SEQ ID NO 20
<211> LENGTH: 501
<212> TYPE: PRT
<213> ORGANISM: Artificial sequence
<220> FEATURE:
<223> OTHER INFORMATION: Chimeric polypeptide
<220> FEATURE:
<221> NAME/KEY: MISC_FEATURE
<222> LOCATION: (1)..(293)
<223> OTHER INFORMATION: Residues 27-319 of S. aureus alpha hemolysin
      (residues 27-319 of SEQ ID NO: 2)
<220> FEATURE:
<221> NAME/KEY: MISC_FEATURE
<222> LOCATION: (294)..(299)
<223> OTHER INFORMATION: GSGGGA linker
<220> FEATURE:
<221> NAME/KEY: MISC_FEATURE
<222> LOCATION: (300)..(501)
<223> OTHER INFORMATION: (SEQ ID NO: 2)

<400> SEQUENCE: 20

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met Leu Lys Lys Val Phe Tyr Ser Phe Ile Asp Asp Lys Asn His
```

-continued

```
            35                  40                  45
Asn Lys Lys Leu Leu Val Ile Arg Thr Lys Gly Thr Ile Ala Gly Gln
 50                  55                  60

Tyr Arg Val Tyr Ser Glu Glu Gly Ala Asn Lys Ser Gly Leu Ala Trp
 65                  70                  75                  80

Pro Ser Ala Phe Lys Val Gln Leu Gln Leu Pro Asp Asn Glu Val Ala
                 85                  90                  95

Gln Ile Ser Asp Tyr Tyr Pro Arg Asn Ser Ile Asp Thr Lys Glu Tyr
                100                 105                 110

Met Ser Thr Leu Thr Tyr Gly Phe Asn Gly Asn Val Thr Gly Asp Asp
                115                 120                 125

Thr Gly Lys Ile Gly Gly Leu Ile Gly Ala Asn Val Ser Ile Gly His
                130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
                180                 185                 190

Asn Gln Leu Phe Met Lys Thr Arg Asn Gly Ser Met Lys Ala Ala Asp
                195                 200                 205

Asn Phe Leu Asp Pro Asn Lys Ala Ser Ser Leu Leu Ser Ser Gly Phe
                210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
                260                 265                 270

Lys Trp Ile Asp Arg Ser Ser Glu Arg Tyr Lys Ile Asp Trp Glu Lys
                275                 280                 285

Glu Glu Met Thr Asn Gly Ser Gly Gly Ala Lys Arg Ile Lys Gln
                290                 295                 300

His Pro Asp Val Gln Lys Val Thr Asp Ala Thr Ser Lys Val Ala Ser
305                 310                 315                 320

Lys Thr Ser Ala Ala Ile Ser Asn Thr Ala Ser Asp Val Lys Glu Tyr
                325                 330                 335

Val Gly Asp Lys Lys Gln Asp Phe Glu Asn Lys Arg Glu Leu Lys Lys
                340                 345                 350

Phe Ala Arg Glu His Asp Pro Ala Tyr Ile Glu Lys Lys Gly Glu Lys
                355                 360                 365

Leu Ala Lys Gln Asn Arg Lys Asp Ala Asp Lys Met Asn Lys Ile Leu
                370                 375                 380

Gln Lys Asn Ile Glu Lys Arg His Lys Glu Glu Gln Lys Ala Arg Glu
385                 390                 395                 400

Lys Asn Glu Ile Gln Arg Ile Lys Asp Met Lys Lys Ser Gln Lys Tyr
                405                 410                 415

Glu Val Lys Ala Gly Leu Thr Pro Asn Lys Leu Asp Glu Lys Thr Glu
                420                 425                 430

Lys Lys Gly Asp Lys Leu Ala Glu Lys Asn Arg Lys Glu Ile Ala Lys
                435                 440                 445

Met Asn Lys Lys Leu Gln Lys Asn Ile Glu Lys Arg His Lys Glu Glu
                450                 455                 460
```

```
Gln Lys Arg Gln Gln Glu Ala Asp Lys Ala Arg Ile Lys Ser Phe Lys
465                 470                 475                 480

Lys Tyr Lys Asp Tyr Val Ala Lys Ser Ala Ser Gln Gln Asn Lys Glu
            485                 490                 495

Asn Asn Thr Glu Ala
            500

<210> SEQ ID NO 21
<211> LENGTH: 15
<212> TYPE: PRT
<213> ORGANISM: Staphylococcus aureus

<400> SEQUENCE: 21

Glu Pro Ile Asn Phe Ile Leu Lys Ser Ser Thr Lys Leu Lys Ala
1               5                   10                  15

<210> SEQ ID NO 22
<211> LENGTH: 15
<212> TYPE: PRT
<213> ORGANISM: Staphylococcus aureus

<400> SEQUENCE: 22

Phe Leu Lys Leu Phe Arg Ile Thr Asn Pro Ile Ala Arg Gly Leu
1               5                   10                  15

<210> SEQ ID NO 23
<211> LENGTH: 15
<212> TYPE: PRT
<213> ORGANISM: Staphylococcus aureus

<400> SEQUENCE: 23

Gly Leu Tyr Phe Val Ala Met Asn Asn Leu Lys Ala Ala Gly Gln
1               5                   10                  15

<210> SEQ ID NO 24
<211> LENGTH: 15
<212> TYPE: PRT
<213> ORGANISM: Staphylococcus aureus

<400> SEQUENCE: 24

Ile Ile Lys Lys Leu Phe Arg Leu Pro Ala Ile Lys Arg Phe Glu
1               5                   10                  15

<210> SEQ ID NO 25
<211> LENGTH: 15
<212> TYPE: PRT
<213> ORGANISM: Staphylococcus aureus

<400> SEQUENCE: 25

Ile Leu Leu Gly Tyr Phe Val Ala Gln Arg Ala Leu Val Lys Ala
1               5                   10                  15

<210> SEQ ID NO 26
<211> LENGTH: 15
<212> TYPE: PRT
<213> ORGANISM: Staphylococcus aureus

<400> SEQUENCE: 26

Lys Ala Asp Ala Leu Lys Ala Ile Thr Ala Leu Lys Leu Gln Met
1               5                   10                  15

<210> SEQ ID NO 27
<211> LENGTH: 15
```

```
<212> TYPE: PRT
<213> ORGANISM: Staphylococcus aureus

<400> SEQUENCE: 27

Lys His Gln Ile Arg Met Leu Ser Ile Pro Arg Asp Thr Ile Ser
1               5                   10                  15

<210> SEQ ID NO 28
<211> LENGTH: 15
<212> TYPE: PRT
<213> ORGANISM: Staphylococcus aureus

<400> SEQUENCE: 28

Lys Arg Ile Phe Lys Met Ser Pro Ile His His Phe Glu Leu
1               5                   10                  15

<210> SEQ ID NO 29
<211> LENGTH: 15
<212> TYPE: PRT
<213> ORGANISM: Staphylococcus aureus

<400> SEQUENCE: 29

Lys Thr Leu Phe Val Ala Leu Asn Asn Lys Ala Arg Ile Pro Glu
1               5                   10                  15

<210> SEQ ID NO 30
<211> LENGTH: 15
<212> TYPE: PRT
<213> ORGANISM: Staphylococcus aureus

<400> SEQUENCE: 30

Leu Asp Gln Ile Ile Ala Gln Ala Asn Leu Arg Leu Ala Thr Met
1               5                   10                  15

<210> SEQ ID NO 31
<211> LENGTH: 15
<212> TYPE: PRT
<213> ORGANISM: Staphylococcus aureus

<400> SEQUENCE: 31

Leu Met Gly Ile Arg Ala Phe Arg Lys Leu Leu Pro Asn Ile Pro
1               5                   10                  15

<210> SEQ ID NO 32
<211> LENGTH: 15
<212> TYPE: PRT
<213> ORGANISM: Staphylococcus aureus

<400> SEQUENCE: 32

Met His Phe Ile Ala Ile Ser Ile Asn His Arg Thr Ala Asp Val
1               5                   10                  15

<210> SEQ ID NO 33
<211> LENGTH: 15
<212> TYPE: PRT
<213> ORGANISM: Staphylococcus aureus

<400> SEQUENCE: 33

Gln Arg His Phe Gln Ile Gly Tyr Asn Arg Ala Ala Arg Ile Ile
1               5                   10                  15

<210> SEQ ID NO 34
<211> LENGTH: 15
<212> TYPE: PRT
<213> ORGANISM: Staphylococcus aureus
```

<400> SEQUENCE: 34

Ser Ser Asn Val Tyr Met Phe Lys Thr Ala Leu Lys Leu Ala Gly
1               5                   10                  15

<210> SEQ ID NO 35
<211> LENGTH: 15
<212> TYPE: PRT
<213> ORGANISM: Staphylococcus aureus

<400> SEQUENCE: 35

Ser Thr Phe Ile Tyr Lys Ile Ala Asn Glu Arg Leu Phe Ser Arg
1               5                   10                  15

<210> SEQ ID NO 36
<211> LENGTH: 15
<212> TYPE: PRT
<213> ORGANISM: Staphylococcus aureus

<400> SEQUENCE: 36

Ser Val Thr Ile Ile Lys Ser Leu Gln Ala Ile Arg Val Pro Phe
1               5                   10                  15

<210> SEQ ID NO 37
<211> LENGTH: 15
<212> TYPE: PRT
<213> ORGANISM: Staphylococcus aureus

<400> SEQUENCE: 37

Thr Ser Gln Phe His Val Leu Arg Ala Leu Arg Leu Ala Gln Lys
1               5                   10                  15

<210> SEQ ID NO 38
<211> LENGTH: 15
<212> TYPE: PRT
<213> ORGANISM: Staphylococcus aureus

<400> SEQUENCE: 38

Val Leu Phe Tyr Leu Arg Ser Asn Lys Arg Gln Ile Ile Glu Lys
1               5                   10                  15

<210> SEQ ID NO 39
<211> LENGTH: 15
<212> TYPE: PRT
<213> ORGANISM: Staphylococcus aureus

<400> SEQUENCE: 39

Trp Lys Arg Ile Gly Arg Leu Lys Ser Ile Pro Ile Phe Met Tyr
1               5                   10                  15

<210> SEQ ID NO 40
<211> LENGTH: 15
<212> TYPE: PRT
<213> ORGANISM: Staphylococcus aureus

<400> SEQUENCE: 40

Tyr Phe Arg Phe Gln Tyr Phe Asn Pro Leu Lys Ser Glu Arg Tyr
1               5                   10                  15

<210> SEQ ID NO 41
<211> LENGTH: 175
<212> TYPE: PRT
<213> ORGANISM: Artificial sequence
<220> FEATURE:
<223> OTHER INFORMATION: Multiple linked epitopes

<400> SEQUENCE: 41

```
Val Leu Phe Tyr Leu Arg Ser Asn Lys Arg Gln Ile Ile Glu Lys Gly
1               5                   10                  15

Pro Gly Pro Gly Glu Pro Ile Asn Phe Ile Leu Lys Ser Ser Thr Lys
            20                  25                  30

Leu Lys Ala Gly Pro Gly Pro Gly Leu Tyr Phe Val Ala Met Asn
        35                  40                  45

Asn Leu Lys Ala Ala Gly Gln Gly Pro Gly Pro Gly Lys Ala Asp Ala
        50                  55                  60

Leu Lys Ala Ile Thr Ala Leu Lys Leu Gln Met Gly Pro Gly Pro Gly
65                  70                  75                  80

Lys His Gln Ile Arg Met Leu Ser Ile Pro Arg Asp Thr Ile Ser Gly
                85                  90                  95

Pro Gly Pro Gly Leu Asp Gln Ile Ile Ala Gln Ala Asn Leu Arg Leu
            100                 105                 110

Ala Thr Met Gly Pro Gly Pro Gly Gln Arg His Phe Gln Ile Gly Tyr
                115                 120                 125

Asn Arg Ala Ala Arg Ile Ile Gly Pro Gly Pro Gly Ser Ser Asn Val
        130                 135                 140

Tyr Met Phe Lys Thr Ala Leu Lys Leu Ala Gly Pro Gly Pro Gly
145                 150                 155                 160

Tyr Phe Arg Phe Gln Tyr Phe Asn Pro Leu Lys Ser Glu Arg Tyr
                165                 170                 175
```

<210> SEQ ID NO 42
<211> LENGTH: 215
<212> TYPE: PRT
<213> ORGANISM: Artificial sequence
<220> FEATURE:
<223> OTHER INFORMATION: Multiple linked epitopes

<400> SEQUENCE: 42

```
Thr Ser Gln Phe His Val Leu Arg Ala Leu Arg Leu Ala Gln Lys Gly
1               5                   10                  15

Pro Gly Pro Gly Phe Leu Lys Leu Phe Arg Ile Thr Asn Pro Ile Ala
            20                  25                  30

Arg Gly Leu Gly Pro Gly Pro Gly Ile Ile Lys Lys Leu Phe Arg Leu
        35                  40                  45

Pro Ala Ile Lys Arg Phe Glu Gly Pro Gly Pro Gly Ile Leu Leu Gly
    50                  55                  60

Tyr Phe Val Ala Gln Arg Ala Leu Val Lys Ala Gly Pro Gly Pro Gly
65                  70                  75                  80

Lys Arg Ile Phe Lys Met Ser Pro Ile His His His Phe Glu Leu Gly
                85                  90                  95

Pro Gly Pro Gly Lys Thr Leu Phe Val Ala Leu Asn Asn Lys Ala Arg
            100                 105                 110

Ile Pro Glu Gly Pro Gly Pro Gly Leu Met Gly Ile Arg Ala Phe Arg
        115                 120                 125

Lys Leu Leu Pro Asn Ile Pro Gly Pro Gly Pro Gly Met His Phe Ile
        130                 135                 140

Ala Ile Ser Ile Asn His Arg Thr Ala Asp Val Gly Pro Gly Pro Gly
145                 150                 155                 160

Ser Thr Phe Ile Tyr Lys Ile Ala Asn Glu Arg Leu Phe Ser Arg Gly
                165                 170                 175
```

```
Pro Gly Pro Gly Ser Val Thr Ile Ile Lys Ser Leu Gln Ala Ile Arg
            180                 185                 190

Val Pro Phe Gly Pro Gly Pro Gly Trp Lys Arg Ile Gly Arg Leu Lys
        195                 200                 205

Ser Ile Pro Ile Phe Met Tyr
    210                 215

<210> SEQ ID NO 43
<211> LENGTH: 453
<212> TYPE: PRT
<213> ORGANISM: Artificial sequence
<220> FEATURE:
<223> OTHER INFORMATION: Scaffold protein with multiple inserted
      epitopes

<400> SEQUENCE: 43

Met Ser Ser Leu Pro Val Gly Pro Val Ala Trp Ser Asp Gly Met Leu
1               5                   10                  15

Ile Glu Thr Gln His Phe Gln Gln Leu Lys Arg Ile Phe Lys Met Ser
            20                  25                  30

Pro Ile His His His Phe Glu Leu Ser Asn His Gly Trp Gly Phe Thr
        35                  40                  45

Leu Leu Asp Leu Asp Gln Asp Gly Leu Gly Leu Gly Arg Leu Met Gly
    50                  55                  60

Ile Arg Ala Phe Arg Lys Leu Leu Pro Asn Ile Pro Phe Ser Leu Pro
65                  70                  75                  80

Ser Asp Asp Pro Leu Pro Pro Pro Leu Glu Thr Glu Leu Ala Gln Ala
                85                  90                  95

Gly Asp Ile Ala Cys Leu Ala Leu Gln Ala Ala Arg Thr Gly Gly Pro
            100                 105                 110

Glu Met Ala Phe Gly Asp Val Glu Leu Ala Ser Arg Tyr Arg Ala Val
        115                 120                 125

Ser Thr Glu Val Pro Asp Leu Ala Val Gly Leu Asp Ala Pro Gly Thr
    130                 135                 140

Pro Phe Leu Lys Leu Phe Arg Ile Thr Asn Pro Ile Ala Arg Gly Leu
145                 150                 155                 160

Trp Lys Arg Ile Gly Arg Leu Lys Ser Ile Pro Ile Phe Met Tyr Arg
                165                 170                 175

Val Ala Gly Arg Asn Ala Ser Arg Thr Val Ser Leu Asp Pro Arg Phe
            180                 185                 190

Ile Pro Pro Lys Thr Leu Phe Val Ala Leu Asn Asn Lys Ala Arg Ile
        195                 200                 205

Pro Glu Glu Leu Gln Ser Thr Ser Val Thr Ile Ile Lys Ser Leu Gln
    210                 215                 220

Ala Ile Arg Val Pro Phe Thr Gly Gly Gly Val Ala Asp Leu Ile Glu
225                 230                 235                 240

Ile Leu Leu Gly Tyr Phe Val Ala Gln Arg Ala Leu Val Lys Ala Asn
                245                 250                 255

Leu Asp Ala Phe Asp Pro Leu Pro Pro Met His Phe Ile Ala Ile Ser
            260                 265                 270

Ile Asn His Arg Thr Ala Asp Val Val Leu Pro Gly Val Asp Glu Glu
        275                 280                 285

Leu Ala Asp Arg Glu Leu Gly Tyr Asp His Asp Asp Leu Gln Thr Ser
    290                 295                 300

Phe Thr Ser Gln Phe His Val Leu Arg Ala Leu Arg Leu Ala Gln Lys
305                 310                 315                 320
```

```
Glu Thr Pro Val Leu Pro Leu Arg Phe Glu Asp Arg Gly Asp Gln Val
                325                 330                 335

His Ile Cys Ile Val Asp Lys Gln Trp Asn Leu Lys Lys Leu Ile Phe
            340                 345                 350

Ala Phe Ser Ile Ile Lys Lys Leu Phe Arg Leu Pro Ala Ile Lys Arg
        355                 360                 365

Phe Glu Thr Lys Leu Gly Ala Val Glu Gln Ile Gln Lys Leu Val Asp
    370                 375                 380

Leu Gln Leu Pro Gly Ala Arg Leu Asn Ala Leu Pro Asn Pro Pro Arg
385                 390                 395                 400

Gln Ile Pro Tyr Tyr Ala Gln Ser Thr Tyr Phe Glu Val Glu Ser Thr
                405                 410                 415

Asp Pro Phe Trp Lys Gln Thr Leu Ala Gly Ser Ala Met Ala Leu Arg
            420                 425                 430

Ile Val Gly Asp Phe Pro Ser Thr Phe Ile Tyr Lys Ile Ala Asn Glu
        435                 440                 445

Arg Leu Phe Ser Arg
    450

<210> SEQ ID NO 44
<211> LENGTH: 453
<212> TYPE: PRT
<213> ORGANISM: Artificial sequence
<220> FEATURE:
<223> OTHER INFORMATION: Scaffold protein with multiple inserted
      epitopes

<400> SEQUENCE: 44

Met Ser Ser Leu Pro Val Gly Pro Val Ala Trp Ser Asp Gly Met Leu
1               5                   10                  15

Ile Glu Thr Gln His Phe Gln Gln Leu Glu Arg His Leu Ala His Gln
            20                  25                  30

Ala Ser Leu Arg Leu Gly Gln Thr Ser Asn His Gly Trp Gly Phe Thr
        35                  40                  45

Leu Leu Asp Leu Asp Gln Asp Gly Leu Gly Leu Gly Arg Leu Gly Leu
    50                  55                  60

Arg Ser Ser Asn Val Tyr Met Phe Lys Thr Ala Leu Lys Leu Ala Gly
65                  70                  75                  80

Ser Asp Asp Pro Leu Pro Pro Pro Leu Glu Thr Glu Leu Ala Gln Ala
                85                  90                  95

Gly Asp Ile Ala Cys Leu Ala Leu Gln Ala Ala Arg Thr Gly Gly Pro
            100                 105                 110

Glu Met Ala Phe Gly Asp Val Glu Leu Ala Ser Arg Tyr Arg Ala Val
        115                 120                 125

Ser Thr Glu Val Pro Asp Leu Ala Val Gly Leu Asp Ala Pro Gly Thr
    130                 135                 140

Pro Arg Arg Leu Thr Ile Glu Thr Gly Gln Leu Val Thr Arg Leu Cys
145                 150                 155                 160

Trp Lys Ser Gln Val Leu Phe Tyr Leu Arg Ser Asn Lys Arg Gln Ile
                165                 170                 175

Ile Glu Lys Arg Asn Ala Ser Arg Thr Val Ser Leu Asp Pro Arg Phe
            180                 185                 190

Ile Pro Pro Glu Pro Ile Asn Phe Ile Leu Lys Ser Ser Thr Lys Leu
        195                 200                 205

Lys Ala Glu Leu Gln Ser Thr Gln Arg His Phe Gln Ile Gly Tyr Asn
```

```
Arg Ala Ala Arg Ile Ile Thr Gly Gly Val Ala Asp Leu Ile Glu
225                 230                 235                 240

Leu Leu Leu Arg Gln Leu Asp Gln Ile Ile Ala Gln Ala Asn Leu Arg
            245                 250                 255

Leu Ala Thr Met Asp Pro Leu Pro Pro Gly Leu Tyr Phe Val Ala Met
        260                 265                 270

Asn Asn Leu Lys Ala Ala Gly Gln Val Leu Pro Gly Val Asp Glu Glu
    275                 280                 285

Leu Ala Asp Arg Glu Leu Gly Tyr Asp His Asp Leu Gln Thr Ser
290                 295                 300

Phe Glu Pro Leu Ala Met Met Leu Arg Gln Ala Leu Ala Arg Val Ile
305                 310                 315                 320

Glu Thr Pro Val Leu Pro Leu Arg Phe Glu Asp Arg Gly Asp Gln Val
            325                 330                 335

His Ile Cys Ile Val Asp Lys Gln Trp Asn Leu Lys Lys Leu Ile Phe
        340                 345                 350

Ala Phe Ser Lys Ala Asp Ala Leu Lys Ala Ile Thr Ala Leu Lys Leu
    355                 360                 365

Gln Met Thr Lys Leu Gly Ala Val Glu Gln Ile Gln Lys Leu Val Asp
370                 375                 380

Leu Gln Leu Pro Gly Ala Arg Leu Asn Ala Leu Pro Asn Pro Arg
385                 390                 395                 400

Gln Ile Pro Tyr Tyr Ala Gln Ser Thr Tyr Phe Glu Val Glu Ser Lys
            405                 410                 415

His Gln Ile Arg Met Leu Ser Ile Pro Arg Asp Thr Ile Ser Leu Arg
        420                 425                 430

Ile Val Gly Asp Tyr Phe Arg Phe Gln Tyr Phe Asn Pro Leu Lys Ser
    435                 440                 445

Glu Arg Tyr Val Ala
    450

<210> SEQ ID NO 45
<211> LENGTH: 5
<212> TYPE: PRT
<213> ORGANISM: Artificial sequence
<220> FEATURE:
<223> OTHER INFORMATION: Peptide linker

<400> SEQUENCE: 45

Gly Pro Gly Pro Gly
1               5

<210> SEQ ID NO 46
<211> LENGTH: 1854
<212> TYPE: DNA
<213> ORGANISM: Artificial sequence
<220> FEATURE:
<223> OTHER INFORMATION: Recombinant DNA encoding chimeric protein

<400> SEQUENCE: 46
atggatattg gtaaaaaaca tgtaattcct aaaagtcagt accgacgtaa gcgtcgtgaa      60
ttcttccaca acgaagacag agaagaaaat ttaaatcaac atcaagataa acaaaatata     120
gataatacaa catcaaaaaa agcagataag caaatacata agattcaat tgataagcac      180 gaacgtttta aaaatagttt atcatcgcat ttagaacaga gaaaccgtga tgttaatgag     240
aataaagctg aagaaagtaa agtaatcag gatagtaagt cagcatataa cagagatcat     300
```

```
tatttaacag acgatgtatc taaaaaacaa aattcattag attcagtgga ccaagataca       360
gagaaatcaa aatattatga gcaaaattct gaagcgactt tatcaactaa atcaaccgat       420
aaagtagaat caactgaaat gagaaagcta agttcagata aaaacaaagt tggtcatgaa       480
gagcaacatg tactttctaa accttcagaa catgataaag agactagaat tgattctgag       540
tcttcaagaa ctgattcaga cagctcgatg cagacagaga aaataaaaaa agacagttca       600
gatggaaata aaagtagtaa tctgaaatct gaagtaatat cagacaaatc aaatacagta       660
ccaaaattgt cggaatctga tgatgaagta aataatcaga agccattaac tttaccggaa       720
gaacagaaat tgaaaagaca gcaaagtcaa aatgagcaaa caaaaaccta tacatatggt       780
gatagcgaac aaaatgacaa gtctaatcat gaaaatgatt taagtcatca tataccatcg       840
ataagtgatg ataaagataa cgtcatgaga gaaaatcata ttgttgacga taatcctgat       900
aatgatatca atacaccatc attatcaaaa acagatgacg atcgaaaact tgatgaaaaa       960
attcatgttg aagataaaca taaacaaaat gcagactcgt ctgaaacggt gggatatcaa      1020
agtcagtcaa ctgcatctca tcgtagcact gaaaaaagaa atatttctat taatgaccat      1080
gataaattaa acggtcaaaa aacaaataca aagacatcgg caaataataa tcaaaaaaag      1140
gctacatcaa aattgaacaa agggcgcgct acgaataata attatagtga cattttgaaa      1200
aagttttgga tgatgtattg gcctaaaggt tctggcggag gggctaaacg tatcaaacaa      1260
catccggacg tacaaaaagt tacagatgct acaagtaaag ttgcttcaaa acatctgca       1320
gcaatcagta acacagcgag tgatgttaaa gaatatgtcg gcgataaaaa acaagatttt      1380
gaaaataagc gtgaacttaa aaagtttgct agagaacatg atcctgccta tattgagaaa      1440
aaaggcgaaa aattagctaa acaaaatcgt aaagacgctg ataaaatgaa taaaatactt      1500
caaaaaaata tcgaaaagcg tcataaagaa gagcaaaaag cccgcgaaaa gaatgaaata      1560
caacgtatta aagatatgaa aaagtcacaa aaatacgaag taaaagcagg cttaacacct      1620
aataaattag atgagaaaac tgagaaaaaa ggcgataaac tagctgaaaa aaatcgcaaa      1680
gaaatcgcta aaatgaataa aaagttacaa aaaatattg aaaaacgaca caagaagaa       1740
caaaaacgcc aacaagaagc tgataaagca cgcatcaagt catttaaaaa atataaagat      1800
tatgttgcca aaagcgcctc tcaacaaaat aaagaaaaca atacagaggc ataa            1854
```

<210> SEQ ID NO 47
<211> LENGTH: 2394
<212> TYPE: DNA
<213> ORGANISM: Artificial sequence
<220> FEATURE:
<223> OTHER INFORMATION: Recombinant DNA encoding chimeric protein

<400> SEQUENCE: 47

```
atgactgaaa agaaaaaaat gttagcagaa aaatggtacg atgcaaactt tgatcaagac        60
ttaatcaatg aacgtgcacg agcgaaagat atttgctttg aattaaatca tacaaagccg       120
agtgacaaaa ataaaagaaa ggaattaatc gatgaattat ttcaaacaac aacagacaat       180
gtaagtattt cgattccttt tgatacagat tatggttgga acgttaaact aggaaaaaat       240
gtctatgtaa acaccaattg ttattttatg atggtggac agattacaat tggcgataat        300
gttttatag gacctaattg tggattctac acagcaacac atccacttaa ttttcatcat       360
agaaatgaag gatttgaaaa agcaggacca attaatattg cagtaatac ttggtttggc        420
ggacatgtag ccgtgcttcc gggagtgacg attggagaag gcagtgtgat tggtgctggt       480
```

-continued

| | |
|---|---|
| agtgttgtca ccaaagatat tccgccacac agtttagcgg ttggaaaccc ttgtaaagtc | 540 |
| gttcgtaaaa ttgataatga ggtaccatca gaagcattga acgatgaaac actaaatggt | 600 |
| tctggcggag gggctgatac acctcaaaaa gatactacag ctaagacaac atctcatgat | 660 |
| tcaaaaaaat ctaatgacga tgaaacttct aaggatacta caagtaaaga tattgataaa | 720 |
| gcagacaaca ataatacaag taaccaagac aataacgaca aaaatttaa aactatagac | 780 |
| gacagcactt cagactctaa caatatcatt gattttattt ataagaattt accacaaacc | 840 |
| aatataaacc aattgctaac caaaaataaa tacgatgata attactcatt aacaactta | 900 |
| atccaaaacc tattcaattt aaattcggat atttctgatt acgaacaacc tcgtaatggc | 960 |
| gaaaagtcaa caaatgattc gaataaaaac agtgacaata gcatcaaaaa tgacactgat | 1020 |
| acgcaatcat ctaaacaaga taaagcagac aatcaaaaag cacctaaatc aaacaataca | 1080 |
| aaaccaagta catctaataa gcaaccaaat tcgccaaagc caacacaacc taatcaatca | 1140 |
| aatagtcaac cagcaagtga cgataaagca aatcaaaaat cttcatcgaa agataatcaa | 1200 |
| tcaatgtcag attcggcttt agactctatt ttggatcaat acagtgaaga tgcaaagaaa | 1260 |
| acacaaaaag attatgcatc tcaatctaaa aaagacaaaa atgaaaaatc taatacaaag | 1320 |
| aatccacagt taccaacaca agatgaattg aaacataaat ctaaacctgc tcaatcattc | 1380 |
| aataacgatg ttaatcaaaa ggatacacgt gcaacatcat tattcgaaac agatcctagt | 1440 |
| atatctaaca atgatgatag cggacaattt aacgttgttg actcaaaaga tacacgtcaa | 1500 |
| tttgtcaaat caattgctaa agatgcacat cgcattggtc aagataacga tatttatgcg | 1560 |
| tctgtcatga ttgcccaagc aatcttagaa tctgactcag gtcgtagtgc tttagctaag | 1620 |
| tcaccaaacc ataatttatt cggtatcaaa ggtgcttttg aagggaattc tgttccttt | 1680 |
| aacacattag aagctgatgg taataaattg tatagtatta atgctggatt ccgaaaatat | 1740 |
| ccaagcacga aagaatcact aaaagattac tctgacctta ttaaaaatgg tattgatggc | 1800 |
| aatcgaacaa tttataaacc aacatggaaa tcggaagccg attcttataa agatgcaaca | 1860 |
| tcacacttat ctaaaacata tgctacagat ccaaactatg ctaagaaatt aaacagtatt | 1920 |
| attaaacact atcaattaac tcagtttgac gatgaacgca tgccagattt agataaatat | 1980 |
| gaacgttcta tcaaggatta tgatgattca tcagatgaat tcaaaccttt ccgtgaggta | 2040 |
| tctgatagta tgccatatcc acatggtcaa tgtacttggt acgtatataa ccgtatgaaa | 2100 |
| caatttggta catctatctc aggtgattta ggtgatgcac ataattggaa taatcgagct | 2160 |
| caataccgtg attatcaagt aagtcataca ccaaaacgtc atgctgctgt tgtatttgag | 2220 |
| gctggacaat tggtgcaga tcaacattac ggtcatgtag catttgttga aaaagttaac | 2280 |
| agtgatggtt ctatcgttat ttcagaatcc aatgttaaag gattaggtat catttctcat | 2340 |
| agaactatca atgcagctgc cgctgaagaa ttatcatata ttacaggtaa ataa | 2394 |

<210> SEQ ID NO 48
<211> LENGTH: 2445
<212> TYPE: DNA
<213> ORGANISM: Artificial sequence
<220> FEATURE:
<223> OTHER INFORMATION: Recombinant DNA encoding chimeric protein

<400> SEQUENCE: 48

| | |
|---|---|
| attgattcaa aaaataaacc agctaattct gatattaaat ttgaggtgac tcaaaagagt | 60 |
| gatgcggtca agcattaaaa agaattgcct aaatccgaaa atgtaaaaaa tatttatcaa | 120 |
| gattacgctg ttactgatgt aaaaactgat aaaaaaggat ttacgcatta tacattgcaa | 180 |

```
ccgagtgttg atggtgttca tgcacctgac aaagaagtga agtacacgc agacaaatca      240 ggaaaagtcg ttttaatcaa tggggatact gatgcgaaga aagtaaagcc aacgaataaa      300
gtgacattaa gtaaagatga cgcagccgac aaagcattta agcagttaa gattgataag      360 aataaagcga aaaatcttaa agataaagtc attaaagaaa acaaagttga aatcgatggt      420
gacagtaata aatacgttta taatgttgag ttaattacag tgacaccaga aatttcacat      480
tggaaagtta aaattgatgc tcaaactggc gaaattttag aaaaaatgaa cttagttaaa      540
gaagctgcag aaactggtaa aggaaaggt gtacttggcg atacaaaaga tatcaatatc      600
aatagtattg acggtggatt tagcctagaa gatttaacgc atcaaggtaa attatcagca      660 tttagctta atgatcaaac aggtcaagca acattgatta ctaatgaaga tgaaaacttc      720
gtaaaagatg agcaacgtgc tggcgtagat gcaaattatt acgctaaaca aacatatgat      780
tattacaaag acacatttgg tcgtgaatca tatgacaacc aaggtagtcc aattgtttca      840
ttaacgcatg ttaataacta cggtggtcaa gataacagaa ataatgccgc atggatcggt      900
gacaaaatga tctatggtga tggtgatggt cgcacattca caagtttatc gggtgcaaat      960
gacgtagtag cacacgaatt aacacacggt gtgacacaag agacagcgaa cttagaatat     1020
aaggaccagt caggcgctct aaatgaaagc ttttcagatg ttttttggata ctttgtagat     1080 gacgaggatt tcttaatggg tgaagatgtc tacacacctg aaaagaggg agacgcttta     1140 cgcagcatgt caaacccaga acaatttggt caaccagctc atatgaaaga ctatgtattc     1200
actgaaaaag ataatggtgg cgtacatacg aattctggtt ctggcggagg ggctggaagt     1260
ggtgggggcg ccaaagttgc caaacaaggg cagtataaaa atcaagaccc tatcgtgtta     1320
gtgcatggtt tcaatggatt tacagatgat attaatcctt cagtgttagc tcattattgg     1380
ggcggtaata aaatgaacat tcgccaagat ttagaagaaa atggttacaa agcttatgaa     1440
gcaagtataa gtgctttgg aagtaactat gaccgcgcag ttgaactta ttattatatc     1500 aaaggcggtc gtgtagatta tggtgcagca catgcagcaa aatatggaca tgaacgttat     1560
ggaaaaacat acgaaggaat ttacaaagac tggaaaccag acagaaggt acacctagtt     1620 ggacatagta tgggtggtca aacgatacgt caactagaag aattactgcg taatggtagt     1680
cgtgaagaaa tagagtatca aaagaaacat ggtggcgaaa tttctccact attcaaaggt     1740
aataatgaca atatgatttc atcaattact actttaggaa cgccacataa tggaacgcat     1800
gcttcagatt tagctggtaa tgaagcttta gtgagacaaa ttgtatttga tatcggtaaa     1860
atgtttggta ataaaaactc tagagtagac ttcgggttgg ctcaatgggg tctaaaacag     1920
aagccaaatg aatcatacat tgattatgtc aaacgcgtta acaatctaa tttatggaaa     1980 tcaaaagata atggatttta cgatctgacg cgtgagggtg caacagattt aaatcgtaaa     2040
acgtcgttga accctaacat tgtgtataaa acatacactg gtgaagcaac gcacaaagca     2100
ttaaatagcg atagacaaaa agcagactta aatatgtttt tcccatttgt gattactggt     2160
aacttaatcg gtaaagctac tgaaaaagaa tggcgagaaa acgatggttt agtatccgtt     2220
atttcttctc agcatccatt taatcaagct tatacaaatg cgacggataa aattcaaaaa     2280
ggcatttggc aagtaacgcc tacaaaacat gattgggatc atgttgattt tgtcggacaa     2340
gatagttctg atacagtgcg cacaagagaa gaattacaag attttggca tcatttagca     2400 gacgatttag tgaaaactga aaaggtgact gatactaagc aataa                     2445
```

<210> SEQ ID NO 49

<211> LENGTH: 2967
<212> TYPE: DNA
<213> ORGANISM: Artificial sequence
<220> FEATURE:
<223> OTHER INFORMATION: Recombinant DNA encoding chimeric protein

<400> SEQUENCE: 49

| | | | | | |
|---|---|---|---|---|---|
| gatacacctc | aaaaagatac | tacagctaag | acaacatctc | atgattcaaa | aaaatctaat | 60 |
| gacgatgaaa | cttctaagga | tactacaagt | aaagatattg | ataaagcaga | caacaataat | 120 |
| acaagtaacc | aagacaataa | cgacaaaaaa | tttaaaacta | tagacgacag | cacttcagac | 180 |
| tctaacaata | tcattgattt | tatttataag | aatttaccac | aaaccaatat | aaaccaattg | 240 |
| ctaaccaaaa | ataaatacga | tgataattac | tcattaacaa | ctttaatcca | aaacctattc | 300 |
| aatttaaatt | cggatatttc | tgattacgaa | caacctcgta | atggcgaaaa | gtcaacaaat | 360 |
| gattcgaata | aaaacagtga | caatagcatc | aaaaatgaca | ctgatacgca | atcatctaaa | 420 |
| caagataaag | cagacaatca | aaaagcacct | aaatcaaaca | atacaaaacc | aagtacatct | 480 |
| aataagcaac | caaattcgcc | aaagccaaca | caacctaatc | aatcaaatag | tcaaccagca | 540 |
| agtgacgata | aagcaaatca | aaaatcttca | tcgaaagata | atcaatcaat | gtcagattcg | 600 |
| gctttagact | ctattttgga | tcaatacagt | gaagatgcaa | agaaaacaca | aaaagattat | 660 |
| gcatctcaat | ctaaaaaaga | caaaaatgaa | aaatctaata | caagaatcc | acagttacca | 720 |
| acacaagatg | aattgaaaca | taaatctaaa | cctgctcaat | cattcaataa | cgatgttaat | 780 |
| caaaaggata | cacgtgcaac | atcattattc | gaaacagatc | ctagtatatc | taacaatgat | 840 |
| gatagcggac | aatttaacgt | tgttgactca | aaagatacac | gtcaatttgt | caaatcaatt | 900 |
| gctaaagatg | cacatcgcat | tggtcaagat | aacgatattt | atgcgtctgt | catgattgcc | 960 |
| caagcaatct | agaatctga | ctcaggtcgt | agtgctttag | ctaagtcacc | aaaccataat | 1020 |
| ttattcggta | tcaaaggtgc | ttttgaaggg | aattctgttc | cttttaacac | attagaagct | 1080 |
| gatggtaata | aattgtatag | tattaatgct | ggattccgaa | atatccaag | cacgaaagaa | 1140 |
| tcactaaaag | attactctga | ccttattaaa | aatggtattg | atggcaatcg | aacaatttat | 1200 |
| aaaccaacat | ggaaatcgga | agccgattct | tataaagatg | caacatcaca | cttatctaaa | 1260 |
| acatatgcta | cagatccaaa | ctatgctaag | aaattaaaca | gtattattaa | acactatcaa | 1320 |
| ttaactcagt | ttgacgatga | acgcatgcca | gatttagata | aatatgaacg | ttctatcaag | 1380 |
| gattatgatg | attcatcaga | tgaattcaaa | cctttccgtg | aggtatctga | tagtatgcca | 1440 |
| tatccacatg | gtcaatgtac | ttggtacgta | tataaccgta | tgaaacaatt | tggtacatct | 1500 |
| atctcaggtg | atttaggtga | tgcacataat | tggaataatc | gagctcaata | ccgtgattat | 1560 |
| caagtaagtc | atacaccaaa | acgtcatgct | gctgttgtat | ttgaggctgg | acaatttggt | 1620 |
| gcagatcaac | attacggtca | tgtagcattt | gttgaaaaag | ttaacagtga | tggttctatc | 1680 |
| gttatttcag | aatccaatgt | taaaggatta | ggtatcattt | ctcatagaac | tatcaatgca | 1740 |
| gctgccgctg | aagaattatc | atatattaca | ggtaaaggtt | ctggcggagg | ggctaaagtt | 1800 |
| gccaaacaag | ggcagtataa | aaatcaagac | cctatcgtgt | tagtgcatgg | tttcaatgga | 1860 |
| tttacagatg | atattaatcc | ttcagtgtta | gctcattatt | ggggcggtaa | taaaatgaac | 1920 |
| attcgccaag | atttagaaga | aatggttac | aaagcttatg | aagcaagtat | aagtgctttt | 1980 |
| ggaagtaact | atgaccgcgc | agttgaactt | tattattata | tcaaaggcgg | tcgtgtagat | 2040 |
| tatggtgcag | cacatgcagc | aaaatatgga | catgaacgtt | atggaaaaac | atacgaagga | 2100 |
| atttacaaag | actggaaacc | aggacagaag | gtacacctag | ttggacatag | tatgggtggt | 2160 |

-continued

| | |
|---|---|
| caaacgatac gtcaactaga agaattactg cgtaatggta gtcgtgaaga aatagagtat | 2220 |
| caaaagaaac atggtggcga aatttctcca ctattcaaag gtaataatga caatatgatt | 2280 |
| tcatcaatta ctactttagg aacgccacat aatggaacgc atgcttcaga tttagctggt | 2340 |
| aatgaagctt tagtgagaca aattgtattt gatatcggta aaatgtttgg taataaaaac | 2400 |
| tctagagtag acttcgggtt ggctcaatgg ggtctaaaac agaagccaaa tgaatcatac | 2460 |
| attgattatg tcaaacgcgt taaacaatct aatttatgga aatcaaaaga taatggattt | 2520 |
| tacgatctga cgcgtgaggg tgcaacagat ttaaatcgta aaacgtcgtt gaaccctaac | 2580 |
| attgtgtata aacatacac tggtgaagca acgcacaaag cattaaatag cgatagacaa | 2640 |
| aaagcagact taaatatgtt tttcccatttt gtgattactg gtaacttaat cggtaaagct | 2700 |
| actgaaaaag aatggcgaga aaacgatggt ttagtatccg ttatttcttc tcagcatcca | 2760 |
| tttaatcaag cttatacaaa tgcgacggat aaaattcaaa aaggcatttg gcaagtaacg | 2820 |
| cctacaaaac atgattggga tcatgttgat tttgtcggac aagatagttc tgatacagtg | 2880 |
| cgcacaagag aagaattaca agattttttgg catcatttag cagacgattt agtgaaaact | 2940 |
| gaaaaggtga ctgatactaa gcaataa | 2967 |

<210> SEQ ID NO 50
<211> LENGTH: 2169
<212> TYPE: DNA
<213> ORGANISM: Artificial sequence
<220> FEATURE:
<223> OTHER INFORMATION: Recombinant DNA encoding chimeric protein

<400> SEQUENCE: 50

| | |
|---|---|
| gcaaaggata acttaaatgg agaaaagcca acgactaatt tgaatcataa tgtaacttca | 60 |
| ccatcagtaa atagtgaaat gaataataat gagactggga cacctcacga atcaaatcaa | 120 |
| gctggtaatg aaggaactgg ttcgaatagt cgtgatgcta atcctgattc gaataatgtg | 180 |
| aagccagact caaacaacca aaacccaagt ccagattcaa aacctgaccc aaataaccca | 240 |
| aacccaggtc cgaatccgaa gccagaccca gataagccga aaccaaatcc ggaaccaaag | 300 |
| ccagacccaa agccagaccc agataaacca aagccaaatc cggatccaaa gccagaccca | 360 |
| gataagccga aaccaaatcc ggatccaaaa ccagatccag acaaaccgaa gccaaatccg | 420 |
| gatccaaaac cagatccaaa tccgaatcca aaaccagacc ctaataagcc aaatccaaat | 480 |
| ccgtctccaa atcccaatca acctggggat tccaatcaat ctggtggctc gaaaaatggg | 540 |
| gggacatgga acccaaatgc ttcagatgga tctaatcaag gtcaatggca accaaatgga | 600 |
| aatcaaggaa actcacaaaa tcctactggt aatgattttg tatcccaacg attttttagcc | 660 |
| ttggcgaatg gggcttacaa gtataatccg tatattttaa atcaaattaa tcaattgggg | 720 |
| aaagaatatg gtgaggtaac tgatgaagat atctacaata tcatccgtaa acaaaacttc | 780 |
| agcgaaaatg catatttaaa tggattacaa cagcaatcga attactttag attccaatat | 840 |
| ttcaatccat tgaaatcaga aaggtactat cgtaatttag atgaacaagt actcgcatta | 900 |
| attactggcg aaattggatc aatgccagat ttgaaaaagc ccgaagataa gccggattca | 960 |
| aaacaacgtt catttgagcc tcatgaaaaa gatgatttta cagttgtaaa aaacaagaa | 1020 |
| gataataaga aagtgcgtc aactgcatat agtggttctg gcggagggc tggatttta | 1080 |
| aacaaatcta aaatgagca agcggcatta aaggcacaac aagcagcgat aaagaagaa | 1140 |
| gcaagtgcaa ataatttaag tgatacatca caagaagcac aagagattca agaagctaaa | 1200 |

| | |
|---|---|
| agagaagcac aagcagaagc ggataaaagt gtggctgtat caaataaaga atcaaaagca | 1260 |
| gtggcattga agcacaaca agcagcgata aaagaagaag caagtgcaaa taatttgagt | 1320 |
| gatacatcac aagaggcaca agagattcaa gaagctaaaa aagaagcaca agcagaaaca | 1380 |
| gataaaagtg cagctgtatc aaatgaagaa ccaaaagcag tggcattgaa agcacaacaa | 1440 |
| gcagcgataa aagaagaagc aagtgcaaat aatttaagtg atatatcaca agaggcacaa | 1500 |
| gaggttcaag aagctaaaaa agaagcacaa gcagagaaag acagtgacac attaactaaa | 1560 |
| gatgcaagtg cagcaaaggt agaagtatca aaaccagagt cacaagctga agattagca | 1620 |
| aacgctgcaa aacagaagca agctaaatta acaccaggtt caaagagag tcaattaact | 1680 |
| gaagcgttat ttgcagaaaa accagttgct aaaaatgact tgaaagaaat tcctcaatta | 1740 |
| gttactaaaa agaatgatgt atcagagaca gagacggtta atatagataa taaagacact | 1800 |
| gttaaacaaa aagaagctaa atttgaaaat ggtgttatta cacgtaaagc tgatgaaaaa | 1860 |
| acaactaata atacagctgt tgacaagaaa tcaggtaaac aatctaaaaa aacaacacct | 1920 |
| tcaaataaac gaaatgcatc aaaagcatct acaaataaaa cttcaggtca gaaaaagcaa | 1980 |
| cataataaga aatcatcaca aggtgcaaag aaacaaagta gttcaagtaa gtcaactcaa | 2040 |
| aagaataatc aaactagtaa taagaattca aaaacaacaa atgctaaatc atccaatgca | 2100 |
| tcaaaaacgc caaatgctaa agttgagaaa gctaaaagta aaatagagaa acgtacattc | 2160 |
| aatgactaa | 2169 |

<210> SEQ ID NO 51
<211> LENGTH: 1863
<212> TYPE: DNA
<213> ORGANISM: Artificial sequence
<220> FEATURE:
<223> OTHER INFORMATION: Recombinant DNA encoding chimeric protein

<400> SEQUENCE: 51

| | |
|---|---|
| atggatattg gtaaaaaaca tgtaattcct aaaagtcagt accgacgtaa gcgtcgtgaa | 60 |
| ttcttccaca cgaagacag agaagaaat ttaaatcaac atcaagataa acaaaatata | 120 |
| gataatacaa catcaaaaaa agcagataag caaatacata aagattcaat tgataagcac | 180 |
| gaacgtttta aaaatagttt atcatcgcat ttagaacaga gaaaccgtga tgttaatgag | 240 |
| aataaagctg aagaaagtaa aagtaatcag gatagtaagt cagcatataa cagagatcat | 300 |
| tatttaacag acgatgtatc taaaaaacaa aattcattag attcagtgga ccaagataca | 360 |
| gagaaatcaa aatattatga gcaaaattct gaagcgactt tatcaactaa atcaaccgat | 420 |
| aaagtagaat caactgaaat gagaaagcta agttcagata aaaacaaagt tggtcatgaa | 480 |
| gagcaacatg tactttctaa accttcagaa catgataaag agactagaat tgattctgag | 540 |
| tcttcaagaa ctgattcaga cagctcgatg cagacagaga aataaaaaa agacagttca | 600 |
| gatggaaata aagtagtaa tctgaaatct gaagtaatat cagacaaatc aaatacagta | 660 |
| ccaaaattgt cggaatctga tgatgaagta ataatcaga agccattaac tttaccggaa | 720 |
| gaacagaaat tgaaaagaca gcaaagtcaa aatgagcaaa caaaaaccta tacatatggt | 780 |
| gatagcgaac aaaatgacaa gtctaatcat gaaaatgatt taagtcatca tataccatcg | 840 |
| ataagtgatg ataaagataa cgtcatgaga gaaaatcata ttgttgacga taatcctgat | 900 |
| aatgatatca atacaccatc attatcaaaa acagatgacg atcgaaaact tgatgaaaaa | 960 |
| attcatgttg aagataaaca taaacaaaat gcagactcgt ctgaaacggt gggatatcaa | 1020 |
| agtcagtcaa ctgcatctca tcgtagcact gaaaaaagaa atatttctat taatgaccat | 1080 |

```
gataaattaa acggtcaaaa aacaaataca aagacatcgg caaataataa tcaaaaaaag   1140
gctacatcaa aattgaacaa agggcgcgct acgaataata attatagtga cattttgaaa   1200
aagttttgga tgatgtattg gcctaaaggt tctggcggag gggctggaag tggtgggggc   1260
gccatgactg aaaagaaaa aatgttagca gaaaatggt acgatgcaaa ctttgatcaa    1320
gacttaatca atgaacgtgc acgagcgaaa gatatttgct ttgaattaaa tcatacaaag   1380
ccgagtgaca aaaataaaag aaaggaatta atcgatgaat tatttcaaac aacaacagac   1440
aatgtaagta tttcgattcc ttttgataca gattatggtt ggaacgttaa actaggaaaa   1500
aatgtctatg taaacaccaa ttgttatttt atggatggtg acagattac aattggcgat    1560 aatgttttta taggacctaa ttgtggattc tacacagcaa cacatccact taattttcat   1620
catagaaatg aaggatttga aaaagcagga ccaattaata ttggcagtaa tacttggttt   1680
ggcggacatg tagccgtgct tccgggagtg acgattggag aaggcagtgt gattggtgct   1740
ggtagtgttg tcaccaaaga tattccgcca cacagtttag cggttggaaa cccttgtaaa   1800
gtcgttcgta aaattgataa tgaggtacca tcagaagcat tgaacgatga aacactaaat   1860
tag                                                                1863
```

<210> SEQ ID NO 52
<211> LENGTH: 1497
<212> TYPE: DNA
<213> ORGANISM: Artificial sequence
<220> FEATURE:
<223> OTHER INFORMATION: Recombinant DNA encoding chimeric protein

<400> SEQUENCE: 52

```
gcagattctg atattaatat taaaaccggt actacagata ttggaagcaa tactacagta     60
aaaacaggtg atttagtcac ttatgataaa gaaaatggca tgttaaaaaa agtatttat    120 agttttatcg atgataaaaa tcataataaa aaactgctag ttattagaac gaaaggtacc    180
attgctggtc aatatagagt ttatagcgaa gaaggtgcta caaaagtgg tttagcctgg    240 ccttcagcct ttaaggtaca gttgcaacta cctgataatg aagtagctca atatctgat    300 tactatccaa gaaattcgat tgatacaaaa gagtatatga gtactttaac ttatggattc    360
aacggtaatg ttactggtga tgatacagga aaaattggcg gccttattgg tgcaaatgtt    420
tcgattggtc atacactgaa atatgttcaa cctgatttca aaacaatttt agagagccca    480
actgataaaa aagtaggctg gaaagtgata tttaacaata tggtgaatca aaattgggga    540
ccatatgata gagattcttg gaacccggta tatggcaatc aacttttcat gaaaactaga    600
aatggctcta tgaaagcagc agataacttc cttgatccta acaaagcaag ttctctatta    660
tcttcagggt tttcaccaga cttcgctaca gttattacta tggatagaaa agcatccaaa    720
caacaaacaa atatagatgt aatatacgaa cgagttcgtg atgactacca attgcactgg    780
acttcaacaa attggaaagg taccaatact aaagataaat ggatagatcg ttcttcagaa    840
agatataaaa tcgattggga aaaagaagaa atgacaaatg gttctggcgg aggggctatg    900
actgaaaaag aaaaaatgtt agcagaaaaa tggtacgatg caaactttga tcaagactta    960
atcaatgaac gtgcacgagc gaaagatatt tgctttgaat aaatcatac aaagccgagt    1020 gacaaaaata aagaaagga attaatcgat gaattatttc aaacaacaac agacaatgta   1080
agtatttcga ttccttttga tacagattat ggttggaacg ttaaactagg aaaaatgtc   1140 tatgtaaaca ccaattgtta ttttatggat ggtgacagat tacaattgg cgataatgtt    1200
```

| | |
|---|---|
| tttataggac ctaattgtgg attctacaca gcaacacatc cacttaattt tcatcataga | 1260 |
| aatgaaggat ttgaaaaagc aggaccaatt aatattggca gtaatacttg gtttggcgga | 1320 |
| catgtagccg tgcttccggg agtgacgatt ggagaaggca gtgtgattgg tgctggtagt | 1380 |
| gttgtcacca aagatattcc gccacacagt ttagcggttg gaaacccttg taaagtcgtt | 1440 |
| cgtaaaattg ataatgaggt accatcagaa gcattgaacg atgaaacact aaattag | 1497 |

<210> SEQ ID NO 53
<211> LENGTH: 2070
<212> TYPE: DNA
<213> ORGANISM: Artificial sequence
<220> FEATURE:
<223> OTHER INFORMATION: Recombinant DNA encoding chimeric protein

<400> SEQUENCE: 53

| | |
|---|---|
| gcagattctg atattaatat taaaaccggt actacagata ttggaagcaa tactacagta | 60 |
| aaaacaggtg atttagtcac ttatgataaa gaaaatggca tgttaaaaaa agtattttat | 120 |
| agttttatcg atgataaaaa tcataataaa aaactgctag ttattagaac gaaaggtacc | 180 |
| attgctggtc aatatagagt ttatagcgaa gaaggtgcta acaaaagtgg tttagcctgg | 240 |
| ccttcagcct ttaaggtaca gttgcaacta cctgataatg aagtagctca aatatctgat | 300 |
| tactatccaa gaaattcgat tgatacaaaa gagtatatga gtactttaac ttatggattc | 360 |
| aacggtaatg ttactggtga tgatacagga aaaattggcg gccttattgg tgcaaatgtt | 420 |
| tcgattggtc atacactgaa atatgttcaa cctgatttca aaacaatttt agagagccca | 480 |
| actgataaaa aagtaggctg aaagtgata tttaacaata tggtgaatca aaattgggga | 540 |
| ccatatgata gagattcttg gaacccggta tatggcaatc aacttttcat gaaaactaga | 600 |
| aatggctcta tgaaagcagc agataacttc cttgatccta caaaagcaag ttctctatta | 660 |
| tcttcagggt tttcaccaga cttcgctaca gttattacta tggatagaaa agcatccaaa | 720 |
| caacaaacaa atatagatgt aatatacgaa cgagttcgtg atgactacca attgcactgg | 780 |
| acttcaacaa attggaaagg taccaatact aaagataaat ggatagatcg ttcttcagaa | 840 |
| agatataaaa tcgattggga aaagaagaa atgacaaatg ttctggcgg aggggctaaa | 900 |
| gttgccaaac aagggcagta taaaaatcaa gaccctatcg tgttagtgca tggtttcaat | 960 |
| ggatttacag atgatattaa tccttcagtg ttagctcatt attggggcgg taataaaatg | 1020 |
| aacattcgcc aagatttaga agaaaatggt tacaaagctt atgaagcaag tataagtgct | 1080 |
| tttgaagta actatgaccg cgcagttgaa ctttattatt atatcaaagg cggtcgtgta | 1140 |
| gattatggtg cagcacatgc agcaaaatat ggacatgaac gttatggaaa aacatacgaa | 1200 |
| ggaattaca aagactggaa accaggacag aaggtacacc tagttggaca tagtatgggt | 1260 |
| ggtcaaacga tacgtcaact agaagaatta ctgcgtaatg gtagtcgtga agaaatagag | 1320 |
| tatcaaaaga aacatggtgg cgaaatttct ccactattca aggtaataa tgacaatatg | 1380 |
| atttcatcaa ttactacttt aggaacgcca cataatggaa cgcatgcttc agatttagct | 1440 |
| ggtaatgaag ctttagtgag acaaattgta tttgatatcg gtaaaatgtt tggtaataaa | 1500 |
| aactctagag tagacttcgg gttggctcaa tggggtctaa acagaagcc aaatgaatca | 1560 |
| tacattgatt atgtcaaacg cgttaaacaa tctaatttat ggaaatcaaa agataatgga | 1620 |
| ttttacgatc tgacgcgtga gggtgcaaca gatttaaatc gtaaacgtc gttgaaccct | 1680 |
| aacattgtgt ataaaacata cactggtgaa gcaacgcaca aagcattaaa tagcgataga | 1740 |
| caaaaagcag acttaaatat gttttttccca tttgtgatta ctggtaactt aatcggtaaa | 1800 |

```
gctactgaaa aagaatggcg agaaaacgat ggtttagtat ccgttatttc ttctcagcat    1860
ccatttaatc aagcttatac aaatgcgacg gataaaattc aaaaaggcat ttggcaagta    1920
acgcctacaa aacatgattg ggatcatgtt gattttgtcg gacaagatag ttctgataca    1980
gtgcgcacaa gagaagaatt acaagatttt tggcatcatt tagcagacga tttagtgaaa    2040
actgaaaagg tgactgatac taagcaataa                                     2070

<210> SEQ ID NO 54
<211> LENGTH: 1506
<212> TYPE: DNA
<213> ORGANISM: Artificial sequence
<220> FEATURE:
<223> OTHER INFORMATION: Recombinant DNA encoding chimeric protein

<400> SEQUENCE: 54
gcagattctg atattaatat taaaaccggt actacagata ttggaagcaa tactacagta      60
aaaacaggtg atttagtcac ttatgataaa gaaaatggca tgttaaaaaa agtatttat     120 agttttatcg atgataaaaa tcataataaa aaactgctag ttattagaac gaaaggtacc     180
attgctggtc aatatagagt ttatagcgaa gaaggtgcta acaaaagtgg tttagcctgg     240
ccttcagcct ttaaggtaca gttgcaacta cctgataatg aagtagctca aatatctgat     300
tactatccaa gaaattcgat tgatacaaaa gagtatatga gtactttaac ttatggattc     360
aacggtaatg ttactggtga tgatacagga aaaattggcg gccttattgg tgcaaatgtt     420
tcgattggtc atacactgaa atatgttcaa cctgatttca aaacaatttt agagagccca     480
actgataaaa aagtaggctg gaaagtgata tttaacaata tggtgaatca aaattgggga     540
ccatatgata gagattcttg gaacccggta tatggcaatc aactttttcat gaaaactaga     600 aatggctcta tgaaagcagc agataacttc cttgatccta caaagcaag ttctctatta     660 tcttcagggt tttccaccaga cttcgctaca gttattacta tggatagaaa agcatccaaa     720
caacaaacaa atatagatgt aatatacgaa cgagttcgtg atgactacca attgcactgg     780
acttcaacaa attggaaagg taccaatact aaagataaat ggatagatcg ttcttcagaa     840
agatataaaa tcgattggga aaaagaagaa atgacaaatg gttctggcgg agggctaaa     900 cgtatcaaac aacatccgga cgtacaaaaa gttacagatg ctacaagtaa agttgcttca     960 aaacatctg cagcaatcag taacacacgc agtgatgtta agaatatgt cggcgataaa    1020 aaacaagatt ttgaaaataa gcgtgaactt aaaagtttg ctagagaaca tgatcctgcc    1080
tatattgaga aaaaggcga aaaattagct aaacaaaatc gtaaagacgc tgataaaatg    1140
aataaaatac ttcaaaaaaa tatcgaaaag cgtcataaag aagagcaaaa agcccgcgaa    1200
aagaatgaaa tacaacgtat taagatatg aaaaagtcac aaaatacga agtaaaagca    1260 ggcttaacac ctaataaatt agatgagaaa actgagaaaa aaggcgataa actagctgaa    1320 aaaatcgca aagaaatcgc taaatgaat aaaaagttac aaaaaatat tgaaaaacga    1380 cacaaagaag aacaaaaacg ccaacaagaa gctgataaag cacgcatcaa gtcatttaaa    1440
aaatataaag attatgttgc caaaagcgcc tctcaacaaa ataaagaaaa caatacagag    1500
gcataa                                                               1506

<210> SEQ ID NO 55
<211> LENGTH: 528
<212> TYPE: DNA
<213> ORGANISM: Artificial sequence
<220> FEATURE:
```

<223> OTHER INFORMATION: Recombinant DNA encoding chimeric protein

<400> SEQUENCE: 55

| | |
|---|---|
| gtgctgttttt atctgcgcag caacaaacgc cagattattg aaaaaggccc gggcccgggc | 60 |
| gaaccgatta actttattct gaaaagcagc accaaaactga aagcgggccc gggcccgggc | 120 |
| ggcctgtatt ttgtggcgat gaacaacctg aaagcggcgg gccagggccc gggcccgggc | 180 |
| aaagcggatg cgctgaaagc gattaccgcg ctgaaactgc agatgggccc gggcccgggc | 240 |
| aaacatcaga ttcgcatgct gagcattccg cgcgatacca ttagcggccc gggcccgggc | 300 |
| ctggatcaga ttattgcgca ggcgaacctg cgcctggcga ccatgggccc gggcccgggc | 360 |
| cagcgccatt ttcagattgg ctataaccgc gcggcgcgca ttattggccc gggcccgggc | 420 |
| agcagcaacg tgtatatgtt taaaaccgcg ctgaaactgg cgggcggccc gggcccgggc | 480 |
| tattttcgct ttcagtattt taacccgctg aaaagcgaac gctattaa | 528 |

<210> SEQ ID NO 56
<211> LENGTH: 648
<212> TYPE: DNA
<213> ORGANISM: Artificial sequence
<220> FEATURE:
<223> OTHER INFORMATION: Recombinant DNA encoding chimeric protein

<400> SEQUENCE: 56

| | |
|---|---|
| accagccagt tcatgtgct gcgcgcgctg cgcctggcgc agaaaggccc gggcccgggc | 60 |
| tttctgaaac tgtttcgcat taccaacccg attgcgcgcg gcctgggccc gggcccgggc | 120 |
| attattaaaa aactgtttcg cctgccggcg attaaacgct ttgaaggccc gggcccgggc | 180 |
| attctgctgg gctattttgt ggcgcagcgc gcgctggtga aagcgggccc gggcccgggc | 240 |
| aaacgcattt ttaaaatgag cccgattcat catcattttg aactgggccc gggcccgggc | 300 |
| aaaaccctgt tgtggcgct gaacaacaaa gcgcgcattc cggaaggccc gggcccgggc | 360 |
| ctgatgggca ttcgcgcgtt tcgcaaactg ctgccgaaca ttccgggccc gggcccgggc | 420 |
| atgcatttta ttgcgattag cattaaccat cgcaccgcgg atgtgggccc gggcccgggc | 480 |
| agcacccttta tttataaaat tgcgaacgaa cgcctgttta gccgcggccc gggcccgggc | 540 |
| agcgtgacca ttattaaaag cctgcaggcg attcgcgtgc cgtttggccc gggcccgggc | 600 |
| tggaaacgca ttggccgcct gaaaagcatt ccgatttta tgtattaa | 648 |

<210> SEQ ID NO 57
<211> LENGTH: 1362
<212> TYPE: DNA
<213> ORGANISM: Artificial sequence
<220> FEATURE:
<223> OTHER INFORMATION: Recombinant DNA encoding chimeric protein

<400> SEQUENCE: 57

| | |
|---|---|
| atgagcagcc tgccggtggg cccggtggcg tggagcgatg gcatgctgat tgaaacccag | 60 |
| cattttcagc agctgaaacg cattttaaaa atgagcccga ttcatcatca ttttgaactg | 120 |
| agcaaccatg gctgggggctt taccctgctg atctggatc aggatggcct gggcctgggc | 180 |
| cgcctgatgg gcattcgcgc gtttcgcaaa ctgctgccga cattccgtt tagcctgccg | 240 |
| agcgatgatc cgctgccgcc gccgctggaa accgaactgg cgcaggcggg cgatattgcg | 300 |
| tgcctggcgc tgcaggcggc gcgcaccggc ggcccggaaa tggcgtttgg cgatgtggaa | 360 |
| ctggcgagcc gctatcgcgc ggtgagcacc gaagtgccgg atctggcggt gggcctggat | 420 |
| gcgccgggca ccccgtttct gaaactgttt cgcattacca acccgattgc gcgcggcctg | 480 |

```
tggaaacgca ttggccgcct gaaaagcatt ccgatttta tgtatcgcgt ggcgggccgc      540
aacgcgagcc gcaccgtgag cctggatccg cgctttattc cgccgaaaac cctgtttgtg      600
gcgctgaaca acaaagcgcg cattccggaa gaactgcaga gcaccagcgt gaccattatt      660
aaaagcctgc aggcgattcg cgtgccgttt accggcggcg cgtggcgga tctgattgaa       720 attctgctgg gctatttgt ggcgcagcgc gcgctggtga aagcgaacct ggatgcgttt       780
gatccgctgc cgccgatgca tttattgcg attagcatta accatcgcac cgcggatgtg       840
gtgctgccgg gcgtggatga agaactggcg gatcgcgaac tgggctatga tcatgatgat      900
ctgcagacca gctttaccag ccagtttcat gtgctgcgcg cgctgcgcct ggcgcagaaa      960
gaaaccccgg tgctgccgct gcgctttgaa gatcgcggcg atcaggtgca tatttgcatt     1020
gtggataaac agtggaacct gaaaaaactg attttgcgt ttagcattat aaaaaactg       1080 tttcgcctgc cggcgattaa acgctttgaa accaaactgg gcgcggtgga acagattcag     1140
aaactggtgg atctgcagct gccgggcgcg cgcctgaacg cgctgccgaa cccgccgcgc     1200
cagattccgt attatgcgca gagcacctat tttgaagtgg aaagcaccga tccgttttgg     1260
aaacagaccc tggcgggcag cgcgatgcg ctgcgcattg tgggcgattt tccgagcacc      1320
tttatttata aaattgcgaa cgaacgcctg tttagccgct aa                        1362
```

<210> SEQ ID NO 58
<211> LENGTH: 1362
<212> TYPE: DNA
<213> ORGANISM: Artificial sequence
<220> FEATURE:
<223> OTHER INFORMATION: Recombinant DNA encoding chimeric protein

<400> SEQUENCE: 58

```
atgagcagcc tgccggtggg cccggtggcg tggagcgatg gcatgctgat tgaaacccag      60
cattttcagc agctggaacg ccatctggcg catcaggcga gcctgcgcct gggccagacc     120
agcaaccatg gctgggcgtt taccctgctg gatctggatc aggatggcct gggcctgggc     180
cgcctgggcc tgcgcagcag caacgtgtat atgtttaaaa ccgcgctgaa actggcgggc     240
agcgatgatc cgctgccgcc gccgctggaa accgaactgg cgcaggcggg cgatattgcg     300
tgcctggcgc tgcaggcggc gcgcaccggc ggcccggaaa tggcgtttgg cgatgtggaa     360
ctggcgagcg gctatcgcgc ggtgagcacc gaagtgccgg atctggcggt gggcctggat     420
gcgccgggca ccccgcgccg cctgaccatt gaaaccggcc agctggtgac cgcctgtgc      480 tggaaaagcc aggtgctgtt ttatctgcgc agcaacaaac gccagattat tgaaaaacgc     540
aacgcgagcc gcaccgtgag cctggatccg cgctttattc gccggaaccc gattaacttt     600
attctgaaaa gcagcaccaa actgaaagcg gaactgcaga gcacccagcg ccattttcag     660
attggctata accgcgcggc gcgcattatt accggcggcg cgtggcgga tctgattgaa      720 ctgctgctgc cccagctgga tcagattatt gcgcaggcga acctgcgcct ggcgaccatg     780
gatccgctgc cgccgggcct gtattttgtg gcgatgaaca acctgaaagc ggcgggccag     840
gtgctgccgg gcgtggatga agaactggcg gatcgcgaac tgggctatga tcatgatgat     900
ctgcagacca gctttgaacc gctggcgatg atgctgcgcc aggcgctggc gcgcgtgatt     960
gaaaccccgg tgctgccgct gcgctttgaa gatcgcggcg atcaggtgca tatttgcatt    1020
gtggataaac agtggaacct gaaaaaactg attttgcgt ttagcaaagc ggatgcgctg     1080
aaagcgatta ccgcgctgaa actgcagatg accaaactgg gcgcggtgga acagattcag    1140
```

-continued

```
aaactggtgg atctgcagct gccgggcgcg cgcctgaacg cgctgccgaa cccgccgcgc    1200
cagattccgt attatgcgca gagcacctat tttgaagtgg aaagcaaaca tcagattcgc    1260
atgctgagca ttccgcgcga taccattagc ctgcgcattg tgggcgatta ttttcgcttt    1320
cagtatttta acccgctgaa aagcgaacgc tatgtggcgt aa                       1362
```

<210> SEQ ID NO 59
<211> LENGTH: 623
<212> TYPE: PRT
<213> ORGANISM: Artificial sequence
<220> FEATURE:
<223> OTHER INFORMATION: Chimeric polypeptide

<400> SEQUENCE: 59

```
Lys Arg Ile Lys Gln His Pro Asp Val Gln Lys Val Thr Asp Ala Thr
1               5                   10                  15

Ser Lys Val Ala Ser Lys Thr Ser Ala Ala Ile Ser Asn Thr Ala Ser
            20                  25                  30

Asp Val Lys Glu Tyr Val Gly Asp Lys Lys Gln Asp Phe Glu Asn Lys
        35                  40                  45

Arg Glu Leu Lys Lys Phe Ala Arg Glu His Asp Pro Ala Tyr Ile Glu
    50                  55                  60

Lys Lys Gly Glu Lys Leu Ala Lys Gln Asn Arg Lys Asp Ala Asp Lys
65                  70                  75                  80

Met Asn Lys Ile Leu Gln Lys Asn Ile Glu Lys Arg His Lys Glu Glu
                85                  90                  95

Gln Lys Ala Arg Glu Lys Asn Glu Ile Gln Arg Ile Lys Asp Met Lys
            100                 105                 110

Lys Ser Gln Lys Tyr Glu Val Lys Ala Gly Leu Thr Pro Asn Lys Leu
        115                 120                 125

Asp Glu Lys Thr Glu Lys Lys Gly Asp Lys Leu Ala Glu Lys Asn Arg
    130                 135                 140

Lys Glu Ile Ala Lys Met Asn Lys Lys Leu Gln Lys Asn Ile Glu Lys
145                 150                 155                 160

Arg His Lys Glu Glu Gln Lys Arg Gln Gln Glu Ala Asp Lys Ala Arg
                165                 170                 175

Ile Lys Ser Phe Lys Lys Tyr Lys Asp Tyr Val Ala Lys Ser Ala Ser
            180                 185                 190

Gln Gln Asn Lys Glu Asn Asn Thr Glu Ala Gly Ser Gly Gly Gly Ala
        195                 200                 205

Gly Ser Gly Gly Gly Ala Met Asp Ile Gly Lys Lys His Val Ile Pro
    210                 215                 220

Lys Ser Gln Tyr Arg Arg Lys Arg Arg Glu Phe Phe His Asn Glu Asp
225                 230                 235                 240

Arg Glu Glu Asn Leu Asn Gln His Gln Asp Lys Gln Asn Ile Asp Asn
                245                 250                 255

Thr Thr Ser Lys Lys Ala Asp Lys Gln Ile His Lys Asp Ser Ile Asp
            260                 265                 270

Lys His Glu Arg Phe Lys Asn Ser Leu Ser Ser His Leu Glu Gln Arg
        275                 280                 285

Asn Arg Asp Val Asn Glu Lys Ala Glu Glu Ser Lys Ser Asn Gln
    290                 295                 300

Asp Ser Lys Ser Ala Tyr Asn Arg Asp His Tyr Leu Thr Asp Val
305                 310                 315                 320

Ser Lys Lys Gln Asn Ser Leu Asp Ser Val Asp Gln Asp Thr Glu Lys
```

325                 330                 335
Ser Lys Tyr Tyr Glu Gln Asn Ser Glu Ala Thr Leu Ser Thr Lys Ser
                340                 345                 350

Thr Asp Lys Val Glu Ser Thr Glu Met Arg Lys Leu Ser Ser Asp Lys
            355                 360                 365

Asn Lys Val Gly His Glu Glu Gln His Val Leu Ser Lys Pro Ser Glu
        370                 375                 380

His Asp Lys Glu Thr Arg Ile Asp Ser Glu Ser Ser Arg Thr Asp Ser
385                 390                 395                 400

Asp Ser Ser Met Gln Thr Glu Lys Ile Lys Asp Ser Ser Asp Gly
                405                 410                 415

Asn Lys Ser Ser Asn Leu Lys Ser Glu Val Ile Ser Asp Lys Ser Asn
                420                 425                 430

Thr Val Pro Lys Leu Ser Glu Ser Asp Glu Val Asn Asn Gln Lys
            435                 440                 445

Pro Leu Thr Leu Pro Glu Glu Gln Lys Leu Lys Arg Gln Gln Ser Gln
                450                 455                 460

Asn Glu Gln Thr Lys Thr Tyr Thr Tyr Gly Asp Ser Glu Gln Asn Asp
465                 470                 475                 480

Lys Ser Asn His Glu Asn Asp Leu Ser His Ile Pro Ser Ile Ser
                485                 490                 495

Asp Asp Lys Asp Asn Val Met Arg Glu Asn His Ile Val Asp Asp Asn
                500                 505                 510

Pro Asp Asn Asp Ile Asn Thr Pro Ser Leu Ser Lys Thr Asp Asp Asp
            515                 520                 525

Arg Lys Leu Asp Glu Lys Ile His Val Glu Asp Lys His Lys Gln Asn
        530                 535                 540

Ala Asp Ser Ser Glu Thr Val Gly Tyr Gln Ser Gln Ser Thr Ala Ser
545                 550                 555                 560

His Arg Ser Thr Glu Lys Arg Asn Ile Ser Ile Asn Asp His Asp Lys
                565                 570                 575

Leu Asn Gly Gln Lys Thr Asn Thr Lys Thr Ser Ala Asn Asn Asn Gln
            580                 585                 590

Lys Lys Ala Thr Ser Lys Leu Asn Lys Gly Arg Ala Thr Asn Asn Asn
        595                 600                 605

Tyr Ser Asp Ile Leu Lys Lys Phe Trp Met Met Tyr Trp Pro Lys
    610                 615                 620

<210> SEQ ID NO 60
<211> LENGTH: 623
<212> TYPE: PRT
<213> ORGANISM: Artificial sequence
<220> FEATURE:
<223> OTHER INFORMATION: Chimeric polypeptide

<400> SEQUENCE: 60

Met Asp Ile Gly Lys Lys His Val Ile Pro Lys Ser Gln Tyr Arg Arg
1               5                   10                  15

Lys Arg Arg Glu Phe Phe His Asn Glu Asp Arg Glu Glu Asn Leu Asn
            20                  25                  30

Gln His Gln Asp Lys Gln Asn Ile Asp Asn Thr Thr Ser Lys Lys Ala
        35                  40                  45

Asp Lys Gln Ile His Lys Asp Ser Ile Asp Lys His Glu Arg Phe Lys
    50                  55                  60

Asn Ser Leu Ser Ser His Leu Glu Gln Arg Asn Arg Asp Val Asn Glu

```
             65                  70                  75                  80
Asn Lys Ala Glu Glu Ser Lys Ser Asn Gln Asp Ser Lys Ser Ala Tyr
                    85                  90                  95

Asn Arg Asp His Tyr Leu Thr Asp Asp Val Ser Lys Lys Gln Asn Ser
                100                 105                 110

Leu Asp Ser Val Asp Gln Asp Thr Glu Lys Ser Lys Tyr Tyr Glu Gln
            115                 120                 125

Asn Ser Glu Ala Thr Leu Ser Thr Lys Ser Thr Asp Lys Val Glu Ser
        130                 135                 140

Thr Glu Met Arg Lys Leu Ser Ser Asp Lys Asn Lys Val Gly His Glu
145                 150                 155                 160

Glu Gln His Val Leu Ser Lys Pro Ser Glu His Asp Lys Glu Thr Arg
                165                 170                 175

Ile Asp Ser Glu Ser Ser Arg Thr Asp Ser Asp Ser Ser Met Gln Thr
                180                 185                 190

Glu Lys Ile Lys Lys Asp Ser Ser Asp Gly Asn Lys Ser Ser Asn Leu
            195                 200                 205

Lys Ser Glu Val Ile Ser Asp Lys Ser Asn Thr Val Pro Lys Leu Ser
        210                 215                 220

Glu Ser Asp Asp Glu Val Asn Asn Gln Lys Pro Leu Thr Leu Pro Glu
225                 230                 235                 240

Glu Gln Lys Leu Lys Arg Gln Gln Ser Gln Asn Glu Gln Thr Lys Thr
                245                 250                 255

Tyr Thr Tyr Gly Asp Ser Glu Gln Asn Asp Lys Ser Asn His Glu Asn
                260                 265                 270

Asp Leu Ser His His Ile Pro Ser Ile Ser Asp Asp Lys Asp Asn Val
            275                 280                 285

Met Arg Glu Asn His Ile Val Asp Asp Asn Pro Asp Asn Asp Ile Asn
        290                 295                 300

Thr Pro Ser Leu Ser Lys Thr Asp Asp Asp Arg Lys Leu Asp Glu Lys
305                 310                 315                 320

Ile His Val Glu Asp Lys His Lys Gln Asn Ala Asp Ser Ser Glu Thr
                325                 330                 335

Val Gly Tyr Gln Ser Gln Ser Thr Ala Ser His Arg Ser Thr Glu Lys
                340                 345                 350

Arg Asn Ile Ser Ile Asn Asp His Asp Lys Leu Asn Gly Gln Lys Thr
            355                 360                 365

Asn Thr Lys Thr Ser Ala Asn Asn Gln Lys Lys Ala Thr Ser Lys
        370                 375                 380

Leu Asn Lys Gly Arg Ala Thr Asn Asn Asn Tyr Ser Asp Ile Leu Lys
385                 390                 395                 400

Lys Phe Trp Met Met Tyr Trp Pro Lys Gly Ser Gly Gly Gly Ala Gly
                405                 410                 415

Ser Gly Gly Gly Ala Lys Arg Ile Lys Gln His Pro Asp Val Gln Lys
            420                 425                 430

Val Thr Asp Ala Thr Ser Lys Val Ala Ser Lys Thr Ser Ala Ala Ile
        435                 440                 445

Ser Asn Thr Ala Ser Asp Val Lys Glu Tyr Val Gly Asp Lys Lys Gln
    450                 455                 460

Asp Phe Glu Asn Lys Arg Glu Leu Lys Lys Phe Ala Arg Glu His Asp
465                 470                 475                 480

Pro Ala Tyr Ile Glu Lys Lys Gly Glu Lys Leu Ala Lys Gln Asn Arg
                485                 490                 495
```

```
Lys Asp Ala Asp Lys Met Asn Lys Ile Leu Gln Lys Asn Ile Glu Lys
            500                 505                 510

Arg His Lys Glu Glu Gln Lys Ala Arg Glu Lys Asn Glu Ile Gln Arg
        515                 520                 525

Ile Lys Asp Met Lys Lys Ser Gln Lys Tyr Glu Val Lys Ala Gly Leu
    530                 535                 540

Thr Pro Asn Lys Leu Asp Glu Lys Thr Glu Lys Lys Gly Asp Lys Leu
545                 550                 555                 560

Ala Glu Lys Asn Arg Lys Glu Ile Ala Lys Met Asn Lys Lys Leu Gln
                565                 570                 575

Lys Asn Ile Glu Lys Arg His Lys Glu Glu Gln Lys Arg Gln Gln Glu
            580                 585                 590

Ala Asp Lys Ala Arg Ile Lys Ser Phe Lys Lys Tyr Lys Asp Tyr Val
        595                 600                 605

Ala Lys Ser Ala Ser Gln Gln Asn Lys Glu Asn Asn Thr Glu Ala
    610                 615                 620

<210> SEQ ID NO 61
<211> LENGTH: 617
<212> TYPE: PRT
<213> ORGANISM: Artificial sequence
<220> FEATURE:
<223> OTHER INFORMATION: Chimeric polypeptide

<400> SEQUENCE: 61

Met Asp Ile Gly Lys Lys His Val Ile Pro Lys Ser Gln Tyr Arg Arg
1               5                   10                  15

Lys Arg Arg Glu Phe Phe His Asn Glu Asp Arg Glu Asn Leu Asn
            20                  25                  30

Gln His Gln Asp Lys Gln Asn Ile Asp Asn Thr Thr Ser Lys Lys Ala
        35                  40                  45

Asp Lys Gln Ile His Lys Asp Ser Ile Asp Lys His Glu Arg Phe Lys
    50                  55                  60

Asn Ser Leu Ser Ser His Leu Glu Gln Arg Asn Arg Asp Val Asn Glu
65                  70                  75                  80

Asn Lys Ala Glu Glu Ser Lys Ser Asn Gln Asp Ser Lys Ser Ala Tyr
                85                  90                  95

Asn Arg Asp His Tyr Leu Thr Asp Val Ser Lys Lys Gln Asn Ser
            100                 105                 110

Leu Asp Ser Val Asp Gln Asp Thr Glu Lys Ser Lys Tyr Tyr Glu Gln
        115                 120                 125

Asn Ser Glu Ala Thr Leu Ser Thr Lys Ser Thr Asp Lys Val Glu Ser
    130                 135                 140

Thr Glu Met Arg Lys Leu Ser Ser Asp Lys Lys Val Gly His Glu
145                 150                 155                 160

Glu Gln His Val Leu Ser Lys Pro Ser Glu His Asp Lys Glu Thr Arg
                165                 170                 175

Ile Asp Ser Glu Ser Ser Arg Thr Asp Ser Asp Ser Met Gln Thr
            180                 185                 190

Glu Lys Ile Lys Lys Asp Ser Asp Gly Asn Lys Ser Ser Asn Leu
        195                 200                 205

Lys Ser Glu Val Ile Ser Asp Lys Ser Asn Thr Val Pro Lys Leu Ser
    210                 215                 220

Glu Ser Asp Asp Glu Val Asn Asn Gln Lys Pro Leu Thr Leu Pro Glu
225                 230                 235                 240
```

```
Glu Gln Lys Leu Lys Arg Gln Gln Ser Gln Asn Gln Thr Lys Thr
                245                 250                 255

Tyr Thr Tyr Gly Asp Ser Glu Gln Asn Asp Lys Ser Asn His Glu Asn
            260                 265                 270

Asp Leu Ser His His Ile Pro Ser Ile Ser Asp Lys Asp Asn Val
        275                 280                 285

Met Arg Glu Asn His Ile Val Asp Asp Asn Pro Asp Asn Asp Ile Asn
290                 295                 300

Thr Pro Ser Leu Ser Lys Thr Asp Asp Asp Arg Lys Leu Asp Glu Lys
305                 310                 315                 320

Ile His Val Glu Asp Lys His Lys Gln Asn Ala Asp Ser Ser Glu Thr
                325                 330                 335

Val Gly Tyr Gln Ser Gln Ser Thr Ala Ser His Arg Ser Thr Glu Lys
            340                 345                 350

Arg Asn Ile Ser Ile Asn Asp His Asp Lys Leu Asn Gly Gln Lys Thr
        355                 360                 365

Asn Thr Lys Thr Ser Ala Asn Asn Gln Lys Lys Ala Thr Ser Lys
370                 375                 380

Leu Asn Lys Gly Arg Ala Thr Asn Asn Asn Tyr Ser Asp Ile Leu Lys
385                 390                 395                 400

Lys Phe Trp Met Met Tyr Trp Pro Lys Gly Ser Gly Gly Ala Lys
                405                 410                 415

Arg Ile Lys Gln His Pro Asp Val Gln Lys Val Thr Asp Ala Thr Ser
            420                 425                 430

Lys Val Ala Ser Lys Thr Ser Ala Ala Ile Ser Asn Thr Ala Ser Asp
        435                 440                 445

Val Lys Glu Tyr Val Gly Asp Lys Lys Gln Asp Phe Glu Asn Lys Arg
450                 455                 460

Glu Leu Lys Lys Phe Ala Arg Glu His Asp Pro Ala Tyr Ile Glu Lys
465                 470                 475                 480

Lys Gly Glu Lys Leu Ala Lys Gln Asn Arg Lys Asp Ala Asp Lys Met
                485                 490                 495

Asn Lys Ile Leu Gln Lys Asn Ile Glu Lys Arg His Lys Glu Glu Gln
            500                 505                 510

Lys Ala Arg Glu Lys Asn Glu Ile Gln Arg Ile Lys Asp Met Lys Lys
        515                 520                 525

Ser Gln Lys Tyr Glu Val Lys Ala Gly Leu Thr Pro Asn Lys Leu Asp
530                 535                 540

Glu Lys Thr Glu Lys Lys Gly Asp Lys Leu Ala Glu Lys Asn Arg Lys
545                 550                 555                 560

Glu Ile Ala Lys Met Asn Lys Lys Leu Gln Lys Asn Ile Glu Lys Arg
                565                 570                 575

His Lys Glu Glu Gln Lys Arg Gln Gln Glu Ala Asp Lys Ala Arg Ile
            580                 585                 590

Lys Ser Phe Lys Lys Tyr Lys Asp Tyr Val Ala Lys Ser Ala Ser Gln
        595                 600                 605

Gln Asn Lys Glu Asn Asn Thr Glu Ala
    610                 615

<210> SEQ ID NO 62
<211> LENGTH: 620
<212> TYPE: PRT
<213> ORGANISM: Artificial sequence
<220> FEATURE:
```

<223> OTHER INFORMATION: Chimeric polypeptide

<400> SEQUENCE: 62

Met Asp Ile Gly Lys Lys His Val Ile Pro Lys Ser Gln Tyr Arg Arg
1               5                   10                  15

Lys Arg Arg Glu Phe Phe His Asn Glu Asp Arg Glu Glu Asn Leu Asn
            20                  25                  30

Gln His Gln Asp Lys Gln Asn Ile Asp Asn Thr Thr Ser Lys Lys Ala
        35                  40                  45

Asp Lys Gln Ile His Lys Asp Ser Ile Asp Lys His Glu Arg Phe Lys
    50                  55                  60

Asn Ser Leu Ser Ser His Leu Glu Gln Arg Asn Arg Asp Val Asn Glu
65                  70                  75                  80

Asn Lys Ala Glu Glu Ser Lys Ser Asn Gln Asp Ser Lys Ser Ala Tyr
                85                  90                  95

Asn Arg Asp His Tyr Leu Thr Asp Val Ser Lys Lys Gln Asn Ser
            100                 105                 110

Leu Asp Ser Val Asp Gln Asp Thr Glu Lys Ser Lys Tyr Tyr Glu Gln
        115                 120                 125

Asn Ser Glu Ala Thr Leu Ser Thr Lys Ser Thr Asp Lys Val Glu Ser
    130                 135                 140

Thr Glu Met Arg Lys Leu Ser Ser Asp Lys Asn Lys Val Gly His Glu
145                 150                 155                 160

Glu Gln His Val Leu Ser Lys Pro Ser Glu His Asp Lys Glu Thr Arg
                165                 170                 175

Ile Asp Ser Glu Ser Ser Arg Thr Asp Ser Asp Ser Ser Met Gln Thr
            180                 185                 190

Glu Lys Ile Lys Lys Asp Ser Ser Asp Gly Asn Lys Ser Ser Asn Leu
        195                 200                 205

Lys Ser Glu Val Ile Ser Asp Lys Ser Asn Thr Val Pro Lys Leu Ser
    210                 215                 220

Glu Ser Asp Asp Glu Val Asn Asn Gln Lys Pro Leu Thr Leu Pro Glu
225                 230                 235                 240

Glu Gln Lys Leu Lys Arg Gln Gln Ser Gln Asn Glu Gln Thr Lys Thr
                245                 250                 255

Tyr Thr Tyr Gly Asp Ser Glu Gln Asn Asp Lys Ser Asn His Glu Asn
            260                 265                 270

Asp Leu Ser His His Ile Pro Ser Ile Ser Asp Lys Asp Asn Val
        275                 280                 285

Met Arg Glu Asn His Ile Val Asp Asp Asn Pro Asp Asn Asp Ile Asn
    290                 295                 300

Thr Pro Ser Leu Ser Lys Thr Asp Asp Arg Lys Leu Asp Glu Lys
305                 310                 315                 320

Ile His Val Glu Asp Lys His Lys Gln Asn Ala Asp Ser Ser Glu Thr
                325                 330                 335

Val Gly Tyr Gln Ser Gln Ser Thr Ala Ser His Arg Ser Thr Glu Lys
            340                 345                 350

Arg Asn Ile Ser Ile Asn Asp His Asp Lys Leu Asn Gly Gln Lys Thr
        355                 360                 365

Asn Thr Lys Thr Ser Ala Asn Asn Gln Lys Lys Ala Thr Ser Lys
    370                 375                 380

Leu Asn Lys Gly Arg Ala Thr Asn Asn Tyr Ser Asp Ile Leu Lys
385                 390                 395                 400

```
Lys Phe Trp Met Met Tyr Trp Pro Lys Gly Ser Gly Gly Ala Gly
                405                 410                 415

Ser Gly Gly Gly Ala Met Thr Glu Lys Glu Lys Met Leu Ala Glu Lys
            420                 425                 430

Trp Tyr Asp Ala Asn Phe Asp Gln Asp Leu Ile Asn Glu Arg Ala Arg
            435                 440                 445

Ala Lys Asp Ile Cys Phe Glu Leu Asn His Thr Lys Pro Ser Asp Lys
    450                 455                 460

Asn Lys Arg Lys Glu Leu Ile Asp Glu Leu Phe Gln Thr Thr Thr Asp
465                 470                 475                 480

Asn Val Ser Ile Ser Ile Pro Phe Asp Thr Asp Tyr Gly Trp Asn Val
                485                 490                 495

Lys Leu Gly Lys Asn Val Tyr Val Asn Thr Asn Cys Tyr Phe Met Asp
            500                 505                 510

Gly Gly Gln Ile Thr Ile Gly Asp Asn Val Phe Ile Gly Pro Asn Cys
            515                 520                 525

Gly Phe Tyr Thr Ala Thr His Pro Leu Asn Phe His His Arg Asn Glu
            530                 535                 540

Gly Phe Glu Lys Ala Gly Pro Ile Asn Ile Gly Ser Asn Thr Trp Phe
545                 550                 555                 560

Gly Gly His Val Ala Val Leu Pro Gly Val Thr Ile Gly Glu Gly Ser
                565                 570                 575

Val Ile Gly Ala Gly Ser Val Val Thr Lys Asp Ile Pro Pro His Ser
            580                 585                 590

Leu Ala Val Gly Asn Pro Cys Lys Val Val Arg Lys Ile Asp Asn Glu
            595                 600                 605

Val Pro Ser Glu Ala Leu Asn Asp Glu Thr Leu Asn
    610                 615                 620

<210> SEQ ID NO 63
<211> LENGTH: 614
<212> TYPE: PRT
<213> ORGANISM: Artificial sequence
<220> FEATURE:
<223> OTHER INFORMATION: Chimeric polypeptide

<400> SEQUENCE: 63

Met Asp Ile Gly Lys Lys His Val Ile Pro Lys Ser Gln Tyr Arg Arg
1               5                   10                  15

Lys Arg Arg Glu Phe Phe His Asn Glu Asp Arg Glu Glu Asn Leu Asn
            20                  25                  30

Gln His Gln Asp Lys Gln Asn Ile Asp Asn Thr Thr Ser Lys Lys Ala
        35                  40                  45

Asp Lys Gln Ile His Lys Asp Ser Ile Asp Lys His Glu Arg Phe Lys
    50                  55                  60

Asn Ser Leu Ser Ser His Leu Glu Gln Arg Asn Arg Asp Val Asn Glu
65                  70                  75                  80

Asn Lys Ala Glu Glu Ser Lys Ser Asn Gln Asp Ser Lys Ser Ala Tyr
                85                  90                  95

Asn Arg Asp His Tyr Leu Thr Asp Asp Val Ser Lys Lys Gln Asn Ser
            100                 105                 110

Leu Asp Ser Val Asp Gln Asp Thr Glu Lys Ser Lys Tyr Tyr Glu Gln
        115                 120                 125

Asn Ser Glu Ala Thr Leu Ser Thr Lys Ser Thr Asp Lys Val Glu Ser
    130                 135                 140
```

-continued

```
Thr Glu Met Arg Lys Leu Ser Ser Asp Lys Asn Lys Val Gly His Glu
145                 150                 155                 160

Glu Gln His Val Leu Ser Lys Pro Ser Glu His Asp Lys Glu Thr Arg
            165                 170                 175

Ile Asp Ser Glu Ser Ser Arg Thr Asp Ser Asp Ser Ser Met Gln Thr
        180                 185                 190

Glu Lys Ile Lys Lys Asp Ser Ser Asp Gly Asn Lys Ser Ser Asn Leu
    195                 200                 205

Lys Ser Glu Val Ile Ser Asp Lys Ser Asn Thr Val Pro Lys Leu Ser
210                 215                 220

Glu Ser Asp Asp Glu Val Asn Asn Gln Lys Pro Leu Thr Leu Pro Glu
225                 230                 235                 240

Glu Gln Lys Leu Lys Arg Gln Gln Ser Gln Asn Glu Gln Thr Lys Thr
                245                 250                 255

Tyr Thr Tyr Gly Asp Ser Glu Gln Asn Asp Lys Ser Asn His Glu Asn
            260                 265                 270

Asp Leu Ser His His Ile Pro Ser Ile Ser Asp Asp Lys Asp Asn Val
        275                 280                 285

Met Arg Glu Asn His Ile Val Asp Asp Asn Pro Asp Asn Asp Ile Asn
    290                 295                 300

Thr Pro Ser Leu Ser Lys Thr Asp Asp Arg Lys Leu Asp Glu Lys
305                 310                 315                 320

Ile His Val Glu Asp Lys His Lys Gln Asn Ala Asp Ser Ser Glu Thr
                325                 330                 335

Val Gly Tyr Gln Ser Gln Ser Thr Ala Ser His Arg Ser Thr Glu Lys
            340                 345                 350

Arg Asn Ile Ser Ile Asn Asp His Asp Lys Leu Asn Gly Gln Lys Thr
        355                 360                 365

Asn Thr Lys Thr Ser Ala Asn Asn Gln Lys Lys Ala Thr Ser Lys
370                 375                 380

Leu Asn Lys Gly Arg Ala Thr Asn Asn Tyr Ser Asp Ile Leu Lys
385                 390                 395                 400

Lys Phe Trp Met Met Tyr Trp Pro Lys Gly Ser Gly Gly Gly Ala Met
                405                 410                 415

Thr Glu Lys Glu Lys Met Leu Ala Glu Lys Trp Tyr Asp Ala Asn Phe
            420                 425                 430

Asp Gln Asp Leu Ile Asn Glu Arg Ala Arg Ala Lys Asp Ile Cys Phe
        435                 440                 445

Glu Leu Asn His Thr Lys Pro Ser Asp Lys Asn Lys Arg Lys Glu Leu
    450                 455                 460

Ile Asp Glu Leu Phe Gln Thr Thr Asp Asn Val Ser Ile Ser Ile
465                 470                 475                 480

Pro Phe Asp Thr Asp Tyr Gly Trp Asn Val Lys Leu Gly Lys Asn Val
                485                 490                 495

Tyr Val Asn Thr Asn Cys Tyr Phe Met Asp Gly Gly Gln Ile Thr Ile
            500                 505                 510

Gly Asp Asn Val Phe Ile Gly Pro Asn Cys Gly Phe Tyr Thr Ala Thr
        515                 520                 525

His Pro Leu Asn Phe His His Arg Asn Glu Gly Phe Glu Lys Ala Gly
    530                 535                 540

Pro Ile Asn Ile Gly Ser Asn Thr Trp Phe Gly Gly His Val Ala Val
545                 550                 555                 560

Leu Pro Gly Val Thr Ile Gly Glu Gly Ser Val Ile Gly Ala Gly Ser
```

```
                    565                 570                 575
Val Val Thr Lys Asp Ile Pro Pro His Ser Leu Ala Val Gly Asn Pro
            580                 585                 590

Cys Lys Val Val Arg Lys Ile Asp Asn Glu Val Pro Ser Glu Ala Leu
        595                 600                 605

Asn Asp Glu Thr Leu Asn
        610

<210> SEQ ID NO 64
<211> LENGTH: 805
<212> TYPE: PRT
<213> ORGANISM: Artificial sequence
<220> FEATURE:
<223> OTHER INFORMATION: Chimeric polypeptide

<400> SEQUENCE: 64

Met Asp Ile Gly Lys Lys His Val Ile Pro Lys Ser Gln Tyr Arg Arg
1               5                   10                  15

Lys Arg Arg Glu Phe Phe His Asn Glu Asp Arg Glu Glu Asn Leu Asn
            20                  25                  30

Gln His Gln Asp Lys Gln Asn Ile Asp Asn Thr Thr Ser Lys Lys Ala
        35                  40                  45

Asp Lys Gln Ile His Lys Asp Ser Ile Asp Lys His Glu Arg Phe Lys
    50                  55                  60

Asn Ser Leu Ser Ser His Leu Glu Gln Arg Asn Arg Asp Val Asn Glu
65                  70                  75                  80

Asn Lys Ala Glu Glu Ser Lys Ser Asn Gln Asp Ser Lys Ser Ala Tyr
                85                  90                  95

Asn Arg Asp His Tyr Leu Thr Asp Asp Val Ser Lys Lys Gln Asn Ser
            100                 105                 110

Leu Asp Ser Val Asp Gln Asp Thr Glu Lys Ser Lys Tyr Tyr Glu Gln
        115                 120                 125

Asn Ser Glu Ala Thr Leu Ser Thr Lys Ser Thr Asp Lys Val Glu Ser
    130                 135                 140

Thr Glu Met Arg Lys Leu Ser Ser Asp Lys Asn Lys Val Gly His Glu
145                 150                 155                 160

Glu Gln His Val Leu Ser Lys Pro Ser Glu His Asp Lys Glu Thr Arg
                165                 170                 175

Ile Asp Ser Glu Ser Ser Arg Thr Asp Ser Asp Ser Ser Met Gln Thr
            180                 185                 190

Glu Lys Ile Lys Lys Asp Ser Ser Asp Gly Asn Lys Ser Ser Asn Leu
        195                 200                 205

Lys Ser Glu Val Ile Ser Asp Lys Ser Asn Thr Val Pro Lys Leu Ser
    210                 215                 220

Glu Ser Asp Asp Glu Val Asn Asn Gln Lys Pro Leu Thr Leu Pro Glu
225                 230                 235                 240

Glu Gln Lys Leu Lys Arg Gln Gln Ser Gln Asn Glu Gln Thr Lys Thr
                245                 250                 255

Tyr Thr Tyr Gly Asp Ser Glu Gln Asn Asp Lys Ser Asn His Glu Asn
            260                 265                 270

Asp Leu Ser His His Ile Pro Ser Ile Ser Asp Lys Asp Asn Val
        275                 280                 285

Met Arg Glu Asn His Ile Val Asp Asp Asn Pro Asp Asn Asp Ile Asn
    290                 295                 300

Thr Pro Ser Leu Ser Lys Thr Asp Asp Asp Arg Lys Leu Asp Glu Lys
```

```
              305                 310                 315                 320
        Ile His Val Glu Asp Lys His Lys Gln Asn Ala Asp Ser Ser Glu Thr
                        325                 330                 335

Val Gly Tyr Gln Ser Gln Ser Thr Ala Ser His Arg Ser Thr Glu Lys
                        340                 345                 350

Arg Asn Ile Ser Ile Asn Asp His Asp Lys Leu Asn Gly Gln Lys Thr
                        355                 360                 365

Asn Thr Lys Thr Ser Ala Asn Asn Gln Lys Lys Ala Thr Ser Lys
        370                 375                 380

Leu Asn Lys Gly Arg Ala Thr Asn Asn Tyr Ser Asp Ile Leu Lys
        385                 390                 395                 400

Lys Phe Trp Met Met Tyr Trp Pro Lys Gly Ser Gly Gly Ala Lys
                        405                 410                 415

Val Ala Lys Gln Gly Gln Tyr Lys Asn Gln Asp Pro Ile Val Leu Val
                        420                 425                 430

His Gly Phe Asn Gly Phe Thr Asp Asp Ile Asn Pro Ser Val Leu Ala
                        435                 440                 445

His Tyr Trp Gly Gly Asn Lys Met Asn Ile Arg Gln Asp Leu Glu Glu
                        450                 455                 460

Asn Gly Tyr Lys Ala Tyr Glu Ala Ser Ile Ser Ala Phe Gly Ser Asn
        465                 470                 475                 480

Tyr Asp Arg Ala Val Glu Leu Tyr Tyr Ile Lys Gly Gly Arg Val
                        485                 490                 495

Asp Tyr Gly Ala Ala His Ala Ala Lys Tyr Gly His Glu Arg Tyr Gly
                        500                 505                 510

Lys Thr Tyr Glu Gly Ile Tyr Lys Asp Trp Lys Pro Gly Gln Lys Val
                        515                 520                 525

His Leu Val Gly His Ser Met Gly Gly Gln Thr Ile Arg Gln Leu Glu
                        530                 535                 540

Glu Leu Leu Arg Asn Gly Ser Arg Glu Glu Ile Glu Tyr Gln Lys Lys
        545                 550                 555                 560

His Gly Gly Glu Ile Ser Pro Leu Phe Lys Gly Asn Asn Asp Asn Met
                        565                 570                 575

Ile Ser Ser Ile Thr Thr Leu Gly Thr Pro His Asn Gly Thr His Ala
                        580                 585                 590

Ser Asp Leu Ala Gly Asn Glu Ala Leu Val Arg Gln Ile Val Phe Asp
                        595                 600                 605

Ile Gly Lys Met Phe Gly Asn Lys Asn Ser Arg Val Asp Phe Gly Leu
                        610                 615                 620

Ala Gln Trp Gly Leu Lys Gln Lys Pro Asn Glu Ser Tyr Ile Asp Tyr
        625                 630                 635                 640

Val Lys Arg Val Lys Gln Ser Asn Leu Trp Lys Ser Lys Asp Asn Gly
                        645                 650                 655

Phe Tyr Asp Leu Thr Arg Glu Gly Ala Thr Asp Leu Asn Arg Lys Thr
                        660                 665                 670

Ser Leu Asn Pro Asn Ile Val Tyr Lys Thr Tyr Thr Gly Glu Ala Thr
                        675                 680                 685

His Lys Ala Leu Asn Ser Asp Arg Gln Lys Ala Asp Leu Asn Met Phe
                        690                 695                 700

Phe Pro Phe Val Ile Thr Gly Asn Leu Ile Gly Lys Ala Thr Glu Lys
        705                 710                 715                 720

Glu Trp Arg Glu Asn Asp Gly Leu Val Ser Val Ile Ser Ser Gln His
                        725                 730                 735
```

-continued

```
Pro Phe Asn Gln Ala Tyr Thr Asn Ala Thr Asp Lys Ile Gln Lys Gly
                740                 745                 750

Ile Trp Gln Val Thr Pro Thr Lys His Asp Trp Asp His Val Asp Phe
            755                 760                 765

Val Gly Gln Asp Ser Ser Asp Thr Val Arg Thr Arg Glu Glu Leu Gln
770                 775                 780

Asp Phe Trp His His Leu Ala Asp Asp Leu Val Lys Thr Glu Lys Val
785                 790                 795                 800

Thr Asp Thr Lys Gln
                805

<210> SEQ ID NO 65
<211> LENGTH: 1003
<212> TYPE: PRT
<213> ORGANISM: Artificial sequence
<220> FEATURE:
<223> OTHER INFORMATION: Chimeric polypeptide

<400> SEQUENCE: 65

Arg Asn Leu Leu Gln Lys Gln Ser Gln Ala Arg Gln Thr Ala Glu
1               5                   10                  15

Asp Ile Val Asn Gln Ala His Lys Glu Ala Asp Asn Ile Lys Lys Glu
                20                  25                  30

Lys Leu Leu Glu Ala Lys Glu Glu Asn Gln Ile Leu Arg Glu Gln Thr
            35                  40                  45

Glu Ala Glu Leu Arg Glu Arg Arg Ser Glu Leu Gln Arg Gln Glu Thr
        50                  55                  60

Arg Leu Leu Gln Lys Glu Glu Asn Leu Glu Arg Lys Ser Asp Leu Leu
65                  70                  75                  80

Asp Lys Lys Asp Glu Ile Leu Glu Gln Lys Ser Lys Ile Glu Glu
                85                  90                  95

Lys Gln Gln Gln Val Asp Ala Lys Glu Ser Ser Val Gln Thr Leu Ile
            100                 105                 110

Met Lys His Glu Gln Glu Leu Glu Arg Ile Ser Gly Leu Thr Gln Glu
        115                 120                 125

Glu Ala Ile Asn Glu Gln Leu Gln Arg Val Glu Glu Glu Leu Ser Gln
    130                 135                 140

Asp Ile Ala Val Leu Val Lys Glu Lys Glu Lys Glu Ala Lys Glu Lys
145                 150                 155                 160

Val Asp Lys Thr Ala Lys Glu Leu Leu Ala Thr Ala Val Gln Arg Leu
                165                 170                 175

Ala Ala Asp His Thr Ser Glu Ser Thr Val Ser Val Val Asn Leu Pro
            180                 185                 190

Asn Asp Glu Met Lys Gly Arg Ile Ile Gly Arg Glu Gly Arg Asn Ile
        195                 200                 205

Arg Thr Leu Glu Thr Leu Thr Gly Ile Asp Leu Ile Ile Asp Asp Thr
    210                 215                 220

Pro Glu Ala Val Ile Leu Ser Gly Phe Asp Pro Ile Arg Arg Glu Ile
225                 230                 235                 240

Ala Arg Thr Ala Leu Val Asn Leu Val Ser Asp Gly Arg Ile His Pro
                245                 250                 255

Gly Arg Ile Glu Asp Met Val Glu Lys Ala Arg Lys Glu Val Asp Asp
            260                 265                 270

Ile Ile Arg Glu Ala Gly Glu Gln Ala Thr Phe Glu Val Asn Ala His
        275                 280                 285
```

```
Asn Met His Pro Asp Leu Val Lys Ile Val Gly Arg Leu Asn Tyr Arg
    290                 295                 300
Thr Ser Tyr Gly Gln Asn Val Leu Lys His Ser Ile Glu Val Ala His
305                 310                 315                 320
Leu Ala Ser Met Leu Ala Ala Glu Leu Gly Glu Asp Glu Thr Leu Ala
                325                 330                 335
Lys Arg Ala Gly Leu Leu His Asp Val Gly Lys Ala Ile Asp His Glu
                340                 345                 350
Val Glu Gly Ser His Val Glu Ile Gly Val Glu Leu Ala Lys Lys Tyr
                355                 360                 365
Gly Glu Asn Glu Thr Val Ile Asn Ala Ile His Ser His His Gly Asp
    370                 375                 380
Val Glu Pro Thr Ser Ile Ile Ser Ile Leu Val Ala Ala Ala Asp Ala
385                 390                 395                 400
Leu Ser Ala Ala Arg Pro Gly Ala Arg Lys Glu Thr Leu Glu Asn Tyr
                405                 410                 415
Ile Arg Arg Leu Glu Arg Leu Glu Thr Leu Ser Glu Ser Tyr Asp Gly
                420                 425                 430
Val Glu Lys Ala Phe Ala Ile Gln Ala Gly Arg Glu Ile Arg Val Ile
                435                 440                 445
Val Ser Pro Glu Glu Ile Asp Asp Leu Lys Ser Tyr Arg Leu Ala Arg
450                 455                 460
Asp Ile Lys Asn Gln Ile Glu Asp Glu Leu Gln Tyr Pro Gly His Ile
465                 470                 475                 480
Lys Val Thr Val Val Arg Glu Thr Arg Ala Val Glu Tyr Ala Lys Lys
                485                 490                 495
Pro Glu Pro Lys Pro Ala Pro Ala Pro Lys Pro Ala Cys Gly Asn Asp
                500                 505                 510
Asp Gly Lys Asp Lys Asp Gly Lys Val Thr Ile Lys Thr Thr Val Tyr
                515                 520                 525
Pro Leu Gln Ser Phe Ala Glu Gln Ile Gly Gly Lys His Val Lys Val
530                 535                 540
Ser Ser Ile Tyr Pro Ala Gly Thr Asp Leu His Ser Tyr Glu Pro Thr
545                 550                 555                 560
Gln Lys Asp Ile Leu Ser Ala Ser Lys Ser Asp Leu Phe Met Tyr Thr
                565                 570                 575
Gly Asp Asn Leu Asp Pro Val Ala Lys Lys Val Ala Ser Thr Ile Lys
                580                 585                 590
Asp Lys Asp Lys Lys Leu Ser Leu Glu Asp Lys Leu Asp Lys Ala Lys
                595                 600                 605
Leu Leu Thr Asp Gln His Glu His Gly Glu Glu His Glu His Glu Gly
                610                 615                 620
His Asp His Glu Lys Glu Glu His His His Gly Gly Tyr Asp Pro
625                 630                 635                 640
His Val Trp Leu Asp Pro Lys Ile Asn Gln Thr Phe Ala Lys Glu Ile
                645                 650                 655
Lys Asp Glu Leu Val Lys Lys Asp Pro Lys His Lys Asp Asp Tyr Glu
                660                 665                 670
Lys Asn Tyr Lys Lys Leu Asn Asp Asp Leu Lys Lys Ile Asp Asn Asp
                675                 680                 685
Met Lys Gln Val Thr Lys Asp Lys Gln Gly Asn Ala Val Phe Ile Ser
    690                 695                 700
```

His Glu Ser Ile Gly Tyr Leu Ala Asp Arg Tyr Gly Phe Val Gln Lys
705                 710                 715                 720

Gly Ile Gln Asn Met Asn Ala Glu Asp Pro Ser Gln Lys Glu Leu Thr
            725                 730                 735

Lys Ile Val Lys Glu Ile Arg Asp Ser Asn Ala Lys Tyr Ile Leu Tyr
        740                 745                 750

Glu Asp Asn Val Ala Asn Lys Val Thr Glu Thr Ile Arg Lys Glu Thr
    755                 760                 765

Asp Ala Lys Pro Leu Lys Phe Tyr Asn Met Glu Ser Leu Asn Lys Glu
770                 775                 780

Gln Gln Lys Lys Asp Asn Ile Thr Tyr Gln Ser Leu Met Lys Ser Asn
785                 790                 795                 800

Ile Glu Asn Ile Gly Lys Ala Leu Asp Ser Gly Val Lys Val Lys Asp
            805                 810                 815

Asp Lys Ala Glu Ser Lys His Asp Lys Ala Ile Ser Asp Gly Tyr Phe
        820                 825                 830

Lys Asp Glu Gln Val Lys Asp Arg Glu Leu Ser Asp Tyr Ala Gly Glu
    835                 840                 845

Trp Gln Ser Val Tyr Pro Tyr Leu Lys Asp Gly Thr Leu Asp Glu Val
850                 855                 860

Met Glu His Lys Ala Glu Asn Asp Pro Lys Lys Ser Ala Lys Asp Leu
865                 870                 875                 880

Lys Ala Tyr Tyr Asp Lys Gly Tyr Lys Thr Asp Ile Thr Asn Ile Asp
            885                 890                 895

Ile Lys Gly Asn Glu Ile Thr Phe Thr Lys Asp Gly Lys Lys His Thr
        900                 905                 910

Gly Lys Tyr Glu Tyr Asn Gly Lys Lys Thr Leu Lys Tyr Pro Lys Gly
    915                 920                 925

Asn Arg Gly Val Arg Phe Met Phe Lys Leu Val Asp Gly Asn Asp Lys
930                 935                 940

Asp Leu Pro Lys Phe Ile Gln Phe Ser Asp His Asn Ile Ala Pro Lys
945                 950                 955                 960

Lys Ala Glu His Phe His Ile Phe Met Gly Asn Asp Asn Asp Ala Leu
            965                 970                 975

Leu Lys Glu Met Asp Asn Trp Pro Thr Tyr Tyr Pro Ser Lys Leu Asn
        980                 985                 990

Lys Asp Gln Ile Lys Glu Glu Met Leu Ala His
    995                 1000

<210> SEQ ID NO 66
<211> LENGTH: 1009
<212> TYPE: PRT
<213> ORGANISM: Artificial sequence
<220> FEATURE:
<223> OTHER INFORMATION: Chimeric polypeptide

<400> SEQUENCE: 66

Met Asn Glu Lys Val Glu Gly Met Thr Leu Glu Leu Lys Leu Asp His
1               5                   10                  15

Leu Gly Val Gln Glu Gly Met Lys Gly Leu Lys Arg Gln Leu Gly Val
            20                  25                  30

Val Asn Ser Glu Met Lys Ala Asn Leu Ser Ala Phe Asp Lys Ser Glu
        35                  40                  45

Lys Ser Met Glu Lys Tyr Gln Ala Arg Ile Lys Gly Leu Asn Asp Arg
    50                  55                  60

```
Leu Lys Val Gln Lys Lys Met Tyr Ser Gln Val Glu Asp Glu Leu Lys
 65                  70                  75                  80

Gln Val Asn Ala Asn Tyr Gln Lys Ala Lys Ser Ser Val Lys Asp Val
                 85                  90                  95

Glu Lys Ala Tyr Leu Lys Leu Val Glu Ala Asn Lys Lys Glu Lys Leu
                100                 105                 110

Ala Leu Asp Lys Ser Lys Glu Ala Leu Lys Ser Ser Asn Thr Glu Leu
                115                 120                 125

Lys Lys Ala Glu Asn Gln Tyr Lys Arg Thr Asn Gln Arg Lys Gln Asp
130                 135                 140

Ala Tyr Gln Lys Leu Lys Gln Leu Arg Asp Ala Glu Gln Lys Leu Lys
145                 150                 155                 160

Asn Ser Asn Gln Ala Thr Thr Ala Gln Leu Lys Arg Ala Ser Asp Ala
                165                 170                 175

Val Gln Lys Gln Ser Ala Lys His Lys Ala Leu Val Glu Gln Tyr Lys
                180                 185                 190

Gln Glu Gly Asn Gln Val Gln Lys Leu Lys Val Gln Asn Asp Asn Leu
                195                 200                 205

Ser Lys Ser Asn Asp Lys Ile Glu Ser Ser Tyr Ala Lys Thr Asn Thr
210                 215                 220

Lys Leu Lys Gln Thr Glu Lys Glu Phe Asn Asp Leu Asn Asn Thr Ile
225                 230                 235                 240

Lys Asn His Ser Ala Asn Val Ala Lys Ala Glu Thr Ala Val Asn Lys
                245                 250                 255

Glu Lys Ala Ala Leu Asn Asn Leu Glu Arg Ser Ile Asp Lys Ala Ser
                260                 265                 270

Ser Glu Met Lys Thr Phe Asn Lys Glu Gln Met Ile Ala Gln Ser His
                275                 280                 285

Phe Gly Lys Leu Ala Ser Gln Ala Asp Val Met Ser Lys Lys Phe Ser
290                 295                 300

Ser Ile Gly Asp Lys Met Thr Ser Leu Gly Arg Thr Met Thr Met Gly
305                 310                 315                 320

Val Ser Thr Pro Ile Thr Leu Gly Leu Gly Ala Ala Leu Lys Thr Ser
                325                 330                 335

Ala Asp Phe Glu Gly Gln Met Ser Arg Val Gly Ala Ile Ala Gln Ala
                340                 345                 350

Ser Ser Lys Asp Leu Lys Ser Met Ser Asn Gln Ala Val Asp Leu Gly
                355                 360                 365

Ala Lys Thr Ser Lys Ser Ala Asn Glu Val Ala Lys Gly Met Glu Glu
                370                 375                 380

Leu Ala Ala Leu Gly Phe Asn Ala Lys Gln Thr Met Glu Ala Met Pro
385                 390                 395                 400

Gly Val Ile Ser Ala Ala Glu Ala Ser Gly Ala Glu Met Ala Thr Thr
                405                 410                 415

Ala Thr Val Met Ala Ser Ala Ile Asn Ser Phe Gly Leu Lys Ala Ser
                420                 425                 430

Asp Ala Asn His Val Ala Asp Leu Leu Ala Arg Ser Ala Asn Asp Ser
                435                 440                 445

Ala Ala Asp Ile Gln Tyr Met Gly Asp Ala Leu Lys Tyr Ala Gly Thr
                450                 455                 460

Pro Ala Lys Ala Leu Gly Val Ser Ile Glu Asp Thr Ser Ala Ala Ile
465                 470                 475                 480

Glu Val Leu Ser Asn Ser Gly Leu Glu Gly Ser Gln Ala Gly Thr Ala
```

```
                    485             490             495
Leu Arg Ala Ser Phe Ile Arg Leu Ala Asn Pro Ser Lys Asn Thr Ala
                500             505             510

Lys Glu Met Lys Lys Leu Gly Ile His Leu Ser Asp Ala Lys Gly Gln
            515             520             525

Phe Val Gly Met Gly Glu Leu Ile Arg Gln Phe Gln Asp Asn Met Lys
530             535             540

Gly Met Thr Arg Glu Gln Lys Leu Ala Thr Val Ala Thr Ile Val Gly
545             550             555             560

Thr Glu Ala Ala Ser Gly Phe Leu Ala Leu Ile Glu Ala Gly Pro Asp
                565             570             575

Lys Ile Asn Ser Tyr Ser Lys Ser Leu Lys Asn Ser Asn Gly Glu Ser
            580             585             590

Lys Lys Ala Ala Asp Leu Met Lys Asp Asn Leu Lys Gly Ala Leu Glu
        595             600             605

Gln Leu Gly Gly Ala Phe Glu Ser Leu Ala Ile Glu Val Gly Lys Asp
    610             615             620

Leu Thr Pro Met Ile Arg Ala Gly Ala Glu Gly Leu Thr Lys Leu Val
625             630             635             640

Asp Gly Phe Thr His Leu Pro Gly Trp Val Arg Lys Gly Ser Gly Gly
                645             650             655

Gly Ala Ala Lys Asp Asn Leu Asn Gly Glu Lys Pro Thr Thr Asn Leu
            660             665             670

Asn His Asn Val Thr Ser Pro Ser Val Asn Ser Glu Met Asn Asn Asn
        675             680             685

Glu Thr Gly Thr Pro His Glu Ser Asn Gln Ala Gly Asn Glu Gly Thr
    690             695             700

Gly Ser Asn Ser Arg Asp Ala Asn Pro Asp Ser Asn Asn Val Lys Pro
705             710             715             720

Asp Ser Asn Asn Gln Asn Pro Ser Pro Asp Ser Lys Pro Asp Pro Asn
                725             730             735

Asn Pro Asn Pro Gly Pro Asn Pro Lys Pro Asp Pro Asp Lys Pro Lys
            740             745             750

Pro Asn Pro Glu Pro Lys Pro Asp Pro Lys Pro Asp Pro Asp Lys Pro
        755             760             765

Lys Pro Asn Pro Asp Pro Lys Pro Asp Pro Asp Lys Pro Lys Pro Asn
    770             775             780

Pro Asp Pro Lys Pro Asp Pro Asp Lys Pro Lys Pro Asn Pro Asp Pro
785             790             795             800

Lys Pro Asp Pro Asn Pro Asn Pro Lys Pro Asp Pro Asn Lys Pro Asn
                805             810             815

Pro Asn Pro Ser Pro Asn Pro Asn Gln Pro Gly Asp Ser Asn Gln Ser
            820             825             830

Gly Gly Ser Lys Asn Gly Gly Thr Trp Asn Pro Asn Ala Ser Asp Gly
        835             840             845

Ser Asn Gln Gly Gln Trp Gln Pro Asn Gly Asn Gln Gly Asn Ser Gln
    850             855             860

Asn Pro Thr Gly Asn Asp Phe Val Ser Gln Arg Phe Leu Ala Leu Ala
865             870             875             880

Asn Gly Ala Tyr Lys Tyr Asn Pro Tyr Ile Leu Asn Gln Ile Asn Gln
                885             890             895

Leu Gly Lys Glu Tyr Gly Glu Val Thr Asp Glu Asp Ile Tyr Asn Ile
            900             905             910
```

```
Ile Arg Lys Gln Asn Phe Ser Gly Asn Ala Tyr Leu Asn Gly Leu Gln
        915                 920                 925

Gln Gln Ser Asn Tyr Phe Arg Phe Gln Tyr Phe Asn Pro Leu Lys Ser
        930                 935                 940

Glu Arg Tyr Tyr Arg Asn Leu Asp Glu Gln Val Leu Ala Leu Ile Thr
945                 950                 955                 960

Gly Glu Ile Gly Ser Met Pro Asp Leu Lys Lys Pro Glu Asp Lys Pro
                965                 970                 975

Asp Ser Lys Gln Arg Ser Phe Glu Pro His Glu Lys Asp Asp Phe Thr
                980                 985                 990

Val Val Lys Lys Gln Glu Asp Asn  Lys Lys Ser Ala Ser  Thr Ala Tyr
                995                1000                1005

Ser

<210> SEQ ID NO 67
<211> LENGTH: 728
<212> TYPE: PRT
<213> ORGANISM: Artificial sequence
<220> FEATURE:
<223> OTHER INFORMATION: Chimeric polypeptide

<400> SEQUENCE: 67

Gly Phe Leu Asn Lys Ser Lys Asn Glu Gln Ala Ala Leu Lys Ala Gln
1               5                   10                  15

Gln Ala Ala Ile Lys Glu Glu Ala Ser Ala Asn Asn Leu Ser Asp Thr
            20                  25                  30

Ser Gln Glu Ala Gln Glu Ile Gln Glu Ala Lys Arg Glu Ala Gln Ala
        35                  40                  45

Glu Ala Asp Lys Ser Val Ala Val Ser Asn Lys Glu Ser Lys Ala Val
50                  55                  60

Ala Leu Lys Ala Gln Gln Ala Ala Ile Lys Glu Glu Ala Ser Ala Asn
65                  70                  75                  80

Asn Leu Ser Asp Thr Ser Gln Glu Ala Gln Glu Ile Gln Glu Ala Lys
                85                  90                  95

Lys Glu Ala Gln Ala Glu Thr Asp Lys Ser Ala Ala Val Ser Asn Glu
            100                 105                 110

Glu Pro Lys Ala Val Ala Leu Lys Ala Gln Gln Ala Ala Ile Lys Glu
        115                 120                 125

Glu Ala Ser Ala Asn Asn Leu Ser Asp Ile Ser Gln Glu Ala Gln Glu
    130                 135                 140

Val Gln Glu Ala Lys Lys Glu Ala Gln Ala Glu Lys Asp Ser Asp Thr
145                 150                 155                 160

Leu Thr Lys Asp Ala Ser Ala Ala Lys Val Glu Val Ser Lys Pro Glu
                165                 170                 175

Ser Gln Ala Glu Arg Leu Ala Asn Ala Ala Lys Gln Lys Gln Ala Lys
            180                 185                 190

Leu Thr Pro Gly Ser Lys Glu Ser Gln Leu Thr Glu Ala Leu Phe Ala
        195                 200                 205

Glu Lys Pro Val Ala Lys Asn Asp Leu Lys Glu Ile Pro Gln Leu Val
    210                 215                 220

Thr Lys Lys Asn Asp Val Ser Glu Thr Glu Thr Val Asn Ile Asp Asn
225                 230                 235                 240

Lys Asp Thr Val Lys Gln Lys Glu Ala Lys Phe Glu Asn Gly Val Ile
                245                 250                 255
```

```
Thr Arg Lys Ala Asp Glu Lys Thr Thr Asn Asn Thr Ala Val Asp Lys
                260                 265                 270

Lys Ser Gly Lys Gln Ser Lys Lys Thr Thr Pro Ser Asn Lys Arg Asn
    275                 280                 285

Ala Ser Lys Ala Ser Thr Asn Lys Thr Ser Gly Gln Lys Lys Gln His
290                 295                 300

Asn Lys Lys Ser Ser Gln Gly Ala Lys Lys Gln Ser Ser Ser Ser Lys
305                 310                 315                 320

Ser Thr Gln Lys Asn Asn Gln Thr Ser Asn Lys Asn Ser Lys Thr Thr
                325                 330                 335

Asn Ala Lys Ser Ser Asn Ala Ser Lys Thr Pro Asn Ala Lys Val Glu
                340                 345                 350

Lys Ala Lys Ser Lys Ile Glu Lys Arg Thr Phe Asn Asp Gly Ser Gly
                355                 360                 365

Gly Gly Ala Gly Ser Gly Gly Ala Ala Lys Asp Asn Leu Asn Gly
        370                 375                 380

Glu Lys Pro Thr Thr Asn Leu Asn His Asn Val Thr Ser Pro Ser Val
385                 390                 395                 400

Asn Ser Glu Met Asn Asn Asn Glu Thr Gly Thr Pro His Glu Ser Asn
                405                 410                 415

Gln Ala Gly Asn Glu Gly Thr Gly Ser Asn Ser Arg Asp Ala Asn Pro
                420                 425                 430

Asp Ser Asn Asn Val Lys Pro Asp Ser Asn Asn Gln Asn Pro Ser Pro
                435                 440                 445

Asp Ser Lys Pro Asp Pro Asn Asn Pro Asn Pro Gly Pro Asn Pro Lys
450                 455                 460

Pro Asp Pro Asp Lys Pro Lys Pro Asn Pro Glu Pro Lys Pro Asp Pro
465                 470                 475                 480

Lys Pro Asp Pro Asp Lys Pro Lys Pro Asn Pro Asp Pro Lys Pro Asp
                485                 490                 495

Pro Asp Lys Pro Lys Pro Asn Pro Asp Pro Lys Pro Asp Pro Asp Lys
                500                 505                 510

Pro Lys Pro Asn Pro Asp Pro Lys Pro Asp Pro Asn Pro Asn Pro Lys
            515                 520                 525

Pro Asp Pro Asn Lys Pro Asn Pro Asn Pro Ser Pro Asn Pro Asn Gln
        530                 535                 540

Pro Gly Asp Ser Asn Gln Ser Gly Gly Ser Lys Asn Gly Gly Thr Trp
545                 550                 555                 560

Asn Pro Asn Ala Ser Asp Gly Ser Asn Gln Gly Gln Trp Gln Pro Asn
                565                 570                 575

Gly Asn Gln Gly Asn Ser Gln Asn Pro Thr Gly Asn Asp Phe Val Ser
            580                 585                 590

Gln Arg Phe Leu Ala Leu Ala Asn Gly Ala Tyr Lys Tyr Asn Pro Tyr
        595                 600                 605

Ile Leu Asn Gln Ile Asn Gln Leu Gly Lys Glu Tyr Gly Glu Val Thr
        610                 615                 620

Asp Glu Asp Ile Tyr Asn Ile Ile Arg Lys Gln Asn Phe Ser Gly Asn
625                 630                 635                 640

Ala Tyr Leu Asn Gly Leu Gln Gln Ser Asn Tyr Phe Arg Phe Gln
                645                 650                 655

Tyr Phe Asn Pro Leu Lys Ser Glu Arg Tyr Tyr Arg Asn Leu Asp Glu
                660                 665                 670

Gln Val Leu Ala Leu Ile Thr Gly Glu Ile Gly Ser Met Pro Asp Leu
```

```
                     675                 680                 685
Lys Lys Pro Glu Asp Lys Pro Asp Ser Lys Gln Arg Ser Phe Glu Pro
                690                 695                 700
His Glu Lys Asp Asp Phe Thr Val Val Lys Lys Gln Glu Asp Asn Lys
705                 710                 715                 720

Lys Ser Ala Ser Thr Ala Tyr Ser
                725
```

<210> SEQ ID NO 68
<211> LENGTH: 722
<212> TYPE: PRT
<213> ORGANISM: Artificial sequence
<220> FEATURE:
<223> OTHER INFORMATION: Chimeric polypeptide

<400> SEQUENCE: 68

```
Ala Lys Asp Asn Leu Asn Gly Glu Lys Pro Thr Thr Asn Leu Asn His
1               5                   10                  15

Asn Val Thr Ser Pro Ser Val Asn Ser Glu Met Asn Asn Asn Glu Thr
                20                  25                  30

Gly Thr Pro His Glu Ser Asn Gln Ala Gly Asn Glu Gly Thr Gly Ser
                35                  40                  45

Asn Ser Arg Asp Ala Asn Pro Asp Ser Asn Asn Val Lys Pro Asp Ser
        50                  55                  60

Asn Asn Gln Asn Pro Ser Pro Asp Ser Lys Pro Asp Pro Asn Asn Pro
65                  70                  75                  80

Asn Pro Gly Pro Asn Pro Lys Pro Asp Pro Lys Pro Lys Pro Asn
                85                  90                  95

Pro Glu Pro Lys Pro Asp Pro Lys Pro Asp Pro Asp Lys Pro Lys Pro
                100                 105                 110

Asn Pro Asp Pro Lys Pro Asp Pro Lys Pro Lys Pro Asn Pro Asp
            115                 120                 125

Pro Lys Pro Asp Pro Asp Lys Pro Lys Pro Asn Pro Asp Pro Lys Pro
        130                 135                 140

Asp Pro Asn Pro Asn Pro Lys Pro Asp Pro Asn Lys Pro Asn Pro Asn
145                 150                 155                 160

Pro Ser Pro Asn Pro Asn Gln Pro Gly Asp Ser Asn Gln Ser Gly Gly
                165                 170                 175

Ser Lys Asn Gly Gly Thr Trp Asn Pro Asn Ala Ser Asp Gly Ser Asn
                180                 185                 190

Gln Gly Gln Trp Gln Pro Asn Gly Asn Gln Gly Asn Ser Gln Asn Pro
            195                 200                 205

Thr Gly Asn Asp Phe Val Ser Gln Arg Phe Leu Ala Leu Ala Asn Gly
        210                 215                 220

Ala Tyr Lys Tyr Asn Pro Tyr Ile Leu Asn Gln Ile Asn Gln Leu Gly
225                 230                 235                 240

Lys Glu Tyr Gly Glu Val Thr Asp Glu Asp Ile Tyr Asn Ile Ile Arg
                245                 250                 255

Lys Gln Asn Phe Ser Gly Asn Ala Tyr Leu Asn Gly Leu Gln Gln Gln
            260                 265                 270

Ser Asn Tyr Phe Arg Phe Gln Tyr Phe Asn Pro Leu Lys Ser Glu Arg
        275                 280                 285

Tyr Tyr Arg Asn Leu Asp Glu Gln Val Leu Ala Leu Ile Thr Gly Glu
                290                 295                 300

Ile Gly Ser Met Pro Asp Leu Lys Lys Pro Glu Asp Lys Pro Asp Ser
```

```
             305                 310                 315                 320
Lys Gln Arg Ser Phe Glu Pro His Glu Lys Asp Asp Phe Thr Val Val
             325                 330                 335
Lys Lys Gln Glu Asp Asn Lys Lys Ser Ala Ser Thr Ala Tyr Ser Gly
             340                 345                 350
Ser Gly Gly Gly Ala Gly Phe Leu Asn Lys Ser Lys Asn Glu Gln Ala
             355                 360                 365
Ala Leu Lys Ala Gln Gln Ala Ala Ile Lys Glu Glu Ala Ser Ala Asn
             370                 375                 380
Asn Leu Ser Asp Thr Ser Gln Glu Ala Gln Glu Ile Gln Glu Ala Lys
385              390                 395                 400
Arg Glu Ala Gln Ala Glu Ala Asp Lys Ser Val Ala Val Ser Asn Lys
                 405                 410                 415
Glu Ser Lys Ala Val Ala Leu Lys Ala Gln Gln Ala Ala Ile Lys Glu
                 420                 425                 430
Glu Ala Ser Ala Asn Asn Leu Ser Asp Thr Ser Gln Glu Ala Gln Glu
                 435                 440                 445
Ile Gln Glu Ala Lys Lys Glu Ala Gln Ala Glu Thr Asp Lys Ser Ala
             450                 455                 460
Ala Val Ser Asn Glu Glu Pro Lys Ala Val Ala Leu Lys Ala Gln Gln
465              470                 475                 480
Ala Ala Ile Lys Glu Glu Ala Ser Ala Asn Asn Leu Ser Asp Ile Ser
                 485                 490                 495
Gln Glu Ala Gln Glu Val Gln Glu Ala Lys Lys Glu Ala Gln Ala Glu
                 500                 505                 510
Lys Asp Ser Asp Thr Leu Thr Lys Asp Ala Ser Ala Ala Lys Val Glu
                 515                 520                 525
Val Ser Lys Pro Glu Ser Gln Ala Glu Arg Leu Ala Asn Ala Ala Lys
             530                 535                 540
Gln Lys Gln Ala Lys Leu Thr Pro Gly Ser Lys Glu Ser Gln Leu Thr
545              550                 555                 560
Glu Ala Leu Phe Ala Glu Lys Pro Val Ala Lys Asn Asp Leu Lys Glu
                 565                 570                 575
Ile Pro Gln Leu Val Thr Lys Lys Asn Asp Val Ser Glu Thr Glu Thr
             580                 585                 590
Val Asn Ile Asp Asn Lys Asp Thr Val Lys Gln Lys Glu Ala Lys Phe
             595                 600                 605
Glu Asn Gly Val Ile Thr Arg Lys Ala Asp Glu Lys Thr Thr Asn Asn
             610                 615                 620
Thr Ala Val Asp Lys Lys Ser Gly Lys Gln Ser Lys Lys Thr Thr Pro
625              630                 635                 640
Ser Asn Lys Arg Asn Ala Ser Lys Ala Ser Thr Asn Lys Thr Ser Gly
                 645                 650                 655
Gln Lys Lys Gln His Asn Lys Lys Ser Ser Gln Gly Ala Lys Lys Gln
                 660                 665                 670
Ser Ser Ser Ser Lys Ser Thr Gln Lys Asn Asn Gln Thr Ser Asn Lys
             675                 680                 685
Asn Ser Lys Thr Thr Asn Ala Lys Ser Ser Asn Ala Ser Lys Thr Pro
             690                 695                 700
Asn Ala Lys Val Glu Lys Ala Lys Ser Lys Ile Glu Lys Arg Thr Phe
705              710                 715                 720
Asn Asp
```

<210> SEQ ID NO 69
<211> LENGTH: 867
<212> TYPE: PRT
<213> ORGANISM: Artificial sequence
<220> FEATURE:
<223> OTHER INFORMATION: Chimeric polypeptide

<400> SEQUENCE: 69

```
Ala Cys Gly Asn Asp Asp Gly Lys Asp Lys Asp Gly Lys Val Thr Ile
1               5                   10                  15

Lys Thr Thr Val Tyr Pro Leu Gln Ser Phe Ala Glu Gln Ile Gly Gly
                20                  25                  30

Lys His Val Lys Val Ser Ser Ile Tyr Pro Ala Gly Thr Asp Leu His
            35                  40                  45

Ser Tyr Glu Pro Thr Gln Lys Asp Ile Leu Ser Ala Ser Lys Ser Asp
        50                  55                  60

Leu Phe Met Tyr Thr Gly Asp Asn Leu Asp Pro Val Ala Lys Lys Val
65                  70                  75                  80

Ala Ser Thr Ile Lys Asp Lys Asp Lys Leu Ser Leu Glu Asp Lys
                85                  90                  95

Leu Asp Lys Ala Lys Leu Leu Thr Asp Gln His Glu His Gly Glu Glu
            100                 105                 110

His Glu His Glu Gly His Asp His Glu Lys Glu His His His His
        115                 120                 125

Gly Gly Tyr Asp Pro His Val Trp Leu Asp Pro Lys Ile Asn Gln Thr
        130                 135                 140

Phe Ala Lys Glu Ile Lys Asp Glu Leu Val Lys Lys Asp Pro Lys His
145                 150                 155                 160

Lys Asp Asp Tyr Glu Lys Asn Tyr Lys Lys Leu Asn Asp Asp Leu Lys
                165                 170                 175

Lys Ile Asp Asn Asp Met Lys Gln Val Thr Lys Asp Lys Gln Gly Asn
            180                 185                 190

Ala Val Phe Ile Ser His Glu Ser Ile Gly Tyr Leu Ala Asp Arg Tyr
        195                 200                 205

Gly Phe Val Gln Lys Gly Ile Gln Asn Met Asn Ala Glu Asp Pro Ser
        210                 215                 220

Gln Lys Glu Leu Thr Lys Ile Val Lys Glu Ile Arg Asp Ser Asn Ala
225                 230                 235                 240

Lys Tyr Ile Leu Tyr Glu Asp Asn Val Ala Asn Lys Val Thr Glu Thr
                245                 250                 255

Ile Arg Lys Glu Thr Asp Ala Lys Pro Leu Lys Phe Tyr Asn Met Glu
            260                 265                 270

Ser Leu Asn Lys Glu Gln Gln Lys Lys Asp Asn Ile Thr Tyr Gln Ser
        275                 280                 285

Leu Met Lys Ser Asn Ile Glu Asn Ile Gly Lys Ala Leu Asp Ser Gly
        290                 295                 300

Val Lys Val Lys Asp Asp Lys Ala Glu Ser Lys His Asp Lys Ala Ile
305                 310                 315                 320

Ser Asp Gly Tyr Phe Lys Asp Glu Gln Val Lys Asp Arg Glu Leu Ser
                325                 330                 335

Asp Tyr Ala Gly Glu Trp Gln Ser Val Tyr Pro Tyr Leu Lys Asp Gly
            340                 345                 350

Thr Leu Asp Glu Val Met Glu His Lys Ala Glu Asn Asp Pro Lys Lys
        355                 360                 365
```

```
Ser Ala Lys Asp Leu Lys Ala Tyr Tyr Asp Lys Gly Tyr Lys Thr Asp
    370                 375                 380

Ile Thr Asn Ile Asp Ile Lys Gly Asn Glu Ile Thr Phe Thr Lys Asp
385                 390                 395                 400

Gly Lys Lys His Thr Gly Lys Tyr Glu Tyr Asn Gly Lys Lys Thr Leu
                405                 410                 415

Lys Tyr Pro Lys Gly Asn Arg Gly Val Arg Phe Met Phe Lys Leu Val
            420                 425                 430

Asp Gly Asn Asp Lys Asp Leu Pro Lys Phe Ile Gln Phe Ser Asp His
        435                 440                 445

Asn Ile Ala Pro Lys Lys Ala Glu His Phe His Ile Phe Met Gly Asn
    450                 455                 460

Asp Asn Asp Ala Leu Leu Lys Glu Met Asp Asn Trp Pro Thr Tyr Tyr
465                 470                 475                 480

Pro Ser Lys Leu Asn Lys Asp Gln Ile Lys Glu Met Leu Ala His
                485                 490                 495

Gly Ser Gly Gly Gly Ala Gly Phe Leu Asn Lys Ser Lys Asn Glu Gln
            500                 505                 510

Ala Ala Leu Lys Ala Gln Gln Ala Ala Ile Lys Glu Glu Ala Ser Ala
        515                 520                 525

Asn Asn Leu Ser Asp Thr Ser Gln Glu Ala Gln Glu Ile Gln Glu Ala
    530                 535                 540

Lys Arg Glu Ala Gln Ala Glu Ala Asp Lys Ser Val Ala Val Ser Asn
545                 550                 555                 560

Lys Glu Ser Lys Ala Val Ala Leu Lys Ala Gln Gln Ala Ala Ile Lys
                565                 570                 575

Glu Glu Ala Ser Ala Asn Asn Leu Ser Asp Thr Ser Gln Glu Ala Gln
            580                 585                 590

Glu Ile Gln Glu Ala Lys Lys Glu Ala Gln Ala Glu Thr Asp Lys Ser
        595                 600                 605

Ala Ala Val Ser Asn Glu Glu Pro Lys Ala Val Ala Leu Lys Ala Gln
    610                 615                 620

Gln Ala Ala Ile Lys Glu Glu Ala Ser Ala Asn Asn Leu Ser Asp Ile
625                 630                 635                 640

Ser Gln Glu Ala Gln Glu Val Gln Glu Ala Lys Lys Glu Ala Gln Ala
                645                 650                 655

Glu Lys Asp Ser Asp Thr Leu Thr Lys Asp Ala Ser Ala Ala Lys Val
            660                 665                 670

Glu Val Ser Lys Pro Glu Ser Gln Ala Glu Arg Leu Ala Asn Ala Ala
        675                 680                 685

Lys Gln Lys Gln Ala Lys Leu Thr Pro Gly Ser Lys Glu Ser Gln Leu
    690                 695                 700

Thr Glu Ala Leu Phe Ala Glu Lys Pro Val Ala Lys Asn Asp Leu Lys
705                 710                 715                 720

Glu Ile Pro Gln Leu Val Thr Lys Lys Asn Asp Val Ser Glu Thr Glu
                725                 730                 735

Thr Val Asn Ile Asp Asn Lys Asp Thr Val Lys Gln Lys Glu Ala Lys
            740                 745                 750

Phe Glu Asn Gly Val Ile Thr Arg Lys Ala Asp Glu Lys Thr Thr Asn
        755                 760                 765

Asn Thr Ala Val Asp Lys Lys Ser Gly Lys Gln Ser Lys Lys Thr Thr
    770                 775                 780

Pro Ser Asn Lys Arg Asn Ala Ser Lys Ala Ser Thr Asn Lys Thr Ser
```

```
                785                 790                 795                 800
Gly Gln Lys Lys Gln His Asn Lys Ser Ser Gln Gly Ala Lys Lys
                805                 810                 815

Gln Ser Ser Ser Lys Ser Thr Gln Lys Asn Asn Gln Thr Ser Asn
            820                 825                 830

Lys Asn Ser Lys Thr Thr Asn Ala Lys Ser Ser Asn Ala Ser Lys Thr
            835                 840                 845

Pro Asn Ala Lys Val Glu Lys Ala Lys Ser Lys Ile Glu Lys Arg Thr
850                 855                 860

Phe Asn Asp
865

<210> SEQ ID NO 70
<211> LENGTH: 797
<212> TYPE: PRT
<213> ORGANISM: Artificial sequence
<220> FEATURE:
<223> OTHER INFORMATION: Chimeric polypeptide

<400> SEQUENCE: 70

Met Thr Glu Lys Glu Lys Met Leu Ala Glu Lys Trp Tyr Asp Ala Asn
1               5                   10                  15

Phe Asp Gln Asp Leu Ile Asn Glu Arg Ala Arg Ala Lys Asp Ile Cys
            20                  25                  30

Phe Glu Leu Asn His Thr Lys Pro Ser Asp Lys Asn Lys Arg Lys Glu
        35                  40                  45

Leu Ile Asp Glu Leu Phe Gln Thr Thr Thr Asp Asn Val Ser Ile Ser
50                  55                  60

Ile Pro Phe Asp Thr Asp Tyr Gly Trp Asn Val Lys Leu Gly Lys Asn
65                  70                  75                  80

Val Tyr Val Asn Thr Asn Cys Tyr Phe Met Asp Gly Gly Gln Ile Thr
                85                  90                  95

Ile Gly Asp Asn Val Phe Ile Gly Pro Asn Cys Gly Phe Tyr Thr Ala
            100                 105                 110

Thr His Pro Leu Asn Phe His His Arg Asn Glu Gly Phe Glu Lys Ala
        115                 120                 125

Gly Pro Ile Asn Ile Gly Ser Asn Thr Trp Phe Gly Gly His Val Ala
    130                 135                 140

Val Leu Pro Gly Val Thr Ile Gly Glu Gly Ser Val Ile Gly Ala Gly
145                 150                 155                 160

Ser Val Val Thr Lys Asp Ile Pro Pro His Ser Leu Ala Val Gly Asn
                165                 170                 175

Pro Cys Lys Val Val Arg Lys Ile Asp Asn Glu Val Pro Ser Glu Ala
            180                 185                 190

Leu Asn Asp Glu Thr Leu Asn Gly Ser Gly Gly Ala Asp Thr Pro
        195                 200                 205

Gln Lys Asp Thr Thr Ala Lys Thr Thr Ser His Asp Ser Lys Lys Ser
    210                 215                 220

Asn Asp Asp Glu Thr Ser Lys Asp Thr Thr Ser Lys Asp Ile Asp Lys
225                 230                 235                 240

Ala Asp Asn Asn Asn Thr Ser Asn Gln Asp Asn Asn Asp Lys Lys Phe
                245                 250                 255

Lys Thr Ile Asp Asp Ser Thr Ser Asp Ser Asn Asn Ile Ile Asp Phe
            260                 265                 270

Ile Tyr Lys Asn Leu Pro Gln Thr Asn Ile Asn Gln Leu Leu Thr Lys
```

```
            275                 280                 285
Asn Lys Tyr Asp Asp Asn Tyr Ser Leu Thr Thr Leu Ile Gln Asn Leu
    290                 295                 300
Phe Asn Leu Asn Ser Asp Ile Ser Asp Tyr Glu Gln Pro Arg Asn Gly
305                 310                 315                 320
Glu Lys Ser Thr Asn Asp Ser Asn Lys Asn Ser Asp Asn Ser Ile Lys
                325                 330                 335
Asn Asp Thr Asp Thr Gln Ser Ser Lys Gln Asp Lys Ala Asp Asn Gln
                340                 345                 350
Lys Ala Pro Lys Ser Asn Asn Thr Lys Pro Ser Thr Ser Asn Lys Gln
                355                 360                 365
Pro Asn Ser Pro Lys Pro Thr Gln Pro Asn Gln Ser Asn Ser Gln Pro
370                 375                 380
Ala Ser Asp Asp Lys Ala Asn Gln Lys Ser Ser Lys Asp Asn Gln
385                 390                 395                 400
Ser Met Ser Asp Ser Ala Leu Asp Ser Ile Leu Asp Gln Tyr Ser Glu
                405                 410                 415
Asp Ala Lys Lys Thr Gln Lys Asp Tyr Ala Ser Gln Ser Lys Lys Asp
                420                 425                 430
Lys Asn Glu Lys Ser Asn Thr Lys Asn Pro Gln Leu Pro Thr Gln Asp
                435                 440                 445
Glu Leu Lys His Lys Ser Lys Pro Ala Gln Ser Phe Asn Asn Asp Val
    450                 455                 460
Asn Gln Lys Asp Thr Arg Ala Thr Ser Leu Phe Glu Thr Asp Pro Ser
465                 470                 475                 480
Ile Ser Asn Asn Asp Asp Ser Gly Gln Phe Asn Val Val Asp Ser Lys
                485                 490                 495
Asp Thr Arg Gln Phe Val Lys Ser Ile Ala Lys Asp Ala His Arg Ile
                500                 505                 510
Gly Gln Asp Asn Asp Ile Tyr Ala Ser Val Met Ile Ala Gln Ala Ile
                515                 520                 525
Leu Glu Ser Asp Ser Gly Arg Ser Ala Leu Ala Lys Ser Pro Asn His
    530                 535                 540
Asn Leu Phe Gly Ile Lys Gly Ala Phe Glu Gly Asn Ser Val Pro Phe
545                 550                 555                 560
Asn Thr Leu Glu Ala Asp Gly Asn Lys Leu Tyr Ser Ile Asn Ala Gly
                565                 570                 575
Phe Arg Lys Tyr Pro Ser Thr Lys Glu Ser Leu Lys Asp Tyr Ser Asp
                580                 585                 590
Leu Ile Lys Asn Gly Ile Asp Gly Asn Arg Thr Ile Tyr Lys Pro Thr
                595                 600                 605
Trp Lys Ser Glu Ala Asp Ser Tyr Lys Asp Ala Thr Ser His Leu Ser
    610                 615                 620
Lys Thr Tyr Ala Thr Asp Pro Asn Tyr Ala Lys Lys Leu Asn Ser Ile
625                 630                 635                 640
Ile Lys His Tyr Gln Leu Thr Gln Phe Asp Asp Glu Arg Met Pro Asp
                645                 650                 655
Leu Asp Lys Tyr Glu Arg Ser Ile Lys Asp Tyr Asp Asp Ser Ser Asp
                660                 665                 670
Glu Phe Lys Pro Phe Arg Glu Val Ser Asp Ser Met Pro Tyr Pro His
                675                 680                 685
Gly Gln Cys Thr Trp Tyr Val Tyr Asn Arg Met Lys Gln Phe Gly Thr
    690                 695                 700
```

-continued

Ser Ile Ser Gly Asp Leu Gly Asp Ala His Asn Trp Asn Asn Arg Ala
705                 710                 715                 720

Gln Tyr Arg Asp Tyr Gln Val Ser His Thr Pro Lys Arg His Ala Ala
            725                 730                 735

Val Val Phe Glu Ala Gly Gln Phe Gly Ala Asp Gln His Tyr Gly His
        740                 745                 750

Val Ala Phe Val Glu Lys Val Asn Ser Asp Gly Ser Ile Val Ile Ser
    755                 760                 765

Glu Ser Asn Val Lys Gly Leu Gly Ile Ile Ser His Arg Thr Ile Asn
770                 775                 780

Ala Ala Ala Ala Glu Glu Leu Ser Tyr Ile Thr Gly Lys
785                 790                 795

<210> SEQ ID NO 71
<211> LENGTH: 783
<212> TYPE: PRT
<213> ORGANISM: Artificial sequence
<220> FEATURE:
<223> OTHER INFORMATION: Chimeric polypeptide

<400> SEQUENCE: 71

Ile Asp Ser Lys Asn Lys Pro Ala Asn Ser Asp Ile Lys Phe Glu Val
1               5                   10                  15

Thr Gln Lys Ser Asp Ala Val Lys Ala Leu Lys Glu Leu Pro Lys Ser
            20                  25                  30

Glu Asn Val Lys Asn Ile Tyr Gln Asp Tyr Ala Val Thr Asp Val Lys
        35                  40                  45

Thr Asp Lys Lys Gly Phe Thr His Tyr Thr Leu Gln Pro Ser Val Asp
    50                  55                  60

Gly Val His Ala Pro Asp Lys Glu Val Lys Val His Ala Asp Lys Ser
65                  70                  75                  80

Gly Lys Val Val Leu Ile Asn Gly Asp Thr Asp Ala Lys Lys Val Lys
                85                  90                  95

Pro Thr Asn Lys Val Thr Leu Ser Lys Asp Asp Ala Ala Asp Lys Ala
            100                 105                 110

Phe Lys Ala Val Lys Ile Asp Lys Asn Lys Ala Lys Asn Leu Lys Asp
        115                 120                 125

Lys Val Ile Lys Glu Asn Lys Val Glu Ile Asp Gly Asp Ser Asn Lys
    130                 135                 140

Tyr Val Tyr Asn Val Glu Leu Ile Thr Val Thr Pro Glu Ile Ser His
145                 150                 155                 160

Trp Lys Val Lys Ile Asp Ala Gln Thr Gly Glu Ile Leu Glu Lys Met
                165                 170                 175

Asn Leu Val Lys Glu Ala Ala Glu Thr Gly Lys Gly Lys Gly Val Leu
            180                 185                 190

Gly Asp Thr Lys Asp Ile Asn Ile Asn Ser Ile Asp Gly Gly Phe Ser
        195                 200                 205

Leu Glu Asp Leu Thr His Gln Gly Lys Leu Ser Ala Phe Ser Phe Asn
    210                 215                 220

Asp Gln Thr Gly Gln Ala Thr Leu Ile Thr Asn Glu Asp Glu Asn Phe
225                 230                 235                 240

Val Lys Asp Glu Gln Arg Ala Gly Val Asp Ala Asn Tyr Tyr Ala Lys
                245                 250                 255

Gln Thr Tyr Asp Tyr Tyr Lys Asp Thr Phe Gly Arg Glu Ser Tyr Asp
            260                 265                 270

```
Asn Gln Gly Ser Pro Ile Val Ser Leu Thr His Val Asn Asn Tyr Gly
            275                 280                 285
Gly Gln Asp Asn Arg Asn Asn Ala Ala Trp Ile Gly Asp Lys Met Ile
        290                 295                 300
Tyr Gly Asp Gly Asp Gly Arg Thr Phe Thr Ser Leu Ser Gly Ala Asn
305                 310                 315                 320
Asp Val Val Ala His Glu Leu Thr His Gly Val Thr Gln Glu Thr Ala
                325                 330                 335
Asn Leu Glu Tyr Lys Asp Gln Ser Gly Ala Leu Asn Glu Ser Phe Ser
            340                 345                 350
Asp Val Phe Gly Tyr Phe Val Asp Asp Glu Asp Phe Leu Met Gly Glu
        355                 360                 365
Asp Val Tyr Thr Pro Gly Lys Glu Gly Asp Ala Leu Arg Ser Met Ser
370                 375                 380
Asn Pro Glu Gln Phe Gly Gln Pro Ala His Met Lys Asp Tyr Val Phe
385                 390                 395                 400
Thr Glu Lys Asp Asn Gly Gly Val His Thr Asn Ser Gly Ser Gly Gly
                405                 410                 415
Gly Ala Gly Phe Leu Asn Lys Ser Lys Asn Glu Gln Ala Ala Leu Lys
            420                 425                 430
Ala Gln Gln Ala Ala Ile Lys Glu Glu Ala Ser Ala Asn Asn Leu Ser
        435                 440                 445
Asp Thr Ser Gln Glu Ala Gln Glu Ile Gln Glu Ala Lys Arg Glu Ala
    450                 455                 460
Gln Ala Glu Ala Asp Lys Ser Val Ala Val Ser Asn Lys Glu Ser Lys
465                 470                 475                 480
Ala Val Ala Leu Lys Ala Gln Gln Ala Ala Ile Lys Glu Glu Ala Ser
                485                 490                 495
Ala Asn Asn Leu Ser Asp Thr Ser Gln Glu Ala Gln Glu Ile Gln Glu
            500                 505                 510
Ala Lys Lys Glu Ala Gln Ala Glu Thr Asp Lys Ser Ala Ala Val Ser
        515                 520                 525
Asn Glu Glu Pro Lys Ala Val Ala Leu Lys Ala Gln Gln Ala Ala Ile
    530                 535                 540
Lys Glu Glu Ala Ser Ala Asn Asn Leu Ser Asp Ile Ser Gln Glu Ala
545                 550                 555                 560
Gln Glu Val Gln Glu Ala Lys Lys Glu Ala Gln Ala Glu Lys Asp Ser
                565                 570                 575
Asp Thr Leu Thr Lys Asp Ala Ser Ala Lys Val Glu Val Ser Lys
            580                 585                 590
Pro Glu Ser Gln Ala Glu Arg Leu Ala Asn Ala Ala Lys Gln Lys Gln
        595                 600                 605
Ala Lys Leu Thr Pro Gly Ser Lys Glu Ser Gln Leu Thr Glu Ala Leu
    610                 615                 620
Phe Ala Glu Lys Pro Val Ala Lys Asn Asp Leu Lys Glu Ile Pro Gln
625                 630                 635                 640
Leu Val Thr Lys Lys Asn Asp Val Ser Glu Thr Glu Thr Val Asn Ile
                645                 650                 655
Asp Asn Lys Asp Thr Val Lys Gln Lys Glu Ala Lys Phe Glu Asn Gly
            660                 665                 670
Val Ile Thr Arg Lys Ala Asp Glu Lys Thr Thr Asn Asn Thr Ala Val
        675                 680                 685
```

```
Asp Lys Lys Ser Gly Lys Gln Ser Lys Lys Thr Thr Pro Ser Asn Lys
    690             695                 700

Arg Asn Ala Ser Lys Ala Ser Thr Asn Lys Thr Ser Gly Gln Lys Lys
705             710                 715                 720

Gln His Asn Lys Lys Ser Ser Gln Gly Ala Lys Lys Gln Ser Ser Ser
                725                 730                 735

Ser Lys Ser Thr Gln Lys Asn Asn Gln Thr Ser Asn Lys Asn Ser Lys
            740                 745                 750

Thr Thr Asn Ala Lys Ser Ser Asn Ala Ser Lys Thr Pro Asn Ala Lys
            755                 760                 765

Val Glu Lys Ala Lys Ser Lys Ile Glu Lys Arg Thr Phe Asn Asp
770             775                 780

<210> SEQ ID NO 72
<211> LENGTH: 769
<212> TYPE: PRT
<213> ORGANISM: Artificial sequence
<220> FEATURE:
<223> OTHER INFORMATION: Chimeric polypeptide

<400> SEQUENCE: 72

Ile Asp Ser Lys Asn Lys Pro Ala Asn Ser Asp Ile Lys Phe Glu Val
1               5                   10                  15

Thr Gln Lys Ser Asp Ala Val Lys Ala Leu Lys Glu Leu Pro Lys Ser
            20                  25                  30

Glu Asn Val Lys Asn Ile Tyr Gln Asp Tyr Ala Val Thr Asp Val Lys
            35                  40                  45

Thr Asp Lys Lys Gly Phe Thr His Tyr Thr Leu Gln Pro Ser Val Asp
50                  55                  60

Gly Val His Ala Pro Asp Lys Glu Val Lys Val His Ala Asp Lys Ser
65                  70                  75                  80

Gly Lys Val Val Leu Ile Asn Gly Asp Thr Asp Ala Lys Lys Val Lys
                85                  90                  95

Pro Thr Asn Lys Val Thr Leu Ser Lys Asp Asp Ala Ala Asp Lys Ala
            100                 105                 110

Phe Lys Ala Val Lys Ile Asp Lys Asn Lys Ala Lys Asn Leu Lys Asp
            115                 120                 125

Lys Val Ile Lys Glu Asn Lys Val Glu Ile Asp Gly Asp Ser Asn Lys
130                 135                 140

Tyr Val Tyr Asn Val Glu Leu Ile Thr Val Thr Pro Glu Ile Ser His
145                 150                 155                 160

Trp Lys Val Lys Ile Asp Ala Gln Thr Gly Glu Ile Leu Glu Lys Met
                165                 170                 175

Asn Leu Val Lys Glu Ala Ala Glu Thr Gly Lys Gly Lys Gly Val Leu
            180                 185                 190

Gly Asp Thr Lys Asp Ile Asn Ile Asn Ser Ile Asp Gly Gly Phe Ser
            195                 200                 205

Leu Glu Asp Leu Thr His Gln Gly Lys Leu Ser Ala Phe Ser Phe Asn
210                 215                 220

Asp Gln Thr Gly Gln Ala Thr Leu Ile Thr Asn Glu Asp Glu Asn Phe
225                 230                 235                 240

Val Lys Asp Glu Gln Arg Ala Gly Val Asp Ala Asn Tyr Tyr Ala Lys
                245                 250                 255

Gln Thr Tyr Asp Tyr Tyr Lys Asp Thr Phe Gly Arg Glu Ser Tyr Asp
            260                 265                 270
```

-continued

```
Asn Gln Gly Ser Pro Ile Val Ser Leu Thr His Val Asn Asn Tyr Gly
            275                 280                 285
Gly Gln Asp Asn Arg Asn Asn Ala Ala Trp Ile Gly Asp Lys Met Ile
        290                 295                 300
Tyr Gly Asp Gly Asp Gly Arg Thr Phe Thr Ser Leu Ser Gly Ala Asn
305                 310                 315                 320
Asp Val Val Ala His Glu Leu Thr His Gly Val Thr Gln Glu Thr Ala
                325                 330                 335
Asn Leu Glu Tyr Lys Asp Gln Ser Gly Ala Leu Asn Glu Ser Phe Ser
            340                 345                 350
Asp Val Phe Gly Tyr Phe Val Asp Asp Glu Asp Phe Leu Met Gly Glu
        355                 360                 365
Asp Val Tyr Thr Pro Gly Lys Glu Gly Asp Ala Leu Arg Ser Met Ser
370                 375                 380
Asn Pro Glu Gln Phe Gly Gln Pro Ala His Met Lys Asp Tyr Val Phe
385                 390                 395                 400
Thr Glu Lys Asp Asn Gly Val His Thr Asn Ser Gly Ser Gly Gly
                405                 410                 415
Gly Ala Ala Lys Asp Asn Leu Asn Gly Glu Lys Pro Thr Thr Asn Leu
            420                 425                 430
Asn His Asn Val Thr Ser Pro Ser Val Asn Ser Glu Met Asn Asn Asn
        435                 440                 445
Glu Thr Gly Thr Pro His Glu Ser Asn Gln Ala Gly Asn Glu Gly Thr
        450                 455                 460
Gly Ser Asn Ser Arg Asp Ala Asn Pro Asp Ser Asn Asn Val Lys Pro
465                 470                 475                 480
Asp Ser Asn Asn Gln Asn Pro Ser Pro Asp Ser Lys Pro Asp Pro Asn
                485                 490                 495
Asn Pro Asn Pro Gly Pro Asn Pro Lys Pro Asp Pro Asp Lys Pro Lys
            500                 505                 510
Pro Asn Pro Glu Pro Lys Pro Asp Pro Lys Pro Asp Pro Asp Lys Pro
        515                 520                 525
Lys Pro Asn Pro Asp Pro Lys Pro Asp Pro Asp Lys Pro Lys Pro Asn
530                 535                 540
Pro Asp Pro Lys Pro Asp Pro Asp Lys Pro Lys Pro Asn Pro Asp Pro
545                 550                 555                 560
Lys Pro Asp Pro Asn Pro Asn Pro Lys Pro Asp Pro Asn Lys Pro Asn
                565                 570                 575
Pro Asn Pro Ser Pro Asn Pro Asn Gln Pro Gly Asp Ser Asn Gln Ser
            580                 585                 590
Gly Gly Ser Lys Asn Gly Gly Thr Trp Asn Pro Asn Ala Ser Asp Gly
        595                 600                 605
Ser Asn Gln Gly Gln Trp Gln Pro Asn Gly Asn Gln Gly Asn Ser Gln
        610                 615                 620
Asn Pro Thr Gly Asn Asp Phe Val Ser Gln Arg Phe Leu Ala Leu Ala
625                 630                 635                 640
Asn Gly Ala Tyr Lys Tyr Asn Pro Tyr Ile Leu Asn Gln Ile Asn Gln
                645                 650                 655
Leu Gly Lys Glu Tyr Gly Glu Val Thr Asp Glu Asp Ile Tyr Asn Ile
            660                 665                 670
Ile Arg Lys Gln Asn Phe Ser Gly Asn Ala Tyr Leu Asn Gly Leu Gln
        675                 680                 685
Gln Gln Ser Asn Tyr Phe Arg Phe Gln Tyr Phe Asn Pro Leu Lys Ser
```

```
                690             695             700
Glu Arg Tyr Tyr Arg Asn Leu Asp Glu Gln Val Leu Ala Leu Ile Thr
705             710             715             720

Gly Glu Ile Gly Ser Met Pro Asp Leu Lys Lys Pro Glu Asp Lys Pro
            725             730             735

Asp Ser Lys Gln Arg Ser Phe Glu Pro His Glu Lys Asp Asp Phe Thr
            740             745             750

Val Val Lys Lys Gln Glu Asp Asn Lys Lys Ser Ala Ser Thr Ala Tyr
            755             760             765

Ser

<210> SEQ ID NO 73
<211> LENGTH: 814
<212> TYPE: PRT
<213> ORGANISM: Artificial sequence
<220> FEATURE:
<223> OTHER INFORMATION: Chimeric polypeptide

<400> SEQUENCE: 73

Ile Asp Ser Lys Asn Lys Pro Ala Asn Ser Asp Ile Lys Phe Glu Val
1               5                  10                  15

Thr Gln Lys Ser Asp Ala Val Lys Ala Leu Lys Glu Leu Pro Lys Ser
            20                  25                  30

Glu Asn Val Lys Asn Ile Tyr Gln Asp Tyr Ala Val Thr Asp Val Lys
        35                  40                  45

Thr Asp Lys Lys Gly Phe Thr His Tyr Thr Leu Gln Pro Ser Val Asp
    50                  55                  60

Gly Val His Ala Pro Asp Lys Glu Val Lys Val His Ala Asp Lys Ser
65                  70                  75                  80

Gly Lys Val Val Leu Ile Asn Gly Asp Thr Asp Ala Lys Lys Val Lys
                85                  90                  95

Pro Thr Asn Lys Val Thr Leu Ser Lys Asp Asp Ala Ala Asp Lys Ala
            100                 105                 110

Phe Lys Ala Val Lys Ile Asp Lys Asn Lys Ala Lys Asn Leu Lys Asp
        115                 120                 125

Lys Val Ile Lys Glu Asn Lys Val Glu Ile Asp Gly Asp Ser Asn Lys
    130                 135                 140

Tyr Val Tyr Asn Val Glu Leu Ile Thr Val Thr Pro Glu Ile Ser His
145                 150                 155                 160

Trp Lys Val Lys Ile Asp Ala Gln Thr Gly Glu Ile Leu Glu Lys Met
                165                 170                 175

Asn Leu Val Lys Glu Ala Ala Glu Thr Gly Lys Gly Lys Gly Val Leu
            180                 185                 190

Gly Asp Thr Lys Asp Ile Asn Ile Asn Ser Ile Asp Gly Gly Phe Ser
        195                 200                 205

Leu Glu Asp Leu Thr His Gln Gly Lys Leu Ser Ala Phe Ser Phe Asn
    210                 215                 220

Asp Gln Thr Gly Gln Ala Thr Leu Ile Thr Asn Glu Asp Glu Asn Phe
225                 230                 235                 240

Val Lys Asp Glu Gln Arg Ala Gly Val Asp Ala Asn Tyr Tyr Ala Lys
                245                 250                 255

Gln Thr Tyr Asp Tyr Tyr Lys Asp Thr Phe Gly Arg Glu Ser Tyr Asp
            260                 265                 270

Asn Gln Gly Ser Pro Ile Val Ser Leu Thr His Val Asn Asn Tyr Gly
        275                 280                 285
```

-continued

```
Gly Gln Asp Asn Arg Asn Asn Ala Ala Trp Ile Gly Asp Lys Met Ile
    290                 295                 300

Tyr Gly Asp Gly Asp Gly Arg Thr Phe Thr Ser Leu Ser Gly Ala Asn
305                 310                 315                 320

Asp Val Val Ala His Glu Leu Thr His Gly Val Thr Gln Glu Thr Ala
                325                 330                 335

Asn Leu Glu Tyr Lys Asp Gln Ser Gly Ala Leu Asn Glu Ser Phe Ser
            340                 345                 350

Asp Val Phe Gly Tyr Phe Val Asp Asp Glu Asp Phe Leu Met Gly Glu
        355                 360                 365

Asp Val Tyr Thr Pro Gly Lys Glu Gly Asp Ala Leu Arg Ser Met Ser
    370                 375                 380

Asn Pro Glu Gln Phe Gly Gln Pro Ala His Met Lys Asp Tyr Val Phe
385                 390                 395                 400

Thr Glu Lys Asp Asn Gly Gly Val His Thr Asn Ser Gly Ser Gly Gly
                405                 410                 415

Gly Ala Gly Ser Gly Gly Gly Ala Lys Val Ala Lys Gln Gly Gln Tyr
            420                 425                 430

Lys Asn Gln Asp Pro Ile Val Leu Val His Gly Phe Asn Gly Phe Thr
        435                 440                 445

Asp Asp Ile Asn Pro Ser Val Leu Ala His Tyr Trp Gly Gly Asn Lys
    450                 455                 460

Met Asn Ile Arg Gln Asp Leu Glu Glu Asn Gly Tyr Lys Ala Tyr Glu
465                 470                 475                 480

Ala Ser Ile Ser Ala Phe Gly Ser Asn Tyr Asp Arg Ala Val Glu Leu
                485                 490                 495

Tyr Tyr Tyr Ile Lys Gly Gly Arg Val Asp Tyr Gly Ala Ala His Ala
            500                 505                 510

Ala Lys Tyr Gly His Glu Arg Tyr Gly Lys Thr Tyr Glu Gly Ile Tyr
        515                 520                 525

Lys Asp Trp Lys Pro Gly Gln Lys Val His Leu Val Gly His Ser Met
    530                 535                 540

Gly Gly Gln Thr Ile Arg Gln Leu Glu Glu Leu Leu Arg Asn Gly Ser
545                 550                 555                 560

Arg Glu Glu Ile Glu Tyr Gln Lys Lys His Gly Gly Glu Ile Ser Pro
                565                 570                 575

Leu Phe Lys Gly Asn Asn Asp Asn Met Ile Ser Ser Ile Thr Thr Leu
            580                 585                 590

Gly Thr Pro His Asn Gly Thr His Ala Ser Asp Leu Ala Gly Asn Glu
        595                 600                 605

Ala Leu Val Arg Gln Ile Val Phe Asp Ile Gly Lys Met Phe Gly Asn
    610                 615                 620

Lys Asn Ser Arg Val Asp Phe Gly Leu Ala Gln Trp Gly Leu Lys Gln
625                 630                 635                 640

Lys Pro Asn Glu Ser Tyr Ile Asp Tyr Val Lys Arg Val Lys Gln Ser
                645                 650                 655

Asn Leu Trp Lys Ser Lys Asp Asn Gly Phe Tyr Asp Leu Thr Arg Glu
            660                 665                 670

Gly Ala Thr Asp Leu Asn Arg Lys Thr Ser Leu Asn Pro Asn Ile Val
        675                 680                 685

Tyr Lys Thr Tyr Thr Gly Glu Ala Thr His Lys Ala Leu Asn Ser Asp
    690                 695                 700
```

```
Arg Gln Lys Ala Asp Leu Asn Met Phe Phe Pro Phe Val Ile Thr Gly
705                 710                 715                 720

Asn Leu Ile Gly Lys Ala Thr Glu Lys Glu Trp Arg Glu Asn Asp Gly
                725                 730                 735

Leu Val Ser Val Ile Ser Ser Gln His Pro Phe Asn Gln Ala Tyr Thr
            740                 745                 750

Asn Ala Thr Asp Lys Ile Gln Lys Gly Ile Trp Gln Val Thr Pro Thr
        755                 760                 765

Lys His Asp Trp Asp His Val Asp Phe Val Gly Gln Asp Ser Ser Asp
    770                 775                 780

Thr Val Arg Thr Arg Glu Glu Leu Gln Asp Phe Trp His His Leu Ala
785                 790                 795                 800

Asp Asp Leu Val Lys Thr Glu Lys Val Thr Asp Thr Lys Gln
                805                 810

<210> SEQ ID NO 74
<211> LENGTH: 797
<212> TYPE: PRT
<213> ORGANISM: Artificial sequence
<220> FEATURE:
<223> OTHER INFORMATION: Chimeric polypeptide

<400> SEQUENCE: 74

Asp Thr Pro Gln Lys Asp Thr Thr Ala Lys Thr Thr Ser His Asp Ser
1               5                   10                  15

Lys Lys Ser Asn Asp Asp Glu Thr Ser Lys Asp Thr Ser Lys Asp
            20                  25                  30

Ile Asp Lys Ala Asp Asn Asn Thr Ser Asn Gln Asp Asn Asn Asp
        35                  40                  45

Lys Lys Phe Lys Thr Ile Asp Asp Ser Thr Ser Asp Ser Asn Asn Ile
50                  55                  60

Ile Asp Phe Ile Tyr Lys Asn Leu Pro Gln Thr Asn Ile Asn Gln Leu
65                  70                  75                  80

Leu Thr Lys Asn Lys Tyr Asp Asp Asn Tyr Ser Leu Thr Thr Leu Ile
                85                  90                  95

Gln Asn Leu Phe Asn Leu Asn Ser Asp Ile Ser Asp Tyr Glu Gln Pro
            100                 105                 110

Arg Asn Gly Glu Lys Ser Thr Asn Asp Ser Asn Lys Asn Ser Asp Asn
        115                 120                 125

Ser Ile Lys Asn Asp Thr Asp Thr Gln Ser Ser Lys Gln Asp Lys Ala
130                 135                 140

Asp Asn Gln Lys Ala Pro Lys Ser Asn Asn Thr Lys Pro Ser Thr Ser
145                 150                 155                 160

Asn Lys Gln Pro Asn Ser Pro Lys Pro Thr Gln Pro Asn Gln Ser Asn
                165                 170                 175

Ser Gln Pro Ala Ser Asp Asp Lys Ala Asn Gln Lys Ser Ser Ser Lys
            180                 185                 190

Asp Asn Gln Ser Met Ser Asp Ser Ala Leu Asp Ser Ile Leu Asp Gln
        195                 200                 205

Tyr Ser Glu Asp Ala Lys Lys Thr Gln Lys Asp Tyr Ala Ser Gln Ser
210                 215                 220

Lys Lys Asp Lys Asn Glu Lys Ser Asn Thr Lys Asn Pro Gln Leu Pro
225                 230                 235                 240

Thr Gln Asp Glu Leu Lys His Lys Ser Lys Pro Ala Gln Ser Phe Asn
                245                 250                 255
```

```
Asn Asp Val Asn Gln Lys Asp Thr Arg Ala Thr Ser Leu Phe Glu Thr
            260                 265                 270
Asp Pro Ser Ile Ser Asn Asn Asp Asp Ser Gly Gln Phe Asn Val Val
            275                 280             285
Asp Ser Lys Asp Thr Arg Gln Phe Val Lys Ser Ile Ala Lys Asp Ala
            290                 295                 300
His Arg Ile Gly Gln Asp Asn Asp Ile Tyr Ala Ser Val Met Ile Ala
305                 310                 315                 320
Gln Ala Ile Leu Glu Ser Asp Ser Gly Arg Ser Ala Leu Ala Lys Ser
                325                 330                 335
Pro Asn His Asn Leu Phe Gly Ile Lys Gly Ala Phe Glu Gly Asn Ser
            340                 345                 350
Val Pro Phe Asn Thr Leu Glu Ala Asp Gly Asn Lys Leu Tyr Ser Ile
            355                 360                 365
Asn Ala Gly Phe Arg Lys Tyr Pro Ser Thr Lys Glu Ser Leu Lys Asp
            370                 375                 380
Tyr Ser Asp Leu Ile Lys Asn Gly Ile Asp Gly Asn Arg Thr Ile Tyr
385                 390                 395                 400
Lys Pro Thr Trp Lys Ser Glu Ala Asp Ser Tyr Lys Asp Ala Thr Ser
            405                 410                 415
His Leu Ser Lys Thr Tyr Ala Thr Asp Pro Asn Tyr Ala Lys Lys Leu
            420                 425                 430
Asn Ser Ile Ile Lys His Tyr Gln Leu Thr Gln Phe Asp Asp Glu Arg
            435                 440                 445
Met Pro Asp Leu Asp Lys Tyr Glu Arg Ser Ile Lys Asp Tyr Asp Asp
450                 455                 460
Ser Ser Asp Glu Phe Lys Pro Phe Arg Glu Val Ser Asp Ser Met Pro
465                 470                 475                 480
Tyr Pro His Gly Gln Cys Thr Trp Tyr Val Tyr Asn Arg Met Lys Gln
            485                 490                 495
Phe Gly Thr Ser Ile Ser Gly Asp Leu Gly Asp Ala His Asn Trp Asn
            500                 505                 510
Asn Arg Ala Gln Tyr Arg Asp Tyr Gln Val Ser His Thr Pro Lys Arg
            515                 520                 525
His Ala Ala Val Val Phe Glu Ala Gly Gln Phe Gly Ala Asp Gln His
            530                 535                 540
Tyr Gly His Val Ala Phe Val Glu Lys Val Asn Ser Asp Gly Ser Ile
545                 550                 555                 560
Val Ile Ser Glu Ser Asn Val Lys Gly Leu Gly Ile Ile Ser His Arg
            565                 570                 575
Thr Ile Asn Ala Ala Ala Ala Glu Glu Leu Ser Tyr Ile Thr Gly Lys
            580                 585                 590
Gly Ser Gly Gly Gly Ala Met Thr Glu Lys Glu Lys Met Leu Ala Glu
            595                 600                 605
Lys Trp Tyr Asp Ala Asn Phe Asp Gln Asp Leu Ile Asn Glu Arg Ala
            610                 615                 620
Arg Ala Lys Asp Ile Cys Phe Glu Leu Asn His Thr Lys Pro Ser Asp
625                 630                 635                 640
Lys Asn Lys Arg Lys Glu Leu Ile Asp Glu Leu Phe Gln Thr Thr Thr
                645                 650                 655
Asp Asn Val Ser Ile Ser Ile Pro Phe Asp Thr Asp Tyr Gly Trp Asn
            660                 665                 670
Val Lys Leu Gly Lys Asn Val Tyr Val Asn Thr Asn Cys Tyr Phe Met
```

-continued

```
            675                 680                 685
Asp Gly Gly Gln Ile Thr Ile Gly Asp Asn Val Phe Ile Gly Pro Asn
        690                 695                 700

Cys Gly Phe Tyr Thr Ala Thr His Pro Leu Asn Phe His His Arg Asn
705                 710                 715                 720

Glu Gly Phe Glu Lys Ala Gly Pro Ile Asn Ile Gly Ser Asn Thr Trp
                725                 730                 735

Phe Gly His Val Ala Val Leu Pro Gly Val Thr Ile Gly Glu Gly
            740                 745                 750

Ser Val Ile Gly Ala Gly Ser Val Thr Lys Asp Ile Pro Pro His
            755                 760                 765

Ser Leu Ala Val Gly Asn Pro Cys Lys Val Val Arg Lys Ile Asp Asn
        770                 775                 780

Glu Val Pro Ser Glu Ala Leu Asn Asp Glu Thr Leu Asn
785                 790                 795
```

<210> SEQ ID NO 75
<211> LENGTH: 803
<212> TYPE: PRT
<213> ORGANISM: Artificial sequence
<220> FEATURE:
<223> OTHER INFORMATION: Chimeric polypeptide

<400> SEQUENCE: 75

```
Asp Thr Pro Gln Lys Asp Thr Thr Ala Lys Thr Thr Ser His Asp Ser
1               5                   10                  15

Lys Lys Ser Asn Asp Asp Glu Thr Ser Lys Asp Thr Thr Ser Lys Asp
            20                  25                  30

Ile Asp Lys Ala Asp Asn Asn Thr Ser Asn Gln Asp Asn Asn Asp
        35                  40                  45

Lys Lys Phe Lys Thr Ile Asp Asp Ser Thr Ser Asp Ser Asn Asn Ile
    50                  55                  60

Ile Asp Phe Ile Tyr Lys Asn Leu Pro Gln Thr Asn Ile Asn Gln Leu
65                  70                  75                  80

Leu Thr Lys Asn Lys Tyr Asp Asp Asn Tyr Ser Leu Thr Thr Leu Ile
                85                  90                  95

Gln Asn Leu Phe Asn Leu Asn Ser Asp Ile Ser Asp Tyr Glu Gln Pro
            100                 105                 110

Arg Asn Gly Glu Lys Ser Thr Asn Asp Ser Asn Lys Asn Ser Asp Asn
        115                 120                 125

Ser Ile Lys Asn Asp Thr Asp Thr Gln Ser Ser Lys Gln Asp Lys Ala
    130                 135                 140

Asp Asn Gln Lys Ala Pro Lys Ser Asn Asn Thr Lys Pro Ser Thr Ser
145                 150                 155                 160

Asn Lys Gln Pro Asn Ser Pro Lys Pro Thr Gln Pro Asn Gln Ser Asn
                165                 170                 175

Ser Gln Pro Ala Ser Asp Asp Lys Ala Asn Gln Lys Ser Ser Ser Lys
            180                 185                 190

Asp Asn Gln Ser Met Ser Asp Ser Ala Leu Asp Ser Ile Leu Asp Gln
        195                 200                 205

Tyr Ser Glu Asp Ala Lys Lys Thr Gln Lys Asp Tyr Ala Ser Gln Ser
    210                 215                 220

Lys Lys Asp Lys Asn Glu Lys Ser Asn Thr Lys Asn Pro Gln Leu Pro
225                 230                 235                 240

Thr Gln Asp Glu Leu Lys His Lys Ser Lys Pro Ala Gln Ser Phe Asn
```

```
                245                 250                 255
Asn Asp Val Asn Gln Lys Asp Thr Arg Ala Thr Ser Leu Phe Glu Thr
                260                 265                 270

Asp Pro Ser Ile Ser Asn Asn Asp Asp Ser Gly Gln Phe Asn Val Val
                275                 280                 285

Asp Ser Lys Asp Thr Arg Gln Phe Val Lys Ser Ile Ala Lys Asp Ala
            290                 295                 300

His Arg Ile Gly Gln Asp Asn Asp Ile Tyr Ala Ser Val Met Ile Ala
305                 310                 315                 320

Gln Ala Ile Leu Glu Ser Asp Ser Gly Arg Ser Ala Leu Ala Lys Ser
                325                 330                 335

Pro Asn His Asn Leu Phe Gly Ile Lys Gly Ala Phe Glu Gly Asn Ser
                340                 345                 350

Val Pro Phe Asn Thr Leu Glu Ala Asp Gly Asn Lys Leu Tyr Ser Ile
                355                 360                 365

Asn Ala Gly Phe Arg Lys Tyr Pro Ser Thr Lys Glu Ser Leu Lys Asp
            370                 375                 380

Tyr Ser Asp Leu Ile Lys Asn Gly Ile Asp Gly Asn Arg Thr Ile Tyr
385                 390                 395                 400

Lys Pro Thr Trp Lys Ser Glu Ala Asp Ser Tyr Lys Asp Ala Thr Ser
                405                 410                 415

His Leu Ser Lys Thr Tyr Ala Thr Asp Pro Asn Tyr Ala Lys Lys Leu
            420                 425                 430

Asn Ser Ile Ile Lys His Tyr Gln Leu Thr Gln Phe Asp Asp Glu Arg
            435                 440                 445

Met Pro Asp Leu Asp Lys Tyr Glu Arg Ser Ile Lys Asp Tyr Asp Asp
            450                 455                 460

Ser Ser Asp Glu Phe Lys Pro Phe Arg Glu Val Ser Asp Ser Met Pro
465                 470                 475                 480

Tyr Pro His Gly Gln Cys Thr Trp Tyr Val Tyr Asn Arg Met Lys Gln
                485                 490                 495

Phe Gly Thr Ser Ile Ser Gly Asp Leu Gly Asp Ala His Asn Trp Asn
                500                 505                 510

Asn Arg Ala Gln Tyr Arg Asp Tyr Gln Val Ser His Thr Pro Lys Arg
            515                 520                 525

His Ala Ala Val Val Phe Glu Ala Gly Gln Phe Gly Ala Asp Gln His
            530                 535                 540

Tyr Gly His Val Ala Phe Val Glu Lys Val Asn Ser Asp Gly Ser Ile
545                 550                 555                 560

Val Ile Ser Glu Ser Asn Val Lys Gly Leu Gly Ile Ile Ser His Arg
                565                 570                 575

Thr Ile Asn Ala Ala Ala Ala Glu Glu Leu Ser Tyr Ile Thr Gly Lys
            580                 585                 590

Lys Pro Glu Pro Lys Pro Ala Pro Ala Pro Lys Pro Met Thr Glu Lys
            595                 600                 605

Glu Lys Met Leu Ala Glu Lys Trp Tyr Asp Ala Asn Phe Asp Gln Asp
            610                 615                 620

Leu Ile Asn Glu Arg Ala Arg Ala Lys Asp Ile Cys Phe Glu Leu Asn
625                 630                 635                 640

His Thr Lys Pro Ser Asp Lys Asn Lys Arg Lys Glu Leu Ile Asp Glu
            645                 650                 655

Leu Phe Gln Thr Thr Thr Asp Asn Val Ser Ile Ser Ile Pro Phe Asp
            660                 665                 670
```

```
Thr Asp Tyr Gly Trp Asn Val Lys Leu Gly Lys Asn Val Tyr Val Asn
        675                 680                 685

Thr Asn Cys Tyr Phe Met Asp Gly Gly Gln Ile Thr Ile Gly Asp Asn
    690                 695                 700

Val Phe Ile Gly Pro Asn Cys Gly Phe Tyr Thr Ala Thr His Pro Leu
705                 710                 715                 720

Asn Phe His His Arg Asn Glu Gly Phe Glu Lys Ala Gly Pro Ile Asn
            725                 730                 735

Ile Gly Ser Asn Thr Trp Phe Gly Gly His Val Ala Val Leu Pro Gly
            740                 745                 750

Val Thr Ile Gly Glu Gly Ser Val Ile Gly Ala Gly Ser Val Val Thr
            755                 760                 765

Lys Asp Ile Pro Pro His Ser Leu Ala Val Gly Asn Pro Cys Lys Val
            770                 775                 780

Val Arg Lys Ile Asp Asn Glu Val Pro Ser Glu Ala Leu Asn Asp Glu
785                 790                 795                 800

Thr Leu Asn

<210> SEQ ID NO 76
<211> LENGTH: 988
<212> TYPE: PRT
<213> ORGANISM: Artificial sequence
<220> FEATURE:
<223> OTHER INFORMATION: Chimeric polypeptide

<400> SEQUENCE: 76

Asp Thr Pro Gln Lys Asp Thr Thr Ala Lys Thr Thr Ser His Asp Ser
1               5                   10                  15

Lys Lys Ser Asn Asp Asp Glu Thr Ser Lys Asp Thr Thr Ser Lys Asp
            20                  25                  30

Ile Asp Lys Ala Asp Asn Asn Thr Ser Asn Gln Asp Asn Asn Asp
        35                  40                  45

Lys Lys Phe Lys Thr Ile Asp Asp Ser Thr Ser Asp Ser Asn Asn Ile
    50                  55                  60

Ile Asp Phe Ile Tyr Lys Asn Leu Pro Gln Thr Asn Ile Asn Gln Leu
65                  70                  75                  80

Leu Thr Lys Asn Lys Tyr Asp Asp Asn Tyr Ser Leu Thr Thr Leu Ile
            85                  90                  95

Gln Asn Leu Phe Asn Leu Asn Ser Asp Ile Ser Asp Tyr Glu Gln Pro
            100                 105                 110

Arg Asn Gly Glu Lys Ser Thr Asn Asp Ser Asn Lys Asn Ser Asp Asn
        115                 120                 125

Ser Ile Lys Asn Asp Thr Asp Thr Gln Ser Ser Lys Gln Asp Lys Ala
    130                 135                 140

Asp Asn Gln Lys Ala Pro Lys Ser Asn Asn Thr Lys Pro Ser Thr Ser
145                 150                 155                 160

Asn Lys Gln Pro Asn Ser Pro Lys Pro Thr Gln Pro Asn Gln Ser Asn
            165                 170                 175

Ser Gln Pro Ala Ser Asp Asp Lys Ala Asn Gln Lys Ser Ser Ser Lys
        180                 185                 190

Asp Asn Gln Ser Met Ser Asp Ser Ala Leu Asp Ser Ile Leu Asp Gln
    195                 200                 205

Tyr Ser Glu Asp Ala Lys Lys Thr Gln Lys Asp Tyr Ala Ser Gln Ser
    210                 215                 220
```

-continued

```
Lys Lys Asp Lys Asn Glu Lys Ser Asn Thr Lys Asn Pro Gln Leu Pro
225                 230                 235                 240

Thr Gln Asp Glu Leu Lys His Lys Ser Lys Pro Ala Gln Ser Phe Asn
            245                 250                 255

Asn Asp Val Asn Gln Lys Asp Thr Arg Ala Thr Ser Leu Phe Glu Thr
        260                 265                 270

Asp Pro Ser Ile Ser Asn Asn Asp Ser Gly Gln Phe Asn Val Val
    275                 280                 285

Asp Ser Lys Asp Thr Arg Gln Phe Val Lys Ser Ile Ala Lys Asp Ala
    290                 295                 300

His Arg Ile Gly Gln Asp Asn Asp Ile Tyr Ala Ser Val Met Ile Ala
305                 310                 315                 320

Gln Ala Ile Leu Glu Ser Asp Ser Gly Arg Ser Ala Leu Ala Lys Ser
            325                 330                 335

Pro Asn His Asn Leu Phe Gly Ile Lys Gly Ala Phe Glu Gly Asn Ser
            340                 345                 350

Val Pro Phe Asn Thr Leu Glu Ala Asp Gly Asn Lys Leu Tyr Ser Ile
    355                 360                 365

Asn Ala Gly Phe Arg Lys Tyr Pro Ser Thr Lys Glu Ser Leu Lys Asp
    370                 375                 380

Tyr Ser Asp Leu Ile Lys Asn Gly Ile Asp Gly Asn Arg Thr Ile Tyr
385                 390                 395                 400

Lys Pro Thr Trp Lys Ser Glu Ala Asp Ser Tyr Lys Asp Ala Thr Ser
            405                 410                 415

His Leu Ser Lys Thr Tyr Ala Thr Asp Pro Asn Tyr Ala Lys Lys Leu
            420                 425                 430

Asn Ser Ile Ile Lys His Tyr Gln Leu Thr Gln Phe Asp Asp Glu Arg
            435                 440                 445

Met Pro Asp Leu Asp Lys Tyr Glu Arg Ser Ile Lys Asp Tyr Asp Asp
    450                 455                 460

Ser Ser Asp Glu Phe Lys Pro Phe Arg Glu Val Ser Asp Ser Met Pro
465                 470                 475                 480

Tyr Pro His Gly Gln Cys Thr Trp Tyr Val Tyr Asn Arg Met Lys Gln
            485                 490                 495

Phe Gly Thr Ser Ile Ser Gly Asp Leu Gly Asp Ala His Asn Trp Asn
            500                 505                 510

Asn Arg Ala Gln Tyr Arg Asp Tyr Gln Val Ser His Thr Pro Lys Arg
            515                 520                 525

His Ala Ala Val Val Phe Glu Ala Gly Gln Phe Gly Ala Asp Gln His
            530                 535                 540

Tyr Gly His Val Ala Phe Val Glu Lys Val Asn Ser Asp Gly Ser Ile
545                 550                 555                 560

Val Ile Ser Glu Ser Asn Val Lys Gly Leu Gly Ile Ile Ser His Arg
            565                 570                 575

Thr Ile Asn Ala Ala Ala Ala Glu Glu Leu Ser Tyr Ile Thr Gly Lys
            580                 585                 590

Gly Ser Gly Gly Gly Ala Lys Val Ala Lys Gln Gly Gln Tyr Lys Asn
            595                 600                 605

Gln Asp Pro Ile Val Leu Val His Gly Phe Asn Gly Phe Thr Asp Asp
            610                 615                 620

Ile Asn Pro Ser Val Leu Ala His Tyr Trp Gly Gly Asn Lys Met Asn
625                 630                 635                 640

Ile Arg Gln Asp Leu Glu Glu Asn Gly Tyr Lys Ala Tyr Glu Ala Ser
```

```
                645                 650                 655
Ile Ser Ala Phe Gly Ser Asn Tyr Asp Arg Ala Val Glu Leu Tyr Tyr
            660                 665                 670

Tyr Ile Lys Gly Gly Arg Val Asp Tyr Gly Ala Ala His Ala Ala Lys
            675                 680                 685

Tyr Gly His Glu Arg Tyr Gly Lys Thr Tyr Glu Gly Ile Tyr Lys Asp
            690                 695                 700

Trp Lys Pro Gly Gln Lys Val His Leu Val Gly His Ser Met Gly Gly
705                 710                 715                 720

Gln Thr Ile Arg Gln Leu Glu Glu Leu Leu Arg Asn Gly Ser Arg Glu
                725                 730                 735

Glu Ile Glu Tyr Gln Lys Lys His Gly Gly Glu Ile Ser Pro Leu Phe
            740                 745                 750

Lys Gly Asn Asn Asp Asn Met Ile Ser Ile Thr Thr Leu Gly Thr
            755                 760                 765

Pro His Asn Gly Thr His Ala Ser Asp Leu Ala Gly Asn Glu Ala Leu
            770                 775                 780

Val Arg Gln Ile Val Phe Asp Ile Gly Lys Met Phe Gly Asn Lys Asn
785                 790                 795                 800

Ser Arg Val Asp Phe Gly Leu Ala Gln Trp Gly Leu Lys Gln Lys Pro
                805                 810                 815

Asn Glu Ser Tyr Ile Asp Tyr Val Lys Arg Val Lys Gln Ser Asn Leu
            820                 825                 830

Trp Lys Ser Lys Asp Asn Gly Phe Tyr Asp Leu Thr Arg Glu Gly Ala
            835                 840                 845

Thr Asp Leu Asn Arg Lys Thr Ser Leu Asn Pro Asn Ile Val Tyr Lys
850                 855                 860

Thr Tyr Thr Gly Glu Ala Thr His Lys Ala Leu Asn Ser Asp Arg Gln
865                 870                 875                 880

Lys Ala Asp Leu Asn Met Phe Phe Pro Phe Val Ile Thr Gly Asn Leu
                885                 890                 895

Ile Gly Lys Ala Thr Glu Lys Glu Trp Arg Glu Asn Asp Gly Leu Val
            900                 905                 910

Ser Val Ile Ser Ser Gln His Pro Phe Asn Gln Ala Tyr Thr Asn Ala
            915                 920                 925

Thr Asp Lys Ile Gln Lys Gly Ile Trp Gln Val Thr Pro Thr Lys His
            930                 935                 940

Asp Trp Asp His Val Asp Phe Val Gly Gln Asp Ser Ser Asp Thr Val
945                 950                 955                 960

Arg Thr Arg Glu Glu Leu Gln Asp Phe Trp His His Leu Ala Asp Asp
                965                 970                 975

Leu Val Lys Thr Glu Lys Val Asp Thr Lys Gln
            980                 985

<210> SEQ ID NO 77
<211> LENGTH: 784
<212> TYPE: PRT
<213> ORGANISM: Artificial sequence
<220> FEATURE:
<223> OTHER INFORMATION: Chimeric polypeptide

<400> SEQUENCE: 77

Asp Thr Pro Gln Lys Asp Thr Thr Ala Lys Thr Thr Ser His Asp Ser
1               5                   10                  15

Lys Lys Ser Asn Asp Asp Glu Thr Ser Lys Asp Thr Thr Ser Lys Asp
```

```
                 20                  25                  30
Ile Asp Lys Ala Asp Asn Asn Thr Ser Asn Gln Asp Asn Asn Asp
            35                  40                  45
Lys Lys Phe Lys Thr Ile Asp Asp Ser Thr Ser Asp Ser Asn Asn Ile
        50                  55                  60
Ile Asp Phe Ile Tyr Lys Asn Leu Pro Gln Thr Asn Ile Asn Gln Leu
65                  70                  75                  80
Leu Thr Lys Asn Lys Tyr Asp Asp Asn Tyr Ser Leu Thr Thr Leu Ile
                85                  90                  95
Gln Asn Leu Phe Asn Leu Asn Ser Asp Ile Ser Asp Tyr Glu Gln Pro
            100                 105                 110
Arg Asn Gly Glu Lys Ser Thr Asn Asp Ser Asn Lys Asn Ser Asp Asn
        115                 120                 125
Ser Ile Lys Asn Asp Thr Asp Thr Gln Ser Ser Lys Gln Asp Lys Ala
        130                 135                 140
Asp Asn Gln Lys Ala Pro Lys Ser Asn Asn Thr Lys Pro Ser Thr Ser
145                 150                 155                 160
Asn Lys Gln Pro Asn Ser Pro Lys Pro Thr Gln Pro Asn Gln Ser Asn
            165                 170                 175
Ser Gln Pro Ala Ser Asp Lys Ala Asn Gln Lys Ser Ser Ser Lys
        180                 185                 190
Asp Asn Gln Ser Met Ser Asp Ser Ala Leu Asp Ser Ile Leu Asp Gln
        195                 200                 205
Tyr Ser Glu Asp Ala Lys Lys Thr Gln Lys Asp Tyr Ala Ser Gln Ser
        210                 215                 220
Lys Lys Asp Lys Asn Glu Lys Ser Asn Thr Lys Asn Pro Gln Leu Pro
225                 230                 235                 240
Thr Gln Asp Glu Leu Lys His Lys Ser Lys Pro Ala Gln Ser Phe Asn
            245                 250                 255
Asn Asp Val Asn Gln Lys Asp Thr Arg Ala Thr Ser Leu Phe Glu Thr
        260                 265                 270
Asp Pro Ser Ile Ser Asn Asn Asp Ser Gly Gln Phe Asn Val Val
        275                 280                 285
Asp Ser Lys Asp Thr Arg Gln Phe Val Lys Ser Ile Ala Lys Asp Ala
        290                 295                 300
His Arg Ile Gly Gln Asp Asn Asp Ile Tyr Ala Ser Val Met Ile Ala
305                 310                 315                 320
Gln Ala Ile Leu Glu Ser Asp Ser Gly Arg Ser Ala Leu Ala Lys Ser
            325                 330                 335
Pro Asn His Asn Leu Phe Gly Ile Lys Gly Ala Phe Glu Gly Asn Ser
        340                 345                 350
Val Pro Phe Asn Thr Leu Glu Ala Asp Gly Asn Lys Leu Tyr Ser Ile
        355                 360                 365
Asn Ala Gly Phe Arg Lys Tyr Pro Ser Thr Lys Glu Ser Leu Lys Asp
        370                 375                 380
Tyr Ser Asp Leu Ile Lys Asn Gly Ile Asp Gly Asn Arg Thr Ile Tyr
385                 390                 395                 400
Lys Pro Thr Trp Lys Ser Glu Ala Asp Ser Tyr Lys Asp Ala Thr Ser
            405                 410                 415
His Leu Ser Lys Thr Tyr Ala Thr Asp Pro Asn Tyr Ala Lys Lys Leu
        420                 425                 430
Asn Ser Ile Ile Lys His Tyr Gln Leu Thr Gln Phe Asp Asp Glu Arg
        435                 440                 445
```

```
Met Pro Asp Leu Asp Lys Tyr Glu Arg Ser Ile Lys Asp Tyr Asp
        450                 455                 460

Ser Ser Asp Glu Phe Lys Pro Phe Arg Glu Val Ser Asp Ser Met Pro
465                 470                 475                 480

Tyr Pro His Gly Gln Cys Thr Trp Tyr Val Tyr Asn Arg Met Lys Gln
            485                 490                 495

Phe Gly Thr Ser Ile Ser Gly Asp Leu Gly Asp Ala His Asn Trp Asn
            500                 505                 510

Asn Arg Ala Gln Tyr Arg Asp Tyr Gln Val Ser His Thr Pro Lys Arg
            515                 520                 525

His Ala Ala Val Val Phe Glu Ala Gly Gln Phe Gly Ala Asp Gln His
            530                 535                 540

Tyr Gly His Val Ala Phe Val Glu Lys Val Asn Ser Asp Gly Ser Ile
545                 550                 555                 560

Val Ile Ser Glu Ser Asn Val Lys Gly Leu Gly Ile Ile Ser His Arg
                565                 570                 575

Thr Ile Asn Ala Ala Ala Glu Glu Leu Ser Tyr Ile Thr Gly Lys
            580                 585                 590

Gly Ser Gly Gly Ala Lys Val Ala Lys Gln Gly Tyr Lys Asn
    595                 600                 605

Gln Asp Pro Ile Val Leu Val His Gly Phe Asn Gly Phe Thr Asp Asp
610                 615                 620

Ile Asn Pro Ser Val Leu Ala His Tyr Trp Gly Gly Asn Lys Met Asn
625                 630                 635                 640

Ile Arg Gln Asp Leu Glu Glu Asn Gly Tyr Lys Ala Tyr Glu Ala Ser
                645                 650                 655

Ile Ser Ala Phe Gly Ser Asn Tyr Asp Arg Ala Val Glu Leu Tyr Tyr
            660                 665                 670

Tyr Ile Lys Gly Gly Arg Val Asp Tyr Gly Ala Ala His Ala Ala Lys
    675                 680                 685

Tyr Gly His Glu Arg Tyr Gly Lys Thr Tyr Glu Gly Ile Tyr Lys Asp
    690                 695                 700

Trp Lys Pro Gly Gln Lys Val His Leu Val Gly His Ser Met Gly Gly
705                 710                 715                 720

Gln Thr Ile Arg Gln Leu Glu Glu Leu Arg Asn Gly Ser Arg Glu
                725                 730                 735

Glu Ile Glu Tyr Gln Lys Lys His Gly Gly Glu Ile Ser Pro Leu Phe
            740                 745                 750

Lys Gly Asn Asn Asp Asn Met Ile Ser Ser Ile Thr Thr Leu Gly Thr
            755                 760                 765

Pro His Asn Gly Thr His Ala Ser Asp Leu Ala Gly Asn Glu Ala Leu
    770                 775                 780

<210> SEQ ID NO 78
<211> LENGTH: 501
<212> TYPE: PRT
<213> ORGANISM: Artificial sequence
<220> FEATURE:
<223> OTHER INFORMATION: Chimeric polypeptide

<400> SEQUENCE: 78

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30
```

```
Gly Met Leu Lys Lys Val Phe Tyr Ser Phe Ile Asp Asp Lys Asn His
         35                  40                  45

Asn Lys Lys Leu Leu Val Ile Arg Thr Lys Gly Thr Ile Ala Gly Gln
 50                  55                  60

Tyr Arg Val Tyr Ser Glu Glu Gly Ala Asn Lys Ser Gly Leu Ala Trp
 65                  70                  75                  80

Pro Ser Ala Phe Lys Val Gln Leu Gln Leu Pro Asp Asn Glu Val Ala
                 85                  90                  95

Gln Ile Ser Asp Tyr Tyr Pro Arg Asn Ser Ile Asp Thr Lys Glu Tyr
                100                 105                 110

Met Ser Thr Leu Thr Tyr Gly Phe Asn Gly Asn Val Thr Gly Asp Asp
             115                 120                 125

Thr Gly Lys Ile Gly Gly Leu Ile Gly Ala Asn Val Ser Ile Gly His
         130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                 165                 170                 175

Gln Asn Trp Gly Pro Tyr Asp Arg Asp Ser Trp Asn Pro Val Tyr Gly
             180                 185                 190

Asn Gln Leu Phe Met Lys Thr Arg Asn Gly Ser Met Lys Ala Ala Asp
         195                 200                 205

Asn Phe Leu Asp Pro Asn Lys Ala Ser Ser Leu Leu Ser Ser Gly Phe
     210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                 245                 250                 255

Gln Leu His Trp Thr Ser Thr Asn Trp Lys Gly Thr Asn Thr Lys Asp
             260                 265                 270

Lys Trp Ile Asp Arg Ser Ser Glu Arg Tyr Lys Ile Asp Trp Glu Lys
         275                 280                 285

Glu Glu Met Thr Asn Gly Ser Gly Gly Ala Lys Arg Ile Lys Gln
     290                 295                 300

His Pro Asp Val Gln Lys Val Thr Asp Ala Thr Ser Lys Val Ala Ser
305                 310                 315                 320

Lys Thr Ser Ala Ala Ile Ser Asn Thr Ala Ser Asp Val Lys Glu Tyr
                 325                 330                 335

Val Gly Asp Lys Lys Gln Asp Phe Glu Asn Lys Arg Glu Leu Lys Lys
             340                 345                 350

Phe Ala Arg Glu His Asp Pro Ala Tyr Ile Glu Lys Lys Gly Glu Lys
         355                 360                 365

Leu Ala Lys Gln Asn Arg Lys Asp Ala Asp Lys Met Asn Lys Ile Leu
     370                 375                 380

Gln Lys Asn Ile Glu Lys Arg His Lys Glu Glu Gln Lys Ala Arg Glu
385                 390                 395                 400

Lys Asn Glu Ile Gln Arg Ile Lys Asp Met Lys Lys Ser Gln Lys Tyr
                 405                 410                 415

Glu Val Lys Ala Gly Leu Thr Pro Asn Lys Leu Asp Glu Lys Thr Glu
             420                 425                 430

Lys Lys Gly Asp Lys Leu Ala Glu Lys Asn Arg Lys Glu Ile Ala Lys
         435                 440                 445
```

Met Asn Lys Lys Leu Gln Lys Asn Ile Glu Lys Arg His Lys Glu Glu
450                 455                 460

Gln Lys Arg Gln Gln Glu Ala Asp Lys Ala Arg Ile Lys Ser Phe Lys
465                 470                 475                 480

Lys Tyr Lys Asp Tyr Val Ala Lys Ser Ala Ser Gln Gln Asn Lys Glu
                485                 490                 495

Asn Asn Thr Glu Ala
            500

<210> SEQ ID NO 79
<211> LENGTH: 498
<212> TYPE: PRT
<213> ORGANISM: Artificial sequence
<220> FEATURE:
<223> OTHER INFORMATION: Chimeric polypeptide

<400> SEQUENCE: 79

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
                20                  25                  30

Gly Met Leu Lys Lys Val Phe Tyr Ser Phe Ile Asp Asp Lys Asn His
            35                  40                  45

Asn Lys Lys Leu Leu Val Ile Arg Thr Lys Gly Thr Ile Ala Gly Gln
50                  55                  60

Tyr Arg Val Tyr Ser Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

Met Ser Thr Leu Thr Tyr Gly Phe Asn Gly Asn Val Thr Gly Asp Asp
            115                 120                 125

Thr Gly Lys Ile Gly Gly Leu Ile Gly Ala Asn Val Ser Ile Gly His
130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
            195                 200                 205

Asn Phe Leu Asp Pro Asn Lys Ala Ser Ser Leu Leu Ser Ser Gly Phe
210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Ile Asp Arg Ser Ser Glu Arg Tyr Lys Ile Asp Trp Glu Lys
            275                 280                 285

Glu Glu Met Thr Asn Gly Ser Gly Gly Gly Ala Met Thr Glu Lys Glu
            290                 295                 300

-continued

```
Lys Met Leu Ala Glu Lys Trp Tyr Asp Ala Asn Phe Asp Gln Asp Leu
305                 310                 315                 320

Ile Asn Glu Arg Ala Arg Ala Lys Asp Ile Cys Phe Glu Leu Asn His
                325                 330                 335

Thr Lys Pro Ser Asp Lys Asn Lys Arg Lys Glu Leu Ile Asp Glu Leu
            340                 345                 350

Phe Gln Thr Thr Thr Asp Asn Val Ser Ile Ser Ile Pro Phe Asp Thr
        355                 360                 365

Asp Tyr Gly Trp Asn Val Lys Leu Gly Lys Asn Val Tyr Val Asn Thr
370                 375                 380

Asn Cys Tyr Phe Met Asp Gly Gln Ile Thr Ile Gly Asp Asn Val
385                 390                 395                 400

Phe Ile Gly Pro Asn Cys Gly Phe Tyr Thr Ala Thr His Pro Leu Asn
                405                 410                 415

Phe His His Arg Asn Glu Gly Phe Glu Lys Ala Gly Pro Ile Asn Ile
                420                 425                 430

Gly Ser Asn Thr Trp Phe Gly Gly His Val Ala Val Leu Pro Gly Val
            435                 440                 445

Thr Ile Gly Glu Gly Ser Val Ile Gly Ala Gly Ser Val Val Thr Lys
        450                 455                 460

Asp Ile Pro Pro His Ser Leu Ala Val Gly Asn Pro Cys Lys Val Val
465                 470                 475                 480

Arg Lys Ile Asp Asn Glu Val Pro Ser Glu Ala Leu Asn Asp Glu Thr
                485                 490                 495

Leu Asn
```

<210> SEQ ID NO 80
<211> LENGTH: 689
<212> TYPE: PRT
<213> ORGANISM: Artificial sequence
<220> FEATURE:
<223> OTHER INFORMATION: Chimeric polypeptide

<400> SEQUENCE: 80

```
Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
                20                  25                  30

Gly Met Leu Lys Lys Val Phe Tyr Ser Phe Ile Asp Asp Lys Asn His
            35                  40                  45

Asn Lys Lys Leu Leu Val Ile Arg Thr Lys Gly Thr Ile Ala Gly Gln
50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly His
    130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
```

-continued

```
                165                 170                 175
Gln Asn Trp Gly Pro Tyr Asp Arg Asp Ser Trp Asn Pro Val Tyr Gly
                180                 185                 190

Asn Gln Leu Phe Met Lys Thr Arg Asn Gly Ser Met Lys Ala Ala Asp
                195                 200                 205

Asn Phe Leu Asp Pro Asn Lys Ala Ser Ser Leu Leu Ser Ser Gly Phe
                210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
                260                 265                 270

Lys Trp Ile Asp Arg Ser Glu Arg Tyr Lys Ile Asp Trp Glu Lys
                275                 280                 285

Glu Glu Met Thr Asn Gly Ser Gly Gly Ala Lys Val Ala Lys Gln
                290                 295                 300

Gly Gln Tyr Lys Asn Gln Asp Pro Ile Val Leu Val His Gly Phe Asn
305                 310                 315                 320

Gly Phe Thr Asp Asp Ile Asn Pro Ser Val Leu Ala His Tyr Trp Gly
                325                 330                 335

Gly Asn Lys Met Asn Ile Arg Gln Asp Leu Glu Glu Asn Gly Tyr Lys
                340                 345                 350

Ala Tyr Glu Ala Ser Ile Ser Ala Phe Gly Ser Asn Tyr Asp Arg Ala
                355                 360                 365

Val Glu Leu Tyr Tyr Tyr Ile Lys Gly Gly Arg Val Asp Tyr Gly Ala
                370                 375                 380

Ala His Ala Ala Lys Tyr Gly His Glu Arg Tyr Gly Lys Thr Tyr Glu
385                 390                 395                 400

Gly Ile Tyr Lys Asp Trp Lys Pro Gly Gln Lys Val His Leu Val Gly
                405                 410                 415

His Ser Met Gly Gly Gln Thr Ile Arg Gln Leu Glu Glu Leu Leu Arg
                420                 425                 430

Asn Gly Ser Arg Glu Glu Ile Glu Tyr Gln Lys Lys His Gly Gly Glu
                435                 440                 445

Ile Ser Pro Leu Phe Lys Gly Asn Asn Asp Asn Met Ile Ser Ser Ile
450                 455                 460

Thr Thr Leu Gly Thr Pro His Asn Gly Thr His Ala Ser Asp Leu Ala
465                 470                 475                 480

Gly Asn Glu Ala Leu Val Arg Gln Ile Val Phe Asp Ile Gly Lys Met
                485                 490                 495

Phe Gly Asn Lys Asn Ser Arg Val Asp Phe Gly Leu Ala Gln Trp Gly
                500                 505                 510

Leu Lys Gln Lys Pro Asn Glu Ser Tyr Ile Asp Tyr Val Lys Arg Val
                515                 520                 525

Lys Gln Ser Asn Leu Trp Lys Ser Lys Asp Asn Gly Phe Tyr Asp Leu
                530                 535                 540

Thr Arg Glu Gly Ala Thr Asp Leu Asn Arg Lys Thr Ser Leu Asn Pro
545                 550                 555                 560

Asn Ile Val Tyr Lys Thr Tyr Thr Gly Glu Ala Thr His Lys Ala Leu
                565                 570                 575

Asn Ser Asp Arg Gln Lys Ala Asp Leu Asn Met Phe Phe Pro Phe Val
                580                 585                 590
```

-continued

```
Ile Thr Gly Asn Leu Ile Gly Lys Ala Thr Glu Lys Glu Trp Arg Glu
                595                 600                 605

Asn Asp Gly Leu Val Ser Val Ile Ser Ser Gln His Pro Phe Asn Gln
            610                 615                 620

Ala Tyr Thr Asn Ala Thr Asp Lys Ile Gln Lys Gly Ile Trp Gln Val
625                 630                 635                 640

Thr Pro Thr Lys His Asp Trp Asp His Val Asp Phe Val Gly Gln Asp
                645                 650                 655

Ser Ser Asp Thr Val Arg Thr Arg Glu Glu Leu Gln Asp Phe Trp His
            660                 665                 670

His Leu Ala Asp Asp Leu Val Lys Thr Glu Lys Val Thr Asp Thr Lys
675                 680                 685

Gln

<210> SEQ ID NO 81
<211> LENGTH: 390
<212> TYPE: PRT
<213> ORGANISM: Artificial sequence
<220> FEATURE:
<223> OTHER INFORMATION: Chimeric polypeptide

<400> SEQUENCE: 81

Lys Val Ala Lys Gln Gly Gln Tyr Lys Asn Gln Asp Pro Ile Val Leu
1               5                   10                  15

Val His Gly Phe Asn Gly Phe Thr Asp Asp Ile Asn Pro Ser Val Leu
            20                  25                  30

Ala His Tyr Trp Gly Gly Asn Lys Met Asn Ile Arg Gln Asp Leu Glu
        35                  40                  45

Glu Asn Gly Tyr Lys Ala Tyr Glu Ala Ser Ile Ser Ala Phe Gly Ser
    50                  55                  60

Asn Tyr Asp Arg Ala Val Glu Leu Tyr Tyr Ile Lys Gly Gly Arg
65                  70                  75                  80

Val Asp Tyr Gly Ala Ala His Ala Ala Lys Tyr Gly His Glu Arg Tyr
                85                  90                  95

Gly Lys Thr Tyr Glu Gly Ile Tyr Lys Asp Trp Lys Pro Gly Gln Lys
            100                 105                 110

Val His Leu Val Gly His Ser Met Gly Gly Gln Thr Ile Arg Gln Leu
        115                 120                 125

Glu Glu Leu Leu Arg Asn Gly Ser Arg Glu Glu Ile Glu Tyr Gln Lys
    130                 135                 140

Lys His Gly Gly Glu Ile Ser Pro Leu Phe Lys Gly Asn Asn Asp Asn
145                 150                 155                 160

Met Ile Ser Ser Ile Thr Thr Leu Gly Thr Pro His Asn Gly Thr His
                165                 170                 175

Ala Ser Asp Leu Ala Gly Asn Glu Ala Leu Val Arg Gln Ile Val Phe
            180                 185                 190

Asp Ile Gly Lys Met Phe Gly Asn Lys Asn Ser Arg Val Asp Phe Gly
        195                 200                 205

Leu Ala Gln Trp Gly Leu Lys Gln Lys Pro Asn Glu Ser Tyr Ile Asp
    210                 215                 220

Tyr Val Lys Arg Val Lys Gln Ser Asn Leu Trp Lys Ser Lys Asp Asn
225                 230                 235                 240

Gly Phe Tyr Asp Leu Thr Arg Glu Gly Ala Thr Asp Leu Asn Arg Lys
                245                 250                 255
```

Thr Ser Leu Asn Pro Asn Ile Val Tyr Lys Thr Tyr Thr Gly Glu Ala
            260                 265                 270

Thr His Lys Ala Leu Asn Ser Asp Arg Gln Lys Ala Asp Leu Asn Met
        275                 280                 285

Phe Phe Pro Phe Val Ile Thr Gly Asn Leu Ile Gly Lys Ala Thr Glu
    290                 295                 300

Lys Glu Trp Arg Glu Asn Asp Gly Leu Val Ser Val Ile Ser Ser Gln
305                 310                 315                 320

His Pro Phe Asn Gln Ala Tyr Thr Asn Ala Thr Asp Lys Ile Gln Lys
                325                 330                 335

Gly Ile Trp Gln Val Thr Pro Thr Lys His Asp Trp Asp His Val Asp
            340                 345                 350

Phe Val Gly Gln Asp Ser Ser Asp Thr Val Arg Thr Arg Glu Glu Leu
        355                 360                 365

Gln Asp Phe Trp His His Leu Ala Asp Asp Leu Val Lys Thr Glu Lys
    370                 375                 380

Val Thr Asp Thr Lys Gln
385                 390

<210> SEQ ID NO 82
<211> LENGTH: 186
<212> TYPE: PRT
<213> ORGANISM: Artificial sequence
<220> FEATURE:
<223> OTHER INFORMATION: Chimeric polypeptide

<400> SEQUENCE: 82

Lys Val Ala Lys Gln Gly Gln Tyr Lys Asn Gln Asp Pro Ile Val Leu
1               5                   10                  15

Val His Gly Phe Asn Gly Phe Thr Asp Asp Ile Asn Pro Ser Val Leu
            20                  25                  30

Ala His Tyr Trp Gly Gly Asn Lys Met Asn Ile Arg Gln Asp Leu Glu
        35                  40                  45

Glu Asn Gly Tyr Lys Ala Tyr Glu Ala Ser Ile Ser Ala Phe Gly Ser
    50                  55                  60

Asn Tyr Asp Arg Ala Val Glu Leu Tyr Tyr Ile Lys Gly Gly Arg
65                  70                  75                  80

Val Asp Tyr Gly Ala Ala His Ala Ala Lys Tyr Gly His Glu Arg Tyr
                85                  90                  95

Gly Lys Thr Tyr Glu Gly Ile Tyr Lys Asp Trp Lys Pro Gly Gln Lys
            100                 105                 110

Val His Leu Val Gly His Ser Met Gly Gly Gln Thr Ile Arg Gln Leu
        115                 120                 125

Glu Glu Leu Leu Arg Asn Gly Ser Arg Glu Glu Ile Glu Tyr Gln Lys
    130                 135                 140

Lys His Gly Gly Glu Ile Ser Pro Leu Phe Lys Gly Asn Asn Asp Asn
145                 150                 155                 160

Met Ile Ser Ser Ile Thr Thr Leu Gly Thr Pro His Asn Gly Thr His
                165                 170                 175

Ala Ser Asp Leu Ala Gly Asn Glu Ala Leu
            180                 185

<210> SEQ ID NO 83
<211> LENGTH: 293
<212> TYPE: PRT
<213> ORGANISM: Artificial sequence
<220> FEATURE:

<223> OTHER INFORMATION: Chimeric polypeptide

<400> SEQUENCE: 83

```
Ala Asp Ser Asp Ile Asn Ile Lys Thr Gly Thr Thr Asp Ile Gly Ser
1               5                   10                  15

Asn Thr Val Lys Thr Gly Asp Leu Val Thr Tyr Asp Lys Glu Asn
            20                  25                  30

Gly Met Leu Lys Lys Val Phe Tyr Ser Phe Ile Asp Asp Lys Asn His
        35                  40                  45

Asn Lys Lys Leu Leu Val Ile Arg Thr Lys Gly Thr Ile Ala Gly Gln
    50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly His
    130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Ile Asp Arg Ser Ser Glu Arg Tyr Lys Ile Asp Trp Glu Lys
        275                 280                 285

Glu Glu Met Thr Asn
    290
```

<210> SEQ ID NO 84
<211> LENGTH: 573
<212> TYPE: PRT
<213> ORGANISM: Artificial sequence
<220> FEATURE:
<223> OTHER INFORMATION: Chimeric polypeptide

<400> SEQUENCE: 84

```
Ala Ala Glu Glu Thr Gly Gly Asn Thr Glu Ala Gln Pro Lys Thr
1               5                   10                  15

Glu Ala Val Ala Ser Pro Thr Thr Thr Ser Glu Lys Ala Pro Glu Thr
            20                  25                  30

Lys Pro Val Ala Asn Ala Val Ser Val Ser Asn Lys Glu Val Glu Ala
        35                  40                  45
```

-continued

```
Pro Thr Ser Glu Thr Lys Glu Ala Lys Glu Val Lys Glu Val Lys Ala
 50                  55                  60

Pro Lys Glu Thr Lys Glu Val Lys Pro Ala Ala Lys Ala Thr Asn Asn
 65                  70                  75                  80

Thr Tyr Pro Ile Leu Asn Gln Glu Leu Arg Glu Ala Ile Lys Asn Pro
                 85                  90                  95

Ala Ile Lys Asp Lys Asp His Ser Ala Pro Asn Ser Arg Pro Ile Asp
            100                 105                 110

Phe Glu Met Lys Lys Asp Gly Thr Gln Gln Phe Tyr His Tyr Ala
            115                 120                 125

Ser Ser Val Lys Pro Ala Arg Val Ile Phe Thr Asp Ser Lys Pro Glu
130                 135                 140

Ile Glu Leu Gly Leu Gln Ser Gly Gln Phe Trp Arg Lys Phe Glu Val
145                 150                 155                 160

Tyr Glu Gly Asp Lys Lys Leu Pro Ile Lys Leu Val Ser Tyr Asp Thr
                165                 170                 175

Val Lys Asp Tyr Ala Tyr Ile Arg Phe Ser Val Ser Asn Gly Thr Lys
            180                 185                 190

Ala Val Lys Ile Val Ser Ser Thr His Phe Asn Asn Lys Glu Glu Lys
            195                 200                 205

Tyr Asp Tyr Thr Leu Met Glu Phe Ala Gln Pro Ile Tyr Asn Ser Ala
210                 215                 220

Asp Lys Phe Lys Thr Glu Glu Asp Tyr Lys Ala Glu Lys Leu Leu Ala
225                 230                 235                 240

Pro Tyr Lys Lys Ala Lys Thr Leu Glu Arg Gln Val Tyr Glu Leu Asn
                245                 250                 255

Lys Ile Gln Asp Lys Leu Pro Glu Lys Leu Lys Ala Glu Tyr Lys Lys
            260                 265                 270

Lys Leu Glu Asp Thr Lys Lys Ala Leu Asp Glu Gln Val Lys Ser Ala
            275                 280                 285

Ile Thr Glu Phe Gln Asn Val Gln Pro Thr Asn Glu Lys Met Thr Asp
290                 295                 300

Leu Gln Asp Thr Lys Tyr Val Val Tyr Glu Ser Val Glu Asn Asn Glu
305                 310                 315                 320

Ser Met Met Asp Thr Phe Val Lys His Pro Ile Lys Thr Gly Met Leu
                325                 330                 335

Asn Gly Lys Lys Tyr Met Val Met Glu Thr Thr Asn Asp Asp Tyr Trp
            340                 345                 350

Lys Asp Phe Met Val Glu Gly Gln Arg Val Arg Thr Ile Ser Lys Asp
            355                 360                 365

Ala Lys Asn Asn Thr Arg Thr Ile Ile Phe Pro Tyr Val Glu Gly Lys
370                 375                 380

Thr Leu Tyr Asp Ala Ile Val Lys Val His Val Lys Thr Ile Asp Tyr
385                 390                 395                 400

Asp Gly Gln Tyr His Val Arg Ile Val Asp Lys Glu Ala Phe Thr Lys
                405                 410                 415

Ala Asn Thr Asp Lys Ser Asn Lys Lys Glu Gln Gln Asp Asn Ser Ala
            420                 425                 430

Lys Lys Glu Ala Thr Pro Ala Thr Pro Ser Lys Pro Thr Pro Ser Pro
            435                 440                 445

Val Glu Lys Glu Ser Gln Lys Gln Asp Ser Gln Lys Asp Asp Asn Lys
450                 455                 460
```

```
Gln Leu Pro Ser Val Glu Lys Glu Asn Asp Ala Ser Glu Ser Gly
465                 470                 475                 480

Lys Asp Lys Thr Pro Ala Thr Lys Pro Thr Lys Gly Glu Val Glu Ser
            485                 490                 495

Ser Ser Thr Thr Pro Thr Lys Val Val Ser Thr Thr Gln Asn Val Ala
            500                 505                 510

Lys Pro Thr Thr Ala Ser Ser Lys Thr Thr Lys Asp Val Val Gln Thr
            515                 520                 525

Ser Ala Gly Ser Ser Glu Ala Lys Asp Ser Ala Pro Leu Gln Lys Ala
            530                 535                 540

Asn Ile Lys Asn Thr Asn Asp Gly His Thr Gln Ser Gln Asn Asn Lys
545                 550                 555                 560

Asn Thr Gln Glu Asn Lys Ala Lys Ser Leu Pro Gln Thr
                565                 570

<210> SEQ ID NO 85
<211> LENGTH: 409
<212> TYPE: PRT
<213> ORGANISM: Artificial sequence
<220> FEATURE:
<223> OTHER INFORMATION: Chimeric polypeptide

<400> SEQUENCE: 85

Met Asp Ile Gly Lys Lys His Val Ile Pro Lys Ser Gln Tyr Arg Arg
1               5                   10                  15

Lys Arg Arg Glu Phe Phe His Asn Glu Asp Arg Glu Glu Asn Leu Asn
                20                  25                  30

Gln His Gln Asp Lys Gln Asn Ile Asp Asn Thr Thr Ser Lys Lys Ala
            35                  40                  45

Asp Lys Gln Ile His Lys Asp Ser Ile Asp Lys His Glu Arg Phe Lys
        50                  55                  60

Asn Ser Leu Ser Ser His Leu Glu Gln Arg Asn Arg Asp Val Asn Glu
65                  70                  75                  80

Asn Lys Ala Glu Glu Ser Lys Ser Asn Gln Asp Ser Lys Ser Ala Tyr
                85                  90                  95

Asn Arg Asp His Tyr Leu Thr Asp Val Ser Lys Lys Gln Asn Ser
            100                 105                 110

Leu Asp Ser Val Asp Gln Asp Thr Glu Lys Ser Lys Tyr Tyr Glu Gln
        115                 120                 125

Asn Ser Glu Ala Thr Leu Ser Thr Lys Ser Thr Asp Lys Val Glu Ser
130                 135                 140

Thr Glu Met Arg Lys Leu Ser Ser Asp Lys Asn Lys Val Gly His Glu
145                 150                 155                 160

Glu Gln His Val Leu Ser Lys Pro Ser Glu His Asp Lys Glu Thr Arg
                165                 170                 175

Ile Asp Ser Glu Ser Ser Arg Thr Asp Ser Asp Ser Met Gln Thr
            180                 185                 190

Glu Lys Ile Lys Lys Asp Ser Ser Asp Gly Asn Lys Ser Ser Asn Leu
        195                 200                 205

Lys Ser Glu Val Ile Ser Asp Lys Ser Asn Thr Val Pro Lys Leu Ser
210                 215                 220

Glu Ser Asp Asp Glu Val Asn Asn Gln Lys Pro Leu Thr Leu Pro Glu
225                 230                 235                 240

Glu Gln Lys Leu Lys Arg Gln Gln Ser Gln Asn Glu Gln Thr Lys Thr
                245                 250                 255
```

```
Tyr Thr Tyr Gly Asp Ser Glu Gln Asn Asp Lys Ser Asn His Glu Asn
                260                 265                 270

Asp Leu Ser His His Ile Pro Ser Ile Ser Asp Lys Asp Asn Val
        275                 280                 285

Met Arg Glu Asn His Ile Val Asp Asp Asn Pro Asp Asn Asp Ile Asn
    290                 295                 300

Thr Pro Ser Leu Ser Lys Thr Asp Asp Arg Lys Leu Asp Glu Lys
305                 310                 315                 320

Ile His Val Glu Asp Lys His Lys Gln Asn Ala Asp Ser Ser Glu Thr
                325                 330                 335

Val Gly Tyr Gln Ser Gln Ser Thr Ala Ser His Arg Ser Thr Glu Lys
                340                 345                 350

Arg Asn Ile Ser Ile Asn Asp His Asp Lys Leu Asn Gly Gln Lys Thr
                355                 360                 365

Asn Thr Lys Thr Ser Ala Asn Asn Gln Lys Lys Ala Thr Ser Lys
                370                 375                 380

Leu Asn Lys Gly Arg Ala Thr Asn Asn Tyr Ser Asp Ile Leu Lys
385                 390                 395                 400

Lys Phe Trp Met Met Tyr Trp Pro Lys
                405

<210> SEQ ID NO 86
<211> LENGTH: 592
<212> TYPE: PRT
<213> ORGANISM: Artificial sequence
<220> FEATURE:
<223> OTHER INFORMATION: Chimeric polypeptide

<400> SEQUENCE: 86

Asp Thr Pro Gln Lys Asp Thr Thr Ala Lys Thr Thr Ser His Asp Ser
1               5                   10                  15

Lys Lys Ser Asn Asp Asp Glu Thr Ser Lys Asp Thr Ser Lys Asp
                20                  25                  30

Ile Asp Lys Ala Asp Asn Asn Asn Thr Ser Asn Gln Asp Asn Asn Asp
                35                  40                  45

Lys Lys Phe Lys Thr Ile Asp Asp Ser Thr Ser Asp Ser Asn Asn Ile
    50                  55                  60

Ile Asp Phe Ile Tyr Lys Asn Leu Pro Gln Thr Asn Ile Asn Gln Leu
65                  70                  75                  80

Leu Thr Lys Asn Lys Tyr Asp Asp Asn Tyr Ser Leu Thr Thr Leu Ile
                85                  90                  95

Gln Asn Leu Phe Asn Leu Asn Ser Asp Ile Ser Asp Tyr Glu Gln Pro
                100                 105                 110

Arg Asn Gly Glu Lys Ser Thr Asn Asp Ser Asn Lys Asn Ser Asp Asn
                115                 120                 125

Ser Ile Lys Asn Asp Thr Asp Thr Gln Ser Ser Lys Gln Asp Lys Ala
130                 135                 140

Asp Asn Gln Lys Ala Pro Lys Ser Asn Asn Thr Lys Pro Ser Thr Ser
145                 150                 155                 160

Asn Lys Gln Pro Asn Ser Pro Lys Pro Thr Gln Pro Asn Gln Ser Asn
                165                 170                 175

Ser Gln Pro Ala Ser Asp Asp Lys Ala Asn Gln Lys Ser Ser Ser Lys
                180                 185                 190

Asp Asn Gln Ser Met Ser Asp Ser Ala Leu Asp Ser Ile Leu Asp Gln
                195                 200                 205
```

Tyr Ser Glu Asp Ala Lys Lys Thr Gln Lys Asp Tyr Ala Ser Gln Ser
        210                 215                 220
Lys Lys Asp Lys Asn Glu Lys Ser Asn Thr Lys Asn Pro Gln Leu Pro
225                 230                 235                 240
Thr Gln Asp Glu Leu Lys His Lys Ser Lys Pro Ala Gln Ser Phe Asn
                245                 250                 255
Asn Asp Val Asn Gln Lys Asp Thr Arg Ala Thr Ser Leu Phe Glu Thr
            260                 265                 270
Asp Pro Ser Ile Ser Asn Asn Asp Asp Ser Gly Gln Phe Asn Val Val
        275                 280                 285
Asp Ser Lys Asp Thr Arg Gln Phe Val Lys Ser Ile Ala Lys Asp Ala
    290                 295                 300
His Arg Ile Gly Gln Asp Asn Asp Ile Tyr Ala Ser Val Met Ile Ala
305                 310                 315                 320
Gln Ala Ile Leu Glu Ser Asp Ser Gly Arg Ser Ala Leu Ala Lys Ser
                325                 330                 335
Pro Asn His Asn Leu Phe Gly Ile Lys Gly Ala Phe Glu Gly Asn Ser
            340                 345                 350
Val Pro Phe Asn Thr Leu Glu Ala Asp Gly Asn Lys Leu Tyr Ser Ile
        355                 360                 365
Asn Ala Gly Phe Arg Lys Tyr Pro Ser Thr Lys Glu Ser Leu Lys Asp
370                 375                 380
Tyr Ser Asp Leu Ile Lys Asn Gly Ile Asp Gly Asn Arg Thr Ile Tyr
385                 390                 395                 400
Lys Pro Thr Trp Lys Ser Glu Ala Asp Ser Tyr Lys Asp Ala Thr Ser
                405                 410                 415
His Leu Ser Lys Thr Tyr Ala Thr Asp Pro Asn Tyr Ala Lys Lys Leu
            420                 425                 430
Asn Ser Ile Ile Lys His Tyr Gln Leu Thr Gln Phe Asp Asp Glu Arg
        435                 440                 445
Met Pro Asp Leu Asp Lys Tyr Glu Arg Ser Ile Lys Tyr Asp
    450                 455                 460
Ser Ser Asp Glu Phe Lys Pro Phe Arg Glu Val Ser Asp Ser Met Pro
465                 470                 475                 480
Tyr Pro His Gly Gln Cys Thr Trp Tyr Val Tyr Asn Arg Met Lys Gln
                485                 490                 495
Phe Gly Thr Ser Ile Ser Gly Asp Leu Gly Asp Ala His Asn Trp Asn
            500                 505                 510
Asn Arg Ala Gln Tyr Arg Asp Tyr Gln Val Ser His Thr Pro Lys Arg
        515                 520                 525
His Ala Ala Val Val Phe Glu Ala Gly Gln Phe Gly Ala Asp Gln His
    530                 535                 540
Tyr Gly His Val Ala Phe Val Glu Lys Val Asn Ser Asp Gly Ser Ile
545                 550                 555                 560
Val Ile Ser Glu Ser Asn Val Lys Gly Leu Gly Ile Ile Ser His Arg
                565                 570                 575
Thr Ile Asn Ala Ala Ala Ala Glu Glu Leu Ser Tyr Ile Thr Gly Lys
            580                 585                 590

<210> SEQ ID NO 87
<211> LENGTH: 793
<212> TYPE: PRT
<213> ORGANISM: Staphylococcus aureus

<400> SEQUENCE: 87

```
Gln Thr Lys Tyr Gly Asp Gln Ser Glu Lys Gly Ser Gln Ser Val Ser
1               5                   10                  15

Asn Lys Asn Asn Lys Ile His Ile Ala Ile Val Asn Glu Asp Gln Pro
            20                  25                  30

Thr Thr Tyr Asn Gly Lys Lys Val Glu Leu Gly Gln Ala Phe Ile Lys
            35                  40                  45

Arg Leu Ala Asn Glu Lys Asn Tyr Lys Phe Glu Thr Val Thr Arg Asn
50                  55                  60

Val Ala Glu Ser Gly Leu Lys Asn Gly Gly Tyr Gln Val Met Ile Val
65                  70                  75                  80

Ile Pro Glu Asn Phe Ser Lys Leu Ala Met Gln Leu Asp Ala Lys Thr
                85                  90                  95

Pro Ser Lys Ile Ser Leu Gln Tyr Lys Thr Ala Val Gly Gln Lys Glu
                100                 105                 110

Glu Val Ala Lys Asn Thr Glu Lys Val Val Ser Asn Val Leu Asn Asp
            115                 120                 125

Phe Asn Lys Asn Leu Val Glu Ile Tyr Leu Thr Ser Ile Ile Asp Asn
            130                 135                 140

Leu His Asn Ala Gln Lys Asn Val Gly Ala Ile Met Thr Arg Glu His
145                 150                 155                 160

Gly Val Asn Ser Lys Phe Ser Asn Tyr Leu Leu Asn Pro Ile Asn Asp
                165                 170                 175

Phe Pro Glu Leu Phe Thr Asp Thr Leu Val Asn Ser Ile Ser Ala Asn
                180                 185                 190

Lys Asp Ile Thr Lys Trp Phe Gln Thr Tyr Asn Lys Ser Leu Leu Ser
                195                 200                 205

Ala Asn Ser Asp Thr Phe Arg Val Asn Thr Asp Tyr Asn Val Ser Thr
210                 215                 220

Leu Ile Glu Lys Gln Asn Ser Leu Phe Asp Glu His Asn Thr Ala Met
225                 230                 235                 240

Asp Lys Met Leu Gln Asp Tyr Lys Ser Gln Lys Asp Ser Val Glu Leu
                245                 250                 255

Asp Asn Tyr Ile Asn Ala Leu Lys Gln Met Asp Ser Gln Ile Asp Gln
                260                 265                 270

Gln Ser Ser Met Gln Asp Thr Gly Lys Glu Glu Tyr Lys Gln Thr Val
            275                 280                 285

Lys Glu Asn Leu Asp Lys Leu Arg Glu Ile Ile Gln Ser Gln Glu Ser
            290                 295                 300

Pro Phe Ser Lys Gly Met Ile Glu Asp Tyr Arg Lys Gln Leu Thr Glu
305                 310                 315                 320

Ser Leu Gln Asp Glu Leu Ala Asn Asn Lys Asp Leu Gln Asp Ala Leu
                325                 330                 335

Asn Ser Ile Lys Met Asn Asn Ala Gln Phe Ala Glu Asn Leu Glu Lys
                340                 345                 350

Gln Leu His Asp Asp Ile Val Lys Glu Pro Asp Ser Asp Thr Thr Phe
                355                 360                 365

Ile Tyr Asn Met Ser Lys Gln Asp Phe Ile Ala Ala Gly Leu Asn Glu
                370                 375                 380

Asp Glu Ala Asn Lys Tyr Glu Ala Ile Val Lys Glu Ala Lys Arg Tyr
385                 390                 395                 400

Lys Asn Glu Tyr Asn Leu Lys Lys Pro Leu Ala Glu His Ile Asn Leu
                405                 410                 415
```

Thr Asp Tyr Asp Asn Gln Val Ala Gln Asp Thr Ser Ser Leu Ile Asn
            420                 425                 430

Asp Gly Val Lys Val Gln Arg Thr Glu Thr Ile Lys Ser Asn Asp Ile
            435                 440                 445

Asn Gln Leu Thr Val Ala Thr Asp Pro His Phe Asn Phe Glu Gly Asp
            450                 455                 460

Ile Lys Ile Asn Gly Lys Lys Tyr Asp Ile Lys Asp Gln Ser Val Gln
465                 470                 475                 480

Leu Asp Thr Ser Asn Lys Glu Tyr Lys Val Glu Val Asn Gly Val Ala
                    485                 490                 495

Lys Leu Lys Lys Asp Ala Glu Lys Asp Phe Leu Lys Asp Lys Thr Met
                500                 505                 510

His Leu Gln Leu Leu Phe Gly Gln Ala Asn Arg Gln Asp Glu Pro Asn
                515                 520                 525

Asp Lys Lys Ala Thr Ser Val Val Asp Val Thr Leu Asn His Asn Leu
            530                 535                 540

Asp Gly Arg Leu Ser Lys Asp Ala Leu Ser Gln Gln Leu Ser Ala Leu
545                 550                 555                 560

Ser Arg Phe Asp Ala His Tyr Lys Met Tyr Thr Asp Thr Lys Gly Arg
                    565                 570                 575

Glu Asp Lys Pro Phe Asp Asn Lys Arg Leu Ile Asp Met Met Val Asp
                580                 585                 590

Gln Val Ile Asn Asp Met Glu Ser Phe Lys Asp Lys Val Ala Val
                595                 600                 605

Leu His Gln Ile Asp Ser Met Glu Gly Asn Ser Asp Lys Leu Ile Asp
            610                 615                 620

Asp Ile Leu Asn Asn Lys Lys Asn Thr Thr Lys Asn Lys Glu Asp Ile
625                 630                 635                 640

Ser Lys Leu Ile Asp Gln Leu Glu Asn Val Lys Lys Thr Phe Ala Glu
                    645                 650                 655

Glu Pro Gln Glu Pro Lys Ile Asp Lys Gly Lys Asn Asp Glu Phe Asn
                660                 665                 670

Thr Met Ser Ser Asn Leu Asp Lys Glu Ile Ser Arg Ile Ser Glu Lys
                675                 680                 685

Ser Thr Gln Leu Leu Ser Asp Thr Gln Glu Ser Lys Thr Ile Ala Asp
            690                 695                 700

Ser Val Ser Gly Gln Leu Asn Gln Leu Asp Asn Asn Val Asn Lys Leu
705                 710                 715                 720

His Ala Thr Gly Arg Ala Leu Gly Val Arg Ala Asn Asp Leu Asn Arg
                    725                 730                 735

Gln Met Ala Lys Asn Asp Lys Asp Asn Glu Leu Phe Ala Lys Glu Phe
                740                 745                 750

Lys Lys Val Leu Gln Asn Ser Lys Asp Gly Asp Arg Gln Asn Gln Ala
                755                 760                 765

Leu Lys Ala Phe Met Ser Asn Pro Val Gln Lys Asn Leu Glu Asn
            770                 775                 780

Val Leu Ala Asn Asn Gly Asn Thr Asp
785                 790

<210> SEQ ID NO 88
<211> LENGTH: 202
<212> TYPE: PRT
<213> ORGANISM: Staphylococcus aureus

<400> SEQUENCE: 88

```
Lys Arg Ile Lys Gln His Pro Asp Val Gln Lys Val Thr Asp Ala Thr
1               5                   10                  15

Ser Lys Val Ala Ser Lys Thr Ser Ala Ala Ile Ser Asn Thr Ala Ser
            20                  25                  30

Asp Val Lys Glu Tyr Val Gly Asp Lys Lys Gln Asp Phe Glu Asn Lys
        35                  40                  45

Arg Glu Leu Lys Lys Phe Ala Arg Glu His Asp Pro Ala Tyr Ile Glu
    50                  55                  60

Lys Lys Gly Glu Lys Leu Ala Lys Gln Asn Arg Lys Asp Ala Asp Lys
65                  70                  75                  80

Met Asn Lys Ile Leu Gln Lys Asn Ile Glu Lys Arg His Lys Glu Glu
                85                  90                  95

Gln Lys Ala Arg Glu Lys Asn Glu Ile Gln Arg Ile Lys Asp Met Lys
            100                 105                 110

Lys Ser Gln Lys Tyr Glu Val Lys Ala Gly Leu Thr Pro Asn Lys Leu
        115                 120                 125

Asp Glu Lys Thr Glu Lys Lys Gly Asp Lys Leu Ala Glu Lys Asn Arg
    130                 135                 140

Lys Glu Ile Ala Lys Met Asn Lys Lys Leu Gln Lys Asn Ile Glu Lys
145                 150                 155                 160

Arg His Lys Glu Glu Gln Lys Arg Gln Gln Glu Ala Asp Lys Ala Arg
                165                 170                 175

Ile Lys Ser Phe Lys Lys Tyr Lys Asp Tyr Val Ala Lys Ser Ala Ser
            180                 185                 190

Gln Gln Asn Lys Glu Asn Asn Thr Glu Ala
            195                 200

<210> SEQ ID NO 89
<211> LENGTH: 409
<212> TYPE: PRT
<213> ORGANISM: Staphylococcus aureus

<400> SEQUENCE: 89

Met Asp Ile Gly Lys Lys His Val Ile Pro Lys Ser Gln Tyr Arg Arg
1               5                   10                  15

Lys Arg Arg Glu Phe Phe His Asn Glu Asp Arg Glu Glu Asn Leu Asn
            20                  25                  30

Gln His Gln Asp Lys Gln Asn Ile Asp Asn Thr Thr Ser Lys Lys Ala
        35                  40                  45

Asp Lys Gln Ile His Lys Asp Ser Ile Asp Lys His Glu Arg Phe Lys
    50                  55                  60

Asn Ser Leu Ser Ser His Leu Glu Gln Arg Asn Arg Asp Val Asn Glu
65                  70                  75                  80

Asn Lys Ala Glu Glu Ser Lys Ser Asn Gln Gly Ser Lys Ser Ala Tyr
                85                  90                  95

Asn Lys Asp His Tyr Leu Thr Asp Val Ser Lys Lys Gln Asn Ser
            100                 105                 110

Leu Asp Ser Val Asp Gln Asp Thr Glu Lys Ser Lys Tyr Tyr Glu Gln
        115                 120                 125

Asn Thr Glu Ala Thr Leu Ser Thr Asn Ser Thr Asp Lys Val Glu Ser
    130                 135                 140

Thr Asp Met Arg Lys Leu Ser Ser Asp Lys Asn Lys Val Gly His Glu
145                 150                 155                 160

Glu Gln His Val Leu Ser Lys Pro Ser Glu His Asp Lys Glu Thr Arg
```

```
                165                 170                 175
Ile Asp Phe Glu Ser Ser Arg Thr Asp Ser Asp Ser Met Gln Thr
                180                 185                 190

Glu Lys Ile Lys Lys Asp Ser Ser Asp Gly Asn Lys Ser Ser Asn Leu
                195                 200                 205

Lys Ser Glu Val Ile Ser Asp Lys Ser Asn Ser Val Pro Ile Leu Ser
            210                 215                 220

Glu Ser Asp Asp Glu Val Asn Asn Gln Lys Pro Leu Thr Leu Pro Glu
225                 230                 235                 240

Glu Gln Lys Leu Lys Arg Gln Gln Ser Gln Asn Glu Gln Thr Lys Thr
                245                 250                 255

Tyr Thr Tyr Gly Asp Ser Glu Gln Asn Asp Lys Ser Asn His Glu Asn
                260                 265                 270

Asp Leu Ser His His Thr Pro Ser Ile Ser Asp Lys Asp Tyr Val
            275                 280                 285

Met Arg Glu Asp His Ile Val Asp Asp Asn Pro Asp Asn Asp Ile Asn
            290                 295                 300

Thr Pro Ser Leu Ser Lys Ile Asp Asp Arg Lys Leu Asp Glu Lys
305                 310                 315                 320

Ile His Val Glu Asp Lys His Lys Gln Asn Ala Asp Ser Ser Glu Thr
                325                 330                 335

Val Gly Tyr Gln Ser Gln Ser Ser Ala Ser His Arg Ser Thr Glu Lys
            340                 345                 350

Arg Asn Met Ala Ile Asn Asp His Asp Lys Leu Asn Gly Gln Lys Pro
                355                 360                 365

Asn Thr Lys Thr Ser Ala Asn Asn Gln Lys Lys Ala Thr Ser Lys
            370                 375                 380

Leu Asn Lys Gly Arg Ala Thr Asn Asn Asn Tyr Ser Ala Ile Leu Lys
385                 390                 395                 400

Lys Phe Trp Met Met Tyr Trp Pro Lys
                405

<210> SEQ ID NO 90
<211> LENGTH: 495
<212> TYPE: PRT
<213> ORGANISM: Staphylococcus aureus

<400> SEQUENCE: 90

Arg Asn Leu Leu Leu Gln Lys Gln Ser Gln Ala Arg Gln Thr Ala Glu
1               5                   10                  15

Asp Ile Val Asn Gln Ala His Lys Glu Ala Asp Asn Ile Lys Lys Glu
                20                  25                  30

Lys Leu Leu Glu Ala Lys Glu Glu Asn Gln Ile Leu Arg Glu Gln Thr
            35                  40                  45

Glu Ala Glu Leu Arg Glu Arg Arg Ser Glu Leu Gln Arg Gln Glu Thr
        50                  55                  60

Arg Leu Leu Gln Lys Glu Glu Asn Leu Glu Arg Lys Ser Asp Leu Leu
65              70                  75                  80

Asp Lys Lys Asp Glu Ile Leu Glu Gln Lys Glu Ser Lys Ile Glu Glu
                85                  90                  95

Lys Gln Gln Gln Val Asp Ala Lys Glu Ser Ser Val Gln Thr Leu Ile
            100                 105                 110

Met Lys His Glu Gln Glu Leu Glu Arg Ile Ser Gly Leu Thr Gln Glu
        115                 120                 125
```

Glu Ala Ile Asn Glu Gln Leu Gln Arg Val Glu Glu Leu Ser Gln
130                 135                 140

Asp Ile Ala Val Leu Val Lys Glu Lys Glu Ala Lys Glu Lys
145                 150                 155                 160

Val Asp Lys Thr Ala Lys Glu Leu Leu Ala Thr Ala Val Gln Arg Leu
                165                 170                 175

Ala Ala Asp His Thr Ser Glu Ser Thr Val Ser Val Val Asn Leu Pro
                180                 185                 190

Asn Asp Glu Met Lys Gly Arg Ile Ile Gly Arg Glu Gly Arg Asn Ile
                195                 200                 205

Arg Thr Leu Glu Thr Leu Thr Gly Ile Asp Leu Ile Ile Asp Asp Thr
210                 215                 220

Pro Glu Ala Val Ile Leu Ser Gly Phe Asp Pro Ile Arg Arg Glu Ile
225                 230                 235                 240

Ala Arg Thr Ala Leu Val Asn Leu Val Ser Asp Gly Arg Ile His Pro
                245                 250                 255

Gly Arg Ile Glu Asp Met Val Glu Lys Ala Arg Lys Glu Val Asp Asp
                260                 265                 270

Ile Ile Arg Glu Ala Gly Glu Gln Ala Thr Phe Glu Val Asn Ala His
                275                 280                 285

Asn Met His Pro Asp Leu Val Lys Ile Val Gly Arg Leu Asn Tyr Arg
290                 295                 300

Thr Ser Tyr Gly Gln Asn Val Leu Lys His Ser Ile Glu Val Ala His
305                 310                 315                 320

Leu Ala Ser Met Leu Ala Ala Glu Leu Gly Glu Asp Glu Thr Leu Ala
                325                 330                 335

Lys Arg Ala Gly Leu Leu His Asp Val Gly Lys Ala Ile Asp His Glu
                340                 345                 350

Val Glu Gly Ser His Val Glu Ile Gly Val Glu Leu Ala Lys Lys Tyr
                355                 360                 365

Gly Glu Asn Glu Thr Val Ile Asn Ala Ile His Ser His His Gly Asp
                370                 375                 380

Val Glu Pro Thr Ser Ile Ile Ser Ile Leu Val Ala Ala Ala Asp Ala
385                 390                 395                 400

Leu Ser Ala Ala Arg Pro Gly Ala Arg Lys Glu Thr Leu Glu Asn Tyr
                405                 410                 415

Ile Arg Arg Leu Glu Arg Leu Glu Thr Leu Ser Glu Ser Tyr Asp Gly
                420                 425                 430

Val Glu Lys Ala Phe Ala Ile Gln Ala Gly Arg Glu Ile Arg Val Ile
                435                 440                 445

Val Ser Pro Glu Glu Ile Asp Asp Leu Lys Ser Tyr Arg Leu Ala Arg
450                 455                 460

Asp Ile Lys Asn Gln Ile Glu Asp Glu Leu Gln Tyr Pro Gly His Ile
465                 470                 475                 480

Lys Val Thr Val Val Arg Glu Thr Arg Ala Val Glu Tyr Ala Lys
                485                 490                 495

<210> SEQ ID NO 91
<211> LENGTH: 144
<212> TYPE: PRT
<213> ORGANISM: Staphylococcus aureus

<400> SEQUENCE: 91

Asn Asn His Asn Asn Gly Thr Lys Glu Asn Lys Ile Ala Asn Thr Asn
1               5                   10                  15

Lys Asn Asn Ala Asp Glu Ser Lys Asp Lys Asp Thr Ser Lys Asp Ala
            20                  25                  30

Ser Lys Asp Lys Ser Lys Ser Thr Asp Ser Asp Lys Ser Lys Asp Asp
        35                  40                  45

Gln Asp Lys Ala Thr Lys Asp Glu Ser Asp Asn Asp Gln Asn Asn Ala
50                  55                  60

Asn Gln Ala Asn Gln Ala Gln Asn Gln Asn Gln Gln Gln Ala
65                  70                  75                  80

Asn Gln Asn Gln Gln Gln Gln Gln Arg Gln Gly Gly Gln Arg
                85                  90                  95

His Thr Val Asn Gly Gln Glu Asn Leu Tyr Arg Ile Ala Ile Gln Tyr
            100                 105                 110

Tyr Gly Ser Gly Ser Pro Glu Asn Val Glu Lys Ile Arg Arg Ala Asn
        115                 120                 125

Gly Leu Ser Gly Asn Asn Ile Arg Asn Gly Gln Gln Ile Val Ile Pro
130                 135                 140

<210> SEQ ID NO 92
<211> LENGTH: 652
<212> TYPE: PRT
<213> ORGANISM: Staphylococcus aureus

<400> SEQUENCE: 92

Met Asn Glu Lys Val Glu Gly Met Thr Leu Glu Leu Lys Leu Asp His
1               5                   10                  15

Leu Gly Val Gln Glu Gly Met Lys Gly Leu Lys Arg Gln Leu Gly Val
            20                  25                  30

Val Asn Ser Glu Met Lys Ala Asn Leu Ser Ala Phe Asp Lys Ser Glu
        35                  40                  45

Lys Ser Met Glu Lys Tyr Gln Ala Arg Ile Lys Gly Leu Asn Asp Arg
    50                  55                  60

Leu Lys Val Gln Lys Lys Met Tyr Ser Gln Val Glu Asp Glu Leu Lys
65                  70                  75                  80

Gln Val Asn Ala Asn Tyr Gln Lys Ala Lys Ser Ser Val Lys Asp Val
                85                  90                  95

Glu Lys Ala Tyr Leu Lys Leu Val Glu Ala Asn Lys Glu Lys Leu
            100                 105                 110

Ala Leu Asp Lys Ser Lys Glu Ala Leu Lys Ser Ser Asn Thr Glu Leu
        115                 120                 125

Lys Lys Ala Glu Asn Gln Tyr Lys Arg Thr Asn Gln Arg Lys Gln Asp
130                 135                 140

Ala Tyr Gln Lys Leu Lys Gln Leu Arg Asp Ala Glu Gln Lys Leu Lys
145                 150                 155                 160

Asn Ser Asn Gln Ala Thr Thr Ala Gln Leu Lys Arg Ala Ser Asp Ala
                165                 170                 175

Val Gln Lys Gln Ser Ala Lys His Lys Ala Leu Val Glu Gln Tyr Lys
            180                 185                 190

Gln Glu Gly Asn Gln Val Gln Lys Leu Lys Val Gln Asn Asp Asn Leu
        195                 200                 205

Ser Lys Ser Asn Asp Lys Ile Glu Ser Ser Tyr Ala Lys Thr Asn Thr
    210                 215                 220

Lys Leu Lys Gln Thr Glu Lys Glu Phe Asn Asp Leu Asn Asn Thr Ile
225                 230                 235                 240

Lys Asn His Ser Ala Asn Val Ala Lys Ala Glu Thr Ala Val Asn Lys

```
            245                 250                 255
Glu Lys Ala Ala Leu Asn Asn Leu Glu Arg Ser Ile Asp Lys Ala Ser
            260                 265                 270

Ser Glu Met Lys Thr Phe Asn Lys Glu Gln Met Ile Ala Gln Ser His
        275                 280                 285

Phe Gly Lys Leu Ala Ser Gln Ala Asp Val Met Ser Lys Lys Phe Ser
    290                 295                 300

Ser Ile Gly Asp Lys Met Thr Ser Leu Gly Arg Thr Met Thr Met Gly
305                 310                 315                 320

Val Ser Thr Pro Ile Thr Leu Gly Leu Gly Ala Ala Leu Lys Thr Ser
                325                 330                 335

Ala Asp Phe Glu Gly Gln Met Ser Arg Val Gly Ala Ile Ala Gln Ala
            340                 345                 350

Ser Ser Lys Asp Leu Lys Ser Met Ser Asn Gln Ala Val Asp Leu Gly
        355                 360                 365

Ala Lys Thr Ser Lys Ser Ala Asn Glu Val Ala Lys Gly Met Glu Glu
    370                 375                 380

Leu Ala Leu Gly Phe Asn Ala Lys Gln Thr Met Glu Ala Met Pro
385                 390                 395                 400

Gly Val Ile Ser Ala Ala Glu Ala Ser Gly Ala Glu Met Ala Thr Thr
                405                 410                 415

Ala Thr Val Met Ala Ser Ala Ile Asn Ser Phe Gly Leu Lys Ala Ser
            420                 425                 430

Asp Ala Asn His Val Ala Asp Leu Leu Ala Arg Ser Ala Asn Asp Ser
        435                 440                 445

Ala Ala Asp Ile Gln Tyr Met Gly Asp Ala Leu Lys Tyr Ala Gly Thr
    450                 455                 460

Pro Ala Lys Ala Leu Gly Val Ser Ile Glu Asp Thr Ser Ala Ala Ile
465                 470                 475                 480

Glu Val Leu Ser Asn Ser Gly Leu Glu Gly Ser Gln Ala Gly Thr Ala
                485                 490                 495

Leu Arg Ala Ser Phe Ile Arg Leu Ala Asn Pro Ser Lys Asn Thr Ala
            500                 505                 510

Lys Glu Met Lys Lys Leu Gly Ile His Leu Ser Asp Ala Lys Gly Gln
        515                 520                 525

Phe Val Gly Met Gly Glu Leu Ile Arg Gln Phe Gln Asp Asn Met Lys
    530                 535                 540

Gly Met Thr Arg Glu Gln Lys Leu Ala Thr Val Ala Thr Ile Val Gly
545                 550                 555                 560

Thr Glu Ala Ala Ser Gly Phe Leu Ala Leu Ile Glu Ala Gly Pro Asp
                565                 570                 575

Lys Ile Asn Ser Tyr Ser Lys Ser Leu Lys Asn Ser Asn Gly Glu Ser
            580                 585                 590

Lys Lys Ala Ala Asp Leu Met Lys Asp Asn Leu Lys Gly Ala Leu Glu
        595                 600                 605

Gln Leu Gly Gly Ala Phe Glu Ser Leu Ala Ile Glu Val Gly Lys Asp
    610                 615                 620

Leu Thr Pro Met Ile Arg Ala Gly Ala Glu Gly Leu Thr Lys Leu Val
625                 630                 635                 640

Asp Gly Phe Thr His Leu Pro Gly Trp Val Arg Lys
                645                 650

<210> SEQ ID NO 93
```

```
<211> LENGTH: 199
<212> TYPE: PRT
<213> ORGANISM: Staphylococcus aureus

<400> SEQUENCE: 93

Met Thr Glu Lys Glu Lys Met Leu Ala Glu Lys Trp Tyr Asp Ala Asn
1               5                   10                  15

Phe Asp Gln Asp Leu Ile Asn Glu Arg Ala Arg Ala Lys Asp Ile Cys
            20                  25                  30

Phe Glu Leu Asn His Thr Lys Pro Ser Asp Lys Asn Lys Arg Lys Glu
        35                  40                  45

Leu Ile Asp Glu Leu Phe Gln Thr Thr Thr Asp Asn Val Ser Ile Ser
50                  55                  60

Ile Pro Phe Asp Thr Asp Tyr Gly Trp Asn Val Lys Leu Gly Lys Asn
65                  70                  75                  80

Val Tyr Val Asn Thr Asn Cys Tyr Phe Met Asp Gly Gln Ile Thr
                85                  90                  95

Ile Gly Asp Asn Val Phe Ile Gly Pro Asn Cys Gly Phe Tyr Thr Ala
                100                 105                 110

Thr His Pro Leu Asn Phe His His Arg Asn Glu Gly Phe Glu Lys Ala
            115                 120                 125

Gly Pro Ile Asn Ile Gly Ser Asn Thr Trp Phe Gly His Val Ala
130                 135                 140

Val Leu Pro Gly Val Thr Ile Gly Glu Gly Ser Val Ile Gly Ala Gly
145                 150                 155                 160

Ser Val Val Thr Lys Asp Ile Pro Pro His Ser Leu Ala Val Gly Asn
                165                 170                 175

Pro Cys Lys Val Val Arg Lys Ile Asp Asn Glu Val Pro Ser Glu Ala
            180                 185                 190

Leu Asn Asp Glu Thr Leu Asn
            195

<210> SEQ ID NO 94
<211> LENGTH: 592
<212> TYPE: PRT
<213> ORGANISM: Staphylococcus aureus

<400> SEQUENCE: 94

Asp Thr Pro Gln Lys Asp Thr Thr Ala Lys Thr Thr Ser His Asp Ser
1               5                   10                  15

Lys Lys Ser Thr Asp Asp Glu Thr Ser Lys Asp Thr Thr Ser Lys Asp
            20                  25                  30

Ile Asp Lys Ala Asp Asn Asn Thr Ser Asn Gln Asp Asn Asn Asp
        35                  40                  45

Lys Lys Val Lys Thr Ile Asp Asp Ser Thr Ser Asp Ser Asn Asn Ile
    50                  55                  60

Ile Asp Phe Ile Tyr Lys Asn Leu Pro Gln Thr Asn Ile Asn Gln Leu
65                  70                  75                  80

Leu Thr Lys Asn Lys Tyr Asp Asp Asn Tyr Ser Leu Thr Thr Leu Ile
                85                  90                  95

Gln Asn Leu Phe Asn Leu Asn Ser Asp Ile Ser Asp Tyr Glu Gln Pro
                100                 105                 110

Arg Asn Gly Glu Lys Ser Thr Asn Asp Ser Asn Lys Asn Ser Asp Asn
            115                 120                 125

Ser Ile Lys Asn Asp Thr Asp Thr Gln Ser Ser Lys Gln Asp Lys Ala
        130                 135                 140
```

```
Asp Asn Gln Lys Ala Pro Lys Ser Asn Asn Thr Lys Pro Ser Thr Ser
145                 150                 155                 160

Asn Lys Gln Pro Asn Ser Pro Lys Pro Thr Gln Pro Asn Gln Ser Asn
                165                 170                 175

Ser Gln Pro Ala Ser Asp Asp Lys Val Asn Gln Lys Ser Ser Ser Lys
            180                 185                 190

Asp Asn Gln Ser Met Ser Asp Ser Ala Leu Asp Ser Ile Leu Asp Gln
        195                 200                 205

Tyr Ser Glu Asp Ala Lys Lys Thr Gln Lys Asp Tyr Ala Ser Gln Ser
    210                 215                 220

Lys Lys Asp Lys Asn Glu Lys Ser Asn Thr Lys Asn Pro Gln Leu Pro
225                 230                 235                 240

Thr Gln Asp Glu Leu Lys His Lys Ser Lys Pro Ala Gln Ser Phe Asn
                245                 250                 255

Asn Asp Val Asn Gln Lys Asp Thr Arg Ala Thr Ser Leu Phe Glu Thr
            260                 265                 270

Asp Pro Ser Ile Ser Asn Asn Asp Ser Gly Gln Phe Asn Val Val
        275                 280                 285

Asp Ser Lys Asp Thr Arg Gln Phe Val Lys Ser Ile Ala Lys Asp Ala
    290                 295                 300

His Arg Ile Gly Gln Asp Asn Asp Ile Tyr Ala Ser Val Met Ile Ala
305                 310                 315                 320

Gln Ala Ile Leu Glu Ser Asp Ser Gly Arg Ser Ala Leu Ala Lys Ser
                325                 330                 335

Pro Asn His Asn Leu Phe Gly Ile Lys Gly Ala Phe Glu Gly Asn Ser
            340                 345                 350

Val Pro Phe Asn Thr Leu Glu Ala Asp Gly Asn Gln Leu Tyr Ser Ile
        355                 360                 365

Asn Ala Gly Phe Arg Lys Tyr Pro Ser Thr Lys Glu Ser Leu Lys Asp
    370                 375                 380

Tyr Ser Asp Leu Ile Lys Asn Gly Ile Asp Gly Asn Arg Thr Ile Tyr
385                 390                 395                 400

Lys Pro Thr Trp Lys Ser Glu Ala Asp Ser Tyr Lys Asp Ala Thr Ser
                405                 410                 415

His Leu Ser Lys Thr Tyr Ala Thr Asp Pro Asn Tyr Ala Lys Lys Leu
            420                 425                 430

Asn Ser Ile Ile Lys His Tyr Gln Leu Thr Gln Phe Asp Asp Glu Arg
        435                 440                 445

Met Pro Asp Leu Asp Lys Tyr Glu Arg Ser Ile Lys Asp Tyr Asp Asp
    450                 455                 460

Ser Ser Asp Glu Phe Lys Pro Phe Arg Glu Val Ser Asp Asn Met Pro
465                 470                 475                 480

Tyr Pro His Gly Gln Cys Thr Trp Tyr Val Tyr Asn Arg Met Lys Gln
                485                 490                 495

Phe Gly Thr Ser Ile Ser Gly Asp Leu Gly Asp Ala His Asn Trp Asn
            500                 505                 510

Asn Arg Ala Gln Tyr Arg Asp Tyr Gln Val Ser His Thr Pro Lys Arg
        515                 520                 525

His Ala Ala Val Val Phe Glu Ala Gly Gln Phe Gly Ala Asp Gln His
    530                 535                 540

Tyr Gly His Val Ala Phe Val Glu Lys Val Asn Ser Asp Gly Ser Ile
545                 550                 555                 560
```

Val Ile Ser Glu Ser Asn Val Lys Gly Leu Gly Ile Ser His Arg
                565                 570                 575

Thr Ile Asn Ala Ala Ala Glu Glu Leu Ser Tyr Ile Thr Gly Lys
            580                 585                 590

<210> SEQ ID NO 95
<211> LENGTH: 441
<212> TYPE: PRT
<213> ORGANISM: Staphylococcus aureus

<400> SEQUENCE: 95

Ala Glu Lys Gln Val Asn Met Gly Asn Ser Gln Glu Asp Thr Val Thr
1               5                   10                  15

Ala Gln Ser Ile Gly Asp Gln Gln Thr Arg Glu Asn Ala Asn Tyr Gln
            20                  25                  30

Arg Glu Asn Gly Val Asp Glu Gln Gln His Thr Glu Asn Leu Thr Lys
        35                  40                  45

Asn Leu His Asn Asp Lys Thr Ile Ser Glu Glu Asn His Arg Lys Thr
    50                  55                  60

Asp Asp Leu Asn Lys Asp Gln Leu Lys Asp Asp Lys Lys Ser Ser Leu
65                  70                  75                  80

Asn Asn Lys Asn Ile Gln Arg Asp Thr Thr Lys Asn Asn Asn Ala Asn
                85                  90                  95

Pro Arg Asp Val Asn Gln Gly Leu Glu Gln Ala Ile Asn Asp Gly Lys
            100                 105                 110

Gln Ser Lys Val Ala Ser Gln Gln Ser Lys Glu Ala Asp Asn Ser
        115                 120                 125

Gln Asp Leu Asn Ala Asn Asn Asn Leu Pro Ser Gln Ser Arg Thr Lys
    130                 135                 140

Val Ser Pro Ser Leu Asn Lys Ser Asp Gln Thr Ser Gln Arg Glu Ile
145                 150                 155                 160

Val Asn Glu Thr Glu Ile Glu Lys Val Gln Pro Gln Gln Lys Asn Gln
                165                 170                 175

Ala Asn Asp Lys Ile Thr Asp His Asn Phe Asn Asn Glu Gln Glu Val
            180                 185                 190

Lys Pro Gln Lys Asp Glu Lys Thr Leu Ser Val Ser Asp Leu Lys Asn
        195                 200                 205

Asn Gln Lys Ser Pro Val Glu Pro Thr Lys Asp Asn Asp Lys Lys Asn
    210                 215                 220

Gly Leu Asn Leu Leu Lys Ser Ser Ala Val Ala Thr Leu Pro Asn Lys
225                 230                 235                 240

Gly Thr Lys Glu Leu Thr Ala Lys Ala Lys Gly Asp Gln Thr Asn Lys
                245                 250                 255

Val Ala Lys Gln Gly Gln Tyr Lys Asn Gln Asp Pro Ile Val Leu Val
            260                 265                 270

His Gly Phe Asn Gly Phe Thr Asp Asp Ile Asn Pro Ser Val Leu Ala
        275                 280                 285

His Tyr Trp Gly Gly Asn Lys Met Asn Ile Arg Gln Asp Leu Glu Glu
    290                 295                 300

Asn Gly Tyr Lys Ala Tyr Glu Ala Ser Ile Ser Ala Phe Gly Ser Asn
305                 310                 315                 320

Tyr Asp Arg Ala Val Glu Leu Tyr Tyr Ile Lys Gly Gly Arg Val
                325                 330                 335

Asp Tyr Gly Ala Ala His Ala Ala Lys Tyr Gly His Glu Arg Tyr Gly
            340                 345                 350

```
Lys Thr Tyr Glu Gly Ile Tyr Lys Asp Trp Lys Pro Gly Gln Lys Val
            355                 360                 365

His Leu Val Gly His Ser Met Gly Gly Gln Thr Ile Arg Gln Leu Glu
        370                 375                 380

Glu Leu Leu Arg Asn Gly Ser Arg Glu Ile Glu Tyr Gln Lys Lys
385                 390                 395                 400

His Ser Gly Glu Ile Ser Pro Leu Phe Lys Gly Asn Asn Asp Asn Met
                405                 410                 415

Ile Ser Ser Ile Thr Thr Leu Gly Thr Pro His Asn Gly Thr His Ala
                420                 425                 430

Ser Asp Leu Ala Gly Asn Glu Ala Leu
            435                 440

<210> SEQ ID NO 96
<211> LENGTH: 365
<212> TYPE: PRT
<213> ORGANISM: Staphylococcus aureus

<400> SEQUENCE: 96

Gly Phe Leu Asn Lys Ser Lys Asn Glu Gln Ala Ala Leu Lys Ala Gln
1               5                   10                  15

Gln Ala Ala Ile Lys Glu Glu Ala Ser Ala Asn Asn Leu Ser Asp Thr
            20                  25                  30

Ser Gln Glu Ala Gln Glu Ile Gln Glu Ala Lys Arg Glu Ala Gln Ala
        35                  40                  45

Glu Ala Asp Lys Ser Val Ala Val Ser Asn Lys Glu Ser Lys Ala Val
    50                  55                  60

Ala Leu Lys Ala Gln Gln Ala Ala Ile Lys Glu Glu Ala Ser Ala Asn
65                  70                  75                  80

Asn Leu Ser Asp Thr Ser Gln Glu Ala Gln Glu Ile Gln Glu Ala Lys
                85                  90                  95

Lys Glu Ala Gln Ala Glu Thr Asp Lys Ser Ala Ala Val Ser Asn Glu
            100                 105                 110

Glu Pro Lys Ala Val Ala Leu Lys Ala Gln Gln Ala Ala Ile Lys Glu
        115                 120                 125

Glu Ala Ser Ala Asn Asn Leu Ser Asp Ile Ser Gln Glu Ala Gln Glu
    130                 135                 140

Val Gln Glu Ala Lys Lys Glu Ala Gln Ala Glu Lys Asp Ser Asp Thr
145                 150                 155                 160

Leu Thr Lys Asp Ala Ser Ala Ala Lys Val Glu Val Ser Lys Pro Glu
                165                 170                 175

Ser Gln Ala Glu Arg Leu Ala Asn Ala Ala Lys Gln Lys Gln Ala Lys
            180                 185                 190

Leu Thr Pro Gly Ser Lys Glu Ser Gln Leu Thr Glu Ala Leu Phe Ala
        195                 200                 205

Glu Lys Pro Val Ala Lys Asn Asp Leu Lys Glu Ile Pro Gln Leu Val
    210                 215                 220

Thr Lys Lys Asn Asp Val Ser Glu Thr Glu Val Asn Ile Asp Asn
225                 230                 235                 240

Lys Asp Thr Val Lys Gln Lys Glu Ala Lys Phe Glu Asn Gly Val Ile
                245                 250                 255

Thr Arg Lys Ala Asp Glu Lys Thr Thr Asn Asn Thr Ala Val Asp Lys
            260                 265                 270

Lys Ser Gly Lys Gln Ser Lys Lys Thr Thr Pro Ser Asn Lys Arg Asn
```

```
            275                 280                 285
Ala Ser Lys Ala Ser Thr Asn Lys Thr Ser Gly Gln Lys Lys Gln His
        290                 295                 300

Asn Lys Lys Ser Ser Gln Gly Ala Lys Lys Gln Ser Ser Ser Ser Lys
305                 310                 315                 320

Ser Thr Gln Lys Asn Asn Gln Thr Ser Asn Lys Asn Ser Lys Thr Thr
                325                 330                 335

Asn Ala Lys Ser Ser Asn Ala Ser Lys Thr Pro Asn Ala Lys Val Glu
            340                 345                 350

Lys Ala Lys Ser Lys Ile Glu Lys Arg Thr Phe Asn Asp
            355                 360                 365

<210> SEQ ID NO 97
<211> LENGTH: 351
<212> TYPE: PRT
<213> ORGANISM: Staphylococcus aureus

<400> SEQUENCE: 97

Lys Asp Asn Leu Asn Gly Glu Lys Pro Thr Thr Asn Leu Asn His Asn
1               5                   10                  15

Ile Thr Ser Pro Ser Val Asn Ser Glu Met Asn Asn Asn Glu Thr Gly
            20                  25                  30

Thr Pro His Glu Ser Asn Gln Thr Gly Asn Glu Gly Thr Gly Ser Asn
        35                  40                  45

Ser Arg Asp Ala Asn Pro Asp Ser Asn Asn Val Lys Pro Asp Ser Asn
    50                  55                  60

Asn Gln Asn Pro Ser Thr Asp Ser Lys Pro Asp Pro Asn Asn Gln Asn
65                  70                  75                  80

Pro Ser Pro Asn Pro Lys Pro Asp Pro Asp Asn Pro Lys Pro Lys Pro
                85                  90                  95

Asp Pro Lys Pro Asp Pro Asp Lys Pro Lys Pro Asn Pro Asp Pro Lys
            100                 105                 110

Pro Asp Pro Asp Asn Pro Lys Pro Asn Pro Asp Pro Lys Pro Asp Pro
        115                 120                 125

Asn Lys Pro Asn Pro Asp Pro Lys Pro Asp Pro Asp Lys Pro Lys Pro
    130                 135                 140

Asn Pro Asn Pro Lys Pro Asp Pro Asn Lys Pro Asn Pro Asn Pro Ser
145                 150                 155                 160

Pro Asp Pro Asp Gln Pro Gly Asp Ser Asn His Ser Gly Gly Ser Lys
                165                 170                 175

Asn Gly Gly Thr Trp Asn Pro Asn Ala Ser Asp Gly Ser Asn Gln Gly
            180                 185                 190

Gln Trp Gln Pro Asn Gly Asn Gln Gly Asn Ser Gln Asn Pro Thr Gly
        195                 200                 205

Asn Asp Phe Val Ser Gln Arg Phe Leu Ala Leu Ala Asn Gly Ala Tyr
    210                 215                 220

Lys Tyr Asn Pro Tyr Ile Leu Asn Gln Ile Asn Lys Leu Gly Lys Asp
225                 230                 235                 240

Tyr Gly Glu Val Thr Asp Glu Asp Ile Tyr Asn Ile Ile Arg Lys Gln
                245                 250                 255

Asn Phe Ser Gly Asn Ala Tyr Leu Asn Gly Leu Gln Gln Ser Asn
            260                 265                 270

Tyr Phe Arg Phe Gln Tyr Phe Asn Pro Leu Lys Ser Glu Arg Tyr Tyr
        275                 280                 285
```

Arg Asn Leu Asp Glu Gln Val Leu Ala Leu Ile Thr Gly Glu Ile Gly
290                 295                 300

Ser Met Pro Asp Leu Lys Lys Pro Glu Asp Lys Pro Asp Ser Lys Gln
305                 310                 315                 320

Arg Ser Phe Glu Pro His Glu Lys Asp Asp Phe Thr Val Val Lys Lys
                325                 330                 335

Gln Glu Asp Asn Lys Lys Ser Ala Ser Thr Ala Tyr Ser Lys Ser
                340                 345                 350

<210> SEQ ID NO 98
<211> LENGTH: 412
<212> TYPE: PRT
<213> ORGANISM: Staphylococcus aureus

<400> SEQUENCE: 98

Ile Asp Ser Lys Asn Lys Pro Ala Asn Ser Asp Ile Lys Phe Glu Val
1               5                   10                  15

Thr Gln Lys Ser Asp Ala Val Lys Ala Leu Lys Glu Leu Pro Lys Ser
                20                  25                  30

Glu Asn Val Lys Asn Ile Tyr Gln Asp Tyr Ala Val Thr Asp Val Lys
                35                  40                  45

Thr Asp Lys Lys Gly Phe Thr His Tyr Thr Leu Gln Pro Ser Val Asp
50                  55                  60

Gly Val His Ala Pro Asp Lys Glu Val Lys Val His Ala Asp Lys Ser
65                  70                  75                  80

Gly Lys Val Val Leu Ile Asn Gly Asp Thr Asp Ala Lys Lys Val Lys
                85                  90                  95

Pro Thr Asn Lys Val Thr Leu Ser Lys Asp Asp Ala Ala Asp Lys Ala
                100                 105                 110

Phe Lys Ala Val Lys Ile Asp Lys Asn Lys Ala Lys Asn Leu Lys Asp
                115                 120                 125

Lys Val Ile Lys Glu Asn Lys Val Glu Ile Asp Gly Asp Ser Asn Lys
130                 135                 140

Tyr Val Tyr Asn Val Glu Leu Ile Thr Val Thr Pro Glu Ile Ser His
145                 150                 155                 160

Trp Lys Val Lys Ile Asp Ala Gln Thr Gly Glu Ile Leu Glu Lys Met
                165                 170                 175

Asn Leu Val Lys Glu Ala Ala Glu Thr Gly Lys Gly Lys Gly Val Leu
                180                 185                 190

Gly Asp Thr Lys Asp Ile Asn Ile Asn Ser Ile Asp Gly Gly Phe Ser
                195                 200                 205

Leu Glu Asp Leu Thr His Gln Gly Lys Leu Ser Ala Phe Ser Phe Asn
210                 215                 220

Asp Gln Thr Gly Gln Ala Thr Leu Ile Thr Asn Glu Asp Glu Asn Phe
225                 230                 235                 240

Val Lys Asp Glu Gln Arg Ala Gly Val Asp Ala Asn Tyr Tyr Ala Lys
                245                 250                 255

Gln Thr Tyr Asp Tyr Tyr Lys Asp Thr Phe Gly Arg Glu Ser Tyr Asp
                260                 265                 270

Asn Gln Gly Ser Pro Ile Val Ser Leu Thr His Val Asn Asn Tyr Gly
                275                 280                 285

Gly Gln Asp Asn Arg Asn Asn Ala Ala Trp Ile Gly Asp Lys Met Ile
                290                 295                 300

Tyr Gly Asp Gly Asp Gly Arg Thr Phe Thr Ser Leu Ser Gly Ala Asn
305                 310                 315                 320

```
Asp Val Val Ala His Glu Leu Thr His Gly Val Thr Gln Glu Thr Ala
                325                 330                 335

Asn Leu Glu Tyr Lys Asp Gln Ser Gly Ala Leu Asn Glu Ser Phe Ser
            340                 345                 350

Asp Val Phe Gly Tyr Phe Val Asp Asp Glu Asp Phe Leu Met Gly Glu
        355                 360                 365

Asp Val Tyr Thr Pro Gly Lys Glu Gly Asp Ala Leu Arg Ser Met Ser
    370                 375                 380

Asn Pro Glu Gln Phe Gly Gln Pro Ala His Met Lys Asp Tyr Val Phe
385                 390                 395                 400

Thr Glu Lys Asp Asn Gly Gly Val His Thr Asn Ser
                405                 410

<210> SEQ ID NO 99
<211> LENGTH: 1872
<212> TYPE: DNA
<213> ORGANISM: Artificial sequence
<220> FEATURE:
<223> OTHER INFORMATION: DNA construct

<400> SEQUENCE: 99
aaacgtatca acaacatcc ggacgtacaa aaagttacag atgctacaag taaagttgct      60
tcaaaaacat ctgcagcaat cagtaacaca gcgagtgatg ttaaagaata tgtcggcgat     120
aaaaaacaag attttgaaaa taagcgtgaa cttaaaaagt ttgctagaga acatgatcct     180
gcctatattg agaaaaaagg cgaaaaatta gctaaacaaa atcgtaaaga cgctgataaa     240
atgaataaaa tacttcaaaa aaatatcgaa aagcgtcata agaagagca aaaagcccgc     300 gaaaagaatg aaatacaacg tattaaagat atgaaaagt cacaaaaata cgaagtaaaa     360
gcaggcttaa cacctaataa attagatgag aaaactgaga aaaaaggcga taaactagct     420
gaaaaaaatc gcaaagaaat cgctaaaatg aataaaaagt tacaaaaaaa tattgaaaaa     480
cgacacaaag aagaacaaaa acgccaacaa gaagctgata agcacgcat caagtcattt     540 aaaaaatata agattatgt tgccaaaagc gcctctcaac aaaataaaga aaacaataca     600
gaggcaggtt ctggcggagg ggctggaagt ggtgggggcg ccatggatat tggtaaaaaa     660
catgtaattc ctaaaagtca gtaccgacgt aagcgtcgtg aattcttcca caacgaagac     720
agagaagaaa atttaaatca acatcaagat aaacaaaata tagataatac aacatcaaaa     780
aaagcagata agcaaataca taaagattca attgataagc acgaacgttt taaaaatagt     840
ttatcatcgc atttagaaca gagaaaccgt gatgttaatg agaataaagc tgaagaaagt     900
aaaagtaatc aggatagtaa gtcagcatat aacagagatc attatttaac agacgatgta     960
tctaaaaaac aaaattcatt agattcagtg gaccaagata cagagaaatc aaaatattat    1020
gagcaaaatt ctgaagcgac tttatcaact aaatcaaccg ataaagtaga atcaactgaa    1080
atgagaaagc taagttcaga taaaacaaa gttggtcatg aagagcaaca tgtactttct    1140
aaaccttcag aacatgataa agagactaga attgattctg agtcttcaag aactgattca    1200
gacagctcga tgcagacaga gaaaataaaa aaagacagtt cagatggaaa taaaagtagt    1260
aatctgaaat ctgaagtaat atcagacaaa tcaaatacag taccaaaatt gtcggaatct    1320
gatgatgaag taataatca gaagccatta actttaccgg aagaacagaa attgaaaaga    1380
cagcaaagtc aaaatgagca aacaaaaacc tatacatatg gtgatagcga acaaaatgac    1440
aagtctaatc atgaaaatga tttaagtcat catataccat cgataagtga tgataaagat    1500
```

```
aacgtcatga gagaaaatca tattgttgac gataatcctg ataatgatat caatacacca    1560
tcattatcaa aaacagatga cgatcgaaaa cttgatgaaa aaattcatgt tgaagataaa    1620
cataaacaaa atgcagactc gtctgaaacg gtgggatatc aaagtcagtc aactgcatct    1680
catcgtagca ctgaaaaaag aaatatttct attaatgacc atgataaatt aaacggtcaa    1740 aaacaaata caaagacatc ggcaaataat aatcaaaaaa aggctacatc aaaattgaac    1800
aaagggcgcg ctacgaataa taattatagt gacattttga aaaagttttg gatgatgtat    1860
tggcctaaat aa                                                       1872

<210> SEQ ID NO 100
<211> LENGTH: 1872
<212> TYPE: DNA
<213> ORGANISM: Artificial sequence
<220> FEATURE:
<223> OTHER INFORMATION: DNA construct

<400> SEQUENCE: 100
atggatattg gtaaaaaaca tgtaattcct aaaagtcagt accgacgtaa gcgtcgtgaa      60
ttcttccaca acgaagacag agaagaaaat ttaaatcaac atcaagataa acaaaatata     120
gataatacaa catcaaaaaa agcagataag caaatacata aagattcaat tgataagcac     180
gaacgtttta aaaatagttt atcatcgcat ttagaacaga gaaaccgtga tgttaatgag     240
aataaagctg aagaaagtaa aagtaatcag gatagtaagt cagcatataa cagagatcat     300
tatttaacag acgatgtatc taaaaaacaa aattcattag attcagtgga ccaagataca     360
gagaaatcaa atattatga gcaaaattct gaagcgactt tatcaactaa atcaaccgat     420
aaagtagaat caactgaaat gagaaagcta agttcagata aaacaaagt tggtcatgaa     480 gagcaacatg tactttctaa accttcagaa catgataaag agactagaat tgattctgag     540
tcttcaagaa ctgattcaga cagctcgatg cagacagaga aaataaaaaa agacagttca     600 gatgaaata aaagtagtaa tctgaaatct gaagtaatat cagacaaatc aaatacagta     660
ccaaaattgt cggaatctga tgatgaagta aataatcaga agccattaac tttaccggaa     720
gaacagaaat tgaaaagaca gcaaagtcaa aatgagcaaa caaaaaccta acatatggt     780 gatagcgaac aaaatgacaa gtctaatcat gaaaatgatt taagtcatca tataccatcg     840
ataagtgatg ataaagataa cgtcatgaga gaaaatcata ttgttgacga taatcctgat     900
aatgatatca atacaccatc attatcaaaa acagatgacg atcgaaaact tgatgaaaaa     960
attcatgttg aagataaaca taaacaaaat gcagactcgt ctgaaacggt gggatatcaa    1020
agtcagtcaa ctgcatctca tcgtagcact gaaaaaagaa atatttctat taatgaccat    1080
gataaattaa acggtcaaaa aacaaataca aagacatcgg caaataataa tcaaaaaaag    1140
gctacatcaa aattgaacaa agggcgcgct acgaataata attatagtga cattttgaaa    1200
aagttttgga tgatgtattg gcctaaaggt tctggcggag gggctggaag tggtgggggc    1260
gccaaacgta tcaaacaaca tccggacgta caaaaagtta cagatgctac aagtaaagtt    1320
gcttcaaaaa catctgcagc aatcagtaac acagcgagtg atgttaaaga atatgtcggc    1380
gataaaaaac aagattttga aaataagcgt gaacttaaaa agtttgctag agaacatgat    1440
cctgcctata ttgagaaaaa aggcgaaaaa ttagctaaac aaaatcgtaa agacgctgat    1500
aaaatgaata aaatacttca aaaaaatatc gaaaagcgtc ataagaaga gcaaaaagcc    1560 cgcgaaaaga atgaaataca acgtattaaa gatatgaaaa agtcacaaaa atacgaagta    1620
aaagcaggct taacacctaa taaattagat gagaaaactg agaaaaaagg cgataaacta    1680
```

```
gctgaaaaaa atcgcaaaga aatcgctaaa atgaataaaa agttacaaaa aaatattgaa    1740
aaacgacaca aagaagaaca aaaacgccaa caagaagctg ataaagcacg catcaagtca    1800
tttaaaaaat ataaagatta tgttgccaaa agcgcctctc aacaaaataa agaaaacaat    1860
acagaggcat aa                                                        1872

<210> SEQ ID NO 101
<211> LENGTH: 1854
<212> TYPE: DNA
<213> ORGANISM: Artificial sequence
<220> FEATURE:
<223> OTHER INFORMATION: DNA construct

<400> SEQUENCE: 101
atggatattg gtaaaaaaca tgtaattcct aaaagtcagt accgacgtaa gcgtcgtgaa      60
ttcttccaca acgaagacag agaagaaaat ttaaatcaac atcaagataa acaaaatata     120
gataatacaa catcaaaaaa agcagataag caaatacata aagattcaat tgataagcac     180
gaacgtttta aaaatagttt atcatcgcat ttagaacaga gaaaccgtga tgttaatgag     240
aataaagctg aagaaagtaa aagtaatcag gatagtaagt cagcatataa cagagatcat     300
tatttaacag acgatgtatc taaaaaacaa aattcattag attcagtgga ccaagataca     360
gagaaatcaa atattatga gcaaaattct gaagcgactt tatcaactaa atcaaccgat     420
aaagtagaat caactgaaat gagaaagcta agttcagata aaaacaaagt tggtcatgaa     480
gagcaacatg tactttctaa accttcagaa catgataaag agactagaat tgattctgag     540
tcttcaagaa ctgattcaga cagctcgatg cagacagaga aaataaaaaa agacagttca     600
gatggaaata aagtagtaa tctgaaatct gaagtaatat cagacaaatc aaatacagta     660
ccaaaattgt cggaatctga tgatgaagta aataatcaga agccattaac tttaccggaa     720
gaacagaaat tgaaaagaca gcaaagtcaa aatgagcaaa caaaaaccta tacatatggt     780
gatagcgaac aaaatgacaa gtctaatcat gaaaatgatt taagtcatca tataccatcg     840
ataagtgatg ataaagataa cgtcatgaga gaaaatcata ttgttgacga taatcctgat     900
aatgatatca atacaccatc attatcaaaa acagatgacg atcgaaaact tgatgaaaaa     960
attcatgttg aagataaaca taaacaaat gcagactcgt ctgaaacggt gggatatcaa    1020
agtcagtcaa ctgcatctca tcgtagcact gaaaaaagaa atatttctat taatgaccat    1080
gataaattaa acggtcaaaa acaaatacaa aagacatcgg caaataataa tcaaaaaaag    1140
gctacatcaa aattgaacaa agggcgcgct acgaataata attatagtga catttttgaaa    1200 aagttttgga tgatgtattg gcctaaaggt tctggcggag gggctaaacg tatcaaacaa    1260
catccggacg tacaaaaagt tacagatgct acaagtaaag ttgcttcaaa aacatctgca    1320
gcaatcagta acacagcgag tgatgttaaa gaatatgtcg gcgataaaaa acaagatttt    1380
gaaaataagc gtgaacttaa aaagtttgct agagaacatg atcctgccta tattgagaaa    1440
aaaggcgaaa aattagctaa acaaaatcgt aaagacgctg ataaaatgaa taaaatactt    1500
caaaaaaata tcgaaaagcg tcataaagaa gagcaaaaag cccgcgaaaa gaatgaaata    1560
caacgtatta aagatatgaa aaagtcacaa aaatacgaag taaaagcagg cttaacacct    1620
aataaattag atgagaaaac tgagaaaaaa ggcgataaac tagctgaaaa aaatcgcaaa    1680
gaaatcgcta aatgaataaa aaagttacaa aaaatattg aaaaacgaca caagaagaa    1740 caaaaacgcc aacaagaagc tgataaagca cgcatcaagt catttaaaaa atataaagat    1800
```
tatgttgcca aaagcgcctc tcaacaaaat aaagaaaaca atacagaggc ataa    1854

<210> SEQ ID NO 102
<211> LENGTH: 1863
<212> TYPE: DNA
<213> ORGANISM: Artificial sequence
<220> FEATURE:
<223> OTHER INFORMATION: DNA construct

<400> SEQUENCE: 102
atggatattg gtaaaaaaca tgtaattcct aaaagtcagt accgacgtaa gcgtcgtgaa    60
ttcttccaca acgaagacag agaagaaaat ttaaatcaac atcaagataa acaaaatata   120
gataatacaa catcaaaaaa agcagataag caaatacata aagattcaat tgataagcac   180
gaacgtttta aaaatagttt atcatcgcat ttagaacaga gaaaccgtga tgttaatgag   240
aataaagctg aagaaagtaa aagtaatcag gatagtaagt cagcatataa cagagatcat   300
tatttaacag acgatgtatc taaaaaacaa aattcattag attcagtgga ccaagataca   360
gagaaatcaa aatattatga gcaaaattct gaagcgactt tatcaactaa atcaaccgat   420
aaagtagaat caactgaaat gagaaagcta agttcagata aaaacaaagt tggtcatgaa   480
gagcaacatg tactttctaa accttcagaa catgataaag agactagaat tgattctgag   540
tcttcaagaa ctgattcaga cagctcgatg cagacagaga aaataaaaaa agacagttca   600
gatgaaaata aagtagtaa tctgaaatct gaagtaatat cagacaaatc aaatacagta   660
ccaaaattgt cggaatctga tgatgaagta ataatcaga agccattaac tttaccggaa   720
gaacagaaat tgaaaagaca gcaaagtcaa atgagcaaa caaaaaccta acatatggt    780
gatagcgaac aaaatgacaa gtctaatcat gaaaatgatt taagtcatca tataccatcg   840
ataagtgatg ataaagataa cgtcatgaga gaaaatcata ttgttgacga taatcctgat   900
atgatatca atacaccatc attatcaaaa acagatgacg atcgaaaact tgatgaaaaa   960
attcatgttg aagataaaca taaacaaaat gcagactcgt ctgaaacggt gggatatcaa  1020
agtcagtcaa ctgcatctca tcgtagcact gaaaaaagaa atatttctat taatgaccat  1080
gataaattaa acggtcaaaa aacaaataca aagacatcgg caaataataa tcaaaaaaag  1140
gctacatcaa aattgaacaa agggcgcgct acgaataata attatagtga catttttgaaa  1200
aagtttttgga tgatgtattg gcctaaaggt tctggcggag gggctggaag tggtgggggc  1260
gccatgactg aaaaagaaaa aatgttagca gaaaaatggt acgatgcaaa ctttgatcaa  1320
gacttaatca tgaacgtgc acgagcgaaa gatatttgct ttgaattaaa tcatacaaag  1380
ccgagtgaca aaataaaag aaaggaatta atcgatgaat tatttcaaac aacaacagac  1440
aatgtaagta tttcgattcc ttttgataca gattatggtt ggaacgttaa actaggaaaa  1500
aatgtctatg taaacaccaa ttgttatttt atggatggtg gacagattac aattggcgat  1560
aatgtttta taggacctaa ttgtggattc tacacagcaa cacatccact taatttcat   1620
catagaaatg aaggatttga aaaagcagga ccaattaata ttggcagtaa tacttggttt  1680
ggcggacatg tagccgtgct tccgggagtg acgattggag aaggcagtgt gattggtgct  1740
ggtagtgttg tcaccaaaga tattccgcca cacagtttag cggttggaaa cccttgtaaa  1800
gtcgttcgta aaattgataa tgaggtacca tcagaagcat tgaacgatga aacactaaat  1860
tag                                                                 1863

<210> SEQ ID NO 103
<211> LENGTH: 1845

<212> TYPE: DNA
<213> ORGANISM: Artificial sequence
<220> FEATURE:
<223> OTHER INFORMATION: DNA construct

<400> SEQUENCE: 103

```
atggatattg gtaaaaaaca tgtaattcct aaaagtcagt accgacgtaa gcgtcgtgaa      60
ttcttccaca acgaagacag agaagaaaat ttaaatcaac atcaagataa acaaatata     120
gataatacaa catcaaaaaa agcagataag caaatacata aagattcaat tgataagcac    180
gaacgtttta aaaatagttt atcatcgcat ttagaacaga gaaaccgtga tgttaatgag    240
aataaagctg aagaaagtaa aagtaatcag gatagtaagt cagcatataa cagagatcat    300
tatttaacag acgatgtatc taaaaaacaa aattcattag attcagtgga ccaagataca    360
gagaaatcaa atattatga gcaaaattct gaagcgactt tatcaactaa atcaaccgat    420
aaagtagaat caactgaaat gagaaagcta agttcagata aaaacaaagt tggtcatgaa    480
gagcaacatg tactttctaa accttcagaa catgataaag agactagaat tgattctgag    540
tcttcaagaa ctgattcaga cagctcgatg cagacagaga aataaaaaa agacagttca    600
gatggaaata aaagtagtaa tctgaaatct gaagtaatat cagacaaatc aaatacagta    660
ccaaaattgt cggaatctga tgatgaagta aataatcaga agccattaac tttaccggaa    720
gaacagaaat tgaaaagaca gcaaagtcaa atgagcaaa caaaaaccta acatatggt    780
gatagcgaac aaaatgacaa gtctaatcat gaaaatgatt taagtcatca tataccatcg    840
ataagtgatg ataaagataa cgtcatgaga gaaaatcata ttgttgacga taatcctgat    900
aatgatatca atacaccatc attatcaaaa acagatgacg atcgaaaact tgatgaaaaa    960
attcatgttg aagataaaca taaacaaaat gcagactcgt ctgaaacggt gggatatcaa   1020
agtcagtcaa ctgcatctca tcgtagcact gaaaaaagaa atatttctat taatgaccat   1080
gataaattaa acggtcaaaa aacaaataca aagacatcgg caaataataa tcaaaaaaag   1140
gctacatcaa aattgaacaa agggcgcgct acgaataata attatagtga catttttgaaa  1200
aagttttgga tgatgtattg gcctaaaggt tctggcggag gggctatgac tgaaaaagaa   1260
aaaatgttag cagaaaaatg gtacgatgca aactttgatc aagacttaat caatgaacgt   1320
gcacgagcga aagatatttg cttttgaatta aatcatacaa agccgagtga caaaaataaa   1380
agaaaggaat taatcgatga attatttcaa acaacaacag acaatgtaag tatttcgatt   1440
cctttttgata cagattatgg ttggaacgtt aaactaggaa aaaatgtcta tgtaaacacc   1500
aattgttatt ttatgatgg tggacagatt acaattggcg ataatgtttt tataggacct   1560
aattgtggat tctacacagc aacacatcca cttaattttc atcatagaaa tgaaggattt   1620
gaaaaagcag gaccaattaa tattggcagt aatacttggt ttggcggaca tgtagccgtg   1680
cttccgggag tgacgattgg agaaggcagt gtgattggtg ctggtagtgt tgtcaccaaa   1740
gatattccgc cacacagttt agcggttgga aaccccttgta aagtcgttcg taaaattgat   1800
aatgaggtac catcagaagc attgaacgat gaaacactaa attag               1845
```

<210> SEQ ID NO 104
<211> LENGTH: 2418
<212> TYPE: DNA
<213> ORGANISM: Artificial sequence
<220> FEATURE:
<223> OTHER INFORMATION: DNA construct

<400> SEQUENCE: 104

```
atggatattg gtaaaaaaca tgtaattcct aaaagtcagt accgacgtaa gcgtcgtgaa    60
ttcttccaca acgaagacag agaagaaaat ttaaatcaac atcaagataa acaaaatata   120
gataatacaa catcaaaaaa agcagataag caaatacata aagattcaat tgataagcac   180
gaacgtttta aaaatagttt atcatcgcat ttagaacaga gaaaccgtga tgttaatgag   240
aataaagctg aagaaagtaa aagtaatcag gatagtaagt cagcatataa cagagatcat   300
tatttaacag acgatgtatc taaaaaacaa aattcattag attcagtgga ccaagataca   360
gagaaatcaa atattatga gcaaaattct gaagcgactt tatcaactaa atcaaccgat   420
aaagtagaat caactgaaat gagaaagcta agttcagata aaacaaagt tggtcatgaa   480
gagcaacatg tactttctaa accttcagaa catgataaag agactagaat tgattctgag   540
tcttcaagaa ctgattcaga cagctcgatg cagacagaga aaataaaaaa agacagttca   600
gatggaaata aaagtagtaa tctgaaatct gaagtaatat cagacaaatc aaatacagta   660
ccaaaattgt cggaatctga tgatgaagta aataatcaga agccattaac tttaccggaa   720
gaacagaaat tgaaaagaca gcaaagtcaa aatgagcaaa caaaaaccta tacatatggt   780
gatagcgaac aaaatgacaa gtctaatcat gaaaatgatt taagtcatca tataccatcg   840
ataagtgatg ataaagataa cgtcatgaga gaaaatcata ttgttgacga taatcctgat   900
aatgatatca atacaccatc attatcaaaa acagatgacg atcgaaaact tgatgaaaaa   960
attcatgttg aagataaaca taaacaaaat gcagactcgt ctgaaacggt gggatatcaa  1020
agtcagtcaa ctgcatctca tcgtagcact gaaaaaagaa atatttctat taatgaccat  1080
gataaattaa acggtcaaaa aacaaataca aagacatcgg caaataataa tcaaaaaaag  1140
gctacatcaa aattgaacaa agggcgcgct acgaataata attatagtga cattttgaaa  1200
aagtttttgga tgatgtattg gcctaaaggt tctggcggag gggctaaagt tgccaaacaa  1260
gggcagtata aaaatcaaga ccctatcgtg ttagtgcatg gtttcaatgg atttacagat  1320
gatattaatc cttcagtgtt agctcattat tggggcggta aaaaatgaa cattcgccaa  1380
gatttagaag aaaatggtta caaagcttat gaagcaagta aagtgctttt tggaagtaac  1440
tatgaccgcg cagttgaact ttattattat atcaaaggcg gtcgtgtaga ttatggtgca  1500
gcacatgcag caaaatatgg acatgaacgt tatggaaaaa catacgaagg aatttacaaa  1560
gactggaaac caggacagaa ggtacaccta gttggacata gtatgggtgg tcaaacgata  1620
cgtcaactag aagaattact gcgtaatggt agtcgtgaag aaatagagta tcaaaagaaa  1680
catggtggcg aaatttctcc actattcaaa ggtaataatg acaatatgat ttcatcaatt  1740
actactttag gaacgccaca taatggaacg catgcttcag atttagctgg taatgaagct  1800
ttagtgagac aaattgtatt tgatatcggt aaaatgtttg gtaataaaaa ctctagagta  1860
gacttcgggt tggctcaatg gggtctaaaa cagaagccaa atgaatcata cattgattat  1920
gtcaaacgcg ttaaacaatc taatttatgg aaatcaaaag ataatggatt ttacgatctg  1980
acgcgtgagg gtgcaacaga tttaaatcgt aaaacgtcgt tgaaccctaa cattgtgtat  2040
aaaacataca ctggtgaagc aacgcacaaa gcattaaata gcgatagaca aaaagcagac  2100
ttaaatatgt ttttcccatt tgtgattact ggtaacttaa tcggtaaagc tactgaaaaa  2160
gaatggcgag aaaacgatgg tttagtatcc gttatttctt ctcagcatcc atttaatcaa  2220
gcttatacaa atgcgacgga taaaattcaa aaaggcattt ggcaagtaac gcctacaaaa  2280
catgattggg atcatgttga ttttgtcgga caagatagtt ctgatacagt gcgcacaaga  2340
gaagaattac aagattttg gcatcattta gcagacgatt tagtgaaaac tgaaaaggtg  2400
```
actgatacta agcaataa 2418

<210> SEQ ID NO 105
<211> LENGTH: 3012
<212> TYPE: DNA
<213> ORGANISM: Artificial sequence
<220> FEATURE:
<223> OTHER INFORMATION: DNA construct

<400> SEQUENCE: 105

| | |
|---|---|
| cgaaatttgt tgcttcaaaa gcaatcacaa gctagacaaa ctgccgaaga tattgtaaat | 60 |
| caagcacata aagaagctga caatatcaaa aaagagaaat tacttgaggc aaaagaagaa | 120 |
| aaccaaatcc taagagaaca aactgaagca gaactacgag aaagacgtag cgaacttcaa | 180 |
| agacaagaaa cccgacttct tcaaaaagaa gaaaacttag agcgtaaatc tgatctatta | 240 |
| gataaaaaag atgagatttt agagcaaaaa gaatcaaaaa ttgaagaaaa acaacaacaa | 300 |
| gtagatgcaa aagagagtag tgttcaaacg ttaataatga agcatgaaca agaattagaa | 360 |
| cgcatctccg gtctcactca agaagaagct attaatgagc aacttcaaag agtagaggaa | 420 |
| gaactgtcac aagatattgc agtacttgtt aaagaaaaag aaaaagaagc taagaaaaaa | 480 |
| gttgataaaa cagcaaaaga attattagct acagcagtac aaagattagc agcagatcac | 540 |
| acaagtgaat caacggtatc agtagttaac ttacctaatg atgagatgaa aggtcgaatc | 600 |
| attggacgtg aaggacgaaa catccgtaca cttgaaactt taactggcat tgatttaatt | 660 |
| attgatgaca caccgaagc agttatatta tctggttttg atccaataag aagagaaatt | 720 |
| gctagaacag cacttgttaa cttagtatct gatggacgta ttcatccagg tagaattgaa | 780 |
| gatatggtcg aaaagctag aaaagaagta gacgatatta aagagaagc aggtgaacaa | 840 |
| gctacatttg aagtgaacgc acataatatg catcctgact tagtaaaaat tgtagggcgt | 900 |
| ttaaactatc gtacaagtta cggtcaaaat gtacttaaac attcaattga agttgcgcat | 960 |
| cttgctagta tgttagctgc tgagctaggc gaagatgaga cattagcgaa acgagctgga | 1020 |
| cttttacatg atgttggtaa agcaattgat catgaagtag aaggtagtca tgttgaaatc | 1080 |
| ggtgtagaat tagcgaaaaa atatggtgaa aatgaaacag ttattaatgc aatccattct | 1140 |
| caccatggtg atgttgaacc tacatctatt atatctatcc ttgttgctgc tgcagatgca | 1200 |
| ttgtctgcgg ctcgtccagg tgcaagaaaa gaaacattag agaattatat cgtcgatta | 1260 |
| gaacgtttag aaacgttatc agaaagttat gatggtgtag aaaaagcatt tgcgattcag | 1320 |
| gcaggtagag aaatccgagt gattgtatct cctgaagaaa ttgatgattt aaaatcttat | 1380 |
| cgattggcta gagatattaa aaatcagatt gaagatgaat tacaatatcc tggtcatatc | 1440 |
| aaggtgacag ttgttcgaga gactagagca gtagaatatg cgaaaaaacc tgagccgaaa | 1500 |
| ccagctcccg cccctaagcc agcatgtggg aatgatgatg gaaaagataa agatggcaag | 1560 |
| gtaacaatta aaacgacagt ttatccattg caatcatttg cagagcaaat tggtggaaaa | 1620 |
| cacgtgaagg tatcatcaat ctatccagca gggacagatt tacatagcta tgaaccaaca | 1680 |
| caaaaagata tattaagtgc aagcaaatca gacttgttta tgtatacagg ggataattta | 1740 |
| gatccggttg ctaagaaagt tgcatctact atcaaagata aagataaaaa actgtcttta | 1800 |
| gaagataaat tagataaagc aaagctttta actgatcaac acgaacatgg tgaagagcat | 1860 |
| gaacatgagg acatgatca tgagaaagaa gaacatcatc atcatggcgg atatgatcca | 1920 |
| cacgtatggt tagatcctaa aattaaccaa actttcgcta agaaattaa agatgaatta | 1980 |

```
gtgaagaaag atccaaaaca taaagatgac tatgagaaaa actacaaaaa attaaacgac    2040
gatcttaaga aaattgataa cgatatgaag caagttacaa aagataagca aggtaatgca    2100
gtattcattt cacatgaatc aattggatac ttagctgatc gttatggttt tgttcaaaaa    2160
ggtattcaaa acatgaatgc tgaagatcca tcacaaaaag aattaactaa aattgttaaa    2220
gaaattagag atagcaatgc aaaatatatt ctttatgaag ataatgttgc gaataaagtg    2280
actgaaacaa ttcgtaaaga aacagatgcg aagcctttaa aattctacaa catggagtct    2340
ttaaataaag aacaacagaa aaaagataat attacgtatc aatcattaat gaaatcgaat    2400
attgaaaata tcggtaaagc tttagacagt ggtgttaaag tgaaagacga taaagctgaa    2460
agtaaacacg acaaagcaat ttctgatggg tattttaaag atgagcaagt taaagaccgt    2520
gaattaagcg attatgctgg tgaatggcaa tctgtttacc cttacttaaa agacggtacg    2580
cttgatgaag tgatggaaca taaagctgaa aatgatccga agaaatctgc taaagattta    2640
aaagcttatt atgacaaagg atataaaact gatattacta acattgatat aaaaggaaat    2700
gaaattacat ttactaaaga tggtaagaaa cacactggta aatatgaata caatggtaag    2760
aaaacattga aatatcctaa aggtaaccgt ggcgtgagat ttatgtttaa attggtcgat    2820
ggtaatgata aagacttacc gaaattcatc caatttagcg atcacaacat tgcacctaaa    2880
aaggcagaac acttccatat ctttatgggt aatgataatg acgcgttatt aaaagaaatg    2940
gataactggc caacatatta tccttcaaaa ttaaataaag accaaatcaa agaagaaatg    3000
ttagcgcatt aa    3012

<210> SEQ ID NO 106
<211> LENGTH: 3030
<212> TYPE: DNA
<213> ORGANISM: Artificial sequence
<220> FEATURE:
<223> OTHER INFORMATION: DNA construct

<400> SEQUENCE: 106
atgaatgaaa agtagaagg catgaccttg agctgaaat tagaccattt aggtgtccaa      60
gaaggcatga aggtttaaa gcgacaatta ggtgttgtta atagtgaaat gaaagctaat     120
ctgtcagcat ttgataagtc tgaaaaatca atggaaaaat atcaggcgag aattaagggg    180
ttaaatgata ggcttaaagt tcaaaaaaag atgtattctc aagtagaaga tgagcttaaa    240
caagttaacg ctaattacca aaaagctaaa tccagtgtaa aagatgttga aaagcatat     300 ttaaagttag tagaagccaa taaaaagaa aaattagctc ttgataaatc taaagaagcc    360
ttaaaatcat cgaatacaga acttaaaaaa gctgaaaatc aatataaacg tacaaatcaa    420
cgtaaacaag atgcgtatca aaacttaaa cagttgagag atgcagaaca aaagcttaag    480
aatagtaacc aagctactac tgcacaacta aaaagagcaa gtgacgcagt acagaagcag    540
tccgctaagc ataaagcact tgttgaacaa tataaacaag aaggcaatca agttcaaaaa    600
ctaaaagtgc aaaatgacaa tcttcaaaa tcaaatgata aaattgaaag ttcttacgct    660
aaaactaata ctaaattaaa gcaaacagaa aaagaattta atgatttaaa caatactatt    720
aagaatcata cgctaatgt cgcaaaagct gaaacagctg ttaataaga aaagctgct     780 ttaaataatt tggagcgttc aatagataaa gcttcatccg aaatgaagac ttttaacaaa    840
gaacaaatga tagctcaaag tcatttcggt aaacttgcaa gtcaagcgga tgtcatgtca    900 aagaaatta gttctattgg agacaaaatg acttccctgg gacgtacaat gacgatgggc    960
gtatctacac caattacttt agggttaggt gcagcattaa aaacaagtgc agactttgaa    1020
```

```
ggccaaatgt ctcgagttgg agcgattgcg caagcaagca gtaaagactt gaaaagcatg    1080
tctaatcaag cagttgactt aggagctaaa accagtaaaa gtgctaacga agttgctaaa    1140
ggtatggaag aattggcagc tttaggcttt aatgccaaac aaacaatgga ggctatgcca    1200
ggtgttatca gtgcagcaga agcaagtggt gcagaaatgg ctacaactgc aactgtaatg    1260
gcttcagcga ttaactcttt cggttttaaaa gcatctgatg caaatcatgt tgctgattta    1320
cttgcgagat cagcaaatga tagtgctgca gatattcagt acatgggaga tgcattgaag    1380
tatgctggta ctcctgcaaa agcattagga gtttcaatag aggacacttc cgcagcaatt    1440
gaagttttat ctaactcagg tttagagggt tctcaagcag gtactgccct aagagcttca    1500
tttatcaggc tagctaatcc aagtaaaaat acagctaagg aaatgaaaaa attaggtatt    1560
catttgtctg atgctaaagg tcaatttgtt ggcatgggtg aattgattag acagttccaa    1620
gataatatga aaggcatgac gagagaacaa aaactagcta cagtggctac aatagttggt    1680
actgaagcag caagtggatt tttagccttg attgaagcgg gaccagataa aattaatagc    1740
tatagtaaat ccttaaagaa ttccaatggc gaaagtaaaa aagcagcaga tttgatgaaa    1800
gataatctca aaggcgctct ggaacaatta ggtggcgctt ttgaatcatt agcaatcgaa    1860
gtcggtaaag atttaacgcc tatgattaga gcaggagcgg aaggtttaac aaaattagtt    1920
gatggattta cacatctccc tggttgggtt agaaaaggtt ctggcggagg ggctgcaaag    1980
gataacttaa atggagaaaa gccaacgact aatttgaatc ataatgtaac ttcaccatca    2040
gtaaatagtg aaatgaataa taatgagact gggacacctc acgaatcaaa tcaagctggt    2100
aatgaaggaa ctggttcgaa tagtcgtgat gctaatcctg attcgaataa tgtgaagcca    2160
gactcaaaca accaaaaccc aagtccagat tcaaaacctg acccaaataa cccaaaccca    2220
ggtccgaatc cgaagccaga cccagataag ccgaaaccaa atccggaacc aaagccagac    2280
ccaaagccag acccagataa accaaagcca atccggatcc aaagccagac ccagataag    2340 ccgaaaccaa atccggatcc aaaaccagat ccagacaaac cgaagccaaa tccggatcca    2400
aaaccagatc caaatccgaa tccaaaacca gaccctaata agccaaatcc aaatccgtct    2460
ccaaatccca atcaacctgg ggattccaat caatctggtg gctcgaaaaa tgggggaca    2520 tggaacccaa atgcttcaga tggatctaat caaggtcaat ggcaaccaaa tggaaatcaa    2580
ggaaactcac aaaatcctac tggtaatgat tttgtatccc aacgattttt agccttggcg    2640
aatgggcttt acaagtataa tccgtatatt ttaaatcaaa ttaatcaatt ggggaaagaa    2700
tatggtgagg taactgatga agatatctac aatatcatcc gtaaacaaaa cttcagcgga    2760
aatgcatatt taaatggatt acaacagcaa tcgaattact ttagattcca atatttcaat    2820
ccattgaaat cagaaaggta ctatcgtaat ttagatgaac aagtactcgc attaattact    2880
ggcgaaattg gatcaatgcc agatttgaaa aagcccgaag ataagccgga ttcaaaacaa    2940
cgttcatttg agcctcatga aaagatgat tttacagttg taaaaaaaca agaagataat    3000
aagaaaagtg cgtcaactgc atatagttaa                                    3030
```

<210> SEQ ID NO 107
<211> LENGTH: 2187
<212> TYPE: DNA
<213> ORGANISM: Artificial sequence
<220> FEATURE:
<223> OTHER INFORMATION: DNA construct

<400> SEQUENCE: 107

```
ggattttttaa acaaatctaa aaatgagcaa gcggcattaa aggcacaaca agcagcgata      60
aaagaagaag caagtgcaaa taatttaagt gatacatcac aagaagcaca agagattcaa     120
gaagctaaaa gagaagcaca agcagaagcg ataaaagtg tggctgtatc aaataaagaa     180
tcaaaagcag tggcattgaa agcacaacaa gcagcgataa aagaagaagc aagtgcaaat     240
aatttgagtg atacatcaca agaggcacaa gagattcaag aagctaaaaa agaagcacaa     300
gcagaaacag ataaaagtgc agctgtatca aatgaagaac caaaagcagt ggcattgaaa     360
gcacaacaag cagcgataaa agaagaagca agtgcaaata atttaagtga tatatcacaa     420
gaggcacaag aggttcaaga agctaaaaaa gaagcacaag cagagaaaga cagtgacaca     480
ttaactaaag atgcaagtgc agcaaaggta gaagtatcaa aaccagagtc acaagctgaa     540
agattagcaa acgctgcaaa acagaagcaa gctaaattaa caccaggttc aaaagagagt     600
caattaactg aagcgttatt tgcagaaaaa ccagttgcta aaaatgactt gaaagaaatt     660
cctcaattag ttactaaaaa gaatgatgta tcagagacag agacggttaa tatagataat     720
aaagacactg ttaaacaaaa agaagctaaa tttgaaaatg gtgttattac acgtaaagct     780
gatgaaaaaa caactaataa tacagctgtt gacaagaaat caggtaaaca atctaaaaaa     840
acaacacctt caaataaacg aaatgcatca aaagcatcta caaataaaac ttcaggtcag     900
aaaaagcaac ataataagaa atcatcacaa ggtgcaaaga acaaagtag ttcaagtaag     960 tcaactcaaa agaataatca aactagtaat aagaattcaa aaacaacaaa tgctaaatca    1020
tccaatgcat caaaaacgcc aaatgctaaa gttgagaaag ctaaaagtaa aatagagaaa    1080
cgtacattca atgacggttc tggcggaggg gctggaagtg gtgggggcgc cgcaaaggat    1140
aacttaaatg gagaaaagcc aacgactaat ttgaatcata atgtaacttc accatcagta    1200
aatagtgaaa tgaataataa tgagactggg acacctcacg aatcaaatca agctggtaat    1260
gaaggaactg gttcgaatag tcgtgatgct aatcctgatt cgaataatgt gaagccagac    1320
tcaaacaacc aaaacccaag tccagattca aaacctgacc caaataaccc aaacccaggt    1380
ccgaatccga agccagaccc agataagccg aaaccaaatc cggaaccaaa gccagaccca    1440
aagccagacc cagataaacc aaagccaaat ccggatccaa agccagaccc agataagccg    1500
aaaccaaatc cggatccaaa accagatcca gacaaaccga agccaaatcc ggatccaaaa    1560
ccagatccaa atccgaatcc aaaaccagac cctaataagc caaatccaaa tccgtctcca    1620
aatcccaatc aacctgggga ttccaatcaa tctggtggct cgaaaaatgg ggggacatgg    1680
aacccaaatg cttcagatgg atctaatcaa ggtcaatggc aaccaaatgg aaatcaagga    1740
aactcacaaa atcctactgg taatgatttt gtatcccaac gattttttagc cttggcgaat    1800 ggggcttaca agtataatcc gtataatttta aatcaaatta atcaattggg gaaagaatat    1860
ggtgaggtaa ctgatgaaga tatctacaat atcatccgta acaaaactt cagcggaaat    1920 gcatatttaa atggattaca acagcaatcg aattactta gattccaata tttcaatcca    1980
ttgaaatcag aaaggtacta tcgtaattta gatgaacaag tactcgcatt aattactggc    2040
gaaattggat caatgccaga tttgaaaaag cccgaagata agccggattc aaaacaacgt    2100
tcatttgagc ctcatgaaaa agatgatttt acagttgtaa aaaacaagaa agataataag    2160
aaaagtgcgt caactgcata tagttaa                                        2187

<210> SEQ ID NO 108
<211> LENGTH: 2169
<212> TYPE: DNA
<213> ORGANISM: Artificial sequence
```

<220> FEATURE:
<223> OTHER INFORMATION: DNA construct

<400> SEQUENCE: 108

```
gcaaaggata acttaaatgg agaaaagcca acgactaatt tgaatcataa tgtaacttca      60
ccatcagtaa atagtgaaat gaataataat gagactggga cacctcacga atcaaatcaa     120
gctggtaatg aaggaactgg ttcgaatagt cgtgatgcta atcctgattc gaataatgtg     180
aagccagact caaacaacca aacccaagt ccagattcaa aacctgaccc aaataaccca      240
aacccaggtc cgaatccgaa gccagaccca gataagccga aaccaaatcc ggaaccaaag     300
ccagacccaa agccagaccc agataaacca aagccaaatc cggatccaaa gccagaccca     360
gataagccga aaccaaatcc ggatccaaaa ccagatccag acaaaccgaa gccaaatccg     420
gatccaaaac cagatccaaa tccgaatcca aaaccagacc ctaataagcc aaatccaaat     480
ccgtctccaa atcccaatca acctggggat tccaatcaat ctggtggctc gaaaaatggg     540
gggacatgga acccaaatgc ttcagatgga tctaatcaag gtcaatggca accaaatgga     600
aatcaaggaa actcacaaaa tcctactggt aatgattttg tatcccaacg attttttagcc    660
ttggcgaatg gggcttacaa gtataatccg tatattttaa atcaaattaa tcaattgggg     720
aaagaatatg gtgaggtaac tgatgaagat atctacaata tcatccgtaa acaaaacttc     780
agcggaaatg catatttaaa tggattacaa cagcaatcga attactttag attccaatat     840
ttcaatccat tgaaatcaga aaggtactat cgtaatttag atgaacaagt actcgcatta     900
attactggcg aaattggatc aatgccagat ttgaaaaagc ccgaagataa gccggattca     960
aaacaacgtt catttgagcc tcatgaaaaa gatgatttta cagttgtaaa aaacaagaa     1020
gataataaga aaagtgcgtc aactgcatat agtggttctg gcggagggggc tggattttta    1080
aacaaatcta aaaatgagca agcggcatta aaggcacaac aagcagcgat aaaagaagaa    1140
gcaagtgcaa ataatttaag tgatacatca caagaagcac aagagattca agaagctaaa    1200
agagaagcac aagcagaagc ggataaaagt gtggctgtat caaataaaga atcaaaagca    1260
gtggcattga agcacaaca agcagcgata aagaagaag caagtgcaaa taatttgagt     1320
gatacatcac aagaggcaca agagattcaa gaagctaaaa agaagcaca agcagaaaca    1380
gataaaagtg cagctgtatc aaatgaagaa ccaaaagcag tggcattgaa agcacaacaa    1440
gcagcgataa aagaagaagc aagtgcaaat aatttaagtg atatatcaca agaggcacaa    1500
gaggttcaag aagctaaaaa agaagcacaa gcagagaaag acagtgacac attaactaaa    1560
gatgcaagtg cagcaaaggt agaagtatca aaaccagagt cacaagctga agattagca    1620
aacgctgcaa acagaagca agctaaatta acaccaggtt caaaagagag tcaattaact    1680
gaagcgttat ttgcagaaaa accagttgct aaaaatgact tgaaagaaat tcctcaatta    1740
gttactaaaa agaatgatgt atcagagaca gagacggtta atatagataa taaagacact    1800
gttaaacaaa aagaagctaa atttgaaaat ggtgttatta cacgtaaagc tgatgaaaaa    1860
acaactaata tacagctgt tgacaagaaa tcaggtaaac aatctaaaaa acaacacct    1920
tcaaataaac gaaatgcatc aaaagcatct acaaatataaa cttcaggtca gaaaaagcaa    1980
cataataaga aatcatcaca aggtgcaaag aaacaaagta gttcaagtaa gtcaactcaa    2040
aagaataatc aaactagtaa taagaattca aaaacaacaa atgctaaatc atccaatgca    2100
tcaaaaacgc caaatgctaa agttgagaaa gctaaaagta aaatagagaa acgtacattc    2160
aatgactaa                                                             2169
```

<210> SEQ ID NO 109
<211> LENGTH: 2604
<212> TYPE: DNA
<213> ORGANISM: Artificial sequence
<220> FEATURE:
<223> OTHER INFORMATION: DNA construct

<400> SEQUENCE: 109

| | | | | | |
|---|---|---|---|---|---|
| gcatgtggga | atgatgatgg | aaaagataaa | gatggcaagg | taacaattaa | aacgacagtt | 60 |
| tatccattgc | aatcatttgc | agagcaaatt | ggtggaaaac | acgtgaaggt | atcatcaatc | 120 |
| tatccagcag | ggacagattt | acatagctat | gaaccaacac | aaaaagatat | attaagtgca | 180 |
| agcaaatcag | acttgtttat | gtatacaggg | gataatttag | atccggttgc | taagaaagtt | 240 |
| gcatctacta | tcaaagataa | agataaaaaa | ctgtctttag | aagataaatt | agataaagca | 300 |
| aagcttttaa | ctgatcaaca | cgaacatggt | gaagagcatg | aacatgaggg | acatgatcat | 360 |
| gagaagaag | aacatcatca | tcatggcgga | tatgatccac | acgtatggtt | agatcctaaa | 420 |
| attaaccaaa | ctttcgctaa | agaaattaaa | gatgaattag | tgaagaaaga | tccaaaacat | 480 |
| aaagatgact | atgagaaaaa | ctacaaaaaa | ttaaacgacg | atcttaagaa | aattgataac | 540 |
| gatatgaagc | aagttacaaa | agataagcaa | ggtaatgcag | tattcatttc | acatgaatca | 600 |
| attggatact | tagctgatcg | ttatggtttt | gttcaaaaag | gtattcaaaa | catgaatgct | 660 |
| gaagatccat | cacaaaaaga | attaactaaa | attgttaaag | aattagaga | tagcaatgca | 720 |
| aaatatattc | tttatgaaga | taatgttgcg | aataaagtga | ctgaaacaat | tcgtaaagaa | 780 |
| acagatgcga | agccttttaaa | attctacaac | atggagtctt | taaataaaga | acaacagaaa | 840 |
| aaagataata | ttacgtatca | atcattaatg | aaatcgaata | ttgaaaatat | cggtaaagct | 900 |
| ttagacagtg | tgttaaagt | gaaagacgat | aaagctgaaa | gtaaacacga | caaagcaatt | 960 |
| tctgatgggt | attttaaaga | tgagcaagtt | aaagaccgtg | aattaagcga | ttatgctggt | 1020 |
| gaatggcaat | ctgtttaccc | ttacttaaaa | gacggtacgc | ttgatgaagt | gatggaacat | 1080 |
| aaagctgaaa | atgatccgaa | gaaatctgct | aaagatttaa | aagcttatta | tgacaaagga | 1140 |
| tataaaactg | atattactaa | cattgatata | aaaggaaatg | aaattacatt | tactaaagat | 1200 |
| ggtaagaaac | acactggtaa | atatgaatac | aatggtaaga | aacattgaa | atatcctaaa | 1260 |
| ggtaaccgtg | gcgtgagatt | tatgtttaaa | ttggtcgatg | gtaatgataa | agacttaccg | 1320 |
| aaattcatcc | aatttagcga | tcacaacatt | gcacctaaaa | aggcagaaca | cttccatatc | 1380 |
| tttatgggta | atgataatga | cgcgttatta | aagaaatgg | ataactggcc | aacatattat | 1440 |
| ccttcaaaat | taaataaaga | ccaaatcaaa | gaagaaatgt | tagcgcatgg | ttctggcgga | 1500 |
| ggggctggat | ttttaaacaa | atctaaaaat | gagcaagcgg | cattaaaggc | acaacaagca | 1560 |
| gcgataaaag | aagaagcaag | tgcaaataat | ttaagtgata | catcacaaga | agcacaagag | 1620 |
| attcaagaag | ctaaaagaga | agcacaagca | gaagcggata | aaagtgtggc | tgtatcaaat | 1680 |
| aaagaatcaa | aagcagtggc | attgaaagca | caacaagcag | cgataaaaga | agaagcaagt | 1740 |
| gcaaataatt | tgagtgatac | atcacaagag | gcacaagaga | ttcaagaagc | taaaaaagaa | 1800 |
| gcacaagcag | aaacagataa | aagtgcagct | gtatcaaatg | aagaaccaaa | agcagtggca | 1860 |
| ttgaaagcac | aacaagcagc | gataaaagaa | gaagcaagtg | caaataattt | aagtgatata | 1920 |
| tcacaagagg | cacaagaggt | tcaagaagct | aaaaaagaag | cacaagcaga | gaaagacagt | 1980 |
| gacacattaa | ctaagatgc | aagtgcagca | aaggtagaag | tatcaaaacc | agagtcacaa | 2040 |
| gctgaaagat | tagcaaacgc | tgcaaaacag | aagcaagcta | aattaacacc | aggttcaaaa | 2100 |

```
gagagtcaat taactgaagc gttatttgca gaaaaaccag ttgctaaaaa tgacttgaaa    2160
gaaattcctc aattagttac taaaaagaat gatgtatcag agacagagac ggttaatata    2220
gataataaag acactgttaa acaaaaagaa gctaaatttg aaaatggtgt tattacacgt    2280
aaagctgatg aaaaaacaac taataataca gctgttgaca agaaatcagg taaacaatct    2340
aaaaaaacaa caccttcaaa taaacgaaat gcatcaaaag catctacaaa taaaacttca    2400
ggtcagaaaa agcaacataa taagaaatca tcacaaggtg caaagaaaca aagtagttca    2460
agtaagtcaa ctcaaaagaa taatcaaact agtaataaga attcaaaaac aacaaatgct    2520 aaaatcatcca atgcatcaaa aacgccaaat gctaaagttg agaaagctaa aagtaaaata    2580
gagaaacgta cattcaatga ctaa                                           2604
```

<210> SEQ ID NO 110
<211> LENGTH: 2394
<212> TYPE: DNA
<213> ORGANISM: Artificial sequence
<220> FEATURE:
<223> OTHER INFORMATION: DNA construct

<400> SEQUENCE: 110

```
atgactgaaa agaaaaaaat gttagcagaa aaatggtacg atgcaaactt tgatcaagac      60
ttaatcaatg aacgtgcacg agcgaaagat atttgctttg aattaaatca tacaaagccg     120
agtgacaaaa ataaaagaaa ggaattaatc gatgaattat ttcaaacaac aacagacaat     180
gtaagtattt cgattccttt tgatacagat tatggttgga acgttaaact aggaaaaaat     240
gtctatgtaa acaccaattg ttattttatg gatggtggac agattacaat tggcgataat     300 gttttttatag gacctaattg tggattctac acagcaacac atccacttaa ttttcatcat     360
agaaatgaag gatttgaaaa agcaggacca attaatattg cagtaatac  ttggtttggc     420 ggacatgtag ccgtgcttcc gggagtgacg attggagaag cagtgtgat  tggtgctggt     480 agtgttgtca ccaaagatat tccgccacac agtttagcgg ttggaaaccc  ttgtaaagtc     540
gttcgtaaaa ttgataatga ggtaccatca gaagcattga acgatgaaac  actaaatggt     600
tctggcggag gggctgatac acctcaaaaa gatactacag ctaagacaac  atctcatgat     660
tcaaaaaaat ctaatgacga tgaaacttct aaggatacta caagtaaaga  tattgataaa     720
gcagacaaca ataatacaag taaccaagac aataacgaca aaaatttaa  actatagac      780 gacagcactt cagactctaa caatatcatt gattttattt ataagaattt  accacaaacc     840
aatataaacc aattgctaac caaaaataaa tacgatgata attactcatt  aacaacttta     900 atccaaaaacc tattcaattt aaattcggat atttctgatt acgaacaacc  tcgtaatggc     960
gaaaagtcaa caaatgattc gaataaaaac agtgacaata gcatcaaaaa  tgacactgat    1020
acgcaatcat ctaaacaaga taaagcagac aatcaaaaag cacctaaatc  aaacaataca    1080
aaaccaagta catctaataa gcaaccaaat tcgccaaagc caacacaacc  taatcaatca    1140
aatagtcaac cagcaagtga cgataaagca atcaaaaat  cttcatcgaa  agataatcaa    1200
tcaatgtcag attcggcttt agactctatt ttggatcaat acagtgaaga  tgcaagaaa     1260 acacaaaaag attatgcatc tcaatctaaa aaagacaaaa atgaaaaatc  taatacaaag    1320
aatccacagt taccaacaca agatgaattg aaacataaat  ctaaacctgc  tcaatcattc    1380
aataacgatg ttaatcaaaa ggatacacgt gcaacatcat  tattcgaaac  agatcctagt    1440
atatctaaca atgatgatag cggacaattt aacgttgttg  actcaaaaga  tacacgtcaa    1500
```

| | |
|---|---|
| tttgtcaaat caattgctaa agatgcacat cgcattggtc aagataacga tatttatgcg | 1560 |
| tctgtcatga ttgcccaagc aatcttagaa tctgactcag gtcgtagtgc tttagctaag | 1620 |
| tcaccaaacc ataatttatt cggtatcaaa ggtgcttttg aagggaattc tgttcctttt | 1680 |
| aacacattag aagctgatgg taataaattg tatagtatta atgctggatt ccgaaaatat | 1740 |
| ccaagcacga aagaatcact aaaagattac tctgacccta ttaaaaatgg tattgatggc | 1800 |
| aatcgaacaa tttataaacc aacatggaaa tcggaagccg attcttataa agatgcaaca | 1860 |
| tcacacttat ctaaaacata tgctacagat ccaaactatg ctaagaaatt aaacagtatt | 1920 |
| attaaacact atcaattaac tcagtttgac gatgaacgca tgccagattt agataaatat | 1980 |
| gaacgttcta tcaaggatta tgatgattca tcagatgaat caaacccttt ccgtgaggta | 2040 |
| tctgatagta tgccatatcc acatggtcaa tgtacttggt acgtatataa ccgtatgaaa | 2100 |
| caatttggta catctatctc aggtgattta ggtgatgcac ataattggaa taatcgagct | 2160 |
| caataccgtg attatcaagt aagtcataca ccaaaacgtc atgctgctgt tgtatttgag | 2220 |
| gctggacaat ttggtgcaga tcaacattac ggtcatgtag catttgttga aaaagttaac | 2280 |
| agtgatggtt ctatcgttat ttcagaatcc aatgttaaag gattaggtat catttctcat | 2340 |
| agaactatca atgcagctgc cgctgaagaa ttatcatata ttacaggtaa ataa | 2394 |

<210> SEQ ID NO 111
<211> LENGTH: 2352
<212> TYPE: DNA
<213> ORGANISM: Artificial sequence
<220> FEATURE:
<223> OTHER INFORMATION: DNA construct

<400> SEQUENCE: 111

| | |
|---|---|
| attgattcaa aaataaaacc agctaattct gatattaaat ttgaggtgac tcaaaagagt | 60 |
| gatgcggtca agcattaaa agaattgcct aaatccgaaa atgtaaaaaa tatttatcaa | 120 |
| gattacgctg ttactgatgt aaaaactgat aaaaaaggat ttacgcatta tacattgcaa | 180 |
| ccgagtgttg atggtgttca tgcacctgac aaagaagtga agtacacgc agacaaatca | 240 |
| ggaaaagtcg ttttaatcaa tgggggatact gatgcgaaga agtaaagcc aacgaataaa | 300 |
| gtgacattaa gtaaagatga cgcagccgac aaagcattta agcagttaa gattgataag | 360 |
| aataaagcga aaatcttaa agataaagtc attaaagaaa acaaagttga atcgatggt | 420 |
| gacagtaata aatacgttta taatgttgag ttaattacag tgacaccaga aatttcacat | 480 |
| tggaaagtta aaattgatgc tcaaactggc gaaattttag aaaaaatgaa cttagttaaa | 540 |
| gaagctgcag aaactggtaa aggaaaaggt gtacttggcg atacaaaaga tatcaatatc | 600 |
| aatagtattg acggtggatt tagcctagaa gatttaacgc atcaaggtaa attatcagca | 660 |
| tttagcttta atgatcaaac aggtcaagca acattgatta ctaatgaaga tgaaaacttc | 720 |
| gtaaagatg agcaacgtgc tggcgtagat gcaaattatt acgctaaaca aacatatgat | 780 |
| tattacaaag acacatttgg tcgtgaatca tatgacaacc aaggtagtcc aattgtttca | 840 |
| ttaacgcatg ttaataacta cggtggtcaa gataacagaa ataatgccgc atggatcggt | 900 |
| gacaaaatga tctatggtga tgtgatggt cgcacattca aagtttatc gggtgcaaat | 960 |
| gacgtagtag cacacgaatt aacacacggt gtgacacaag agacagcgaa cttagaatat | 1020 |
| aaggaccagt caggcgctct aaatgaaagc ttttcagatg ttttggata ctttgtagat | 1080 |
| gacgaggatt tcttaatggg tgaagatgtc tacacacctg gaaagagggg agacgcttta | 1140 |
| cgcagcatgt caaacccaga acaatttggt caaccagctc atatgaaaga ctatgtattc | 1200 |

-continued

| | |
|---|---|
| actgaaaaag ataatggtgg cgtacatacg aattctggtt ctggcggagg ggctggattt | 1260 |
| ttaaacaaat ctaaaaatga gcaagcggca ttaaaggcac aacaagcagc gataaaagaa | 1320 |
| gaagcaagtg caaataattt aagtgataca tcacaagaag cacaagagat tcaagaagct | 1380 |
| aaaagagaag cacaagcaga agcggataaa agtgtggctg tatcaaataa agaatcaaaa | 1440 |
| gcagtggcat tgaaagcaca acaagcagcg ataaaagaag aagcaagtgc aaataatttg | 1500 |
| agtgatacat cacaagaggc acaagagatt caagaagcta aaaagaagc acaagcagaa | 1560 |
| acagataaaa gtgcagctgt atcaaatgaa gaaccaaaag cagtggcatt gaaagcacaa | 1620 |
| caagcagcga taaagaaga agcaagtgca ataatttaa gtgatatatc acaagaggca | 1680 |
| caagaggttc aagaagctaa aaagaagca caagcagaga agacagtga cacattaact | 1740 |
| aaagatgcaa gtgcagcaaa ggtagaagta tcaaaaccag agtcacaagc tgaaagatta | 1800 |
| gcaaacgctg caaaacagaa gcaagctaaa ttaacaccag gttcaaaaga gagtcaatta | 1860 |
| actgaagcgt tatttgcaga aaaaccagtt gctaaaaatg acttgaaaga aattcctcaa | 1920 |
| ttagttacta aaagaatga tgtatcagag acagagacgg ttaatataga taataaagac | 1980 |
| actgttaaac aaaagaagc taaatttgaa atggtgtta ttacacgtaa agctgatgaa | 2040 |
| aaaacaacta ataatacagc tgttgacaag aaatcaggta acaatctaa aaaaacaaca | 2100 |
| ccttcaaata aacgaaatgc atcaaaagca tctacaaata aaacttcagg tcagaaaaag | 2160 |
| caacataata agaaatcatc acaaggtgca aagaaacaaa gtagttcaag taagtcaact | 2220 |
| caaaagaata atcaaactag taataagaat tcaaaaacaa caaatgctaa atcatccaat | 2280 |
| gcatcaaaaa cgccaaatgc taaagttgag aaagctaaaa gtaaaataga gaaacgtaca | 2340 |
| ttcaatgact aa | 2352 |

<210> SEQ ID NO 112
<211> LENGTH: 2310
<212> TYPE: DNA
<213> ORGANISM: Artificial sequence
<220> FEATURE:
<223> OTHER INFORMATION: DNA construct

<400> SEQUENCE: 112

| | |
|---|---|
| attgattcaa aaaataaacc agctaattct gatattaaat ttgaggtgac tcaaaagagt | 60 |
| gatgcggtca agcattaaaa agaattgcct aaatccgaaa atgtaaaaaa tatttatcaa | 120 |
| gattacgctg ttactgatgt aaaaactgat aaaaaaggat ttacgcatta tacattgcaa | 180 |
| ccgagtgttg atggtgttca tgcacctgac aaagaagtga agtacacgc agacaaatca | 240 |
| ggaaaagtcg tttaatcaa tggggatact gatgcgaaga agtaaagcc aacgaataaa | 300 |
| gtgacattaa gtaagatga cgcagccgac aaagcattta agcagttaa gattgataag | 360 |
| aataaagcga aaaatcttaa agataaagtc attaaagaaa acaaagttga atcgatggt | 420 |
| gacagtaata aatacgttta taatgttgag ttaattacag tgacaccaga aatttcacat | 480 |
| tggaaagtta aaattgatgc tcaaactggc gaaattttag aaaaaatgaa cttagttaaa | 540 |
| gaagctgcag aaactggtaa aggaaaaggt gtacttggcg atacaaaaga tatcaatatc | 600 |
| aatagtattg acggtggatt tagcctagaa gatttacgc atcaaggtaa attatcagca | 660 |
| tttagcttta atgatcaaac aggtcaagca acattgatta ctaatgaaga tgaaaacttc | 720 |
| gtaaaagatg agcaacgtgc tggcgtagat gcaaattatt acgctaaaca acatatgat | 780 |
| tattacaaag acacatttgg tcgtgaatca tatgacaacc aaggtagtcc aattgtttca | 840 |

```
ttaacgcatg ttaataacta cggtggtcaa gataacagaa ataatgccgc atggatcggt      900
gacaaaatga tctatggtga tggtgatggt cgcacattca aagtttatc gggtgcaaat       960
gacgtagtag cacacgaatt aacacacggt gtgacacaag agacagcgaa cttagaatat     1020
aaggaccagt caggcgctct aaatgaaagc ttttcagatg ttttttggata ctttgtagat    1080
gacgaggatt tcttaatggg tgaagatgtc tacacacctg aaaagaggg agacgcttta     1140
cgcagcatgt caaacccaga acaatttggt caaccagctc atatgaaaga ctatgtattc   1200
actgaaaaag ataatggtgg cgtacatacg aattctggtt ctggcggagg ggctgcaaag  1260
gataacttaa atggagaaaa gccaacgact aatttgaatc ataatgtaac ttcaccatca    1320
gtaaatagtg aaatgaataa taatgagact gggacacctc acgaatcaaa tcaagctggt    1380
aatgaaggaa ctggttcgaa tagtcgtgat gctaatcctg attcgaataa tgtgaagcca   1440
gactcaaaca accaaaaccc aagtccagat tcaaaacctg acccaaataa cccaaaccca    1500
ggtccgaatc cgaagccaga cccagataag ccgaaaccaa atccggaacc aaagccagac   1560
ccaaagccag acccagataa accaaagcca atccggatc caaagccaga cccagataag    1620
ccgaaaccaa atccggatcc aaaaccagat ccagacaaac cgaagccaaa tccggatcca   1680
aaaccagatc caaatccgaa tccaaaacca gaccctaata agccaaatcc aaatccgtct    1740
ccaaatccca atcaacctgg ggattccaat caatctggtg gctcgaaaaa tgggggaca    1800
tggaacccaa atgcttcaga tggatctaat caaggtcaat ggcaaccaaa tggaaatcaa    1860
ggaaactcac aaaatcctac tggtaatgat tttgtatccc aacgattttt agccttggcg    1920
aatgggctt acaagtataa tccgtatatt ttaaatcaaa ttaatcaatt ggggaaagaa     1980
tatggtgagg taactgatga agatatctac aatatcatcc gtaaacaaaa cttcagcgga    2040
aatgcatatt taaatggatt acaacagcaa tcgaattact ttagattcca atatttcaat   2100
ccattgaaat cagaaaggta ctatcgtaat ttagatgaac aagtactcgc attaattact    2160
ggcgaaattg gatcaatgcc agatttgaaa aagcccgaag ataagccgga ttcaaaacaa   2220
cgttcatttg agcctcatga aaaagatgat tttacagttg taaaaaaaca agaagataat   2280
aagaaaagtg cgtcaactgc atatagttaa                                    2310
```

<210> SEQ ID NO 113
<211> LENGTH: 2445
<212> TYPE: DNA
<213> ORGANISM: Artificial sequence
<220> FEATURE:
<223> OTHER INFORMATION: DNA construct

<400> SEQUENCE: 113

```
attgattcaa aaaataaacc agctaattct gatattaaat ttgaggtgac tcaaaagagt       60
gatgcggtca aagcattaaa agaattgcct aaatccgaaa atgtaaaaaa tatttatcaa      120
gattacgctg ttactgatgt aaaaactgat aaaaaaggat ttacgcatta tacattgcaa     180
ccgagtgttg atggtgttca tgcacctgac aaagaagtga agtacacgc agacaaatca     240
ggaaaagtcg tttaatcaa tggggatact gatgcgaaga agtaaagcc aacgaataaa      300
gtgacattaa gtaaagatga cgcagccgac aaagcattta agcagttaa gattgataag    360
aataaagcga aaatcttaa agataaagtc attaaagaaa acaagttga atcgatggt        420
gacagtaata aatacgttta taatgttgag ttaattacag tgacaccaga atttcacat     480
tggaaagtta aaattgatgc tcaaactggc gaaattttag aaaaaatgaa cttagttaaa    540
gaagctgcag aaactggtaa aggaaaaggt gtacttggcg atacaaaaga tatcaatatc    600
```

```
aatagtattg acggtggatt tagcctagaa gatttaacgc atcaaggtaa attatcagca    660 tttagctttta atgatcaaac aggtcaagca acattgatta ctaatgaaga tgaaaacttc    720
gtaaaagatg agcaacgtgc tggcgtagat gcaaattatt acgctaaaca aacatatgat    780
tattacaaag acacatttgg tcgtgaatca tatgacaacc aaggtagtcc aattgtttca    840
ttaacgcatg ttaataacta cggtggtcaa gataacagaa ataatgccgc atggatcggt    900
gacaaaatga tctatggtga tggtgatggt cgcacattca aagtttatc gggtgcaaat    960 gacgtagtag cacacgaatt aacacacggt gtgacacaag agacagcgaa cttagaatat    1020
aaggaccagt caggcgctct aaatgaaagc ttttcagatg ttttttggata ctttgtagat    1080 gacgaggatt tcttaatggg tgaagatgtc tacacacctg aaaagagg agacgcttta    1140 cgcagcatgt caaacccaga acaatttggt caaccagctc atatgaaaga ctatgtattc    1200
actgaaaaag ataatggtgg cgtacatacg aattctggtt ctggcggagg ggctggaagt    1260 ggtggggggcg ccaaagttgc caaacaaggg cagtataaaa atcaagaccc tatcgtgtta    1320
gtgcatggtt tcaatggatt tacagatgat attaatcctt cagtgttagc tcattattgg    1380
ggcggtaata aaatgaacat tcgccaagat ttagaagaaa atggttacaa agcttatgaa    1440
gcaagtataa gtgcttttgg aagtaactat gaccgcgcag ttgaacttta ttattatatc    1500
aaaggcggtc gtgtagatta tggtgcagca catgcagcaa aatatggaca tgaacgttat    1560
ggaaaaacat acgaaggaat ttacaaagac tggaaaccag gacagaaggt acacctagtt    1620
ggacatagta tgggtggtca aacgatacgt caactagaag aattactgcg taatggtagt    1680
cgtgaagaaa tagagtatca aaagaaacat ggtggcgaaa tttctccact attcaaaggt    1740
aataatgaca atatgatttc atcaattact actttaggaa cgccacataa tggaacgcat    1800
gcttcagatt tagctggtaa tgaagcttta gtgagacaaa ttgtatttga tatcggtaaa    1860
atgtttggta taaaaactc tagagtagac ttcgggttgg ctcaatgggg tctaaaacag    1920
aagccaaatg aatcatacat tgattatgtc aaacgcgtta acaatctaa tttatggaaa    1980 tcaaaagata atggattta cgatctgacg cgtgagggtg caacagattt aaatcgtaaa    2040
acgtcgttga accctaacat tgtgtataaa acatacactg gtgaagcaac gcacaaagca    2100
ttaaatagcg atagacaaaa agcagactta aatatgtttt tcccatttgt gattactggt    2160
aacttaatcg gtaaagctac tgaaaaagaa tggcgagaaa acgatggttt agtatccgtt    2220
atttcttctc agcatccatt taatcaagct tatacaaatg cgacggataa aattcaaaaa    2280
ggcatttggc aagtaacgcc tacaaaacat gattgggatc atgttgattt tgtcggacaa    2340
gatagttctg atacagtgcg cacaagagaa gaattacaag attttttggca tcatttagca    2400 gacgatttag tgaaaactga aaaggtgact gatactaagc aataa    2445
```

<210> SEQ ID NO 114
<211> LENGTH: 2394
<212> TYPE: DNA
<213> ORGANISM: Artificial sequence
<220> FEATURE:
<223> OTHER INFORMATION: DNA construct

<400> SEQUENCE: 114

```
gatacacctc aaaaagatac tacagctaag acaacatctc atgattcaaa aaaatctaat    60
gacgatgaaa cttctaagga tactacaagt aaagatattg ataaagcaga caacaataat    120
acaagtaacc aagacaataa cgacaaaaaa tttaaaacta tagacgacag cacttcagac    180
```

```
tctaacaata tcattgattt tatttataag aatttaccac aaaccaatat aaaccaattg    240
ctaaccaaaa ataaatacga tgataattac tcattaacaa ctttaatcca aaacctattc    300
aatttaaatt cggatatttc tgattacgaa caacctcgta atggcgaaaa gtcaacaaat    360
gattcgaata aaaacagtga caatagcatc aaaaatgaca ctgatacgca atcatctaaa    420
caagataaag cagacaatca aaaagcacct aaatcaaaca atacaaaacc aagtacatct    480
aataagcaac caaattcgcc aaagccaaca caacctaatc aatcaaatag tcaaccagca    540
agtgacgata aagcaaatca aaaatcttca tcgaaagata atcaatcaat gtcagattcg    600
gctttagact ctattttgga tcaatacagt gaagatgcaa agaaaacaca aaagagattat    660 gcatctcaat ctaaaaaaga caaaaatgaa aaatctaata caagaatcc acagttacca    720 acacaagatg aattgaaaca taaatctaaa cctgctcaat cattcaataa cgatgttaat    780
caaaaggata cacgtgcaac atcattattc gaaacagatc ctagtatatc taacaatgat    840
gatagcggac aatttaacgt tgttgactca aaagatacac gtcaatttgt caaatcaatt    900
gctaaagatg cacatcgcat tggtcaagat aacgatattt atgcgtctgt catgattgcc    960
caagcaatct tagaatctga ctcaggtcgt agtgctttag ctaagtcacc aaaccataat   1020
ttattcggta tcaaaggtgc ttttgaaggg aattctgttc ctttaacac attagaagct   1080 gatggtaata aattgtatag tattaatgct ggattccgaa atatccaag cacgaaagaa   1140 tcactaaaag attactctga ccttattaaa atggtattg atggcaatcg aacaatttat   1200
aaaccaacat ggaaatcgga agccgattct tataaagatg caacatcaca cttatctaaa   1260
acatatgcta cagatccaaa ctatgctaag aaattaaaca gtattattaa acactatcaa   1320
ttaactcagt ttgacgatga acgcatgcca gatttagata aatatgaacg ttctatcaag   1380
gattatgatg attcatcaga tgaattcaaa cctttccgtg aggtatctga tagtatgcca   1440
tatccacatg gtcaatgtac ttggtacgta tataaccgta tgaaacaatt tggtacatct   1500
atctcaggtg atttaggtga tgcacataat tggaataatc gagctcaata ccgtgattat   1560
caagtaagtc atacaccaaa acgtcatgct gctgttgtat ttgaggctgg acaatttggt   1620
gcagatcaac attacggtca tgtagcattt gttgaaaaag ttaacagtga tggttctatc   1680
gttatttcag aatccaatgt taaaggatta ggtatcattt ctcatagaac tatcaatgca   1740
gctgccgctg aagaattatc atatattaca ggtaaaggtt ctggcggagg ggctatgact   1800
gaaaaagaaa aaatgttagc agaaaaatgg tacgatgcaa actttgatca agacttaatc   1860
aatgaacgtg cacgagcgaa agatatttgc tttgaattaa atcatacaaa gccgagtgac   1920
aaaaataaaa gaaggaatt aatcgatgaa ttatttcaaa caacaacaga caatgtaagt   1980
atttcgattc cttttgatac agattatggt tggaacgtta aactaggaaa aaatgtctat   2040
gtaaacacca attgttattt tatggatggt ggacagatta caattggcga taatgttttt   2100
ataggaccta attgtggatt ctacacagca acacatccac ttaattttca tcatagaaat   2160
gaaggatttg aaaaagcagg accaattaat attggcagta atacttggtt tggcggacat   2220
gtagccgtgc ttccgggagt gacgattgga gaaggcagtg tgattggtgc tggtagtgtt   2280
gtcaccaaag atattccgcc acacagttta gcggttggaa acccttgtaa agtcgttcgt   2340
aaaattgata atgaggtacc atcagaagca ttgaacgatg aaacactaaa ttag         2394
```

<210> SEQ ID NO 115
<211> LENGTH: 2412
<212> TYPE: DNA
<213> ORGANISM: Artificial sequence
<220> FEATURE:
<223> OTHER INFORMATION: DNA construct

<400> SEQUENCE: 115

```
gatacacctc aaaaagatac tacagctaag acaacatctc atgattcaaa aaaatctaat      60
gacgatgaaa cttctaagga tactacaagt aaagatattg ataaagcaga caacaataat     120
acaagtaacc aagacaataa cgacaaaaaa tttaaaacta tagacgacag cacttcagac     180
tctaacaata tcattgattt tatttataag aatttaccac aaaccaatat aaaccaattg     240
ctaaccaaaa ataaatacga tgataattac tcattaacaa ctttaatcca aaacctattc     300
aatttaaatt cggatatttc tgattacgaa caacctcgta atggcgaaaa gtcaacaaat     360
gattcgaata aaaacagtga caatagcatc aaaaatgaca ctgatacgca atcatctaaa     420
caagataaag cagacaatca aaaagcacct aaatcaaaca atacaaaacc aagtacatct     480
aataagcaac caaattcgcc aaagccaaca caacctaatc aatcaaatag tcaaccagca     540
agtgacgata aagcaaatca aaaatcttca tcgaaagata atcaatcaat gtcagattcg     600
gctttagact ctattttgga tcaatacagt gaagatgcaa agaaaacaca aaaagattat     660
gcatctcaat ctaaaaaaga caaaaatgaa aaatctaata caagaatcc acagttacca      720
acacaagatg aattgaaaca taaatctaaa cctgctcaat cattcaataa cgatgttaat     780
caaaaggata cacgtgcaac atcattattc gaaacagatc ctagtatatc taacaatgat     840
gatagcggac aatttaacgt tgttgactca aaagatacac gtcaatttgt caaatcaatt     900
gctaaagatg cacatcgcat tggtcaagat aacgatattt atgcgtctgt catgattgcc     960
caagcaatct tagaatctga ctcaggtcgt agtgctttag ctaagtcacc aaaccataat    1020
ttattcggta tcaaaggtgc ttttgaaggg aattctgttc cttttaacac attagaagct    1080
gatggtaata aattgtatag tattaatgct ggattccgaa aatatccaag cacgaaagaa    1140
tcactaaaag attactctga ccttattaaa aatggtattg atggcaatcg aacaatttat    1200
aaaccaacat ggaaatcgga agccgattct tataaagatg caacatcaca cttatctaaa    1260
acatatgcta cagatccaaa ctatgctaag aaattaaaca gtattattaa acactatcaa    1320
ttaactcagt ttgacgatga acgcatgcca gatttagata aatatgaacg ttctatcaag    1380
gattatgatg attcatcaga tgaattcaaa ccttttccgtg aggtatctga tagtatgcca    1440
tatccacatg gtcaatgtac ttggtacgta tataaccgta tgaaacaatt tggtacatct    1500
atctcaggtg atttaggtga tgcacataat tggaataatc gagctcaata ccgtgattat    1560
caagtaagtc atacaccaaa acgtcatgct gctgttgtat ttgaggctgg acaatttggt    1620
gcagatcaac attacggtca tgtagcattt gttgaaaaag ttaacagtga tggttctatc    1680
gttatttcag aatccaatgt taaggatta ggtatcattt ctcatagaac tatcaatgca    1740
gctgccgctg aagaattatc atatattaca ggtaaaaaac ctgagccgaa accagctccc    1800
gcccctaagc caatgactga aaagaaaaa atgttagcag aaaaatggta cgatgcaaac    1860
tttgatcaag acttaatcaa tgaacgtgca cgagcgaaag atatttgctt tgaattaaat    1920
catacaaagc cgagtgacaa aaataaaaga aaggaattaa tcgatgaatt atttcaaaca    1980
acaacagaca atgtaagtat ttcgattcct tttgatacag attatggttg aacgttaaa     2040
ctaggaaaaa atgtctatgt aaacaccaat tgttattta tggatggtgg acagattaca    2100
attggcgata atgttttat aggacctaat tgtggattct acacagcaac acatccactt    2160
aattttcatc atagaaatga aggatttgaa aaagcaggac caattaatat tggcagtaat    2220
```

```
acttggtttg cggacatgt agccgtgctt ccgggagtga cgattggaga aggcagtgtg    2280
attggtgctg gtagtgttgt caccaaagat attccgccac acagtttagc ggttggaaac    2340
ccttgtaaag tcgttcgtaa aattgataat gaggtaccat cagaagcatt gaacgatgaa    2400
acactaaatt ag                                                        2412

<210> SEQ ID NO 116
<211> LENGTH: 2967
<212> TYPE: DNA
<213> ORGANISM: Artificial sequence
<220> FEATURE:
<223> OTHER INFORMATION: DNA construct

<400> SEQUENCE: 116
gatacacctc aaaagatac tacagctaag caacatctc atgattcaaa aaaatctaat        60
gacgatgaaa cttctaagga tactacaagt aaagatattg ataaagcaga caacaataat      120
acaagtaacc aagacaataa cgacaaaaaa tttaaaacta tagacgacag cacttcagac      180
tctaacaata tcattgattt tatttataag aatttaccac aaaccaatat aaaccaattg      240
ctaaccaaaa ataaatacga tgataattac tcattaacaa ctttaatcca aaacctattc      300
aatttaaatt cggatatttc tgattacgaa caacctcgta atggcgaaaa gtcaacaaat      360
gattcgaata aaacagtga caatagcatc aaaaatgaca ctgatacgca atcatctaaa       420
caagataaag cagacaatca aaaagcacct aaatcaaaca atacaaaacc aagtacatct      480
aataagcaac caaattcgcc aaagccaaca caacctaatc aatcaaatag tcaaccagca      540
agtgacgata aagcaaatca aaaatcttca tcgaaagata atcaatcaat gtcagattcg      600
gctttagact ctattttgga tcaatacagt gaagatgcaa agaaaacaca aaaagattat      660
gcatctcaat ctaaaaaaga caaaaatgaa aaatctaata caaagaatcc acagttacca      720
acacaagatg aattgaaaca taaatctaaa cctgctcaat cattcaataa cgatgttaat      780
caaaaggata cacgtgcaac atcattattc gaaacagatc ctagtatatc taacaatgat      840
gatagcggac aatttaacgt tgttgactca aaagatacac gtcaatttgt caaatcaatt      900
gctaaagatg cacatcgcat tggtcaagat aacgatattt atgcgtctgt catgattgcc      960
caagcaatct tagaatctga ctcaggtcgt agtgctttag ctaagtcacc aaaccataat     1020
ttattcggta tcaaaggtgc ttttgaaggg aattctgttc cttttaacac attagaagct     1080
gatggtaata aattgtatag tattaatgct ggattccgaa aatatccaag cacgaaagaa     1140
tcactaaaag attactctga ccttattaaa aatggtattg atggcaatcg aacaatttat     1200
aaaccaacat ggaaatcgga agccgattct tataaagatg caacatcaca cttatctaaa     1260
acatatgcta cagatccaaa ctatgctaag aaattaaaca gtattattaa acactatcaa     1320
ttaactcagt ttgacgatga acgcatgcca gatttagata aatatgaacg ttctatcaag     1380
gattatgatg attcatcaga tgaattcaaa ccttttccgtg aggtatctga tagtatgcca     1440
tatccacatg gtcaatgtac ttggtacgta tataaccgta tgaaacaatt tggtacatct     1500
atctcaggtg atttaggtga tgcacataat tggaataatc gagctcaata ccgtgattat     1560
caagtaagtc atacaccaaa acgtcatgct gctgttgtat ttgaggctgg acaatttggt     1620
gcagatcaac attacggtca tgtagcattt gttgaaaaag ttaacagtga tggttctatc     1680
gttatttcag aatccaatgt taaaggatta ggtatcattt ctcatagaac tatcaatgca     1740
gctgccgctg aagaattatc atatattaca ggtaaaggtt ctggcggagg gctaaagtt     1800 gccaaacaag ggcagtataa aaaatcaagac cctatcgtgt tagtgcatgg tttcaatgga     1860
```

```
tttacagatg atattaatcc ttcagtgtta gctcattatt ggggcggtaa taaaatgaac    1920
attcgccaag atttagaaga aaatggttac aaagcttatg aagcaagtat aagtgctttt    1980
ggaagtaact atgaccgcgc agttgaactt tattattata tcaaaggcgg tcgtgtagat    2040
tatggtgcag cacatgcagc aaaatatgga catgaacgtt atggaaaaac atacgaagga    2100
atttacaaag actggaaacc aggacagaag gtacacctag ttggacatag tatgggtggt    2160
caaacgatac gtcaactaga agaattactg cgtaatggta gtcgtgaaga aatagagtat    2220
caaaagaaac atggtggcga aatttctcca ctattcaaag gtaataatga caatatgatt    2280
tcatcaatta ctactttagg aacgccacat aatggaacgc atgcttcaga tttagctggt    2340
aatgaagctt tagtgagaca aattgtattt gatatcggta aaatgtttgg taataaaaac    2400
tctagagtag acttcgggtt ggctcaatgg ggtctaaaac agaagccaaa tgaatcatac    2460
attgattatg tcaaacgcgt taaacaatct aatttatgga aatcaaaaga taatggattt    2520
tacgatctga cgcgtgaggg tgcaacagat ttaaatcgta aaacgtcgtt gaaccctaac    2580
attgtgtata aaacatacac tggtgaagca acgcacaaag cattaaatag cgatagacaa    2640
aaagcagact taaatatgtt tttcccattt gtgattactg gtaacttaat cggtaaagct    2700
actgaaaaag aatggcgaga aaacgatggt ttagtatccg ttatttcttc tcagcatcca    2760
tttaatcaag cttatacaaa tgcgacggat aaaattcaaa aaggcatttg gcaagtaacg    2820
cctacaaaac atgattggga tcatgttgat tttgtcggac aagatagttc tgatacagtg    2880
cgcacaagag aagaattaca agattttttgg catcatttag cagacgattt agtgaaaact    2940
gaaaaggtga ctgatactaa gcaataa                                        2967

<210> SEQ ID NO 117
<211> LENGTH: 2355
<212> TYPE: DNA
<213> ORGANISM: Artificial sequence
<220> FEATURE:
<223> OTHER INFORMATION: DNA construct

<400> SEQUENCE: 117
gatacacctc aaaaagatac tacagctaag acaacatctc atgattcaaa aaaatctaat      60
gacgatgaaa cttctaagga tactacaagt aaagatattg ataaagcaga caacaataat     120
acaagtaacc aagacaataa cgacaaaaaa tttaaaacta tagacgacag cacttcagac     180
tctaacaata tcattgatttt tatttataag aatttaccac aaaccaatat aaaccaattg     240
ctaaccaaaa ataaatacga tgataattac tcattaacaa ctttaatcca aaacctattc     300
aatttaaatt cggatatttc tgattacgaa caacctcgta atggcgaaaa gtcaacaaat     360
gattcgaata aaaacagtga caatagcatc aaaaatgaca ctgatacgca atcatctaaa     420
caagataaag cagacaatca aaaagcacct aaatcaaaca atacaaaacc aagtacatct     480
aataagcaac caaattcgcc aaagccaaca caacctaatc aatcaaatag tcaaccagca     540
agtgacgata aagcaaatca aaaatcttca tcgaaagata atcaatcaat gtcagattcg     600
gctttagact ctatttttgga tcaatacagt gaagatgcaa agaaaacaca aaaagattat     660
gcatctcaat ctaaaaaaga caaaaatgaa aaatctaata caagaatcc acagttacca     720 acacaagatg aattgaaaca taaatctaaa cctgctcaat cattcaataa cgatgttaat     780
caaaaggata cacgtgcaac atcattattc gaaacagatc ctagtatatc taacaatgat     840
gatagcggac aatttaacgt tgttgactca aaagatacac gtcaatttgt caaatcaatt     900
```

```
gctaaagatg cacatcgcat tggtcaagat aacgatattt atgcgtctgt catgattgcc      960
caagcaatct tagaatctga ctcaggtcgt agtgctttag ctaagtcacc aaaccataat     1020
ttattcggta tcaaaggtgc ttttgaaggg aattctgttc cttttaacac attagaagct     1080
gatggtaata aattgtatag tattaatgct ggattccgaa atatccaag  cacgaaagaa     1140
tcactaaaag attactctga ccttattaaa aatggtattg atggcaatcg aacaatttat     1200
aaaccaacat ggaaatcgga agccgattct tataaagatg caacatcaca cttatctaaa     1260
acatatgcta cagatccaaa ctatgctaag aaattaaaca gtattattaa acactatcaa     1320
ttaactcagt ttgacgatga acgcatgcca gatttagata aatatgaacg ttctatcaag     1380
gattatgatg attcatcaga tgaattcaaa cctttccgtg aggtatctga tagtatgcca     1440
tatccacatg gtcaatgtac ttggtacgta tataaccgta tgaaacaatt tggtacatct     1500
atctcaggtg atttaggtga tgcacataat tggaataatc gagctcaata ccgtgattat     1560
caagtaagtc atacaccaaa acgtcatgct gctgttgtat ttgaggctgg acaatttggt     1620
gcagatcaac attacggtca tgtagcattt gttgaaaaag ttaacagtga tggttctatc     1680
gttatttcag aatccaatgt taaaggatta ggtatcattt ctcatagaac tatcaatgca     1740
gctgccgctg aagaattatc atatattaca ggtaaaggtt ctggcggagg ggctaaagtt     1800
gccaaacaag ggcagtataa aaatcaagac cctatcgtgt tagtgcatgg tttcaatgga     1860
tttacagatg atattaatcc ttcagtgtta gctcattatt ggggcggtaa taaaatgaac     1920
attcgccaag atttagaaga aaatggttac aaagcttatg aagcaagtat aagtgctttt     1980
ggaagtaact atgaccgcgc agttgaactt tattattata tcaaaggcgg tcgtgtagat     2040
tatggtgcag cacatgcagc aaaatatgga catgaacgtt atggaaaaac atacgaagga     2100
atttacaaag actggaaacc aggacagaag gtacacctag ttggacatag tatgggtggt     2160
caaacgatac gtcaactaga agaattactg cgtaatggta gtcgtgaaga aatagagtat     2220
caaaagaaac atggtggcga aatttctcca ctattcaaag gtaataatga caatatgatt     2280
tcatcaatta ctactttagg aacgccacat aatggaacgc atgcttcaga tttagctggt     2340
aatgaagctt tataa                                                     2355

<210> SEQ ID NO 118
<211> LENGTH: 1506
<212> TYPE: DNA
<213> ORGANISM: Artificial sequence
<220> FEATURE:
<223> OTHER INFORMATION: DNA construct

<400> SEQUENCE: 118
gcagattctg atattaatat taaaaccggt actacagata ttggaagcaa tactacagta       60
aaaacaggtg atttagtcac ttatgataaa gaaaatggca tgttaaaaaa agtatttat      120
agttttatcg atgataaaaa tcataataaa aaactgctag ttattagaac gaaaggtacc      180
attgctggtc aatatagagt ttatagcgaa gaaggtgcta caaaagtgg  tttagcctgg      240
ccttcagcct ttaaggtaca gttgcaacta cctgataatg aagtagctca aatatctgat      300
tactatccaa gaaattcgat tgatacaaaa gagtatatga gtactttaac ttatggattc      360
aacggtaatg ttactggtga tgatacagga aaaattggcg gccttattgg tgcaaatgtt      420
tcgattggtc atacactgaa atatgttcaa cctgatttca aaacaatttt agagagccca      480
actgataaaa aagtaggctg gaaagtgata tttaacaata tggtgaatca aaattgggga      540
ccatatgata gagattcttg gaacccggta tatggcaatc aacttttcat gaaaactaga      600
```

```
aatggctcta tgaaagcagc agataacttc cttgatccta acaaagcaag ttctctatta      660
tcttcagggt tttcaccaga cttcgctaca gttattacta tggatagaaa agcatccaaa      720
caacaaacaa atatagatgt aatatacgaa cgagttcgtg atgactacca attgcactgg      780
acttcaacaa attggaaagg taccaatact aaagataaat ggatagatcg ttcttcagaa      840
agatataaaa tcgattggga aaaagaagaa atgacaaatg gttctggcgg aggggctaaa      900
cgtatcaaac aacatccgga cgtacaaaaa gttacagatg ctacaagtaa agttgcttca      960
aaaacatctg cagcaatcag taacacagcg agtgatgtta agaatatgt cggcgataaa     1020 aaacaagatt ttgaaaataa gcgtgaactt aaaaagtttg ctagagaaca tgatcctgcc     1080
tatattgaga aaaaggcga aaaattagct aaacaaaatc gtaaagacgc tgataaaatg     1140
aataaaatac ttcaaaaaaa tatcgaaaag cgtcataaag aagagcaaaa agcccgcgaa     1200
aagaatgaaa tacaacgtat taagatatg aaaaagtcac aaaaatacga agtaaaagca     1260
ggcttaacac ctaataaatt agatgagaaa actgagaaaa aaggcgataa actagctgaa     1320
aaaaatcgca agaaatcgc taaaatgaat aaaaagttac aaaaaaatat tgaaaaacga     1380
cacaaagaag aacaaaaacg ccaacaagaa gctgataaag cacgcatcaa gtcatttaaa     1440
aaatataaag attatgttgc caaagcgcc tctcaacaaa ataaagaaaa caatacagag     1500
gcataa                                                               1506

<210> SEQ ID NO 119
<211> LENGTH: 1497
<212> TYPE: DNA
<213> ORGANISM: Artificial sequence
<220> FEATURE:
<223> OTHER INFORMATION: DNA construct

<400> SEQUENCE: 119
gcagattctg atattaatat taaaaccggt actacagata ttggaagcaa tactacagta       60
aaaacaggtg atttagtcac ttatgataaa gaaaatggca tgttaaaaaa agtatttat      120 agttttatcg atgataaaaa tcataataaa aaactgctag ttattagaac gaaaggtacc      180
attgctggtc aatatagagt ttatagcgaa gaaggtgcta caaaagtgg tttagcctgg      240 ccttcagcct ttaaggtaca gttgcaacta cctgataatg aagtagctca aatatctgat      300
tactatccaa gaaattcgat tgatacaaaa gagtatatga gtactttaac ttatggattc      360
aacggtaatg ttactggtga tgatacagga aaaattggcg gccttattgg tgcaaatgtt      420
tcgattggtc atacactgaa atatgttcaa cctgatttca aaacaatttt agagagccca      480
actgataaaa aagtaggctg gaaagtgata tttaacaata tggtgaatca aaattgggga      540
ccatatgata gagattcttg gaacccggta tatggcaatc aacttttcat gaaaactaga      600
aatggctcta tgaaagcagc agataacttc cttgatccta acaaagcaag ttctctatta      660
tcttcagggt tttcaccaga cttcgctaca gttattacta tggatagaaa agcatccaaa      720
caacaaacaa atatagatgt aatatacgaa cgagttcgtg atgactacca attgcactgg      780
acttcaacaa attggaaagg taccaatact aaagataaat ggatagatcg ttcttcagaa      840
agatataaaa tcgattggga aaaagaagaa atgacaaatg gttctggcgg aggggctatg      900
actgaaaaag aaaaaatgtt agcagaaaaa tggtacgatg caaactttga tcaagactta      960
atcaatgaac gtgcacgagc gaaagatatt tgctttgaat taaatcatac aaagccgagt     1020
gacaaaaata aagaaaagga attaatcgat gaattatttc aaacaacaac agacaatgta     1080
```

| | |
|---|---|
| agtatttcga ttccttttga tacagattat ggttggaacg ttaaactagg aaaaaatgtc | 1140 |
| tatgtaaaca ccaattgtta ttttatggat ggtggacaga ttacaattgg cgataatgtt | 1200 |
| tttataggac ctaattgtgg attctacaca gcaacacatc cacttaattt tcatcataga | 1260 |
| aatgaaggat tgaaaaagc aggaccaatt aatattggca gtaatacttg gtttggcgga | 1320 |
| catgtagccg tgcttccggg agtgacgatt ggagaaggca gtgtgattgg tgctggtagt | 1380 |
| gttgtcacca agatattcc gccacacagt ttagcggttg gaaacccttg taaagtcgtt | 1440 |
| cgtaaaattg ataatgaggt accatcagaa gcattgaacg atgaaacact aaattag | 1497 |

<210> SEQ ID NO 120
<211> LENGTH: 2070
<212> TYPE: DNA
<213> ORGANISM: Artificial sequence
<220> FEATURE:
<223> OTHER INFORMATION: DNA construct

<400> SEQUENCE: 120

| | |
|---|---|
| gcagattctg atattaatat taaaaccggt actacagata ttggaagcaa tactacagta | 60 |
| aaaacaggtg atttagtcac ttatgataaa gaaaatggca tgttaaaaaa agtattttat | 120 |
| agttttatcg atgataaaaa tcataataaa aaactgctag ttattagaac gaaaggtacc | 180 |
| attgctggtc aatatagagt ttatagcgaa gaaggtgcta acaaaagtgg tttagcctgg | 240 |
| ccttcagcct ttaaggtaca gttgcaacta cctgataatg aagtagctca atatctgat | 300 |
| tactatccaa gaaattcgat tgatacaaaa gagtatatga gtactttaac ttatggattc | 360 |
| aacggtaatg ttactggtga tgatacagga aaaattggcg gccttattgg tgcaaatgtt | 420 |
| tcgattggtc atacactgaa atatgttcaa cctgatttca aaacaatttt agagagccca | 480 |
| actgataaaa aagtaggctg gaaagtgata tttaacaata tggtgaatca aaattgggga | 540 |
| ccatatgata gagattcttg gaacccggta tatggcaatc aacttttcat gaaaactaga | 600 |
| aatggctcta tgaaagcagc agataacttc cttgatccta caaaagcaag ttctctatta | 660 |
| tcttcagggt tttcaccaga cttcgctaca gttattacta tggatagaaa agcatccaaa | 720 |
| caacaaacaa atatagatgt aatatacgaa cgagttcgtg atgactacca attgcactgg | 780 |
| acttcaacaa attggaaagg taccaatact aaagataaat ggatagatcg ttcttcagaa | 840 |
| agatataaaa tcgattggga aaagaagaa atgacaaatg ttctggcgg aggggctaaa | 900 |
| gttgccaaac aagggcagta taaaaatcaa gaccctatcg tgttagtgca tggtttcaat | 960 |
| ggatttacag atgatattaa tccttcagtg ttagctcatt attggggcgg taataaaatg | 1020 |
| aacattcgcc aagatttaga agaaaatggt tacaaagctt atgaagcaag tataagtgct | 1080 |
| tttgaagta actatgaccg cgcagttgaa ctttattatt atatcaaagg cggtcgtgta | 1140 |
| gattatggtg cagcacatgc agcaaaatat ggacatgaac gttatggaaa aacatacgaa | 1200 |
| ggaatttaca aagactggaa accaggacag aaggtacacc tagttggaca tagtatgggt | 1260 |
| ggtcaaacga tacgtcaact agaagaatta ctgcgtaatg gtagtcgtga agaaatagag | 1320 |
| tatcaaaaga acatggtgg cgaaatttct ccactattca aaggtaataa tgacaatatg | 1380 |
| atttcatcaa ttactacttt aggaacgcca cataatggaa cgcatgcttc agatttagct | 1440 |
| ggtaatgaag ctttagtgag acaaattgta tttgatatcg gtaaaatgtt tggtaataaa | 1500 |
| aactctagag tagacttcgg gttggctcaa tggggtctaa acagaagcc aaatgaatca | 1560 |
| tacattgatt atgtcaaacg cgttaaacaa tctaatttat ggaaatcaaa agataatgga | 1620 |
| ttttacgatc tgacgcgtga gggtgcaaca gatttaaatc gtaaaacgtc gttgaaccct | 1680 |

| aacattgtgt ataaaacata cactggtgaa gcaacgcaca aagcattaaa tagcgataga | 1740 |
| caaaaagcag acttaaatat gttttccca tttgtgatta ctggtaactt aatcggtaaa | 1800 |
| gctactgaaa aagaatggcg agaaaacgat ggtttagtat ccgttatttc ttctcagcat | 1860 |
| ccatttaatc aagcttatac aaatgcgacg gataaaattc aaaaaggcat ttggcaagta | 1920 |
| acgcctacaa aacatgattg ggatcatgtt gattttgtcg acaagatag ttctgataca | 1980 |
| gtgcgcacaa gagaagaatt acaagatttt tggcatcatt tagcagacga tttagtgaaa | 2040 |
| actgaaaagg tgactgatac taagcaataa | 2070 |

<210> SEQ ID NO 121  
<211> LENGTH: 1173  
<212> TYPE: DNA  
<213> ORGANISM: Artificial sequence  
<220> FEATURE:  
<223> OTHER INFORMATION: DNA construct

<400> SEQUENCE: 121

| aaagttgcca acaagggca gtataaaaat caagacccta tcgtgttagt gcatggtttc | 60 |
| aatggattta cagatgatat taatccttca gtgttagctc attattgggg cggtaataaa | 120 |
| atgaacattc gccaagattt agaagaaaat ggttacaaag cttatgaagc aagtataagt | 180 |
| gcttttggaa gtaactatga ccgcgcagtt gaactttatt attatatcaa aggcggtcgt | 240 |
| gtagattatg gtgcagcaca tgcagcaaaa tatggacatg aacgttatgg aaaaacatac | 300 |
| gaaggaattt acaagactg gaaaccagga cagaaggtac acctagttgg acatagtatg | 360 |
| ggtggtcaaa cgatacgtca actagaagaa ttactgcgta atggtagtcg tgaagaaata | 420 |
| gagtatcaaa agaaacatgg tggcgaaatt tctccactat tcaaaggtaa taatgacaat | 480 |
| atgatttcat caattactac tttaggaacg ccacataatg gaacgcatgc ttcagattta | 540 |
| gctggtaatg aagctttagt gagacaaatt gtatttgata tcggtaaaat gtttggtaat | 600 |
| aaaaactcta gagtagactt cgggttggct caatggggtc taaaacagaa gccaaatgaa | 660 |
| tcatacattg attatgtcaa acgcgttaaa caatctaatt tatggaaatc aaaagataat | 720 |
| ggatttacg atctgacgcg tgagggtgca acagatttaa atcgtaaaac gtcgttgaac | 780 |
| cctaacattg tgtataaaac atacactggt gaagcaacgc acaaagcatt aaatagcgat | 840 |
| agacaaaaag cagacttaaa tatgtttttc ccatttgtga ttactggtaa cttaatcggt | 900 |
| aaagctactg aaaagaatg gcgagaaaac gatggtttag tatccgttat ttcttctcag | 960 |
| catccattta tcaagctta tacaaatgcg acggataaaa ttcaaaaagg catttggcaa | 1020 |
| gtaacgccta caaaacatga ttgggatcat gttgattttg tcggacaaga tagttctgat | 1080 |
| acagtgcgca caagagaaga attacaagat ttttggcatc attagcaga cgatttagtg | 1140 |
| aaaactgaaa aggtgactga tactaagcaa taa | 1173 |

<210> SEQ ID NO 122  
<211> LENGTH: 561  
<212> TYPE: DNA  
<213> ORGANISM: Artificial sequence  
<220> FEATURE:  
<223> OTHER INFORMATION: DNA construct

<400> SEQUENCE: 122

| aaagttgcca acaagggca gtataaaaat caagacccta tcgtgttagt gcatggtttc | 60 |
| aatggattta cagatgatat taatccttca gtgttagctc attattgggg cggtaataaa | 120 |

| | |
|---|---|
| atgaacattc gccaagattt agaagaaaat ggttacaaag cttatgaagc aagtataagt | 180 |
| gcttttggaa gtaactatga ccgcgcagtt gaactttatt attatatcaa aggcggtcgt | 240 |
| gtagattatg gtgcagcaca tgcagcaaaa tatggacatg aacgttatgg aaaaacatac | 300 |
| gaaggaattt acaaagactg aaaccagga cagaaggtac acctagttgg acatagtatg | 360 |
| ggtggtcaaa cgatacgtca actagaagaa ttactgcgta atggtagtcg tgaagaaata | 420 |
| gagtatcaaa agaaacatgg tggcgaaatt tctccactat tcaaaggtaa taatgacaat | 480 |
| atgatttcat caattactac tttaggaacg ccacataatg gaacgcatgc ttcagattta | 540 |
| gctggtaatg aagctttata a | 561 |

<210> SEQ ID NO 123
<211> LENGTH: 882
<212> TYPE: DNA
<213> ORGANISM: Artificial sequence
<220> FEATURE:
<223> OTHER INFORMATION: DNA construct

<400> SEQUENCE: 123

| | |
|---|---|
| gcagattctg atattaatat taaaaccggt actacagata ttggaagcaa tactacagta | 60 |
| aaaacaggtg atttagtcac ttatgataaa gaaaatggca tgttaaaaaa agtattttat | 120 |
| agttttatcg atgataaaaa tcataataaa aaactgctag ttattagaac gaaaggtacc | 180 |
| attgctggtc aatatagagt ttatagcgaa gaaggtgcta caaaagtggt ttagcctggg | 240 |
| ccttcagcct ttaaggtaca gttgcaacta cctgataatg aagtagctca aatatctgat | 300 |
| tactatccaa gaaattcgat tgatacaaaa gagtatatga gtactttaac ttatggattc | 360 |
| aacggtaatg ttactggtga tgatacagga aaaattggcg gccttattgg tgcaaatgtt | 420 |
| tcgattggtc atacactgaa atatgttcaa cctgatttca aaacaatttt agagagccca | 480 |
| actgataaaa aagtaggctg gaaagtgata tttaacaata tggtgaatca aaattgggga | 540 |
| ccatatgata gagattcttg gaacccggta tatggcaatc aacttttcat gaaaactaga | 600 |
| aatggctcta tgaaagcagc agataacttc cttgatccta caaagcaag ttctctatta | 660 |
| tcttcagggt tttcaccaga cttcgctaca gttattacta tggatagaaa agcatccaaa | 720 |
| caacaaacaa atatagatgt aatatacgaa cgagttcgtg atgactacca attgcactgg | 780 |
| acttcaacaa attggaaagg taccaatact aaagataaat ggatagatcg ttcttcagaa | 840 |
| agatataaaa tcgattggga aaaagaagaa atgacaaatt aa | 882 |

<210> SEQ ID NO 124
<211> LENGTH: 1722
<212> TYPE: DNA
<213> ORGANISM: Artificial sequence
<220> FEATURE:
<223> OTHER INFORMATION: DNA construct

<400> SEQUENCE: 124

| | |
|---|---|
| gcagctgaag aaacaggtgg tacaaataca gaagcacaac caaaaactga agcagttgca | 60 |
| agtccaacaa caacatctga aaaagctcca gaaactaaac cagtagctaa tgctgtctca | 120 |
| gtatctaata agaagttga ggcccctact tctgaaacaa agaagctaa agaagttaaa | 180 |
| gaagttaaag cccctaagga acaaaagaa gttaaaccag cagcaaaagc cactaacaat | 240 |
| acatatccta tttttgaatca ggaacttaga gaagcgatta aaaaccctgc aataaaagac | 300 |
| aaagatcata gcgcaccaaa ctctcgtcca attgattttg aaatgaaaaa gaaagatgga | 360 |
| actcaacagt tttatcatta tgcaagttct gttaaacctg ctagagttat tttcactgat | 420 |

```
tcaaaaccag aaattgaatt aggattacaa tcaggtcaat tttggagaaa atttgaagtt    480
tatgaaggtg acaaaaagtt gccaattaaa ttagtatcat acgatactgt taaagattat    540
gcttacattc gcttctctgt atcaaacgga acaaaagctg ttaaaattgt tagttcaaca    600
cacttcaata acaagaaga aaaatacgat tacacattaa tggaattcgc acaaccaatt     660
tataacagtg cagataaatt caaaactgaa gaagattata aagctgaaaa attattagcg    720
ccatataaaa aagcgaaaac actagaaaga caagtttatg aattaaataa aattcaagat    780
aaacttcctg aaaaattaaa ggctgagtac aagaagaaat tagaggatac aaagaaagct    840
ttagatgagc aagtgaaatc agctattact gaattccaaa atgtacaacc aacaaatgaa    900
aaaatgactg atttacaaga tacaaaatat gttgtttatg aaagtgttga gaataacgaa    960
tctatgatgg atacttttgt taaacaccct attaaaacag gtatgcttaa cggcaaaaaa   1020
tatatggtca tggaaactac taatgacgat tactggaaag atttcatggt tgaaggtcaa   1080
cgtgttagaa ctataagcaa agatgctaaa aataatacta gaacaattat tttcccatat   1140
gttgaaggta aaactctata tgatgctatc gttaaagttc acgtaaaaac gattgattat   1200
gatggacaat accatgtcag aatcgttgat aagaagcat ttacaaaagc caataccgat    1260
aaatctaaca aaaagaaca acaagataac tcagctaaga aggaagctac tccagctacg   1320
cctagcaaac caacaccatc acctgttgaa aaagaatcac aaaaacaaga cagccaaaaa   1380
gatgacaata acaattacc aagtgttgaa aaagaaaatg acgcatctag tgagtcaggt    1440
aaagacaaaa cgcctgctac aaaaccaact aaaggtgaag tagaatcaag tagtacaact   1500
ccaactaagg tagtatctac gactcaaaat gttgcaaaac caacaactgc ttcatcaaaa   1560
acaacaaaag atgttgttca aacttcagca ggttctagcg aagcaaaaga tagtgctcca   1620
ttacaaaaag caaacattaa aaacacaaat gatggacaca ctcaaagcca aacaataaa    1680 aatacacaag aaaataaagc aaaatcatta ccacaaactt aa                       1722
```

<210> SEQ ID NO 125
<211> LENGTH: 1230
<212> TYPE: DNA
<213> ORGANISM: Artificial sequence
<220> FEATURE:
<223> OTHER INFORMATION: DNA construct

<400> SEQUENCE: 125

```
atggatattg gtaaaaaaca tgtaattcct aaaagtcagt accgacgtaa gcgtcgtgaa      60
ttcttccaca acgaagacag agaagaaaat ttaaatcaac atcaagataa acaaaatata    120
gataatacaa catcaaaaaa agcagataag caaatacata agattcaat tgataagcac     180 gaacgtttta aaaatagttt atcatcgcat ttagaacaga gaaaccgtga tgttaatgag    240
aataaagctg aagaagtaa aagtaatcag gatagtaagt cagcatataa cagagatcat    300
tatttaacag acgatgtatc taaaaaacaa aattcattag attcagtgga ccaagataca    360
gagaaatcaa atattatga gcaaaattct gaagcgactt tatcaactaa atcaaccgat    420
aaagtagaat caactgaaat gagaaagcta agttcagata aaaacaaagt tggtcatgaa   480
gagcaacatg tactttctaa accttcagaa catgataaag agactagaat tgattctgag    540
tcttcaagaa ctgattcaga cagctcgatg cagacagaga aataaaaaa agacagttca   600 gatggaaata aagtagtaa tctgaaatct gaagtaatat cagacaaatc aaatacagta    660
ccaaaattgt cggaatctga tgatgaagta aataatcaga agccattaac tttaccggaa   720
```

| | |
|---|---|
| gaacagaaat tgaaaagaca gcaaagtcaa aatgagcaaa caaaaaccta tacatatggt | 780 |
| gatagcgaac aaaatgacaa gtctaatcat gaaaatgatt taagtcatca tataccatcg | 840 |
| ataagtgatg ataaagataa cgtcatgaga gaaaatcata ttgttgacga taatcctgat | 900 |
| aatgatatca atacaccatc attatcaaaa acagatgacg atcgaaaact tgatgaaaaa | 960 |
| attcatgttg aagataaaca taaacaaaat gcagactcgt ctgaaacggt gggatatcaa | 1020 |
| agtcagtcaa ctgcatctca tcgtagcact gaaaaaagaa atatttctat taatgaccat | 1080 |
| gataaattaa acggtcaaaa aacaaataca aagacatcgg caaataataa tcaaaaaaag | 1140 |
| gctacatcaa aattgaacaa agggcgcgct acgaataata attatagtga cattttgaaa | 1200 |
| aagttttgga tgatgtattg gcctaaataa | 1230 |

<210> SEQ ID NO 126
<211> LENGTH: 1779
<212> TYPE: DNA
<213> ORGANISM: Artificial sequence
<220> FEATURE:
<223> OTHER INFORMATION: DNA construct

<400> SEQUENCE: 126

| | |
|---|---|
| gatacacctc aaaagatac tacagctaag acaaacatctc atgattcaaa aaaatctaat | 60 |
| gacgatgaaa cttctaagga tactacaagt aaagatattg ataaagcaga caacaataat | 120 |
| acaagtaacc aagacaataa cgacaaaaaa tttaaaacta tagacgacag cacttcagac | 180 |
| tctaacaata tcattgattt tatttataag aatttaccac aaaccaatat aaaccaattg | 240 |
| ctaaccaaaa ataaatacga tgataattac tcattaacaa ctttaatcca aaacctattc | 300 |
| aatttaaatt cggatatttc tgattacgaa caacctcgta atggcgaaaa gtcaacaaat | 360 |
| gattcgaata aaaacagtga caatagcatc aaaaatgaca ctgatacgca atcatctaaa | 420 |
| caagataaag cagacaatca aaaagcacct aaatcaaaca atacaaaacc aagtacatct | 480 |
| aataagcaac caaattcgcc aaagccaaca caacctaatc aatcaaatag tcaaccagca | 540 |
| agtgacgata aagcaaatca aaaatcttca tcgaaagata atcaatcaat gtcagattcg | 600 |
| gctttagact ctattttgga tcaatacagt gaagatgcaa agaaaacaca aaaagattat | 660 |
| gcatctcaat ctaaaaaaga caaaaatgaa aaatctaata caaagaatcc acagttacca | 720 |
| acacaagatg aattgaaaca taaatctaaa cctgctcaat cattcaataa cgatgttaat | 780 |
| caaaaggata cacgtgcaac atcattattc gaaacagatc ctagtatatc taacaatgat | 840 |
| gatagcggac aatttaacgt tgttgactca aaagatacac gtcaatttgt caaatcaatt | 900 |
| gctaaagatg cacatcgcat tggtcaagat aacgatattt atgcgtctgt catgattgcc | 960 |
| caagcaatct tagaatctga ctcaggtcgt agtgctttag ctaagtcacc aaaccataat | 1020 |
| ttattcggta tcaaaggtgc ttttgaaggg aattctgttc cttttaacac attagaagct | 1080 |
| gatggtaata aattgtatag tattaatgct ggattccgaa atatccaag cacgaaagaa | 1140 |
| tcactaaaag attactctga ccttattaaa aatggtattg atggcaatcg aacaatttat | 1200 |
| aaaccaacat ggaaatcgga agccgattct tataaagatg caacatcaca cttatctaaa | 1260 |
| acatatgcta cagatccaaa ctatgctaag aaattaaaca gtattattaa acactatcaa | 1320 |
| ttaactcagt ttgacgatga acgcatgcca gatttagata aatatgaacg ttctatcaag | 1380 |
| gattatgatg attcatcaga tgaattcaaa ccttccgtg aggtatctga tagtatgcca | 1440 |
| tatccacatg gtcaatgtac ttggtacgta tataaccgta tgaaacaatt tggtacatct | 1500 |
| atctcaggtg atttaggtga tgcacataat tggaataatc gagctcaata ccgtgattat | 1560 |

```
caagtaagtc atacaccaaa acgtcatgct gctgttgtat ttgaggctgg acaatttggt   1620
gcagatcaac attacggtca tgtagcattt gttgaaaaag ttaacagtga tggttctatc   1680
gttatttcag aatccaatgt taaaggatta ggtatcattt ctcatagaac tatcaatgca   1740
gctgccgctg aagaattatc atatattaca ggtaaataa                          1779

<210> SEQ ID NO 127
<211> LENGTH: 2382
<212> TYPE: DNA
<213> ORGANISM: Artificial sequence
<220> FEATURE:
<223> OTHER INFORMATION: DNA construct

<400> SEQUENCE: 127
caaacaaaat atggagatca atcagaaaaa ggatcccaaa gtgtaagtaa taaaaataat     60
aaaatacata tcgcaattgt taacgaggat caaccaacga catataacgg taaaaaggtt    120
gagctgggtc aagcatttat taaaaggtta gcaaatgaga aaaactataa atttgaaaca    180
gtaacaagaa acgttgctga gtctggtttg aaaaatggcg ataccaagt catgattgtt     240 atcccagaaa acttttcaaa attggcaatg caattagacg ctaaaacacc atcgaaaata    300
tcactacagt ataaaacagc tgtaggacaa aaagaagaag tagctaaaaa cacagaaaaa    360
gttgtaagta atgtacttaa cgactttaac aaaaacttgg tcgaaattta tttaacaagc    420
atcattgata atttacataa tgcacaaaaa aatgttggcg ctattatgac gcgtgaacat    480
ggtgtgaata gtaaattctc gaattactta ttaaatccaa ttaacgactt cccggaatta    540
tttacagata cgcttgtaaa ttcgatttct gcaaacaaag atattacaaa atggttccaa    600
acatacaata aatcattact gagtgcgaat tcagatacat tcagagtgaa cacagattat    660
aatgtttcga ctttaattga aaaacaaaat tcattatttg acgaacacaa tacagcgatg    720
gataaaatgt tacaagatta taaatcgcaa aaagatagcg tggaacttga taactatatc    780
aatgcattaa aacagatgga cagccaaatt gatcaacaat caagtatgca agatacaggt    840
aaagaagaat ataaacaaac tgttaaagaa aacttagata aattaagaga atcattcaa     900 tcacaagagt caccattttc aaaaggtatg attgaagact atcgtaagca attaacagaa    960
tcactccaag atgagcttgc aaacaacaaa gacttacaag atgcgctaaa tagcattaaa   1020
atgaacaatg ctcaattcgc tgaaaactta gagaaacaac ttcatgatga tattgtcaaa   1080
gaacctgatt cagatacaac atttatctat aacatgtcta acaagactt tatagctgca    1140 ggtttaaatg aggatgaagc taataaatac gaagcaattg tcaaagaagc aaaacgttat   1200
aaaaacgaat ataatttgaa aaaaccgtta gcagaacaca ttaatttaac agattacgat   1260
aaccaagttg cgcaagacac aagtagtttg attaatgatg gtgtgaaagt gcaacgtact   1320
gaaacgatta aagtaatga tattaatcaa ttaactgttg caacagatcc tcattttaat    1380
tttgaaggcg acattaaaat taatggtaaa aaatatgaca ttaaggatca aagtgttcaa   1440
ctcgatacat ctaacaagga atataaagtt gaagtcaatg gcgttgctaa attgaaaaag   1500
gatgctgaga aagatttctt aaaagataaa acaatgcatt tacaattgtt atttggacaa   1560
gcaaatcgtc aagatgaacc aaatgataag aaagcaacga gtgttgtgga tgtaacattg   1620
aatcataacc ttgatggtcg cttatcgaaa gatgcattaa gccagcaatt gagtgcatta   1680
tctaggtttg atgcgcatta taaaatgtac acagatacaa aaggcagaga agataaacca   1740
ttcgacaaca aacgtttaat tgatatgatg gttgaccaag ttatcaatga catggaaagt   1800
```

| | |
|---|---:|
| ttcaaagacg ataaagtagc tgtgttacat caaattgatt caatggaaga aaactcagac | 1860 |
| aaactgattg atgacatttt aaataacaaa aagaatacaa caaaaaataa agaagatatt | 1920 |
| tctaagctga ttgatcagtt agaaaacgtt aaaaagactt ttgctgaaga gccacaagaa | 1980 |
| ccaaaaattg ataaaggcaa aaatgatgaa tttaatacga tgtcttcaaa tttagataaa | 2040 |
| gaaattagta gaatttctga gaaaagtacg caattgctat cagatacaca agaatcaaaa | 2100 |
| acaattgcag attcagttag tggacaatta aatcaattag ataataatgt gaataaacta | 2160 |
| catgcgacag gtcgagcatt aggcgtaaga gcgaatgatt tgaaccgtca aatggctaaa | 2220 |
| aacgataaag ataatgagtt attcgctaaa gagtttaaaa aagtattaca aaattctaaa | 2280 |
| gatggcgaca gacaaaacca agcattaaaa gcatttatga gtaatccggt tcaaaagaaa | 2340 |
| aacttagaaa atgttttagc taataatggt aatacagact aa | 2382 |

<210> SEQ ID NO 128
<211> LENGTH: 609
<212> TYPE: DNA
<213> ORGANISM: Artificial sequence
<220> FEATURE:
<223> OTHER INFORMATION: DNA construct

<400> SEQUENCE: 128

| | |
|---|---:|
| aaacgtatca acaacatcc ggacgtacaa aaagttacag atgctacaag taaagttgct | 60 |
| tcaaaaacat ctgcagcaat cagtaacaca gcgagtgatg ttaaagaata tgtcggcgat | 120 |
| aaaaaacaag attttgaaaa taagcgtgaa cttaaaaagt ttgctagaga acatgatcct | 180 |
| gcctatattg agaaaaaagg cgaaaaatta gctaaacaaa atcgtaaaga cgctgataaa | 240 |
| atgaataaaa tacttcaaaa aaatatcgaa aagcgtcata agaagagca aaaagcccgc | 300 |
| gaaaagaatg aaatacaacg tattaaagat atgaaaaagt cacaaaaata cgaagtaaaa | 360 |
| gcaggcttaa cacctaataa attagatgag aaaactgaga aaaaggcga taaactagct | 420 |
| gaaaaaaatc gcaaagaaat cgctaaaatg aataaaaagt tacaaaaaaa tattgaaaaa | 480 |
| cgacacaaag aagaacaaaa acgccaacaa gaagctgata agcacgcat caagtcattt | 540 |
| aaaaaatata aagattatgt tgccaaaagc gcctctcaac aaaataaaga aaacaataca | 600 |
| gaggcataa | 609 |

<210> SEQ ID NO 129
<211> LENGTH: 1230
<212> TYPE: DNA
<213> ORGANISM: Artificial sequence
<220> FEATURE:
<223> OTHER INFORMATION: DNA construct

<400> SEQUENCE: 129

| | |
|---|---:|
| gtggatattg gtaaaaaaca tgtaattcct aaaagtcagt accgacgtaa gcgtcgtgaa | 60 |
| ttcttccaca acgaagacag agaagaaaat ttaaatcaac atcaagataa acaaaatata | 120 |
| gataatacaa catcaaaaaa agcagataag caaatacata aagattcaat tgataagcac | 180 |
| gaacgtttta aaaatagttt atcatcgcat ttagaacaga gaaaccgtga tgtgaatgag | 240 |
| aacaaagctg aagaaagtaa aagtaatcag ggtagtaagt cagcatataa caaagatcat | 300 |
| tatttaacag acgatgtatc taaaaaacaa aattcattag attcagtaga ccaagataca | 360 |
| gagaaatcaa aatattatga gcaaatatact gaagcgactt tatcaactaa ttcaaccgat | 420 |
| aaagtagaat caactgacat gagaaagcta agttcagata aaaacaaagt tggtcatgaa | 480 |
| gagcaacatg tactttctaa accttcagaa catgataaag agactagaat tgattttgag | 540 |

```
tcttcaagaa ctgattcaga cagctcgatg cagacagaga aaataaaaaa agacagttca        600
gatggaaata aaagtagtaa tctgaaatct gaagtaatat cagacaaatc aaattcagta        660
ccaatattgt cggaatctga tgatgaagta aataatcaga agccattaac tttgccggaa        720
gaacagaaat tgaaaaggca gcaaagtcaa atgagcaaa caaaaactta tacatatggt         780
gatagcgaac aaaatgacaa gtctaatcat gaaaatgatt taagtcatca tacaccatcg        840
ataagtgatg ataaagatta cgttatgaga gaagatcata ttgttgacga taatcctgat        900
aatgatatca atacaccatc attatcaaaa atagatgacg atcgaaaact tgatgaaaaa        960
attcatgtcg aagataaaca taaacaaaat gcagactcat ctgaaacggt gggatatcaa       1020
agtcagtcaa gtgcatctca tcgtagcact gaaaaaagaa atatggctat taatgaccat       1080
gataaattaa acggtcaaaa accaaataca aagacatcgg caaataataa tcaaaaaaag       1140
gctacatcaa aattgaacaa agggcgcgct acaaataata attatagcgc cattttgaaa       1200
aagttttgga tgatgtattg gcctaaataa                                         1230
```

<210> SEQ ID NO 130
<211> LENGTH: 1488
<212> TYPE: DNA
<213> ORGANISM: Artificial sequence
<220> FEATURE:
<223> OTHER INFORMATION: DNA construct

<400> SEQUENCE: 130

```
cgaaatttgt tgcttcaaaa gcaatcacaa gctagacaaa ctgccgaaga tattgtaaat         60
caagcacata aagaagctga caatatcaaa aaagagaaat tacttgaggc aaaagaagaa        120
aaccaaatcc taagagaaca aactgaagca gaactacgag aaagacgtag cgaacttcaa        180
agacaagaaa cccgacttct tcaaaaagaa gaaaacttag agcgtaaatc tgatctatta        240
gataaaaaag atgagatttt agagcaaaaa gaatcaaaaa ttgaagaaaa acaacaacaa        300
gtagatgcaa aagagagtag tgttcaaacg ttaataatga agcatgaaca agaattagaa        360
cgcatctccg gtctcactca agaagaagct attaatgagc aacttcaaag agtagaggaa        420
gaactgtcac aagatattgc agtacttgtt aaagaaaaag aaaagaagc taagaaaaa         480 gttgataaaa cagcaaaaga attattagct acagcagtac aaagattagc agcagatcac       540
acaagtgaat caacggtatc agtagttaac ttacctaatg atgagatgaa aggtcgaatc       600
attggacgtg aaggacgaaa catccgtaca cttgaaactt taactggcat tgatttaatt       660
attgatgaca caccagaagc agttatatta tctggttttg atccaataag aagagaaatt       720
gctagaacag cacttgttaa cttagtatct gatggacgta ttcatccagg tagaattgaa       780
gatatggtcg aaaaagctag aaaagaagta gacgatatta agagaagc aggtgaacaa        840 gctacatttg aagtgaacgc acataatatg catcctgact agtaaaaat tgtagggcgt         900 ttaaactatc gtacaagtta cggtcaaaat gtacttaaac attcaattga agttgcgcat       960
cttgctagta tgttagctgc tgagctaggc gaagatgaga cattagcgaa acgagctgga      1020
cttttacatg atgttggtaa agcaattgat catgaagtag aaggtagtca tgttgaaatc      1080
ggtgtagaat tagcgaaaaa atatggtgaa aatgaaacag ttattaatgc aatccattct      1140
caccatggtg atgttgaacc tacatctatt atatctatcc ttgttgctgc tgcagatgca      1200
ttgtctgcgg ctcgtccagg tgcaagaaaa gaaacattag agaattatat tcgtcgatta      1260
gaacgtttag aaacgttatc agaaagttat gatggtgtag aaaaagcatt tgcgattcag      1320
```

| | |
|---|---:|
| gcaggtagag aaatccgagt gattgtatct cctgaagaaa ttgatgattt aaaatcttat | 1380 |
| cgattggcta gagatattaa aaatcagatt gaagatgaat tacaatatcc tggtcatatc | 1440 |
| aaggtgacag ttgttcgaga gactagagca gtagaatatg cgaaataa | 1488 |

<210> SEQ ID NO 131
<211> LENGTH: 435
<212> TYPE: DNA
<213> ORGANISM: Artificial sequence
<220> FEATURE:
<223> OTHER INFORMATION: DNA construct

<400> SEQUENCE: 131

| | |
|---|---:|
| aacaatcata ataatggtac aaaagaaaat aaaatcgcga atacaaataa aaataatgct | 60 |
| gatgaaagta aagataaaga cacatctaaa gacgcttcta aagataaatc aaaatctaca | 120 |
| gacagtgata aatcaaaaga tgatcaagac aaagcgacta aagatgaatc tgataatgat | 180 |
| caaaacaacg ctaatcaagc gaacaatcaa gcacaaaata tcaaaatca acaacaagct | 240 |
| aatcaaaatc aacaacagca acaacaacgt caaggtggtg ccaaagaca tacagtgaat | 300 |
| ggtcaagaaa acttataccg tatcgcaatt caatactacg gttcaggttc accggaaaat | 360 |
| gttgaaaaaa ttagacgtgc caatggttta agtggtaaca atattagaaa cggtcaacaa | 420 |
| atcgttattc cataa | 435 |

<210> SEQ ID NO 132
<211> LENGTH: 1959
<212> TYPE: DNA
<213> ORGANISM: Artificial sequence
<220> FEATURE:
<223> OTHER INFORMATION: DNA construct

<400> SEQUENCE: 132

| | |
|---|---:|
| atgaatgaaa aagtagaagg catgaccttg gagctgaaat tagaccattt aggtgtccaa | 60 |
| gaaggcatga aggtttaaa gcgacaatta ggtgttgtta atagtgaaat gaaagctaat | 120 |
| ctgtcagcat ttgataagtc tgaaaaatca atggaaaaat atcaggcgag aattaagggg | 180 |
| ttaaatgata ggcttaaagt tcaaaaaaag atgtattctc aagtagaaga tgagcttaaa | 240 |
| caagttaacg ctaattacca aaaagctaaa tccagtgtaa aagatgttga aaagcatat | 300 |
| ttaaagttag tagaagccaa taaaaagaa aaattagctc ttgataaatc taagaagcc | 360 |
| ttaaaatcat cgaatacaga acttaaaaaa gctgaaaatc aatataaacg tacaaatcaa | 420 |
| cgtaaacaag atgcgtatca aaaacttaaa cagttgagag atgcagaaca aaagcttaag | 480 |
| aatagtaacc aagctactac tgcacaacta aaaagagcaa gtgacgcagt acagaagcag | 540 |
| tccgctaagc ataaagcact tgttgaacaa tataaacaag aaggcaatca agttcaaaaa | 600 |
| ctaaaagtgc aaaatgacaa tctttcaaaa tcaaatgata aaattgaaag ttcttacgct | 660 |
| aaaactaata ctaaattaaa gcaaacagaa aaagaattta atgatttaaa caatactatt | 720 |
| aagaatcata gcgctaatgt cgcaaaagct gaaacagctg ttaataaaga aaagctgct | 780 |
| ttaaataatt tggagcgttc aatagataaa gcttcatccg aaatgaagac ttttaacaaa | 840 |
| gaacaaatga tagctcaaag tcatttcggt aaacttgcaa gtcaagcgga tgtcatgtca | 900 |
| aagaaattta gttctattgg agacaaaatg acttccctgg acgtacaat gacgatgggc | 960 |
| gtatctacac caattacttt agggttaggt gcagcattaa aaacaagtgc agactttgaa | 1020 |
| ggccaaatgt ctcgagttgg agcgattgcg caagcaagca gtaaagactt gaaaagcatg | 1080 |
| tctaatcaag cagttgactt aggagctaaa accagtaaaa gtgctaacga agttgctaaa | 1140 |

```
ggtatggaag aattggcagc tttaggcttt aatgccaaac aaacaatgga ggctatgcca    1200
ggtgttatca gtgcagcaga agcaagtggt gcagaaatgg ctacaactgc aactgtaatg    1260
gcttcagcga ttaactcttt cggttttaaaa gcatctgatg caaatcatgt tgctgattta    1320
cttgcgagat cagcaaatga tagtgctgca gatattcagt acatgggaga tgcattgaag    1380
tatgctggta ctcctgcaaa agcattagga gtttcaatag aggacacttc cgcagcaatt    1440
gaagttttat ctaactcagg tttagagggt tctcaagcag gtactgccct aagagcttca    1500
tttatcaggc tagctaatcc aagtaaaaat acagctaagg aaatgaaaaa attaggtatt    1560
catttgtctg atgctaaagg tcaatttgtt ggcatgggtg aattgattag acagttccaa    1620
gataatatga aaggcatgac gagagaacaa aaactagcta cagtggctac aatagttggt    1680
actgaagcag caagtggatt tttagccttg attgaagcgg gaccagataa aattaatagc    1740
tatagtaaat ccttaaagaa ttccaatggc gaaagtaaaa aagcagcaga tttgatgaaa    1800
gataatctca aaggcgctct ggaacaatta ggtggcgctt ttgaatcatt agcaatcgaa    1860
gtcggtaaag atttaacgcc tatgattaga gcaggagcgg aaggtttaac aaaattagtt    1920
gatggattta cacatctccc tggttgggtt agaaaataa                           1959

<210> SEQ ID NO 133
<211> LENGTH: 600
<212> TYPE: DNA
<213> ORGANISM: Artificial sequence
<220> FEATURE:
<223> OTHER INFORMATION: DNA construct

<400> SEQUENCE: 133
atgactgaaa aagaaaaaat gttagcagaa aaatggtacg atgcaaactt tgatcaagac      60
ttaatcaatg aacgtgcacg agcgaaagat atttgctttg aattaaatca tacaaagccg     120
agtgacaaaa ataaaagaaa ggaattaatc gatgaattat ttcaaacaac aacagacaat     180
gtaagtattt cgattccttt tgatacagat tatggttgga acgttaaact aggaaaaaat     240
gtctatgtaa acaccaattg ttattttatg gatggtggac agattacaat tggcgataat     300 gttttttatag gacctaattg tggattctac acagcaacac atccacttaa tttttcatcat   360 agaaatgaag gatttgaaaa agcaggacca attaatattg gcagtaatac ttggtttggc     420
ggacatgtag ccgtgcttcc gggagtgacg attggagaag gcagtgtgat tggtgctggt     480
agtgttgtca ccaaagatat tccgccacac agtttagcgg ttggaaaccc ttgtaaagtc     540
gttcgtaaaa ttgataatga ggtaccatca gaagcattga acgatgaaac actaaattag    600

<210> SEQ ID NO 134
<211> LENGTH: 1779
<212> TYPE: DNA
<213> ORGANISM: Artificial sequence
<220> FEATURE:
<223> OTHER INFORMATION: DNA construct

<400> SEQUENCE: 134
gacacacctc aaaagatac tacagctaag acaacatctc atgattccaa aaaatctact       60
gatgatgaaa cttctaagga tactacaagt aaagatattg ataaagcaga caacaataat     120
actagtaacc aagacaataa cgacaaaaaa gttaaaacta tagacgacag cacttcagac     180
tctaacaata tcattgattt tatttataag aatttaccac aaaccaatat aaaccaattg     240
ctaaccaaaa ataaatacga tgataattac tcattaacaa cttaatccaa aaacttattc     300
```

| | |
|---|---|
| aatttaaatt cggatatttc tgattacgaa caacctcgta atggtgaaaa gtcaacaaat | 360 |
| gattcgaata aaaacagtga taatagcatc aaaaatgata cggatacgca atcatctaaa | 420 |
| caagataaag cagacaatca aaaagcacct aaatcaaaca atacaaaacc aagtacatct | 480 |
| aataagcaac caaattcgcc aaagccaaca caaccaaatc aatcaaatag tcaaccagca | 540 |
| agtgacgata aagtaaatca aaaatcttca tcgaaagata atcaatcaat gtcagattcg | 600 |
| gctttagatt ctattttgga tcaatacagt gaagatgcaa agaaaacaca aaagattac | 660 |
| gcatctcaat ctaaaaaaga caaaaatgaa aaatctaata caaagaatcc acagttacca | 720 |
| acacaagatg aattgaaaca taaatctaaa cctgctcaat cattcaataa cgatgttaat | 780 |
| caaaaggata cacgtgcaac atcactattc gaaacagatc ctagtatatc taacaatgat | 840 |
| gatagtggac aatttaacgt tgttgactca aaagatacac gtcaatttgt caaatcaatt | 900 |
| gctaaagatg cacaccgcat tggtcaagat aacgatattt atgcgtctgt catgattgcc | 960 |
| caagcaatct tagaatctga ctcaggtcgt agtgctttag ctaagtcacc aaaccataat | 1020 |
| ttattcggta tcaaaggtgc ttttgaaggg aattctgttc cttttaacac attagaagct | 1080 |
| gatggtaatc aattgtatag tattaatgct ggattccgaa aatatccaag cacgaaagaa | 1140 |
| tcactaaaag attactctga ccttattaaa aatggtattg atggcaatcg aacaatttat | 1200 |
| aaaccaacat ggaaatcgga agccgattct tataaagatg caacatcaca cttatctaaa | 1260 |
| acatatgcta cagatccaaa ctatgctaag aaattaaaca gtattattaa acactatcaa | 1320 |
| ttaactcagt tgacgatga acgtatgcca gatttagata aatatgaacg ttctatcaag | 1380 |
| gattatgatg attcatcaga tgaattcaaa cctttccgcg aggtatctga taatatgcca | 1440 |
| tatccacatg gccaatgtac ttggtacgta tataaccgta tgaaacaatt tggtacatct | 1500 |
| atctcaggtg atttaggtga tgcacataat tggaataatc gagctcaata ccgtgattat | 1560 |
| caagtaagtc atacaccaaa acgtcatgct gctgttgtat ttgaggctgg acaatttggt | 1620 |
| gcagatcaac attacggtca tgtagcattt gttgaaaaag ttaacagtga tggttctatc | 1680 |
| gttatttcag aatccaatgt aaaggatta ggtatcattt ctcatagaac tatcaatgca | 1740 |
| gctgccgctg aagaattatc atatattaca ggtaaataa | 1779 |

<210> SEQ ID NO 135
<211> LENGTH: 1326
<212> TYPE: DNA
<213> ORGANISM: Artificial sequence
<220> FEATURE:
<223> OTHER INFORMATION: DNA construct

<400> SEQUENCE: 135

| | |
|---|---|
| gctgagaagc aagtgaatat gggaaattca caggaggata cagttacagc acaatctatt | 60 |
| ggggatcaac aaactaggga aaatgctaat tatcaacgtg aaaacggtgt tgacgaacag | 120 |
| caacatactg aaaatttaac taagaacttg cataatgata aaacaatatc agaagaaaat | 180 |
| catcgtaaaa cagatgattt gaataaagat caactaaagg atgataaaaa atcatcgctt | 240 |
| aataataaaa atattcaacg tgatacaaca aaaaataaca atgctaatcc tagggatgta | 300 |
| aatcaagggt tagaacaggc tattaatgat ggcaaacaaa gtaaagtggc gtcacagcaa | 360 |
| cagtcaaaag aggcagataa tagtcaagac ttaaacgcta ataacaatct accttcacaa | 420 |
| agtcgaacaa aggtatcacc atcattaaat aagtcagatc aaacaagtca acgagaaatt | 480 |
| gttaatgaga cagaaataga gaaagtacaa ccgcaacaaa agaatcaagc gatgataaaa | 540 |
| attactgacc acaatttaa caatgaacaa gaagtgaaac ctcaaaaaga cgaaaaaaca | 600 |

```
ctatcagttt cagatttaaa aaacaatcaa aaatcaccag ttgaaccaac aaaggacaat        660
gacaagaaaa atggattaaa tttattaaaa agtagtgcaa tagcaacgtt accaaacaaa        720
gggacaaagg aacttactgc aaaagcgaaa ggtgatcaaa cgaataaagt tgccaaacaa        780
gggcagtata aaaatcaaga tcctatagtt ttagtgcatg gtttcaatgg gtttacagat        840
gatattaatc cttcagtgtt agctcattat tggggcggta ataaaatgaa cattcgccaa        900
gatttagaag aaaatggtta caaagcttat gaagcaagta taagtgcttt tggaagtaac        960
tatgaccgcg cagttgaact ttattattat atcaaaggcg gtcgtgtaga ttatggtgca       1020
gcacatgcag caaatatgg acatgaacgt tatggaaaaa catacgaagg aatttacaaa       1080
gactggaaac caggacagaa ggtacacctt gttggacata gtatgggtgg tcaaacgata       1140
cgtcaactag aagaattact gcgtaatggt agtcgtgaag aaatagagta tcaaaagaaa       1200
catagtggcg aaatttctcc actattcaaa ggtaataatg acaatatgat ttcatcaatt       1260
actactttag gaacgccaca taatggaacg catgcttcag atttagctgg taatgaagct       1320
ttataa                                                                  1326

<210> SEQ ID NO 136
<211> LENGTH: 1098
<212> TYPE: DNA
<213> ORGANISM: Artificial sequence
<220> FEATURE:
<223> OTHER INFORMATION: DNA construct

<400> SEQUENCE: 136
ggatttttaa acaaatctaa aaatgagcaa gcggcattaa aggcacaaca agcagcgata         60 aagaagaag caagtgcaaa taatttaagt gatacatcac aagaagcaca agagattcaa        120
gaagctaaaa gagaagcaca agcagaagcg ataaaagtg tggctgtatc aaataaagaa        180
tcaaaagcag tggcattgaa agcacaacaa gcagcgataa aagaagaagc aagtgcaaat        240
aatttgagtg atacatcaca agaggcacaa gagattcaag aagctaaaaa agaagcacaa        300
gcagaaacag ataaaagtgc agctgtatca aatgaagaac caaaagcagt ggcattgaaa        360
gcacaacaag cagcgataaa agaagaagca agtgcaaata atttaagtga tatatcacaa        420
gaggcacaag aggttcaaga agctaaaaaa gaagcacaag cagagaaaga cagtgacaca        480
ttaactaaag atgcaagtgc agcaaaggta gaagtatcaa aaccgagtc acaagctgaa        540 agattagcaa acgctgcaaa acagaagcaa gctaaattaa caccaggttc aaaagagagt        600
caattaactg aagcgttatt tgcagaaaaa ccagttgcta aaaatgactt gaaagaaatt        660
cctcaattag ttactaaaaa gaatgatgta tcagagacag agacggttaa tatagataat        720
aaagacactg ttaaacaaaa agaagctaaa tttgaaaatg gtgttattac acgtaaagct        780
gatgaaaaaa caactaataa tacagctgtt gacaagaaat caggtaaaca atctaaaaaa        840
acaacacctt caaatatacg aaatgcatca aaagcatcta caatataaac ttcaggtcag        900
aaaaagcaac ataataagaa atcatcacaa ggtgcaaaga aacaaagtag ttcaagtaag        960
tcaactcaaa agaataatca aactagtaat aagaattcaa aaacaacaaa tgctaaatca       1020
tccaatgcat caaaaacgcc aaatgctaaa gttgagaaag ctaaagtaa aatagagaaa       1080 cgtacattca atgactaa                                                    1098

<210> SEQ ID NO 137
<211> LENGTH: 1056
<212> TYPE: DNA
```

<213> ORGANISM: Artificial sequence
<220> FEATURE:
<223> OTHER INFORMATION: DNA construct

<400> SEQUENCE: 137

| | | | | | |
|---|---|---|---|---|---|
| aaggataact | taaatggaga | aaaaccaact | actaatttga | atcataatat | aacttcacca | 60 |
| tcagtaaata | gtgaaatgaa | taataatgag | actgggacac | ctcacgaatc | aaatcaaacg | 120 |
| ggtaatgaag | gaacaggttc | gaatagtcgt | gatgctaatc | ctgattcgaa | taatgtgaag | 180 |
| ccagactcaa | acaaccaaaa | cccaagtaca | gattcaaaac | cagacccaaa | taaccaaaac | 240 |
| ccaagtccga | atcctaaacc | agatccagat | aacccgaaac | caaaaccgga | tccaaaacca | 300 |
| gacccagata | accaaagcc | aaatccggat | ccaaaaccag | atccagataa | cccgaaacca | 360 |
| aatccagatc | caaaaccaga | ccctaataag | ccaaatccgg | atccaaaacc | agatccagat | 420 |
| aaaccaaagc | caaatccgaa | tccaaaacca | gaccctaata | agccaaatcc | taacccgtca | 480 |
| ccagatcccg | atcaacctgg | ggattccaat | cattctggtg | gctcgaaaaa | tgggggaca | 540 |
| tggaacccaa | atgcttcaga | tggatctaat | caaggtcaat | ggcaaccaaa | tgggaatcaa | 600 |
| ggaaactcac | aaaatcctac | tggtaatgat | tttgtatccc | aacgattttt | agccttggca | 660 |
| aatgggctt | acaagtataa | tccgtatatt | ttaaatcaaa | ttaataagtt | gggcaaagat | 720 |
| tatggagaag | ttactgatga | agacatttat | aatattattc | gaaaacaaaa | tttcagcgga | 780 |
| aatgcatatt | taaatggatt | acaacagcaa | tcgaattact | ttagattcca | atatttcaat | 840 |
| ccattgaaat | cagaaaggta | ctatcgtaat | ttagatgaac | aagtactcgc | attaattact | 900 |
| ggtgaaattg | gatcaatgcc | agatttgaaa | agcccgaag | ataagccgga | ttcaaaacaa | 960 |
| cgctcatttg | aaccgcatga | aaaagacgat | tttacagtag | ttaaaaaaca | agaagataat | 1020 |
| aagaaaagtg | cgtcaactgc | atatagtaaa | agttaa | | | 1056 |

<210> SEQ ID NO 138
<211> LENGTH: 1239
<212> TYPE: DNA
<213> ORGANISM: Artificial sequence
<220> FEATURE:
<223> OTHER INFORMATION: DNA construct

<400> SEQUENCE: 138

| | | | | | |
|---|---|---|---|---|---|
| attgattcaa | aaaataaacc | agctaattct | gatattaaat | ttgaggtgac | tcaaaagagt | 60 |
| gatgcggtca | aagcattaaa | agaattgcct | aaatccgaaa | atgtaaaaaa | tatttatcaa | 120 |
| gattacgctg | ttactgatgt | aaaaactgat | aaaaaaggat | ttacgcatta | tacattgcaa | 180 |
| ccgagtgttg | atggtgttca | tgcacctgac | aaagaagtga | agtacacgc | agacaaatca | 240 |
| ggaaaagtcg | ttttaatcaa | tgggatact | gatgcgaaga | agtaaagcc | aacgaataaa | 300 |
| gtgacattaa | gtaaagatga | cgcagccgac | aaagcattta | agcagttaa | gattgataag | 360 |
| aataaagcga | aaaatcttaa | agataaagtc | attaaagaaa | acaaagttga | atcgatggt | 420 |
| gacagtaata | aatacgttta | taatgttgag | ttaattacag | tgcaccaga | aatttcacat | 480 |
| tggaaagtta | aaattgatgc | tcaaactggc | gaaattttag | aaaaaatgaa | cttagttaaa | 540 |
| gaagctgcag | aaactggtaa | aggaaaaggt | gtacttggcg | atacaaaaga | tatcaatatc | 600 |
| aatagtattg | acggtggatt | tagcctagaa | gatttaacgc | atcaaggtaa | attatcagca | 660 |
| tttagcttta | atgatcaaac | aggtcaagca | acattgatta | ctaatgaaga | tgaaaacttc | 720 |
| gtaaaagatg | agcaacgtgc | tggcgtagat | gcaaattatt | acgctaaaca | aacatatgat | 780 |
| tattacaaag | acacatttgg | tcgtgaatca | tatgacaacc | aaggtagtcc | aattgtttca | 840 |

```
ttaacgcatg ttaataacta cggtggtcaa gataacagaa ataatgccgc atggatcggt     900
gacaaaatga tctatggtga tggtgatggt cgcacattca caagtttatc gggtgcaaat     960
gacgtagtag cacacgaatt aacacacggt gtgacacaag agacagcgaa cttagaatat    1020
aaggaccagt caggcgctct aaatgaaagc ttttcagatg tttttggata ctttgtagat    1080
gacgaggatt tcttaatggg tgaagatgtc tacacacctg aaaagaggg agacgcttta     1140 cgcagcatgt caaacccaga acaatttggt caaccagctc atatgaaaga ctatgtattc    1200
actgaaaaag ataatggtgg cgtacatacg aattcttaa                            1239
```

<210> SEQ ID NO 139
<211> LENGTH: 319
<212> TYPE: PRT
<213> ORGANISM: Staphylococcus aureus

<400> SEQUENCE: 139

```
Met Lys Thr Arg Ile Val Ser Ser Val Thr Thr Thr Leu Leu Leu Gly
1               5                   10                  15

Ser Ile Leu Met Asn Pro Val Ala Asn Ala Ala Asp Ser Asp Ile Asn
            20                  25                  30

Ile Lys Thr Gly Thr Thr Asp Ile Gly Ser Asn Thr Thr Val Lys Thr
        35                  40                  45

Gly Asp Leu Val Thr Tyr Asp Lys Glu Asn Gly Met Leu Lys Lys Val
    50                  55                  60

Phe Tyr Ser Phe Ile Asp Asp Lys Asn His Asn Lys Lys Leu Leu Val
65                  70                  75                  80

Ile Arg Thr Lys Gly Thr Ile Ala Gly Gln Tyr Arg Val Tyr Ser Glu
                85                  90                  95

Glu Gly Ala Asn Lys Ser Gly Leu Ala Trp Pro Ser Ala Phe Lys Val
            100                 105                 110

Gln Leu Gln Leu Pro Asp Asn Glu Val Ala Gln Ile Ser Asp Tyr Tyr
        115                 120                 125

Pro Arg Asn Ser Ile Asp Thr Lys Glu Tyr Met Ser Thr Leu Thr Tyr
    130                 135                 140

Gly Phe Asn Gly Asn Val Thr Gly Asp Asp Thr Gly Lys Ile Gly Gly
145                 150                 155                 160

Leu Ile Gly Ala Asn Val Ser Ile Gly His Thr Leu Lys Tyr Val Gln
                165                 170                 175

Pro Asp Phe Lys Thr Ile Leu Glu Ser Pro Thr Asp Lys Lys Val Gly
            180                 185                 190

Trp Lys Val Ile Phe Asn Asn Met Val Asn Gln Asn Trp Gly Pro Tyr
        195                 200                 205

Asp Arg Asp Ser Trp Asn Pro Val Tyr Gly Asn Gln Leu Phe Met Lys
    210                 215                 220

Thr Arg Asn Gly Ser Met Lys Ala Ala Asp Asn Phe Leu Asp Pro Asn
225                 230                 235                 240

Lys Ala Ser Ser Leu Leu Ser Ser Gly Phe Ser Pro Asp Phe Ala Thr
                245                 250                 255

Val Ile Thr Met Asp Arg Lys Ala Ser Lys Gln Gln Thr Asn Ile Asp
            260                 265                 270

Val Ile Tyr Glu Arg Val Arg Asp Asp Tyr Gln Leu His Trp Thr Ser
        275                 280                 285

Thr Asn Trp Lys Gly Thr Asn Thr Lys Asp Lys Trp Ile Asp Arg Ser
    290                 295                 300
```

Ser Glu Arg Tyr Lys Ile Asp Trp Glu Lys Glu Glu Met Thr Asn
305                 310                 315

<210> SEQ ID NO 140
<211> LENGTH: 515
<212> TYPE: PRT
<213> ORGANISM: Staphylococcus aureus

<400> SEQUENCE: 140

Met Lys Lys Lys Leu Gly Met Leu Leu Val Pro Ala Val Thr Leu
1               5                   10                  15

Ser Leu Ala Ala Cys Gly Asn Asp Asp Gly Lys Asp Lys Asp Gly Lys
            20                  25                  30

Val Thr Ile Lys Thr Thr Val Tyr Pro Leu Gln Ser Phe Ala Glu Gln
            35                  40                  45

Ile Gly Gly Lys His Val Lys Val Ser Ser Ile Tyr Pro Ala Gly Thr
    50                  55                  60

Asp Leu His Ser Tyr Glu Pro Thr Gln Lys Asp Ile Leu Ser Ala Ser
65              70                  75                  80

Lys Ser Asp Leu Phe Met Tyr Thr Gly Asp Asn Leu Asp Pro Val Ala
                85                  90                  95

Lys Lys Val Ala Ser Thr Ile Lys Asp Lys Asp Lys Lys Leu Ser Leu
            100                 105                 110

Glu Asp Lys Leu Asp Lys Ala Lys Leu Leu Thr Asp Gln His Glu His
            115                 120                 125

Gly Glu Glu His Glu His Glu Gly His Asp His Gly Lys Glu Glu His
130                 135                 140

His His His Gly Gly Tyr Asp Pro His Val Trp Leu Asp Pro Lys Ile
145                 150                 155                 160

Asn Gln Thr Phe Ala Lys Glu Ile Lys Asp Glu Leu Val Lys Lys Asp
                165                 170                 175

Pro Lys His Lys Asp Asp Tyr Glu Lys Asn Tyr Lys Lys Leu Asn Asp
            180                 185                 190

Asp Leu Lys Lys Ile Asp Asn Asp Met Lys Gln Val Thr Lys Asp Lys
            195                 200                 205

Gln Gly Asn Ala Val Phe Ile Ser His Glu Ser Ile Gly Tyr Leu Ala
210                 215                 220

Asp Arg Tyr Gly Phe Val Gln Lys Gly Ile Gln Asn Met Asn Ala Glu
225                 230                 235                 240

Asp Pro Ser Gln Lys Glu Leu Thr Lys Ile Val Lys Glu Ile Arg Asp
                245                 250                 255

Ser Asn Ala Lys Tyr Ile Leu Tyr Glu Asp Asn Val Ala Asn Lys Val
            260                 265                 270

Thr Glu Thr Ile Arg Lys Glu Thr Asp Ala Lys Pro Leu Lys Phe Tyr
            275                 280                 285

Asn Met Glu Ser Leu Asn Lys Glu Gln Gln Lys Lys Asp Asn Ile Thr
290                 295                 300

Tyr Gln Ser Leu Met Lys Ser Asn Ile Glu Asn Ile Gly Lys Ala Leu
305                 310                 315                 320

Asp Ser Gly Val Lys Val Lys Asp Lys Ala Glu Ser Lys His Asp
                325                 330                 335

Lys Ala Ile Ser Asp Gly Tyr Phe Lys Asp Glu Gln Val Lys Asp Arg
            340                 345                 350

Glu Leu Ser Asp Tyr Ala Gly Glu Trp Gln Ser Val Tyr Pro Tyr Leu

```
                    355                 360                 365
Lys Asp Gly Thr Leu Asp Glu Val Met Glu His Lys Ala Glu Asn Asp
            370                 375                 380

Pro Lys Lys Ser Ala Lys Asp Leu Lys Ala Tyr Tyr Asp Lys Gly Tyr
385                 390                 395                 400

Lys Thr Asp Ile Thr Asn Ile Asp Ile Lys Gly Asn Glu Ile Thr Phe
                    405                 410                 415

Thr Lys Asp Gly Thr Lys His Thr Gly Lys Tyr Glu Tyr Asn Gly Lys
            420                 425                 430

Lys Thr Leu Lys Tyr Pro Lys Gly Asn Arg Gly Val Arg Phe Met Phe
            435                 440                 445

Lys Leu Val Asp Gly Asn Asp Lys Asp Leu Pro Lys Phe Ile Gln Phe
            450                 455                 460

Ser Asp His Asn Ile Ala Pro Lys Lys Ala Glu His Phe His Ile Phe
465                 470                 475                 480

Met Gly Asn Asp Asn Asp Ala Leu Leu Lys Glu Met Asp Asn Trp Pro
                    485                 490                 495

Thr Tyr Tyr Pro Ser Lys Leu Asn Lys Asp Gln Ile Lys Glu Glu Met
                500                 505                 510

Leu Ala His
        515
```

<210> SEQ ID NO 141
<211> LENGTH: 519
<212> TYPE: PRT
<213> ORGANISM: Staphylococcus aureus

<400> SEQUENCE: 141

```
Met Asn Leu Leu Ser Leu Leu Ile Leu Gly Ile Ile Leu Gly
1               5                   10                  15

Val Val Gly Gly Tyr Val Val Ala Arg Asn Leu Leu Gln Lys Gln
                    20                  25                  30

Ser Gln Ala Arg Gln Thr Ala Glu Asp Ile Val Asn Gln Ala His Lys
                35                  40                  45

Glu Ala Asp Asn Ile Lys Lys Glu Lys Leu Leu Glu Ala Lys Glu Glu
            50                  55                  60

Asn Gln Ile Leu Arg Glu Gln Thr Glu Ala Glu Leu Arg Glu Arg Arg
65                  70                  75                  80

Ser Glu Leu Gln Arg Gln Glu Thr Arg Leu Leu Gln Lys Glu Glu Asn
                    85                  90                  95

Leu Glu Arg Lys Ser Asp Leu Leu Asp Lys Lys Asp Glu Ile Leu Glu
                100                 105                 110

Gln Lys Glu Ser Lys Ile Glu Glu Lys Gln Gln Val Asp Ala Lys
            115                 120                 125

Glu Ser Ser Val Gln Thr Leu Ile Met Lys His Glu Gln Glu Leu Glu
130                 135                 140

Arg Ile Ser Gly Leu Thr Gln Glu Glu Ala Ile Asn Glu Gln Leu Gln
145                 150                 155                 160

Arg Val Glu Glu Glu Leu Ser Gln Asp Ile Ala Val Leu Val Lys Glu
                    165                 170                 175

Lys Glu Lys Glu Ala Lys Glu Lys Val Asp Lys Thr Ala Lys Glu Leu
                180                 185                 190

Leu Ala Thr Ala Val Gln Arg Leu Ala Ala Asp His Thr Ser Glu Ser
            195                 200                 205
```

Thr Val Ser Val Val Asn Leu Pro Asn Asp Glu Met Lys Gly Arg Ile
210                 215                 220

Ile Gly Arg Glu Gly Arg Asn Ile Arg Thr Leu Glu Thr Leu Thr Gly
225                 230                 235                 240

Ile Asp Leu Ile Ile Asp Asp Thr Pro Glu Ala Val Ile Leu Ser Gly
            245                 250                 255

Phe Asp Pro Ile Arg Arg Glu Ile Ala Arg Thr Ala Leu Val Asn Leu
            260                 265                 270

Val Ser Asp Gly Arg Ile His Pro Gly Arg Ile Glu Asp Met Val Glu
        275                 280                 285

Lys Ala Arg Lys Glu Val Asp Asp Ile Ile Arg Glu Ala Gly Glu Gln
290                 295                 300

Ala Thr Phe Glu Val Asn Ala His Asn Met His Pro Asp Leu Val Lys
305                 310                 315                 320

Ile Val Gly Arg Leu Asn Tyr Arg Thr Ser Tyr Gly Gln Asn Val Leu
            325                 330                 335

Lys His Ser Ile Glu Val Ala His Leu Ala Ser Met Leu Ala Ala Glu
        340                 345                 350

Leu Gly Glu Asp Glu Thr Leu Ala Lys Arg Ala Gly Leu Leu His Asp
        355                 360                 365

Val Gly Lys Ala Ile Asp His Glu Val Glu Gly Ser His Val Glu Ile
370                 375                 380

Gly Val Glu Leu Ala Lys Lys Tyr Gly Glu Asn Glu Thr Val Ile Asn
385                 390                 395                 400

Ala Ile His Ser His His Gly Asp Val Glu Pro Thr Ser Ile Ile Ser
            405                 410                 415

Ile Leu Val Ala Ala Ala Asp Ala Leu Ser Ala Ala Arg Pro Gly Ala
            420                 425                 430

Arg Lys Glu Thr Leu Glu Asn Tyr Ile Arg Arg Leu Glu Arg Leu Glu
        435                 440                 445

Thr Leu Ser Glu Ser Tyr Asp Gly Val Glu Lys Ala Phe Ala Ile Gln
        450                 455                 460

Ala Gly Arg Glu Ile Arg Val Ile Val Ser Pro Glu Glu Ile Asp Asp
465                 470                 475                 480

Leu Lys Ser Tyr Arg Leu Ala Arg Asp Ile Lys Asn Gln Ile Glu Asp
            485                 490                 495

Glu Leu Gln Tyr Pro Gly His Ile Lys Val Thr Val Val Arg Glu Thr
        500                 505                 510

Arg Ala Val Glu Tyr Ala Lys
        515

<210> SEQ ID NO 142
<211> LENGTH: 619
<212> TYPE: PRT
<213> ORGANISM: Staphylococcus aureus

<400> SEQUENCE: 142

Met Pro Lys Asn Lys Ile Leu Ile Tyr Leu Leu Ser Thr Thr Leu Val
1               5                   10                  15

Leu Pro Thr Leu Val Ser Pro Thr Ala Tyr Ala Asp Thr Pro Gln Lys
            20                  25                  30

Asp Thr Thr Ala Lys Thr Thr Ser His Asp Ser Lys Lys Ser Asn Asp
        35                  40                  45

Asp Glu Thr Ser Lys Asp Thr Thr Ser Lys Asp Ile Asp Lys Ala Asp
    50                  55                  60

```
Asn Asn Asn Thr Ser Asn Gln Asp Asn Asp Lys Phe Lys Thr
65                  70                  75                  80

Ile Asp Asp Ser Thr Ser Asp Ser Asn Asn Ile Ile Asp Phe Ile Tyr
                85                  90                  95

Lys Asn Leu Pro Gln Thr Asn Ile Asn Gln Leu Leu Thr Lys Asn Lys
            100                 105                 110

Tyr Asp Asp Asn Tyr Ser Leu Thr Thr Leu Ile Gln Asn Leu Phe Asn
        115                 120                 125

Leu Asn Ser Asp Ile Ser Asp Tyr Glu Gln Pro Arg Asn Gly Glu Lys
    130                 135                 140

Ser Thr Asn Asp Ser Asn Lys Asn Ser Asp Asn Ser Ile Lys Asn Asp
145                 150                 155                 160

Thr Asp Thr Gln Ser Ser Lys Gln Asp Lys Ala Asp Asn Gln Lys Ala
                165                 170                 175

Pro Lys Ser Asn Asn Thr Lys Pro Ser Thr Ser Asn Lys Gln Pro Asn
            180                 185                 190

Ser Pro Lys Pro Thr Gln Pro Asn Gln Ser Asn Ser Gln Pro Ala Ser
        195                 200                 205

Asp Asp Lys Ala Asn Gln Lys Ser Ser Ser Lys Asp Asn Gln Ser Met
    210                 215                 220

Ser Asp Ser Ala Leu Asp Ser Ile Leu Asp Gln Tyr Ser Glu Asp Ala
225                 230                 235                 240

Lys Lys Thr Gln Lys Asp Tyr Ala Ser Gln Ser Lys Lys Asp Lys Asn
                245                 250                 255

Glu Lys Ser Asn Thr Lys Asn Pro Gln Leu Pro Thr Gln Asp Glu Leu
            260                 265                 270

Lys His Lys Ser Lys Pro Ala Gln Ser Phe Asn Asn Asp Val Asn Gln
        275                 280                 285

Lys Asp Thr Arg Ala Thr Ser Leu Phe Glu Thr Asp Pro Ser Ile Ser
    290                 295                 300

Asn Asn Asp Asp Ser Gly Gln Phe Asn Val Val Asp Ser Lys Asp Thr
305                 310                 315                 320

Arg Gln Phe Val Lys Ser Ile Ala Lys Asp Ala His Arg Ile Gly Gln
                325                 330                 335

Asp Asn Asp Ile Tyr Ala Ser Val Met Ile Ala Gln Ala Ile Leu Glu
            340                 345                 350

Ser Asp Ser Gly Arg Ser Ala Leu Ala Lys Ser Pro Asn His Asn Leu
        355                 360                 365

Phe Gly Ile Lys Gly Ala Phe Glu Gly Asn Ser Val Pro Phe Asn Thr
    370                 375                 380

Leu Glu Ala Asp Gly Asn Lys Leu Tyr Ser Ile Asn Ala Gly Phe Arg
385                 390                 395                 400

Lys Tyr Pro Ser Thr Lys Glu Ser Leu Lys Asp Tyr Ser Asp Leu Ile
                405                 410                 415

Lys Asn Gly Ile Asp Gly Asn Arg Thr Ile Tyr Lys Pro Thr Trp Lys
            420                 425                 430

Ser Glu Ala Asp Ser Tyr Lys Asp Ala Thr Ser His Leu Ser Lys Thr
        435                 440                 445

Tyr Ala Thr Asp Pro Asn Tyr Ala Lys Lys Leu Asn Ser Ile Ile Lys
    450                 455                 460

His Tyr Gln Leu Thr Gln Phe Asp Asp Glu Arg Met Pro Asp Leu Asp
465                 470                 475                 480
```

-continued

Lys Tyr Glu Arg Ser Ile Lys Asp Tyr Asp Ser Ser Asp Glu Phe
                485                 490                 495

Lys Pro Phe Arg Glu Val Ser Asp Ser Met Pro Tyr Pro His Gly Gln
            500                 505                 510

Cys Thr Trp Tyr Val Tyr Asn Arg Met Lys Gln Phe Gly Thr Ser Ile
            515                 520                 525

Ser Gly Asp Leu Gly Asp Ala His Asn Trp Asn Asn Arg Ala Gln Tyr
        530                 535                 540

Arg Asp Tyr Gln Val Ser His Thr Pro Lys Arg His Ala Ala Val Val
545                 550                 555                 560

Phe Glu Ala Gly Gln Phe Gly Ala Asp Gln His Tyr Gly His Val Ala
                565                 570                 575

Phe Val Glu Lys Val Asn Ser Asp Gly Ser Ile Val Ile Ser Glu Ser
            580                 585                 590

Asn Val Lys Gly Leu Gly Ile Ile Ser His Arg Thr Ile Asn Ala Ala
        595                 600                 605

Ala Ala Glu Glu Leu Ser Tyr Ile Thr Gly Lys
    610                 615

<210> SEQ ID NO 143
<211> LENGTH: 645
<212> TYPE: PRT
<213> ORGANISM: Staphylococcus aureus

<400> SEQUENCE: 143

Met Asn Lys Gln Gln Lys Glu Phe Lys Ser Phe Tyr Ser Ile Arg Lys
1               5                   10                  15

Ser Ser Leu Gly Val Ala Ser Val Ala Ile Ser Thr Leu Leu Leu Leu
            20                  25                  30

Met Ser Asn Gly Glu Ala Gln Ala Ala Ala Glu Glu Thr Gly Gly Thr
        35                  40                  45

Asn Thr Glu Ala Gln Pro Lys Thr Glu Ala Val Ala Ser Pro Thr Thr
    50                  55                  60

Thr Ser Glu Lys Ala Pro Glu Thr Lys Pro Val Ala Asn Ala Val Ser
65                  70                  75                  80

Val Ser Asn Lys Glu Val Glu Ala Pro Thr Ser Glu Thr Lys Glu Ala
                85                  90                  95

Lys Glu Val Lys Glu Val Lys Ala Pro Lys Glu Thr Lys Glu Val Lys
            100                 105                 110

Pro Ala Ala Lys Ala Thr Asn Asn Thr Tyr Pro Ile Leu Asn Gln Glu
        115                 120                 125

Leu Arg Glu Ala Ile Lys Asn Pro Ala Ile Lys Asp Lys Asp His Ser
    130                 135                 140

Ala Pro Asn Ser Arg Pro Ile Asp Phe Glu Met Lys Lys Lys Asp Gly
145                 150                 155                 160

Thr Gln Gln Phe Tyr His Tyr Ala Ser Ser Val Lys Pro Ala Arg Val
                165                 170                 175

Ile Phe Thr Asp Ser Lys Pro Glu Ile Glu Leu Gly Leu Gln Ser Gly
            180                 185                 190

Gln Phe Trp Arg Lys Phe Glu Val Tyr Glu Gly Asp Lys Lys Leu Pro
        195                 200                 205

Ile Lys Leu Val Ser Tyr Asp Thr Val Lys Asp Tyr Ala Tyr Ile Arg
    210                 215                 220

Phe Ser Val Ser Asn Gly Thr Lys Ala Val Lys Ile Val Ser Ser Thr
225                 230                 235                 240

```
His Phe Asn Asn Lys Glu Glu Lys Tyr Asp Tyr Thr Leu Met Glu Phe
                245                 250                 255

Ala Gln Pro Ile Tyr Asn Ser Ala Asp Lys Phe Lys Thr Glu Glu Asp
            260                 265                 270

Tyr Lys Ala Glu Lys Leu Leu Ala Pro Tyr Lys Ala Lys Thr Leu
        275                 280                 285

Glu Arg Gln Val Tyr Glu Leu Asn Lys Ile Gln Asp Lys Leu Pro Glu
    290                 295                 300

Lys Leu Lys Ala Glu Tyr Lys Lys Leu Glu Asp Thr Lys Lys Ala
305                 310                 315                 320

Leu Asp Glu Gln Val Lys Ser Ala Ile Thr Glu Phe Gln Asn Val Gln
                325                 330                 335

Pro Thr Asn Glu Lys Met Thr Asp Leu Gln Asp Thr Lys Tyr Val Val
            340                 345                 350

Tyr Glu Ser Val Glu Asn Asn Glu Ser Met Met Asp Thr Phe Val Lys
        355                 360                 365

His Pro Ile Lys Thr Gly Met Leu Asn Gly Lys Lys Tyr Met Val Met
    370                 375                 380

Glu Thr Thr Asn Asp Asp Tyr Trp Lys Asp Phe Met Val Glu Gly Gln
385                 390                 395                 400

Arg Val Arg Thr Ile Ser Lys Asp Ala Lys Asn Asn Thr Arg Thr Ile
                405                 410                 415

Ile Phe Pro Tyr Val Glu Gly Lys Thr Leu Tyr Asp Ala Ile Val Lys
            420                 425                 430

Val His Val Lys Thr Ile Asp Tyr Asp Gly Gln Tyr His Val Arg Ile
        435                 440                 445

Val Asp Lys Glu Ala Phe Thr Lys Ala Asn Thr Asp Lys Ser Asn Lys
    450                 455                 460

Lys Glu Gln Gln Asp Asn Ser Ala Lys Lys Glu Ala Thr Pro Ala Thr
465                 470                 475                 480

Pro Ser Lys Pro Thr Pro Ser Pro Val Glu Lys Glu Ser Gln Lys Gln
                485                 490                 495

Asp Ser Gln Lys Asp Asp Asn Lys Gln Leu Pro Ser Val Glu Lys Glu
            500                 505                 510

Asn Asp Ala Ser Ser Glu Ser Gly Lys Asp Lys Thr Pro Ala Thr Lys
        515                 520                 525

Pro Thr Lys Gly Glu Val Glu Ser Ser Ser Thr Thr Pro Thr Lys Val
    530                 535                 540

Val Ser Thr Thr Gln Asn Val Ala Lys Pro Thr Thr Ala Ser Ser Lys
545                 550                 555                 560

Thr Thr Lys Asp Val Val Gln Thr Ser Ala Gly Ser Ser Glu Ala Lys
                565                 570                 575

Asp Ser Ala Pro Leu Gln Lys Ala Asn Ile Lys Asn Thr Asn Asp Gly
            580                 585                 590

His Thr Gln Ser Gln Asn Asn Lys Asn Thr Gln Glu Asn Lys Ala Lys
        595                 600                 605

Ser Leu Pro Gln Thr Gly Glu Glu Ser Asn Lys Asp Met Thr Leu Pro
    610                 615                 620

Leu Met Ala Leu Leu Ala Leu Ser Ser Ile Val Ala Phe Val Leu Pro
625                 630                 635                 640

Arg Lys Arg Lys Asn
                645
```

```
<210> SEQ ID NO 144
<211> LENGTH: 681
<212> TYPE: PRT
<213> ORGANISM: Staphylococcus aureus

<400> SEQUENCE: 144

Met Met Lys Ser Gln Asn Lys Tyr Ser Ile Arg Lys Phe Ser Val Gly
1               5                   10                  15

Ala Ser Ser Ile Leu Ile Ala Thr Leu Leu Phe Leu Ser Gly Gly Gln
            20                  25                  30

Ala Gln Ala Ala Glu Lys Gln Val Asn Met Gly Asn Ser Gln Glu Asp
        35                  40                  45

Thr Val Thr Ala Gln Ser Ile Gly Asp Gln Gln Thr Arg Glu Asn Ala
50                  55                  60

Asn Tyr Gln Arg Glu Asn Gly Val Asp Glu Gln Gln His Thr Glu Asn
65                  70                  75                  80

Leu Thr Lys Asn Leu His Asn Asp Lys Thr Ile Ser Glu Glu Asn His
                85                  90                  95

Arg Lys Thr Asp Asp Leu Asn Lys Asp Gln Leu Lys Asp Asp Lys Lys
            100                 105                 110

Ser Ser Arg Asn Asn Lys Asn Ile Gln Arg Asp Thr Thr Lys Asn Asn
        115                 120                 125

Asn Ala Asn Pro Ser Asp Val Asn Gln Gly Leu Glu Gln Ala Ile Asn
130                 135                 140

Asp Gly Lys Gln Ser Lys Val Ala Ser Gln Gln Ser Lys Glu Ala
145                 150                 155                 160

Asp Asn Ser Gln Asp Ser Asn Ala Asn Asn Asn Leu Pro Ser Gln Ser
                165                 170                 175

Arg Thr Lys Glu Ala Pro Ser Leu Asn Lys Leu Asp Gln Thr Ser Gln
            180                 185                 190

Arg Glu Ile Val Asn Glu Thr Glu Ile Glu Lys Val Gln Pro Gln Gln
        195                 200                 205

Asn Asn Gln Ala Asn Asp Lys Ile Thr Asn Tyr Asn Phe Asn Asn Glu
210                 215                 220

Gln Glu Val Lys Pro Gln Lys Asp Glu Lys Thr Leu Ser Val Ser Asp
225                 230                 235                 240

Leu Lys Asn Asn Gln Lys Ser Pro Val Glu Pro Thr Lys Asp Asn Asp
                245                 250                 255

Lys Lys Asn Gly Leu Asn Leu Leu Lys Ser Ser Ala Val Ala Thr Leu
            260                 265                 270

Pro Asn Lys Gly Thr Lys Glu Leu Thr Ala Lys Ala Lys Asp Asp Gln
        275                 280                 285

Thr Asn Lys Val Ala Lys Gly Gln Tyr Lys Asn Gln Asp Pro Ile
290                 295                 300

Val Leu Val His Gly Phe Asn Gly Phe Thr Asp Asp Ile Asn Pro Ser
305                 310                 315                 320

Val Leu Ala His Tyr Trp Gly Gly Asn Lys Met Asn Ile Arg Gln Asp
                325                 330                 335

Leu Glu Glu Asn Gly Tyr Lys Ala Tyr Glu Ala Ser Ile Ser Ala Phe
            340                 345                 350

Gly Ser Asn Tyr Asp Arg Ala Val Glu Leu Tyr Tyr Ile Lys Gly
        355                 360                 365

Gly Arg Val Asp Tyr Gly Ala Ala His Ala Ala Lys Tyr Gly His Glu
370                 375                 380
```

```
Arg Tyr Gly Lys Thr Tyr Glu Gly Ile Tyr Lys Asp Trp Lys Pro Gly
385                 390                 395                 400

Gln Lys Val His Leu Val Gly His Ser Met Gly Gly Gln Thr Ile Arg
            405                 410                 415

Gln Leu Glu Glu Leu Leu Arg Asn Gly Ser Arg Glu Glu Ile Glu Tyr
        420                 425                 430

Gln Lys Lys His Gly Gly Glu Ile Ser Pro Leu Phe Lys Gly Asn Asn
    435                 440                 445

Asp Asn Met Ile Ser Ser Ile Thr Thr Leu Gly Thr Pro His Asn Gly
    450                 455                 460

Thr His Ala Ser Asp Leu Ala Gly Asn Glu Ala Leu Val Arg Gln Ile
465                 470                 475                 480

Val Phe Asp Ile Gly Lys Met Phe Gly Asn Lys Asn Ser Arg Val Asp
                485                 490                 495

Phe Gly Leu Ala Gln Trp Gly Leu Lys Gln Lys Pro Asn Glu Ser Tyr
            500                 505                 510

Ile Asp Tyr Val Lys Arg Val Lys Gln Ser Asn Leu Trp Lys Ser Lys
        515                 520                 525

Asp Asn Gly Phe Tyr Asp Leu Thr Arg Glu Gly Ala Thr Asp Leu Asn
530                 535                 540

Arg Lys Thr Ser Leu Asn Pro Asn Ile Val Tyr Lys Thr Tyr Thr Gly
545                 550                 555                 560

Glu Ala Thr His Lys Ala Leu Asn Ser Asp Arg Gln Lys Ala Asp Leu
                565                 570                 575

Asn Met Phe Phe Pro Phe Val Ile Thr Gly Asn Leu Ile Gly Lys Ala
            580                 585                 590

Thr Glu Lys Glu Trp Arg Glu Asn Asp Gly Leu Val Ser Val Ile Ser
        595                 600                 605

Ser Gln His Pro Phe Asn Gln Ala Tyr Thr Asn Ala Thr Asp Lys Ile
            610                 615                 620

Gln Lys Gly Ile Trp Gln Val Thr Pro Thr Lys His Asp Trp Asp His
625                 630                 635                 640

Val Asp Phe Val Gly Gln Asp Ser Ser Asp Thr Val Arg Thr Arg Glu
                645                 650                 655

Glu Leu Gln Asp Phe Trp His His Leu Ala Asp Asp Leu Val Lys Thr
            660                 665                 670

Glu Lys Val Thr Asp Thr Lys Gln Ala
        675                 680

<210> SEQ ID NO 145
<211> LENGTH: 769
<212> TYPE: PRT
<213> ORGANISM: Staphylococcus aureus

<400> SEQUENCE: 145

Met Asp Ile Gly Lys Lys His Val Ile Pro Lys Ser Gln Tyr Arg Arg
1               5                   10                  15

Lys Arg Arg Glu Phe Phe His Asn Glu Asp Arg Glu Glu Asn Leu Asn
            20                  25                  30

Gln His Gln Asp Lys Gln Asn Ile Asp Asn Thr Thr Ser Lys Lys Ala
        35                  40                  45

Asp Lys Gln Ile His Lys Asp Ser Ile Asp Lys His Glu Arg Phe Lys
    50                  55                  60

Asn Ser Leu Ser Ser His Leu Glu Gln Arg Asn Arg Asp Val Asn Glu
```

```
              65                  70                  75                  80
Asn Lys Ala Glu Glu Ser Lys Ser Asn Gln Asp Ser Lys Ser Ala Tyr
                        85                  90                  95

Asn Arg Asp His Tyr Leu Thr Asp Asp Val Ser Lys Lys Gln Asn Ser
                       100                 105                 110

Leu Asp Ser Val Asp Gln Asp Thr Glu Lys Ser Lys Tyr Tyr Glu Gln
                       115                 120                 125

Asn Ser Glu Ala Thr Leu Ser Thr Lys Ser Thr Asp Lys Val Glu Ser
            130                 135                 140

Thr Glu Met Arg Lys Leu Ser Ser Asp Lys Asn Lys Val Gly His Glu
145                 150                 155                 160

Glu Gln His Val Leu Ser Lys Pro Ser Glu His Asp Lys Glu Thr Arg
                        165                 170                 175

Ile Asp Ser Glu Ser Ser Arg Thr Asp Ser Asp Ser Ser Met Gln Thr
                       180                 185                 190

Glu Lys Ile Lys Lys Asp Ser Ser Asp Gly Asn Lys Ser Ser Asn Leu
                       195                 200                 205

Lys Ser Glu Val Ile Ser Asp Lys Ser Asn Thr Val Pro Lys Leu Ser
            210                 215                 220

Glu Ser Asp Asp Glu Val Asn Asn Gln Lys Pro Leu Thr Leu Pro Glu
225                 230                 235                 240

Glu Gln Lys Leu Lys Arg Gln Gln Ser Gln Asn Glu Gln Thr Lys Thr
                        245                 250                 255

Tyr Thr Tyr Gly Asp Ser Glu Gln Asn Asp Lys Ser Asn His Glu Asn
                       260                 265                 270

Asp Leu Ser His His Ile Pro Ser Ile Ser Asp Asp Lys Asp Asn Val
                       275                 280                 285

Met Arg Glu Asn His Ile Val Asp Asp Asn Pro Asp Asn Asp Ile Asn
            290                 295                 300

Thr Pro Ser Leu Ser Lys Thr Asp Asp Arg Lys Leu Asp Glu Lys
305                 310                 315                 320

Ile His Val Glu Asp Lys His Lys Gln Asn Ala Asp Ser Ser Glu Thr
                        325                 330                 335

Val Gly Tyr Gln Ser Gln Ser Thr Ala Ser His Arg Ser Thr Glu Lys
                       340                 345                 350

Arg Asn Ile Ser Ile Asn Asp His Asp Lys Leu Asn Gly Gln Lys Thr
                       355                 360                 365

Asn Thr Lys Thr Ser Ala Asn Asn Gln Lys Lys Ala Thr Ser Lys
            370                 375                 380

Leu Asn Lys Gly Arg Ala Thr Asn Asn Tyr Ser Asp Ile Leu Lys
385                 390                 395                 400

Lys Phe Trp Met Met Tyr Trp Pro Lys Leu Val Ile Leu Met Gly Ile
                        405                 410                 415

Ile Ile Leu Ile Val Ile Leu Asn Ala Ile Phe Asn Asn Val Asn Lys
                       420                 425                 430

Asn Asp Arg Met Asn Asp Asn Asp Ala Asp Ala Gln Lys Tyr Thr
            435                 440                 445

Thr Thr Met Lys Asn Ala Asn Asn Thr Val Lys Ser Val Val Thr Val
            450                 455                 460

Glu Asn Glu Thr Ser Lys Asp Ser Ser Leu Pro Lys Asp Lys Ala Ser
465                 470                 475                 480

Gln Asp Glu Val Gly Ser Gly Val Val Tyr Lys Lys Ser Gly Asp Thr
                        485                 490                 495
```

Leu Tyr Ile Val Thr Asn Ala His Val Val Gly Asp Lys Glu Asn Gln
            500                 505                 510

Lys Ile Thr Phe Ser Asn Asn Lys Ser Val Val Gly Lys Val Leu Gly
            515                 520                 525

Lys Asp Lys Trp Ser Asp Leu Ala Val Val Lys Ala Thr Ser Ser Asp
530                 535                 540

Ser Ser Val Lys Glu Ile Ala Ile Gly Asp Ser Asn Asn Leu Val Leu
545                 550                 555                 560

Gly Glu Pro Ile Leu Val Val Gly Asn Pro Leu Gly Val Asp Phe Lys
            565                 570                 575

Gly Thr Val Thr Glu Gly Ile Ile Ser Gly Leu Asn Arg Asn Val Pro
            580                 585                 590

Ile Asp Phe Asp Lys Asp Asn Lys Tyr Asp Met Leu Met Lys Ala Phe
            595                 600                 605

Gln Ile Asp Ala Ser Val Asn Pro Gly Asn Ser Gly Gly Ala Val Val
            610                 615                 620

Asn Arg Glu Gly Lys Leu Ile Gly Val Val Ala Ala Lys Ile Ser Met
625                 630                 635                 640

Pro Asn Val Glu Asn Met Ser Phe Ala Ile Pro Val Asn Glu Val Gln
            645                 650                 655

Lys Ile Val Lys Asp Leu Glu Thr Lys Gly Lys Ile Asp Tyr Pro Asp
            660                 665                 670

Val Gly Val Lys Met Lys Asn Ile Ala Ser Leu Asn Ser Phe Glu Arg
            675                 680                 685

Gln Ala Val Lys Leu Pro Gly Lys Val Lys Asn Gly Val Val Val Asp
            690                 695                 700

Gln Val Asp Asn Asn Gly Leu Ala Asp Gln Ser Gly Leu Lys Lys Gly
705                 710                 715                 720

Asp Val Ile Thr Glu Leu Asp Gly Lys Leu Leu Glu Asp Asp Leu Arg
            725                 730                 735

Phe Arg Gln Ile Ile Phe Ser His Lys Asp Asp Leu Lys Ser Ile Thr
            740                 745                 750

Ala Lys Ile Tyr Arg Asp Gly Lys Glu Lys Glu Ile Asn Ile Lys Leu
            755                 760                 765

Lys

<210> SEQ ID NO 146
<211> LENGTH: 2066
<212> TYPE: PRT
<213> ORGANISM: Staphylococcus aureus

<400> SEQUENCE: 146

Met Asn Glu Lys Val Glu Gly Met Thr Leu Glu Leu Lys Leu Asp His
1               5                   10                  15

Leu Gly Val Gln Glu Gly Met Lys Gly Leu Lys Arg Gln Leu Gly Val
            20                  25                  30

Val Asn Ser Glu Met Lys Ala Asn Leu Ser Ala Phe Asp Lys Ser Glu
        35                  40                  45

Lys Ser Met Glu Lys Tyr Gln Ala Arg Ile Lys Gly Leu Asn Asp Arg
    50                  55                  60

Leu Lys Val Gln Lys Lys Met Tyr Ser Gln Val Glu Asp Glu Leu Lys
65                  70                  75                  80

Gln Val Asn Ala Asn Tyr Gln Lys Ala Lys Ser Ser Val Lys Asp Val
            85                  90                  95

```
Glu Lys Ala Tyr Leu Lys Leu Val Glu Ala Asn Lys Lys Glu Lys Leu
            100                 105                 110

Ala Leu Asp Lys Ser Lys Glu Ala Leu Lys Ser Ser Asn Thr Glu Leu
            115                 120                 125

Lys Lys Ala Glu Asn Gln Tyr Lys Arg Thr Asn Gln Arg Lys Gln Asp
            130                 135                 140

Ala Tyr Gln Lys Leu Lys Gln Leu Arg Asp Ala Glu Gln Lys Leu Lys
145                 150                 155                 160

Asn Ser Asn Gln Ala Thr Thr Ala Gln Leu Lys Arg Ala Ser Asp Ala
                165                 170                 175

Val Gln Lys Gln Ser Ala Lys His Lys Ala Leu Val Glu Gln Tyr Lys
            180                 185                 190

Gln Glu Gly Asn Gln Val Gln Lys Leu Lys Val Gln Asn Asp Asn Leu
            195                 200                 205

Ser Lys Ser Asn Asp Lys Ile Glu Ser Ser Tyr Ala Lys Thr Asn Thr
            210                 215                 220

Lys Leu Lys Gln Thr Glu Lys Glu Phe Asn Asp Leu Asn Asn Thr Ile
225                 230                 235                 240

Lys Asn His Ser Ala Asn Val Ala Lys Ala Glu Thr Ala Val Asn Lys
                245                 250                 255

Glu Lys Ala Ala Leu Asn Asn Leu Glu Arg Ser Ile Asp Lys Ala Ser
            260                 265                 270

Ser Glu Met Lys Thr Phe Asn Lys Glu Gln Met Ile Ala Gln Ser His
            275                 280                 285

Phe Gly Lys Leu Ala Ser Gln Ala Asp Val Met Ser Lys Lys Phe Ser
            290                 295                 300

Ser Ile Gly Asp Lys Met Thr Ser Leu Gly Arg Thr Met Thr Met Gly
305                 310                 315                 320

Val Ser Thr Pro Ile Thr Leu Gly Leu Gly Ala Ala Leu Lys Thr Ser
                325                 330                 335

Ala Asp Phe Glu Gly Gln Met Ser Arg Val Gly Ala Ile Ala Gln Ala
            340                 345                 350

Ser Ser Lys Asp Leu Lys Ser Met Ser Asn Gln Ala Val Asp Leu Gly
            355                 360                 365

Ala Lys Thr Ser Lys Ser Ala Asn Glu Val Ala Lys Gly Met Glu Glu
            370                 375                 380

Leu Ala Ala Leu Gly Phe Asn Ala Lys Gln Thr Met Glu Ala Met Pro
385                 390                 395                 400

Gly Val Ile Ser Ala Ala Glu Ala Ser Gly Ala Glu Met Ala Thr Thr
                405                 410                 415

Ala Thr Val Met Ala Ser Ala Ile Asn Ser Phe Gly Leu Lys Ala Ser
            420                 425                 430

Asp Ala Asn His Val Ala Asp Leu Leu Ala Arg Ser Ala Asn Asp Ser
            435                 440                 445

Ala Ala Asp Ile Gln Tyr Met Gly Asp Ala Leu Lys Tyr Ala Gly Thr
            450                 455                 460

Pro Ala Lys Ala Leu Gly Val Ser Ile Glu Asp Thr Ser Ala Ala Ile
465                 470                 475                 480

Glu Val Leu Ser Asn Ser Gly Leu Glu Gly Ser Gln Ala Gly Thr Ala
                485                 490                 495

Leu Arg Ala Ser Phe Ile Arg Leu Ala Asn Pro Ser Lys Asn Thr Ala
            500                 505                 510
```

```
Lys Glu Met Lys Lys Leu Gly Ile His Leu Ser Asp Ala Lys Gly Gln
            515                 520                 525

Phe Val Gly Met Gly Glu Leu Ile Arg Gln Phe Gln Asp Asn Met Lys
            530                 535                 540

Gly Met Thr Arg Glu Gln Lys Leu Ala Thr Val Ala Thr Ile Val Gly
545                 550                 555                 560

Thr Glu Ala Ala Ser Gly Phe Leu Ala Leu Ile Glu Ala Gly Pro Asp
                565                 570                 575

Lys Ile Asn Ser Tyr Ser Lys Ser Leu Lys Asn Ser Asn Gly Glu Ser
            580                 585                 590

Lys Lys Ala Ala Asp Leu Met Lys Asp Asn Leu Lys Gly Ala Leu Glu
            595                 600                 605

Gln Leu Gly Gly Ala Phe Glu Ser Leu Ala Ile Glu Val Gly Lys Asp
            610                 615                 620

Leu Thr Pro Met Ile Arg Ala Gly Ala Glu Gly Leu Thr Lys Leu Val
625                 630                 635                 640

Asp Gly Phe Thr His Leu Pro Gly Trp Val Arg Lys Ala Ser Val Gly
                645                 650                 655

Leu Ala Leu Phe Gly Ala Ser Ile Gly Pro Ala Val Leu Ala Gly Gly
                660                 665                 670

Leu Leu Ile Arg Ala Val Gly Ser Ala Ala Lys Gly Tyr Ala Ser Leu
            675                 680                 685

Asn Arg Arg Ile Ala Glu Asn Thr Ile Leu Ser Asn Thr Asn Ser Lys
            690                 695                 700

Ala Met Lys Ser Leu Gly Leu Gln Thr Leu Phe Leu Gly Ser Thr Thr
705                 710                 715                 720

Gly Lys Thr Ser Lys Gly Phe Lys Gly Leu Ala Gly Ala Met Leu Phe
                725                 730                 735

Asn Leu Lys Pro Ile Asn Val Leu Lys Asn Ser Ala Lys Leu Ala Ile
            740                 745                 750

Leu Pro Phe Lys Leu Leu Lys Asn Gly Leu Gly Leu Ala Ala Lys Ser
            755                 760                 765

Leu Phe Ala Val Ser Gly Gly Ala Arg Phe Ala Gly Val Ala Leu Lys
            770                 775                 780

Phe Leu Thr Gly Pro Ile Gly Ala Thr Ile Thr Ala Ile Thr Ile Ala
785                 790                 795                 800

Tyr Lys Val Phe Lys Thr Ala Tyr Asp Arg Val Glu Trp Phe Arg Asn
                805                 810                 815

Gly Ile Asn Gly Leu Gly Glu Thr Ile Lys Phe Phe Gly Gly Lys Ile
            820                 825                 830

Ile Gly Gly Ala Val Arg Lys Leu Gly Glu Phe Lys Asn Tyr Leu Gly
            835                 840                 845

Ser Ile Gly Lys Ser Phe Lys Glu Lys Phe Ser Lys Asp Met Lys Asp
850                 855                 860

Gly Tyr Lys Ser Leu Ser Asp Asp Leu Leu Lys Val Gly Val Asn
865                 870                 875                 880

Lys Phe Lys Gly Phe Met Gln Thr Met Gly Thr Ala Ser Lys Lys Ala
                885                 890                 895

Ser Asp Thr Val Lys Val Leu Gly Lys Gly Val Ser Lys Glu Thr Glu
                900                 905                 910

Lys Ala Leu Glu Lys Tyr Val His Tyr Ser Glu Glu Asn Asn Arg Ile
            915                 920                 925

Met Glu Lys Val Arg Leu Asn Ser Gly Gln Ile Thr Glu Asp Lys Ala
```

```
                930             935             940
Lys Lys Leu Leu Lys Ile Glu Ala Asp Leu Ser Asn Asn Leu Ile Ala
945             950             955             960

Glu Ile Glu Lys Arg Asn Lys Lys Glu Leu Glu Lys Thr Gln Glu Leu
            965             970             975

Ile Asp Lys Tyr Ser Ala Phe Asp Glu Gln Glu Lys Gln Asn Ile Leu
            980             985             990

Thr Arg Thr Lys Glu Lys Asn Asp Leu Arg Ile Lys Lys Glu Gln Glu
            995             1000            1005

Leu Asn Gln Lys Ile Lys Glu Leu Lys Glu Lys Ala Leu Ser Asp
    1010            1015            1020

Gly Gln Ile Ser Glu Asn Glu Arg Lys Glu Ile Glu Lys Leu Glu
    1025            1030            1035

Asn Gln Arg Arg Asp Ile Thr Val Lys Glu Leu Ser Lys Thr Glu
    1040            1045            1050

Lys Glu Gln Glu Arg Ile Leu Val Arg Met Gln Arg Asn Arg Asn
    1055            1060            1065

Ser Tyr Ser Ile Asp Glu Ala Ser Lys Ala Ile Lys Glu Ala Glu
    1070            1075            1080

Lys Ala Arg Lys Ala Lys Lys Lys Glu Val Asp Lys Gln Tyr Glu
    1085            1090            1095

Asp Asp Val Ile Ala Ile Lys Asn Asn Val Asn Leu Ser Lys Ser
    1100            1105            1110

Glu Lys Asp Lys Leu Leu Ala Ile Ala Asp Gln Arg His Lys Asp
    1115            1120            1125

Glu Val Arg Lys Ala Lys Ser Lys Lys Asp Ala Val Val Asp Val
    1130            1135            1140

Val Lys Lys Gln Asn Lys Asp Ile Asp Lys Glu Met Asp Leu Ser
    1145            1150            1155

Ser Gly Arg Val Tyr Lys Asn Thr Glu Lys Trp Trp Asn Gly Leu
    1160            1165            1170

Lys Ser Trp Trp Ser Asn Phe Arg Glu Asp Gln Lys Lys Lys Ser
    1175            1180            1185

Asp Lys Tyr Ala Lys Glu Gln Glu Thr Ala Arg Arg Asn Arg
    1190            1195            1200

Glu Asn Ile Lys Lys Trp Phe Gly Asn Ala Trp Asp Gly Val Lys
    1205            1210            1215

Ser Lys Thr Gly Glu Ala Phe Ser Lys Met Gly Arg Asn Ala Asn
    1220            1225            1230

His Phe Gly Gly Glu Met Lys Met Trp Ser Gly Ile Lys Gly
    1235            1240            1245

Ile Pro Ser Lys Leu Ser Ser Gly Trp Ser Ser Ala Lys Ser Ser
    1250            1255            1260

Val Gly Tyr His Thr Lys Ala Ile Ala Asn Ser Thr Gly Lys Trp
    1265            1270            1275

Phe Gly Lys Ala Trp Gln Ser Val Lys Ser Thr Thr Gly Ser Ile
    1280            1285            1290

Tyr Asn Gln Thr Lys Gln Lys Tyr Ser Asp Ala Ser Asp Lys Ala
    1295            1300            1305

Trp Ala His Ser Lys Ser Ile Trp Lys Gly Thr Ser Lys Trp Phe
    1310            1315            1320

Ser Asn Ala Tyr Lys Ser Ala Lys Gly Trp Leu Thr Asp Met Ala
    1325            1330            1335
```

Asn Lys Ser Arg Ser Lys Trp Asp Asn Ile Ser Ser Thr Ala Trp
1340            1345                1350

Ser Asn Ala Lys Ser Val Trp Lys Gly Thr Ser Lys Trp Phe Ser
1355            1360                1365

Asn Ser Tyr Lys Ser Leu Lys Gly Trp Thr Gly Asp Met Tyr Ser
1370            1375                1380

Arg Ala His Asp Arg Phe Asp Ala Ile Ser Ser Ala Trp Ser
1385            1390                1395

Asn Ala Lys Ser Val Phe Asn Gly Phe Arg Lys Trp Leu Ser Arg
1400            1405                1410

Thr Tyr Glu Trp Ile Arg Asp Ile Gly Lys Asp Met Gly Arg Ala
1415            1420                1425

Ala Ala Asp Leu Gly Lys Asn Val Ala Asn Lys Ala Ile Gly Gly
1430            1435                1440

Leu Asn Ser Met Ile Gly Gly Ile Asn Lys Ile Ser Lys Ala Ile
1445            1450                1455

Thr Asp Lys Asn Leu Ile Lys Pro Ile Pro Thr Leu Ser Thr Gly
1460            1465                1470

Thr Leu Ala Gly Lys Gly Val Ala Thr Asp Asn Ser Gly Ala Leu
1475            1480                1485

Thr Gln Pro Thr Phe Ala Val Leu Asn Asp Arg Gly Ser Gly Asn
1490            1495                1500

Ala Pro Gly Gly Gly Val Gln Glu Val Ile His Arg Ala Asp Gly
1505            1510                1515

Thr Phe His Ala Pro Gln Gly Arg Asp Val Val Val Pro Leu Gly
1520            1525                1530

Val Gly Asp Ser Val Ile Asn Ala Asn Asp Thr Leu Lys Leu Gln
1535            1540                1545

Arg Met Gly Val Leu Pro Lys Phe His Gly Gly Thr Lys Lys Lys
1550            1555                1560

Lys Trp Met Glu Gln Val Thr Glu Asn Leu Gly Lys Lys Ala Gly
1565            1570                1575

Asp Phe Gly Ser Lys Ala Lys Asn Thr Ala His Asn Ile Lys Lys
1580            1585                1590

Gly Ala Glu Glu Met Val Glu Ala Ala Gly Asp Lys Ile Lys Asp
1595            1600                1605

Gly Ala Ser Trp Leu Gly Asp Lys Ile Gly Asp Val Trp Asp Tyr
1610            1615                1620

Val Gln His Pro Gly Lys Leu Val Asn Lys Val Met Ser Gly Leu
1625            1630                1635

Asn Ile Asn Phe Gly Gly Gly Ala Asn Ala Thr Val Lys Ile Ala
1640            1645                1650

Lys Gly Ala Tyr Ser Leu Leu Lys Lys Lys Leu Val Asp Lys Val
1655            1660                1665

Lys Ser Trp Phe Glu Asp Phe Gly Gly Gly Gly Asp Gly Ser Tyr
1670            1675                1680

Leu Phe Asp His Pro Ile Trp Gln Arg Phe Gly Ser Tyr Thr Gly
1685            1690                1695

Gly Leu Asn Phe Asn Gly Gly Arg His Tyr Gly Ile Asp Phe Gln
1700            1705                1710

Met Pro Thr Gly Thr Asn Ile Tyr Ala Val Lys Gly Gly Ile Ala
1715            1720                1725

```
Asp Lys Val Trp Thr Asp Tyr Gly Gly Gly Asn Ser Ile Gln Ile
    1730            1735                1740

Lys Thr Gly Ala Asn Glu Trp Asn Trp Tyr Met His Leu Ser Lys
    1745            1750                1755

Gln Leu Ala Arg Gln Gly Gln Arg Ile Lys Ala Gly Gln Leu Ile
    1760            1765                1770

Gly Lys Ser Gly Ala Thr Gly Asn Phe Val Arg Gly Ala His Leu
    1775            1780                1785

His Phe Gln Leu Met Gln Gly Ser His Pro Gly Asn Asp Thr Ala
    1790            1795                1800

Lys Asp Pro Glu Lys Trp Leu Lys Ser Leu Lys Gly Ser Gly Val
    1805            1810                1815

Arg Ser Gly Ser Gly Val Asn Lys Ala Ala Ser Ala Trp Ala Gly
    1820            1825                1830

Asp Ile Arg Arg Ala Ala Lys Arg Met Gly Val Asn Val Thr Ser
    1835            1840                1845

Gly Asp Val Gly Asn Ile Ile Ser Leu Ile Gln His Glu Ser Gly
    1850            1855                1860

Gly Asn Ala Gly Ile Thr Gln Ser Ser Ala Leu Arg Asp Ile Asn
    1865            1870                1875

Val Leu Gln Gly Asn Pro Ala Lys Gly Leu Leu Gln Tyr Ile Pro
    1880            1885                1890

Gln Thr Phe Arg His Tyr Ala Val Arg Gly His Asn Asn Ile Tyr
    1895            1900                1905

Ser Gly Tyr Asp Gln Leu Leu Ala Phe Phe Asn Ser Tyr Trp
    1910            1915                1920

Arg Ser Gln Phe Asn Pro Arg Gly Gly Trp Ser Pro Ser Gly Pro
    1925            1930                1935

Arg Arg Tyr Ala Asn Gly Gly Leu Ile Thr Lys His Gln Leu Ala
    1940            1945                1950

Glu Val Gly Glu Gly Asp Lys Gln Glu Met Val Ile Pro Leu Thr
    1955            1960                1965

Arg Arg Lys Arg Ala Ile Gln Leu Thr Glu Gln Val Met Arg Ile
    1970            1975                1980

Ile Gly Met Asp Gly Lys Pro Asn Asn Ile Thr Val Asn Asn Asp
    1985            1990                1995

Thr Ser Thr Val Glu Lys Leu Leu Lys Gln Ile Val Met Leu Ser
    2000            2005                2010

Asp Lys Gly Asn Lys Leu Thr Asp Ala Leu Ile Gln Thr Val Ser
    2015            2020                2025

Ser Gln Asp Asn Asn Leu Gly Ser Asn Asp Ala Ile Arg Gly Leu
    2030            2035                2040

Glu Lys Ile Leu Ser Lys Gln Ser Gly His Arg Ala Asn Ala Asn
    2045            2050                2055

Asn Tyr Met Gly Gly Leu Thr Asn
    2060            2065
```

CHIMERIC PROTEINS FOR INDUCING IMMUNITY TOWARDS INFECTION WITH *S. AUREUS*

CROSS REFERENCE TO RELATED APPLICATIONS

This is a national stage filing in accordance with 35 U.S.C. § 371 of PCT/EP2017/068694, filed Jul. 24, 2017, which claims the benefit of the priority of European Patent Application No. 16180748.2, filed Jul. 22, 2016, the contents of each are incorporated herein by reference.

FIELD OF THE INVENTION

The present invention relates to the field of antimicrobial prophylaxis and therapy. In particular the present invention relates to novel recombinant chimeric polypeptides and polynucleotides derived from *Staphylococcus aureus*. The invention further relates to vectors comprising the polynucleotides, transformed host organisms expressing the polynucleotides, as well as prophylactic and therapeutic uses and methods. Finally, also methods of preparation are part of the invention.

BACKGROUND OF THE INVENTION

Bacterial infections are in most instances successfully treated by administration of antibiotics to patients in need thereof. However, due to careless or thoughtless use of powerful antibiotics, many pathological germs become resistant against antibiotics over time. One threatening example is *Staphyloccocus aureus*. In particular in hospitals this bacterium is of relevance. So-called Methicillin Resistant *S. Aureus* (MRSA) strains jeopardize patient's survival in hospitals, in particular after surgery.

Vaccination is considered to be a very effective method of preventing infectious diseases in human and veterinary health care. Vaccination is the administration of effective amounts of antigenic material (the vaccine) to produce immunity to a disease/disease-causing pathogenic agent. Vaccines have contributed to the eradication of smallpox, the near eradication of polio, and the control of a variety of diseases, including rubella, measles, mumps, chickenpox, typhoid fever.

Before "the genomic era", vaccines were based on killed or live attenuated, microorganisms, or parts purified from them. Subunit vaccines are considered as a modern upgrade of these types of vaccine, as the subunit vaccines contain one or more protective antigens, which are more or less the weak spot of the pathogen. Hence, in order to develop subunit vaccines, it is critical to identify the proteins, which are important for inducing protection and to eliminate others.

An antigen is said to be protective if it is able to induce protection from subsequent challenge by a disease-causing infectious agent in an appropriate animal model following immunization.

The empirical approach to subunit vaccine development, which includes several steps, begins with pathogen cultivation, followed by purification into components, and then testing of antigens for protection. Apart from being time and labour consuming, this approach has several limitations that can lead to failure. It is not possible to develop vaccines using this approach for microorganisms, which cannot easily be cultured and only allows for the identification of the antigens, which can be obtained in sufficient quantities. The empirical approach has a tendency to focus on the most abundant proteins, which in some cases are not immunoprotective. In other cases, the antigen expressed during in vivo infection is not expressed during in vitro cultivation. Furthermore, antigen discovery by use of the empirical approach demands an extreme amount of proteins in order to discover the protective antigens, which are like finding needles in the haystack. This renders it a very expensive approach, and it limits the vaccine development around diseases, which is caused by pathogens with a large genome or disease areas, which perform badly in a cost-effective perspective.

The present applicant has previously filed patent applications relating to induction of immunity against *Staphylococcus aureus*. In international patent application publications WO 2012/136653 and WO 2015/053899 and in European patent application No. 16156786.2 are disclosed a number of polypeptides, nucleic acids, vectors, and compositions that are useful as vaccine agents.

OBJECT OF THE INVENTION

It is an object of embodiments of the invention to provide further polypeptides, nucleic acids, vectors, and compositions that are useful as vaccine agents that are able to induce protective immunity against infections with *S. aureus*. It is also an object of embodiments of the invention to provide useful tools for the recombinant production of such vaccine agents.

SUMMARY OF THE INVENTION

The present invention provides chimeric polypeptides that include antigenic material from several different proteins derived from *S. aureus*. These chimeric polypeptides are useful as (vaccine) immunogens per se but also in combination with any one of the immunogens disclosed in WO 2012/136653 and/or WO 2015/053899 and/or European patent application No. 16156786.2.

Hence, in a first aspect the present invention relates to a chimeric polypeptide comprising formula I

$$a^1\text{-}A^1\text{-}L\text{-}A^2\text{-}a^1 \qquad (I)$$

wherein
$A^1$ is selected from the group consisting of
an amino acid sequence constituted by at least or exactly 5 contiguous amino acid residues present in any one of SEQ ID Nos: 1-9 and 139-146, and
an amino acid sequence with at least 80% sequence identity with an amino acid sequence constituted by at least or exactly 5 contiguous amino acid residues present in any one of SEQ ID Nos: 1-9 and 139-146,
$A^2$ is selected from the group consisting of
an amino acid sequence constituted by at least or exactly 5 contiguous amino acid residues present in any one of SEQ ID Nos: 1-9 and 139-146, and
an amino acid sequence with at least 80% sequence identity with an amino acid sequence constituted by at least or exactly 5 contiguous amino acid residues present in any one of SEQ ID Nos: 1-9 and 139-146,
L is an optional amino acid sequence,
$a^1$ is an optional amino acid sequence, and
$b^1$ is an optional amino acid sequence.

A second aspect of the invention relates to a chimeric polypeptide comprising at least 2 non-identical amino acid sequences, where each of said at least 2 non-identical amino acid sequences consists of any one of SEQ ID NOs: 21-40, wherein 0, 1, 2, or 3 amino acid residues can be substituted.

A third aspect of the invention relates to an isolated nucleic acid fragment, which comprises
  i) a nucleotide sequence encoding a chimeric polypeptide according to the first or second aspect of the invention as well as any embodiments of these aspects, or
  ii) a nucleotide sequence consisting part of any one of SEQ ID NOs: 46-58 and 99-138, or the RNA equivalent thereof, that encodes a chimeric polypeptide,
  iii) a nucleotide sequence consisting of at least or exactly or at most 10 consecutive nucleotides in part of any one of SEQ ID NOs: 46-58 and 99-138, or the RNA equivalent thereof, that encodes a chimeric polypeptide,
  iv) a nucleotide sequence having a sequence identity of at least 60% with the nucleotide sequence in i) or ii),
  v) a nucleotide sequence having a sequence identity of at least 60% with the nucleotide sequence in iii),
  vi) a nucleotide sequence complementary to the nucleotide sequence in i)-v), or
  vii) a nucleotide sequence which hybridizes under stringent conditions with the nucleotide sequence in i)-vi).

A fourth aspect of the invention relates to a vector comprising the nucleic acid of the third aspect of the invention or of any embodiments of the third aspect, such as a cloning vector or an expression vector.

A fifth aspect of the invention relates to a cell which is transformed so as to carry the vector of 1) the fourth aspect of the present invention or 2) any embodiments of the fourth aspect. Also part of this aspect is a cell line derived from such a transformed cell of the present invention.

A sixth aspect of the invention relates to a pharmaceutical composition comprising a chimeric polypeptide of the first or second aspect of the invention as well as any embodiments of these 2 aspects, a nucleic acid fragment of the third aspect of the invention or the embodiments of the $3^{rd}$ aspect, a vector of the fourth aspect of the invention or of any embodiments thereof, or a cell of the fifth aspect of the invention and any embodiments of the fifth aspect, and a pharmaceutically acceptable carrier, vehicle or diluent A $7^{th}$ aspects of the invention relates to a method for inducing immunity in an animal by administering at least once an immunogenically effective amount of a chimeric polypeptide of the first or second aspect of the invention as well as of embodiments of these 2 aspects, a nucleic acid fragment of the third aspect of the invention as well as any embodiment of the third aspect, a vector of the fourth aspect of the invention as well as any embodiment of the fourth aspect, a cell of the fifth aspect of the invention as well as any embodiment thereof, or a pharmaceutical composition of the sixth aspect of the invention as well as any embodiment thereof, so as to induce adaptive immunity against S. aureus in the animal.

An $8^{th}$ aspect of the present invention relates to a method for the preparation of the chimeric polypeptide of the first aspect of the invention as well as any embodiment thereof, comprising
  culturing a transformed cell of the fifth aspect of the invention as well as embodiments thereof (insofar as these relate to cells expressing the nucleic acid fragment of the invention) under conditions that facilitate that the transformed cell expresses the nucleic acid fragment of the third aspect of the invention and the embodiments thereof and subsequently recovering said chimeric polypeptide, or
  preparing said chimeric polypeptide by means of solid or liquid phase peptide synthesis.

Finally, in separate aspect relating to the $7^{th}$ aspect, the present invention also relates to the chimeric polypeptides of the invention, the nucleic acid or vector of the invention, the cells of the invention, or the pharmaceutical compositions of the invention for use as a pharmaceutical, in particular for use in the treatment, prophylaxis or amelioration of infection with S. aureus.

LEGENDS TO THE FIGURE

FIG. 1 shows survival plots after challenge infection in mice immunized with immunogens of the invention in a peritonitis model. Dotted lines indicates control, full lines indicates immunogen.
  A: Survival plots for CHIM_2635_2723_FS, CHIM_Hla_2635_FS, and CHIM_2716_2753_FL.
  B: Survival plots for CHIM_2723_2753_L_FL, CHIM_0992_0735_FL, and
    CHIM_0992_2635_FL.
  C: Survival plots for CHIM_1816_2119_FL, CHIM_1262_2496_RS, and CHIM_Hla_2753_FS.

FIG. 2 shows survival plots after challenge infection in mice immunized with immunogens of the invention in a peritonitis model. Dotted lines indicates control, full lines indicates immunogen.
  A: Survival plots for SAR2635-1-199, USA300HOU_2637-28-439, and SAR2723-28-619.
  B: Survival plots for M3496_SAR2723-28-619, SAR2753-36-476, and USA300HOU_2027-33-383.
  C: Survival plots for USA300HOU_1728-88-452, SAR1507-1-652, and SAR1489-343-486.
  D: Survival plots for SAR1262-25-519 and CHIM_0992_0735_FS.

FIG. 3 shows survival plots after challenge infection in mice immunized with immunogens of the invention in a peritonitis model. Dotted lines indicates control, full lines indicates immunogen.
  A: Survival plots for CHIM_2723_2753_S_FS, CHIM_2723_2753_L_FS, and CHIM_Hla_2753_FS.
  B: Survival plots for CHIM_Hla_0735_FS, IsdB_USA300-41-613, and SAR0280-28-820.
  C: Survival plots for SAR0992-1-409, M2683_SAR0992-1-409, and SAR0735-26-227.

FIG. 4 shows survival plots after challenge infection in mice immunized with immunogens of the invention in a peritonitis model. Dotted lines indicates control, full lines indicates immunogen.
  A: Survival plots for CHIM_2119_1816_FS, CHIM_1816_2119_FL, and CHIM_2716_2119_FS.
  B: Survival plots for CHIM_2496_1816_FS, CHIM_1262_2496_RS, and CHIM_1507_2119_FS
  C: Survival plots for CHIM_HLa_2635_FS, CHIM_2716_2753_FL, and HL461_SAR2753-291-476
  D: Survival plot for HL461_SAR2753_291-680.

FIG. 5 shows survival plots after challenge infection in mice immunized with immunogens of the invention in a peritonitis model. Dotted lines indicates control, full lines indicates immunogen.
  A: Survival plots for CHIM_0992_0735_FS, CHIM_0992_0735_FL, and CHIM_0735_0992_FL.
  B: Survival plots for CHIM_0992_2635_FS, CHIM_0992_2635_FL, and CHIM_0992_2753_FS.
  C: Survival plots for CHIM_2723_2635_FS, CHIM_2723_2635_RL, and CHIM_2635_2723_FS.
  D: Survival plot for CHIM_2716_1816_FS.

DETAILED DISCLOSURE OF THE INVENTION

Definitions

The term "polypeptide" is in the present context intended to mean both short peptides of from 2 to 10 amino acid residues, oligopeptides of from 11 to 100 amino acid residues, and polypeptides of more than 100 amino acid residues. Furthermore, the term is also intended to include proteins, i.e. functional biomolecules comprising at least one polypeptide; when comprising at least two polypeptides, these may form complexes, be covalently linked, or may be non-covalently linked. The polypeptide (s) in a protein can be glycosylated and/or lipidated and/or comprise prosthetic groups.

The term "subsequence" means any consecutive stretch of at least 3 amino acids or, when relevant, of at least 3 nucleotides, derived directly from a reference amino acid sequence or nucleic acid sequence, respectively The term "amino acid sequence" is the order in which amino acid residues, connected by peptide bonds, lie in the chain in peptides and proteins.

The term "adjuvant" or "immunological adjuvant" has its usual meaning in the art of vaccine technology, i.e. a substance or a composition of matter which is 1) not in itself capable of mounting a specific immune response against the immunogen of the vaccine, but which is 2) nevertheless capable of enhancing the immune response against the immunogen. Or, in other words, vaccination with the adjuvant alone does not provide an immune response against the immunogen, vaccination with the immunogen may or may not give rise to an immune response against the immunogen, but the combined vaccination with immunogen and adjuvant induces an immune response against the immunogen which is stronger than that induced by the immunogen alone.

"Sequence identity" is in the context of the present invention determined by comparing 2 aligned sequences of equal length (e.g. DNA, RNA or amino acid) according to the following formula: $(N_{ref}-N_{dif}) \cdot 100/N_{ref}$, wherein $N_{ref}$ is the number of residues in one of the 2 sequences and $N_{dif}$ is the number of residues which are non-identical in the two sequences when they are aligned over their entire lengths and in the same direction. So, two sequences 5'-ATTCG-GAAC-3' and 5'-ATACGGGAC-3' will provide the sequence identity 77.78% ($N_{ref}=9$ and $N_{dif}=2$). It will be understood that such a sequence identity determination requires that the two aligned sequences are aligned so that there are no overhangs between the two sequences: each amino acid in each sequence will have to be matched with a counterpart in the other sequence.

An "assembly of amino acids" means two or more amino acids bound together by physical or chemical means.

The "3D conformation" is the 3 dimensional structure of a biomolecule such as a protein. In monomeric polypeptides/proteins, the 3D conformation is also termed "the tertiary structure" and denotes the relative locations in 3 dimensional space of the amino acid residues forming the polypeptide.

"An immunogenic carrier" is a molecule or moiety to which an immunogen or a hapten can be coupled in order to enhance or enable the elicitation of an immune response against the immunogen/hapten. Immunogenic carriers are in classical cases relatively large molecules (such as tetanus toxoid, KLH, diphtheria toxoid etc.) which can be fused or conjugated to an immunogen/hapten, which is not sufficiently immunogenic in its own right—typically, the immunogenic carrier is capable of eliciting a strong cellular immune response against the combined substance constituted by the immunogen and the immunogenic carrier, and this in turn provides for improved responses against the immunogen antibody producing cells and cytotoxic cells. More recently, the large carrier molecules have to a certain extent been substituted by so-called promiscuous epitopes, i.e. shorter peptides that are recognized by a large fraction of MHC-haplotypes in a population, and which elicit antigen specific cellular immune responses.

An "immunogen" is a substance of matter which is capable of inducing an adaptive immune response in a host, whose immune system is exposed to the immunogen. As such, immunogens are a subset of the larger genus "antigens", which are substances that can be recognized specifically by the immune system but which are not necessarily capable of inducing immunity—an antigen is, however, always capable of eliciting immunity, meaning that a host that has an established memory immunity against the antigen will mount a specific immune response against the antigen.

A "hapten" is a (typically) small molecule, which can neither induce nor elicit an immune response, but if conjugated to an immunogenic carrier, a specific adaptive immune response can be induced against a hapten upon exposure of the immune system with the hapten carrier conjugate.

An "adaptive immune response" is an immune response in response to exposure to an antigen or immunogen, where the immune response is specific for antigenic determinants of the antigen/immunogen—examples of adaptive immune responses are induction of antigen specific antibody production or antigen specific induction/activation of cellular immune responses.

A "protective, adaptive immune response" is an antigen-specific immune response induced in a subject as a reaction to immunization (artificial or natural) with an antigen, where the immune response is capable of protecting the subject against subsequent challenges with the antigen or a pathology-related agent that includes the antigen. Typically, prophylactic vaccination aims at establishing a protective adaptive immune response against one or several pathogens.

"Stimulation of the immune system" means that a substance or composition of matter exhibits a general, non-specific immunostimulatory effect. A number of adjuvants and putative adjuvants (such as certain cytokines) share the ability to stimulate the immune system. The result of using an immunostimulating agent is an increased "alertness" of the immune system meaning that simultaneous or subsequent immunization with an immunogen induces a significantly more effective immune response compared to isolated use of the immunogen.

Hybridization under "stringent conditions" is herein defined as hybridization performed under conditions by which a probe will hybridize to its target sequence, to a detectably greater degree than to other sequences. Stringent conditions are target-sequence-dependent and will differ depending on the structure of the polynucleotide. By controlling the stringency of the hybridization and/or washing conditions, target sequences can be identified which are 100% complementary to a probe (homologous probing). Alternatively, stringency conditions can be adjusted to allow some mismatching in sequences so that lower degrees of similarity are detected (heterologous probing). Specificity is typically the function of post-hybridization washes, the critical factors being the ionic strength and temperature of the final wash solution. Generally, stringent wash temperature conditions are selected to be about 5° C. to about 2° C. lower than the melting point (Tm) for the specific sequence at a defined ionic strength and pH. The melting point, or denaturation, of DNA occurs over a narrow temperature range and represents the disruption of the double helix into its complementary single strands. The process is described by the temperature of the midpoint of transition, Tm, which is also called the melting temperature. Formulas are available in the art for the determination of melting temperatures.

As used herein, the term "antibody" refers to a polypeptide or group of polypeptides composed of at least one antibody combining site. An "antibody combining site" is the three-dimensional binding space with an internal surface shape and charge distribution complementary to the features of an epitope of an antigen, which allows a binding of the antibody with the antigen. "Antibody" includes, for example, vertebrate antibodies, hybrid antibodies, chimeric antibodies, humanised antibodies, altered antibodies, univalent antibodies, Fab proteins, and single domain antibodies.

"Specific binding" denotes binding between two substances which goes beyond binding of either substance to randomly chosen substances and also goes beyond simple association between substances that tend to aggregate because they share the same overall hydrophobicity or hydrophilicity. As such, specific binding usually involves a combination of electrostatic and other interactions between two conformationally complementary areas on the two substances, meaning that the substances can "recognize" each other in a complex mixture.

The term "vector" is used to refer to a carrier nucleic acid molecule into which a heterologous nucleic acid sequence can be inserted for introduction into a cell where it can be replicated and expressed. The term further denotes certain biological vehicles useful for the same purpose, e.g. viral and bacterial vectors—both these infectious agents are capable of introducing a heterologous nucleic acid sequence into a host and effect subsequence expression of a nucleic acid in the host.

The term "expression vector" refers to a vector containing a nucleic acid sequence coding for at least part of a gene product capable of being transcribed. In some cases, when the transcription product is an mRNA molecule, this is in turn translated into a protein, polypeptide, or peptide.

A "chimeric polypeptide" is a polypeptide as defined above, which is constituted by amino acid stretches derived from at least two different proteins, where these at least two stretches are fused to each other, optionally via a linker. By nature, a chimeric polypeptide does not occur in nature.

A "linker" or "peptide linker" is a stretch of amino acids that are interspersed between two peptides in a fusion polypeptide (such as a chimeric polypeptide). Linkers are widely used in recombinant biotechnology and are reviewed in Chen X et al. (2013), Advanced drug delivery reviews 65(10): 1357-1369. doi:10.1016/j.addr.2012.09.039. Typical linkers are flexible, meaning that they allow the joint polypeptides in a fusion construct to have a high degree of movement. Such flexible linkers are often rich in small, non-polar amino acid residues (such as glycine residues) but will often incorporate small polar amino acid residues such as serine or threonine residues, too. Such linkers are known as GS linkers.

SPECIFIC EMBODIMENTS OF THE INVENTION

The Chimeric Polypeptides of the Invention—the First and Second Aspects of the Invention Chimeric polypeptides of the first aspect of the invention comprise or consist of an amino acid sequence that has the general formula:

$$a^1\text{-}A^1\text{-}L\text{-}A^2\text{-}a^1 \qquad (I)$$

This formula is generally defined above in the summary of the invention section. The core of the amino acid sequence is constituted by the 2 amino acid sequences $A^1$ and $A^2$, which are both—independently—derived from SEQ ID NOs: 1-9 and 139-146. L can be either a linker (see below) or absent, the latter meaning that $A^1$ and $A^2$ are joined directly, typically via a peptide bond. Both $a^1$ and $a^2$ are optional and can e.g. constitute various functional amino acid sequences or in certain embodiments amino acid sequences that occur adjacent to SEQ ID NOs: 1-9 or 139-146.

Typically, $A^1$ and $A^2$ are in important embodiments of the first aspect of the invention non-identical and it is preferred that they are not derived from the same sequence among SEQ ID NOs: 1-9 and 139-146.

Thus if $A^1$ is an amino acid sequence constituted by at least or exactly 5 contiguous amino acid residues present in SEQ ID NO: 1 or an amino acid sequence with at least 80% sequence identity with an amino acid sequence constituted by at least or exactly 5 contiguous amino acid residues present in SEQ ID NO: 1, then $A^2$ is an amino acid sequence with at least 80% sequence identity with any one of SEQ ID Nos: 2-9 and 139-146 or an amino acid sequence with at least 80% sequence identity with an amino acid sequence constituted by at least or exactly 5 contiguous amino acid residues present in any one of SEQ ID NOs: 2-9 and 139-146; and if $A^1$ is an amino acid sequence constituted by at least or exactly 5 contiguous amino acid residues present in SEQ ID NO: 2 or an amino acid sequence with at least 80% sequence identity with an amino acid sequence constituted by at least or exactly 5 contiguous amino acid residues present in SEQ ID NO: 2, then $A^2$ is an amino acid sequence constituted by at least or exactly 5 contiguous amino acid residues present in any one of SEQ ID Nos: 1, 3-9, and 139-146 or an amino acid sequence with at least 80% sequence identity with an amino acid sequence constituted by at least or exactly 5 contiguous amino acid residues present in any one of SEQ ID NOs: 1, 3-9, and 139-146; and if $A^1$ is an amino acid sequence constituted by at least or exactly 5 contiguous amino acid residues present in SEQ ID NO: 3 or an amino acid sequence with at least 80% sequence identity with an amino acid sequence constituted by at least or exactly 5 contiguous amino acid residues present in SEQ ID NO: 3, then $A^2$ is an amino acid sequence constituted by at least or exactly 5 contiguous amino acid residues present in any one of SEQ ID Nos: 1, 2, 4-9, and 139-146 or an amino acid sequence with at least 80% sequence identity with an amino acid sequence constituted by at least or exactly 5 contiguous amino acid residues present in any one of SEQ ID NOs: 1, 2, 4-9, and 139-146; and if $A^1$ is an amino acid sequence constituted by at least or exactly 5 contiguous amino acid residues present in SEQ ID NO: 4 or an amino acid sequence with at least 80% sequence identity with an amino acid sequence constituted by at least or exactly 5 contiguous amino acid residues present in SEQ ID NO: 4, then $A^2$ is an amino acid sequence constituted by at least or exactly 5 contiguous amino acid residues present in any one of SEQ ID Nos: 1-3, 5-9, and 139-146 or an amino acid sequence with at least 80% sequence identity with an amino acid sequence constituted by at least or exactly 5 contiguous amino acid residues present in any one of SEQ ID NOs: 1-3, 5-9, and 139-146; and if $A^1$ is an amino acid sequence constituted by at least or exactly 5 contiguous amino acid residues present in SEQ ID NO: 5 or an amino acid sequence with at least 80% sequence identity with an amino acid sequence constituted by at least or exactly 5 contiguous amino acid residues present in SEQ ID NO: 5, then A² is an amino acid sequence constituted by at least or exactly 5 contiguous amino acid residues present in any one of SEQ ID Nos: 1-4, 6-9, and 139-146 or an amino acid sequence with at least 80% sequence identity with an amino acid sequence constituted by at least or exactly 5 contiguous amino acid residues present in any one of SEQ ID NOs: 1-4, 6-9, and 139-146; and if A¹ is an amino acid sequence constituted by at least or exactly 5 contiguous amino acid residues present in SEQ ID NO: 6 or an amino acid sequence with at least 80% sequence identity with an amino acid sequence constituted by at least or exactly 5 contiguous amino acid residues present in SEQ ID NO: 6, then A² is an amino acid sequence constituted by at least or exactly 5 contiguous amino acid residues present in any one of SEQ ID Nos: 1-5, 7-9, and 139-146 or an amino acid sequence with at least 80% sequence identity with an amino acid sequence constituted by at least or exactly 5 contiguous amino acid residues present in any one of SEQ ID NOs: 1-5 and 7-9 and 139-146; and if A¹ is an amino acid sequence constituted by at least or exactly 5 contiguous amino acid residues present in SEQ ID NO: 7 or an amino acid sequence with at least 80% sequence identity with an amino acid sequence constituted by at least or exactly 5 contiguous amino acid residues present in SEQ ID NO: 7, then A² is an amino acid sequence constituted by at least or exactly 5 contiguous amino acid residues present in any one of SEQ ID Nos: 1-6, 8, 9, and 139-146 or an amino acid sequence with at least 80% sequence identity with an amino acid sequence constituted by at least or exactly 5 contiguous amino acid residues present in any one of SEQ ID NOs: 1-6, 8, 9, and 139-146; and if A¹ is an amino acid sequence constituted by at least or exactly 5 contiguous amino acid residues present in SEQ ID NO: 8 or an amino acid sequence with at least 80% sequence identity with an amino acid sequence constituted by at least or exactly 5 contiguous amino acid residues present in SEQ ID NO: 8, then A² is an amino acid sequence constituted by at least or exactly 5 contiguous amino acid residues present in any one of SEQ ID Nos: 1-7, 9, and 139-146 or an amino acid sequence with at least 80% sequence identity with an amino acid sequence constituted by at least or exactly 5 contiguous amino acid residues present in any one of SEQ ID NOs: 1-7, 9, and 139-146; and if A¹ is an amino acid sequence constituted by at least or exactly 5 contiguous amino acid residues present in SEQ ID NO: 9 or an amino acid sequence with at least 80% sequence identity with an amino acid sequence constituted by at least or exactly 5 contiguous amino acid residues present in SEQ ID NO: 9, then A² is an amino acid sequence constituted by at least or exactly 5 contiguous amino acid residues present in any one of SEQ ID Nos: 1-8 and 139-146 or an amino acid sequence with at least 80% sequence identity with an amino acid sequence constituted by at least or exactly 5 contiguous amino acid residues present in any one of SEQ ID NOs: 1-8 and 139-146; and P if A¹ is an amino acid sequence constituted by at least or exactly 5 contiguous amino acid residues present in SEQ ID NO: 139 or an amino acid sequence with at least 80% sequence identity with an amino acid sequence constituted by at least or exactly 5 contiguous amino acid residues present in SEQ ID NO: 139, then A² is an amino acid sequence constituted by at least or exactly 5 contiguous amino acid residues present in any one of SEQ ID Nos: 1-9 and 140-146 or an amino acid sequence with at least 80% sequence identity with an amino acid sequence constituted by at least or exactly 5 contiguous amino acid residues present in any one of SEQ ID NOs: 1-9 and 140-146; and if A¹ is an amino acid sequence constituted by at least or exactly 5 contiguous amino acid residues present in SEQ ID NO: 140 or an amino acid sequence with at least 80% sequence identity with an amino acid sequence constituted by at least or exactly 5 contiguous amino acid residues present in SEQ ID NO: 140, then A² is an amino acid sequence constituted by at least or exactly 5 contiguous amino acid residues present in any one of SEQ ID Nos: 1-9, 139, and 141-146 or an amino acid sequence with at least 80% sequence identity with an amino acid sequence constituted by at least or exactly 5 contiguous amino acid residues present in any one of SEQ ID NOs: 1-9, 139, and 141-146; and if A¹ is an amino acid sequence constituted by at least or exactly 5 contiguous amino acid residues present in SEQ ID NO: 141 or an amino acid sequence with at least 80% sequence identity with an amino acid sequence constituted by at least or exactly 5 contiguous amino acid residues present in SEQ ID NO: 141, then A² is an amino acid sequence constituted by at least or exactly 5 contiguous amino acid residues present in any one of SEQ ID Nos: 1-9 and 139, 140, and 142-146 or an amino acid sequence with at least 80% sequence identity with an amino acid sequence constituted by at least or exactly 5 contiguous amino acid residues present in any one of SEQ ID NOs: 1-9, 139, 140, and 142-146; and if A¹ is an amino acid sequence constituted by at least or exactly 5 contiguous amino acid residues present in SEQ ID NO: 142 or an amino acid sequence with at least 80% sequence identity with an amino acid sequence constituted by at least or exactly 5 contiguous amino acid residues present in SEQ ID NO: 142, then A² is an amino acid sequence constituted by at least or exactly 5 contiguous amino acid residues present in any one of SEQ ID Nos: 1-9 and 139-141 and 143-146 or an amino acid sequence with at least 80% sequence identity with an amino acid sequence constituted by at least or exactly 5 contiguous amino acid residues present in any one of SEQ ID NOs: 1-9 and 139-141 and 143-146; and if A¹ is an amino acid sequence constituted by at least or exactly 5 contiguous amino acid residues present in SEQ ID NO: 143 or an amino acid sequence with at least 80% sequence identity with an amino acid sequence constituted by at least or exactly 5 contiguous amino acid residues present in SEQ ID NO: 143, then A² is an amino acid sequence constituted by at least or exactly 5 contiguous amino acid residues present in any one of SEQ ID Nos: 1-9 and 139-142 and 144-146 or an amino acid sequence with at least 80% sequence identity with an amino acid sequence constituted by at least or exactly 5 contiguous amino acid residues present in any one of SEQ ID NOs: 1-9 and 139-142 and 144-146; and if A¹ is an amino acid sequence constituted by at least or exactly 5 contiguous amino acid residues present in SEQ ID NO: 144 or an amino acid sequence with at least 80% sequence identity with an amino acid sequence constituted by at least or exactly 5 contiguous amino acid residues present in SEQ ID NO: 144, then A² is an amino acid sequence constituted by at least or exactly 5 contiguous amino acid residues present in any one of SEQ ID Nos: 1-9 and 139-143, 145, and 146 or an amino acid sequence with at least 80% sequence identity with an amino acid sequence constituted by at least or exactly 5 contiguous amino acid residues present in any one of SEQ ID NOs: 1-9 and 139-143, 145, and 146; and if A¹ is an amino acid sequence constituted by at least or exactly 5 contiguous amino acid residues present in SEQ ID NO:

145 or an amino acid sequence with at least 80% sequence identity with an amino acid sequence constituted by at least or exactly 5 contiguous amino acid residues present in SEQ ID NO: 145, then $A^2$ is an amino acid sequence constituted by at least or exactly 5 contiguous amino acid residues present in any one of SEQ ID Nos: 1-9, 139-144, and 146 or an amino acid sequence with at least 80% sequence identity with an amino acid sequence constituted by at least or exactly 5 contiguous amino acid residues present in any one of SEQ ID NOs: 1-9, 139-144, and 146; and if $A^1$ is an amino acid sequence constituted by at least or exactly 5 contiguous amino acid residues present in SEQ ID NO: 146 or an amino acid sequence with at least 80% sequence identity with an amino acid sequence constituted by at least or exactly 5 contiguous amino acid residues present in SEQ ID NO: 146, then $A^2$ is an amino acid sequence constituted by at least or exactly 5 contiguous amino acid residues present in any one of SEQ ID Nos: 1-9 and 139-145 or an amino acid sequence with at least 80% sequence identity with an amino acid sequence constituted by at least or exactly 5 contiguous amino acid residues present in any one of SEQ ID NOs: 1-9 and 139-145.

As is clear from the claims, $A^1$ and $A^2$ can be modified independently in formula I but are defined in the same manner.

For instance, $A^1$ and $A^2$ are independently each an amino acid sequence with at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with an amino acid sequence constituted by at least or exactly 5 contiguous amino acid residues present in any one of SEQ ID NOs: 1-9 and 139-146. This applies to all embodiments of the first aspect of the invention discussed above.

Also the at least or exactly 5 contiguous amino acid residues present in any one of SEQ ID NOs: 1-9 and 139-146 in the definition of $A^1$ and $A^2$ are at least or exactly or at most 6, at least or exactly or at most 7, at least or exactly or at most 8, at least or exactly or at most 9, at least or exactly or at most 10, at least or exactly or at most 11, at least or exactly or at most 12, at least or exactly or at most 13, at least or exactly or at most 14, at least or exactly or at most 15, at least or exactly or at most 16, at least or exactly or at most 17, at least or exactly or at most 18, at least or exactly or at most 19, at least or exactly or at most 20, at least or exactly or at most 21, at least or exactly or at most 22, at least or exactly or at most 23, at least or exactly or at most 24, at least or exactly or at most 25, at least or exactly or at most 26, at least or exactly or at most 27, at least or exactly or at most 28, at least or exactly or at most 29, at least or exactly or at most 30, at least or exactly or at most 31, at least or exactly or at most 32, at least or exactly or at most 33, at least or exactly or at most 34, at least or exactly or at most 35, at least or exactly or at most 36, at least or exactly or at most 37, at least or exactly or at most 38, at least or exactly or at most 39, at least or exactly or at most 40, at least or exactly or at most 41, at least or exactly or at most 42, at least or exactly or at most 43, at least or exactly or at most 44, at least or exactly or at most 45, at least or exactly or at most 46, at least or exactly or at most 47, at least or exactly or at most 48, at least or exactly or at most 49, at least or exactly or at most 50, at least or exactly or at most 51, at least or exactly or at most 52, at least or exactly or at most 53, at least or exactly or at most 54, at least or exactly or at most 55, at least or exactly or at most 56, at least or exactly or at most 57, at least or exactly or at most 58, at least or exactly or at most 59, at least or exactly or at most 60, at least or exactly or at most 61, at least or exactly or at most 62, at least or exactly or at most 63, at least or exactly or at most 64, at least or exactly or at most 65, at least or exactly or at most 66, at least or exactly or at most 67, at least or exactly or at most 68, at least or exactly or at most 69, at least or exactly or at most 70, at least or exactly or at most 71, at least or exactly or at most 72, at least or exactly or at most 73, at least or exactly or at most 74, at least or exactly or at most 75, at least or exactly or at most 76, at least or exactly or at most 77, at least or exactly or at most 78, at least or exactly or at most 79, at least or exactly or at most 80, at least or exactly or at most 81, at least or exactly or at most 82, at least or exactly or at most 83, at least or exactly or at most 84, at least or exactly or at most 85, at least or exactly or at most 86, at least or exactly or at most 87, at least or exactly or at most 88, at least or exactly or at most 89, at least or exactly or at most 90, at least or exactly or at most 91, at least or exactly or at most 92, at least or exactly or at most 93, at least or exactly or at most 94, at least or exactly or at most 95, at least or exactly or at most 96, at least or exactly or at most 97, at least or exactly or at most 98, at least or exactly or at most 99, at least or exactly or at most 100, at least or exactly or at most 101, at least or exactly or at most 102, at least or exactly or at most 103, at least or exactly or at most 104, at least or exactly or at most 105, at least or exactly or at most 106, at least or exactly or at most 107, at least or exactly or at most 108, at least or exactly or at most 109, at least or exactly or at most 110, at least or exactly or at most 111, at least or exactly or at most 112, at least or exactly or at most 113, at least or exactly or at most 114, at least or exactly or at most 115, at least or exactly or at most 116, at least or exactly or at most 117, at least or exactly or at most 118, at least or exactly or at most 119, at least or exactly or at most 120, at least or exactly or at most 121, at least or exactly or at most 122, at least or exactly or at most 123, at least or exactly or at most 124, at least or exactly or at most 125, at least or exactly or at most 126, at least or exactly or at most 127, at least or exactly or at most 128, at least or exactly or at most 129, at least or exactly or at most 130, at least or exactly or at most 131, at least or exactly or at most 132, at least or exactly or at most 133, at least or exactly or at most 134, at least or exactly or at most 135, at least or exactly or at most 136, at least or exactly or at most 137, at least or exactly or at most 138, at least or exactly or at most 139, at least or exactly or at most 140, at least or exactly or at most 141, at least or exactly or at most 142, at least or exactly or at most 143, at least or exactly or at most 144, at least or exactly or at most 145, at least or exactly or at most 146, at least or exactly or at most 147, at least or exactly or at most 148, at least or exactly or at most 149, at least or exactly or at most 150, at least or exactly or at most 151, at least or exactly or at most 152, at least or exactly or at most 153, at least or exactly or at most 154, at least or exactly or at most 155, at least or exactly or at most 156, at least or exactly or at most 157, at least or exactly or at most 158, at least or exactly or at most 159, at least or exactly or at most 160, at least or exactly or at most 161, at least or exactly or at most 162, at least or exactly or at most 163, at least or exactly or at most 164, at least or exactly or at most 165, at least or exactly or at most 166, at least or exactly or at most 167, at least or exactly or at most 168, at least or exactly or at most 169, at least or exactly or at most 170, at least or exactly or at most 171, at least or exactly or at most 172, at least or exactly or at most 173, at least or exactly or at most 174, at least or exactly or at most 175, at least or exactly or at most 176, at least or exactly or at most 177, at least or exactly or at most 178, at least or exactly or at most 179, at least or exactly or at most 180, at least or exactly or at most 181, at least or exactly or at most 182, at least or exactly or at most 183, at least or exactly or at most 184, at least or exactly or at most 185, at least or exactly or at most 186, at least or exactly or at most 187, at least or exactly or at most 188, at least or exactly or at most 189, at least or exactly or at most 190, at least or exactly or at most 191, at least or exactly or at most 192, at least or exactly or at most 193, at least or exactly or at most 194, at least or exactly or at most 195, at least or exactly or at most 196, at least or exactly or at most 197, at least or exactly or at most 198, or at least or exactly or at most 199 amino acid residues in any one of SEQ ID NOs: 1-9 and 139-146; or the at least or exactly 5 contiguous amino acid residues present in any one of SEQ ID NOs: 2-9 and 139-146 in the definition of $A^1$ and $A^2$ are at least or exactly or at most 200, at least or exactly or at most 201, or at least or exactly or at most 202 amino acid residues in any one of SEQ ID NOs: 2-9 and 139-146; or the at least or exactly 5 contiguous amino acid residues present in any one of SEQ ID NOs: 3-9 and 139-146 in the definition of $A^1$ and $A^2$ are at least or exactly or at most 203, at least or exactly or at most 204, at least or exactly or at most 205, at least or exactly or at most 206, at least or exactly or at most 207, at least or exactly or at most 208, at least or exactly or at most 209, at least or exactly or at most 210, at least or exactly or at most 211, at least or exactly or at most 212, at least or exactly or at most 213, at least or exactly or at most 214, at least or exactly or at most 215, at least or exactly or at most 216, at least or exactly or at most 217, at least or exactly or at most 218, at least or exactly or at most 219, at least or exactly or at most 220, at least or exactly or at most 221, at least or exactly or at most 222, at least or exactly or at most 223, at least or exactly or at most 224, at least or exactly or at most 225, at least or exactly or at most 226, at least or exactly or at most 227, at least or exactly or at most 228, at least or exactly or at most 229, at least or exactly or at most 230, at least or exactly or at most 231, at least or exactly or at most 232, at least or exactly or at most 233, at least or exactly or at most 234, at least or exactly or at most 235, at least or exactly or at most 236, at least or exactly or at most 237, at least or exactly or at most 238, at least or exactly or at most 239, at least or exactly or at most 240, at least or exactly or at most 241, at least or exactly or at most 242, at least or exactly or at most 243, at least or exactly or at most 244, at least or exactly or at most 245, at least or exactly or at most 246, at least or exactly or at most 247, at least or exactly or at most 248, at least or exactly or at most 249, at least or exactly or at most 250, at least or exactly or at most 251, at least or exactly or at most 252, at least or exactly or at most 253, at least or exactly or at most 254, at least or exactly or at most 255, at least or exactly or at most 256, at least or exactly or at most 257, at least or exactly or at most 258, at least or exactly or at most 259, at least or exactly or at most 260, at least or exactly or at most 261, at least or exactly or at most 262, at least or exactly or at most 263, at least or exactly or at most 264, at least or exactly or at most 265, at least or exactly or at most 266, at least or exactly or at most 267, at least or exactly or at most 268, at least or exactly or at most 269, at least or exactly or at most 270, at least or exactly or at most 271, at least or exactly or at most 272, at least or exactly or at most 273, at least or exactly or at most 274, at least or exactly or at most 275, at least or exactly or at most 276, at least or exactly or at most 277, at least or exactly or at most 278, at least or exactly or at most 279, at least or exactly or at most 280, at least or exactly or at most 281, at least or exactly or at most 282, at least or exactly or at most 283, at least or exactly or at most 284, at least or exactly or at most 285, at least or exactly or at most 286, at least or exactly or at most 287, at least or exactly or at most 288, at least or exactly or at most 289, at least or exactly or at most 290, at least or exactly or at most 291, at least or exactly or at most 292, or at least or exactly or at most 293 amino acid residues in any one of SEQ ID NOs: 3-9 and 139-146; or the at least or exactly 5 contiguous amino acid residues present in any one of SEQ ID NOs: 4-9 and 139-146 in the definition of $A^1$ and $A^2$ are at least or exactly or at most 294, at least or exactly or at most 295, at least or exactly or at most 296, at least or exactly or at most 297, at least or exactly or at most 298, at least or exactly or at most 299, at least or exactly or at most 300, at least or exactly or at most 301, at least or exactly or at most 302, at least or exactly or at most 303, at least or exactly or at most 304, at least or exactly or at most 305, at least or exactly or at most 306, at least or exactly or at most 307, at least or exactly or at most 308, at least or exactly or at most 309, at least or exactly or at most 310, at least or exactly or at most 311, at least or exactly or at most 312, at least or exactly or at most 313, at least or exactly or at most 314, at least or exactly or at most 315, at least or exactly or at most 316, at least or exactly or at most 317, at least or exactly or at most 318, or at least or exactly or at most 319 amino acid residues in any one of SEQ ID NOs: 4-9 and 139-146; or the at least or exactly 5 contiguous amino acid residues present in any one of SEQ ID NOs: 4-9 and 140-146 in the definition of $A^1$ and $A^2$ are at least or exactly or at most 320, at least or exactly or at most 321, at least or exactly or at most 322, at least or exactly or at most 323, at least or exactly or at most 324, at least or exactly or at most 325, at least or exactly or at most 326, at least or exactly or at most 327, at least or exactly or at most 328, at least or exactly or at most 329, at least or exactly or at most 330, at least or exactly or at most 331, at least or exactly or at most 332, at least or exactly or at most 333, at least or exactly or at most 334, at least or exactly or at most 335, at least or exactly or at most 336, at least or exactly or at most 337, at least or exactly or at most 338, at least or exactly or at most 339, at least or exactly or at most 340, at least or exactly or at most 341, at least or exactly or at most 342, at least or exactly or at most 343, at least or exactly or at most 344, at least or exactly or at most 345, at least or exactly or at most 346, at least or exactly or at most 347, at least or exactly or at most 348, at least or exactly or at most 349, at least or exactly or at most 350, or at least or exactly or at most 351 amino acid residues in any one of SEQ ID NOs: 4-9 and 140-146; or the at least or exactly 5 contiguous amino acid residues present in any one of SEQ ID NOs: 5-9 and 140-146 in the definition of $A^1$ and $A^2$ are at least or exactly or at most 352, at least or exactly or at most 353, at least or exactly or at most 354, at least or exactly or at most 355, at least or exactly or at most 356, at least or exactly or at most 357, at least or exactly or at most 358, at least or exactly or at most 359, at least or exactly or at most 360, at least or exactly or at most 361, at least or exactly or at most 362, at least or exactly or at most 363, at least or exactly or at most 364, or at least or exactly or at most 365 amino acid residues in any one of SEQ ID NOs: 5-9 and 140-146; or the at least or exactly 5 contiguous amino acid residues present in any one of SEQ ID NOs: 6-9 and 140-146 in the definition of $A^1$ and $A^2$ are at least or exactly or at most 366, at least or exactly or at most 367, at least or exactly or at most 368, at least or exactly or at most 369, at least or exactly or at most 370, at least or exactly or at most 371, at least or exactly or at most 372, at least or exactly or at most 373, at least or exactly or at most 374, at least or exactly or at most 375, at least or exactly or at most 376, at least or exactly or at most 377, at least or exactly or at most 378, at least or exactly or at most 379, at least or exactly or at most 380, at least or exactly or at most 381, at least or exactly or at most 382, at least or exactly or at most 383, at least or exactly or at most 384, at least or exactly or at most 385, at least or exactly or at most 386, at least or exactly or at most 387, at least or exactly or at most 388, at least or exactly or at most 389, or at least or exactly or at most 390 amino acid residues in any one of SEQ ID NOs: 6-9 and 140-146; or the at least or exactly 5 contiguous amino acid residues present in any one of SEQ ID NOs: 7-9 and 140-146 in the definition of $A^1$ and $A^2$ are at least or exactly or at most 391, at least or exactly or at most 392, at least or exactly or at most 393, at least or exactly or at most 394, at least or exactly or at most 395, at least or exactly or at most 396, at least or exactly or at most 397, at least or exactly or at most 398, at least or exactly or at most 399, at least or exactly or at most 400, at least or exactly or at most 401, at least or exactly or at most 402, at least or exactly or at most 403, or at least or exactly or at most 404, at least or exactly or at most 405, at least or exactly or at most 406, at least or exactly or at most 407, at least or exactly or at most 408, or at least or exactly or at most 409 amino acid residues in any one of SEQ ID NOs: 7-9 and 140-146; or the at least or exactly 5 contiguous amino acid residues present in any one of SEQ ID NOs: 8, 9 and 140-146 in the definition of $A^1$ and $A^2$ are at least or exactly or at most 410, at least or exactly or at most 411, or at least or exactly or at most 412 amino acid residues in any one of SEQ ID NO: 8, 9 and 140-146; or the at least or exactly 5 contiguous amino acid residues present in any one of SEQ ID NOs: 9 and 140-146 in the definition of $A^1$ and $A^2$ are at least or exactly or at most 413, at least or exactly or at most 414, at least or exactly or at most 415, at least or exactly or at most 416, at least or exactly or at most 417, at least or exactly or at most 418, at least or exactly or at most 419, at least or exactly or at most 420, at least or exactly or at most 421, at least or exactly or at most 422, at least or exactly or at most 423, at least or exactly or at most 424, at least or exactly or at most 425, at least or exactly or at most 426, at least or exactly or at most 427, at least or exactly or at most 428, at least or exactly or at most 429, at least or exactly or at most 430, at least or exactly or at most 431, at least or exactly or at most 432, at least or exactly or at most 433, at least or exactly or at most 434, at least or exactly or at most 435, at least or exactly or at most 436, at least or exactly or at most 437, at least or exactly or at most 438, at least or exactly or at most 439, at least or exactly or at most 440, at least or exactly or at most 441, at least or exactly or at most 442, at least or exactly or at most 443, at least or exactly or at most 444, at least or exactly or at most 445, at least or exactly or at most 446, at least or exactly or at most 447, at least or exactly or at most 448, at least or exactly or at most 449, at least or exactly or at most 450, at least or exactly or at most 451, at least or exactly or at most 452, at least or exactly or at most 453, at least or exactly or at most 454, at least or exactly or at most 455, at least or exactly or at most 456, at least or exactly or at most 457, at least or exactly or at most 458, at least or exactly or at most 459, at least or exactly or at most 460, at least or exactly or at most 461, at least or exactly or at most 462, at least or exactly or at most 463, at least or exactly or at most 464, at least or exactly or at most 465, at least or exactly or at most 466, at least or exactly or at most 467, at least or exactly or at most 468, at least or exactly or at most 469, at least or exactly or at most 470, at least or exactly or at most 471, at least or exactly or at most 472, at least or exactly or at most 473, at least or exactly or at most 474, at least or exactly or at most 475, at least or exactly or at most 476, at least or exactly or at most 477, at least or exactly or at most 478, at least or exactly or at most 479, at least or exactly or at most 480, at least or exactly or at most 481, at least or exactly or at most 482, at least or exactly or at most 483, at least or exactly or at most 484, at least or exactly or at most 485, at least or exactly or at most 486, at least or exactly or at most 487, at least or exactly or at most 488, at least or exactly or at most 489, at least or exactly or at most 490, at least or exactly or at most 491, at least or exactly or at most 492, at least or exactly or at most 493, at least or exactly or at most 494, at least or exactly or at most 495, at least or exactly or at most 496, at least or exactly or at most 497, at least or exactly or at most 498, at least or exactly or at most 499, at least or exactly or at most 500, at least or exactly or at most 501, at least or exactly or at most 502, at least or exactly or at most 503, at least or exactly or at most 504, at least or exactly or at most 505, at least or exactly or at most 506, at least or exactly or at most 507, at least or exactly or at most 508, at least or exactly or at most 509, at least or exactly or at most 510, at least or exactly or at most 511, at least or exactly or at most 512, at least or exactly or at most 513, at least or exactly or at most 514, or at least or exactly or at most 515 amino acid residues in any one of SEQ ID NO: 9 and 140-146; or the at least or exactly 5 contiguous amino acid residues present in any one of SEQ ID NOs: 9 and 141-146 in the definition of $A^1$ and $A^2$ are at least or exactly or at most 516, at least or exactly or at most 517, at least or exactly or at most 518, or at least or exactly or at most 519 amino acid residues in any one of SEQ ID NO: 9 and 141-146; or the at least or exactly 5 contiguous amino acid residues present in any one of SEQ ID NOs: 9 and 142-146 in the definition of $A^1$ and $A^2$ are at least or exactly or at most 520, at least or exactly or at most 521, at least or exactly or at most 522, at least or exactly or at most 523, at least or exactly or at most 524, at least or exactly or at most 525, at least or exactly or at most 526, at least or exactly or at most 527, at least or exactly or at most 528, at least or exactly or at most 529, at least or exactly or at most 530, at least or exactly or at most 531, at least or exactly or at most 532, at least or exactly or at most 533, at least or exactly or at most 534, at least or exactly or at most 535, at least or exactly or at most 536, at least or exactly or at most 537, at least or exactly or at most 538, at least or exactly or at most 539, at least or exactly or at most 540, at least or exactly or at most 541, at least or exactly or at most 542, at least or exactly or at most 543, at least or exactly or at most 544, at least or exactly or at most 545, at least or exactly or at most 546, at least or exactly or at most 547, at least or exactly or at most 548, at least or exactly or at most 549, at least or exactly or at most 550, at least or exactly or at most 551, at least or exactly or at most 552, at least or exactly or at most 553, at least or exactly or at most 554, at least or exactly or at most 555, at least or exactly or at most 556, at least or exactly or at most 557, at least or exactly or at most 558, at least or exactly or at most 559, at least or exactly or at most 560, at least or exactly or at most 561, at least or exactly or at most 562, at least or exactly or at most 563, at least or exactly or at most 564, at least or exactly or at most 565, at least or exactly or at most 566, at least or exactly or at most 567, at least or exactly or at most 568, at least or exactly or at most 569, at least or exactly or at most 570, at least or exactly or at most 571, at least or exactly or at most 572, at least or exactly or at most 573, at least or exactly or at most 574, at least or exactly or at most 575, at least or exactly or at most 576, at least or exactly or at most 577, at least or exactly or at most 578, at least or exactly or at most 579, at least or exactly or at most 580, at least or exactly or at most 581, at least or exactly or at most 582, at least or exactly or at most 583, at least or exactly or at most 584, at least or exactly or at most 585, at least or exactly or at most 586, at least or exactly or at most 587, at least or exactly or at most 588, at least or exactly or at most 589, at least or exactly or at most 590, at least or exactly or at most 591, or at least or exactly or at most 592 amino acid residues in any one of SEQ ID NOs: 9 and 142-146; or the at least or exactly 5 contiguous amino acid residues present in any one of SEQ ID NOs: 142-146 in the definition of $A^1$ and $A^2$ are at least or exactly or at most 593, at least or exactly or at most 594, at least or exactly or at most 595, at least or exactly or at most 596, at least or exactly or at most 597, at least or exactly or at most 598, at least or exactly or at most 599, at least or exactly or at most 600, at least or exactly or at most 601, at least or exactly or at most 602, at least or exactly or at most 603, at least or exactly or at most 604, at least or exactly or at most 605, at least or exactly or at most 606, at least or exactly or at most 607, at least or exactly or at most 608, at least or exactly or at most 609, at least or exactly or at most 610, at least or exactly or at most 611, at least or exactly or at most 612, at least or exactly or at most 613, at least or exactly or at most 614, at least or exactly or at most 615, at least or exactly or at most 616, at least or exactly or at most 617, at least or exactly or at most 618, or at least or exactly or at most 619 amino acid residues in any one of SEQ ID NOs: 142-146; or the at least or exactly 5 contiguous amino acid residues present in any one of SEQ ID NOs: 143-146 in the definition of $A^1$ and $A^2$ are at least or exactly or at most 620, at least or exactly or at most 621, at least or exactly or at most 622, at least or exactly or at most 623, at least or exactly or at most 624, at least or exactly or at most 625, at least or exactly or at most 626, at least or exactly or at most 627, at least or exactly or at most 628, at least or exactly or at most 629, at least or exactly or at most 630, at least or exactly or at most 631, at least or exactly or at most 632, at least or exactly or at most 633, at least or exactly or at most 634, at least or exactly or at most 635, at least or exactly or at most 636, at least or exactly or at most 637, at least or exactly or at most 638, at least or exactly or at most 639, at least or exactly or at most 640, at least or exactly or at most 641, at least or exactly or at most 642, at least or exactly or at most 643, at least or exactly or at most 644, or at least or exactly or at most 645 amino acid residues in any one of SEQ ID NOs: 143-146; or the at least or exactly 5 contiguous amino acid residues present in any one of SEQ ID NOs: 144-146 in the definition of $A^1$ and $A^2$ are at least or exactly or at most 646, at least or exactly or at most 647, at least or exactly or at most 648, at least or exactly or at most 649, at least or exactly or at most 650, at least or exactly or at most 651, at least or exactly or at most 652, at least or exactly or at most 653, at least or exactly or at most 654, at least or exactly or at most 655, at least or exactly or at most 656, at least or exactly or at most 657, at least or exactly or at most 658, at least or exactly or at most 659, at least or exactly or at most 660, at least or exactly or at most 661, at least or exactly or at most 662, at least or exactly or at most 663, at least or exactly or at most 664, at least or exactly or at most 665, at least or exactly or at most 666, at least or exactly or at most 667, at least or exactly or at most 668, at least or exactly or at most 669, at least or exactly or at most 670, at least or exactly or at most 671, at least or exactly or at most 672, at least or exactly or at most 673, at least or exactly or at most 674, at least or exactly or at most 675, at least or exactly or at most 676, at least or exactly or at most 677, at least or exactly or at most 678, at least or exactly or at most 679, at least or exactly or at most 680, or at least or exactly or at most 681 amino acid residues in any one of SEQ ID NOs: 144-146; or the at least or exactly 5 contiguous amino acid residues present in any one of SEQ ID NO: 145 or 146 in the definition of $A^1$ and $A^2$ are at least or exactly or at most 682, at least or exactly or at most 683, at least or exactly or at most 684, at least or exactly or at most 685, at least or exactly or at most 686, at least or exactly or at most 687, at least or exactly or at most 688, at least or exactly or at most 689, at least or exactly or at most 690, at least or exactly or at most 691, at least or exactly or at most 692, at least or exactly or at most 693, at least or exactly or at most 694, at least or exactly or at most 695, at least or exactly or at most 696, at least or exactly or at most 697, at least or exactly or at most 698, at least or exactly or at most 699, at least or exactly or at most 700, at least or exactly or at most 701, at least or exactly or at most 702, at least or exactly or at most 703, at least or exactly or at most 704, at least or exactly or at most 705, at least or exactly or at most 706, at least or exactly or at most 707, at least or exactly or at most 708, at least or exactly or at most 709, at least or exactly or at most 710, at least or exactly or at most 711, at least or exactly or at most 712, at least or exactly or at most 713, at least or exactly or at most 714, at least or exactly or at most 715, at least or exactly or at most 716, at least or exactly or at most 717, at least or exactly or at most 718, at least or exactly or at most 719, at least or exactly or at most 720, at least or exactly or at most 721, at least or exactly or at most 722, at least or exactly or at most 723, at least or exactly or at most 724, at least or exactly or at most 725, at least or exactly or at most 726, at least or exactly or at most 727, at least or exactly or at most 728, at least or exactly or at most 729, at least or exactly or at most 730, at least or exactly or at most 731, at least or exactly or at most 732, at least or exactly or at most 733, at least or exactly or at most 734, at least or exactly or at most 735, at least or exactly or at most 736, at least or exactly or at most 737, at least or exactly or at most 738, at least or exactly or at most 739, at least or exactly or at most 740, at least or exactly or at most 741, at least or exactly or at most 742, at least or exactly or at most 743, at least or exactly or at most 744, at least or exactly or at most 745, at least or exactly or at most 746, at least or exactly or at most 747, at least or exactly or at most 748, at least or exactly or at most 749, at least or exactly or at most 750, at least or exactly or at most 751, at least or exactly or at most 752, at least or exactly or at most 753, at least or exactly or at most 754, at least or exactly or at most 755, at least or exactly or at most 756, at least or exactly or at most 757, at least or exactly or at most 758, at least or exactly or at most 759, at least or exactly or at most 760, at least or exactly or at most 761, at least or exactly or at most 762, at least or exactly or at most 763, at least or exactly or at most 764, at least or exactly or at most 765, at least or exactly or at most 766, at least or exactly or at most 767, at least or exactly or at most 768, or at least or exactly or at most 769 amino acid residues in SEQ ID NO: 145 or 146; or the at least or exactly 5 contiguous amino acid residues present in SEQ ID NO: 146 in the definition of $A^1$ and $A^2$ are at least or exactly or at most 770, at least or exactly or at most 771, at least or exactly or at most 772, at least or exactly or at most 773, at least or exactly or at most 774, at least or exactly or at most 775, at least or exactly or at most 776, at least or exactly or at most 777, at least or exactly or at most 778, at least or exactly or at most 779, at least or exactly or at most 780, at least or exactly or at most 781, at least or exactly or at most 782, at least or exactly or at most 783, at least or exactly or at most 784, at least or exactly or at most 785, at least or exactly or at most 786, at least or exactly or at most 787, at least or exactly or at most 788, at least or exactly or at most 789, at least or exactly or at most 790, at least or exactly or at most 791, at least or exactly or at most 792, at least or exactly or at most 793, at least or exactly or at most 794, at least or exactly or at most 795, at least or exactly or at most 796, at least or exactly or at most 797, at least or exactly or at most 798, at least or exactly or at most 799, at least or exactly or at most 800, at least or exactly or at most 801, at least or exactly or at most 802, at least or exactly or at most 803, at least or exactly or at most 804, at least or exactly or at most 805, at least or exactly or at most 806, at least or exactly or at most 807, at least or exactly or at most 808, at least or exactly or at most 809, at least or exactly or at most 810, at least or exactly or at most 811, at least or exactly or at most 812, at least or exactly or at most 813, at least or exactly or at most 814, at least or exactly or at most 815, at least or exactly or at most 816, at least or exactly or at most 817, at least or exactly or at most 818, at least or exactly or at most 819, at least or exactly or at most 820, at least or exactly or at most 821, at least or exactly or at most 822, at least or exactly or at most 823, at least or exactly or at most 824, at least or exactly or at most 825, at least or exactly or at most 826, at least or exactly or at most 827, at least or exactly or at most 828, at least or exactly or at most 829, at least or exactly or at most 830, at least or exactly or at most 831, at least or exactly or at most 832, at least or exactly or at most 833, at least or exactly or at most 834, at least or exactly or at most 835, at least or exactly or at most 836, at least or exactly or at most 837, at least or exactly or at most 838, at least or exactly or at most 839, at least or exactly or at most 840, at least or exactly or at most 841, at least or exactly or at most 842, at least or exactly or at most 843, at least or exactly or at most 844, at least or exactly or at most 845, at least or exactly or at most 846, at least or exactly or at most 847, at least or exactly or at most 848, at least or exactly or at most 849, at least or exactly or at most 850, at least or exactly or at most 851, at least or exactly or at most 852, at least or exactly or at most 853, at least or exactly or at most 854, at least or exactly or at most 855, at least or exactly or at most 856, at least or exactly or at most 857, at least or exactly or at most 858, at least or exactly or at most 859, at least or exactly or at most 860, at least or exactly or at most 861, at least or exactly or at most 862, at least or exactly or at most 863, at least or exactly or at most 864, at least or exactly or at most 865, at least or exactly or at most 866, at least or exactly or at most 867, at least or exactly or at most 868, at least or exactly or at most 869, at least or exactly or at most 870, at least or exactly or at most 871, at least or exactly or at most 872, at least or exactly or at most 873, at least or exactly or at most 874, at least or exactly or at most 875, at least or exactly or at most 876, at least or exactly or at most 877, at least or exactly or at most 878, at least or exactly or at most 879, at least or exactly or at most 880, at least or exactly or at most 881, at least or exactly or at most 882, at least or exactly or at most 883, at least or exactly or at most 884, at least or exactly or at most 885, at least or exactly or at most 886, at least or exactly or at most 887, at least or exactly or at most 888, at least or exactly or at most 889, at least or exactly or at most 890, at least or exactly or at most 891, at least or exactly or at most 892, at least or exactly or at most 893, at least or exactly or at most 894, at least or exactly or at most 895, at least or exactly or at most 896, at least or exactly or at most 897, at least or exactly or at most 898, at least or exactly or at most 899, at least or exactly or at most 900, at least or exactly or at most 901, at least or exactly or at most 902, at least or exactly or at most 903, at least or exactly or at most 904, at least or exactly or at most 905, at least or exactly or at most 906, at least or exactly or at most 907, at least or exactly or at most 908, at least or exactly or at most 909, at least or exactly or at most 910, at least or exactly or at most 911, at least or exactly or at most 912, at least or exactly or at most 913, at least or exactly or at most 914, at least or exactly or at most 915, at least or exactly or at most 916, at least or exactly or at most 917, at least or exactly or at most 918, at least or exactly or at most 919, at least or exactly or at most 920, at least or exactly or at most 921, at least or exactly or at most 922, at least or exactly or at most 923, at least or exactly or at most 924, at least or exactly or at most 925, at least or exactly or at most 926, at least or exactly or at most 927, at least or exactly or at most 928, at least or exactly or at most 929, at least or exactly or at most 930, at least or exactly or at most 931, at least or exactly or at most 932, at least or exactly or at most 933, at least or exactly or at most 934, at least or exactly or at most 935, at least or exactly or at most 936, at least or exactly or at most 937, at least or exactly or at most 938, at least or exactly or at most 939, at least or exactly or at most 940, at least or exactly or at most 941, at least or exactly or at most 942, at least or exactly or at most 943, at least or exactly or at most 944, at least or exactly or at most 945, at least or exactly or at most 946, at least or exactly or at most 947, at least or exactly or at most 948, at least or exactly or at most 949, at least or exactly or at most 950, at least or exactly or at most 951, at least or exactly or at most 952, at least or exactly or at most 953, at least or exactly or at most 954, at least or exactly or at most 955, at least or exactly or at most 956, at least or exactly or at most 957, at least or exactly or at most 958, at least or exactly or at most 959, at least or exactly or at most 960, at least or exactly or at most 961, at least or exactly or at most 962, at least or exactly or at most 963, at least or exactly or at most 964, at least or exactly or at most 965, at least or exactly or at most 966, at least or exactly or at most 967, at least or exactly or at most 968, at least or exactly or at most 969, at least or exactly or at most 970, at least or exactly or at most 971, at least or exactly or at most 972, at least or exactly or at most 973, at least or exactly or at most 974, at least or exactly or at most 975, at least or exactly or at most 976, at least or exactly or at most 977, at least or exactly or at most 978, at least or exactly or at most 979, at least or exactly or at most 980, at least or exactly or at most 981, at least or exactly or at most 982, at least or exactly or at most 983, at least or exactly or at most 984, at least or exactly or at most 985, at least or exactly or at most 986, at least or exactly or at most 987, at least or exactly or at most 988, at least or exactly or at most 989, at least or exactly or at most 990, at least or exactly or at most 991, at least or exactly or at most 992, at least or exactly or at most 993, at least or exactly or at most 994, at least or exactly or at most 995, at least or exactly or at most 996, at least or exactly or at most 997, at least or exactly or at most 998, at least or exactly or at most 999, at least or exactly or at most 1000, at least or exactly or at most 1001, at least or exactly or at most 1002, at least or exactly or at most 1003, at least or exactly or at most 1004, at least or exactly or at most 1005, at least or exactly or at most 1006, at least or exactly or at most 1007, at least or exactly or at most 1008, at least or exactly or at most 1009, at least or exactly or at most 1010, at least or exactly or at most 1011, at least or exactly or at most 1012, at least or exactly or at most 1013, at least or exactly or at most 1014, at least or exactly or at most 1015, at least or exactly or at most 1016, at least or exactly or at most 1017, at least or exactly or at most 1018, at least or exactly or at most 1019, at least or exactly or at most 1020, at least or exactly or at most 1021, at least or exactly or at most 1022, at least or exactly or at most 1023, at least or exactly or at most 1024, at least or exactly or at most 1025, at least or exactly or at most 1026, at least or exactly or at most 1027, at least or exactly or at most 1028, at least or exactly or at most 1029, at least or exactly or at most 1030, at least or exactly or at most 1031, at least or exactly or at most 1032, at least or exactly or at most 1033, at least or exactly or at most 1034, at least or exactly or at most 1035, at least or exactly or at most 1036, at least or exactly or at most 1037, at least or exactly or at most 1038, at least or exactly or at most 1039, at least or exactly or at most 1040, at least or exactly or at most 1041, at least or exactly or at most 1042, at least or exactly or at most 1043, at least or exactly or at most 1044, at least or exactly or at most 1045, at least or exactly or at most 1046, at least or exactly or at most 1047, at least or exactly or at most 1048, at least or exactly or at most 1049, at least or exactly or at most 1050, at least or exactly or at most 1051, at least or exactly or at most 1052, at least or exactly or at most 1053, at least or exactly or at most 1054, at least or exactly or at most 1055, at least or exactly or at most 1056, at least or exactly or at most 1057, at least or exactly or at most 1058, at least or exactly or at most 1059, at least or exactly or at most 1060, at least or exactly or at most 1061, at least or exactly or at most 1062, at least or exactly or at most 1063, at least or exactly or at most 1064, at least or exactly or at most 1065, at least or exactly or at most 1066, at least or exactly or at most 1067, at least or exactly or at most 1068, at least or exactly or at most 1069, at least or exactly or at most 1070, at least or exactly or at most 1071, at least or exactly or at most 1072, at least or exactly or at most 1073, at least or exactly or at most 1074, at least or exactly or at most 1075, at least or exactly or at most 1076, at least or exactly or at most 1077, at least or exactly or at most 1078, at least or exactly or at most 1079, at least or exactly or at most 1080, at least or exactly or at most 1081, at least or exactly or at most 1082, at least or exactly or at most 1083, at least or exactly or at most 1084, at least or exactly or at most 1085, at least or exactly or at most 1086, at least or exactly or at most 1087, at least or exactly or at most 1088, at least or exactly or at most 1089, at least or exactly or at most 1090, at least or exactly or at most 1091, at least or exactly or at most 1092, at least or exactly or at most 1093, at least or exactly or at most 1094, at least or exactly or at most 1095, at least or exactly or at most 1096, at least or exactly or at most 1097, at least or exactly or at most 1098, at least or exactly or at most 1099, at least or exactly or at most 1100, at least or exactly or at most 1101, at least or exactly or at most 1102, at least or exactly or at most 1103, at least or exactly or at most 1104, at least or exactly or at most 1105, at least or exactly or at most 1106, at least or exactly or at most 1107, at least or exactly or at most 1108, at least or exactly or at most 1109, at least or exactly or at most 1110, at least or exactly or at most 1111, at least or exactly or at most 1112, at least or exactly or at most 1113, at least or exactly or at most 1114, at least or exactly or at most 1115, at least or exactly or at most 1116, at least or exactly or at most 1117, at least or exactly or at most 1118, at least or exactly or at most 1119, at least or exactly or at most 1120, at least or exactly or at most 1121, at least or exactly or at most 1122, at least or exactly or at most 1123, at least or exactly or at most 1124, at least or exactly or at most 1125, at least or exactly or at most 1126, at least or exactly or at most 1127, at least or exactly or at most 1128, at least or exactly or at most 1129, at least or exactly or at most 1130, at least or exactly or at most 1131, at least or exactly or at most 1132, at least or exactly or at most 1133, at least or exactly or at most 1134, at least or exactly or at most 1135, at least or exactly or at most 1136, at least or exactly or at most 1137, at least or exactly or at most 1138, at least or exactly or at most 1139, at least or exactly or at most 1140, at least or exactly or at most 1141, at least or exactly or at most 1142, at least or exactly or at most 1143, at least or exactly or at most 1144, at least or exactly or at most 1145, at least or exactly or at most 1146, at least or exactly or at most 1147, at least or exactly or at most 1148, at least or exactly or at most 1149, at least or exactly or at most 1150, at least or exactly or at most 1151, at least or exactly or at most 1152, at least or exactly or at most 1153, at least or exactly or at most 1154, at least or exactly or at most 1155, at least or exactly or at most 1156, at least or exactly or at most 1157, at least or exactly or at most 1158, at least or exactly or at most 1159, at least or exactly or at most 1160, at least or exactly or at most 1161, at least or exactly or at most 1162, at least or exactly or at most 1163, at least or exactly or at most 1164, at least or exactly or at most 1165, at least or exactly or at most 1166, at least or exactly or at most 1167, at least or exactly or at most 1168, at least or exactly or at most 1169, at least or exactly or at most 1170, at least or exactly or at most 1171, at least or exactly or at most 1172, at least or exactly or at most 1173, at least or exactly or at most 1174, at least or exactly or at most 1175, at least or exactly or at most 1176, at least or exactly or at most 1177, at least or exactly or at most 1178, at least or exactly or at most 1179, at least or exactly or at most 1180, at least or exactly or at most 1181, at least or exactly or at most 1182, at least or exactly or at most 1183, at least or exactly or at most 1184, at least or exactly or at most 1185, at least or exactly or at most 1186, at least or exactly or at most 1187, at least or exactly or at most 1188, at least or exactly or at most 1189, at least or exactly or at most 1190, at least or exactly or at most 1191, at least or exactly or at most 1192, at least or exactly or at most 1193, at least or exactly or at most 1194, at least or exactly or at most 1195, at least or exactly or at most 1196, at least or exactly or at most 1197, at least or exactly or at most 1198, at least or exactly or at most 1199, at least or exactly or at most 1200, at least or exactly or at most 1201, at least or exactly or at most 1202, at least or exactly or at most 1203, at least or exactly or at most 1204, at least or exactly or at most 1205, at least or exactly or at most 1206, at least or exactly or at most 1207, at least or exactly or at most 1208, at least or exactly or at most 1209, at least or exactly or at most 1210, at least or exactly or at most 1211, at least or exactly or at most 1212, at least or exactly or at most 1213, at least or exactly or at most 1214, at least or exactly or at most 1215, at least or exactly or at most 1216, at least or exactly or at most 1217, at least or exactly or at most 1218, at least or exactly or at most 1219, at least or exactly or at most 1220, at least or exactly or at most 1221, at least or exactly or at most 1222, at least or exactly or at most 1223, at least or exactly or at most 1224, at least or exactly or at most 1225, at least or exactly or at most 1226, at least or exactly or at most 1227, at least or exactly or at most 1228, at least or exactly or at most 1229, at least or exactly or at most 1230, at least or exactly or at most 1231, at least or exactly or at most 1232, at least or exactly or at most 1233, at least or exactly or at most 1234, at least or exactly or at most 1235, at least or exactly or at most 1236, at least or exactly or at most 1237, at least or exactly or at most 1238, at least or exactly or at most 1239, at least or exactly or at most 1240, at least or exactly or at most 1241, at least or exactly or at most 1242, at least or exactly or at most 1243, at least or exactly or at most 1244, at least or exactly or at most 1245, at least or exactly or at most 1246, at least or exactly or at most 1247, at least or exactly or at most 1248, at least or exactly or at most 1249, at least or exactly or at most 1250, at least or exactly or at most 1251, at least or exactly or at most 1252, at least or exactly or at most 1253, at least or exactly or at most 1254, at least or exactly or at most 1255, at least or exactly or at most 1256, at least or exactly or at most 1257, at least or exactly or at most 1258, at least or exactly or at most 1259, at least or exactly or at most 1260, at least or exactly or at most 1261, at least or exactly or at most 1262, at least or exactly or at most 1263, at least or exactly or at most 1264, at least or exactly or at most 1265, at least or exactly or at most 1266, at least or exactly or at most 1267, at least or exactly or at most 1268, at least or exactly or at most 1269, at least or exactly or at most 1270, at least or exactly or at most 1271, at least or exactly or at most 1272, at least or exactly or at most 1273, at least or exactly or at most 1274, at least or exactly or at most 1275, at least or exactly or at most 1276, at least or exactly or at most 1277, at least or exactly or at most 1278, at least or exactly or at most 1279, at least or exactly or at most 1280, at least or exactly or at most 1281, at least or exactly or at most 1282, at least or exactly or at most 1283, at least or exactly or at most 1284, at least or exactly or at most 1285, at least or exactly or at most 1286, at least or exactly or at most 1287, at least or exactly or at most 1288, at least or exactly or at most 1289, at least or exactly or at most 1290, at least or exactly or at most 1291, at least or exactly or at most 1292, at least or exactly or at most 1293, at least or exactly or at most 1294, at least or exactly or at most 1295, at least or exactly or at most 1296, at least or exactly or at most 1297, at least or exactly or at most 1298, at least or exactly or at most 1299, at least or exactly or at most 1300, at least or exactly or at most 1301, at least or exactly or at most 1302, at least or exactly or at most 1303, at least or exactly or at most 1304, at least or exactly or at most 1305, at least or exactly or at most 1306, at least or exactly or at most 1307, at least or exactly or at most 1308, at least or exactly or at most 1309, at least or exactly or at most 1310, at least or exactly or at most 1311, at least or exactly or at most 1312, at least or exactly or at most 1313, at least or exactly or at most 1314, at least or exactly or at most 1315, at least or exactly or at most 1316, at least or exactly or at most 1317, at least or exactly or at most 1318, at least or exactly or at most 1319, at least or exactly or at most 1320, at least or exactly or at most 1321, at least or exactly or at most 1322, at least or exactly or at most 1323, at least or exactly or at most 1324, at least or exactly or at most 1325, at least or exactly or at most 1326, at least or exactly or at most 1327, at least or exactly or at most 1328, at least or exactly or at most 1329, at least or exactly or at most 1330, at least or exactly or at most 1331, at least or exactly or at most 1332, at least or exactly or at most 1333, at least or exactly or at most 1334, at least or exactly or at most 1335, at least or exactly or at most 1336, at least or exactly or at most 1337, at least or exactly or at most 1338, at least or exactly or at most 1339, at least or exactly or at most 1340, at least or exactly or at most 1341, at least or exactly or at most 1342, at least or exactly or at most 1343, at least or exactly or at most 1344, at least or exactly or at most 1345, at least or exactly or at most 1346, at least or exactly or at most 1347, at least or exactly or at most 1348, at least or exactly or at most 1349, at least or exactly or at most 1350, at least or exactly or at most 1351, at least or exactly or at most 1352, at least or exactly or at most 1353, at least or exactly or at most 1354, at least or exactly or at most 1355, at least or exactly or at most 1356, at least or exactly or at most 1357, at least or exactly or at most 1358, at least or exactly or at most 1359, at least or exactly or at most 1360, at least or exactly or at most 1361, at least or exactly or at most 1362, at least or exactly or at most 1363, at least or exactly or at most 1364, at least or exactly or at most 1365, at least or exactly or at most 1366, at least or exactly or at most 1367, at least or exactly or at most 1368, at least or exactly or at most 1369, at least or exactly or at most 1370, at least or exactly or at most 1371, at least or exactly or at most 1372, at least or exactly or at most 1373, at least or exactly or at most 1374, at least or exactly or at most 1375, at least or exactly or at most 1376, at least or exactly or at most 1377, at least or exactly or at most 1378, at least or exactly or at most 1379, at least or exactly or at most 1380, at least or exactly or at most 1381, at least or exactly or at most 1382, at least or exactly or at most 1383, at least or exactly or at most 1384, at least or exactly or at most 1385, at least or exactly or at most 1386, at least or exactly or at most 1387, at least or exactly or at most 1388, at least or exactly or at most 1389, at least or exactly or at most 1390, at least or exactly or at most 1391, at least or exactly or at most 1392, at least or exactly or at most 1393, at least or exactly or at most 1394, at least or exactly or at most 1395, at least or exactly or at most 1396, at least or exactly or at most 1397, at least or exactly or at most 1398, at least or exactly or at most 1399, at least or exactly or at most 1400, at least or exactly or at most 1401, at least or exactly or at most 1402, at least or exactly or at most 1403, at least or exactly or at most 1404, at least or exactly or at most 1405, at least or exactly or at most 1406, at least or exactly or at most 1407, at least or exactly or at most 1408, at least or exactly or at most 1409, at least or exactly or at most 1410, at least or exactly or at most 1411, at least or exactly or at most 1412, at least or exactly or at most 1413, at least or exactly or at most 1414, at least or exactly or at most 1415, at least or exactly or at most 1416, at least or exactly or at most 1417, at least or exactly or at most 1418, at least or exactly or at most 1419, at least or exactly or at most 1420, at least or exactly or at most 1421, at least or exactly or at most 1422, at least or exactly or at most 1423, at least or exactly or at most 1424, at least or exactly or at most 1425, at least or exactly or at most 1426, at least or exactly or at most 1427, at least or exactly or at most 1428, at least or exactly or at most 1429, at least or exactly or at most 1430, at least or exactly or at most 1431, at least or exactly or at most 1432, at least or exactly or at most 1433, at least or exactly or at most 1434, at least or exactly or at most 1435, at least or exactly or at most 1436, at least or exactly or at most 1437, at least or exactly or at most 1438, at least or exactly or at most 1439, at least or exactly or at most 1440, at least or exactly or at most 1441, at least or exactly or at most 1442, at least or exactly or at most 1443, at least or exactly or at most 1444, at least or exactly or at most 1445, at least or exactly or at most 1446, at least or exactly or at most 1447, at least or exactly or at most 1448, at least or exactly or at most 1449, at least or exactly or at most 1450, at least or exactly or at most 1451, at least or exactly or at most 1452, at least or exactly or at most 1453, at least or exactly or at most 1454, at least or exactly or at most 1455, at least or exactly or at most 1456, at least or exactly or at most 1457, at least or exactly or at most 1458, at least or exactly or at most 1459, at least or exactly or at most 1460, at least or exactly or at most 1461, at least or exactly or at most 1462, at least or exactly or at most 1463, at least or exactly or at most 1464, at least or exactly or at most 1465, at least or exactly or at most 1466, at least or exactly or at most 1467, at least or exactly or at most 1468, at least or exactly or at most 1469, at least or exactly or at most 1470, at least or exactly or at most 1471, at least or exactly or at most 1472, at least or exactly or at most 1473, at least or exactly or at most 1474, at least or exactly or at most 1475, at least or exactly or at most 1476, at least or exactly or at most 1477, at least or exactly or at most 1478, at least or exactly or at most 1479, at least or exactly or at most 1480, at least or exactly or at most 1481, at least or exactly or at most 1482, at least or exactly or at most 1483, at least or exactly or at most 1484, at least or exactly or at most 1485, at least or exactly or at most 1486, at least or exactly or at most 1487, at least or exactly or at most 1488, at least or exactly or at most 1489, at least or exactly or at most 1490, at least or exactly or at most 1491, at least or exactly or at most 1492, at least or exactly or at most 1493, at least or exactly or at most 1494, at least or exactly or at most 1495, at least or exactly or at most 1496, at least or exactly or at most 1497, at least or exactly or at most 1498, at least or exactly or at most 1499, at least or exactly or at most 1500, at least or exactly or at most 1501, at least or exactly or at most 1502, at least or exactly or at most 1503, at least or exactly or at most 1504, at least or exactly or at most 1505, at least or exactly or at most 1506, at least or exactly or at most 1507, at least or exactly or at most 1508, at least or exactly or at most 1509, at least or exactly or at most 1510, at least or exactly or at most 1511, at least or exactly or at most 1512, at least or exactly or at most 1513, at least or exactly or at most 1514, at least or exactly or at most 1515, at least or exactly or at most 1516, at least or exactly or at most 1517, at least or exactly or at most 1518, at least or exactly or at most 1519, at least or exactly or at most 1520, at least or exactly or at most 1521, at least or exactly or at most 1522, at least or exactly or at most 1523, at least or exactly or at most 1524, at least or exactly or at most 1525, at least or exactly or at most 1526, at least or exactly or at most 1527, at least or exactly or at most 1528, at least or exactly or at most 1529, at least or exactly or at most 1530, at least or exactly or at most 1531, at least or exactly or at most 1532, at least or exactly or at most 1533, at least or exactly or at most 1534, at least or exactly or at most 1535, at least or exactly or at most 1536, at least or exactly or at most 1537, at least or exactly or at most 1538, at least or exactly or at most 1539, at least or exactly or at most 1540, at least or exactly or at most 1541, at least or exactly or at most 1542, at least or exactly or at most 1543, at least or exactly or at most 1544, at least or exactly or at most 1545, at least or exactly or at most 1546, at least or exactly or at most 1547, at least or exactly or at most 1548, at least or exactly or at most 1549, at least or exactly or at most 1550, at least or exactly or at most 1551, at least or exactly or at most 1552, at least or exactly or at most 1553, at least or exactly or at most 1554, at least or exactly or at most 1555, at least or exactly or at most 1556, at least or exactly or at most 1557, at least or exactly or at most 1558, at least or exactly or at most 1559, at least or exactly or at most 1560, at least or exactly or at most 1561, at least or exactly or at most 1562, at least or exactly or at most 1563, at least or exactly or at most 1564, at least or exactly or at most 1565, at least or exactly or at most 1566, at least or exactly or at most 1567, at least or exactly or at most 1568, at least or exactly or at most 1569, at least or exactly or at most 1570, at least or exactly or at most 1571, at least or exactly or at most 1572, at least or exactly or at most 1573, at least or exactly or at most 1574, at least or exactly or at most 1575, at least or exactly or at most 1576, at least or exactly or at most 1577, at least or exactly or at most 1578, at least or exactly or at most 1579, at least or exactly or at most 1580, at least or exactly or at most 1581, at least or exactly or at most 1582, at least or exactly or at most 1583, at least or exactly or at most 1584, at least or exactly or at most 1585, at least or exactly or at most 1586, at least or exactly or at most 1587, at least or exactly or at most 1588, at least or exactly or at most 1589, at least or exactly or at most 1590, at least or exactly or at most 1591, at least or exactly or at most 1592, at least or exactly or at most 1593, at least or exactly or at most 1594, at least or exactly or at most 1595, at least or exactly or at most 1596, at least or exactly or at most 1597, at least or exactly or at most 1598, at least or exactly or at most 1599, at least or exactly or at most 1600, at least or exactly or at most 1601, at least or exactly or at most 1602, at least or exactly or at most 1603, at least or exactly or at most 1604, at least or exactly or at most 1605, at least or exactly or at most 1606, at least or exactly or at most 1607, at least or exactly or at most 1608, at least or exactly or at most 1609, at least or exactly or at most 1610, at least or exactly or at most 1611, at least or exactly or at most 1612, at least or exactly or at most 1613, at least or exactly or at most 1614, at least or exactly or at most 1615, at least or exactly or at most 1616, at least or exactly or at most 1617, at least or exactly or at most 1618, at least or exactly or at most 1619, at least or exactly or at most 1620, at least or exactly or at most 1621, at least or exactly or at most 1622, at least or exactly or at most 1623, at least or exactly or at most 1624, at least or exactly or at most 1625, at least or exactly or at most 1626, at least or exactly or at most 1627, at least or exactly or at most 1628, at least or exactly or at most 1629, at least or exactly or at most 1630, at least or exactly or at most 1631, at least or exactly or at most 1632, at least or exactly or at most 1633, at least or exactly or at most 1634, at least or exactly or at most 1635, at least or exactly or at most 1636, at least or exactly or at most 1637, at least or exactly or at most 1638, at least or exactly or at most 1639, at least or exactly or at most 1640, at least or exactly or at most 1641, at least or exactly or at most 1642, at least or exactly or at most 1643, at least or exactly or at most 1644, at least or exactly or at most 1645, at least or exactly or at most 1646, at least or exactly or at most 1647, at least or exactly or at most 1648, at least or exactly or at most 1649, at least or exactly or at most 1650, at least or exactly or at most 1651, at least or exactly or at most 1652, at least or exactly or at most 1653, at least or exactly or at most 1654, at least or exactly or at most 1655, at least or exactly or at most 1656, at least or exactly or at most 1657, at least or exactly or at most 1658, at least or exactly or at most 1659, at least or exactly or at most 1660, at least or exactly or at most 1661, at least or exactly or at most 1662, at least or exactly or at most 1663, at least or exactly or at most 1664, at least or exactly or at most 1665, at least or exactly or at most 1666, at least or exactly or at most 1667, at least or exactly or at most 1668, at least or exactly or at most 1669, at least or exactly or at most 1670, at least or exactly or at most 1671, at least or exactly or at most 1672, at least or exactly or at most 1673, at least or exactly or at most 1674, at least or exactly or at most 1675, at least or exactly or at most 1676, at least or exactly or at most 1677, at least or exactly or at most 1678, at least or exactly or at most 1679, at least or exactly or at most 1680, at least or exactly or at most 1681, at least or exactly or at most 1682, at least or exactly or at most 1683, at least or exactly or at most 1684, at least or exactly or at most 1685, at least or exactly or at most 1686, at least or exactly or at most 1687, at least or exactly or at most 1688, at least or exactly or at most 1689, at least or exactly or at most 1690, at least or exactly or at most 1691, at least or exactly or at most 1692, at least or exactly or at most 1693, at least or exactly or at most 1694, at least or exactly or at most 1695, at least or exactly or at most 1696, at least or exactly or at most 1697, at least or exactly or at most 1698, at least or exactly or at most 1699, at least or exactly or at most 1700, at least or exactly or at most 1701, at least or exactly or at most 1702, at least or exactly or at most 1703, at least or exactly or at most 1704, at least or exactly or at most 1705, at least or exactly or at most 1706, at least or exactly or at most 1707, at least or exactly or at most 1708, at least or exactly or at most 1709, at least or exactly or at most 1710, at least or exactly or at most 1711, at least or exactly or at most 1712, at least or exactly or at most 1713, at least or exactly or at most 1714, at least or exactly or at most 1715, at least or exactly or at most 1716, at least or exactly or at most 1717, at least or exactly or at most 1718, at least or exactly or at most 1719, at least or exactly or at most 1720, at least or exactly or at most 1721, at least or exactly or at most 1722, at least or exactly or at most 1723, at least or exactly or at most 1724, at least or exactly or at most 1725, at least or exactly or at most 1726, at least or exactly or at most 1727, at least or exactly or at most 1728, at least or exactly or at most 1729, at least or exactly or at most 1730, at least or exactly or at most 1731, at least or exactly or at most 1732, at least or exactly or at most 1733, at least or exactly or at most 1734, at least or exactly or at most 1735, at least or exactly or at most 1736, at least or exactly or at most 1737, at least or exactly or at most 1738, at least or exactly or at most 1739, at least or exactly or at most 1740, at least or exactly or at most 1741, at least or exactly or at most 1742, at least or exactly or at most 1743, at least or exactly or at most 1744, at least or exactly or at most 1745, at least or exactly or at most 1746, at least or exactly or at most 1747, at least or exactly or at most 1748, at least or exactly or at most 1749, at least or exactly or at most 1750, at least or exactly or at most 1751, at least or exactly or at most 1752, at least or exactly or at most 1753, at least or exactly or at most 1754, at least or exactly or at most 1755, at least or exactly or at most 1756, at least or exactly or at most 1757, at least or exactly or at most 1758, at least or exactly or at most 1759, at least or exactly or at most 1760, at least or exactly or at most 1761, at least or exactly or at most 1762, at least or exactly or at most 1763, at least or exactly or at most 1764, at least or exactly or at most 1765, at least or exactly or at most 1766, at least or exactly or at most 1767, at least or exactly or at most 1768, at least or exactly or at most 1769, at least or exactly or at most 1770, at least or exactly or at most 1771, at least or exactly or at most 1772, at least or exactly or at most 1773, at least or exactly or at most 1774, at least or exactly or at most 1775, at least or exactly or at most 1776, at least or exactly or at most 1777, at least or exactly or at most 1778, at least or exactly or at most 1779, at least or exactly or at most 1780, at least or exactly or at most 1781, at least or exactly or at most 1782, at least or exactly or at most 1783, at least or exactly or at most 1784, at least or exactly or at most 1785, at least or exactly or at most 1786, at least or exactly or at most 1787, at least or exactly or at most 1788, at least or exactly or at most 1789, at least or exactly or at most 1790, at least or exactly or at most 1791, at least or exactly or at most 1792, at least or exactly or at most 1793, at least or exactly or at most 1794, at least or exactly or at most 1795, at least or exactly or at most 1796, at least or exactly or at most 1797, at least or exactly or at most 1798, at least or exactly or at most 1799, at least or exactly or at most 1800, at least or exactly or at most 1801, at least or exactly or at most 1802, at least or exactly or at most 1803, at least or exactly or at most 1804, at least or exactly or at most 1805, at least or exactly or at most 1806, at least or exactly or at most 1807, at least or exactly or at most 1808, at least or exactly or at most 1809, at least or exactly or at most 1810, at least or exactly or at most 1811, at least or exactly or at most 1812, at least or exactly or at most 1813, at least or exactly or at most 1814, at least or exactly or at most 1815, at least or exactly or at most 1816, at least or exactly or at most 1817, at least or exactly or at most 1818, at least or exactly or at most 1819, at least or exactly or at most 1820, at least or exactly or at most 1821, at least or exactly or at most 1822, at least or exactly or at most 1823, at least or exactly or at most 1824, at least or exactly or at most 1825, at least or exactly or at most 1826, at least or exactly or at most 1827, at least or exactly or at most 1828, at least or exactly or at most 1829, at least or exactly or at most 1830, at least or exactly or at most 1831, at least or exactly or at most 1832, at least or exactly or at most 1833, at least or exactly or at most 1834, at least or exactly or at most 1835, at least or exactly or at most 1836, at least or exactly or at most 1837, at least or exactly or at most 1838, at least or exactly or at most 1839, at least or exactly or at most 1840, at least or exactly or at most 1841, at least or exactly or at most 1842, at least or exactly or at most 1843, at least or exactly or at most 1844, at least or exactly or at most 1845, at least or exactly or at most 1846, at least or exactly or at most 1847, at least or exactly or at most 1848, at least or exactly or at most 1849, at least or exactly or at most 1850, at least or exactly or at most 1851, at least or exactly or at most 1852, at least or exactly or at most 1853, at least or exactly or at most 1854, at least or exactly or at most 1855, at least or exactly or at most 1856, at least or exactly or at most 1857, at least or exactly or at most 1858, at least or exactly or at most 1859, at least or exactly or at most 1860, at least or exactly or at most 1861, at least or exactly or at most 1862, at least or exactly or at most 1863, at least or exactly or at most 1864, at least or exactly or at most 1865, at least or exactly or at most 1866, at least or exactly or at most 1867, at least or exactly or at most 1868, at least or exactly or at most 1869, at least or exactly or at most 1870, at least or exactly or at most 1871, at least or exactly or at most 1872, at least or exactly or at most 1873, at least or exactly or at most 1874, at least or exactly or at most 1875, at least or exactly or at most 1876, at least or exactly or at most 1877, at least or exactly or at most 1878, at least or exactly or at most 1879, at least or exactly or at most 1880, at least or exactly or at most 1881, at least or exactly or at most 1882, at least or exactly or at most 1883, at least or exactly or at most 1884, at least or exactly or at most 1885, at least or exactly or at most 1886, at least or exactly or at most 1887, at least or exactly or at most 1888, at least or exactly or at most 1889, at least or exactly or at most 1890, at least or exactly or at most 1891, at least or exactly or at most 1892, at least or exactly or at most 1893, at least or exactly or at most 1894, at least or exactly or at most 1895, at least or exactly or at most 1896, at least or exactly or at most 1897, at least or exactly or at most 1898, at least or exactly or at most 1899, at least or exactly or at most 1900, at least or exactly or at most 1901, at least or exactly or at most 1902, at least or exactly or at most 1903, at least or exactly or at most 1904, at least or exactly or at most 1905, at least or exactly or at most 1906, at least or exactly or at most 1907, at least or exactly or at most 1908, at least or exactly or at most 1909, at least or exactly or at most 1910, at least or exactly or at most 1911, at least or exactly or at most 1912, at least or exactly or at most 1913, at least or exactly or at most 1914, at least or exactly or at most 1915, at least or exactly or at most 1916, at least or exactly or at most 1917, at least or exactly or at most 1918, at least or exactly or at most 1919, at least or exactly or at most 1920, at least or exactly or at most 1921, at least or exactly or at most 1922, at least or exactly or at most 1923, at least or exactly or at most 1924, at least or exactly or at most 1925, at least or exactly or at most 1926, at least or exactly or at most 1927, at least or exactly or at most 1928, at least or exactly or at most 1929, at least or exactly or at most 1930, at least or exactly or at most 1931, at least or exactly or at most 1932, at least or exactly or at most 1933, at least or exactly or at most 1934, at least or exactly or at most 1935, at least or exactly or at most 1936, at least or exactly or at most 1937, at least or exactly or at most 1938, at least or exactly or at most 1939, at least or exactly or at most 1940, at least or exactly or at most 1941, at least or exactly or at most 1942, at least or exactly or at most 1943, at least or exactly or at most 1944, at least or exactly or at most 1945, at least or exactly or at most 1946, at least or exactly or at most 1947, at least or exactly or at most 1948, at least or exactly or at most 1949, at least or exactly or at most 1950, at least or exactly or at most 1951, at least or exactly or at most 1952, at least or exactly or at most 1953, at least or exactly or at most 1954, at least or exactly or at most 1955, at least or exactly or at most 1956, at least or exactly or at most 1957, at least or exactly or at most 1958, at least or exactly or at most 1959, at least or exactly or at most 1960, at least or exactly or at most 1961, at least or exactly or at most 1962, at least or exactly or at most 1963, at least or exactly or at most 1964, at least or exactly or at most 1965, at least or exactly or at most 1966, at least or exactly or at most 1967, at least or exactly or at most 1968, at least or exactly or at most 1969, at least or exactly or at most 1970, at least or exactly or at most 1971, at least or exactly or at most 1972, at least or exactly or at most 1973, at least or exactly or at most 1974, at least or exactly or at most 1975, at least or exactly or at most 1976, at least or exactly or at most 1977, at least or exactly or at most 1978, at least or exactly or at most 1979, at least or exactly or at most 1980, at least or exactly or at most 1981, at least or exactly or at most 1982, at least or exactly or at most 1983, at least or exactly or at most 1984, at least or exactly or at most 1985, at least or exactly or at most 1986, at least or exactly or at most 1987, at least or exactly or at most 1988, at least or exactly or at most 1989, at least or exactly or at most 1990, at least or exactly or at most 1991, at least or exactly or at most 1992, at least or exactly or at most 1993, at least or exactly or at most 1994, at least or exactly or at most 1995, at least or exactly or at most 1996, at least or exactly or at most 1997, at least or exactly or at most 1998, at least or exactly or at most 1999, at least or exactly or at most 2000, at least or exactly or at most 2001, at least or exactly or at most 2002, at least or exactly or at most 2003, at least or exactly or at most 2004, at least or exactly or at most 2005, at least or exactly or at most 2006, at least or exactly or at most 2007, at least or exactly or at most 2008, at least or exactly or at most 2009, at least or exactly or at most 2010, at least or exactly or at most 2011, at least or exactly or at most 2012, at least or exactly or at most 2013, at least or exactly or at most 2014, at least or exactly or at most 2015, at least or exactly or at most 2016, at least or exactly or at most 2017, at least or exactly or at most 2018, at least or exactly or at most 2019, at least or exactly or at most 2020, at least or exactly or at most 2021, at least or exactly or at most 2022, at least or exactly or at most 2023, at least or exactly or at most 2024, at least or exactly or at most 2025, at least or exactly or at most 2026, at least or exactly or at most 2027, at least or exactly or at most 2028, at least or exactly or at most 2029, at least or exactly or at most 2030, at least or exactly or at most 2031, at least or exactly or at most 2032, at least or exactly or at most 2033, at least or exactly or at most 2034, at least or exactly or at most 2035, at least or exactly or at most 2036, at least or exactly or at most 2037, at least or exactly or at most 2038, at least or exactly or at most 2039, at least or exactly or at most 2040, at least or exactly or at most 2041, at least or exactly or at most 2042, at least or exactly or at most 2043, at least or exactly or at most 2044, at least or exactly or at most 2045, at least or exactly or at most 2046, at least or exactly or at most 2047, at least or exactly or at most 2048, at least or exactly or at most 2049, at least or exactly or at most 2050, at least or exactly or at most 2051, at least or exactly or at most 2052, at least or exactly or at most 2053, at least or exactly or at most 2054, at least or exactly or at most 2055, at least or exactly or at most 2056, at least or exactly or at most 2057, at least or exactly or at most 2058, at least or exactly or at most 2059, at least or exactly or at most 2060, at least or exactly or at most 2061, at least or exactly or at most 2062, at least or exactly or at most 2063, at least or exactly or at most 2064, at least or exactly or at most 2065, or at least or exactly or at most 2066 amino acid residues in SEQ ID NO: 146.

Another way to phrase this is that for each of the definitions of $A^1$ and $A^2$ the number of the contiguous amino acid residues derived from SEQ ID NO: 1-9 and 139-146 is at least or exactly or at most N-n, where N is the length of the sequence ID in question and n is any integer ranging from N-5 and 0; that is, the at least 5 contiguous amino acids can be at least any number between 5 and the length of the reference sequence minus one, in increments of one.

In the embodiments of the first aspect of the invention discussed above, the at least or exactly 5 contiguous amino acid residues present in any one of SEQ ID NOs: 1-9 and 139-146 in the definition of $A^1$ and $A^2$ can independently commence at any one of amino acid residues 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, and 194 in any one of SEQ ID NOs: 1-9 and 139-146, with the proviso that the number of the selected commencing amino acid residue satisfies the formula N≤L−n+1, where N is the number of the selected residue, L is the number of amino acid residues in the sequence selected from SEQ ID NOs: 1-9 and 139-146 from which the at least 5 contiguous amino acid residues are selected, and n is the number of contiguous amino acid residues, or the at least or exactly 5 contiguous amino acid residues present in any one of SEQ ID NOs: 2-9 and 139-146 in the definition of $A^1$ and $A^2$ can independently commence at any one of amino acid residues 195, 196, 197, and 198 in any one of SEQ ID NOs: 2-9 and 139-146, with the proviso that the number of the selected commencing amino acid residue satisfies the formula N≤L−n+1, where N is the number of the selected residue, L is the number of amino acid residues in the sequence selected from SEQ ID NOs: 2-9 and 139-146 from which the at least 5 contiguous amino acid residues are selected, and n is the number of contiguous amino acid residues; or the at least or exactly 5 contiguous amino acid residues present in any one of SEQ ID NOs: 3-9 and 139-146 in the definition of $A^1$ and $A^2$ can independently commence at any one of amino acid residues 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, and 289 in any one of SEQ ID NOs: 3-9 and 139-146, with the proviso that the number of the selected commencing amino acid residue satisfies the formula N≤L−n+1, where N is the number of the selected residue, L is the number of amino acid residues in the sequence selected from SEQ ID NOs: 3-9 and 139-146 from which the at least 5 contiguous amino acid residues are selected, and n is the number of contiguous amino acid residues; or the least or exactly 5 contiguous amino acid residues present in any one of SEQ ID NOs: 4-9 and 139-146 in the definition of $A^1$ and $A^2$ can independently commence at any one of amino acid residues 290, 291, 292, 293, 294, 295, 296, 297, 298, 299, 300, 301, 302, 303, 304, 305, 306, 307, 308, 309, 310, 311, 312, 313, 314, and 315 in any one of SEQ ID NOs: 4-9 and 139-146, with the proviso that the number of the selected commencing amino acid residue satisfies the formula N≤L−n+1, where N is the number of the selected residue, L is the number of amino acid residues in the sequence selected from SEQ ID NOs: 4-9 and 139-146 from which the at least 5 contiguous amino acid residues are selected, and n is the number of contiguous amino acid residues; or the at least or exactly 5 contiguous amino acid residues present in any one of SEQ ID NOs: 4-9 and 140-146 in the definition of $A^1$ and $A^2$ can independently commence at any one of amino acid residues 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, and 347 in any one of SEQ ID NOs: 4-9 and 140-146, with the proviso that the number of the selected commencing amino acid residue satisfies the formula N≤L−n+1, where N is the number of the selected residue, L is the number of amino acid residues in the sequence selected from SEQ ID NOs: 4-9 and 140-146 from which the at least 5 contiguous amino acid residues are selected, and n is the number of contiguous amino acid residues; or the at least or exactly 5 contiguous amino acid residues present in any one of SEQ ID NOs: 5-9 and 140-146 in the definition of $A^1$ and $A^2$ can independently commence at any one of amino acid residues 348, 349, 350, 351, 352, 353, 354, 355, 356, 357, 358, 359, 360, and 361 in any one of SEQ ID NOs: 5-9 and 140-146, with the proviso that the number of the selected commencing amino acid residue satisfies the formula N≤L−n+1, where N is the number of the selected residue, L is the number of amino acid residues in the sequence selected from SEQ ID NOs: 5-9 and 140-146 from which the at least 5 contiguous amino acid residues are selected, and n is the number of contiguous amino acid residues; or the at least or exactly 5 contiguous amino acid residues present in any one of SEQ ID NOs: 6-9 and 140-146 in the definition of $A^1$ and $A^2$ can independently commence at any one of amino acid residues 362, 363, 364, 365, 366, 367, 368, 369, 370, 371, 372, 373, 374, 375, 376, 377, 378, 379, 380, 381, 382, 383, 384, 385, and 386 in any one of SEQ ID NOs: 6-9 and 140-146, with the proviso that the number of the selected commencing amino acid residue satisfies the formula N≤L−n+1, where N is the number of the selected residue, L is the number of amino acid residues in the sequence selected from SEQ ID NOs: 6-9 and 140-146 from which the at least 5 contiguous amino acid residues are selected, and n is the number of contiguous amino acid residues; or the at least or exactly 5 contiguous amino acid residues present in any one of SEQ ID NOs: 7-9 and 140-146 in the definition of $A^1$ and $A^2$ can independently commence at any one of amino acid residues 387, 388, 389, 390, 391, 392, 393, 394, 395, 396, 397, 398, 399, 400, 401, 402, 403, 404, and 405 in any one of SEQ ID NOs: 7-9 and 140-146, with the proviso that the number of the selected commencing amino acid residue satisfies the formula N≤L−n+1, where N is the number of the selected residue, L is the number of amino acid residues in the sequence selected from SEQ ID NOs: 7-9 and 140-146 from which the at least 5 contiguous amino acid residues are selected, and n is the number of contiguous amino acid residues; or the at least or exactly 5 contiguous amino acid residues present in any one of SEQ ID NOs: 8, 9 and 140-146 in the definition of $A^1$ and $A^2$ can independently commence at any one of amino acid residues 406, 407, and 408 in any one of SEQ ID NOs: 8, 9 and 140-146, with the proviso that the number of the selected commencing amino acid residue satisfies the formula N≤L−n+1, where N is the number of the selected residue, L is the number of amino acid residues in the sequence selected from SEQ ID NOs: 8, 9 and 140-146 from which the at least 5 contiguous amino acid residues are selected, and n is the number of contiguous amino acid residues; or the at least or exactly 5 contiguous amino acid residues present in any one of SEQ ID NOs: 9 and 140-146 in the definition of $A^1$ and $A^2$ can independently commence at any one of amino acid residues 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, and 511 in any one of SEQ ID NOs: 9 and 140-146, with the proviso that the number of the selected commencing amino acid residue satisfies the formula N≤L−n+1, where N is the number of the selected residue, L is the number of amino acid residues in the sequence selected from SEQ ID NOs: 9 and 140-146 from which the at least 5 contiguous amino acid residues are selected, and n is the number of contiguous amino acid residues; or the at least or exactly 5 contiguous amino acid residues present in any one of SEQ ID NOs: 9 and 141-146 in the definition of $A^1$ and $A^2$ can independently commence at any one of amino acid residues 512, 513, 514, and 515 in any one of SEQ ID NOs: 9 and 141-146, with the proviso that the number of the selected commencing amino acid residue satisfies the formula $N \leq L-n+1$, where N is the number of the selected residue, L is the number of amino acid residues in the sequence selected from SEQ ID NOs: 9 and 141-146 from which the at least 5 contiguous amino acid residues are selected, and n is the number of contiguous amino acid residues; or the at least or exactly 5 contiguous amino acid residues present in any one of SEQ ID NOs: 9 and 142-146 in the definition of $A^1$ and $A^2$ can independently commence at any one of amino acid residues 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, and 588 in any one of SEQ ID NOs: 9 and 142-146, with the proviso that the number of the selected commencing amino acid residue satisfies the formula $N \leq L-n+1$, where N is the number of the selected residue in SEQ ID NOs: 9 and 142-146, and n is the number of contiguous amino acid residues; or the at least or exactly 5 contiguous amino acid residues present in any one of SEQ ID NOs: 142-146 in the definition of $A^1$ and $A^2$ can independently commence at any one of amino acid residues 589, 590, 591, 592, 593, 594, 595, 596, 597, 598, 599, 600, 601, 602, 603, 604, 605, 606, 607, 608, 609, 610, 611, 612, 613, 614, and 615 in any one of SEQ ID NOs: 142-146, with the proviso that the number of the selected commencing amino acid residue satisfies the formula $N \leq L-n+1$, where N is the number of the selected residue in SEQ ID NO: 142-146, and n is the number of contiguous amino acid residues; or the at least or exactly 5 contiguous amino acid residues present in any one of SEQ ID NOs: 143-146 in the definition of $A^1$ and $A^2$ can independently commence at any one of amino acid residues 616, 617, 618, 619, 620, 621, 622, 623, 624, 625, 626, 627, 628, 629, 630, 631, 632, 633, 634, 635, 636, 637, 638, 639, 640, and 641 in any one of SEQ ID NOs: 143-146, with the proviso that the number of the selected commencing amino acid residue satisfies the formula $N \leq L-n+1$, where N is the number of the selected residue in SEQ ID NO: 143-146, and n is the number of contiguous amino acid residues; or the at least or exactly 5 contiguous amino acid residues present in any one of SEQ ID NOs: 144-146 in the definition of $A^1$ and $A^2$ can independently commence at any one of amino acid residues 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, and 677 in any one of SEQ ID NOs: 144-146, with the proviso that the number of the selected commencing amino acid residue satisfies the formula $N \leq L-n+1$, where N is the number of the selected residue in SEQ ID NO: 144-146, and n is the number of contiguous amino acid residues; or the at least or exactly 5 contiguous amino acid residues present in any one of SEQ ID NOs: 145 or 146 in the definition of $A^1$ and $A^2$ can independently commence at any one of amino acid residues 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, and 765 in any one of SEQ ID NOs: 145 or 146, with the proviso that the number of the selected commencing amino acid residue satisfies the formula $N \leq L-n+1$, where N is the number of the selected residue in SEQ ID NO: 142-146, and n is the number of contiguous amino acid residues; or the at least or exactly 5 contiguous amino acid residues present in SEQ ID NO: 146 in the definition of $A^1$ and $A^2$ can independently commence at any one of amino acid residues 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980, 981, 982, 983, 984, 985, 986, 987, 988, 989, 990, 991, 992, 993, 994, 995, 996, 997, 998, 999, 1000, 1001, 1002, 1003, 1004, 1005, 1006, 1007, 1008, 1009, 1010, 1011, 1012, 1013, 1014, 1015, 1016, 1017, 1018, 1019, 1020, 1021, 1022, 1023, 1024, 1025, 1026, 1027, 1028, 1029, 1030, 1031, 1032, 1033, 1034, 1035, 1036, 1037, 1038, 1039, 1040, 1041, 1042, 1043, 1044, 1045, 1046, 1047, 1048, 1049, 1050, 1051, 1052, 1053, 1054, 1055, 1056, 1057, 1058, 1059, 1060, 1061, 1062, 1063, 1064, 1065, 1066, 1067, 1068, 1069, 1070, 1071, 1072, 1073, 1074, 1075, 1076, 1077, 1078, 1079, 1080, 1081, 1082, 1083, 1084, 1085, 1086, 1087, 1088, 1089, 1090, 1091, 1092, 1093, 1094, 1095, 1096, 1097, 1098, 1099, 1100, 1101, 1102, 1103, 1104, 1105, 1106, 1107, 1108, 1109, 1110, 1111, 1112, 1113, 1114, 1115, 1116, 1117, 1118, 1119, 1120, 1121, 1122, 1123, 1124, 1125, 1126, 1127, 1128, 1129, 1130, 1131, 1132, 1133, 1134, 1135, 1136, 1137, 1138, 1139, 1140, 1141, 1142, 1143, 1144, 1145, 1146, 1147, 1148, 1149, 1150, 1151, 1152, 1153, 1154, 1155, 1156, 1157, 1158, 1159, 1160, 1161, 1162, 1163, 1164, 1165, 1166, 1167, 1168, 1169, 1170, 1171, 1172, 1173, 1174, 1175, 1176, 1177, 1178, 1179, 1180, 1181, 1182, 1183, 1184, 1185, 1186, 1187, 1188, 1189, 1190, 1191, 1192, 1193, 1194, 1195, 1196, 1197, 1198, 1199, 1200, 1201, 1202, 1203, 1204, 1205, 1206, 1207, 1208, 1209, 1210, 1211, 1212, 1213, 1214, 1215, 1216, 1217, 1218, 1219, 1220, 1221, 1222, 1223, 1224, 1225, 1226, 1227, 1228, 1229, 1230, 1231, 1232, 1233, 1234, 1235, 1236, 1237, 1238, 1239, 1240, 1241, 1242, 1243, 1244, 1245, 1246, 1247, 1248, 1249, 1250, 1251, 1252, 1253, 1254, 1255, 1256, 1257, 1258, 1259, 1260, 1261, 1262, 1263, 1264, 1265, 1266, 1267, 1268, 1269, 1270, 1271, 1272, 1273, 1274, 1275, 1276, 1277, 1278, 1279, 1280, 1281, 1282, 1283, 1284, 1285, 1286, 1287, 1288, 1289, 1290, 1291, 1292, 1293, 1294, 1295, 1296, 1297, 1298, 1299, 1300, 1301, 1302, 1303, 1304, 1305, 1306, 1307, 1308, 1309, 1310, 1311, 1312, 1313, 1314, 1315, 1316, 1317, 1318, 1319, 1320, 1321, 1322, 1323, 1324, 1325, 1326, 1327, 1328, 1329, 1330, 1331, 1332, 1333, 1334, 1335, 1336, 1337, 1338, 1339, 1340, 1341, 1342, 1343, 1344, 1345, 1346, 1347, 1348, 1349, 1350, 1351, 1352, 1353, 1354, 1355, 1356, 1357, 1358, 1359, 1360, 1361, 1362, 1363, 1364, 1365, 1366, 1367, 1368, 1369, 1370, 1371, 1372, 1373, 1374, 1375, 1376, 1377, 1378, 1379, 1380, 1381, 1382, 1383, 1384, 1385, 1386, 1387, 1388, 1389, 1390, 1391, 1392, 1393, 1394, 1395, 1396, 1397, 1398, 1399, 1400, 1401, 1402, 1403, 1404, 1405, 1406, 1407, 1408, 1409, 1410, 1411, 1412, 1413, 1414, 1415, 1416, 1417, 1418, 1419, 1420, 1421, 1422, 1423, 1424, 1425, 1426, 1427, 1428, 1429, 1430, 1431, 1432, 1433, 1434, 1435, 1436, 1437, 1438, 1439, 1440, 1441, 1442, 1443, 1444, 1445, 1446, 1447, 1448, 1449, 1450, 1451, 1452, 1453, 1454, 1455, 1456, 1457, 1458, 1459, 1460, 1461, 1462, 1463, 1464, 1465, 1466, 1467, 1468, 1469, 1470, 1471, 1472, 1473, 1474, 1475, 1476, 1477, 1478, 1479, 1480, 1481, 1482, 1483, 1484, 1485, 1486, 1487, 1488, 1489, 1490, 1491, 1492, 1493, 1494, 1495, 1496, 1497, 1498, 1499, 1500, 1501, 1502, 1503, 1504, 1505, 1506, 1507, 1508, 1509, 1510, 1511, 1512, 1513, 1514, 1515, 1516, 1517, 1518, 1519, 1520, 1521, 1522, 1523, 1524, 1525, 1526, 1527, 1528, 1529, 1530, 1531, 1532, 1533, 1534, 1535, 1536, 1537, 1538, 1539, 1540, 1541, 1542, 1543, 1544, 1545, 1546, 1547, 1548, 1549, 1550, 1551, 1552, 1553, 1554, 1555, 1556, 1557, 1558, 1559, 1560, 1561, 1562, 1563, 1564, 1565, 1566, 1567, 1568, 1569, 1570, 1571, 1572, 1573, 1574, 1575, 1576, 1577, 1578, 1579, 1580, 1581, 1582, 1583, 1584, 1585, 1586, 1587, 1588, 1589, 1590, 1591, 1592, 1593, 1594, 1595, 1596, 1597, 1598, 1599, 1600, 1601, 1602, 1603, 1604, 1605, 1606, 1607, 1608, 1609, 1610, 1611, 1612, 1613, 1614, 1615, 1616, 1617, 1618, 1619, 1620, 1621, 1622, 1623, 1624, 1625, 1626, 1627, 1628, 1629, 1630, 1631, 1632, 1633, 1634, 1635, 1636, 1637, 1638, 1639, 1640, 1641, 1642, 1643, 1644, 1645, 1646, 1647, 1648, 1649, 1650, 1651, 1652, 1653, 1654, 1655, 1656, 1657, 1658, 1659, 1660, 1661, 1662, 1663, 1664, 1665, 1666, 1667, 1668, 1669, 1670, 1671, 1672, 1673, 1674, 1675, 1676, 1677, 1678, 1679, 1680, 1681, 1682, 1683, 1684, 1685, 1686, 1687, 1688, 1689, 1690, 1691, 1692, 1693, 1694, 1695, 1696, 1697, 1698, 1699, 1700, 1701, 1702, 1703, 1704, 1705, 1706, 1707, 1708, 1709, 1710, 1711, 1712, 1713, 1714, 1715, 1716, 1717, 1718, 1719, 1720, 1721, 1722, 1723, 1724, 1725, 1726, 1727, 1728, 1729, 1730, 1731, 1732, 1733, 1734, 1735, 1736, 1737, 1738, 1739, 1740, 1741, 1742, 1743, 1744, 1745, 1746, 1747, 1748, 1749, 1750, 1751, 1752, 1753, 1754, 1755, 1756, 1757, 1758, 1759, 1760, 1761, 1762, 1763, 1764, 1765, 1766, 1767, 1768, 1769, 1770, 1771, 1772, 1773, 1774, 1775, 1776, 1777, 1778, 1779, 1780, 1781, 1782, 1783, 1784, 1785, 1786, 1787, 1788, 1789, 1790, 1791, 1792, 1793, 1794, 1795, 1796, 1797, 1798, 1799, 1800, 1801, 1802, 1803, 1804, 1805, 1806, 1807, 1808, 1809, 1810, 1811, 1812, 1813, 1814, 1815, 1816, 1817, 1818, 1819, 1820, 1821, 1822, 1823, 1824, 1825, 1826, 1827, 1828, 1829, 1830, 1831, 1832, 1833, 1834, 1835, 1836, 1837, 1838, 1839, 1840, 1841, 1842, 1843, 1844, 1845, 1846, 1847, 1848, 1849, 1850, 1851, 1852, 1853, 1854, 1855, 1856, 1857, 1858, 1859, 1860, 1861, 1862, 1863, 1864, 1865, 1866, 1867, 1868, 1869, 1870, 1871, 1872, 1873, 1874, 1875, 1876, 1877, 1878, 1879, 1880, 1881, 1882, 1883, 1884, 1885, 1886, 1887, 1888, 1889, 1890, 1891, 1892, 1893, 1894, 1895, 1896, 1897, 1898, 1899, 1900, 1901, 1902, 1903, 1904, 1905, 1906, 1907, 1908, 1909, 1910, 1911, 1912, 1913, 1914, 1915, 1916, 1917, 1918, 1919, 1920, 1921, 1922, 1923, 1924, 1925, 1926, 1927, 1928, 1929, 1930, 1931, 1932, 1933, 1934, 1935, 1936, 1937, 1938, 1939, 1940, 1941, 1942, 1943, 1944, 1945, 1946, 1947, 1948, 1949, 1950, 1951, 1952, 1953, 1954, 1955, 1956, 1957, 1958, 1959, 1960, 1961, 1962, 1963, 1964, 1965, 1966, 1967, 1968, 1969, 1970, 1971, 1972, 1973, 1974, 1975, 1976, 1977, 1978, 1979, 1980, 1981, 1982, 1983, 1984, 1985, 1986, 1987, 1988, 1989, 1990, 1991, 1992, 1993, 1994, 1995, 1996, 1997, 1998, 1999, 2000, 2001, 2002, 2003, 2004, 2005, 2006, 2007, 2008, 2009, 2010, 2011, 2012, 2013, 2014, 2015, 2016, 2017, 2018, 2019, 2020, 2021, 2022, 2023, 2024, 2025, 2026, 2027, 2028, 2029, 2030, 2031, 2032, 2033, 2034, 2035, 2036, 2037, 2038, 2039, 2040, 2041, 2042, 2043, 2044, 2045, 2046, 2047, 2048, 2049, 2050, 2051, 2052, 2053, 2054, 2055, 2056, 2057, 2058, 2059, 2060, 2061, 2062 in SEQ ID NO 146, with the proviso that the number of the selected commencing amino acid residue satisfies the formula $N \leq L-n+1$, where N is the number of the selected residue in SEQ ID NO: 146, and n is the number of contiguous amino acid residues.

For instance, if the number of the contiguous amino acid residues defined for $A^1$ and $A^2$ is exactly 30 and the sequence in question is SEQ ID NO: 1, the N-terminal first residue can hence not be higher numbered than 199−30+1=170, meaning that the 30 amino acid residues in that case will be constituted by amino acid residues 170-199 of SEQ ID NO: 1.

The chimeric polypeptide as disclosed in any of the embodiments above may include an amino acid sequence $A^1$ and $A^2$, which can be any suitable fusion partner. In certain embodiments $A^1$ and $A^2$ is selected from the group consisting of 1) a methionine residue, 2) an amino acid sequence located, or directly linked, N-terminally to the amino acid sequence selected from any one of SEQ ID NOs: 1-9 from which $A^1$ and $A^2$ is derived, 3) an amino acid sequence that comprises or constitutes a purification tag, 4) an amino acid sequence that comprises or constitutes an immunogenic carrier molecule, 5) an amino acid sequence that exerts adjuvant activity; and 6) any combination of 1-5.

This means that when $A^1$ and $A^2$ is an amino acid sequence (as in 2-6) then $A^1$ and $A^2$ further may include an N-terminal methionine residue, cf. option 1.

The chimeric polypeptide may also include an amino acid sequence $a^2$, which can be any suitable fusion partner. In certain embodiments, $a^2$ is selected from the group consisting of i) an amino acid sequence located, or directly linked, C-terminally to the amino acid sequence selected from any one of SEQ ID NOs: 1-9 from which $A^2$ is derived, ii) an amino acid sequence that comprises or constitutes a purification tag, iii) an amino acid sequence that comprises or constitutes an immunogenic carrier molecule, iv) an amino acid sequence that exerts adjuvant activity, and v) any combination of i-iv.

In the definition of the chimeric polypeptide in any of the embodiments described above L may constitute a linker.

Typical linkers are flexible, and the ones that art particularly preferred are linkers that comprise glycine and/or serine residues. In particular, the linker may be any linker disclosed in Chen X et al. (2013), Advanced drug delivery reviews 65(10): 1357-1369. doi:10.1016/j.addr.2012.09.039. Particularly preferred linkers comprise or consist of the amino acid sequence GSGGGA (SEQ ID NO: 10) or GSGG-GAGSGGGA (SEQ ID NO: 11).

A further embodiment of the first aspect is that one or more of the amino acid sequences derived from SEQ ID NOs: 21-40 (see the second aspect of the invention) can be introduced into chimeric polypeptides of the first aspect of the present invention. Thus, such sequences can be part of or constitute $a^1$, L, and/or $a^2$ in formula I.

The presently exemplified chimeric polypeptides of the first aspect of the invention are those that comprise or consist of the amino acid sequence SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, or SEQ ID NO: 20, or SEQ ID NO: 59, or SEQ ID NO: 60, or SEQ ID NO: 61, or SEQ ID NO: 62, or SEQ ID NO: 63, or SEQ ID NO: 64, or SEQ ID NO: 65, or SEQ ID NO: 66, or SEQ ID NO: 67, or SEQ ID NO: 68, or SEQ ID NO: 69, or SEQ ID NO: 70, or SEQ ID NO: 71, or SEQ ID NO: 72, or SEQ ID NO: 73, or SEQ ID NO: 74, or SEQ ID NO: 75, or SEQ ID NO: 76, or SEQ ID NO: 77, or SEQ ID NO: 78, or SEQ ID NO: 79, or SEQ ID NO: 80, or SEQ ID NO: 81, or SEQ ID NO: 82, or SEQ ID NO: 83, or SEQ ID NO: 84, or SEQ ID NO: 85, or SEQ ID NO: 86.

The chimeric polypeptide of the second aspect of the invention focusses on inclusion of MHC Class II binding peptides derived from *S. aureus* into peptide constructs. As shown in the example below, the present inventors have identified 20 *S. aureus* derived peptides (SEQ ID NOs: 21-40) that exert binding to multiple MHC Class II molecules (DRB1*01:01; DRB1*04:01; and DRB5*01:01), and these have been introduced into chimeric peptide constructs. Hence, the second aspect of the invention relates to a chimeric polypeptide comprising at least 2 non-identical amino acid sequences, where each of said at least 2 non-identical amino acid sequences consists of any one of SEQ ID NOs: 21-40, wherein 0, 1, 2, or 3 amino acid residues can be substituted. In other words, each of SEQ ID NOs 21-40 can be modified with up to 3 amino acid substitutions, thereby providing for features such as increased stability of binding to MHC Class II, broader population coverage, changed solubility in either water or organic solvents, and increased stability towards proteolytic breakdown.

The chimeric polypeptide of the second aspect typically comprises at least or exactly 3 or at least or exactly 4 or at least or exactly 5 or at least or exactly 6 or at least or exactly 7 or at least or exactly 8 or at least or exactly 9 or at least or exactly 10 or at least or exactly 11 or at least or exactly 11 or at least or exactly 12 or at least or exactly 13 or at least or exactly 14 or at least or exactly 15 or at least or exactly 16 or at least or exactly 17 or at least or exactly 18 or at least or exactly 19 or at least or exactly 20 of said non-identical amino acid sequences. In particularly interesting embodiments of the second aspect, 2 or more of said at least 2 non-identical amino acid sequences are not derivable from the same of SEQ ID NOs: 21-40 by introducing 0, 1, 2, or 3 amino acid substitutions. This means that 2 or more of the non-identical amino acid sequences are unrelated in the sense that their sequences cannot be arrived at when starting out with one and the same of SEQ ID NOs: 21-40 and introducing 0, 1, 2, or 3 amino acid substitutions. In an embodiment, 3 or 4 or 5 or 6 or 7 or 8 or 9 or 10 or 11 or 12 or 13 or 14 or 15 or 16 or 17 or 19 or 20 of said at least 2 non-identical amino acid sequences are not derivable from the same of SEQ ID NOs: 21-40 by introducing 0, 1, 2, or 3 amino acid substitutions. "Derivable from SEQ ID NO: 21-40" thus means that if an amino acid sequence can be defined by introducing 0, 1, 2 or 3 amino acid substitutions in a sequence selected from one of SEQ ID NOs: 21-40, then this amino acid sequence is derivable from that sequence selected from SEQ ID NOs: 21-40.

In some embodiments of the $2^{nd}$ aspect of the invention, including the embodiments disclosed above, the chimeric polypeptide includes amino acid sequences derivable from the group consisting of SEQ ID NO: 21, 23, 26, 27, 30, 33, 34, 38, and 40, but none derivable from the group selected from SEQ ID NOs: 22, 24, 25, 28, 29, 31, 32, 35-37, and 39. Alternatively, some embodiments relate to chimeric polypeptide that do not include amino acid sequences derivable from the group consisting of SEQ ID NO: 21, 23, 26, 27, 30, 33, 34, 38, and 40, but does include amino acid sequences derivable from the groups selected from SEQ ID NOs: 22, 24, 25, 28, 29, 31, 32, 35-37, and 39.

The chimeric polypeptide of the second aspect can include that the individual sequences derived from SEQ ID NOs: 21-40 are directly jointed, but in important embodiments some or all of the sequences are separated. One possibility is to separate via use of peptide linkers (cf. above for details) but another possibility is to use a scaffold protein or polypeptide, where the sequences derived from SEQ ID NOs: 21-40 are introduced via insertion and/or substitution in the scaffold's amino acid sequence. A particularly interesting linker for use in the second aspect is SEQ ID NO: 45 (-GPGPG-), cf. SEQ ID NOs: 41 and 42. With respect to the scaffold protein, it may be any suitable scaffold. In the present application, the protein having the NCBI identifier: 53721566 has been used as scaffold, cf. SEQ ID NOs: 43 and 44.

A further embodiment of the second aspect is that one or more of the amino acid sequences derived from SEQ ID NOs: 21-40 can be introduced into chimeric polypeptides of the first aspect of the present invention. Thus, such sequences can be part of or constitute $a^1$, L, and/or $a^2$ in formula I. Thus, in such embodiments, $A^1$ and/or $A^2$ can constitute scaffolds as discussed herein.

The chimeric polypeptide of the invention is in certain embodiments also covalently linked (i.e. fused or conjugated) to an immunogenic carrier molecule; or, phrased otherwise, the polypeptide of the invention also includes such an immunogenic carrier molecule in addition to the chimeric polypeptides of the present invention. The immunogenic carrier molecule is a typically polypeptide that induces T-helper lymphocyte responses in a majority of humans, such as immunogenic carrier proteins selected from the group consisting of keyhole limpet hemocyanino or a fragment thereof, tetanus toxoid or a fragment thereof, dipththeria toxoid or a fragment thereof. Other suitable carrier molecules are discussed infra. One further fusion partner, which is preferably incorporated is a "His tag", i.e. a stretch of amino acids, which is rich or only consists of histidinyl residues so as to facilitate protein purification.

In preferred embodiments, the polypeptide of the invention detailed above is capable of inducing an adaptive immune response against the chimeric polypeptide in a mammal, in particular in a human being. Preferably, the adaptive immune response is a protective adaptive immune response against infection with *S. aureus*, in particular multi-resistant *S. aureus*. The polypeptide may in these cases induce a humeral and/or a cellular immune response.

It is believed that the presently presented T-helper epitopes are inventive in their own right.

Hence, related to the second aspect of the invention—and part of the invention—is a peptide selected from SEQ ID NOs. 21-40 and peptides having an amino acid sequence set forth in any one of SEQ ID NOs: 21-40 wherein 1, 2, or 3 amino acids have been substituted. Also included in the invention is peptides having up to 30 amino acid residues and comprising 1) an amino acid selected from SEQ ID NOs. 21-40 2) an amino acid sequence set forth in any one of SEQ ID NOs: 21-40 wherein 1, 2, or 3 amino acids have been substituted.

Nucleic Acid Fragments of the Invention; Third Aspect

The nucleic acid fragment of the invention referred to above preferably is a DNA fragment or an RNA fragment. Exemplary DNA fragments are provided as SEQ ID NOs: 46-54 (DNA encoding SEQ ID NOs: 12-20, i.e. exemplary polypeptides of the first aspect of the invention) and as SEQ ID NOs: 55-58 (DNA encoding SEQ ID NOs: 41-44, i.e. exemplary polypeptides of the second aspect of the present invention). The RNA equivalents of these sequences are also encompassed by the present invention (i.e. SEQ ID NOs: 46-58, where T is exchanged with U in the sequence notation). Also the complimentary sequences are embraced by the present invention.

Since the presently disclosed chimeric polypeptides can be encoded by a plethora of nucleic acid sequences due to the degeneracy of the genetic code, the skilled person will understand that none single nucleic acid sequence is particularly preferred as long as it encodes a chimeric polypeptide of the present invention. Rather, the skilled person will design suitable coding sequences that are codon optimised with respect to e.g. the expression system wherein recombinant production of the polypeptide is to take place.

Nevertheless, the sequence identity with the nucleotide sequence in i) or ii) or iii) in the definition of the nucleic acid fragment of the invention is preferably at least 65%, such as at least 70%, at least 75%, at least 80%, at least 85%, at least 90%, at least 91%, at least 92%, at least 93%, at least 94%, at least 95%, at least 96%, at least 97%, at least 98%, and at least 99%.

It will be understood that the nucleic acid fragments of the invention may be used for both production, carrier and vaccine purposes—the latter will require that the sequences are included in expression vectors that may lead to production of immunogenic proteins in the host animal receiving the vector.

Fourth Aspect—Vectors of the Invention

It will be understood that the nucleic acid fragments of the invention may be used for both production, carrier and vaccine purposes—the latter will require that the sequences are included in expression vectors that may lead to production of immunogenic proteins in the mammal receiving the vector. Or put differently, the nucleic acid is comprised in a vector capable of expressing the nucleic acid in man upon administration.

Such a vector of the invention often comprises in operable linkage and in the 5'-3' direction, an expression control region comprising an enhancer/promoter for driving expression of the nucleic acid, an optional signal peptide coding sequence, a nucleotide sequence of the invention, and optionally a terminator. Hence, such a vector constitutes an expression vector useful for effecting production in cells of the polypeptide of the invention. Since the polypeptides of the invention are protozoan of origin, recombinant production has to be effected in host cells that can express the coding nucleic acid. Bacterial host cells may be used.

However, if the vector is to drive expression in eukaryotic cell (as would be the case for a nucleic acid vaccine vector), the expression control region should be adapted to this particular use.

For production purposes it is therefore often convenient that the expression control region drives expression in a prokaryotic cell such as a bacterium, e.g. in *E. coli*, or in a eukaryotic cell such as a plant cell, an insect cell, or a mammalian cell. For vaccine purposes, the expression control region has to be able to drive expression in a mammalian, preferably human, cell.

Also, for production purposes, it is practical that the vector is capable of integrating the nucleic acid into the genome of a host cell—this is particularly useful if the vector is use in the production of stably transformed cells, where the progeny will also include the genetic information introduced via the vector. Alternatively, vectors incapable of being integrated into the genome of a piscine host cell are useful in e.g. nucleic acid vaccination.

An interesting production system is the use of plants. For instance, proteins can be produced at low cost in plants using an Agrobacterium transfection system to genetically modify plants to express genes that encode the protein of interest. One commercially available platform are those provided by iBio CMO LLC (8800 HSC Pkwy, Bryan, Tex. 77807, USA) and iBio, Inc (9 Innovatoin Way, Suite 100, Newark, DE 19711, USA) and disclosed in e.g. EP 2 853 599, EP 1 769 068, and EP 2 192 172. Hence, in such systems the vector is an Agrobacterium vector or other vector suitable for transfection of plants.

The vector is typically selected from the group consisting of a virus, such as a virus which is non-pathogenic in mammals and in particular in humans, a bacterium such as a bacterium which is non-pathogenic in mammals such as humans, a plasmid, a minichromosome, and a cosmid.

Interesting vectors are viral vectors (in particular those useful as vaccine agents in humans). These may be selected from the group consisting of a retrovirus vector, such as a lentivirus vector, an adenovirus vector, an adeno-associated virus vector, and a pox virus vector. Certain pox virus vectors are preferred, in particular vaccinia virus vectors. A particularly preferred vaccinia virus vector is a modified vaccinia Ankara (MVA) vector.

Polypeptides of the invention may as indicated be encoded by a nucleic acid molecule comprised in a vector. A nucleic acid sequence can be "heterologous," which means that it is in a context foreign to the cell in which the vector is being introduced, which includes a sequence homologous to a sequence in the cell but in a position within the host cell where it is ordinarily not found.

Vectors include naked DNAs, RNAs, plasmids, cosmids, viruses (bacteriophage, animal viruses, and plant viruses), and artificial chromosomes (e.g., YACs). One of skill in the art would be well equipped to construct a vector through standard recombinant techniques. In addition to encoding the polypeptides of this invention, a vector of the present invention may encode polypeptide sequences such as a "tag" or immunogenicity enhancing peptide (e.g. an immunogenic carrier or a fusion partner that stimulates the immune system, such as a cytokine or active fragment thereof). Useful vectors encoding such fusion proteins include pIN vectors, vectors encoding a stretch of histidines, and pGEX vectors, for use in generating glutathione S-transferase (GST) soluble fusion proteins for later purification and separation or cleavage.

Vectors of the invention may be used in a host cell to produce a polypeptide of the invention that may subsequently be purified for administration or the vector may be purified for direct administration for expression of the protein (as is the case when administering a nucleic acid vaccine).

Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra.

1. Promoters and Enhancers

A "promoter" is a control sequence. The promoter is typically a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and expression of that sequence. A promoter may or may not be used in conjunction with an "enhancer," which refers to a cis-acting regulatory sequence involved in the transcriptional activation of a nucleic acid sequence.

A promoter may be one naturally associated with a gene or sequence, as may be obtained by isolating the 5' non-coding sequences located upstream of the coding segment or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural state. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including polymerase chain reaction in connection with the compositions disclosed herein.

It may be important to employ a promoter and/or enhancer that effectively direct(s) the expression of the DNA segment in the cell type or organism chosen for expression. Those of skill in the art of molecular biology generally know the use of promoters, enhancers, and cell type combinations for protein expression. The promoters employed may be constitutive, tissue-specific, or inducible and in certain embodiments may direct high level expression of the introduced DNA segment under specified conditions, such as large-scale production of recombinant proteins or peptides.

Examples of inducible elements, which are regions of a nucleic acid sequence that can be activated in response to a specific stimulus, include but are not limited to Immunoglobulin Heavy Chain, Immunoglobulin Light Chain, T Cell Receptor, HLA DQα and/or DQβ, β-Interferon, Interleukin-2, Interleukin-2 Receptor, MHC Class II 5, MHC Class II HLA-DRα, β-Actin, Muscle Creatine Kinase (MCK), Pre-albumin (Transthyretin), Elastase I, Metallothionein (MTII), Collagenase, Albumin, α-Fetoprotein, γ-Globin, β-Globin, c-fos, c-HA-ras, Insulin, Neural Cell Adhesion Molecule (NCAM), α1-Antitrypain, H2B (TH2B) Histone, Mouse and/or Type I Collagen, Glucose-Regulated Proteins (GRP94 and GRP78), Rat Growth Hormone, Human Serum Amyloid A (SAA), Troponin I (TN I), Platelet-Derived Growth Factor (PDGF), Duchenne Muscular Dystrophy, SV40, Polyoma, Retroviruses, Papilloma Virus, Hepatitis B Virus, Human Immunodeficiency Virus, Cytomegalovirus (CMV) IE, and Gibbon Ape Leukemia Virus.

Inducible Elements include MT II—Phorbol Ester (TFA)/ Heavy metals; MMTV (mouse mammary tumor virus)—Glucocorticoids; β-Interferon—poly(rl)x/poly(rc); Adenovirus 5 E2-EIA; Collagenase—Phorbol Ester (TPA); Stromelysin—Phorbol Ester (TPA); SV40—Phorbol Ester (TPA); Murine MX Gene—Interferon, Newcastle Disease Virus; GRP78 Gene—A23187; α-2-Macroglobulin—IL-6; Vimentin—Serum; MHC Class I Gene H-2κb—Interferon; HSP70-EIA/SV40 Large T Antigen; Proliferin—Phorbol Ester/TPA; Tumor Necrosis Factor—PMA; and Thyroid Stimulating Hormoneα Gene—Thyroid Hormone.

Also contemplated as useful in the present invention are the dectin-1 and dectin-2 promoters. Additionally any promoter/enhancer combination (as per the Eukaryotic Promoter Data Base EPDB) could also be used to drive expression of structural genes encoding oligosaccharide processing enzymes, protein folding accessory proteins, selectable marker proteins or a heterologous protein of interest.

The particular promoter that is employed to control the expression of peptide or protein encoding polynucleotide of the invention is not believed to be critical, so long as it is capable of expressing the polynucleotide in a targeted cell. Where a piscine cell is targeted (as is the case in nucleic acid vaccination), it is preferable to position the polynucleotide coding region adjacent to and under the control of a promoter that is capable of being expressed in a piscine cell. Generally speaking, such a promoter might include either a bacterial, piscine or viral promoter as long as the promoter is effective in piscine cells.

In various embodiments—in particular those where recombinant production of the polypeptide of the invention is the aim—the human cytomegalovirus (CMV) immediate early gene promoter, the SV40 early promoter, and the Rous sarcoma virus long terminal repeat can be used to obtain high level expression of a related polynucleotide to this invention. The use of other viral or mammalian cellular or bacterial phage promoters, which are well known in the art, to achieve expression of polynucleotides is contemplated as well.

In embodiments in which a vector is administered to humans for expression of the protein, it is contemplated that a desirable promoter for use with the vector is one that is not down-regulated by cytokines or one that is strong enough that even if down-regulated, it produces an effective amount of the protein/polypeptide of the current invention in humans to elicit an immune response. Non-limiting examples of these are CMV IE and RSV LTR. In other embodiments, a promoter that is up-regulated in the presence of cytokines is employed. The MHC I promoter increases expression in the presence of IFN-γ.

Tissue specific promoters can be used, particularly if expression is in cells in which expression of an antigen is desirable, such as dendritic cells and macrophages. The mammalian MHC I and MHC II promoters are examples of such tissue-specific promoters in man and it is contemplated that corresponding piscine promoters will be effective.

2. Initiation Signals and Internal Ribosome Binding Sites (IRES)

A specific initiation signal also may be required for efficient translation of coding sequences. These signals include the ATG initiation codon or adjacent sequences. Exogenous translational control signals, including the ATG initiation codon, may need to be provided.

One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic and may be operable in bacteria or mammalian cells. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome scanning model of 5' methylated Cap dependent translation and begin translation at internal sites. IRES elements from two members of the picornavirus family (polio and encephalomyocarditis) have been described, as well an IRES from a mammalian message. IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, herein incorporated by reference).

3. Multiple Cloning Sites

Vectors can include a multiple cloning site (MCS), which is a nucleic acid region that contains multiple restriction enzyme sites, any of which can be used in conjunction with standard recombinant technology to digest the vector. Frequently, a vector is linearized or fragmented using a restriction enzyme that cuts within the MCS to enable exogenous sequences to be ligated to the vector. Techniques involving restriction enzymes and ligation reactions are well known to those of skill in the art of recombinant technology.

4. Splicing Sites

Most transcribed eukaryotic RNA molecules will undergo RNA splicing to remove introns from the primary transcripts. If relevant in the context of vectors of the present invention, vectors containing genomic eukaryotic sequences may require donor and/or acceptor splicing sites to ensure proper processing of the transcript for protein expression.

5. Termination Signals

The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (poly A) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message.

Terminators contemplated for use in the invention include any known terminator of transcription described herein or known to one of ordinary skill in the art, including but not limited to, for example, the bovine growth hormone terminator or viral termination sequences, such as the SV40 terminator. In certain embodiments, the termination signal may be a lack of transcribable or translatable sequence, such as due to a sequence truncation.

6. Polyadenylation Signals

In expression, particularly eukaryotic expression (as is relevant in nucleic acid vaccination), one will typically include a polyadenylation signal to effect proper polyadenylation of the transcript. The nature of the polyadenylation signal is not believed to be crucial to the successful practice of the invention, and/or any such sequence may be employed. Preferred embodiments include the SV40 polyadenylation signal and/or the bovine growth hormone polyadenylation signal, convenient and/or known to function well in various target cells. Polyadenylation may increase the stability of the transcript or may facilitate cytoplasmic transport.

7. Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

8. Selectable and Screenable Markers

In certain embodiments of the invention, cells containing a nucleic acid construct of the present invention may be identified in vitro or in vivo by encoding a screenable or selectable marker in the expression vector. When transcribed and translated, a marker confers an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, markers that confer resistance to neomycin, puromycin, hygromycin, DHFR, GPT, zeocin or histidinol are useful selectable markers. In addition to markers conferring a phenotype that allows for the discrimination of transformants based on the implementation of conditions, other types of markers including screenable markers such as GFP for colorimetric analysis. Alternatively, screenable enzymes such as herpes simplex virus thymidine kinase (tk) or chloramphenicol acetyltransferase (CAT) may be utilized. One of skill in the art would also know how to employ immunologic markers that can be used in conjunction with FACS analysis. The marker used is not believed to be important, so long as it is capable of being expressed simultaneously with the nucleic acid encoding a protein of the invention. Further examples of selectable and screenable markers are well known to one of skill in the art.

The Transformed Cells of the Invention—Fifth Aspect

Transformed cells of the invention are useful as organisms for producing the polypeptide of the invention, but also as simple "containers" of nucleic acids and vectors of the invention.

Certain transformed cells of the invention are capable of replicating the nucleic acid fragment defined for option i) of the third aspect of the invention. Preferred transformed cells of the invention are capable of expressing the nucleic acid fragment defined for option i).

For recombinant production it is convenient, but not a prerequisite that the transformed cell according is prokaryotic, such as a bacterium, but generally both prokaryotic cells and eukaryotic cells may be used.

Suitable prokaryotic cells are bacterial cells selected from the group consisting of Escherichia (such as E. coli.), Bacillus [e.g. Bacillus subtilis], Salmonella, and Mycobacterium [preferably non-pathogenic, e.g. M. bovis BCG].

Eukaryotic cells can be in the form of yeasts (such as Saccharomyces cerevisiae) and protozoans. Alternatively, the transformed eukaryotic cells are derived from a multicellular organism such as a fungus, an insect cell, a plant cell, or a mammalian cell.

For production purposes, it is advantageous that the transformed cell of the invention is stably transformed by having the nucleic acid defined above for option i) stably integrated into its genome, and in certain embodiments it is also preferred that the transformed cell secretes or carries on its surface the polypeptide of the invention, since this facilitates recovery of the polypeptides produced. A particular version of this embodiment is one where the transformed cell is a bacterium and secretion of the polypeptide of the invention is into the periplasmic space.

As noted above, stably transformed cells are preferred—these i.a. allows that cell lines comprised of transformed cells as defined herein may be established—such cell lines are partilucarly preferred aspects of the invention.

Further details on cells and cell lines are presented in the following:

Suitable cells for recombinant nucleic acid expression of the nucleic acid fragments of the present invention are prokaryotes and eukaryotes. Examples of prokaryotic cells include E. coli; members of the Staphylococcus genus, such as S. epidermidis; members of the Lactobacillus genus, such as L. plantarum; members of the Lactococcus genus, such as L. lactis; members of the Bacillus genus, such as B. subtilis; members of the Corynebacterium genus such as C. glutamicum; and members of the Pseudomonas genus such as Ps. fluorescens. Examples of eukaryotic cells include mammalian cells; insect cells; yeast cells such as members of the Saccharomyces genus (e.g. S. cerevisiae), members of the Pichia genus (e.g. P. pastoris), members of the Hansenula genus (e.g. H. polymorpha), members of the Kluyveromyces genus (e.g. K. lactis or K. fragilis) and members of the Schizosaccharomyces genus (e.g. S. pombe).

Techniques for recombinant gene production, introduction into a cell, and recombinant gene expression are well known in the art. Examples of such techniques are provided in references such as Ausubel, Current Protocols in Molecular Biology, John Wiley, 1987-2002, and Sambrook et al., Molecular Cloning, A Laboratory Manual, 2 nd Edition, Cold Spring Harbor Laboratory Press, 1989.

As used herein, the terms "cell," "cell line," and "cell culture" may be used interchangeably. All of these terms also include their progeny, which includes any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organism that is capable of replicating a vector or expressing a heterologous gene encoded by a vector. A host cell can, and has been, used as a recipient for vectors or viruses. A host cell may be "transfected" or "transformed," which refers to a process by which exogenous nucleic acid, such as a recombinant protein-encoding sequence, is transferred or introduced into the host cell. A transformed cell includes the primary subject cell and its progeny.

Host cells may be derived from prokaryotes or eukaryotes, including bacteria, yeast cells, insect cells, and mammalian cells for replication of the vector or expression of part or all of the nucleic acid sequence(s). Numerous cell lines and cultures are available for use as a host cell, and they can be obtained through the American Type Culture Collection (ATCC), which is an organization that serves as an archive for living cultures and genetic materials (www.atcc.org) or from other depository institutions such as Deutsche Sammlung vor Micrroorganismen and Zellkulturen (DSM). An appropriate host can be determined by one of skill in the art based on the vector backbone and the desired result. A plasmid or cosmid, for example, can be introduced into a prokaryote host cell for replication of many vectors or expression of encoded proteins. Bacterial cells used as host cells for vector replication and/or expression include Staphylococcus strains, DH5a, JMI 09, and KC8, as well as a number of commercially available bacterial hosts such as SURE(R) Competent Cells and SOLOP ACK™ Gold Cells (STRATAGENE®, La Jolla, Calif.). Alternatively, bacterial cells such as E. coli LE392 could be used as host cells for phage viruses. Appropriate yeast cells include Saccharomyces cerevisiae, Saccharomyces pombe, and Pichia pastoris.

Examples of eukaryotic host cells for replication and/or expression of a vector include HeLa, NIH3T3, Jurkat, 293, Cos, CHO, Saos, and PC12. Many host cells from various cell types and organisms are available and would be known to one of skill in the art. Similarly, a viral vector may be used in conjunction with either a eukaryotic or prokaryotic host cell, particularly one that is permissive for replication or expression of the vector.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

Expression Systems

Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MAXBAC®

2.0 from INVITROGEN® and BACPACK™ Baculovirus expression system from CLONTECH®

In addition to the disclosed expression systems of the invention, other examples of expression systems include STRATAGENE®'s COMPLETE CONTROL™ Inducible Mammalian Expression System, which involves a synthetic ecdysone-inducible receptor, or its pET Expression System, an E. coli expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the Pichia methanolica Expression System, which is designed for high-level production of recombinant proteins in the methylotrophic yeast Pichia methanolica. One of skill in the art would know how to express a vector, such as an expression construct, to produce a nucleic acid sequence or its cognate polypeptide, protein, or peptide.

Methods of Gene Transfer

Suitable methods for nucleic acid delivery to effect expression of compositions of the present invention are believed to include virtually any method by which a nucleic acid (e.g., DNA, including viral and nonviral vectors) can be introduced into a cell, a tissue or an organism, as described herein or as would be known to one of ordinary skill in the art. Such methods include, but are not limited to, direct delivery of DNA such as by injection (U.S. Pat. Nos. 5,994,624, 5,981,274, 5,945,100, 5,780,448, 5,736,524, 5,702,932, 5,656,610, 5,589,466 and 5,580,859), including microinjection (U.S. Pat. No. 5,789,215); by electroporation (U.S. Pat. No. 5,384,253); by calcium phosphate precipitation; by using DEAE dextran followed by polyethylene glycol; by direct sonic loading; by liposome mediated transfection; by microprojectile bombardment (PCT Application Nos. WO 94/09699 and 95/06128; U.S. Pat. Nos. 5,610,042; 5,322,783 5,563,055, 5,550,318, 5,538,877 and 5,538,880); by agitation with silicon carbide fibers (U.S. Pat. Nos. 5,302,523 and 5,464,765); by Agrobacterium mediated transformation (U.S. Pat. Nos. 5,591,616 and 5,563,055); or by PEG mediated transformation of protoplasts (U.S. Pat. Nos. 4,684,611 and 4,952,500); by desiccation/inhibition mediated DNA uptake. Through the application of techniques such as these, organelle(s), cell(s), tissue(s) or organism(s) may be stably or transiently transformed.

Compositions of the Invention; Vaccines

Compositions, in particular vaccines, according to the invention are prophylactic but may also be used therapeutically.

Such vaccines comprise immunising antigen(s), immunogen(s), polypeptide(s), protein(s) or nucleic acid(s), usually in combination with "pharmaceutically acceptable carriers", which include any carrier that does not itself induce the production of antibodies harmful to the individual receiving the composition.

In some embodiments of the invention, the pharmaceutical compositions such as vaccines include merely one single antigen, immunogen, polypeptide, protein, nucleic acid or vector of the invention, but in other embodiments, the pharmaceutical compositions comprise "cocktails" of the antigens or of the immunogens or of the polypeptides or of the protein or of the nucleic acids or of the vectors of the invention.

In particularly interesting embodiments, the pharmaceutical composition is a vector mentioned herein, which encodes and can effect expression of at least 2 nucleic acid fragments of the invention.

Another interesting embodiment of a pharmaceutical composition comprises RNA as the active principle, i.e. at least one mRNA encoding a polypeptide of the invention.

An embodiment of a pharmaceutical composition of the invention at least 2 (such as 2, 3, 4, 5, 6, 7, 8, 9, or 10) distinct chimeric polypeptides of the invention described above.

Another embodiment of the pharmaceutical composition of the invention comprises at least 2 (such as 2, 3, 4, 5, 6, 7, 8, 9, or 10) distinct nucleic acid molecules (such as DNA and RNA) each encoding a chimeric polypeptide of the invention.

Suitable carriers are typically large, slowly metabolized macromolecules such as proteins, polysaccharides, polylactic acids, polyglycolic acids, polymeric amino acids, amino acid copolymers, lipid aggregates (such as oil droplets or liposomes), and inactive virus particles.

Such carriers are well known to those of ordinary skill in the art. Additionally, these carriers may function as immunostimulating agents ("adjuvants"). Furthermore, the antigen or immunogen may be conjugated to a bacterial toxoid, such as a toxoid from diphtheria, tetanus, cholera, H. pylori, etc. pathogen, cf. the description of immunogenic carriers supra.

The pharmaceutical compositions of the invention thus typically contain an immunological adjuvant, which is commonly an aluminium based adjuvant or one of the other adjuvants described in the following:

Preferred adjuvants to enhance effectiveness of the composition include, but are not limited to: (1) aluminum salts (alum), such as aluminum hydroxide, aluminum phosphate, aluminum sulfate, etc; (2) oil-in-water emulsion formulations (with or without other specific immunostimulating agents such as muramyl peptides (see below) or bacterial cell wall components), such as for example (a) MF59 (WO 90/14837; Chapter 10 in Vaccine design: the subunit and adjuvant approach, eds. Powell & Newman, Plenum Press 1995), containing 5% Squalene, 0.5% TWEEN 80, and 0.5% SPAN 85 (optionally containing various amounts of MTP-PE (see below), although not required) formulated into submicron particles using a microfluidizer such as Model 110Y microfluidizer (Microfluidics, Newton, Mass.), (b) SAF, containing 10% Squalane, 0.4% TWEEN 80, 5% PLURONIC blocked polymer L121, and thr-MDP (see below) either microfluidized into a submicron emulsion or vortexed to generate a larger particle size emulsion, and (c) Ribi adjuvant system (RAS), (Ribi Immunochem, Hamilton, Mont.) containing 2% Squalene, 0.2% TWEEN 80, and one or more bacterial cell wall components from the group consisting of monophosphoryl lipid A (MPL), trehalose dimycolate (TDM), and cell wall skeleton (CWS), preferably MPL+CWS (Detox™); (3) saponin adjuvants such as STIMULON (Cambridge Bioscience, Worcester, MA) may be used or particles generated therefrom such as ISCOMs (immunostimulating complexes); (4) Complete Freund's Adjuvant (CFA) and Incomplete Freund's Adjuvant (IFA); (5) cytokines, such as interleukins (eg. IL-1, IL-2, IL-4, IL-5, IL-6, IL-7, IL-12, etc.), interferons (eg. gamma interferon), macrophage colony stimulating factor (M-CSF), tumor necrosis factor (TNF), etc.; and (6) other substances that act as immunostimulating agents to enhance the effectiveness of the composition. Alum and MF59™ adjuvants are preferred together with CFA and IFA.

As mentioned above, muramyl peptides include, but are not limited to, N-acetyl-muramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-alanine-2"-2'-dipalmitoyl-sn-glycero-3-hydroxyphosphoryloxy)-ethylamine (MTP-PE), etc.

Another possibility for a polypeptide vaccine formulation is to include the vaccine polypeptide(s) of the present invention in a virus-like particle, i.e. a non-infectious self-assembling structure composed of envelope or capsid proteins, where the protein(s) of the invention are incorporated. The effect is multiple presentations of the polypeptides of the invention on the surface of the VLP, which in turn provides for improved immune recognition of the polypeptides. Hence, VLPs exert immunological adjuvant effects, too.

The immunogenic compositions (e.g. the immunising antigen or immunogen or polypeptide or protein or nucleic acid, pharmaceutically acceptable carrier, and adjuvant) typically will contain diluents, such as water, saline, glycerol, ethanol, etc. Additionally, auxiliary substances, such as wetting or emulsifying agents, pH buffering substances, and the like, may be present in such vehicles.

Typically, the immunogenic compositions are prepared as injectables, either as liquid solutions or suspensions; solid forms suitable for solution in, or suspension in, liquid vehicles prior to injection may also be prepared. The preparation also may be emulsified or encapsulated in liposomes for enhanced adjuvant effect, as discussed above under pharmaceutically acceptable carriers.

Immunogenic compositions used as vaccines comprise an immunologically effective amount of the antigenic or immunogenic polypeptides, as well as any other of the above-mentioned components, as needed. By "immunologically effective amount", it is meant that the administration of that amount to an individual, either in a single dose or as part of a series, is effective for treatment or prevention. This amount varies depending upon the health and physical condition of the individual to be treated, the taxonomic group of individual to be treated (eg. non-human primate, primate, etc.), the capacity of the individual's immune system to synthesize antibodies or generally mount an immune response, the degree of protection desired, the formulation of the vaccine, the treating doctor's assessment of the medical situation, and other relevant factors. It is expected that the amount of immunogen will fall in a relatively broad range that can be determined through routine trials. However, for the purposes of protein vaccination, the amount administered per immunization is typically in the range between 0.5 µg and 500 mg (however, often not higher than 5,000 µg). The amount of polypeptide of the invention can therefore be between 1 and 400 µg, between 2 and 350 µg, between 4 and 300 µg, between 5 and 250 µg, and between 10 and 200 µg. Hence, the composition will typically contain between 0.1-500 µg of protein of the invention per g of vaccine composition.

The immunogenic compositions are conventionally administered parenterally, eg, by injection, either subcutaneously, intramuscularly, or transdermally/transcutaneously (eg. WO98/20734). Additional formulations suitable for other modes of administration include oral and pulmonary formulations, suppositories, and transdermal applications. In the case of nucleic acid vaccination, also the intravenous or intraarterial routes may be applicable.

Dosage treatment may be a single dose schedule or a multiple dose schedule. The vaccine may be administered in conjunction with other immunoregulatory agents.

As an alternative to protein-based vaccines, DNA vaccination (also termed nucleic acid vaccination or gene vaccination) may be used [eg. Robinson & Torres (1997) Seminars in Immunol 9: 271-283; Donnelly et al. (1997) Avnu Rev Innnunol 15: 617-648; later herein].

A further aspect of the invention is as mentioned above the recognition that combination vaccines can be provided, wherein 2 or more chimeric polypeptide antigens disclosed herein are combined to enhance the immune response by the vaccinated individueal, including to optimize initial immune response and duration of immunity. For the purposes of this aspect of the invention, multiple antigenic fragments derived from the same, longer protein can also be used, such as the use of a combination of different lengths of polypeptide sequence fragments from one protein.

Thus, embodiments of the invention relate to a composition (or the use as a vaccine thereof) comprising 2 distinct (i.e. non-identical) proteinaceous immunogens disclosed herein.

Immunization Methods

The method of this aspect of the invention generally relates to induction of immunity and as such also entails methods that are prophylactic as well as therapeutic.

When immunization methods entail that a chimeric polypeptide of the invention or a composition comprising such a chimeric polypeptide is administered the animal (e.g. the human) typically receives between 0.5 and 5,000 µg of the polypeptide of the invention per administration, cf. the above indications concerning dosages.

In preferred embodiments, the immunization scheme includes that the a primary administration of the chimeric polypeptide(s), the nucleic acids/vectore, or the composition(s) of the invention, but it may be necessary to follow up with one or more booster administrations.

Preferred embodiments comprise that the administration is for the purpose of inducing protective immunity against *S. aureus*. In this embodiment it is particularly preferred that the protective immunity is effective in reducing the risk of attracting infection wit *S. aureus*.

As mentioned herein, the some vaccines of the invention induce humoral immunity, so it is preferred that the administration is for the purpose of inducing antibodies specific for *S. aureus*.

But, as also mentioned the immunization method may also be useful in antibody production, so in other embodiments the administration is for the purpose of inducing antibodies specific for *S. aureus* wherein B-lymphocytes producing said antibodies are subsequently recovered from the animal and used for preparation of monoclonal antibodies.

Compositions for immunization can as mentioned above comprise polypeptides, nucleic acids, or vectors of the invention. The pharmaceutical compositions will comprise a therapeutically effective amount thereof.

The term "therapeutically effective amount" or "prophylactically effective amount" as used herein refers to an amount of a therapeutic agent to treat, ameliorate, or prevent a desired disease or condition, or to exhibit a detectable preventative effect in a group of mammals such as humans The effect can be detected by, for example, chemical markers or antigen levels. Reference is made to the ranges for dosages of immunologically effective amounts of polypeptides, cf. above. However, the effective amount for a given situation can be determined by routine experimentation and is within the judgement of the clinician.

For purposes of the present invention, an effective dose will be from about 0.01 mg/kg to 50 mg/kg or 0.05 mg/kg to about 10 mg/kg of the DNA constructs in the animal to which it is administered.

A pharmaceutical composition can also contain a pharmaceutically acceptable carrier. The term "pharmaceutically acceptable carrier" refers to a carrier for administration of a therapeutic agent, such as antibodies or a polypeptide, genes, and other therapeutic agents. The term refers to any pharmaceutical carrier that does not itself induce the production of antibodies harmful to the individual receiving the composition, and which may be administered without undue toxicity. Suitable carriers may be large, slowly metabolized macromolecules such as proteins, polysaccharides, polylactic acids, polyglycolic acids, polymeric amino acids, amino acid copolymers, and inactive virus particles. Such carriers are well known to those of ordinary skill in the art.

Pharmaceutically acceptable salts can be used therein, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients is available in Remington's Pharmaceutical Sciences (Mack Pub. Co., N. J. 1991).

Pharmaceutically acceptable carriers in therapeutic compositions may contain liquids such as water, saline, glycerol and ethanol. Additionally, auxiliary substances, such as wetting or emulsifying agents, pH buffering substances, and the like, may be present in such vehicles. Typically, the therapeutic compositions are prepared as injectables, either as liquid solutions or suspensions; solid forms suitable for solution in, or suspension in, liquid vehicles prior to injection may also be prepared. Liposomes are included within the definition of a pharmaceutically acceptable carrier.

Example 1

Identification of Amino Acid Sequences Binding to MHC Class II Molecules

A number of 15-mer peptides were initially identified in silico from the S. aureus proteomes.

Also, a number of putative scaffold proteins were identified, leaving out potentially toxic or otherwise harmful scaffold proteins. The initial 15-mer peptides were selected based on the probability that they would bind several MHC Class II allelic variants and also based on their degree of non-similarity with the human proteome. Finally, each 15-mer was mapped to a proteome and evaluated relative to normalized expression data of the proteome member in S. aureus. The total number of 15-mer peptides selected was 50.

The 50 selected peptides were subsequently tested in vitro for MHC Class II binding:

As the peptide:MHCII complex stability has been proven to be the main driver of immunogenicity, the 50 selected epitopes were subjected to analysis by Immunitrack (Biocenter of Copenhagen, Ole Maaloes Vej 5, DK-2200 Copenhagen N, Denmark) by measuring the stability of the peptide:DRB1*01:01 complex, the peptide:DRB1*04:01 complex, and the peptide:DRB5*01:01 complex.

12 out the 50 tested peptides did not form complexes with one or more of the 3 alleles. From the remaining 38 epitopes 20 (SEQ ID NOs: 21-40) were categorized as forming stable or very stable complexes with all 3 alleles and were used for building epitope constructs.

Finally the 9 epitopes having SEQ ID NOs: 21, 23, 26, 27, 30, 33, 34, 38, and 40, and the 11 epitopes having SEQ ID NOs: 22, 24, 25, 28, 29, 31, 32, 35-37, and 39 were compiled into multiple different constructs using either an epitope on a string strategy (epitope-linker-epitope- . . . -) or by replacing known epitopes in the NCBI 53721566 protein with the nearest (in BLOSUM space) identified S. aureus epitope.

The constructs were finally submitted to 3 different solubility prediction servers and the 4 most soluble constructs were ordered from Genscript. The amino acid sequences of the resulting chimeric proteins are set forth in SEQ ID NOs: 41-44 (41 and 42 are "epitopes on a string" constructs, 43 and 44 are "epitopes in scaffold" constructs). For recombinant production, a start codon encoded Met was introduced in the N-terminus of the epitope on a string constructs (not shown in the SEQ ID NOs: 41 and 42).

Hence, 4 S. aureus T-helper cell epitope constructs were developed. Formalized together with the adjuvant CAF01 (Agger E M et al. PLoS ONE. 2008; 3(9): e3116) the constructs can elicit a Th1/Th17 response important for recurrent skin infection in humans, thereby supplementing the primarily antibody driven protection induced by protein vaccines.

Example 2

General Experimental Setup

Proteins of the invention were tested in two animal models: a skin abscess model and a sepsis model. In the following the general experimental details are provided.

1. Murine Model of Subcutaneous Skin Abscess Induced by S. aureus USA300

A number of polypeptides of the present invention were tested for their ability to interfere with subcutaneous skin abscess formation caused by S. aureus USA300; see the examples below.

Abbreviations Used:
BHI Brain-heart infusion
BW Body weight
DPBS Dulbecco's Phosphate-Buffered Saline
CFU Colony forming units
LB Luria-Bertani
ns Not significant
ON Over night
p.i. Post infection
rpm Revolutions per minute
SC Subcutaneous administration
TSA Tryptic Soy Agar
D Study Day
Materials and Methods
Microorganism:
S. aureus USA300 [Staphylococcus aureus subsp. aureus Rosenbach (ATCC® BAA-1717™)], Strain Designations: TCH1516 [USA300-HOU-MR]

Animals:
Female BALB/c Mice, obtained from Charles River Italy. Mice were 5 weeks at arrival. After arrival, the mice we acclimatized for 5 days. The mice were kept at 22° C.±2 and a relative humidity of 55%±10 in cages from TECNIPLAST S.p.A. Italy, (type III, polysulfone cage with a 3-4 cm thick Scobis Duo, Mucedola, Italy with provision of one cotton nestlet for nestmaking and a Des Res paper shelter (Lillico Serving Biotechnology, UK), as well as with ASPEN BLOCKS, MEDIUM (20×20×100 mm), LBS (Serving Biotechnology, UK). Air was changed 15-20 times per hour, and the lighting cycle was 12 hours light (7:00 to 19:00)/12 hours dark (19:00 to 7:00). The mice received ad libitum pelleted food for mice (SDS VRF 1 (P), UK) and ad libitum drinking water. At day 1 in all experiments, the mice were grouped randomly. Each mouse was identified by a number, as well as by a tail mark within the cage. Each single cage had a tag, indicating experiment number, progressive cage and animal numbers. All animals were subjected to a detailed physical examination by a veterinarian to ensure that they were in a good state of health prior to start of the study.

In the study in Example 3, the mice were female Tg (HLA-DRA/H2-Ea,HLA-DRB1*0401/H2-Eb) 1 Kito from Taconic, USA. Other procedures were otherwise as described in the present example.

Materials Used:

Narkamon (100 mg/mL ketamine chloride), Bioveta, a.s. Czech Republic, serial no 095322A, Exp. date 03/2017

Rompun 2%, Bayer, Leverkusen, Germany

Forane, ABBOTT, USA

Microtainer tubes, BD, ref. no. 365950.

CAF01 adjuvant (Agger E M et al. PLoS ONE. 2008; 3(9): e3116)

Bacterial Inoculum:

S. aureus USA300 was plated on blood agar TSA plate. The next day, one 50 mL Falcon tube containing 20 mL of LB broth was inoculated with one colony of S. aureus USA300 grown on blood agar. Bacterial culture was incubated in orbital shaker at 200 rpm/37° C./ON. After the overnight growth in liquid broth, bacteria were subcultured by diluting 1 mL of ON bacterial suspension in 100 mL of LB broth in an Erlenmeyer flask. Bacterial culture was incubated in orbital shaker till mid log phase at 200 rpm/37° C. Mid-log bacterial cultures were centrifuged 3× at 5000 g for 10 min at 4° C. and washed each time with sterile DPBS (without Ca and Mg). Pellet was finally re-suspended in 10× lower volume of sterile PBS (10 mL). One-hundred 100 microliter μL of prepared bacterial suspensions were given SC per animal (confirmed inoculum size was $5.6 \times 10^9$ cfu/animal). Actual inoculum size was confirmed by plating prepared suspensions on surface of Tryptic Soy Agar plate supplemented with 5% defibrinated sheep blood. Plates were incubated at 37° C. ON and colonies counted.

Immunization and Blood Sampling

Mice were immunized on D0, D14 and D28.

Each mouse was immunized with an SC injection of 100 μL of formulation/injection site. The amount of each protein in the formulation was 20 μg/mouse.

At D1 and D37 blood was obtained for serum preparation from all mice by puncturing the tail vein after warming in warming cabinet for 5 min/38° C. Sample size of whole blood was ≤100 μL. After collection, blood was centrifuged at 3500 rpm/15 min. Obtained serum samples were stored at −80° C.

Challenge Infection

Blinding procedure: One day prior to challenge, cages were labelled by a person not involved in the study and the cages were mixed in order. Original labels were marked with the assigned letter and kept away from the researchers performing the measurements. When the challenge had finished and all data collected, the cages/animals were revealed.

D41_preparing mice for the challenge: Mice were anaesthetized with ketamine+xylazine IP injection, the fur was shaved from the back of the mouse (3×4 cm), and the shaved area was disinfected with Pursept A, Schülz, Germany.

D42_challenge: Animals were weighed, 100 μL of bacterial suspension was injected SC into the middle of the shaved area, under light ketamine+xylazine anaesthesia, and mice were observed for 3-5 hours post challenge to ensure that all mice have recovered from anaesthesia.

D43-D52 (D1-D10 post challenge)_Abscess measurements, clinical observations and body weight recordings following challenge: Abscess measurement was performed on 7 time points in total, on study days 43, 44, 45, 46, 47, 48 and 52 (days 1, 2, 3, 4, 5, 6 and 10 following challenge). The measurements were performed under Isoflurane anesthesia using caliper and the values of width and length were captured in Excel spread sheet tables. Mice were monitored once daily for clinical signs and body weights were recorded on the day of challenge (day 42) and then on day 46 and 52. Data were collected into prepared Excel table. D52_Terminal procedures: At D52 mice were weighed and euthanized by CO2 asfixion.

Read-Outs

Abscess area (mm$^2$) (7 time points in total)

Body weights at D0, D42, D46 and D52

Data Analysis

Data was processed using Microsoft Excel SW. Statistical analyses and graphical presentation were performed using GraphPad Prism software (version 5.04). Differences between groups were considered statistically significant when p<0.05.

Animal Welfare

All animal related research was conducted in accordance with 2010/63/EU and National legislation regulating the use of laboratory animals in scientific research and for other purposes (Official Gazette 55/13). An Institutional Committee on Animal Research Ethics (CARE-Zg) oversees that animal related procedures are not compromising the animal welfare.

2. Murine Model of Peritonitis

Female NMRI mice were immunized with recombinant peptides in combination with the adjuvant CAF01 (cf. above). As control, the adjuvant alone was administered. Each mouse was immunized subcutaneously three times at approximately two week intervals. At each immunization the mice were immunized with a formulation of 100 μL CAF01 mixed with 20 μg peptide; protein was added to the adjuvant in small portions, and the tube gently flicked before adding additional protein. When the protein was mixed with the adjuvant 10 mM tris (pH 7.2) was added to attain a total injection volume of 200 μL per ani-mal.

Blood samples were collected from each animal approximately ten days after the last immunization for analysis of antibody titre. Blood samples were collected by tail vein puncture following a short exposure under a heat lamp. The blood was collected in Eppendorf tubes containing 5 μL 0.5 M EDTA and the sample mixed vigorously. The tubes were centrifuged at 1800×g for 10 minutes and the plasma fraction transferred to a new tube and stored at −80° C.

Four days before challenge, temperature transponders (BMDS, cat. no. IPTT-300) were inserted into each mouse. The mice were briefly anaesthetized by inhalation of isoflurane, and a temperature transponder inserted underneath the skin on the lower back or side of the mouse. Using a compatible wireless scanner (BMDS Smart Probe; BMDS, cat. no. DAS-7007s) body temperature could be registered when placing the scanner close to the transponders underneath the skin of the mouse.

Preparation of Bacterial Inoculum

The bacteria used in the animal model of peritonitis were prepared in advance and frozen at −80° C. in aliquots; bacterial matter was streaked out on a blood agar plate and incubated at 37° C. overnight. The following day, a single colony of S. aureus was used for the inoculation of 30 mL tryptic soy broth (TSB) media. The culture was incubated overnight at 37° C., with continuous shaking. The following day 1 L of TSB media was inoculated with 10 mL of the overnight culture and incubated at 37° C. under continuous shaking for 6 hours. The bacterial suspension was centrifuged at 3000×g for 10 minutes and the pellet washed twice in 400 mL sterile PBS. After each wash the bacterial suspension was centrifuged at 3000×g for 10 minutes. The bacterial pellet was resuspended in 10-15 mL PBS and glycerol added to a final concentration of 16%. The suspension was thoroughly mixed, aliquoted in 1 mL aliquots and stored at −80° C. The number of colony forming units (CFU) per mL was determined for the frozen stock, as aliquots were thawed on ice and serially diluted in sterile saline. The dilutions were plated on TSB agar plates and incubated overnight at 37° C. The number of CFU per mL was established the following day. The procedure was repeated with an additional aliquot to confirm homogeny among the aliquots. Immediately prior to challenge, aliquots were thawed and diluted in sterile saline to the desired number of CFU.

Challenge Setup

The mice were housed at the Biomedical Laboratory at the University of Southern Denmark.

The animals were kept in an environment characterized by a 12-hours light-dark cycle and temperature and humidity control. The mice had access to food and water ad libitum. The experimental procedures were carried out in accordance with the guidelines of the Danish National Animal Ethics Committee (license number 2015-15-0201-00680).

The experiments were performed in class 2 certified facilities at the Biomedical Laboratory. Each mouse was challenged intraperitoneally with $3.0 \times 10^9$ CFU *S. aureus* strain MRSA252 (lot #4). The seven days following the challenge, the mice were assessed daily to register symptoms and development of disease. To ensure a consistent evaluation of all animals, each animal was scored individually following the criteria for clinical symptoms set forth here:

0: No symptoms.

1: Decreased spontaneous activity, slightly ruffled fur, weight loss maximum 10%.

2: Decreased provoked activity, ruffled fur, weight loss maximum 15%.

3: Symptoms like 1 or 2 and/or semi-closed eyes, decreased food and water uptake, weight loss maximum 20%.

4: No activity when provoked, cold to the touch, no uptake of food and water, weight loss maximum 20%.

The mice were individually assessed on their physical appearance and behaviour, noting the presence or absence of the given characteristics.

Apart from the registration of clinical symptoms, body weight and temperature of each animal was registered daily following challenge. The weight loss was calculated as a percentage of the body weight registered prior to challenge. Animals were euthanized if either of the following humane endpoints were reached: a body temperature below 34° C. or a weight loss above 20% of the initial body weight. Additionally, mice scored 3 over three successive days, without signs of improvements such as weight gain, or 4 once were euthanized.

Example 3

Subcutaneous Skin Abscess Testing of Immunogens of the Present Invention

The proteins having SEQ ID NOs: 41-44 were subjected to the skin abscess testing described above in Example 2. One group of mice received a cocktail of the proteins having SEQ ID NOs: 41 and 44 ("Eden" group), the other group received a cocktail of the proteins having SEQ ID NOs. 42 and 43 ("NonEden" group). The mice received 50 µg of protein per injection (25 µg of each protein in the cocktail).

The most striking read-out of this study was that the Eden group which was vaccinated with the two immunogens having SEQ ID NO: 41 and 44 exhibited a mean abscess area expressed in $mm^2$ which was significantly ($p<0.05$) smaller than both the nonEden group receiving SEQ ID NO: 42 and 43 and a control group receiving adjuvant only.

Mean abscess area ($mm^2$)

| Group | Day 43 | Day 44 | Day 45 | Day 46 | Day 47 | Day 48 | Day 52 |
|---|---|---|---|---|---|---|---|
| Eden | 404.0 | 330.3 | 307.8 | 295.4 | 283.4 | 257.5 | 117.5 |
| NonEden | 433.2 | 419.3 | 371.3 | 360.6 | 349.8 | 309.4 | 154.2 |
| Control | 487.7 | 461.4 | 423.2 | 371.5 | 359.2 | 322.9 | 181.2 |

Adjuvant Control

The mean abscess areas in the group treated with CAF01 alone slowly decreased from 488 $mm^2$ (D1 p.i.) to 181 $mm^2$ (D10 p.i.).

EDEN and NonEDEN Formulations

In the EDEN immunized group, a maximal mean abscess area was observed at D1 p.i. (404 $mm^2$) and gradually decreased to 117 $mm^2$ on D10 p.i. Significantly smaller abscess areas were observed on D2 and D3 p.i., as compared to CAF01 adjuvant control. A decrease in the mean abscess area of 17% was observed already at D1 p.i. A further reduction in the mean abscess area was observed on D2 p.i. (28%) whilst a 35% of decrease on the last study day was observed, as compared to CAF01 adjuvant control mean abscess area values.

Maximum mean abscess areas in the NonEDEN CD4+ construct immunized group was reached at D1 p.i. (433 $mm^2$) after which it gradually decreased to 154 $mm^2$ at D10 p.i. A decrease in the mean abscess areas ranged from 11% on D1 p.i. to 15% at the end of the study (D10 p.i.), when compared to CAF01 adjuvant control mean abscess area values. However, these differences in mean abscess areas were not significant.

In conclusion, subcutaneous immunization with EDEN construct formulation (a mixture of SEQ ID NO: 41 and SEQ ID NO: 44) exhibited protective effect against *S. aureus* USA300 subcutaneous skin abscess formation in female Tg (HLA-DRA/H2-Ea,HLA-DRB1*0401/H2-Eb) 1 Kito mice.

Example 4

Subcutaneous Skin Abscess Testing of Immunogens of the Present Invention

In a series of experiments, the following constructs of the invention were tested in the skin abscess model detailed in Example 2:

1. CHIM 0992 0735 FS, CHIM 0992 0735 FL, CHIM 0735 0992 FL and CHIM 0992 2753 FS formulations (containing SEQ ID NOs. 12, 60, 59, and 64, respectively):

The recorded data for these formulations were as follows:

| | Average body weight (g) (mean ± SD) | | | | |
|---|---|---|---|---|---|
| Day | SEQ ID NO: 12 | SEQ ID NO: 60 | SEQ ID NO: 59 | SEQ ID NO: 64 | CAF01 |
| 0 | 17.4 ± 1.1 | 17.4 ± 1.1 | 17.5 ± 0.6 | 17.5 ± 1.3 | 17.4 ± 1.0 |
| 42 | 19.3 ± 1.0 | 19.0 ± 1.2 | 19.7 ± 1.1 | 20.0 ± 1.0 | 18.9 ± 1.6 |

-continued

| | Average body weight (g) (mean ± SD) | | | | |
|---|---|---|---|---|---|
| Day | SEQ ID NO: 12 | SEQ ID NO: 60 | SEQ ID NO: 59 | SEQ ID NO: 64 | CAF01 |
| 46 | 18.1 ± 1.0 | 17.8 ± 1.2 | 18.4 ± 1.3 | 18.4 ± 1.2 | 17.7 ± 1.3 |
| 52 | 19.5 ± 1.0 | 19.2 ± 1.3 | 19.7 ± 1.1 | 19.4 ± 1.2 | 18.9 ± 1.6 |

| Group (SEQ ID NO:) | D 43 | D 44 | D 45 | D 46 | D 47 | D 48 | D 52 |
|---|---|---|---|---|---|---|---|
| 12 | 209.9 | 187.5 | 170.9 | 154.9 | 134.5 | 111.4 | 74.6 |
| 60 | 349.2 | 282.8 | 257.9 | 233.7 | 215.2 | 200.9 | 142.0 |
| 59 | 391.7 | 338.0 | 320.2 | 301.3 | 273.6 | 260.4 | 178.1 |
| 64 | 295.3 | 268.0 | 247.6 | 225.2 | 198.9 | 179.2 | 132.8 |
| CAF01 (control) | 329.8 | 308.6 | 259.6 | 226.0 | 202.7 | 173.3 | 121.7 |

Bold letters: statistical significant reduction vs. control.

Observations:

In the CHIM_0992_0735_FS immunized group, a maximum mean abscess area was reached on D1 p.i. (210 mm$^2$) and was significantly smaller compared to the CAF01 control group (36%). The mean abscess area gradually decreased to 75 mm$^2$ at D10 p.i., corresponding to 39% reduction as compared to the CAF01 adjuvant control mean abscess area value. Significantly smaller abscess areas were observed between D1 (36%) and D2 (39%) as compared to the CAF01 adjuvant control group.

A maximum mean abscess area in the CHIM_0992_0735_FL immunized group was reached at D1 p.i. (349 mm$^2$) and when compared to the CAF01 control group, it was increased for 6%. The mean abscess area gradually decreased to 142 mm$^2$ at D10 p.i, increased for 17%, when compared to CAF01 adjuvant control mean abscess area value.

In the CHIM_0735_0992_FL immunized group, a maximum mean abscess area was reached at D1 p.i. (392 mm$^2$) after which it gradually decreased to 178 mm$^2$ at D10 p.i. An increase in the mean abscess areas ranged from 19% on D1 p.i. to 46% at the end of the study (D10 p.i.) was observed as compared to CAF01 adjuvant control mean abscess area value.

The mean abscess areas in the CHIM_0992_2753_FS immunized group reached maximum value on D1 p.i. (295 mm$^2$), and gradually decreased to a value of 133 mm$^2$ on D10 p.i. When compared to the CAF01 adjuvant control mean abscess area values, mean abscess areas ranged from decrease of 10% on D1 p.i. to increase of 9% at the end of the study (D10 p.i.).

A transient body weight loss was observed in all groups following challenge, with no statistical significance compared to the CAF01 control group.

Conclusion:

Single protein immunization with CHIM_0992_0735_FS resulted in statistically significant protection against *S. aureus* USA300 induced skin abscess formation on day 1 and day 2 post challenge, when compared to the CAF01 adjuvant control group, as revealed by the abscess areas measured during the 10-day period following SC challenge.

Immunization with the single protein CHIM_0992_0735_FL and CHIM_0992_2753_FS showed no protective effect against *S. aureus* USA300 induced skin abscess formation since abscess areas were similar to CAF01 control group during the whole course of the infection (10 days). In addition, immunization with single protein CHIM_0735_0992_FL showed no protective effect against *S. aureus* USA300 induced skin abscess formation, since abscess areas were increased when compared to the CAF01 adjuvant control group during the 10-day period following SC challenge.

In conclusion, immunization with the single protein CHIM_0992_0735_FS showed statistically significant protective effect on day 1 and day 2 following challenge with *S. aureus* USA300. Subcutaneous immunization with CHIM_0992_0735_FL, CHIM_0735_0992_FL and CHIM_0992_2753_FS as single protein formulations exhibited no significant protective effect in the same model.

2. M2863_SAR0992-1-409, USA300HOU_2637-28-439, and SAR0992-1-409 formulations (containing SEQ ID NOs. 85, 98, and 89, respectively):

The data obtained with these 3 protein formulations (SEQ ID NOs: 85, 98, and 89) provided no conclusive data, since animals immunized with did no exhibit any significant difference from control immunized animals.

3. Hla_H35L-27-319, SAR2635-1-199, CHIM_Hla_2753 FS, and CHIM_Hla_0735_FS formulations (containing SEQ ID NOs: 83, 93, 80, and 78, respectively):

The recorded data for these formulations were as follows:

| | Average body weight (g) (mean ± SD) | | | | |
|---|---|---|---|---|---|
| Day | SEQ ID NO: 83 | SEQ ID NO: 93 | SEQ ID NO: 80 | SEQ ID NO: 78 | CAF01 |
| 0 | 17.4 ± 1.3 | 18.3 ± 1.2 | 18.0 ± 1.1 | 17.9 ± 1.1 | 17.7 ± 1.6 |
| 42 | 18.9 ± 1.1 | 20.1 ± 0.9 | 19.4 ± 1.6 | 19.3 ± 1.3 | 18.9 ± 1.8 |
| 46 | 18.0 ± 1.3 | 18.6 ± 1.4 | 18.7 ± 1.6 | 18.7 ± 1.3 | 17.5 ± 1.8 |
| 52 | 18.9 ± 1.5 | 18.6 ± 1.4 | 19.8 ± 1.2 | 19.8 ± 1.6 | 17.9 ± 2.0 |

| Group (SEQ ID NO:) | D 43 | D 44 | D 45 | D 46 | D 47 | D 48 | D 52 |
|---|---|---|---|---|---|---|---|
| 83 | 124.7 | 111.2 | 99.4 | 98.5 | 93.4 | 76.0 | 38.8 |
| 93 | 569.6 | 703.1 | 660.5 | 584.8 | 546.5 | 509.8 | 433.8 |
| 80 | 135.6 | 109.4 | 105.7 | 97.3 | 79.0 | 66.9 | 43.3 |
| 78 | 109.9 | 78.3 | 73.8 | 66.4 | 56.9 | 45.9 | 28.3 |
| CAF01 (control) | 536.3 | 578.0 | 569.5 | 531.5 | 481.8 | 451.9 | 366.0 |

Bold letters: statistical significant reduction vs. control.

Observations:

In the SAR2635-1-199 immunized group, a maximal mean abscess area was reached at D2 p.i. (703 mm$^2$) and was significantly higher compared to the CAF01 control group (22%). The mean abscess area gradually decreased to 434 mm$^2$ at D10 p.i. When compared to CAF01 adjuvant control mean abscess area value, it was increased for 19% (not statistically significant).

A maximal mean abscess area in the Hla_H35L-27-319-immunized group was reached at D1 p.i. (125 mm$^2$) after which it gradually decreased to 39 mm$^2$ at D10 p.i. Decreases in the mean abscess areas ranged from 77% on D1 p.i. to 89% at the end of the study (D10 p.i.), when compared to CAF01 adjuvant control mean abscess area values and were statistically significant during the whole post-challenge course.

The mean abscess areas in the CHIM_Hla_2753_FS* immunized group reached a maximal value on D1 (136 mm$^2$), and gradually decreased to a value of 43 mm$^2$ on D10. Significantly smaller abscess areas were observed between D1 (75%) and D10 (88%) as compared to the CAF01 adjuvant control group.

The mean abscess areas in the CHIM_Hla_0735_FS immunized group reached a maximal value on D1 p.i. (110 mm$^2$), and gradually decreased to a value of 28 mm$^2$ at D10 p.i. When compared with CAF01, statistically significant decreases in the abscess areas between D1 (80%) and D10 (92%) were observed.

Conclusions:

A transient body weight loss was observed in all groups following challenge. An evident improvement in clinical status of the protein immunized animals was noticed up to D52, as revealed by the statistically significant increases in body weights in CHIM_Hla_2753_FS* and CHIM_Hla_0735_FS immunized groups on D52.

Immunization with Hla_H35L-27-319, CHIM_Hla_2753_FS or CHIM_Hla_0735_FS as single protein formulations resulted in statistically significant protection against *S. aureus* USA300 induced skin abscess formation, when compared to the CAF01 adjuvant control, as revealed by the abscess areas measured during the 10 day period following SC challenge.

Single protein immunization with SAR2635-1-199 demonstrated no protective effect against *S. aureus* USA300 induced skin abscess formation, when compared to the CAF01 adjuvant control group, since mean abscess areas measured during the 10 day period following SC challenge were similar between these two groups. However, it should be noted that the group immunized with SAR2635-1-199 included only 11 mice in the abscess measurements since 5 mice had died during the course of the experiment (either during the challenge preparation phase or following the challenge).

In conclusion, subcutaneous vaccination with Hla_H35L-27-319, CHIM_Hla_2753_FS or CHIM_Hla_0735_FS as single protein formulations exhibited protective effect against *S. aureus* USA300 subcutaneous skin abscess formation in female BALB/c mice. However, immunization with SAR2635-1-199 formulation showed no protective effect in the same model.

4. CHIM_1262_2496_RS, CHIM_2716_2753_FL, CHIM_2723_2753_S_FS, and CHIM_2723_2753_L_FS formulations (containing SEQ ID NOs: 65, 14, 77, and 15, respectively):

Subcutaneous immunization with CHIM_2723_2753_S_FS, CHIM_1262_2496_RS, CHIM_2716_2753_FL or CHIM_2723_2753_L_FS as single protein formulation exhibited no significant protective effect against *S. aureus* USA 300 subcutaneous skin abscess formation in female BALB/c mice.

5. CHIM_2723_2635_FS, CHIM_2723_2635_RL, CHIM_2635_2723_FS, and CHIM_Hla_2635_FS formulations (containing SEQ ID NOs: 74, 75, 70, and 79, respectively):

The recorded data for these formulations were as follows:

| | Average body weight (g) (mean ± SD) | | | | |
|---|---|---|---|---|---|
| Day | SEQ ID NO: 74 | SEQ ID NO: 75 | SEQ ID NO: 70 | SEQ ID NO: 79 | CAF01 |
| 0 | 18.2 ± 1.2 | 17.6 ± 1.1 | 17.8 ± 0.8 | 18.2 ± 1.0 | 18.1 ± 0.9 |
| 42 | 18.3 ± 1.4 | 18.2 ± 0.9 | 19.1 ± 0.8 | 19.7 ± 1.1 | 18.6 ± 0.8 |
| 46 | 18.7 ± 1.6 | 17.9 ± 1.6 | 18.9 ± 0.8 | 19.7 ± 0.8 | 18.4 ± 1.0 |
| 52 | 19.8 ± 1.6 | 18.6 ± 1.2 | 19.8 ± 0.9 | 20.7 ± 0.9 | 18.8 ± 1.3 |

| Group (SEQ ID NO:) | D 43 | D 44 | D 45 | D 46 | D 47 | D 48 | D 52 |
|---|---|---|---|---|---|---|---|
| 74 | 261.6 | 220.5 | 216.2 | 207.8 | 190.7 | 167.2 | 78.1 |
| 75 | 402.6 | 391.4 | 379.8 | 371.0 | 347.8 | 318.7 | 201.3 |
| 70 | 312.3 | 272.6 | 265.6 | 257.6 | 237.1 | 211.7 | 86.5 |
| 79 | 24.8 | 31.6 | 20.7 | 17.4 | 18.9 | 9.7 | 3.8 |
| CAF01 (control) | 412.0 | 402.5 | 389.5 | 367.3 | 335.2 | 296.2 | 161.3 |

Bold letters: statistical significant reduction vs. control.

Observations:

In the CHIM_2723_2635_FS immunized group, a maximum mean abscess area was reached at D1 p.i. (262 mm$^2$) and gradually decreased to 78 mm$^2$ at D10 p.i. Significantly smaller abscess areas were observed from D1 until D6 p.i., as compared to CAF01 adjuvant control. A decrease in the mean abscess area of 37% was observed already at D1 p.i. A reduction in the mean abscess area continued at D2 p.i. (45%) and ended with a 52% of decrease on the last study day, when compared to CAF01 adjuvant control mean abscess area value.

A maximum mean abscess area in the CHIM_2723_2635_RL*-immunized group was reached at D1 p.i. (403 mm$^2$) after which it gradually decreased to 201 mm$^2$ at D10 p.i. A change in the mean abscess areas ranged from 2% reduction on D1 p.i. to 25% increase at the end of the study (D10 p.i.), when compared to the CAF01 adjuvant control mean abscess area value (not statistically significant).

The mean abscess areas in the CHIM_2635_2723_FS immunized group reached maximum value at D1 (312 mm$^2$), and gradually decreased to value of 87 mm$^2$ at D10. Significantly smaller mean abscess areas were observed on D2 (32%) and D3 (32%) as compared to the CAF01 adjuvant control group.

In the CHIM_Hla_2635_FS immunized group, only three animals developed measurable abscesses after challenge with *S. aureus* USA300 on D42. The mean abscess areas reached maximum value on D2 p.i. (32 mm$^2$), and gradually decreased to value of 3.8 mm$^2$ on D10 p.i. When compared to the CAF01 immunized group, a statistically significant decrease in abscess areas between D1 (94%) and D6 (97%) was observed.

Conclusions:

Immunization with CHIM_2723_2635_FS, CHIM_2635_2723_FS or CHIM_Hla_2635_FS as single protein formulations, resulted in statistically significant protection against *S. aureus* USA300 induced skin abscess formation, when compared to the CAF01 adjuvant control, as revealed by the abscess areas measured during the 10 day period following SC challenge.

Immunization with the single protein CHIM_2723_2635_RL* showed no protective effect against *S. aureus* USA300 induced skin abscess formation, since abscess areas were similar to the CAF01 Control group during the whole course of the infection (10 days).

Although immunizations with CHIM_2723_2635_FS, CHIM_2635_2723_FS or CHIM_Hla_2635_FS as single antigens demonstrated significant protective effects when compared to the CAF01 Control treated group, CHIM_Hla_2635_FS formulation showed superior protective effect compared to the other two. Namely, only three animals of sixteen in this group formed abscesses following bacterial infection.

In conclusion, subcutaneous immunization with CHIM_2723_2635_FS, CHIM_2635_2723_FS or CHIM_Hla_2635_FS as single protein formulations exhibited protective effect against *S. aureus* USA300 subcutaneous skin abscess formation in female BALB/c mice. Immunization with CHIM_Hla_2635_FS showed superior protective effect in comparison to the other single protein vaccines tested in this study.

6. CHIM_2496_1816_FS, CHIM_2716_1816_FS, CHIM_2119_1816_FS, and CHIM_1816_2119_FL formulations (containing SEQ ID NOs: 69, 71, 68, and 67, respectively):

The recorded data for these formulations were as follows:

| | Average body weight (g) (mean ± SD) | | | | |
|---|---|---|---|---|---|
| Day | SEQ ID NO: 69 | SEQ ID NO: 71 | SEQ ID NO: 68 | SEQ ID NO: 67 | CAF01 |
| 0 | 18.8 ± 0.9 | 18.4 ± 1.0 | 18.3 ± 2.2 | 18.0 ± 1.1 | 18.1 ± 1.2 |
| 42 | 19.7 ± 1.2 | 19.5 ± 1.0 | 20.0 ± 1.5 | 19.1 ± 1.1 | 19.7 ± 1.0 |
| 46 | 19.0 ± 1.1 | 18.9 ± 1.2 | 19.2 ± 1.8 | 18.3 ± 1.1 | 18.7 ± 1.2 |
| 52 | 19.4 ± 1.4 | 19.7 ± 1.3 | 19.7 ± 1.9 | 19.0 ± 1.3 | 19.2 ± 1.7 |

| Group (SEQ ID NO:) | D 43 | D 44 | D 45 | D 46 | D 47 | D 48 | D 52 |
|---|---|---|---|---|---|---|---|
| 69 | 318.13 | 323.09 | 316.27 | 318.96 | 293.22 | 267.49 | 151.96 |
| 71 | 238.85 | 251.02 | 238.70 | 234.58 | 211.71 | 184.19 | 101.06 |
| 68 | 285.08 | 290.30 | 282.47 | 271.78 | 249.21 | 198.54 | 106.64 |
| 67 | 349.23 | 367.45 | 343.32 | 342.03 | 323.58 | 271.68 | 170.51 |
| CAF01 (control) | 407.94 | 415.30 | 409.76 | 374.86 | 348.01 | 296.51 | 187.48 |

Bold letters: statistical significant reduction vs. control.

Observations:

In the CHIM_2496_1816_FS vaccinated group, maximum mean abscess area was reached at D2 p.i. (323.09 mm$^2$) and gradually decreased to 151.96 mm$^2$ at D10 p.i. A reduction in the mean abscess areas ranged from 22% on D1 p.i. to 10% at the D6 p.i. and ended with 19% (D10 p.i.), when compared to CAF01 adjuvant control mean abscess area values.

Significantly smaller abscess areas were observed from D1 (238.85 mm$^2$) until D5 (211.71 mm$^2$) p.i. in CHIM_2716_1816_FS vaccined group, as compared to CAF01 adjuvant control. A decrease in the mean abscess area of 41% was observed already at D1 p.i. Reduction in the mean abscess area started from D3 p.i. (42%) and ended with 46% of decrease at the last study day, as compared to CAF01 adjuvant control mean abscess area values.

A maximal mean abscess area in the CHIM_2119_1816_FS vaccine group was reached at D2 p.i. (290.30 mm$^2$) after which it gradually decreased to 106.64 mm$^2$ at D10 p.i. A reduction in the mean abscess areas ranged from 30% on D1 p.i. to 33% at the D6 p.i. and ended with 43% (D10 p.i.), when compared to CAF01 adjuvant control mean abscess area values.

The mean abscess areas in the CHIM_1816_2119_FL vaccinated group reached maximal value at D2 (367.45 mm$^2$), and gradually decreased to value of 170.51 mm$^2$ at D10. When compared to CAF01 adjuvant control mean abscess area values, a reduction in the mean abscess areas ranged from 14% on D1 p.i. and ended with 9% (D10 p.i.).

Conclusions:

A transient body weight loss was observed in all groups following infection. Slight improvement in clinical status and body weight was noticed in all groups up to D52.

Vaccination with CHIM_2496_1816_FS and CHIM_1816_2119_FL single protein vaccine resulted in poor protection of *S. aureus* USA300 induced skin abscess formation, when compared to the respective CAF01 adjuvant control, as revealed by the abscess areas measured during the 10 day period following SC infection. Vaccination with CHIM_2119_1816_FS single protein vaccine resulted in moderate protection of *S. aureus* USA300 induced skin abscess formation, when compared to the respective CAF01 adjuvant control. There was no statistically significant difference in the abscess areas between CHIM_2496_1816_FS, CHIM_2119_1816_FS and CHIM_1816_2119_FL and Control CAF01 group during the whole course of the infection (10 days).

Vaccination with CHIM_2716_1816_FS single protein vaccine resulted in strong, statistically significant protection of *S. aureus* USA300 induced skin abscess formation, when compared to the respective CAF01 adjuvant control.

In conclusion, subcutaneous vaccination with CHIM_2496_1816_FS, CHIM_2119_1816_FS and CHIM_1816_2119_FL single protein vaccine exhibited protective effect against *S. aureus* USA 300 subcutaneous skin abscess formation in BALB/c female mice but it was not statistically significant. In addition, vaccination with CHIM_2716_1816_FS vaccine showed statistically significant and strong protective effect against *S. aureus* USA 300 subcutaneous skin abscess formation in BALB/c female mice.

7. CHIM_0992_2635_FL, CHIM_0992_2635_FS, CHIM_1507_2119_FS, and CHIM_2716_2119_FS formulations (containing SEQ ID NOs: 17, 63, 66, and 72, respectively):

The recorded data for these formulations were as follows:

| | Average body weight (g) (mean ± SD) | | | | |
|---|---|---|---|---|---|
| Day | SEQ ID NO: 17 | SEQ ID NO: 63 | SEQ ID NO: 66 | SEQ ID NO: 72 | CAF01 |
| 0 | 17.5 ± 1.4 | 17.8 ± 1.4 | 16.9 ± 1.4 | 17.6 ± 1.7 | 16.7 ± 1.4 |
| 42 | 18.1 ± 1.7 | 18.8 ± 1.6 | 18.5 ± 1.5 | 19.5 ± 1.5 | 18.5 ± 1.4 |
| 46 | 17.7 ± 1.2 | 18.1 ± 1.6 | 17.5 ± 1.2 | 18.8 ± 1.8 | 17.1 ± 1.5 |
| 52 | 18.4 ± 1.3 | 18.8 ± 1.8 | 18.6 ± 1.4 | 19.1 ± 1.8 | 16.9 ± 1.6 |

| Group (SEQ ID NO:) | D 43 | D 44 | D 45 | D 46 | D 47 | D 48 | D 52 |
|---|---|---|---|---|---|---|---|
| 17 | 286.13 | 303.19 | 283.50 | 291.77 | 295.73 | 276.92 | 174.86 |
| 63 | 358.61 | 409.00 | 412.30 | 411.31 | 388.71 | 330.55 | 231.54 |
| 66 | 345.42 | 366.00 | 313.73 | 316.09 | 294.27 | 249.55 | 169.63 |
| 72 | 346.48 | 350.47 | 303.86 | 293.63 | 273.11 | 222.99 | 142.87 |
| CAF01 (control) | 465.22 | 503.18 | 459.02 | 471.18 | 428.15 | 396.98 | 250.19 |

Bold letters: statistical significant reduction vs. control.

Observations:

In CHIM_0992_2635_FL-vaccinated group, a maximal mean abscess area was reached at D2 p.i. (303.19 mm$^2$) and gradually decreased to 174.86 mm$^2$ at D10 p.i. Significantly smaller abscess areas were observed from D1 until D5 p.i. in CHIM_0992_2635_FL vaccinated group, as compared to CAF01 adjuvant control. A decrease in the mean abscess area of 38% was observed already at D1 p.i. A reduction in the mean abscess area started from D2 p.i. (40%) and ended with a 30% of decrease on the last study day, when compared to CAF01 adjuvant control mean abscess area values.

A maximum mean abscess area in the CHIM_0992_2635_FS vaccine group was reached at D3 p.i. (412.30 mm$^2$) after which it gradually decreased to 231.54 mm$^2$ at D10 p.i. A reduction in the mean abscess areas ranged from 23% on D1 p.i. to 7% at the end of the study (D10 p.i.), when compared to CAF01 adjuvant control mean abscess area values.

The mean abscess areas in the CHIM_1507_2119_FS vaccinated group reached maximal value at D2 (366 mm$^2$), and gradually decreased to value of 169.63 mm$^2$ at D10. Significantly smaller abscess areas were observed between D2 (27%) and D6 (37%) as compared to CAF01 adjuvant control.

The mean abscess areas in the CHIM_2716_2119_FS vaccinated group reached maximal value on D2 p.i. (350.47 mm$^2$), and gradually decreased to value of 142.87 mm$^2$ at D10 p.i. When compared with CAF01, a statistically significant decrease in abscess areas between D2 (30%) and D6 (44%) was observed.

Conclusions:

A transient body weight loss was observed in all groups following infection. However, it was less pronounced in the protein-vaccinated animals. In addition, an evident improvement in clinical status of the protein vaccinated animals was noticed up to D52.

Vaccination with CHIM_0992_2635_FL, CHIM_1507_2119_FS and CHIM_2716_2119_FS single protein vaccine resulted in strong, significant protection of S. aureus USA300 induced skin abscess formation, when compared to respective CAF01 adjuvant controls, as revealed by the abscess areas measured during the 10 day period following SC infection. There was no statistically significant difference in the abscess areas between CHIM_0992_2635_FS and Control CAF01 groups during the whole course of the infection (10 days).

Although vaccinations with these three single proteins resulted in significant protection when compared to Control CAF01 vaccinated group, CHIM_2716_2119_FS vaccine showed superior protective effect to other single proteins vaccines applied.

In conclusion, subcutaneous vaccination with CHIM_0992_2635_FL, CHIM_1507_2119_FS and CHIM_2716_2119_FS single protein vaccine exhibited protective effect against S. aureus USA 300 subcutaneous skin abscess formation in BALB/c female mice. In addition, vaccination with CHIM_2716_2119_FS vaccine showed superior protective effect to the other single proteins vaccines applied.

Example 5

Peritonitis Testing of Immunogens of the Present Invention

Figure 1B:
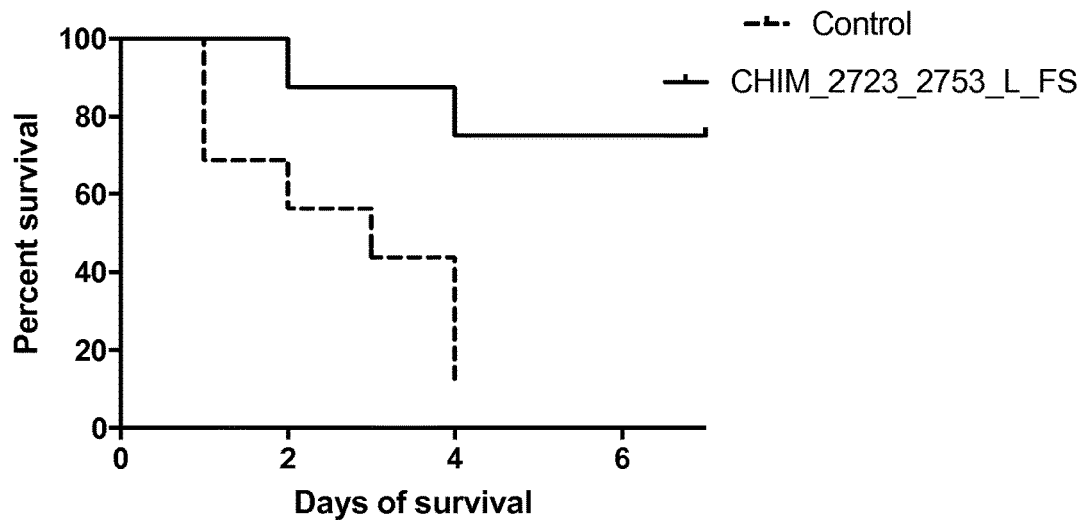
Figure 1B:
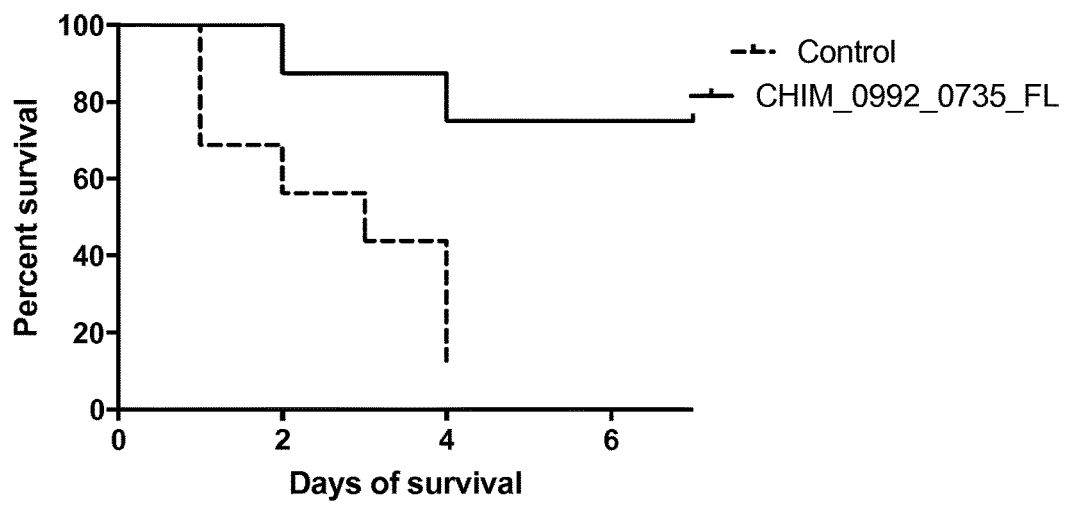
Figure 1B:
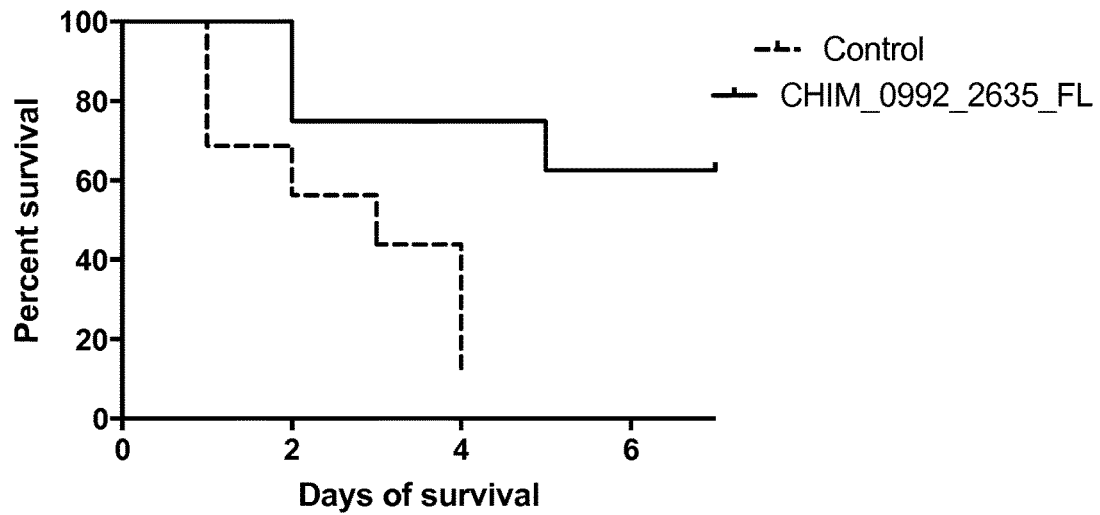
Figure 1C:
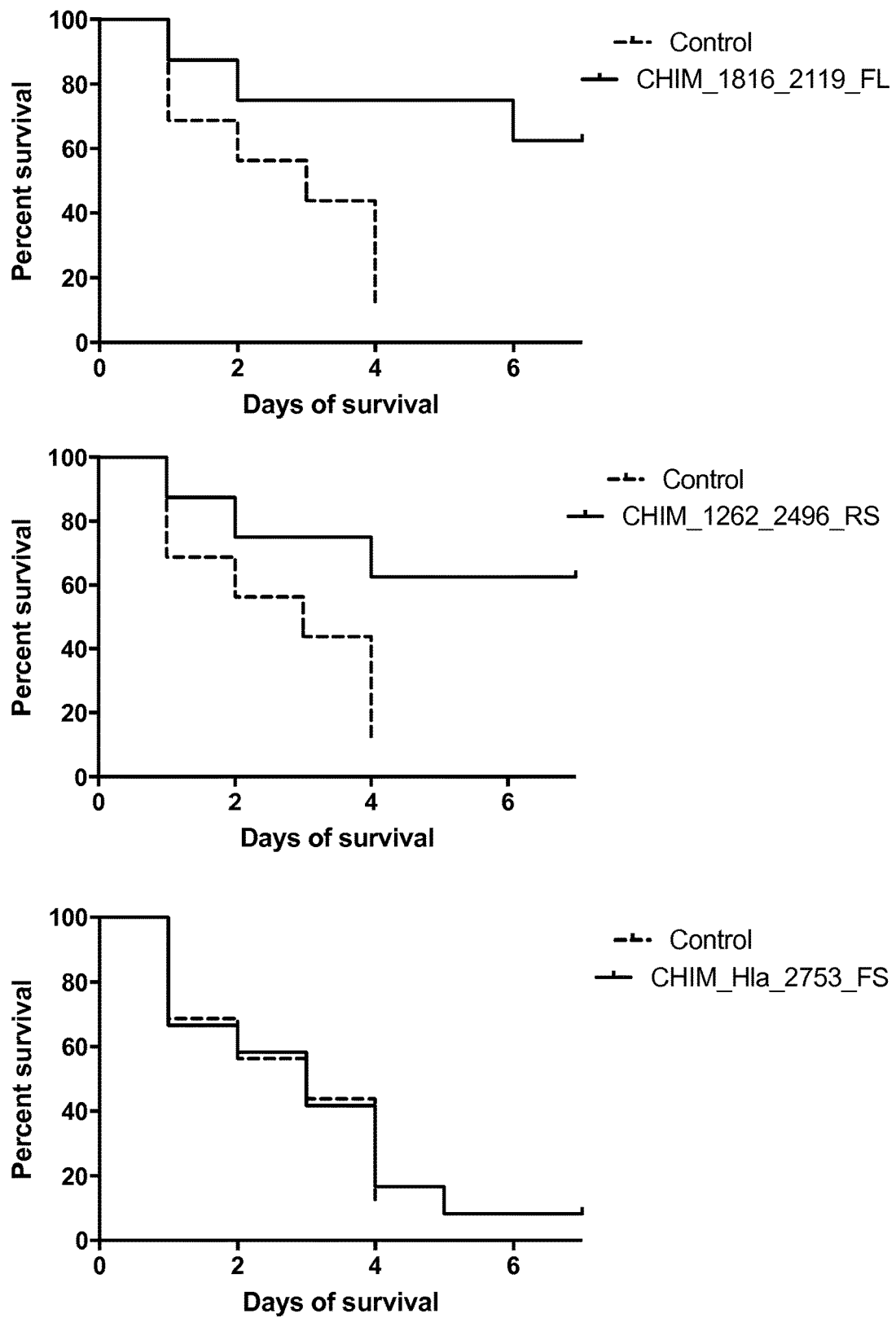
Figure 2A:
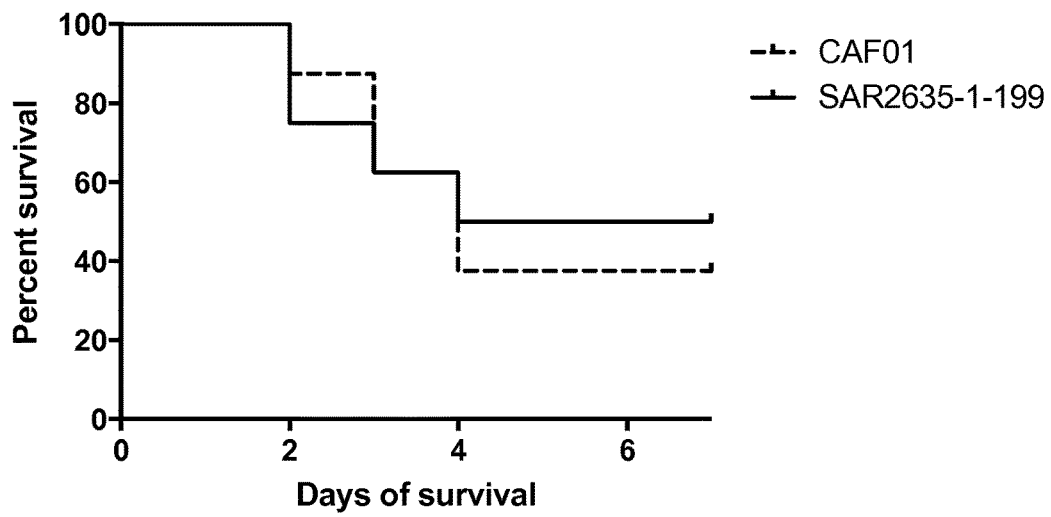
Figure 2A:
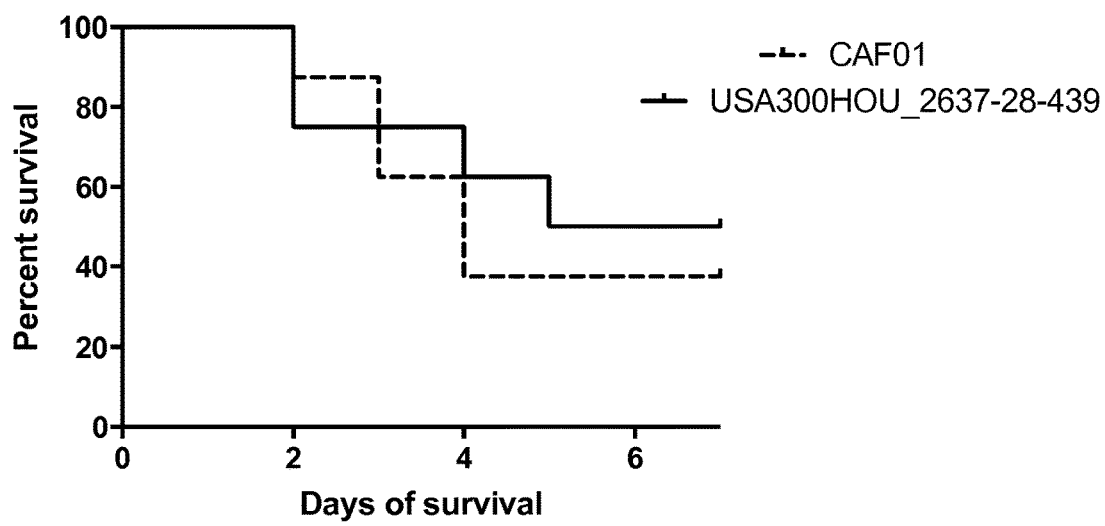
Figure 2A:
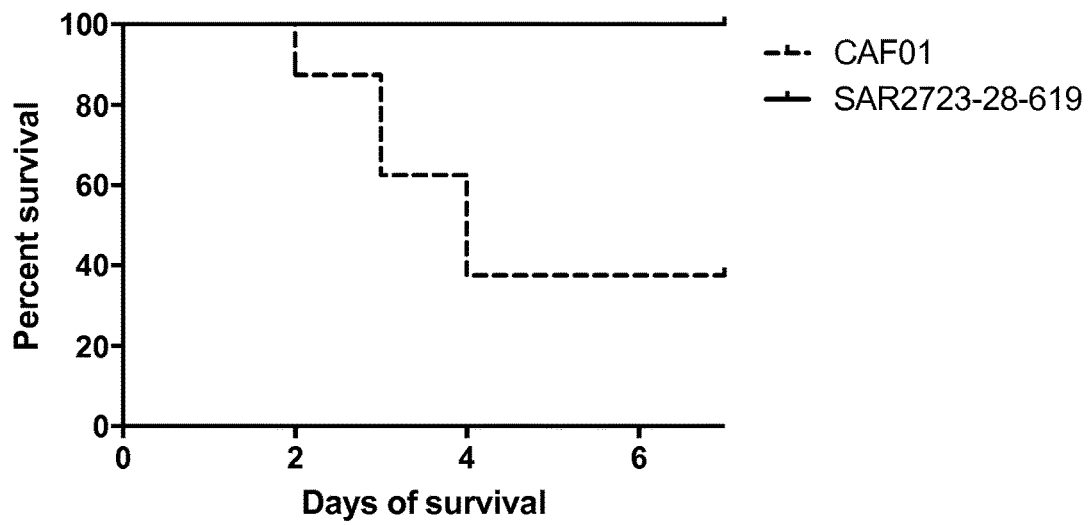
Figure 2B:
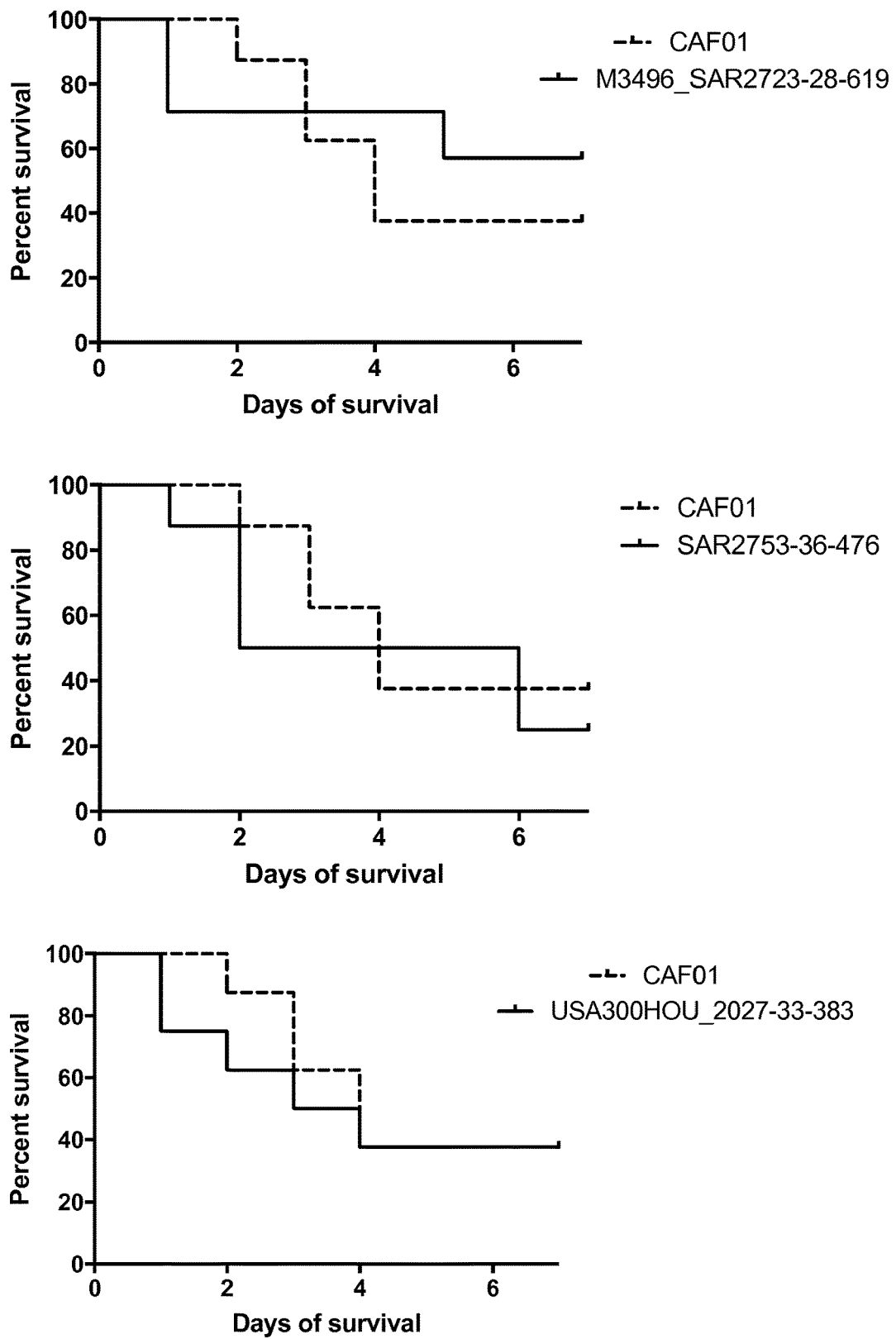
Figure 2C:
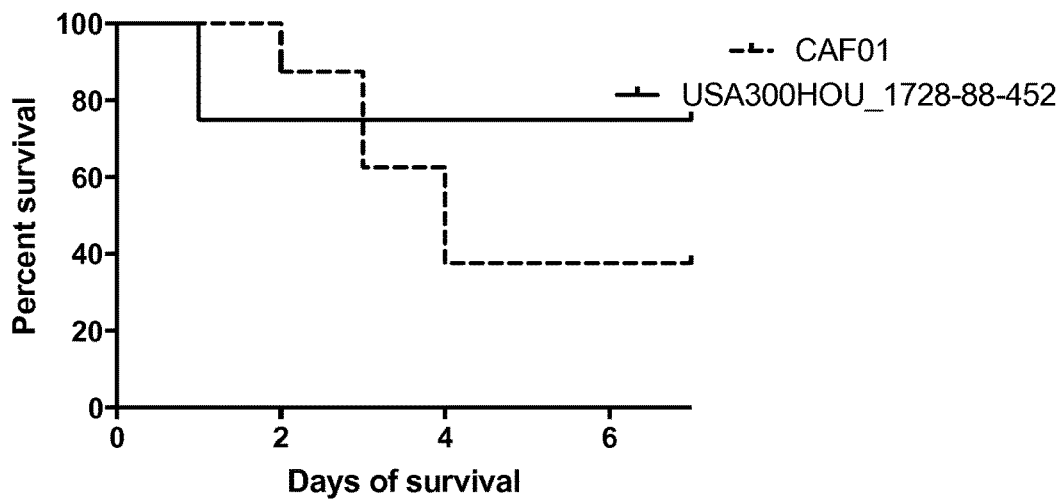
Figure 2C:
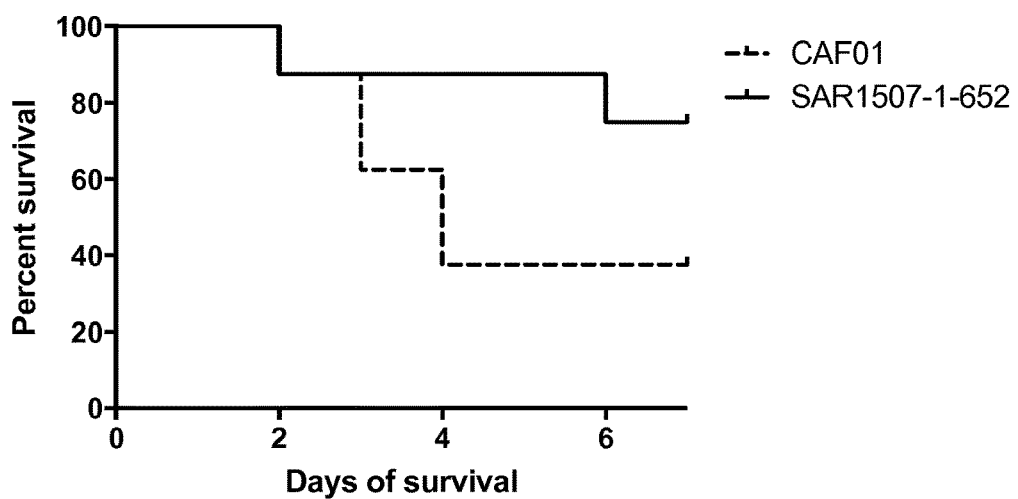
Figure 2C:
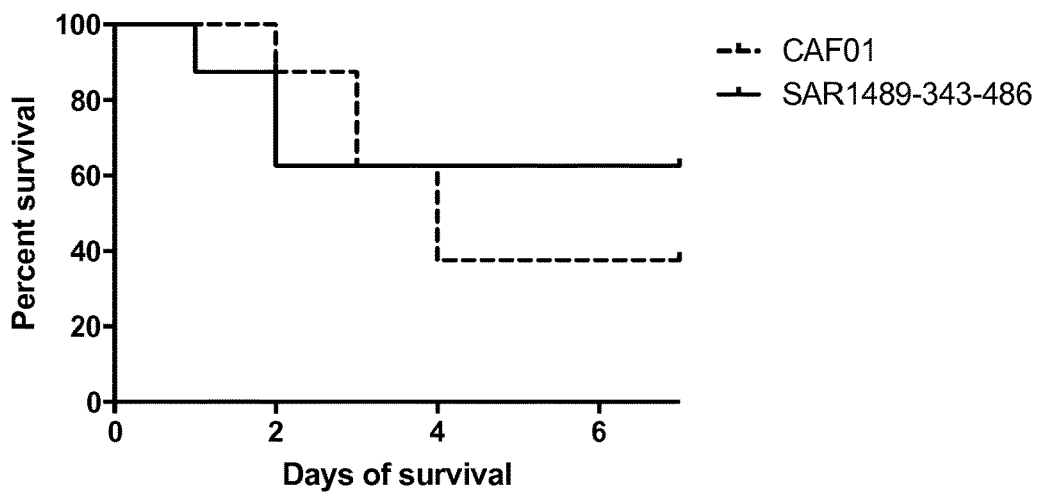
Figure 2D:
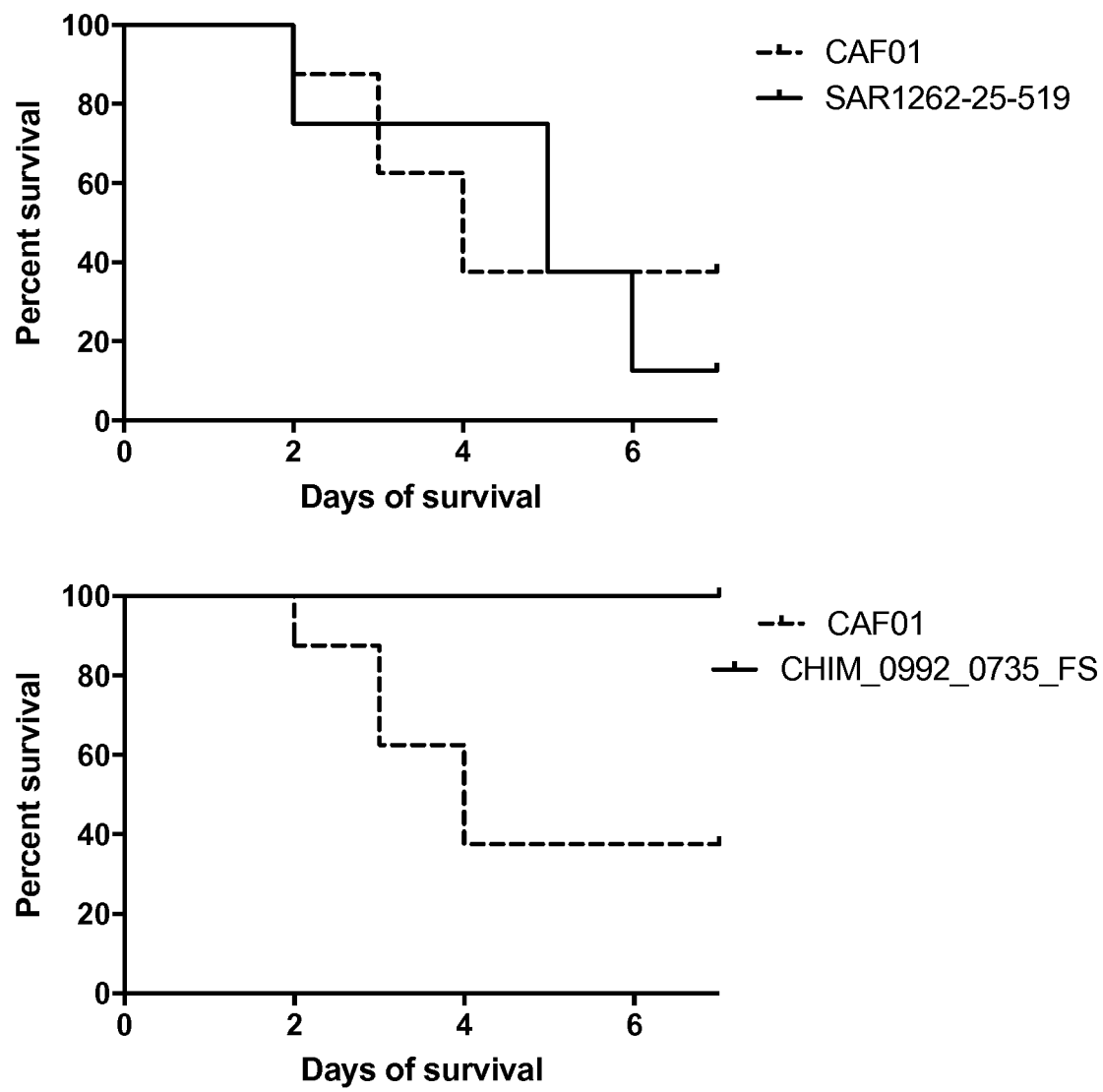

A number of the immunogens disclosed herein were tested in the peritonitis model described in Example 2 above:

1. CHIM_2635_2723_FS, CHIM_Hla_2635_FS, CHIM_2716_2753_FL, CHIM_2723_2753_L_FS, CHIM_0992_0735 FL, CHIM_0992_2635 FL, CHIM_1816_2119_FL, CHIM_1262_2496_RS, and CHIM_Hla_2753_FS formulations (containing SEQ ID NOs: 13, 79, 73, 76, 60, 62, 67, 65, and 80, respectively):

Survival of animals is provided for each of the immunogens in the survival plots in FIG. 1A-FIG. 1C. The results from the experiment show that immunization with either of CHIM_2635_2723_FS, CHIM_Hla_2635_FS, CHIM_2723_2753_L_FL, CHIM_0992_0735_FL, CHIM_0992_2635_FL, CHIM_1816_2119_FL, and CHIM_1262_2496_RS protected mice significantly against a lethal infection with S. aureus MRSA252 as compared to immunization with adjuvant alone.

2. SAR2635-1-199, USA300HOU 2637-28-439, SAR2723-28-619, M3496_SAR2723-28-619, SAR2753-36-476, USA300HOU 2027-33-383, USA300HOU 1728-88-452, SAR1507-1-652, SAR1489-343-486, SAR1262-25-519, and CHIM_0992_0735_FS formulations (containing SEQ ID NOS: 93, 98, 94, 86, 95, 97, 96, 92, 91, 90, and 12, respectively):

Survival of animals is provided for each of the immunogens in the survival plots in FIG. 2A-FIG. 2D. The results from the experiments show that immunization with either SAR2723-28-619 or CHIM_0992_0735_FS protected mice against a lethal challenge with S. aureus MRSA252 as compared to immunization with adjuvant alone.

Figure 3A:
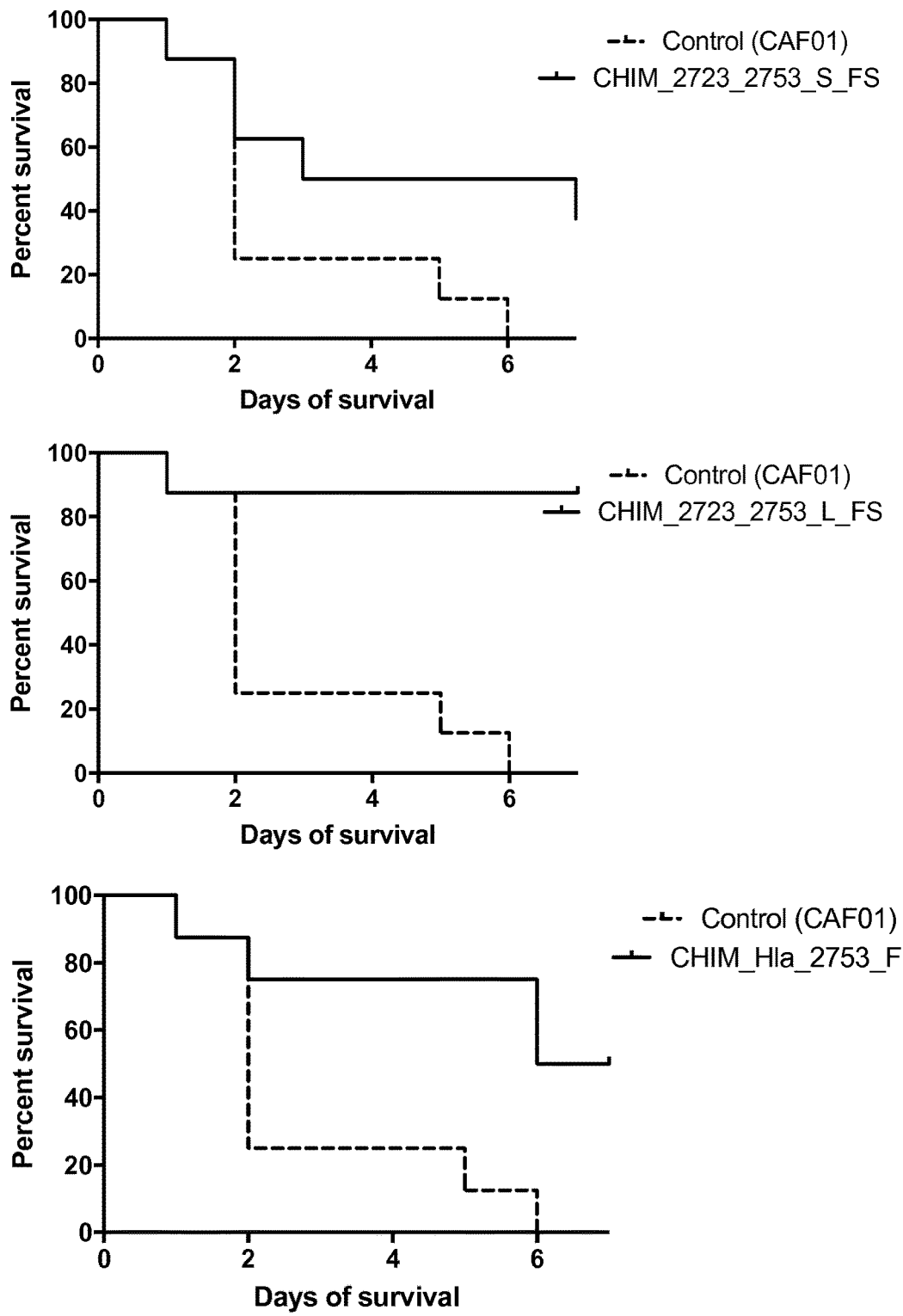
Figure 3B:
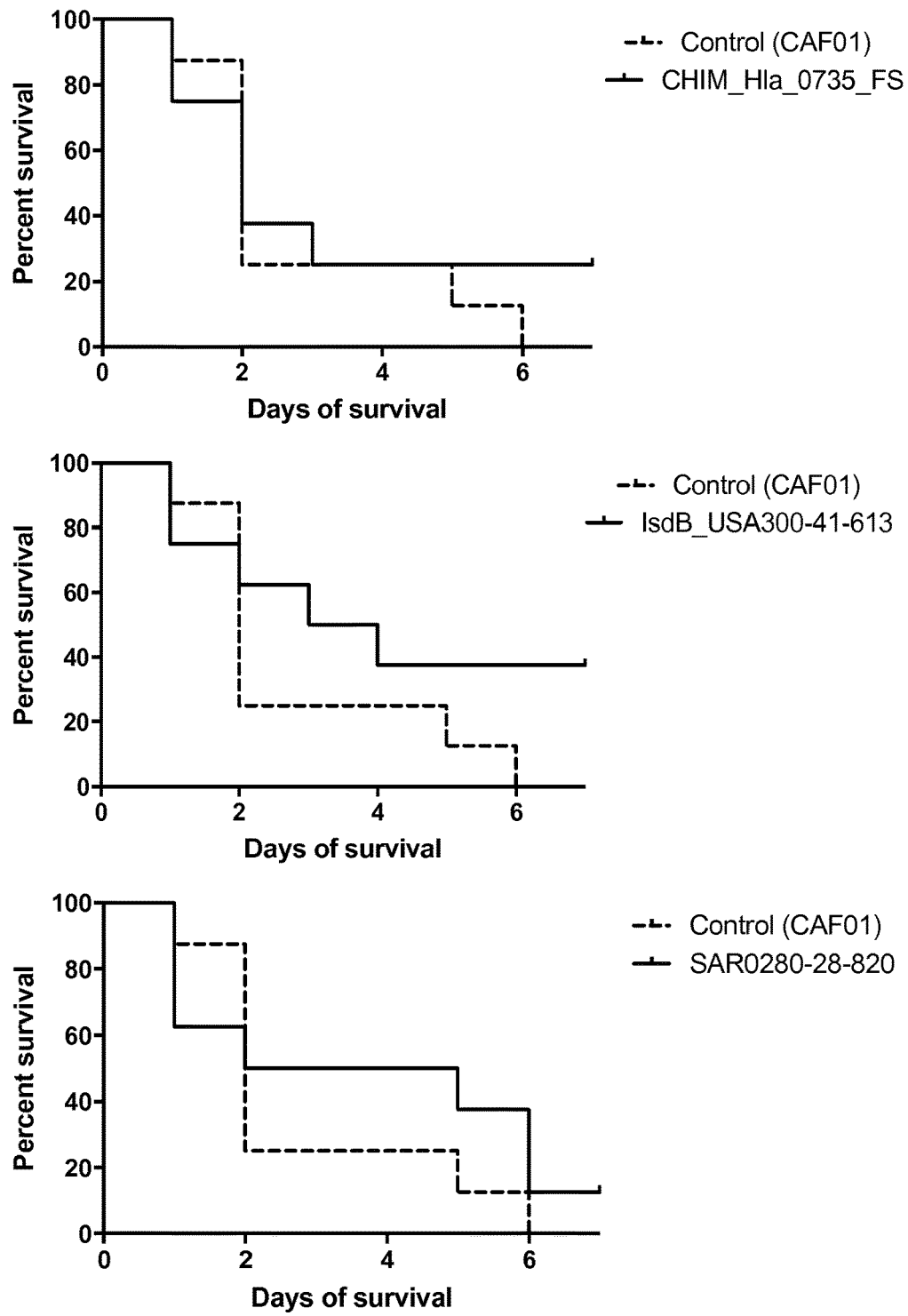
Figure 3C:
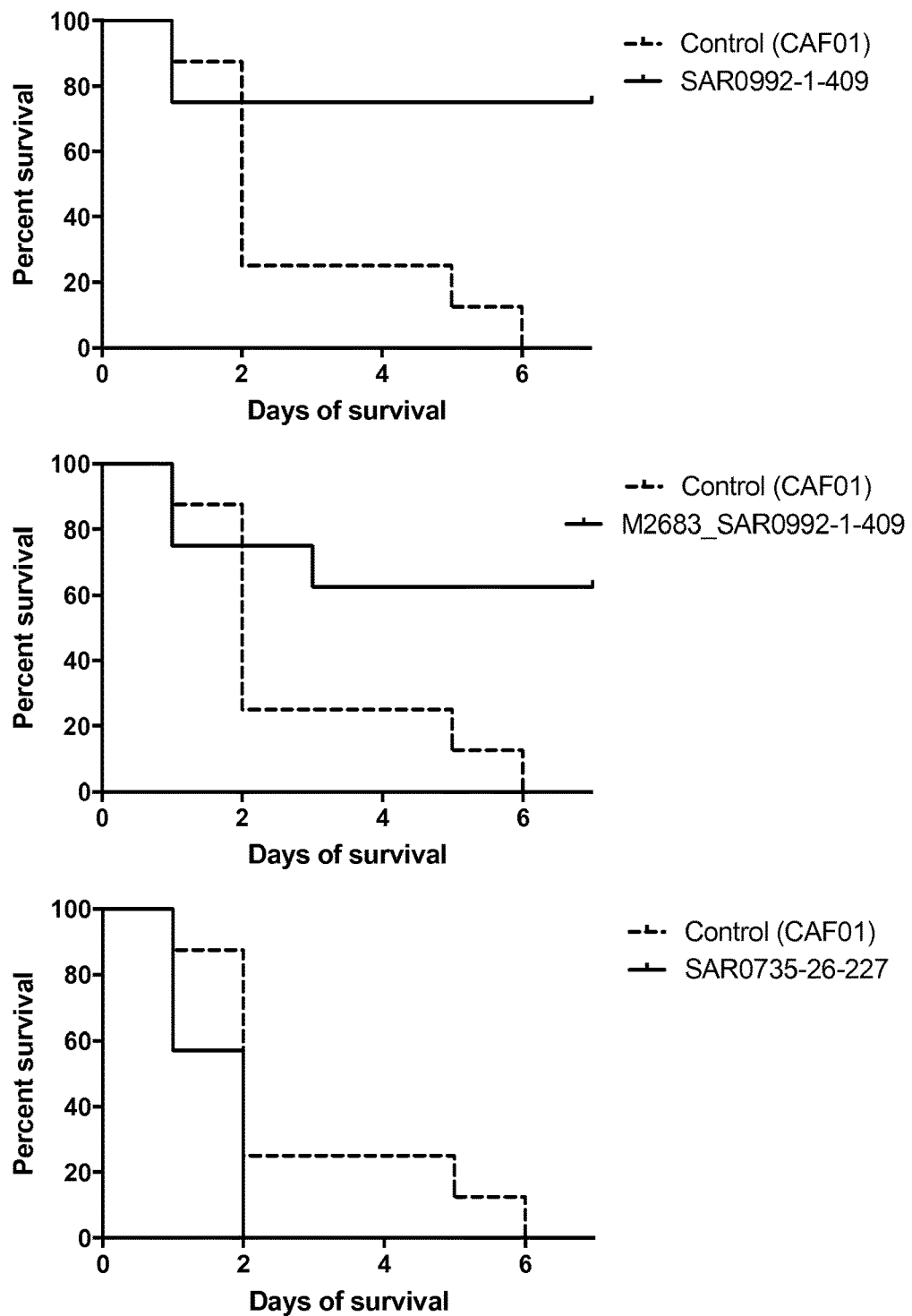
Figure 4A:
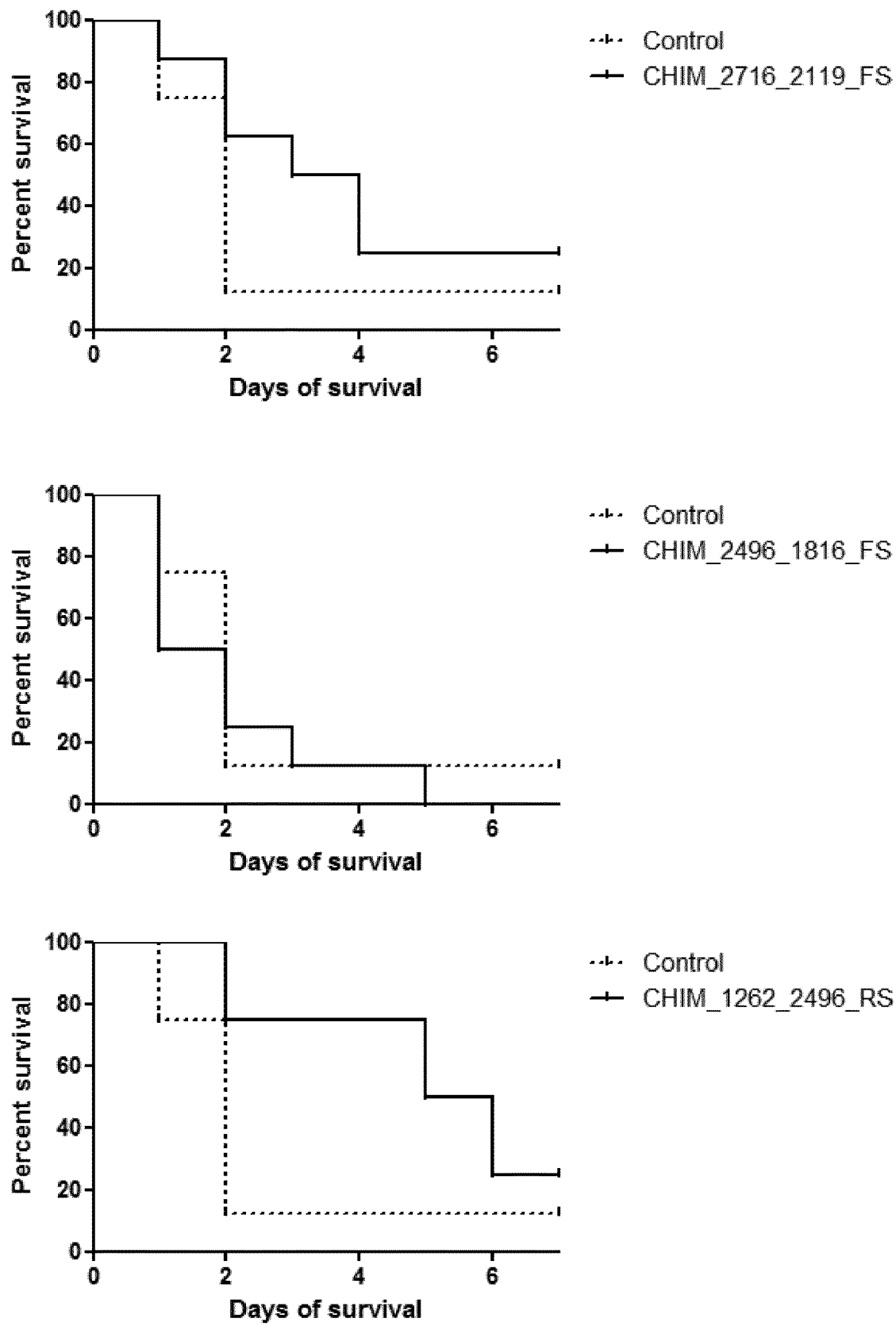
Figure 4B:
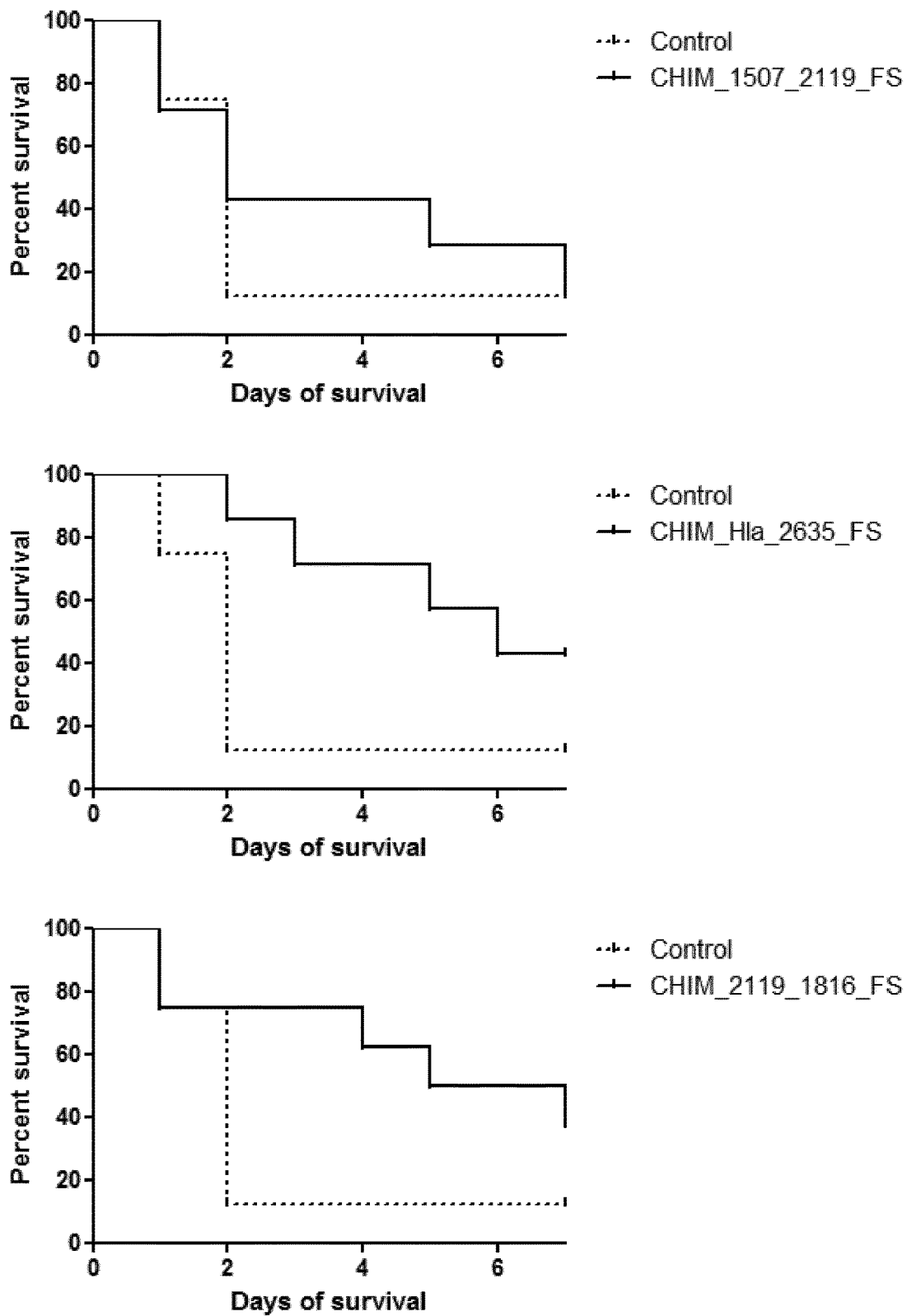
Figure 4C:
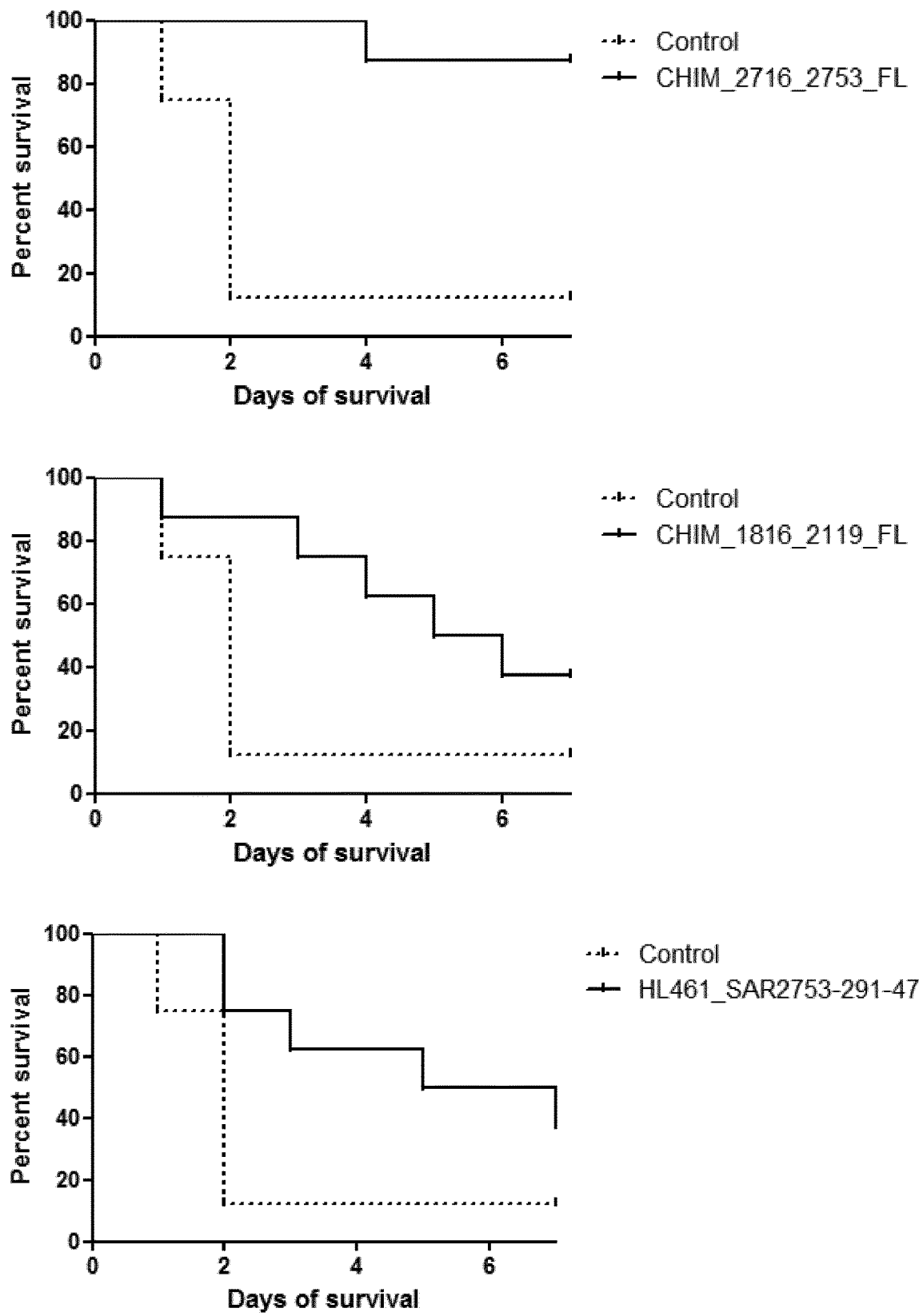
Figure 4D:
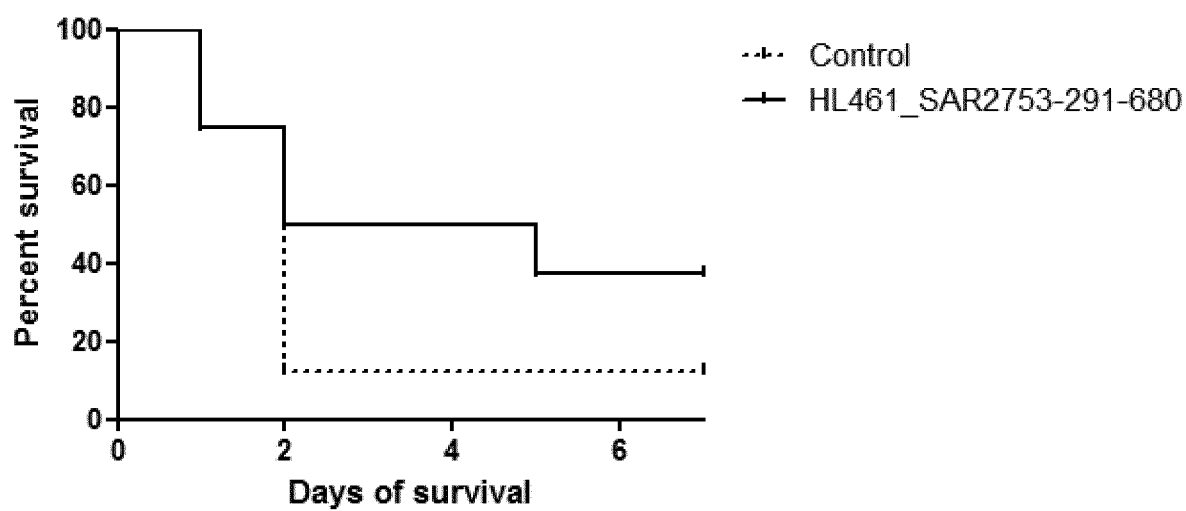
Figure 5A:
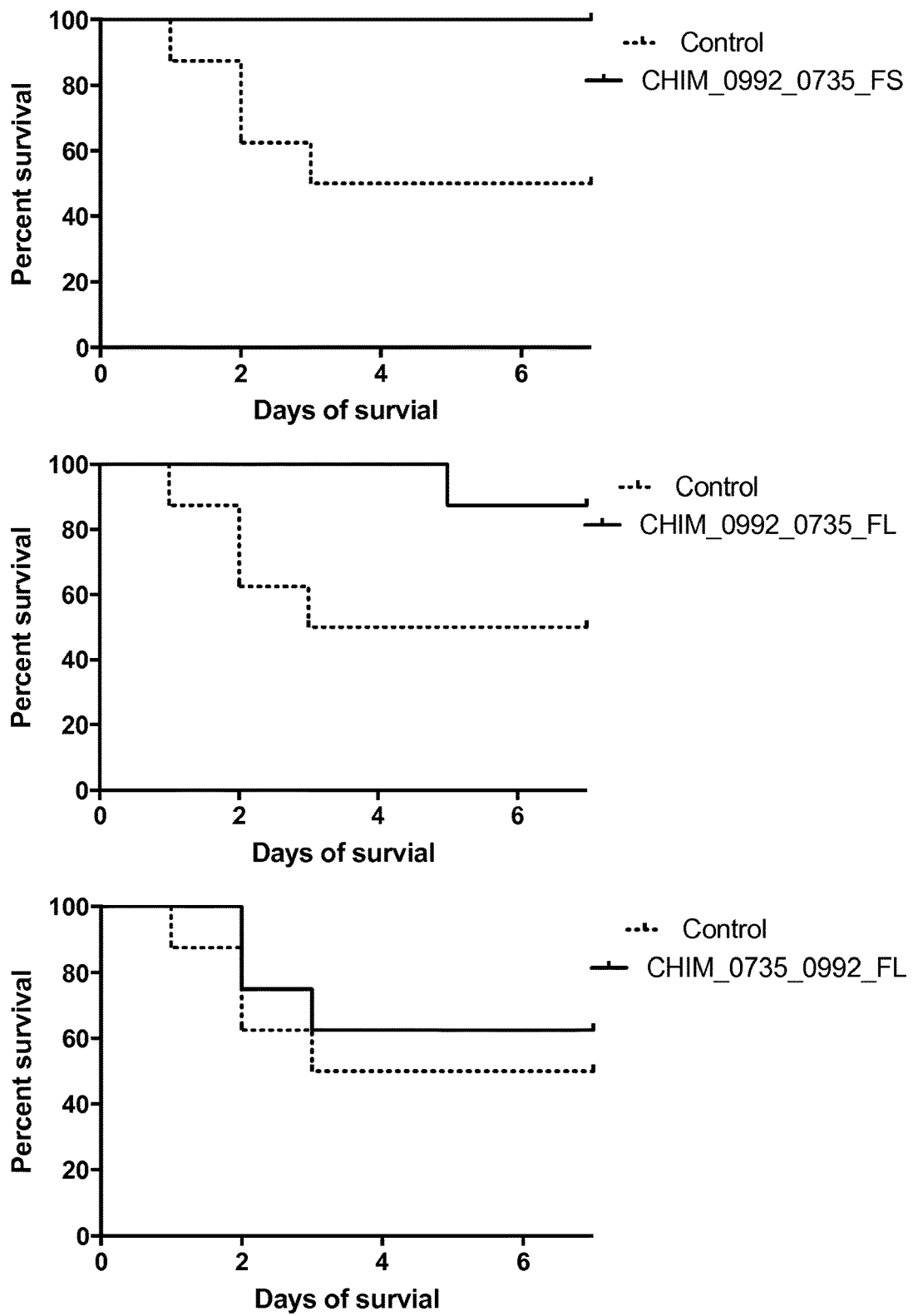
Figure 5B:
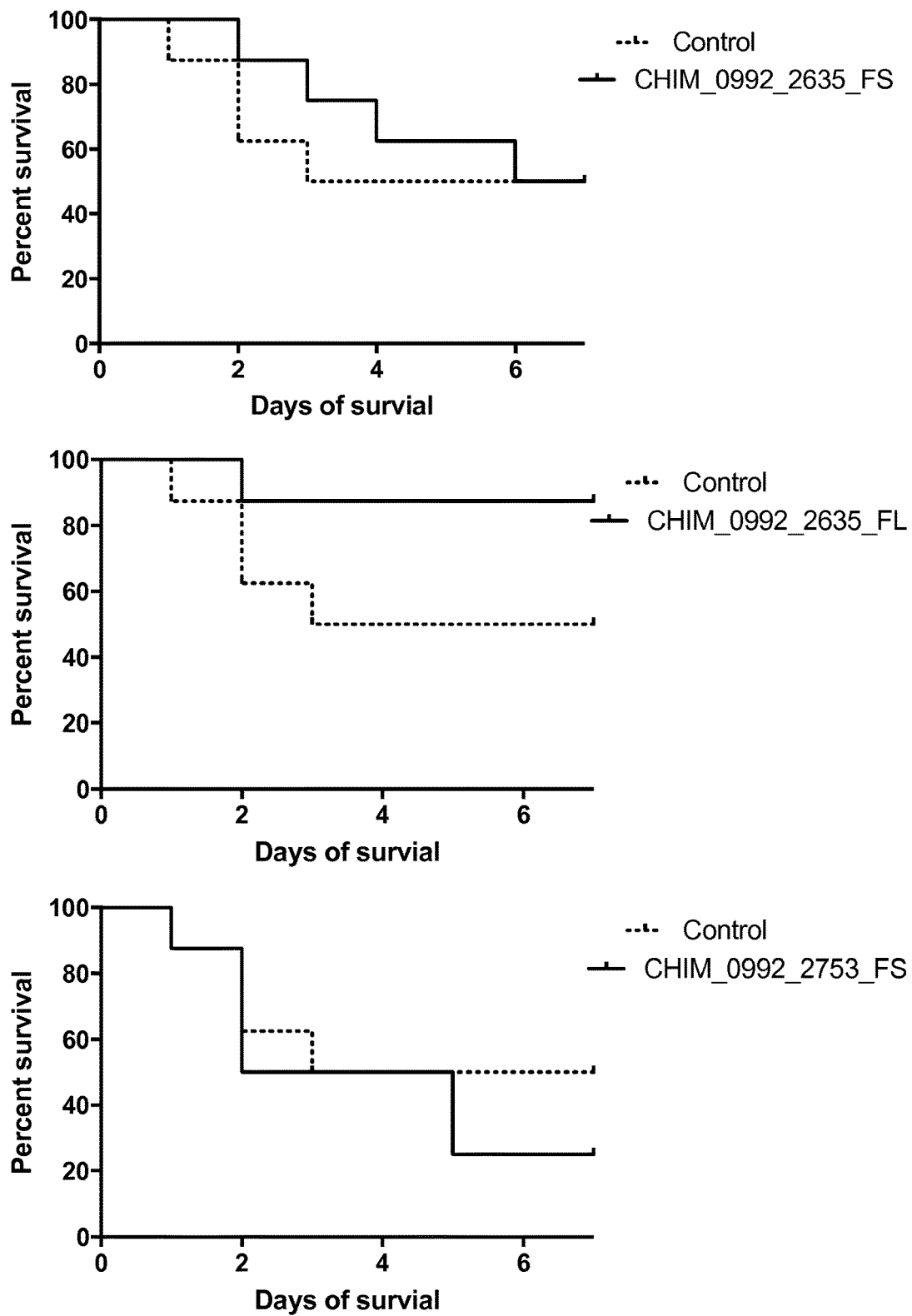
Figure 5C:
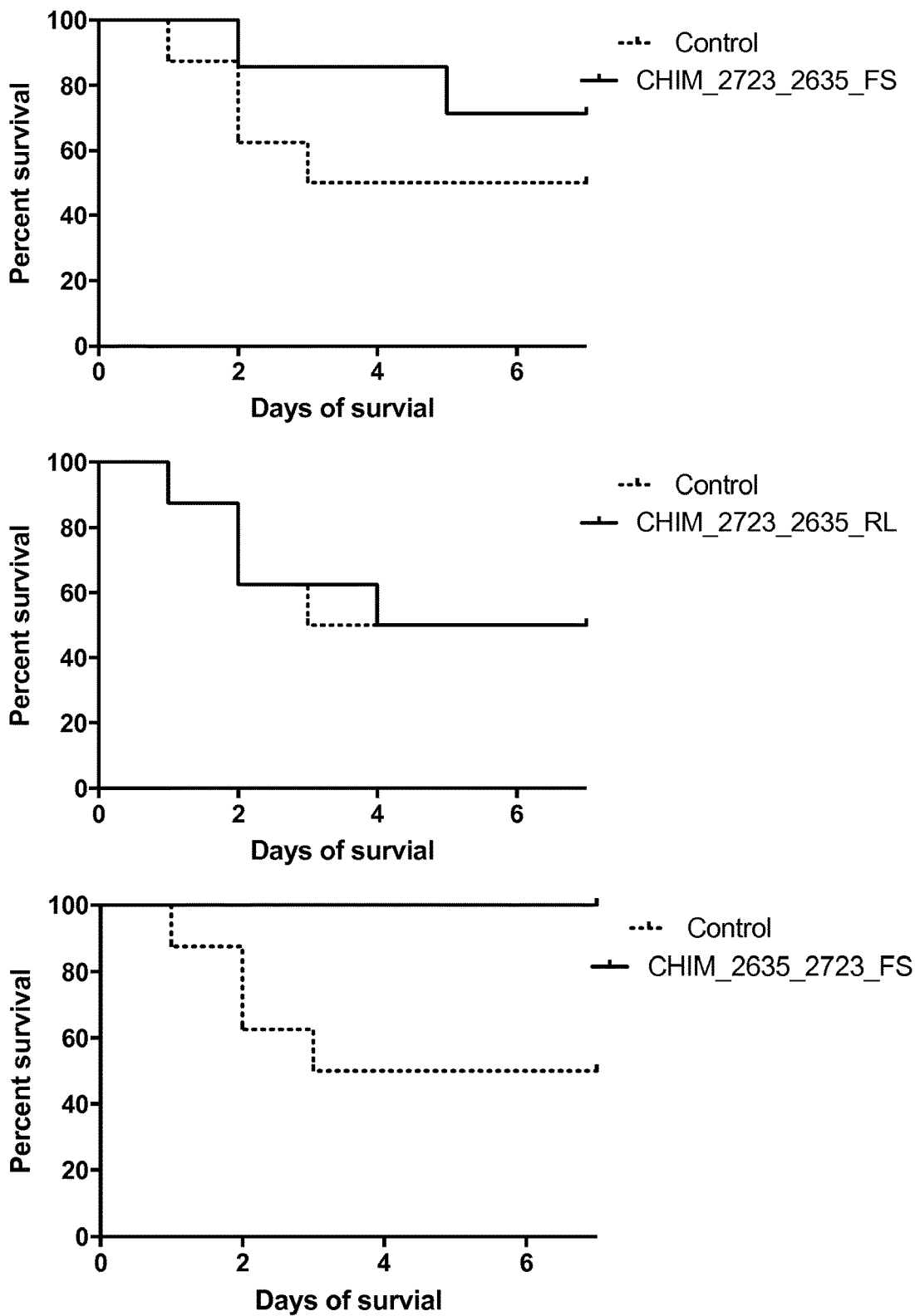
Figure 5D:
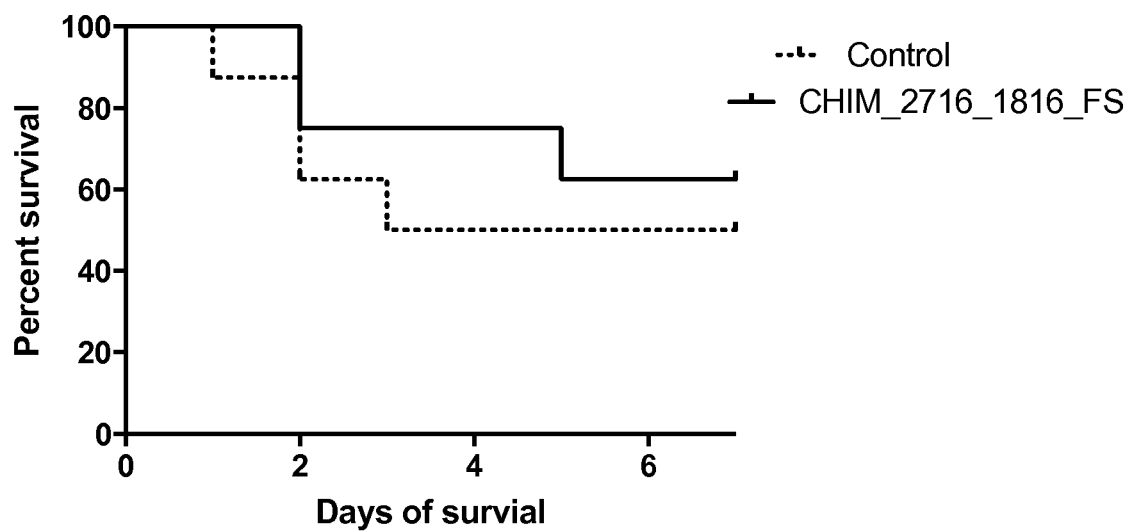

3. CHIM_2723_2753_S_FS, CHIM_2723_2753_L_FS, CHIM_Hla 2753_FS, CHIM_Hla_0735_FS, IsdB_USA300-41-613, SAR0280-28-820, SAR0992-1-409, M2683 SAR0992-1-409 and SAR0735-26-227 formulations (containing SEQ ID NOs: 77, 15, 80, 78, 84, 87, 89, 85, and 88, respectively):

Survival of animals is provided for each of the immunogens in the survival plots in FIG. 3A-FIG. 3C. The results show that immunization with either CHIM_2723_2753_L_FS, CHIM_Hla_2753_FS, SAR0992-1-409 or M2683_SAR0992-1-409 protected mice against a lethal challenge with S. aureus MRSA252. Immunization with the other antigens did not result in significant protection compared to the control group.

4. CHIM_2119_1816_FS, CHIM_1816_2119 FL, CHIM_2716_2119_FS, CHIM_2496_1816_FS, CHIM_1262_2496 RS, CHIM_1507_2119_FS,

CHIM_HLa_2635_FS, CHIM_2716_2753 FL, HL461_SAR2753-291-476, and HL461_SAR2753_291-680 formulations (containing SEQ ID NOs: 68, 67, 72, 69, 65, 66, 79, 73, 82, and 81, respectively):

Survival of animals is provided for each of the immunogens in the survival plots in FIG. 4A-FIG. 4D. The results show that immunization with either CHIM_HLA_2635 or CHIM_2716_2753_FL in combination with the adjuvant CAF01 had a protective effect, resulting in survival of a significant number of the immunized animals.

5. CHIM_0992_0735_FS, CHIM_0992_0735_FL, CHIM_0735_0992_FL, CHIM_0992_2635_FS, CHIM_0992_2635_FL, CHIM_0992_2753_FS, CHIM_2723_2635_FS, CHIM_2723_2635_RL, CHIM_2635_2723_FS and CHIM_2716_1816_FS formulations (containing SEQ ID NOs: 61, 60, 59, 63, 62, 64, 74, 75, 13, and 71, respectively):

Survival of animals is provided for each of the immunogens in the survival plots in FIG. 5A-FIG. 5D. The results show that immunization with either CHIM_0992_0735_FS or CHIM_2635_2723_FS protected mice against a lethal infection with *S. aureus* MRSA252 when compared to adjuvant alone.

Biological Sequences

The amino acid sequences referred to in the present application are the following:

```
                                                      SEQ ID NO: 1
MTEKEKMLAE KWYDANFDQD LINERARAKD ICFELNHTKP SDKNKRKELI DELFQTTTDN

VSISIPFDTD YGWNVKLGKN VYVNTNCYFM DGGQITIGDN VFIGPNCGFY TATHPLNFHH

RNEGFEKAGP INIGSNTWFG GHVAVLPGVT IGEGSVIGAG SVVTKDIPPH SLAVGNPCKV

VRKIDNEVPS EALNDETLN

SEQ ID NO: 2
KRIKQHPDVQ KVTDATSKVA SKTSAAISNT ASDVKEYVGD KKQDFENKRE LKKFAREHDP

AYIEKKGEKL AKQNRKDADK MNKILQKNIE KRHKEEQKAR EKNEIQRIKD MKKSQKYEVK

AGLTPNKLDE KTEKKGDKLA EKNRKEIAKM NKKLQKNIEK RHKEEQKRQQ EADKARIKSF

KKYKDYVAKS ASQQNKENNT EA

SEQ ID NO: 3
ADSDINIKTG TTDIGSNTTV KTGDLVTYDK ENGMLKKVFY SFIDDKNHNK KLLVIRTKGT

IAGQYRVYSE EGANKSGLAW PSAFKVQLQL PDNEVAQISD YYPRNSIDTK EYMSTLTYGF

NGNVTGDDTG KIGGLIGANV SIGHTLKYVQ PDFKTILESP TDKKVGWKVI FNNMVNQNWG

PYDRDSWNPV YGNQLFMKTR NGSMKAADNF LDPNKASSLL SSGFSPDFAT VITMDRKASK

QQTNIDVIYE RVRDDYQLHW TSTNWKGTNT KDKWIDRSSE RYKIDWEKEE MTN

SEQ ID NO: 4
AKDNLNGEKP TTNLNHNVTS PSVNSEMNNN ETGTPHESNQ AGNEGTGSNS RDANPDSNNV

KPDSNNQNPS PDSKPDPNNP NPGPNPKPDP DKPKPNPEPK PDPKPDPDKP KPNPDPKPDP

DKPKPNPDPK PDPDKPKPNP DPKPDPNPNP KPDPNKPNPN PSPNPNQPGD SNQSGGSKNG

GTWNPNASDG SNQGQWQPNG NQGNSQNPTG NDFVSQRFLA LANGAYKYNP YILNQINQLG

KEYGEVTDED IYNIIRKQNF SGNAYLNGLQ QQSNYFRFQY FNPLKSERYY RNLDEQVLAL

ITGEIGSMPD LKKPEDKPDS KQRSFEPHEK DDFTVVKKQE DNKKSASTAY S

SEQ ID NO: 5
GFLNKSKNEQ AALKAQQAAI KEEASANNLS DTSQEAQEIQ EAKREAQAEA DKSVAVSNKE

SKAVALKAQQ AAIKEEASAN NLSDTSQEAQ EIQEAKKEAQ AETDKSAAVS NEEPKAVALK

AQQAAIKEEA SANNLSDISQ EAQEVQEAKK EAQAEKDSDT LTKDASAAKV EVSKPESQAE

RLANAAKQKQ AKLTPGSKES QLTEALFAEK PVAKNDLKEI PQLVTKKNDV SETETVNIDN

KDTVKQKEAK FENGVITRKA DEKTTNNTAV DKKSGKQSKK TTPSNKRNAS KASTNKTSGQ

KKQHNKKSSQ GAKKQSSSSK STQKNNQTSN KNSKTTNAKS SNASKTPNAK VEKAKSKIEK

RTFND

SEQ ID NO: 6
KVAKQGQYKN QDPIVLVHGF NGFTDDINPS VLAHYWGGNK MNIRQDLEEN GYKAYEASIS

AFGSNYDRAV ELYYYIKGGR VDYGAAHAAK YGHERYGKTY EGIYKDWKPG QKVHLVGHSM

GGQTIRQLEE LLRNGSREEI EYQKKHGGEI SPLFKGNNDN MISSITTLGT PHNGTHASDL
```

```
AGNEALVRQI VFDIGKMFGN KNSRVDFGLA QWGLKQKPNE SYIDYVKRVK QSNLWKSKDN

GFYDLTREGA TDLNRKTSLN PNIVYKTYTG EATHKALNSD RQKADLNMFF PFVITGNLIG

KATEKEWREN DGLVSVISSQ HPFNQAYTNA TDKIQKGIWQ VTPTKHDWDH VDFVGQDSSD

TVRTREELQD FWHHLADDLV KTEKVTDTKQ

SEQ ID NO: 7
MDIGKKHVIP KSQYRRKRRE FFHNEDREEN LNQHQDKQNI DNTTSKKADK QIHKDSIDKH

ERFKNSLSSH LEQRNRDVNE NKAEESKSNQ DSKSAYNRDH YLTDDVSKKQ NSLDSVDQDT

EKSKYYEQNS EATLSTKSTD KVESTEMRKL SSDKNKVGHE EQHVLSKPSE HDKETRIDSE

SSRTDSDSSM QTEKIKKDSS DGNKSSNLKS EVISDKSNTV PKLSESDDEV NNQKPLTLPE

EQKLKRQQSQ NEQTKTYTYG DSEQNDKSNH ENDLSHHIPS ISDDKDNVMR ENHIVDDNPD

NDINTPSLSK TDDDRKLDEK IHVEDKHKQN ADSSETVGYQ SQSTASHRST EKRNISINDH

DKLNGQKTNT KTSANNNQKK ATSKLNKGRA TNNNYSDILK KFWMMYWPK

SEQ ID NO: 8
IDSKNKPANS DIKFEVTQKS DAVKALKELP KSENVKNIYQ DYAVTDVKTD KKGFTHYTLQ

PSVDGVHAPD KEVKVHADKS GKVVLINGDT DAKKVKPTNK VTLSKDDAAD KAFKAVKIDK

NKAKNLKDKV IKENKVEIDG DSNKYVYNVE LITVTPEISH WKVKIDAQTG EILEKMNLVK

EAAETGKGKG VLGDTKDINI NSIDGGFSLE DLTHQGKLSA FSFNDQTGQA TLITNEDENF

VKDEQRAGVD ANYYAKQTYD YYKDTFGRES YDNQGSPIVS LTHVNNYGGQ DNRNNAAWIG

DKMIYGDGDG RTFTSLSGAN DVVAHELTHG VTQETANLEY KDQSGALNES FSDVFGYFVD

DEDFLMGEDV YTPGKEGDAL RSMSNPEQFG QPAHMKDYVF TEKDNGGVHT NS

SEQ ID NO: 9
DTPQKDTTAK TTSHDSKKSN DDETSKDTTS KDIDKADNNN TSNQDNNDKK FKTIDDSTSD

SNNIIDFIYK NLPQTNINQL LTKNKYDDNY SLTTLIQNLF NLNSDISDYE QPRNGEKSTN

DSNKNSDNSI KNDTDTQSSK QDKADNQKAP KSNNTKPSTS NKQPNSPKPT QPNQSNSQPA

SDDKANQKSS SKDNQSMSDS ALDSILDQYS EDAKKTQKDY ASQSKKDKNE KSNTKNPQLP

TQDELKHKSK PAQSFNNDVN QKDTRATSLF ETDPSISNND DSGQFNVVDS KDTRQFVKSI

AKDAHRIGQD NDIYASVMIA QAILESDSGR SALAKSPNHN LFGIKGAFEG NSVPFNTLEA

DGNKLYSINA GFRKYPSTKE SLKDYSDLIK NGIDGNRTIY KPTWKSEADS YKDATSHLSK

TYATDPNYAK KLNSIIKHYQ LTQFDDERMP DLDKYERSIK DYDDSSDEFK PFREVSDSMP

YPHGQCTWYV YNRMKQFGTS ISGDLGDAHN WNNRAQYRDY QVSHTPKRHA AVVFEAGQFG

ADQHYGHVAF VEKVNSDGSI VISESNVKGL GIISHRTINA AAAEELSYIT GK

SEQ ID NO: 10
GSGGGA

SEQ ID NO: 11
GSGGGAGSGG GA

SEQ ID NO: 12
MDIGKKHVIP KSQYRRKRRE FFHNEDREEN LNQHQDKQNI DNTTSKKADK QIHKDSIDKH

ERFKNSLSSH LEQRNRDVNE NKAEESKSNQ DSKSAYNRDH YLTDDVSKKQ NSLDSVDQDT

EKSKYYEQNS EATLSTKSTD KVESTEMRKL SSDKNKVGHE EQHVLSKPSE HDKETRIDSE

SSRTDSDSSM QTEKIKKDSS DGNKSSNLKS EVISDKSNTV PKLSESDDEV NNQKPLTLPE

EQKLKRQQSQ NEQTKTYTYG DSEQNDKSNH ENDLSHHIPS ISDDKDNVMR ENHIVDDNPD

NDINTPSLSK TDDDRKLDEK IHVEDKHKQN ADSSETVGYQ SQSTASHRST EKRNISINDH

DKLNGQKTNT KTSANNNQKK ATSKLNKGRA TNNNYSDILK KFWMMYWPKG SGGGAKRIKQ

HPDVQKVTDA TSKVASKTSA AISNTASDVK EYVGDKKQDF ENKRELKKFA REHDPAYIEK
```

```
KGEKLAKQNR KDADKMNKIL QKNIEKRHKE EQKAREKNEI QRIKDMKKSQ KYEVKAGLTP

NKLDEKTEKK GDKLAEKNRK EIAKMNKKLQ KNIEKRHKEE QKRQQEADKA RIKSFKKYKD

YVAKSASQQN KENNTEA
                                                      SEQ ID NO: 13
MTEKEKMLAE KWYDANFDQD LINERARAKD ICFELNHTKP SDKNKRKELI DELFQTTTDN

VSISIPFDTD YGWNVKLGKN VYVNTNCYFM DGGQITIGDN VFIGPNCGFY TATHPLNFHH

RNEGFEKAGP INIGSNTWFG GHVAVLPGVT IGEGSVIGAG SVVTKDIPPH SLAVGNPCKV

VRKIDNEVPS EALNDETLNG SGGGADTPQK DTTAKTTSHD SKKSNDDETS KDTTSKDIDK

ADNNNTSNQD NNDKKFKTID DSTSDSNNII DFIYKNLPQT NINQLLTKNK YDDNYSLTTL

IQNLFNLNSD ISDYEQPRNG EKSTNDSNKN SDNSIKNDTD TQSSKQDKAD NQKAPKSNNT

KPSTSNKQPN SPKPTQPNQS NSQPASDDKA NQKSSSKDNQ SMSDSALDSI LDQYSEDAKK

TQKDYASQSK KDKNEKSNTK NPQLPTQDEL KHKSKPAQSF NNDVNQKDTR ATSLFETDPS

ISNNDDSGQF NVVDSKDTRQ FVKSIAKDAH RIGQDNDIYA SVMIAQAILE SDSGRSALAK

SPNHNLFGIK GAFEGNSVPF NTLEADGNKL YSINAGFRKY PSTKESLKDY SDLIKNGIDG

NRTIYKPTWK SEADSYKDAT SHLSKTYATD PNYAKKLNSI IKHYQLTQFD DERMPDLDKY

ERSIKDYDDS SDEFKPFREV SDSMPYPHGQ CTWYVYNRMK QFGTSISGDL GDAHNWNNRA

QYRDYQVSHT PKRHAAVVFE AGQFGADQHY GHVAFVEKVN SDGSIVISES NVKGLGIISH

RTINAAAAEE LSYITGK
                                                      SEQ ID NO: 14
IDSKNKPANS DIKFEVTQKS DAVKALKELP KSENVKNIYQ DYAVTDVKTD KKGFTHYTLQ

PSVDGVHAPD KEVKVHADKS GKVVLINGDT DAKKVKPTNK VTLSKDDAAD KAFKAVKIDK

NKAKNLKDKV IKENKVEIDG DSNKYVYNVE LITVTPEISH WKVKIDAQTG EILEKMNLVK

EAAETGKGKG VLGDTKDINI NSIDGGFSLE DLTHQGKLSA FSFNDQTGQA TLITNEDENF

VKDEQRAGVD ANYYAKQTYD YYKDTFGRES YDNQGSPIVS LTHVNNYGGQ DNRNNAAWIG

DKMIYGDGDG RTFTSLSGAN DVVAHELTHG VTQETANLEY KDQSGALNES FSDVFGYFVD

DEDFLMGEDV YTPGKEGDAL RSMSNPEQFG QPAHMKDYVF TEKDNGGVHT NSGSGGGAGS

GGGAKVAKQG QYKNQDPIVL VHGFNGFTDD INPSVLAHYW GGNKMNIRQD LEENGYKAYE

ASISAFGSNY DRAVELYYYI KGGRVDYGAA HAAKYGHERY GKTYEGIYKD WKPGQKVHLV

GHSMGGQTIR QLEELLRNGS REEIEYQKKH GGEISPLFKG NNDNMISSIT TLGTPHNGTH

ASDLAGNEAL VRQIVFDIGK MFGNKNSRVD FGLAQWGLKQ KPNESYIDYV KRVKQSNLWK

SKDNGFYDLT REGATDLNRK TSLNPNIVYK TYTGEATHKA LNSDRQKADL NMFFPFVITG

NLIGKATEKE WRENDGLVSV ISSQHPFNQA YTNATDKIQK GIWQVTPTKH DWDHVDFVGQ

DSSDTVRTRE ELQDFWHHLA DDLVKTEKVT DTKQ
                                                      SEQ ID NO: 15
DTPQKDTTAK TTSHDSKKSN DDETSKDTTS KDIDKADNNN TSNQDNNDKK FKTIDDSTSD

SNNIIDFIYK NLPQTNINQL LTKNKYDDNY SLTTLIQNLF NLNSDISDYE QPRNGEKSTN

DSNKNSDNSI KNDTDTQSSK QDKADNQKAP KSNNTKPSTS NKQPNSPKPT QPNQSNSQPA

SDDKANQKSS SKDNQSMSDS ALDSILDQYS EDAKKTQKDY ASQSKKDKNE KSNTKNPQLP

TQDELKHKSK PAQSFNNDVN QKDTRATSLF ETDPSISNND DSGQFNVVDS KDTRQFVKSI

AKDAHRIGQD NDIYASVMIA QAILESDSGR SALAKSPNHN LFGIKGAFEG NSVPFNTLEA

DGNKLYSINA GFRKYPSTKE SLKDYSDLIK NGIDGNRTIY KPTWKSEADS YKDATSHLSK

TYATDPNYAK KLNSIIKHYQ LTQFDDERMP DLDKYERSIK DYDDSSDEFK PFREVSDSMP
```

```
YPHGQCTWYV YNRMKQFGTS ISGDLGDAHN WNNRAQYRDY QVSHTPKRHA AVVFEAGQFG

ADQHYGHVAF VEKVNSDGSI VISESNVKGL GIISHRTINA AAAEELSYIT GKGSGGGAKV

AKQGQYKNQD PIVLVHGFNG FTDDINPSVL AHYWGGNKMN IRQDLEENGY KAYEASISAF

GSNYDRAVEL YYYIKGGRVD YGAAHAAKYG HERYGKTYEG IYKDWKPGQK VHLVGHSMGG

QTIRQLEELL RNGSREEIEY QKKHGGEISP LFKGNNDNMI SSITTLGTPH NGTHASDLAG

NEALVRQIVF DIGKMFGNKN SRVDFGLAQW GLKQKPNESY IDYVKRVKQS NLWKSKDNGF

YDLTREGATD LNRKTSLNPN IVYKTYTGEA THKALNSDRQ KADLNMFFPF VITGNLIGKA

TEKEWRENDG LVSVISSQHP FNQAYTNATD KIQKGIWQVT PTKHDWDHVD FVGQDSSDTV

RTREELQDFW HHLADDLVKT EKVTDTKQ

SEQ ID NO: 16
AKDNLNGEKP TTNLNHNVTS PSVNSEMNNN ETGTPHESNQ AGNEGTGSNS RDANPDSNNV

KPDSNNQNPS PDSKPDPNNP NPGPNPKPDP DKPKPNPEPK PDPKPDPDKP KPNPDPKPDP

DKPKPNPDPK PDPDKPKPNP DPKPDPNPNP KPDPNKPNPN PSPNPNQPGD SNQSGGSKNG

GTWNPNASDG SNQGQWQPNG NQGNSQNPTG NDFVSQRFLA LANGAYKYNP YILNQINQLG

KEYGEVTDED IYNIIRKQNF SGNAYLNGLQ QQSNYFRFQY FNPLKSERYY RNLDEQVLAL

ITGEIGSMPD LKKPEDKPDS KQRSFEPHEK DDFTVVKKQE DNKKSASTAY SGSGGGAGFL

NKSKNEQAAL KAQQAAIKEE ASANNLSDTS QEAQEIQEAK REAQAEADKS VAVSNKESKA

VALKAQQAAI KEEASANNLS DTSQEAQEIQ EAKKEAQAET DKSAAVSNEE PKAVALKAQQ

AAIKEEASAN NLSDISQEAQ EVQEAKKEAQ AEKDSDTLTK DASAAKVEVS KPESQAERLA

NAAKQKQAKL TPGSKESQLT EALFAEKPVA KNDLKEIPQL VTKKNDVSET ETVNIDNKDT

VKQKEAKFEN GVITRKADEK TTNNTAVDKK SGKQSKKTTP SNKRNASKAS TNKTSGQKKQ

HNKKSSQGAK KQSSSSKSTQ KNNQTSNKNS KTTNAKSSNA SKTPNAKVEK AKSKIEKRTF

ND

SEQ ID NO: 17
MDIGKKHVIP KSQYRRKRRE FFHNEDREEN LNQHQDKQNI DNTTSKKADK QIHKDSIDKH

ERFKNSLSSH LEQRNRDVNE NKAEESKSNQ DSKSAYNRDH YLTDDVSKKQ NSLDSVDQDT

EKSKYYEQNS EATLSTKSTD KVESTEMRKL SSDKNKVGHE EQHVLSKPSE HDKETRIDSE

SSRTDSDSSM QTEKIKKDSS DGNKSSNLKS EVISDKSNTV PKLSESDDEV NNQKPLTLPE

EQKLKRQQSQ NEQTKTYTYG DSEQNDKSNH ENDLSHHIPS ISDDKDNVMR ENHIVDDNPD

NDINTPSLSK TDDDRKLDEK IHVEDKHKQN ADSSETVGYQ SQSTASHRST EKRNISINDH

DKLNGQKTNT KTSANNNQKK ATSKLNKGRA TNNNYSDILK KFWMMYWPKG SGGGAGSGGG

AMTEKEKMLA EKWYDANFDQ DLINERARAK DICFELNHTK PSDKNKRKEL IDELFQTTTD

NVSISIPFDT DYGWNVKLGK NVYVNTNCYF MDGGQITIGD NVFIGPNCGF YTATHPLNFH

HRNEGFEKAG PINIGSNTWF GGHVAVLPGV TIGEGSVIGA GSVVTKDIPP HSLAVGNPCK

VVRKIDNEVP SEALNDETLN

SEQ ID NO: 18
ADSDINIKTG TTDIGSNTTV KTGDLVTYDK ENGMLKKVFY SFIDDKNHNK KLLVIRTKGT

IAGQYRVYSE EGANKSGLAW PSAFKVQLQL PDNEVAQISD YYPRNSIDTK EYMSTLTYGF

NGNVTGDDTG KIGGLIGANV SIGHTLKYVQ PDFKTILESP TDKKVGWKVI FNNMVNQNWG

PYDRDSWNPV YGNQLFMKTR NGSMKAADNF LDPNKASSLL SSGFSPDFAT VITMDRKASK

QQTNIDVIYE RVRDDYQLHW TSTNWKGTNT KDKWIDRSSE RYKIDWEKEE MTNGSGGGAM

TEKEKMLAEK WYDANFDQDL INERARAKDI CFELNHTKPS DKNKRKELID ELFQTTTDNV
```

```
SISIPFDTDY GWNVKLGKNV YVNTNCYFMD GGQITIGDNV FIGPNCGFYT ATHPLNFHHR

NEGFEKAGPI NIGSNTWFGG HVAVLPGVTI GEGSVIGAGS VVTKDIPPHS LAVGNPCKVV

RKIDNEVPSE ALNDETLN
```

SEQ ID NO: 19
```
ADSDINIKTG TTDIGSNTTV KTGDLVTYDK ENGMLKKVFY SFIDDKNHNK KLLVIRTKGT

IAGQYRVYSE EGANKSGLAW PSAFKVQLQL PDNEVAQISD YYPRNSIDTK EYMSTLTYGF

NGNVTGDDTG KIGGLIGANV SIGHTLKYVQ PDFKTILESP TDKKVGWKVI FNNMVNQNWG

PYDRDSWNPV YGNQLFMKTR NGSMKAADNF LDPNKASSLL SSGFSPDFAT VITMDRKASK

QQTNIDVIYE RVRDDYQLHW TSTNWKGTNT KDKWIDRSSE RYKIDWEKEE MTNGSGGGAK

VAKQGQYKNQ DPIVLVHGFN GFTDDINPSV LAHYWGGNKM NIRQDLEENG YKAYEASISA

FGSNYDRAVE LYYYIKGGRV DYGAAHAAKY GHERYGKTYE GIYKDWKPGQ KVHLVGHSMG

GQTIRQLEEL LRNGSREEIE YQKKHGGEIS PLFKGNNDNM ISSITTLGTP HNGTHASDLA

GNEALVRQIV FDIGKMFGNK NSRVDFGLAQ WGLKQKPNES YIDYVKRVKQ SNLWKSKDNG

FYDLTREGAT DLNRKTSLNP NIVYKTYTGE ATHKALNSDR QKADLNMFFP FVITGNLIGK

ATEKEWREND GLVSVISSQH PFNQAYTNAT DKIQKGIWQV TPTKHDWDHV DFVGQDSSDT

VRTREELQDF WHHLADDLVK TEKVTDTKQ
```

SEQ ID NO: 20
```
ADSDINIKTG TTDIGSNTTV KTGDLVTYDK ENGMLKKVFY SFIDDKNHNK KLLVIRTKGT

IAGQYRVYSE EGANKSGLAW PSAFKVQLQL PDNEVAQISD YYPRNSIDTK EYMSTLTYGF

NGNVTGDDTG KIGGLIGANV SIGHTLKYVQ PDFKTILESP TDKKVGWKVI FNNMVNQNWG

PYDRDSWNPV YGNQLFMKTR NGSMKAADNF LDPNKASSLL SSGFSPDFAT VITMDRKASK

QQTNIDVIYE RVRDDYQLHW TSTNWKGTNT KDKWIDRSSE RYKIDWEKEE MTNGSGGGAK

RIKQHPDVQK VTDATSKVAS KTSAAISNTA SDVKEYVGDK KQDFENKREL KKFAREHDPA

YIEKKGEKLA KQNRKDADKM NKILQKNIEK RHKEEQKARE KNEIQRIKDM KKSQKYEVKA

GLTPNKLDEK TEKKGDKLAE KNRKEIAKMN KKLQKNIEKR HKEEQKRQQE ADKARIKSFK

KYKDYVAKSA SQQNKENNTE A
```

SEQ ID NO: 21
EPINFILKSSTKLKA

SEQ ID NO: 22
FLKLFRITNPIARGL

SEQ ID NO: 23
GLYFVAMNNLKAAGQ

SEQ ID NO: 24
IIKKLFRLPAIKRFE

SEQ ID NO: 25
ILLGYFVAQRALVKA

SEQ ID NO: 26
KADALKAITALKLQM

SEQ ID NO: 27
KHQIRMLSIPRDTIS

SEQ ID NO: 28
KRIFKMSPIHHHFEL

SEQ ID NO: 29
KTLFVALNNKARIPE

SEQ ID NO: 30
LDQIIAQANLRLATM

-continued

```
                                                            SEQ ID NO: 31
LMGIRAFRKLLPNIP

SEQ ID NO: 32
MHFIAISINHRTADV

SEQ ID NO: 33
QRHFQIGYNRAARII

SEQ ID NO: 34
SSNVYMFKTALKLAG

SEQ ID NO: 35
STFIYKIANERLFSR

SEQ ID NO: 36
SVTIIKSLQAIRVPF

SEQ ID NO: 37
TSQFHVLRALRLAQK

SEQ ID NO: 38
VLFYLRSNKRQIIEK

SEQ ID NO: 39
WKRIGRLKSIPIFMY

SEQ ID NO: 40
YFRFQYFNPLKSERY

SEQ ID NO: 41
VLFYLRSNKR QIIEKGPGPG EPINFILKSS TKLKAGPGPG GLYFVAMNNL KAAGQGPGPG

KADALKAITA LKLQMGPGPG KHQIRMLSIP RDTISGPGPG LDQIIAQANL RLATMGPGPG

QRHFQIGYNR AARIIGPGPG SSNVYMFKTA LKLAGGPGPG YFRFQYFNPL KSERY

SEQ ID NO: 42
TSQFHVLRAL RLAQKGPGPG FLKLFRITNP IARGLGPGPG IIKKLFRLPA IKRFEGPGPG

ILLGYFVAQR ALVKAGPGPG KRIFKMSPIH HHFELGPGPG KTLFVALNNK ARIPEGPGPG

LMGIRAFRKL LPNIPGPGPG MHFIAISINH RTADVGPGPG STFIYKIANE RLFSRGPGPG

SVTIIKSLQA IRVPFGPGPG WKRIGRLKSI PIFMY

SEQ ID NO: 43
MSSLPVGPVA WSDGMLIETQ HFQQLKRIFK MSPIHHHFEL SNHGWGFTLL DLDQDGLGLG

RLMGIRAFRK LLPNIPFSLP SDDPLPPPLE TELAQAGDIA CLALQAARTG GPEMAFGDVE

LASRYRAVST EVPDLAVGLD APGTPFLKLF RITNPIARGL WKRIGRLKSI PIFMYRVAGR

NASRTVSLDP RFIPPKTLFV ALNNKARIPE ELQSTSVTII KSLQAIRVPF TGGGVADLIE

ILLGYFVAQR ALVKANLDAF DPLPPMHFIA ISINHRTADV VLPGVDEELA DRELGYDHDD

LQTSFTSQFH VLRALRLAQK ETPVLPLRFE DRGDQVHICI VDKQWNLKKL IFAFSIIKKL

FRLPAIKRFE TKLGAVEQIQ KLVDQLPGA RLNALPNPPR QIPYYAQSTY FEVESTDPFW

KQTLAGSAMA LRIVGDFPST FIYKIANERL FSR

SEQ ID NO: 44
MSSLPVGPVA WSDGMLIETQ HFQQLERHLA HQASLRLGQT SNHGWGFTLL DLDQDGLGLG

RLGLRSSNVY MFKTALKLAG SDDPLPPPLE TELAQAGDIA CLALQAARTG GPEMAFGDVE

LASRYRAVST EVPDLAVGLD APGTPRRLTI ETGQLVTRLC WKSQVLFYLR SNKRQIIEKR

NASRTVSLDP RFIPPEPINF ILKSSTKLKA ELQSTQRHFQ IGYNRAARII TGGGVADLIE

LLLRQLDQII AQANLRLATM DPLPPGLYFV AMNNLKAAGQ VLPGVDEELA DRELGYDHDD

LQTSFEPLAM MLRQALARVI ETPVLPLRFE DRGDQVHICI VDKQWNLKKL IFAFSKADAL

KAITALKLQM TKLGAVEQIQ KLVDQLPGA RLNALPNPPR QIPYYAQSTY FEVESKHQIR

MLSIPRDTIS LRIVGDYFRF QYFNPLKSER YVA
```

SEQ ID NO: 45
GPGPG

SEQ ID NO: 59
KRIKQHPDVQ KVTDATSKVA SKTSAAISNT ASDVKEYVGD KKQDFENKRE LKKFAREHDP
AYIEKKGEKL AKQNRKDADK MNKILQKNIE KRHKEEQKAR EKNEIQRIKD MKKSQKYEVK
AGLTPNKLDE KTEKKGDKLA EKNRKEIAKM NKKLQKNIEK RHKEEQKRQQ EADKARIKSF
KKYKDYVAKS ASQQNKENNT EAGSGGGAGS GGGAMDIGKK HVIPKSQYRR KRREFFHNED
REENLNQHQD KQNIDNTTSK KADKQIHKDS IDKHERFKNS LSSHLEQRNR DVNENKAEES
KSNQDSKSAY NRDHYLTDDV SKKQNSLDSV DQDTEKSKYY EQNSEATLST KSTDKVESTE
MRKLSSDKNK VGHEEQHVLS KPSEHDKETR IDSESSRTDS DSSMQTEKIK KDSSDGNKSS
NLKSEVISDK SNTVPKLSES DDEVNNQKPL TLPEEQKLKR QQSQNEQTKT YTYGDSEQND
KSNHENDLSH HIPSISDDKD NVMRENHIVD DNPDNDINTP SLSKTDDDRK LDEKIHVEDK
HKQNADSSET VGYQSQSTAS HRSTEKRNIS INDHDKLNGQ KTNTKTSANN NQKKATSKLN
KGRATNNNYS DILKKFWMMY WPK

SEQ ID NO: 60
MDIGKKHVIP KSQYRRKRRE FFHNEDREEN LNQHQDKQNI DNTTSKKADK QIHKDSIDKH
ERFKNSLSSH LEQRNRDVNE NKAEESKSNQ DSKSAYNRDH YLTDDVSKKQ NSLDSVDQDT
EKSKYYEQNS EATLSTKSTD KVESTEMRKL SSDKNKVGHE EQHVLSKPSE HDKETRIDSE
SSRTDSDSSM QTEKIKKDSS DGNKSSNLKS EVISDKSNTV PKLSESDDEV NNQKPLTLPE
EQKLKRQQSQ NEQTKTYTYG DSEQNDKSNH ENDLSHHIPS ISDDKDNVMR ENHIVDDNPD
NDINTPSLSK TDDDRKLDEK IHVEDKHKQN ADSSETVGYQ SQSTASHRST EKRNISINDH
DKLNGQKTNT KTSANNNQKK ATSKLNKGRA TNNNYSDILK KFWMMYWPKG SGGGAGSGGG
AKRIKQHPDV QKVTDATSKV ASKTSAAISN TASDVKEYVG DKKQDFENKR ELKKFAREHD
PAYIEKKGEK LAKQNRKDAD KMNKILQKNI EKRHKEEQKA REKNEIQRIK DMKKSQKYEV
KAGLTPNKLD EKTEKKGDKL AEKNRKEIAK MNKKLQKNIE KRHKEEQKRQ QEADKARIKS
FKKYKDYVAK SASQQNKENN TEA

SEQ ID NO: 61
MDIGKKHVIP KSQYRRKRRE FFHNEDREEN LNQHQDKQNI DNTTSKKADK QIHKDSIDKH
ERFKNSLSSH LEQRNRDVNE NKAEESKSNQ DSKSAYNRDH YLTDDVSKKQ NSLDSVDQDT
EKSKYYEQNS EATLSTKSTD KVESTEMRKL SSDKNKVGHE EQHVLSKPSE HDKETRIDSE
SSRTDSDSSM QTEKIKKDSS DGNKSSNLKS EVISDKSNTV PKLSESDDEV NNQKPLTLPE
EQKLKRQQSQ NEQTKTYTYG DSEQNDKSNH ENDLSHHIPS ISDDKDNVMR ENHIVDDNPD
NDINTPSLSK TDDDRKLDEK IHVEDKHKQN ADSSETVGYQ SQSTASHRST EKRNISINDH
DKLNGQKTNT KTSANNNQKK ATSKLNKGRA TNNNYSDILK KFWMMYWPKG SGGGAKRIKQ
HPDVQKVTDA TSKVASKTSA AISNTASDVK EYVGDKKQDF ENKRELKKFA REHDPAYIEK
KGEKLAKQNR KDADKMNKIL QKNIEKRHKE EQKAREKNEI QRIKDMKKSQ KYEVKAGLTP
NKLDEKTEKK GDKLAEKNRK EIAKMNKKLQ KNIEKRHKEE QKRQQEADKA RIKSFKKYKD
YVAKSASQQN KENNTEA

SEQ ID NO: 62
MDIGKKHVIP KSQYRRKRRE FFHNEDREEN LNQHQDKQNI DNTTSKKADK QIHKDSIDKH
ERFKNSLSSH LEQRNRDVNE NKAEESKSNQ DSKSAYNRDH YLTDDVSKKQ NSLDSVDQDT
EKSKYYEQNS EATLSTKSTD KVESTEMRKL SSDKNKVGHE EQHVLSKPSE HDKETRIDSE
SSRTDSDSSM QTEKIKKDSS DGNKSSNLKS EVISDKSNTV PKLSESDDEV NNQKPLTLPE

```
                                              -continued
EQKLKRQQSQ NEQTKTYTYG DSEQNDKSNH ENDLSHHIPS ISDDKDNVMR ENHIVDDNPD

NDINTPSLSK TDDDRKLDEK IHVEDKHKQN ADSSETVGYQ SQSTASHRST EKRNISINDH

DKLNGQKTNT KTSANNNQKK ATSKLNKGRA TNNNYSDILK KFWMMYWPKG SGGGAGSGGG

AMTEKEKMLA EKWYDANFDQ DLINERARAK DICFELNHTK PSDKNKRKEL IDELFQTTTD

NVSISIPFDT DYGWNVKLGK NVYVNTNCYF MDGGQITIGD NVFIGPNCGF YTATHPLNFH

HRNEGFEKAG PINIGSNTWF GGHVAVLPGV TIGEGSVIGA GSVVTKDIPP HSLAVGNPCK

VVRKIDNEVP SEALNDETLN

SEQ ID NO: 63
MDIGKKHVIP KSQYRRKRRE FFHNEDREEN LNQHQDKQNI DNTTSKKADK QIHKDSIDKH

ERFKNSLSSH LEQRNRDVNE NKAEESKSNQ DSKSAYNRDH YLTDDVSKKQ NSLDSVDQDT

EKSKYYEQNS EATLSTKSTD KVESTEMRKL SSDKNKVGHE EQHVLSKPSE HDKETRIDSE

SSRTDSDSSM QTEKIKKDSS DGNKSSNLKS EVISDKSNTV PKLSESDDEV NNQKPLTLPE

EQKLKRQQSQ NEQTKTYTYG DSEQNDKSNH ENDLSHHIPS ISDDKDNVMR ENHIVDDNPD

NDINTPSLSK TDDDRKLDEK IHVEDKHKQN ADSSETVGYQ SQSTASHRST EKRNISINDH

DKLNGQKTNT KTSANNNQKK ATSKLNKGRA TNNNYSDILK KFWMMYWPKG SGGGAMTEKE

KMLAEKWYDA NFDQDLINER ARAKDICFEL NHTKPSDKNK RKELIDELFQ TTTDNVSISI

PFDTDYGWNV KLGKNVYVNT NCYFMDGGQI TIGDNVFIGP NCGFYTATHP LNFHHRNEGF

EKAGPINIGS NTWFGGHVAV LPGVTIGEGS VIGAGSVVTK DIPPHSLAVG NPCKVVRKID

NEVPSEALND ETLN

SEQ ID NO: 64
MDIGKKHVIP KSQYRRKRRE FFHNEDREEN LNQHQDKQNI DNTTSKKADK QIHKDSIDKH

ERFKNSLSSH LEQRNRDVNE NKAEESKSNQ DSKSAYNRDH YLTDDVSKKQ NSLDSVDQDT

EKSKYYEQNS EATLSTKSTD KVESTEMRKL SSDKNKVGHE EQHVLSKPSE HDKETRIDSE

SSRTDSDSSM QTEKIKKDSS DGNKSSNLKS EVISDKSNTV PKLSESDDEV NNQKPLTLPE

EQKLKRQQSQ NEQTKTYTYG DSEQNDKSNH ENDLSHHIPS ISDDKDNVMR ENHIVDDNPD

NDINTPSLSK TDDDRKLDEK IHVEDKHKQN ADSSETVGYQ SQSTASHRST EKRNISINDH

DKLNGQKTNT KTSANNNQKK ATSKLNKGRA TNNNYSDILK KFWMMYWPKG SGGGAKVAKQ

GQYKNQDPIV LVHGFNGFTD DINPSVLAHY WGGNKMNIRQ DLEENGYKAY EASISAFGSN

YDRAVELYYY IKGGRVDYGA AHAAKYGHER YGKTYEGIYK DWKPGQKVHL VGHSMGGQTI

RQLEELLRNG SREEIEYQKK HGGEISPLFK GNNDNMISSI TTLGTPHNGT HASDLAGNEA

LVRQIVFDIG KMFGNKNSRV DFGLAQWGLK QKPNESYIDY VKRVKQSNLW KSKDNGFYDL

TREGATDLNR KTSLNPNIVY KTYTGEATHK ALNSDRQKAD LNMFFPFVIT GNLIGKATEK

EWRENDGLVS VISSQHPFNQ AYTNATDKIQ KGIWQVTPTK HDWDHVDFVG QDSSDTVRTR

EELQDFWHHL ADDLVKTEKV TDTKQ

SEQ ID NO: 65
RNLLLQKQSQ ARQTAEDIVN QAHKEADNIK KEKLLEAKEE NQILREQTEA ELRERRSELQ

RQETRLLQKE ENLERKSDLL DKKDEILEQK ESKIEEKQQQ VDAKESSVQT LIMKHEQELE

RISGLTQEEA INEQLQRVEE ELSQDIAVLV KEKEKEAKEK VDKTAKELLA TAVQRLAADH

TSESTVSVVN LPNDEMKGRI IGREGRNIRT LETLTGIDLI IDDTPEAVIL SGFDPIRREI

ARTALVNLVS DGRIHPGRIE DMVEKARKEV DDIIREAGEQ ATFEVNAHNM HPDLVKIVGR

LNYRTSYGQN VLKHSIEVAH LASMLAAELG EDETLAKRAG LLHDVGKAID HEVEGSHVEI

GVELAKKYGE NETVINAIHS HHGDVEPTSI ISILVAAADA LSAARPGARK ETLENYIRRL
```

```
ERLETLSESY DGVEKAFAIQ AGREIRVIVS PEEIDDLKSY RLARDIKNQI EDELQYPGHI
KVTVVRETRA VEYAKKPEPK PAPAPKPACG NDDGKDKDGK VTIKTTVYPL QSFAEQIGGK
HVKVSSIYPA GTDLHSYEPT QKDILSASKS DLFMYTGDNL DPVAKKVAST IKDKDKKLSL
EDKLDKAKLL TDQHEHGEEH EHEGHDHEKE EHHHHGGYDP HVWLDPKINQ TFAKEIKDEL
VKKDPKHKDD YEKNYKKLND DLKKIDNDMK QVTKDKQGNA VFISHESIGY LADRYGFVQK
GIQNMNAEDP SQKELTKIVK EIRDSNAKYI LYEDNVANKV TETIRKETDA KPLKFYNMES
LNKEQQKKDN ITYQSLMKSN IENIGKALDS GVKVKDDKAE SKHDKAISDG YFKDEQVKDR
ELSDYAGEWQ SVYPYLKDGT LDEVMEHKAE NDPKKSAKDL KAYYDKGYKT DITNIDIKGN
EITFTKDGKK HTGKYEYNGK KTLKYPKGNR GVRFMFKLVD GNDKDLPKFI QFSDHNIAPK
KAEHFHIFMG NDNDALLKEM DNWPTYYPSK LNKDQIKEEM LAH
                                                        SEQ ID NO: 66
MNEKVEGMTL ELKLDHLGVQ EGMKGLKRQL GVVNSEMKAN LSAFDKSEKS MEKYQARIKG
LNDRLKVQKK MYSQVEDELK QVNANYQKAK SSVKDVEKAY LKLVEANKKE KLALDKSKEA
LKSSNTELKK AENQYKRTNQ RKQDAYQKLK QLRDAEQKLK NSNQATTAQL KRASDAVQKQ
SAKHKALVEQ YKQEGNQVQK LKVQNDNLSK SNDKIESSYA KTNTKLKQTE KEFNDLNNTI
KNHSANVAKA ETAVNKEKAA LNNLERSIDK ASSEMKTFNK EQMIAQSHFG KLASQADVMS
KKFSSIGDKM TSLGRTMTMG VSTPITLGLG AALKTSADFE GQMSRVGAIA QASSKDLKSM
SNQAVDLGAK TSKSANEVAK GMEELAALGF NAKQTMEAMP GVISAAEASG AEMATTATVM
ASAINSFGLK ASDANHVADL LARSANDSAA DIQYMGDALK YAGTPAKALG VSIEDTSAAI
EVLSNSGLEG SQAGTALRAS FIRLANPSKN TAKEMKKLGI HLSDAKGQFV GMGELIRQFQ
DNMKGMTREQ KLATVATIVG TEAASGFLAL IEAGPDKINS YSKSLKNSNG ESKKAADLMK
DNLKGALEQL GGAFESLAIE VGKDLTPMIR AGAEGLTKLV DGFTHLPGWV RKGSGGGAAK
DNLNGEKPTT NLNHNVTSPS VNSEMNNNET GTPHESNQAG NEGTGSNSRD ANPDSNNVKP
DSNNQNPSPD SKPDPNNPNP GPNPKPDPDK PKPNPEPKPD PKPDPDKPKP NPDPKPDPDK
PKPNPDPKPD PDKPKPNPDP KPDPNPNPKP DPNKPNPNPS PNPNQPGDSN QSGGSKNGGT
WNPNASDGSN QGQWQPNGNQ GNSQNPTGND FVSQRFLALA NGAYKYNPYI LNQINQLGKE
YGEVTDEDIY NIIRKQNFSG NAYLNGLQQQ SNYFRFQYFN PLKSERYYRN LDEQVLALIT
GEIGSMPDLK KPEDKPDSKQ RSFEPHEKDD FTVVKKQEDN KKSASTAYS
                                                        SEQ ID NO: 67
GFLNKSKNEQ AALKAQQAAI KEEASANNLS DTSQEAQEIQ EAKREAQAEA DKSVAVSNKE
SKAVALKAQQ AAIKEEASAN NLSDTSQEAQ EIQEAKKEAQ AETDKSAAVS NEEPKAVALK
AQQAAIKEEA SANNLSDISQ EAQEVQEAKK EAQAEKDSDT LTKDASAAKV EVSKPESQAE
RLANAAKQKQ AKLTPGSKES QLTEALFAEK PVAKNDLKEI PQLVTKKNDV SETETVNIDN
KDTVKQKEAK FENGVITRKA DEKTTNNTAV DKKSGKQSKK TTPSNKRNAS KASTNKTSGQ
KKQHNKKSSQ GAKKQSSSSK STQKNNQTSN KNSKTTNAKS SNASKTPNAK VEKAKSKIEK
RTFNDGSGGG AGSGGGAAKD NLNGEKPTTN LNHNVTSPSV NSEMNNNETG TPHESNQAGN
EGTGSNSRDA NPDSNNVKPD SNNQNPSPDS KPDPNNPNPG PNPKPDPDKP KPNPEPKPDP
KPDPDKPKPN PDPKPDPDKP KPNPDPKPDP DKPKPNPDPK PDPNPNPKPD PNKPNPNPSP
NPNQPGDSNQ SGGSKNGGTW NPNASDGSNQ GQWQPNGNQG NSQNPTGNDF VSQRFLALAN
```

-continued

```
GAYKYNPYIL NQINQLGKEY GEVTDEDIYN IIRKQNFSGN AYLNGLQQQS NYFRFQYFNP

LKSERYYRNL DEQVLALITG EIGSMPDLKK PEDKPDSKQR SFEPHEKDDF TVVKKQEDNK

KSASTAYS
                                                        SEQ ID NO: 68
AKDNLNGEKP TTNLNHNVTS PSVNSEMNNN ETGTPHESNQ AGNEGTGSNS RDANPDSNNV

KPDSNNQNPS PDSKPDPNNP NPGPNPKPDP DKPKPNPEPK PDPKPDPDKP KPNPDPKPDP

DKPKPNPDPK PDPDKPKPNP DPKPDPNPNP KPDPNKPNPN PSPNPNQPGD SNQSGGSKNG

GTWNPNASDG SNQGQWQPNG NQGNSQNPTG NDFVSQRFLA LANGAYKYNP YILNQINQLG

KEYGEVTDED IYNIIRKQNF SGNAYLNGLQ QQSNYFRFQY FNPLKSERYY RNLDEQVLAL

ITGEIGSMPD LKKPEDKPDS KQRSFEPHEK DDFTVVKKQE DNKKSASTAY SGSGGGAGFL

NKSKNEQAAL KAQQAAIKEE ASANNLSDTS QEAQEIQEAK REAQAEADKS VAVSNKESKA

VALKAQQAAI KEEASANNLS DTSQEAQEIQ EAKKEAQAET DKSAAVSNEE PKAVALKAQQ

AAIKEEASAN NLSDISQEAQ EVQEAKKEAQ AEKDSDTLTK DASAAKVEVS KPESQAERLA

NAAKQKQAKL TPGSKESQLT EALFAEKPVA KNDLKEIPQL VTKKNDVSET ETVNIDNKDT

VKQKEAKFEN GVITRKADEK TTNNTAVDKK SGKQSKKTTP SNKRNASKAS TNKTSGQKKQ

HNKKSSQGAK KQSSSSKSTQ KNNQTSNKNS KTTNAKSSNA SKTPNAKVEK AKSKIEKRTF

ND
                                                        SEQ ID NO: 69
ACGNDDGKDK DGKVTIKTTV YPLQSFAEQI GGKHVKVSSI YPAGTDLHSY EPTQKDILSA

SKSDLFMYTG DNLDPVAKKV ASTIKDKDKK LSLEDKLDKA KLLTDQHEHG EEHEHEGHDH

EKEEHHHHGG YDPHVWLDPK INQTFAKEIK DELVKKDPKH KDDYEKNYKK LNDDLKKIDN

DMKQVTKDKQ GNAVFISHES IGYLADRYGF VQKGIQNMNA EDPSQKELTK IVKEIRDSNA

KYILYEDNVA NKVTETIRKE TDAKPLKFYN MESLNKEQQK KDNITYQSLM KSNIENIGKA

LDSGVKVKDD KAESKHDKAI SDGYFKDEQV KDRELSDYAG EWQSVYPYLK DGTLDEVMEH

KAENDPKKSA KDLKAYYDKG YKTDITNIDI KGNEITFTKD GKKHTGKYEY NGKKTLKYPK

GNRGVRFMFK LVDGNDKDLP KFIQFSDHNI APKKAEHFHI FMGNDNDALL KEMDNWPTYY

PSKLNKDQIK EEMLAHGSGG GAGFLNKSKN EQAALKAQQA AIKEEASANN LSDTSQEAQE

IQEAKREAQA EADKSVAVSN KESKAVALKA QQAAIKEEAS ANNLSDTSQE AQEIQEAKKE

AQAETDKSAA VSNEEPKAVA LKAQQAAIKE EASANNLSDI SQEAQEVQEA KKEAQAEKDS

DTLTKDASAA KVEVSKPESQ AERLANAAKQ KQAKLTPGSK ESQLTEALFA EKPVAKNDLK

EIPQLVTKKN DVSETETVNI DNKDTVKQKE AKFENGVITR KADEKTTNNT AVDKKSGKQS

KKTTPSNKRN ASKASTNKTS GQKKQHNKKS SQGAKKQSSS SKSTQKNNQT SNKNSKTTNA

KSSNASKTPN AKVEKAKSKI EKRTFND
                                                        SEQ ID NO: 70
MTEKEKMLAE KWYDANFDQD LINERARAKD ICFELNHTKP SDKNKRKELI DELFQTTTDN

VSISIPFDTD YGWNVKLGKN VYVNTNCYFM DGGQITIGDN VFIGPNCGFY TATHPLNFHH

RNEGFEKAGP INIGSNTWFG GHVAVLPGVT IGEGSVIGAG SVVTKDIPPH SLAVGNPCKV

VRKIDNEVPS EALNDETLNG SGGGADTPQK DTTAKTTSHD SKKSNDDETS KDTTSKDIDK

ADNNNTSNQD NNDKKFKTID DSTSDSNNII DFIYKNLPQT NINQLLTKNK YDDNYSLTTL

IQNLFNLNSD ISDYEQPRNG EKSTNDSNKN SDNSIKNDTD TQSSKQDKAD NQKAPKSNNT

KPSTSNKQPN SPKPTQPNQS NSQPASDDKA NQKSSSKDNQ SMSDSALDSI LDQYSEDAKK

TQKDYASQSK KDKNEKSNTK NPQLPTQDEL KHKSKPAQSF NNDVNQKDTR ATSLFETDPS
```

```
ISNNDDSGQF NVVDSKDTRQ FVKSIAKDAH RIGQDNDIYA SVMIAQAILE SDSGRSALAK

SPNHNLFGIK GAFEGNSVPF NTLEADGNKL YSINAGFRKY PSTKESLKDY SDLIKNGIDG

NRTIYKPTWK SEADSYKDAT SHLSKTYATD PNYAKKLNSI IKHYQLTQFD DERMPDLDKY

ERSIKDYDDS SDEFKPFREV SDSMPYPHGQ CTWYVYNRMK QFGTSISGDL GDAHNWNNRA

QYRDYQVSHT PKRHAAVVFE AGQFGADQHY GHVAFVEKVN SDGSIVISES NVKGLGIISH

RTINAAAAEE LSYITGK

SEQ ID NO: 71
IDSKNKPANS DIKFEVTQKS DAVKALKELP KSENVKNIYQ DYAVTDVKTD KKGFTHYTLQ

PSVDGVHAPD KEVKVHADKS GKVVLINGDT DAKKVKPTNK VTLSKDDAAD KAFKAVKIDK

NKAKNLKDKV IKENKVEIDG DSNKYVYNVE LITVTPEISH WKVKIDAQTG EILEKMNLVK

EAAETGKGKG VLGDTKDINI NSIDGGFSLE DLTHQGKLSA FSFNDQTGQA TLITNEDENF

VKDEQRAGVD ANYYAKQTYD YYKDTFGRES YDNQGSPIVS LTHVNNYGGQ DNRNNAAWIG

DKMIYGDGDG RTFTSLSGAN DVVAHELTHG VTQETANLEY KDQSGALNES FSDVFGYFVD

DEDFLMGEDV YTPGKEGDAL RSMSNPEQFG QPAHMKDYVF TEKDNGGVHT NSGSGGGAGF

LNKSKNEQAA LKAQQAAIKE EASANNLSDT SQEAQEIQEA KREAQAEADK SVAVSNKESK

AVALKAQQAA IKEEASANNL SDTSQEAQEI QEAKKEAQAE TDKSAAVSNE EPKAVALKAQ

QAAIKEEASA NNLSDISQEA QEVQEAKKEA QAEKDSDTLT KDASAAKVEV SKPESQAERL

ANAAKQKQAK LTPGSKESQL TEALFAEKPV AKNDLKEIPQ LVTKKNDVSE TETVNIDNKD

TVKQKEAKFE NGVITRKADE KTTNNTAVDK KSGKQSKKTT PSNKRNASKA STNKTSGQKK

QHNKKSSQGA KKQSSSSKST QKNNQTSNKN SKTTNAKSSN ASKTPNAKVE KAKSKIEKRT

END
                                                        SEQ ID NO: 72
IDSKNKPANS DIKFEVTQKS DAVKALKELP KSENVKNIYQ DYAVTDVKTD KKGFTHYTLQ

PSVDGVHAPD KEVKVHADKS GKVVLINGDT DAKKVKPTNK VTLSKDDAAD KAFKAVKIDK

NKAKNLKDKV IKENKVEIDG DSNKYVYNVE LITVTPEISH WKVKIDAQTG EILEKMNLVK

EAAETGKGKG VLGDTKDINI NSIDGGFSLE DLTHQGKLSA FSFNDQTGQA TLITNEDENF

VKDEQRAGVD ANYYAKQTYD YYKDTFGRES YDNQGSPIVS LTHVNNYGGQ DNRNNAAWIG

DKMIYGDGDG RTFTSLSGAN DVVAHELTHG VTQETANLEY KDQSGALNES FSDVFGYFVD

DEDFLMGEDV YTPGKEGDAL RSMSNPEQFG QPAHMKDYVF TEKDNGGVHT NSGSGGGAAK

DNLNGEKPTT NLNHNVTSPS VNSEMNNNET GTPHESNQAG NEGTGSNSRD ANPDSNNVKP

DSNNQNPSPD SKPDPNNPNP GPNPKPDPDK PKPNPEPKPD PKPDPDKPKP NPDPKPDPDK

PKPNPDPKPD PDKPKPNPDP KPDPNPNPKP DPNKPNPNPS PNPNQPGDSN QSGGSKNGGT

WNPNASDGSN QGQWQPNGNQ GNSQNPTGND FVSQRFLALA NGAYKYNPYI LNQINQLGKE

YGEVTDEDIY NIIRKQNFSG NAYLNGLQQQ SNYFRFQYFN PLKSERYYRN LDEQVLALIT

GEIGSMPDLK KPEDKPDSKQ RSFEPHEKDD FTVVKKQEDN KKSASTAYS
                                                        SEQ ID NO: 73
IDSKNKPANS DIKFEVTQKS DAVKALKELP KSENVKNIYQ DYAVTDVKTD KKGFTHYTLQ

PSVDGVHAPD KEVKVHADKS GKVVLINGDT DAKKVKPTNK VTLSKDDAAD KAFKAVKIDK

NKAKNLKDKV IKENKVEIDG DSNKYVYNVE LITVTPEISH WKVKIDAQTG EILEKMNLVK

EAAETGKGKG VLGDTKDINI NSIDGGFSLE DLTHQGKLSA FSFNDQTGQA TLITNEDENF

VKDEQRAGVD ANYYAKQTYD YYKDTFGRES YDNQGSPIVS LTHVNNYGGQ DNRNNAAWIG

DKMIYGDGDG RTFTSLSGAN DVVAHELTHG VTQETANLEY KDQSGALNES FSDVFGYFVD
```

```
DEDFLMGEDV YTPGKEGDAL RSMSNPEQFG QPAHMKDYVF TEKDNGGVHT NSGSGGGAGS

GGGAKVAKQG QYKNQDPIVL VHGFNGFTDD INPSVLAHYW GGNKMNIRQD LEENGYKAYE

ASISAFGSNY DRAVELYYYI KGGRVDYGAA HAAKYGHERY GKTYEGIYKD WKPGQKVHLV

GHSMGGQTIR QLEELLRNGS REEIEYQKKH GGEISPLFKG NNDNMISSIT TLGTPHNGTH

ASDLAGNEAL VRQIVFDIGK MFGNKNSRVD FGLAQWGLKQ KPNESYIDYV KRVKQSNLWK

SKDNGFYDLT REGATDLNRK TSLNPNIVYK TYTGEATHKA LNSDRQKADL NMFFPFVITG

NLIGKATEKE WRENDGLVSV ISSQHPFNQA YTNATDKIQK GIWQVTPTKH DWDHVDFVGQ

DSSDTVRTRE ELQDFWHHLA DDLVKTEKVT DTKQ

SEQ ID NO: 74
DTPQKDTTAK TTSHDSKKSN DDETSKDTTS KDIDKADNNN TSNQDNNDKK FKTIDDSTSD

SNNIIDFIYK NLPQTNINQL LTKNKYDDNY SLTTLIQNLF NLNSDISDYE QPRNGEKSTN

DSNKNSDNSI KNDTDTQSSK QDKADNQKAP KSNNTKPSTS NKQPNSPKPT QPNQSNSQPA

SDDKANQKSS SKDNQSMSDS ALDSILDQYS EDAKKTQKDY ASQSKKDKNE KSNTKNPQLP

TQDELKHKSK PAQSFNNDVN QKDTRATSLF ETDPSISNND DSGQFNVVDS KDTRQFVKSI

AKDAHRIGQD NDIYASVMIA QAILESDSGR SALAKSPNHN LFGIKGAFEG NSVPFNTLEA

DGNKLYSINA GFRKYPSTKE SLKDYSDLIK NGIDGNRTIY KPTWKSEADS YKDATSHLSK

TYATDPNYAK KLNSIIKHYQ LTQFDDERMP DLDKYERSIK DYDDSSDEFK PFREVSDSMP

YPHGQCTWYV YNRMKQFGTS ISGDLGDAHN WNNRAQYRDY QVSHTPKRHA AVVFEAGQFG

ADQHYGHVAF VEKVNSDGSI VISESNVKGL GIISHRTINA AAAEELSYIT GKGSGGGAMT

EKEKMLAEKW YDANFDQDLI NERARAKDIC FELNHTKPSD KNKRKELIDE LFQTTTDNVS

ISIPFDTDYG WNVKLGKNVY VNTNCYFMDG GQITIGDNVF IGPNCGFYTA THPLNFHHRN

EGFEKAGPIN IGSNTWFGGH VAVLPGVTIG EGSVIGAGSV VTKDIPPHSL AVGNPCKVVR

KIDNEVPSEA LNDETLN

SEQ ID NO: 75
DTPQKDTTAK TTSHDSKKSN DDETSKDTTS KDIDKADNNN TSNQDNNDKK FKTIDDSTSD

SNNIIDFIYK NLPQTNINQL LTKNKYDDNY SLTTLIQNLF NLNSDISDYE QPRNGEKSTN

DSNKNSDNSI KNDTDTQSSK QDKADNQKAP KSNNTKPSTS NKQPNSPKPT QPNQSNSQPA

SDDKANQKSS SKDNQSMSDS ALDSILDQYS EDAKKTQKDY ASQSKKDKNE KSNTKNPQLP

TQDELKHKSK PAQSFNNDVN QKDTRATSLF ETDPSISNND DSGQFNVVDS KDTRQFVKSI

AKDAHRIGQD NDIYASVMIA QAILESDSGR SALAKSPNHN LFGIKGAFEG NSVPFNTLEA

DGNKLYSINA GFRKYPSTKE SLKDYSDLIK NGIDGNRTIY KPTWKSEADS YKDATSHLSK

TYATDPNYAK KLNSIIKHYQ LTQFDDERMP DLDKYERSIK DYDDSSDEFK PFREVSDSMP

YPHGQCTWYV YNRMKQFGTS ISGDLGDAHN WNNRAQYRDY QVSHTPKRHA AVVFEAGQFG

ADQHYGHVAF VEKVNSDGSI VISESNVKGL GIISHRTINA AAAEELSYIT GKKPEPKPAP

APKPMTEKEK MLAEKWYDAN FDQDLINERA RAKDICFELN HTKPSDKNKR KELIDELFQT

TTDNVSISIP FDTDYGWNVK LGKNVYVNTN CYFMDGGQIT IGDNVFIGPN CGFYTATHPL

NFHHRNEGFE KAGPINIGSN TWFGGHVAVL PGVTIGEGSV IGAGSVVTKD IPPHSLAVGN

PCKVVRKIDN EVPSEALNDE TLN

SEQ ID NO: 76
DTPQKDTTAK TTSHDSKKSN DDETSKDTTS KDIDKADNNN TSNQDNNDKK FKTIDDSTSD

SNNIIDFIYK NLPQTNINQL LTKNKYDDNY SLTTLIQNLF NLNSDISDYE QPRNGEKSTN

DSNKNSDNSI KNDTDTQSSK QDKADNQKAP KSNNTKPSTS NKQPNSPKPT QPNQSNSQPA
```

-continued

```
SDDKANQKSS SKDNQSMSDS ALDSILDQYS EDAKKTQKDY ASQSKKDKNE KSNTKNPQLP
TQDELKHKSK PAQSFNNDVN QKDTRATSLF ETDPSISNND DSGQFNVVDS KDTRQFVKSI
AKDAHRIGQD NDIYASVMIA QAILESDSGR SALAKSPNHN LFGIKGAFEG NSVPFNTLEA
DGNKLYSINA GFRKYPSTKE SLKDYSDLIK NGIDGNRTIY KPTWKSEADS YKDATSHLSK
TYATDPNYAK KLNSIIKHYQ LTQFDDERMP DLDKYERSIK DYDDSSDEFK PFREVSDSMP
YPHGQCTWYV YNRMKQFGTS ISGDLGDAHN WNNRAQYRDY QVSHTPKRHA AVVFEAGQFG
ADQHYGHVAF VEKVNSDGSI VISESNVKGL GIISHRTINA AAAEELSYIT GKGSGGGAKV
AKQGQYKNQD PIVLVHGFNG FTDDINPSVL AHYWGGNKMN IRQDLEENGY KAYEASISAF
GSNYDRAVEL YYYIKGGRVD YGAAHAAKYG HERYGKTYEG IYKDWKPGQK VHLVGHSMGG
QTIRQLEELL RNGSREEIEY QKKHGGEISP LFKGNNDNMI SSITTLGTPH NGTHASDLAG
NEALVRQIVF DIGKMFGNKN SRVDFGLAQW GLKQKPNESY IDYVKRVKQS NLWKSKDNGF
YDLTREGATD LNRKTSLNPN IVYKTYTGEA THKALNSDRQ KADLNMFFPF VITGNLIGKA
TEKEWRENDG LVSVISSQHP FNQAYTNATD KIQKGIWQVT PTKHDWDHVD FVGQDSSDTV
RTREELQDFW HHLADDLVKT EKVTDTKQ
                                                    SEQ ID NO: 77
DTPQKDTTAK TTSHDSKKSN DDETSKDTTS KDIDKADNNN TSNQDNNDKK FKTIDDSTSD
SNNIIDFIYK NLPQTNINQL LTKNKYDDNY SLTTLIQNLF NLNSDISDYE QPRNGEKSTN
DSNKNSDNSI KNDTDTQSSK QDKADNQKAP KSNNTKPSTS NKQPNSPKPT QPNQSNSQPA
SDDKANQKSS SKDNQSMSDS ALDSILDQYS EDAKKTQKDY ASQSKKDKNE KSNTKNPQLP
TQDELKHKSK PAQSFNNDVN QKDTRATSLF ETDPSISNND DSGQFNVVDS KDTRQFVKSI
AKDAHRIGQD NDIYASVMIA QAILESDSGR SALAKSPNHN LFGIKGAFEG NSVPFNTLEA
DGNKLYSINA GFRKYPSTKE SLKDYSDLIK NGIDGNRTIY KPTWKSEADS YKDATSHLSK
TYATDPNYAK KLNSIIKHYQ LTQFDDERMP DLDKYERSIK DYDDSSDEFK PFREVSDSMP
YPHGQCTWYV YNRMKQFGTS ISGDLGDAHN WNNRAQYRDY QVSHTPKRHA AVVFEAGQFG
ADQHYGHVAF VEKVNSDGSI VISESNVKGL GIISHRTINA AAAEELSYIT GKGSGGGAKV
AKQGQYKNQD PIVLVHGFNG FTDDINPSVL AHYWGGNKMN IRQDLEENGY KAYEASISAF
GSNYDRAVEL YYYIKGGRVD YGAAHAAKYG HERYGKTYEG IYKDWKPGQK VHLVGHSMGG
QTIRQLEELL RNGSREEIEY QKKHGGEISP LFKGNNDNMI SSITTLGTPH NGTHASDLAG
NEAL
                                                    SEQ ID NO: 78
ADSDINIKTG TTDIGSNTTV KTGDLVTYDK ENGMLKKVFY SFIDDKNHNK KLLVIRTKGT
IAGQYRVYSE EGANKSGLAW PSAFKVQLQL PDNEVAQISD YYPRNSIDTK EYMSTLTYGF
NGNVTGDDTG KIGGLIGANV SIGHTLKYVQ PDFKTILESP TDKKVGWKVI FNNMVNQNWG
PYDRDSWNPV YGNQLFMKTR NGSMKAADNF LDPNKASSLL SSGFSPDFAT VITMDRKASK
QQTNIDVIYE RVRDDYQLHW TSTNWKGTNT KDKWIDRSSE RYKIDWEKEE MTNGSGGGAK
RIKQHPDVQK VTDATSKVAS KTSAAISNTA SDVKEYVGDK KQDFENKREL KKFAREHDPA
YIEKKGEKLA KQNRKDADKM NKILQKNIEK RHKEEQKARE KNEIQRIKDM KKSQKYEVKA
GLTPNKLDEK TEKKGDKLAE KNRKEIAKMN KKLQKNIEKR HKEEQKRQQE ADKARIKSFK
KYKDYVAKSA SQQNKENNTE A
                                                    SEQ ID NO: 79
ADSDINIKTG TTDIGSNTTV KTGDLVTYDK ENGMLKKVFY SFIDDKNHNK KLLVIRTKGT
IAGQYRVYSE EGANKSGLAW PSAFKVQLQL PDNEVAQISD YYPRNSIDTK EYMSTLTYGF
```

```
NGNVTGDDTG KIGGLIGANV SIGHTLKYVQ PDFKTILESP TDKKVGWKVI FNNMVNQNWG

PYDRDSWNPV YGNQLFMKTR NGSMKAADNF LDPNKASSLL SSGFSPDFAT VITMDRKASK

QQTNIDVIYE RVRDDYQLHW TSTNWKGTNT KDKWIDRSSE RYKIDWEKEE MTNGSGGGAM

TEKEKMLAEK WYDANFDQDL INERARAKDI CFELNHTKPS DKNKRKELID ELFQTTTDNV

SISIPFDTDY GWNVKLGKNV YVNTNCYFMD GGQITIGDNV FIGPNCGFYT ATHPLNFHHR

NEGFEKAGPI NIGSNTWFGG HVAVLPGVTI GEGSVIGAGS VVTKDIPPHS LAVGNPCKVV

RKIDNEVPSE ALNDETLN

SEQ ID NO: 80
ADSDINIKTG TTDIGSNTTV KTGDLVTYDK ENGMLKKVFY SFIDDKNHNK KLLVIRTKGT

IAGQYRVYSE EGANKSGLAW PSAFKVQLQL PDNEVAQISD YYPRNSIDTK EYMSTLTYGF

NGNVTGDDTG KIGGLIGANV SIGHTLKYVQ PDFKTILESP TDKKVGWKVI FNNMVNQNWG

PYDRDSWNPV YGNQLFMKTR NGSMKAADNF LDPNKASSLL SSGFSPDFAT VITMDRKASK

QQTNIDVIYE RVRDDYQLHW TSTNWKGTNT KDKWIDRSSE RYKIDWEKEE MTNGSGGGAK

VAKQGQYKNQ DPIVLVHGFN GFTDDINPSV LAHYWGGNKM NIRQDLEENG YKAYEASISA

FGSNYDRAVE LYYYIKGGRV DYGAAHAAKY GHERYGKTYE GIYKDWKPGQ KVHLVGHSMG

GQTIRQLEEL LRNGSREEIE YQKKHGGEIS PLFKGNNDNM ISSITTLGTP HNGTHASDLA

GNEALVRQIV FDIGKMFGNK NSRVDFGLAQ WGLKQKPNES YIDYVKRVKQ SNLWKSKDNG

FYDLTREGAT DLNRKTSLNP NIVYKTYTGE ATHKALNSDR QKADLNMFFP FVITGNLIGK

ATEKEWREND GLVSVISSQH PFNQAYTNAT DKIQKGIWQV TPTKHDWDHV DFVGQDSSDT

VRTREELQDF WHHLADDLVK TEKVTDTKQ

SEQ ID NO: 81
KVAKQGQYKN QDPIVLVHGF NGFTDDINPS VLAHYWGGNK MNIRQDLEEN GYKAYEASIS

AFGSNYDRAV ELYYYIKGGR VDYGAAHAAK YGHERYGKTY EGIYKDWKPG QKVHLVGHSM

GGQTIRQLEE LLRNGSREEI EYQKKHGGEI SPLFKGNNDN MISSITTLGT PHNGTHASDL

AGNEALVRQI VFDIGKMFGN KNSRVDFGLA QWGLKQKPNE SYIDYVKRVK QSNLWKSKDN

GFYDLTREGA TDLNRKTSLN PNIVYKTYTG EATHKALNSD RQKADLNMFF PFVITGNLIG

KATEKEWREN DGLVSVISSQ HPFNQAYTNA TDKIQKGIWQ VTPTKHDWDH VDFVGQDSSD

TVRTREELQD FWHHLADDLV KTEKVTDTKQ

SEQ ID NO: 82
KVAKQGQYKN QDPIVLVHGF NGFTDDINPS VLAHYWGGNK MNIRQDLEEN GYKAYEASIS

AFGSNYDRAV ELYYYIKGGR VDYGAAHAAK YGHERYGKTY EGIYKDWKPG QKVHLVGHSM

GGQTIRQLEE LLRNGSREEI EYQKKHGGEI SPLFKGNNDN MISSITTLGT PHNGTHASDL

AGNEAL

SEQ ID NO: 83
ADSDINIKTG TTDIGSNTTV KTGDLVTYDK ENGMLKKVFY SFIDDKNHNK KLLVIRTKGT

IAGQYRVYSE EGANKSGLAW PSAFKVQLQL PDNEVAQISD YYPRNSIDTK EYMSTLTYGF

NGNVTGDDTG KIGGLIGANV SIGHTLKYVQ PDFKTILESP TDKKVGWKVI FNNMVNQNWG

PYDRDSWNPV YGNQLFMKTR NGSMKAADNF LDPNKASSLL SSGFSPDFAT VITMDRKASK

QQTNIDVIYE RVRDDYQLHW TSTNWKGTNT KDKWIDRSSE RYKIDWEKEE MTN

SEQ ID NO: 84
AAEETGGTNT EAQPKTEAVA SPTTTSEKAP ETKPVANAVS VSNKEVEAPT SETKEAKEVK

EVKAPKETKE VKPAAKATNN TYPILNQELR EAIKNPAIKD KDHSAPNSRP IDFEMKKKDG

TQQFYHYASS VKPARVIFTD SKPEIELGLQ SGQFWRKFEV YEGDKKLPIK LVSYDTVKDY
```

```
AYIRFSVSNG TKAVKIVSST HFNNKEEKYD YTLMEFAQPI YNSADKFKTE EDYKAEKLLA

PYKKAKTLER QVYELNKIQD KLPEKLKAEY KKKLEDTKKA LDEQVKSAIT EFQNVQPTNE

KMTDLQDTKY VVYESVENNE SMMDTFVKHP IKTGMLNGKK YMVMETTNDD YWKDFMVEGQ

RVRTISKDAK NNTRTIIFPY VEGKTLYDAI VKVHVKTIDY DGQYHVRIVD KEAFTKANTD

KSNKKEQQDN SAKKEATPAT PSKPTPSPVE KESQKQDSQK DDNKQLPSVE KENDASSESG

KDKTPATKPT KGEVESSSTT PTKVVSTTQN VAKPTTASSK TTKDVVQTSA GSSEAKDSAP

LQKANIKNTN DGHTQSQNNK NTQENKAKSL PQT
                                                     SEQ ID NO: 85
MDIGKKHVIP KSQYRRKRRE FFHNEDREEN LNQHQDKQNI DNTTSKKADK QIHKDSIDKH

ERFKNSLSSH LEQRNRDVNE NKAEESKSNQ DSKSAYNRDH YLTDDVSKKQ NSLDSVDQDT

EKSKYYEQNS EATLSTKSTD KVESTEMRKL SSDKNKVGHE EQHVLSKPSE HDKETRIDSE

SSRTDSDSSM QTEKIKKDSS DGNKSSNLKS EVISDKSNTV PKLSESDDEV NNQKPLTLPE

EQKLKRQQSQ NEQTKTYTYG DSEQNDKSNH ENDLSHHIPS ISDDKDNVMR ENHIVDDNPD

NDINTPSLSK TDDDRKLDEK IHVEDKHKQN ADSSETVGYQ SQSTASHRST EKRNISINDH

DKLNGQKTNT KTSANNNQKK ATSKLNKGRA TNNNYSDILK KFWMMYWPK
                                                     SEQ ID NO: 86
DTPQKDTTAK TTSHDSKKSN DDETSKDTTS KDIDKADNNN TSNQDNNDKK FKTIDDSTSD

SNNIIDFIYK NLPQTNINQL LTKNKYDDNY SLTTLIQNLF NLNSDISDYE QPRNGEKSTN

DSNKNSDNSI KNDTDTQSSK QDKADNQKAP KSNNTKPSTS NKQPNSPKPT QPNQSNSQPA

SDDKANQKSS SKDNQSMSDS ALDSILDQYS EDAKKTQKDY ASQSKKDKNE KSNTKNPQLP

TQDELKHKSK PAQSFNNDVN QKDTRATSLF ETDPSISNND DSGQFNVVDS KDTRQFVKSI

AKDAHRIGQD NDIYASVMIA QAILESDSGR SALAKSPNHN LFGIKGAFEG NSVPFNTLEA

DGNKLYSINA GFRKYPSTKE SLKDYSDLIK NGIDGNRTIY KPTWKSEADS YKDATSHLSK

TYATDPNYAK KLNSIIKHYQ LTQFDDERMP DLDKYERSIK DYDDSSDEFK PFREVSDSMP

YPHGQCTWYV YNRMKQFGTS ISGDLGDAHN WNNRAQYRDY QVSHTPKRHA AVVFEAGQFG

ADQHYGHVAF VEKVNSDGSI VISESNVKGL GIISHRTINA AAAEELSYIT GK
                                                     SEQ ID NO: 87
QTKYGDQSEK GSQSVSNKNN KIHIAIVNED QPTTYNGKKV ELGQAFIKRL ANEKNYKFET

VTRNVAESGL KNGGYQVMIV IPENFSKLAM QLDAKTPSKI SLQYKTAVGQ KEEVAKNTEK

VVSNVLNDFN KNLVEIYLTS IIDNLHNAQK NVGAIMTREH GVNSKFSNYL LNPINDFPEL

FTDTLVNSIS ANKDITKWFQ TYNKSLLSAN SDTFRVNTDY NVSTLIEKQN SLFDEHNTAM

DKMLQDYKSQ KDSVELDNYI NALKQMDSQI DQQSSMQDTG KEEYKQTVKE NLDKLREIIQ

SQESPFSKGM IEDYRKQLTE SLQDELANNK DLQDALNSIK MNNAQFAENL EKQLHDDIVK

EPDSDTTFIY NMSKQDFIAA GLNEDEANKY EAIVKEAKRY KNEYNLKKPL AEHINLTDYD

NQVAQDTSSL INDGVKVQRT ETIKSNDINQ LTVATDPHFN FEGDIKINGK KYDIKDQSVQ

LDTSNKEYKV EVNGVAKLKK DAEKDFLKDK TMHLQLLFGQ ANRQDEPNDK KATSVVDVTL

NHNLDGRLSK DALSQQLSAL SRFDAHYKMY TDTKGREDKP FDNKRLIDMM VDQVINDMES

FKDDKVAVLH QIDSMEENSD KLIDDILNNK KNTTKNKEDI SKLIDQLENV KKTFAEEPQE

PKIDKGKNDE FNTMSSNLDK EISRISEKST QLLSDTQESK TIADSVSGQL NQLDNNVNKL

HATGRALGVR ANDLNRQMAK NDKDNELFAK EFKKVLQNSK DGDRQNQALK AFMSNPVQKK

NLENVLANNG NTD
```

SEQ ID NO: 88
KRIKQHPDVQ KVTDATSKVA SKTSAAISNT ASDVKEYVGD KKQDFENKRE LKKFAREHDP
AYIEKKGEKL AKQNRKDADK MNKILQKNIE KRHKEEQKAR EKNEIQRIKD MKKSQKYEVK
AGLTPNKLDE KTEKKGDKLA EKNRKEIAKM NKKLQKNIEK RHKEEQKRQQ EADKARIKSF
KKYKDYVAKS ASQQNKENNT EA

SEQ ID NO: 89
MDIGKKHVIP KSQYRRKRRE FFHNEDREEN LNQHQDKQNI DNTTSKKADK QIHKDSIDKH
ERFKNSLSSH LEQRNRDVNE NKAEESKSNQ GSKSAYNKDH YLTDDVSKKQ NSLDSVDQDT
EKSKYYEQNT EATLSTNSTD KVESTDMRKL SSDKNKVGHE EQHVLSKPSE HDKETRIDFE
SSRTDSDSSM QTEKIKKDSS DGNKSSNLKS EVISDKSNSV PILSESDDEV NNQKPLTLPE
EQKLKRQQSQ NEQTKTYTYG DSEQNDKSNH ENDLSHHTPS ISDDKDYVMR EDHIVDDNPD
NDINTPSLSK IDDDRKLDEK IHVEDKHKQN ADSSETVGYQ SQSSASHRST EKRNMAINDH
DKLNGQKPNT KTSANNNQKK ATSKLNKGRA TNNNYSAILK KFWMMYWPK

SEQ ID NO: 90
RNLLLQKQSQ ARQTAEDIVN QAHKEADNIK KEKLLEAKEE NQILREQTEA ELRERRSELQ
RQETRLLQKE ENLERKSDLL DKKDEILEQK ESKIEEKQQQ VDAKESSVQT LIMKHEQELE
RISGLTQEEA INEQLQRVEE ELSQDIAVLV KEKEKEAKEK VDKTAKELLA TAVQRLAADH
TSESTVSVVN LPNDEMKGRI IGREGRNIRT LETLTGIDLI IDDTPEAVIL SGFDPIRREI
ARTALVNLVS DGRIHPGRIE DMVEKARKEV DDIIREAGEQ ATFEVNAHNM HPDLVKIVGR
LNYRTSYGQN VLKHSIEVAH LASMLAAELG EDETLAKRAG LLHDVGKAID HEVEGSHVEI
GVELAKKYGE NETVINAIHS HHGDVEPTSI ISILVAAADA LSAARPGARK ETLENYIRRL
ERLETLSESY DGVEKAFAIQ AGREIRVIVS PEEIDDLKSY RLARDIKNQI EDELQYPGHI
KVTVVRETRA VEYAK

SEQ ID NO: 91
NNHNNGTKEN KIANTNKNNA DESKDKDTSK DASKDKSKST DSDKSKDDQD KATKDESDND
QNNANQANNQ AQNNQNQQQA NQNQQQQQQR QGGGQRHTVN GQENLYRIAI QYYGSGSPEN
VEKIRRANGL SGNNIRNGQQ IVIP

SEQ ID NO: 92
MNEKVEGMTL ELKLDHLGVQ EGMKGLKRQL GVVNSEMKAN LSAFDKSEKS MEKYQARIKG
LNDRLKVQKK MYSQVEDELK QVNANYQKAK SSVKDVEKAY LKLVEANKKE KLALDKSKEA
LKSSNTELKK AENQYKRTNQ RKQDAYQKLK QLRDAEQKLK NSNQATTAQL KRASDAVQKQ
SAKHKALVEQ YKQEGNQVQK LKVQNDNLSK SNDKIESSYA KTNTKLKQTE KEFNDLNNTI
KNHSANVAKA ETAVNKEKAA LNNLERSIDK ASSEMKTFNK EQMIAQSHFG KLASQADVMS
KKFSSIGDKM TSLGRTMTMG VSTPITLGLG AALKTSADFE GQMSRVGAIA QASSKDLKSM
SNQAVDLGAK TSKSANEVAK GMEELAALGF NAKQTMEAMP GVISAAEEASG AEMATTATVM
ASAINSFGLK ASDANHVADL LARSANDSAA DIQYMGDALK YAGTPAKALG VSIEDTSAAI
EVLSNSGLEG SQAGTALRAS FIRLANPSKN TAKEMKKLGI HLSDAKGQFV GMGELIRQFQ
DNMKGMTREQ KLATVATIVG TEAASGFLAL IEAGPDKINS YSKSLKNSNG ESKKAADLMK
DNLKGALEQL GGAFESLAIE VGKDLTPMIR AGAEGLTKLV DGFTHLPGWV RK

SEQ ID NO: 93
MTEKEKMLAE KWYDANFDQD LINERARAKD ICFELNHTKP SDKNKRKELI DELFQTTTDN
VSISIPFDTD YGWNVKLGKN VYVNTNCYFM DGGQITIGDN VFIGPNCGFY TATHPLNFHH

```
RNEGFEKAGP INIGSNTWFG GHVAVLPGVT IGEGSVIGAG SVVTKDIPPH SLAVGNPCKV

VRKIDNEVPS EALNDETLN

SEQ ID NO: 94
DTPQKDTTAK TTSHDSKKST DDETSKDTTS KDIDKADNNN TSNQDNNDKK VKTIDDSTSD

SNNIIDFIYK NLPQTNINQL LTKNKYDDNY SLTTLIQNLF NLNSDISDYE QPRNGEKSTN

DSNKNSDNSI KNDTDTQSSK QDKADNQKAP KSNNTKPSTS NKQPNSPKPT QPNQSNSQPA

SDDKVNQKSS SKDNQSMSDS ALDSILDQYS EDAKKTQKDY ASQSKKDKNE KSNTKNPQLP

TQDELKHKSK PAQSFNNDVN QKDTRATSLF ETDPSISNND DSGQFNVVDS KDTRQFVKSI

AKDAHRIGQD NDIYASVMIA QAILESDSGR SALAKSPNHN LFGIKGAFEG NSVPFNTLEA

DGNQLYSINA GFRKYPSTKE SLKDYSDLIK NGIDGNRTIY KPTWKSEADS YKDATSHLSK

TYATDPNYAK KLNSIIKHYQ LTQFDDERMP DLDKYERSIK DYDDSSDEFK PFREVSDNMP

YPHGQCTWYV YNRMKQFGTS ISGDLGDAHN WNNRAQYRDY QVSHTPKRHA AVVFEAGQFG

ADQHYGHVAF VEKVNSDGSI VISESNVKGL GIISHRTINA AAAEELSYIT GK

SEQ ID NO: 95
AEKQVNMGNS QEDTVTAQSI GDQQTRENAN YQRENGVDEQ QHTENLTKNL HNDKTISEEN

HRKTDDLNKD QLKDDKKSSL NNKNIQRDTT KNNNANPRDV NQGLEQAIND GKQSKVASQQ

QSKEADNSQD LNANNNLPSQ SRTKVSPSLN KSDQTSQREI VNETEIEKVQ PQQKNQANDK

ITDHNFNNEQ EVKPQKDEKT LSVSDLKNNQ KSPVEPTKDN DKKNGLNLLK SSAVATLPNK

GTKELTAKAK GDQTNKVAKQ GQYKNQDPIV LVHGFNGFTD DINPSVLAHY WGGNKMNIRQ

DLEENGYKAY EASISAFGSN YDRAVELYYY IKGGRVDYGA AHAAKYGHER YGKTYEGIYK

DWKPGQKVHL VGHSMGGQTI RQLEELLRNG SREEIEYQKK HSGEISPLFK GNNDNMISSI

TTLGTPHNGT HASDLAGNEA L

SEQ ID NO: 96
GFLNKSKNEQ AALKAQQAAI KEEASANNLS DTSQEAQEIQ EAKREAQAEA DKSVAVSNKE

SKAVALKAQQ AAIKEEASAN NLSDTSQEAQ EIQEAKKEAQ AETDKSAAVS NEEPKAVALK

AQQAAIKEEA SANNLSDISQ EAQEVQEAKK EAQAEKDSDT LTKDASAAKV EVSKPESQAE

RLANAAKQKQ AKLTPGSKES QLTEALFAEK PVAKNDLKEI PQLVTKKNDV SETETVNIDN

KDTVKQKEAK FENGVITRKA DEKTTNNTAV DKKSGKQSKK TTPSNKRNAS KASTNKTSGQ

KKQHNKKSSQ GAKKQSSSSK STQKNNQTSN KNSKTTNAKS SNASKTPNAK VEKAKSKIEK

RTFND

SEQ ID NO: 97
KDNLNGEKPT TNLNHNITSP SVNSEMNNNE TGTPHESNQT GNEGTGSNSR DANPDSNNVK

PDSNNQNPST DSKPDPNNQN PSPNPKPDPD NPKPKPDPKP DPDKPKPNPD PKPDPDNPKP

NPDPKPDPNK PNPDPKPDPD KPKPNPNPKP DPNKPNPNPS PDPDQPGDSN HSGGSKNGGT

WNPNASDGSN QGQWQPNGNQ GNSQNPTGND FVSQRFLALA NGAYKYNPYI LNQINKLGKD

YGEVTDEDIY NIIRKQNFSG NAYLNGLQQQ SNYFRFQYFN PLKSERYYRN LDEQVLALIT

GEIGSMPDLK KPEDKPDSKQ RSFEPHEKDD FTVVKKQEDN KKSASTAYSK S

SEQ ID NO: 98
IDSKNKPANS DIKFEVTQKS DAVKALKELP KSENVKNIYQ DYAVTDVKTD KKGFTHYTLQ

PSVDGVHAPD KEVKVHADKS GKVVLINGDT DAKKVKPTNK VTLSKDDAAD KAFKAVKIDK

NKAKNLKDKV IKENKVEIDG DSNKYVYNVE LITVTPEISH WKVKIDAQTG EILEKMNLVK

EAAETGKGKG VLGDTKDINI NSIDGGFSLE DLTHQGKLSA FSFNDQTGQA TLITNEDENF

VKDEQRAGVD ANYYAKQTYD YYKDTFGRES YDNQGSPIVS LTHVNNYGGQ DNRNNAAWIG
```

-continued

```
DKMIYGDGDG RTFTSLSGAN DVVAHELTHG VTQETANLEY KDQSGALNES FSDVFGYFVD

DEDFLMGEDV YTPGKEGDAL RSMSNPEQFG QPAHMKDYVF TEKDNGGVHT NS
```

The DNA sequences encoding SEQ ID NOs: 12-20 and 41-44 are set forth in SEQ ID NO: 46-58 in the same order. The DNA sequence encoding SEQ ID NOs: 59-98 are set forth in SEQ ID NOs: 99-138.

The following table provides the amino acid sequence information relative to constructs disclosed and tested herein:

| Construct name | SEQ ID NO |
| --- | --- |
| CHIM_0992_0735_FS | 12 |
| CHIM_2635_2723_FS | 13 |
| CHIM_2716_2753_FL | 14 |
| CHIM_2723_2753_L_FS | 15 |
| CHIM_2119_1816_FS | 16 |
| CHIM_0992_2635_FL | 17 |
| CHIM_Hla_2635_FS | 18 |
| CHIM_Hla_2753_FS | 19 |
| CHIM_Hla_0735_FS | 20 |
| CHIM_0735_0992_FL | 59 |
| CHIM_0992_0735_FL | 60 |
| CHIM_0992_0735_FS | 61 |
| CHIM_0992_2635_FL | 62 |
| CHIM_0992_2635_FS | 63 |
| CHIM_0992_2753_FS | 64 |
| CHIM_1262_2496_RS | 65 |
| CHIM_1507_2119_FS | 66 |
| CHIM_1816_2119_FL | 67 |
| CHIM_2119_1816_FS | 68 |
| CHIM_2496_1816_FS | 69 |
| CHIM_2635_2723_FS | 70 |
| CHIM_2716_1816_FS | 71 |
| CHIM_2716_2119_FS | 72 |
| CHIM_2716_2753_FL | 73 |
| CHIM_2723_2635_FS | 74 |
| CHIM_2723_2635_RL | 75 |
| CHIM_2723_2753_L_FL | 76 |
| CHIM_2723_2753_S_FS | 77 |
| CHIM_Hla_0735_FS | 78 |
| CHIM_Hla_2635_FS | 79 |
| CHIM_Hla_2753_FS | 80 |
| HL461_SAR2753_291-680 | 81 |
| HL461_SAR2753-291-476 | 82 |
| Hla_H35L-27-319 | 83 |
| IsdB_USA300-41-613 | 84 |
| M2863_SAR0992-1-409 | 85 |
| M3496_SAR2723-28-619 | 86 |
| SAR0280-28-820 | 87 |
| SAR0735-26-227 | 88 |
| SAR0992-1-409 | 89 |
| SAR1262-25-519 | 90 |
| SAR1489-343-486 | 91 |
| SAR1507-1-652 | 92 |
| SAR2635-1-199 | 93 |
| SAR2723-28-619 | 94 |
| SAR2753-36-476 | 95 |
| USA300HOU_1728-88-452 | 96 |
| USA300HOU_2027-33-383 | 97 |
| USA300HOU_2637-28-439 | 98 |

The invention claimed is:

1. A chimeric polypeptide comprising formula I $$a^1\text{-}A^1\text{-}L\text{-}A^2\text{-}a^2 \quad (I)$$

wherein $A^1$ is an amino acid sequence constituted by at least or exactly 35 contiguous amino acid residues present in SEQ ID NO: 6 or an amino acid sequence with at least 80% sequence identity with an amino acid sequence constituted by at least or exactly 35 contiguous amino acid residues present in SEQ ID NO: 6, and, $A^2$ an amino acid sequence constituted by at least or exactly 35 contiguous amino acid residues present in SEQ ID NO: 9 or an amino acid sequence with at least 80% sequence identity with an amino acid sequence constituted by at least or exactly 35 contiguous amino acid residues present in SEQ ID NO: 9, or A¹ is an amino acid sequence constituted by at least or exactly 35 contiguous amino acid residues present in SEQ ID NO: 9 or an amino acid sequence with at least 80% sequence identity with an amino acid sequence constituted by at least or exactly 35 contiguous amino acid residues present in SEQ ID NO: 9, and A² is an amino acid sequence constituted by at least or exactly 35 contiguous amino acid residues present in SEQ ID NO: 6 or an amino acid sequence with at least 80% sequence identity with an amino acid sequence constituted by at least or exactly 35 contiguous amino acid residues present in SEQ ID NO: 6, L is an optional amino acid sequence, a¹ is an optional amino acid sequence, and a² is an optional amino acid sequence.

2. The chimeric polypeptide according to claim 1, wherein A¹ and A² is an amino acid sequence with at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%1, or at least 99% sequence identity with an amino acid sequence constituted by at least or exactly 35 contiguous amino acid residues present in SEQ ID NO: 6 or SEQ ID NO: 9.

3. The chimeric polypeptide according to claim 1, wherein the at least or exactly 35 contiguous amino acid residues present in SEQ ID: 6 or SEQ ID NO: 9 in the definition of A¹ and/or A² are at least or exactly or at most 36 at least or exactly or at most 37, at least or exactly or at most 38, at least or exactly or at most 39, at least or exactly or at most 40, at least or exactly or at most 41, at least or exactly or at most 42, at least or exactly or at most 43, at least Or exactly or at most 44, at least or exactly or at most 45, at least or exactly or at most 46, at least or exactly or at most 47, at least or exactly or at most 48, at least or exactly or at most 49, at least or exactly or at most 50, at least or exactly or at most 51, at least or exactly or at most 52 at least or exactly or at most 53, at least or exactly or at most 54, at least or exactly or at most 55, at least or exactly at most 56 at least or exactly or at most 57, at least or exactly or at most 58, at least or exactly or at most 59 at least or exactly or at most, 60, at least or exactly or at most 61, at least or exactly or at most 62, at least or exactly or at most 63, at least or exactly or at most 64, at least or exactly or at most 65, at least or exactly or at most 66 at least or exactly or at most 67, at least or exactly or at most 68, at least or exactly or at most 69, at least or exactly or at most 70, at least or exactly or at most 71, at least or exactly or at most 72, at least or exactly or at most 73, at least or exactly or at most 74, at least or exactly or at most 75, at least or exactly or at most 76, at least or exactly or at most 77, at least or exactly or at most 78, at least or exactly or at most 79, at least or exactly or at most 80, at least or exactly or at most 81, at least or exactly or at most 82, at least or exactly or at most 83, at least or exactly or at most 84, at least or exactly or at most 85, at least or exactly or at most 86, at least or exactly or at most 87, at least or exactly or at most 88, at least or exactly or at most 89, at least or exactly or at most 90, at least or exactly or at most 91, at least or exactly or at most 92, at least or exactly or at most 93, at least or exactly or at most 94, at least or exactly or at most 95, at least or exactly or at most 96, at least or exactly or at most 97, at least or exactly or at most 98, at least or exactly or at most 99, at least or exactly or at most 100, at least or exactly or at most 101, at least or exactly or at most 102, at least or exactly or at most 103, at least or exactly or at most 104, at least or exactly or at most 105, at least or exactly or at most 106, at least or exactly or at most 107, at least or exactly or at most 108, at least or exactly or at most 109, at least or exactly or at most 110, at least or exactly or at most 111, at least or exactly or at most 112, at least or exactly or at most 113, at least or exactly or at most 114, at least or exactly or at most 115, at least or exactly or at most 116, at least or exactly or at most 117, at least or exactly or at most 118, at least or exactly or at most 119, at least or exactly or at most 120, at least or exactly or at most 121, at least or exactly or at most 122, at least or exactly or at most 123, at least or exactly or at most 124, at least or exactly or at most 125, at least or exactly or at most 126, at least or exactly or at most 127, at least or exactly or at most 128, at least or exactly or at most 129, at least or exactly or at most 130, at least or exactly or at most 131, at least or exactly or at most 132, at least or exactly or at most 133, at least or exactly or at most 134, at least or exactly or at most 135, at least or exactly or at most 136, at least or exactly or at most 137, at least or exactly or at most 138, at least or exactly or at most 139, at least or exactly or at most 140, at least or exactly or at most 141, at least or exactly or at most 142, at least or exactly or at most 143, at least or exactly or at most 144, at least or exactly or at most 145, at least or exactly or at most 146, at least or exactly or at most 147, at least or exactly or at most 148, at least or exactly or at most 149, at least or exactly or at most 150, at least or exactly or at most 151, at least or exactly or at most 152, at least or exactly or at most 153, at least or exactly or at most 154, at least or exactly or at most 155, at least or exactly or at most 156, at least or exactly or at most 157, at least or exactly or at most 158, at least or exactly or at most 159, at least or exactly or at most 160, at least or exactly or at most 161, at least or exactly or at most 162, at least or exactly or at most 163, at least or exactly or at most 164, at least or exactly or at most 165, at least or exactly or at most 166, at least or exactly or at most 167, at least or exactly or at most 168, at least or exactly or at most 169, at least or exactly or at most 170, at least or exactly or at most 171, at least or exactly or at most 172, at least or exactly or at most 173, at least or exactly or at most 174, at least or exactly or at most 175, at least or exactly or at most 176, at least or exactly or at most 177, at least or exactly or at most 178, at least or exactly or at most 179, at least or exactly or at most 180, at least or exactly or at most 181, at least or exactly or at most 182, at least or exactly or at most 183, at least or exactly or at most 184, at least or exactly or at most 185, at least or exactly or at most 186, at least or exactly or at most 187, at least or exactly or at most 188, at least or exactly or at most 189, at least or exactly or at most 190, at least or exactly or at most 191, at least or exactly or at most 192, at least or exactly or at most 193, at least or exactly or at most 194, at least or exactly or at most 195, at least or exactly or at most 196, at least or exactly or at most 197, at least or exactly or at most 198, or at least or exactly or at most 199, at least or exactly or at most 200, at least or exactly or at most 201, at least or exactly or at most 202, at least or exactly or at most 203, at least or exactly or at most 204, at least or exactly or at most 205, at least or exactly or at most 206, at least or exactly or at most 207, at least or exactly or at most 208, at least or exactly or at most 209, at least or exactly or at most 210, at least or exactly or at most 211, at least or exactly or at most 212, at least or exactly or at most 213, at least or exactly or at most 214, at least or exactly or at most 215, at least or exactly or at most 216, at least or exactly or at most 217, at least or exactly or at most 218, at least or exactly or at most 219, at least or exactly or at most 220, at least or exactly or at most 221, at least or exactly or at most 222, at least or exactly or at most 223, at least or exactly or at most 224, at least or exactly or at most 225, at least or exactly or at most 226, at least or exactly or at most 227, at least or exactly or at most 228, at least or exactly or at most 229, at least or exactly or at most 230, at least or exactly or at most 231, at least or exactly or at most 232, at least or exactly or at most 233, at least or exactly or at most 234, at least or exactly or at most 235, at least or exactly or at most 236, at least or exactly or at most 237, at least or exactly or at most 238, at least or exactly or at most 239, at least or exactly or at most 240, at least or exactly or at most 241, at least or exactly or at most 242, at least or exactly or at most 243, at least or exactly or at most 244, at least or exactly or at most 245, at least or exactly or at most 246, at least or exactly or at most 247, at least or exactly or at most 248, at least or exactly or at most 249, at least or exactly or at most 250, at least or exactly or at most 251, at least or exactly or at most 252, at least or exactly or at most 253, at least or exactly or at most 254, at least or exactly or at most 255, at least or exactly or at most 256, at least or exactly or at most 257, at least or exactly or at most 258, at least or exactly or at most 259, at least or exactly or at most 260, at least or exactly or at most 261, at least or exactly or at most 262, at least or exactly or at most 263, at least or exactly or at most 264, at least or exactly or at most 265, at least or exactly or at most 266, at least or exactly or at most 267, at least or exactly or at most 268, at least or exactly or at most 269, at least or exactly or at most 270, at least or exactly or at most 271, at least or exactly or at most 272, at least or exactly or at most 273, at least or exactly or at most 274, at least or exactly or at most 275, at least or exactly or at most 276, at least or exactly or at most 277, at least or exactly or at most 278, at least or exactly or at most 279, at least or exactly or at most 280, at least or exactly or at most 281, at least or exactly or at most 282, at least or exactly or at most 283, at least or exactly or at most 284, at least or exactly or at most 285, at least or exactly or at most 286, at least or exactly or at most 287, at least or exactly or at most 288, at least or exactly or at most 289, at least or exactly or at most 290, at least or exactly or at most 291, at least or exactly or at most 292, at least or exactly or at most 293, at least or exactly or at most 294, at least or exactly or at most 295, at least or exactly or at most 296, at least or exactly or at most 297, at least or exactly or at most 298, at least or exactly or at most 299, at least or exactly or at most 300, at least or exactly or at most 301, at least or exactly or at most 302, at least or exactly or at most 303, at least or exactly or at most 304, at least or exactly or at most 305, at least or exactly or at most 306, at least or exactly or at most 307, at least or exactly or at most 308, at least or exactly or at most 309, at least or exactly or at most 310, at least or exactly or at most 311, at least or exactly or at most 312, at least or exactly or at most 313, at least or exactly or at most 314, at least or exactly or at most 315, at least or exactly or at most 316, at least or exactly or at most 317, at least or exactly or at most 318, or at least or exactly or at most 319, at least or exactly or at most 320, at least or exactly or at most 321, at least or exactly or at most 322, at least or exactly or at most 323, at least or exactly or at most 324, at least or exactly or at most 325, at least or exactly or at most 326, at least or exactly or at most 327, at least or exactly or at most 328, at least or exactly or at most 329, at least or exactly or at most 330, at least or exactly or at most 331, at least or exactly or at most 332, at least or exactly or at most 333, at least or exactly or at most 334, at least or exactly or at most 335, at least or exactly or at most 336, at least or exactly or at most 337, at least or exactly or at most 338, at least or exactly or at most 339, at least or exactly or at most 340, at least or exactly or at most 341, at least or exactly or at most 342, at least or exactly or at most 343, at least or exactly or at most 344, at least or exactly or at most 345, at least or exactly or at most 346, at least or exactly or at most 347, at least or exactly or at most 348, at least or exactly or at most 349, at least or exactly or at most 350, or at least or exactly or at most 351, at least or exactly or at most 352, at least or exactly or at most 353, at least or exactly or at most 354, at least or exactly or at most 355, at least or exactly or at most 356, at least or exactly or at most 357, at least or exactly or at most 358, at least or exactly or at most 359, at least or exactly or at most 360, at least or exactly or at most 361, at least or exactly or at most 362, at least or exactly or at most 363, at least or exactly or at most 364, or at least or exactly or at most 365, at least or exactly or at most 366, at least or exactly or at most 367, at least or exactly or at most 368, at least or exactly or at most 369, at least or exactly or at most 370, at least or exactly or at most 371, at least or exactly or at most 372, at least or exactly or at most 373, at least or exactly or at most 374, at least or exactly or at most 375, at least or exactly or at most 376, at least or exactly or at most 377, at least or exactly or at most 378, at least or exactly or at most 379, at least or exactly or at most 380, at least or exactly or at most 381, at least or exactly or at most 382, at least or exactly or at most 383, at least or exactly or at most 384, at least or exactly or at most 385, at least or exactly or at most 386, at least or exactly or at most 387, at least or exactly or at most 388, at least or exactly or at most 389, or at least or exactly or at most 390 amino acid residues in SEQ ID NO: 6 and/or SEQ ID NO: 9, or wherein the at least or exactly 35 contiguous amino acid residues present in SEQ ID NO: 9 in the definition of $A^1$ and/or $A^2$ are at least or exactly or at most 391, at least or exactly or at most 392, at least or exactly or at most 393, at least or exactly or at most 394, at least or exactly or at most 395, at least or exactly or at most 396, at least or exactly or at most 397, at least or exactly or at most 398, at least or exactly or at most 399, at least or exactly or at most 400, at least or exactly or at most 401, at least or exactly or at most 402, at least or exactly or at most 403, or at least or exactly or at most 404, at least or exactly or at most 405, at least or exactly or at most 406, at least or exactly or at most 407, at least or exactly or at most 408, at least or exactly or at most 409, at least or exactly or at most 410, at least or exactly or at most 411, at least or exactly or at most 412, at least or exactly or at most 413, at least or exactly or at most 414, at least or exactly or at most 415, at least or exactly or at most 416, at least or exactly or at most 417, at least or exactly or at most 418, at least or exactly or at most 419, at least or exactly or at most 420, at least or exactly or at most 421, at least or exactly or at most 422, at least or exactly or at most 423, at least or exactly or at most 424, at least or exactly or at most 425, at least or exactly or at most 426, at least or exactly or at most 427, at least or exactly or at most 428, at least or exactly or at most 429, at least or exactly or at most 430, at least or exactly or at most 431, at least or exactly or at most 432, at least or exactly or at most 433, at least or exactly or at most 434, at least or exactly or at most 435, at least or exactly or at most 436, at least or exactly or at most 437, at least or exactly or at most 438, at least or exactly or at most 439, at least or exactly or at most 440, at least or exactly or at most 441, at least or exactly or at most 442, at least or exactly or at most 443, at least or exactly or at most 444, at least or exactly or at most 445, at least or exactly or at most 446, at least or exactly or at most 447, at least or exactly or at most 448, at least or exactly or at most 449, at least or exactly or at most 450, at least or exactly or at most 451, at least or exactly or at most 452, at least or exactly or at most 453, at least or exactly or at most 454, at least or exactly or at most 455, at least or exactly or at most 456, at least or exactly or at most 457, at least or exactly or at most 458, at least or exactly or at most 459, at least or exactly or at most 460, at least or exactly or at most 461, at least or exactly or at most 462, at least or exactly or at most 463, at least or exactly or at most 464, at least or exactly or at most 465, at least or exactly or at most 466, at least or exactly or at most 467, at least or exactly or at most 468, at least or exactly or at most 469, at least or exactly or at most 470, at least or exactly or at most 471, at least or exactly or at most 472, at least or exactly or at most 473, at least or exactly or at most 474, at least or exactly or at most 475, at least or exactly or at most 476, at least or exactly or at most 477, at least or exactly or at most 478, at least or exactly or at most 479, at least or exactly or at most 480, at least or exactly or at most 481, at least or exactly or at most 482, at least or exactly or at most 483, at least or exactly or at most 484, at least or exactly or at most 485, at least or exactly or at most 486, at least or exactly or at most 487, at least or exactly or at most 488, at least or exactly or at most 489, at least or exactly or at most 490, at least or exactly or at most 491, at least or exactly or at most 492, at least or exactly or at most 493, at least or exactly or at most 494, at least or exactly or at most 495, at least or exactly or at most 496, at least or exactly or at most 497, at least or exactly or at most 498, at least or exactly or at most 499, at least or exactly or at most 500, at least or exactly or at most 501, at least or exactly or at most 502, at least or exactly or at most 503, at least or exactly or at most 504, at least or exactly or at most 505, at least or exactly or at most 506, at least or exactly or at most 507, at least or exactly or at most 508, at least or exactly or at most 509, at least or exactly or at most 510, at least or exactly or at most 511, at least or exactly or at most 512, at least or exactly or at most 513, at least or exactly or at most 514, at least or exactly or at most 515, at least or exactly or at most 516, at least or exactly or at most 517, at least or exactly or at most 518, at least or exactly or at most 519, at least or exactly or at most 520, at least or exactly or at most 521, at least or exactly or at most 522, at least or exactly or at most 523, at least or exactly or at most 524, at least or exactly or at most 525, at least or exactly or at most 526, at least or exactly or at most 527, at least or exactly or at most 528, at least or exactly or at most 529, at least or exactly or at most 530, at least or exactly or at most 531, at least or exactly or at most 532, at least or exactly or at most 533, at least or exactly or at most 534, at least or exactly or at most 535, at least or exactly or at most 536, at least or exactly or at most 537, at least or exactly or at most 538, at least or exactly or at most 539, at least or exactly or at most 540, at least or exactly or at most 541, at least or exactly or at most 542, at least or exactly or at most 543, at least or exactly or at most 544, at least or exactly or at most 545, at least or exactly or at most 546, at least or exactly or at most 547, at least or exactly or at most 548, at least or exactly or at most 549, at least or exactly or at most 550, at least or exactly or at most 551, at least or exactly or at most 552, at least or exactly or at most 553, at least or exactly or at most 554, at least or exactly or at most 555, at least or exactly or at most 556, at least or exactly or at most 557, at least or exactly or at most 558, at least or exactly or at most 559, at least or exactly or at most 560, at least or exactly or at most 561, at least or exactly or at most 562, at least or exactly or at most 563, at least or exactly or at most 564, at least or exactly or at most 565, at least or exactly or at most 566, at least or exactly or at most 567, at least or exactly or at most 568, at least or exactly or at most 569, at least or exactly or at most 570, at least or exactly or at most 571, at least or exactly or at most 572, at least or exactly or at most 573, at least or exactly or at most 574, at least or exactly or at most 575, at least or exactly or at most 576, at least or exactly or at most 577, at least or exactly or at most 578, at least or exactly or at most 579, at least or exactly or at most 580, at least or exactly or at most 581, at least or exactly or at most 582, at least or exactly or at most 583, at least or exactly or at most 584, at least or exactly or at most 585, at least or exactly or at most 586, at least or exactly or at most 587, at least or exactly or at most 588, at least or exactly or at most 589, at least or exactly or at most 590, at least or exactly or at most 591, or at least or exactly or at most 592 amino acid residues in SEQ ID NO: 9.

4. The chimeric polypeptide according to claim 1, wherein the at least or exactly 35 contiguous amino acid residues present in SEQ ID NO: 6 or SEQ ID NO: 9 in the definition of $A^1$ and/or $A^2$ commences at amino acid residue 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 133, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 244, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, or 356 SEQ ID NO: 6 or SEQ ID NO: 9, wherein the at least or exactly 35 contiguous amino acid residues present in SEQ ID NO: 9 n the definition of $A^1$ and/or $A^2$ commences at amino acid residue 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, or 558 in SEQ ID NO: 9, with the proviso that the number of the selected commencing amino acid residue satisfies the formula $N \leq L-n+1$, where N is the number of the selected residue in SEQ ID NO: 6 and/or SEQ ID NO: 9, and n is the number of contiguous amino acid residues.

5. The chimeric polypeptide according to claim 1, wherein $a^1$ is selected from the group consisting of
   1) a methionine residue,
   2) an amino acid sequence located, or directly linked, N-terminally to the $A^1$ amino acid sequence,
   3) an amino acid sequence that comprises or constitutes a purification tag,
   4) an amino acid sequence that comprises or constitutes an immunogenic carrier molecule,
   5) an amino acid sequence that exerts adjuvant activity, and
   6) any combination of 1) to 5).

6. The chimeric polypeptide according to claim 5, wherein, when $a^1$ is the amino acid sequence, then said $a^1$ has an N-terminal methionine residue.

7. The chimeric polypeptide according to claim 1, wherein $a^2$ is selected from the group consisting of
   i) an amino acid sequence located, or directly linked, C-terminally to the $A^2$ amino acid sequence,
   ii) an amino acid sequence that comprises or constitutes a purification tag,
   iii) an amino acid sequence that comprises or constitutes an immunogenic carrier molecule,
   iv) an amino acid sequence that exerts adjuvant activity, and
   v) any combination of i) to iv).

8. The chimeric polypeptide according to claim 1, wherein L is a linker.

9. The chimeric polypeptide according to claim 8, wherein the linker comprises glycine and/or serine residues.

10. The chimeric polypeptide according to claim 9,
    wherein the linker comprises or consists of the amino acid sequence GSGGGA (SEQ ID NO: 10) or GSGG-GAGSGGGA (SEQ ID NO: 11).

11. A chimeric polypeptide which comprises or consists of the amino acid sequence of SEQ ID NO: 15.

12. The chimeric polypeptide according to claim 1, which is further covalently linked to an immunogenic carrier molecule.

13. The chimeric polypeptide according to claim 12, wherein the immunogenic carrier molecule is a polypeptide that induces T-helper lymphocyte responses in a majority of humans.

14. A pharmaceutical composition comprising an immunogenically effective amount of the chimeric polypeptide according to claim 1 and a pharmaceutically acceptable carrier, vehicle or diluent.

15. The pharmaceutical composition according to claim 14, which further comprises an immunological adjuvant.

16. The pharmaceutical composition according to claim 15, wherein the adjuvant is an aluminium based adjuvant.

17. The pharmaceutical composition pharmaceutical composition according to claim 13, wherein the immunogenic carrier molecule is an immunogenic carrier protein selected from the group consisting of keyhole limpet hemocyanin or an immunogenic fragment thereof, tetanus toxoid or an immunogenic fragment thereof, and diphtheria toxoid or an immunogenic fragment thereof.

18. The chimeric polypeptide of claim 1, wherein $A^1$ is an amino acid sequence constituted by at least or exactly 100 contiguous amino acid residues present in SEQ ID NO: 6 or an amino acid sequence with at least 80% sequence identity with an amino acid sequence constituted by at least or exactly 100 contiguous amino acid residues present in SEQ ID NO: 6, and $A^2$ is an amino acid sequence constituted by at least or exactly 100 contiguous amino acid residues present in SEQ ID NO: 9 or an amino acid sequence with at least 80% sequence identity with an amino acid sequence constituted by at least or exactly 100 contiguous amino acid residues present in SEQ ID NO: 9, or $A^1$ is an amino acid sequence constituted by at least or exactly 100 contiguous amino acid residues present in SEQ ID NO: 9 or an amino acid sequence with at least 80% sequence identity with an amino acid sequence constituted by at least or exactly 100 contiguous amino acid residues present in SEQ ID NO: 9, and $A^2$ is an amino acid sequence constituted by at least or exactly 100 contiguous amino acid residues present in SEQ ID NO: 6 or an amino acid sequence with at least 80% sequence identity with an amino acid sequence constituted by at least or exactly 100 contiguous amino acid residues present in SEQ ID NO: 6.

19. The chimeric polypeptide of claim 1, wherein $A^1$ is an amino acid sequence constituted by at least or exactly 200 contiguous amino acid residues present in SEQ ID NO: 6 or an amino acid sequence with at least 80% sequence identity with an amino acid sequence constituted by at least or exactly 200 contiguous amino acid residues present in SEQ ID NO: 6, and $A^2$ is an amino acid sequence constituted by at least or exactly 200 contiguous amino acid residues present in SEQ ID NO: 9 or an amino acid sequence with at least 80% sequence identity with an amino acid sequence constituted by at least or exactly 200 contiguous amino acid residues present in SEQ ID NO: 9, or $A^1$ is an amino acid sequence constituted by at least or exactly 200 contiguous amino acid residues present in SEQ ID NO: 9 or an amino acid sequence with at least 80% sequence identity with an amino acid sequence constituted by at least or exactly 200 contiguous amino acid residues present in SEQ ID NO: 9, and $A^2$ is an amino acid sequence constituted by at least or exactly 200 contiguous amino acid residues present in SEQ ID NO: 6 or an amino acid sequence with at least 80% sequence identity with an amino acid sequence constituted by at least or exactly 200 contiguous amino acid residues present in SEQ ID NO: 6.

20. The chimeric polypeptide of claim 1, wherein $A^1$ is an amino acid sequence constituted by at least or exactly 300 contiguous amino acid residues present in SEQ ID NO: 6 or an amino acid sequence with at least 80% sequence identity with an amino acid sequence constituted by at least or exactly 300 contiguous amino acid residues present in SEQ ID NO: 6, and $A^2$ is an amino acid sequence constituted by at least or exactly 300 contiguous amino acid residues present in SEQ ID NO: 9 or an amino acid sequence with at least 80% sequence identity with an amino acid sequence constituted by at least or exactly 300 contiguous amino acid residues present in SEQ ID NO: 9, or $A^1$ is an amino acid sequence constituted by at least or exactly 300 contiguous amino acid residues present in SEQ ID NO: 9 or an amino acid sequence with at least 80% sequence identity with an amino acid sequence constituted by at least or exactly 300 contiguous amino acid residues present in SEQ ID NO: 9, and $A^2$ is an amino acid sequence constituted by at least or exactly 300 contiguous amino acid residues present in SEQ ID NO: 6 or an amino acid sequence with at least 80% sequence identity with an amino acid sequence constituted by at least or exactly 300 contiguous amino acid residues present in SEQ ID NO: 6.

21. The chimeric polypeptide of claim 1, wherein $A^1$ is an amino acid sequence constituted by at least or exactly 300 contiguous amino acid residues present in SEQ ID NO: 6 or an amino acid sequence with at least 80% sequence identity with an amino acid sequence constituted by at least or exactly 300 contiguous amino acid residues present in SEQ ID NO: 6, and $A^2$ is an amino acid sequence constituted by at least or exactly 400 contiguous amino acid residues present in SEQ ID NO: 9 or an amino acid sequence with at least 80% sequence identity with an amino acid sequence constituted by at least or exactly 400 contiguous amino acid residues present in SEQ ID NO: 9, or $A^1$ is an amino acid sequence constituted by at least or exactly 400 contiguous amino acid residues present in SEQ ID NO: 9 or an amino acid sequence with at least 80% sequence identity with an amino acid sequence constituted by at least or exactly 400 contiguous amino acid residues present in SEQ ID NO: 9, and $A^2$ is an amino acid sequence constituted by at least or exactly 300 contiguous amino acid residues present in SEQ ID NO: 6 or an amino acid sequence with at least 80% sequence identity with an amino acid sequence constituted by at least or exactly 300 contiguous amino acid residues present in SEQ ID NO: 6.

22. The chimeric polypeptide of claim 1, wherein $A^1$ is an amino acid sequence constituted by at least or exactly 300 contiguous amino acid residues present in SEQ ID NO: 6 or an amino acid sequence with at least 80% sequence identity with an amino acid sequence constituted by at least or exactly 300 contiguous amino acid residues present in SEQ ID NO: 6, and $A^2$ is an amino acid sequence constituted by at least or exactly 500 contiguous amino acid residues present in SEQ ID NO: 9 or an amino acid sequence with at least 80% sequence identity with an amino acid sequence constituted by at least or exactly 500 contiguous amino acid residues present in SEQ ID NO: 9, or $A^1$ is an amino acid sequence constituted by at least or exactly 500 contiguous amino acid residues present in SEQ ID NO: 9 or an amino acid sequence with at least 80% sequence identity with an amino acid sequence constituted by at least or exactly 500 contiguous amino acid residues present in SEQ ID NO: 9, and $A^2$ is an amino acid sequence constituted by at least or exactly 300 contiguous amino acid residues present in SEQ ID NO: 6 or an amino acid sequence with at least 80% sequence identity with an amino acid sequence constituted by at least or exactly 300 contiguous amino acid residues present in SEQ ID NO: 6.

23. The chimeric polypeptide according to claim 1, which is capable of inducing an adaptive immune response against the chimeric polypeptide in a mammal.

24. The chimeric polypeptide according to claim 23, wherein the mammal is a human being.

25. The chimeric polypeptide according to claim 23, which is capable of inducing a humoral and/or a cellular immune response.

26. A method of inducing a protective adaptive immune response against *Staphylococcus aureus* in an animal by administering at least once an immunogenically effective amount of the chimeric polypeptide according to claim 11.

27. A method of inducing an immune response in an animal by administering to the animal at least once an immunogenically effective amount of the chimeric polypeptide according to claim 1.

28. The method of claim 27, wherein the animal receives between 0.5 and 5,000 micrograms of the chimeric polypeptide per administration.

29. The method of claim 27, wherein the animal receives a first priming administration of the chimeric polypeptide and one or more booster administrations of the chimeric polypeptide.

30. The method of claim 27, wherein the animal is a human being.

31. The method of claim 27, wherein the administration is for the purpose of inducing antibodies specific to the chimeric polypeptide.

32. A method of inducing an immune response in an animal by administering at least once the pharmaceutical composition of claim 14.

* * * * *